(12) United States Patent
Berry et al.

(10) Patent No.: US 11,607,432 B2
(45) Date of Patent: Mar. 21, 2023

(54) PROBIOTIC COMPOSITIONS CONTAINING CLOSTRIDIALES FOR INHIBITING INFLAMMATION

(71) Applicant: Evelo Biosciences, Inc., Cambridge, MA (US)

(72) Inventors: David Berry, Waban, MA (US); Johanne Kaplan, Sherborn, MA (US); Shaila Rahman, Cambridge, MA (US)

(73) Assignee: Evelo Biosciences, Inc., Cambridge, MA (US)

( * ) Notice: Subject to any disclaimer, the term of this patent is extended or adjusted under 35 U.S.C. 154(b) by 489 days.

(21) Appl. No.: 16/549,950

(22) Filed: Aug. 23, 2019

(65) Prior Publication Data

US 2020/0061129 A1    Feb. 27, 2020

Related U.S. Application Data

(63) Continuation of application No. 16/219,125, filed on Dec. 13, 2018, which is a continuation of application No. 15/438,271, filed on Feb. 21, 2017, now abandoned, which is a continuation of application No. 14/952,895, filed on Nov. 25, 2015, now Pat. No. 9,610,307.

(60) Provisional application No. 62/257,714, filed on Nov. 19, 2015, provisional application No. 62/162,562, filed on May 15, 2015, provisional application No. 62/117,639, filed on Feb. 18, 2015, provisional application No. 62/117,632, filed on Feb. 18, 2015, provisional application No. 62/117,637, filed on Feb. 18, 2015, provisional application No. 62/084,536, filed on Nov. 25, 2014, provisional application No. 62/084,540, filed on Nov. 25, 2014, provisional application No. 62/084,537, filed on Nov. 25, 2014.

(51) Int. Cl.

| | |
|---|---|
| A61K 35/744 | (2015.01) |
| A61K 35/741 | (2015.01) |
| A61K 35/74 | (2015.01) |
| A61P 37/00 | (2006.01) |
| A61K 31/7004 | (2006.01) |
| A61K 31/715 | (2006.01) |
| A61K 38/46 | (2006.01) |
| A61K 35/39 | (2015.01) |
| A61P 29/00 | (2006.01) |
| A61P 43/00 | (2006.01) |
| A61K 9/00 | (2006.01) |
| A61K 35/742 | (2015.01) |
| A61K 35/745 | (2015.01) |
| A61K 35/747 | (2015.01) |
| A61K 9/19 | (2006.01) |
| A61K 31/7016 | (2006.01) |
| A61K 35/00 | (2006.01) |

(52) U.S. Cl.
CPC ............ *A61K 35/74* (2013.01); *A61K 9/0031* (2013.01); *A61K 9/0053* (2013.01); *A61K 9/19* (2013.01); *A61K 31/7004* (2013.01); *A61K 31/7016* (2013.01); *A61K 31/715* (2013.01); *A61K 35/39* (2013.01); *A61K 35/741* (2013.01); *A61K 35/742* (2013.01); *A61K 35/744* (2013.01); *A61K 35/745* (2013.01); *A61K 35/747* (2013.01); *A61K 38/46* (2013.01); *A61P 29/00* (2018.01); *A61P 37/00* (2018.01); *A61P 43/00* (2018.01); *A61K 2035/115* (2013.01); *Y02A 50/30* (2018.01)

(58) Field of Classification Search
CPC .............................. A61K 35/74; A61K 35/744
See application file for complete search history.

(56) References Cited

U.S. PATENT DOCUMENTS

| | | |
|---|---|---|
| 6,506,380 B1 | 1/2003 | Isolauri et al. |
| 7,172,756 B2 | 2/2007 | Isolauri et al. |
| 7,235,395 B2 | 6/2007 | Stadler et al. |
| 7,627,437 B2 | 12/2009 | Forney et al. |
| 7,749,494 B2 | 7/2010 | Renaud et al. |
| 8,318,151 B2 | 11/2012 | Darimont-Nicolau et al. |
| 8,486,668 B2 | 7/2013 | Ritter et al. |
| 9,603,878 B2 | 3/2017 | Berry et al. |
| 9,610,307 B2 | 4/2017 | Berry et al. |
| 9,700,609 B2 | 7/2017 | Larkin et al. |
| 10,869,903 B2 | 12/2020 | Berry et al. |
| 10,980,845 B2 | 4/2021 | Berry et al. |
| 2003/0147858 A1 | 8/2003 | Renaud et al. |
| 2004/0265290 A1 | 12/2004 | Stadler et al. |

(Continued)

FOREIGN PATENT DOCUMENTS

| | | |
|---|---|---|
| CA | 1333564 C | 12/1994 |
| CA | 2966132 A1 | 4/2016 |

(Continued)

OTHER PUBLICATIONS

Ermolenko et al., Bioscience of Microbiota, Food and Health, 2013; 32(2):41-49 (Year: 2013).*

(Continued)

*Primary Examiner* — Brian Gangle
*Assistant Examiner* — Lakia J Jackson-Tongue
(74) *Attorney, Agent, or Firm* — Foley Hoag LLP; Brendan T. Jones; David E. Shore

(57) ABSTRACT

Pharmaceutical compositions containing microbial entities are described herein. The pharmaceutical compositions may optionally contain or be used in conjunction with one or more prebiotics. Uses of the pharmaceutical compositions to treat or prevent disorders of the local or systemic microbiome in a subject are also provided.

14 Claims, 99 Drawing Sheets

Specification includes a Sequence Listing.

(56) References Cited

U.S. PATENT DOCUMENTS

| | | | |
|---|---|---|---|
| 2005/0180961 | A1 | 8/2005 | Pecquet et al. |
| 2006/0088513 | A1 | 4/2006 | Inoue et al. |
| 2007/0128303 | A1 | 6/2007 | Chang et al. |
| 2007/0207132 | A1 | 9/2007 | Speelmans et al. |
| 2007/0280912 | A1* | 12/2007 | Cobb ............... A61P 1/14 424/93.44 |
| 2008/0254058 | A1 | 10/2008 | Glenting et al. |
| 2009/0110664 | A1 | 4/2009 | Moore |
| 2009/0148545 | A1 | 6/2009 | Falk et al. |
| 2010/0074872 | A1 | 3/2010 | Blaser et al. |
| 2010/0310514 | A1 | 12/2010 | Cho et al. |
| 2010/0316617 | A1 | 12/2010 | Renaud et al. |
| 2011/0097361 | A1 | 4/2011 | Tang |
| 2011/0280840 | A1 | 11/2011 | Blaser et al. |
| 2011/0287072 | A1 | 11/2011 | Ritter et al. |
| 2012/0034322 | A1 | 2/2012 | Oda et al. |
| 2012/0149584 | A1 | 6/2012 | Olle et al. |
| 2012/0276149 | A1 | 11/2012 | Littman et al. |
| 2013/0122147 | A1* | 5/2013 | Tissot-Favre ....... A23K 20/158 426/71 |
| 2013/0330414 | A1 | 12/2013 | Santamaria |
| 2014/0199281 | A1 | 7/2014 | Henn et al. |
| 2014/0271721 | A1 | 9/2014 | Walser et al. |
| 2014/0271836 | A1 | 9/2014 | Walser et al. |
| 2014/0328803 | A1 | 11/2014 | McKenzie et al. |
| 2014/0341921 | A1 | 11/2014 | Honda et al. |
| 2014/0363397 | A1 | 12/2014 | Allen-Vercoe et al. |
| 2016/0143961 | A1 | 5/2016 | Berry et al. |
| 2016/0143962 | A1 | 5/2016 | Berry et al. |
| 2016/0193258 | A1 | 7/2016 | Berry et al. |
| 2016/0199424 | A1 | 7/2016 | Berry et al. |
| 2016/0235792 | A1 | 8/2016 | Berry et al. |
| 2016/0271188 | A1 | 9/2016 | Berry et al. |
| 2017/0065554 | A1 | 3/2017 | Heiman et al. |
| 2017/0151291 | A1 | 6/2017 | Henn et al. |
| 2018/0015130 | A1 | 1/2018 | Berry et al. |
| 2018/0046774 | A1 | 2/2018 | Lindahl et al. |
| 2018/0071344 | A1 | 3/2018 | Berry et al. |
| 2018/0169153 | A1 | 6/2018 | Berry et al. |
| 2018/0280454 | A1* | 10/2018 | Garcia-Rodenas ....... A61P 1/12 |
| 2019/0336543 | A1 | 11/2019 | Berry et al. |
| 2020/0061129 | A1 | 2/2020 | Berry et al. |
| 2022/0016185 | A1* | 1/2022 | Hsiao ................ A61K 35/744 |

FOREIGN PATENT DOCUMENTS

| | | |
|---|---|---|
| EP | 2308498 A1 | 4/2011 |
| EP | 2967077 A2 | 1/2016 |
| EP | 3297727 A1 | 3/2018 |
| EP | 3 587 558 A * | 1/2020 |
| JP | 2005058092 A | 3/2005 |
| JP | 2006067881 A | 3/2006 |
| JP | 2006067881 A1 * | 3/2006 |
| JP | 2006104107 A | 4/2006 |
| JP | 2007055986 A | 3/2007 |
| WO | WO-1996/11014 A1 | 4/1996 |
| WO | WO-2001/85187 A1 | 11/2001 |
| WO | WO-2006/091103 A2 | 8/2006 |
| WO | WO-2008/031438 A2 | 3/2008 |
| WO | WO-2011/107481 A2 | 9/2011 |
| WO | WO-2011/110918 A1 | 9/2011 |
| WO | WO-2011/152566 A2 | 12/2011 |
| WO | WO-2012/016287 A2 | 2/2012 |
| WO | WO-2012/024638 A2 | 2/2012 |
| WO | WO-2012/142605 A1 | 10/2012 |
| WO | WO-2013/037068 A1 | 3/2013 |
| WO | WO-2013/050792 A1 | 4/2013 |
| WO | WO-2013/053836 A1 | 4/2013 |
| WO | WO-2013/080561 A1 | 6/2013 |
| WO | WO-2014/078911 A | 5/2014 |
| WO | WO-2014/088982 A1 | 6/2014 |
| WO | WO-2014/121298 A2 | 8/2014 |
| WO | WO-2014/121302 A2 | 8/2014 |
| WO | WO-2014/121304 A1 | 8/2014 |
| WO | WO-2014/145958 A2 | 9/2014 |
| WO | WO-2014/150094 A1 | 9/2014 |
| WO | WO-2014/152338 A1 | 9/2014 |
| WO | WO-2014/153194 A2 | 9/2014 |
| WO | WO-2014/201037 A2 | 12/2014 |
| WO | WO-2015/006355 A2 | 1/2015 |
| WO | WO 2015/077794 A1 * | 5/2015 |
| WO | WO-2015/082151 A1 | 6/2015 |
| WO | WO-2015/095241 A2 | 6/2015 |
| WO | WO-2016/033439 A2 | 3/2016 |
| WO | WO-2016/086209 A8 | 6/2016 |
| WO | WO-2016/086206 A8 | 7/2016 |
| WO | WO-2016/203218 A1 | 12/2016 |
| WO | WO-2017/115001 A1 | 7/2017 |
| WO | WO-2017/152137 A2 | 9/2017 |
| WO | WO-2018/106845 A1 | 6/2018 |
| WO | WO-2018/109461 A1 | 6/2018 |

OTHER PUBLICATIONS

Pascal et al., Frontiers in Immunology, 2018; 9(1584):1-9 (Year: 2018).*
Hughes et al., Curr Neurol Neurosci Rep, 2019; 18(11): 1-22 (Year: 2019).*
Adamu et al., Bacteriotherapy for the treatment of intestinal dysbiosis caused by Clostridium difficile infection. Curr Opin Microbiol. Oct. 2013;16(5):596-601.
Aguilera et al., Aga1, the first alpha-Galactosidase from the human bacteria Ruminococcus gnavus E1, efficiently transcribed in gut conditions. Res Microbiol. Jan. 2012;163(1):14-21.
Andermann et al., Microbiota Manipulation With Prebiotics and Probiotics in Patients Undergoing Stem Cell Transplantation. Curr Hematol Malig Rep. Feb. 2016;11(1):19-28.
Aristilde et al., Hierarchy in pentose sugar metabolism in Clostridium acetobutylicum. Appl Environ Microbiol. Feb. 2015;81(4):1452-62.
Arumugam et al., Enterotypes of the human gut microbiome. Nature. May 12, 2011;473(7346):174-80.
Atarashi et al., Induction of Colonic Regulatory T Cells by Indigenous *clostridium* Species. Sciencexpress. 9 pages, Dec. 23, 2010.
Atarashi et al., Treg induction by a rationally selected mixture of Clostridia strains from the human microbiota. Nature. Aug. 8, 2013;500(7461):232-6.
Atarod et al., Elevated level of HSPA1L mRNA correlates with graft-versus-host disease. Transpl Immunol. Jun. 2015;32(3):188-94.
Baxter et al., Structure of the gut microbiome following colonization with human feces determines colonic tumor burden. Microbiome. Jun. 17, 2014;2:20, 11 pages.
Beelen et al., Influence of intestinal bacterial decontamination using metronidazole and ciprofloxacin or ciprofloxacin alone on the development of acute graft-versus-host disease after marrow transplantation in patients with hematologic malignancies: final results and long-term follow-up of an open-label prospective randomized trial. Blood. May 15, 1999;93(10):3267-75.
Bercik et al., Microbes and the gut-brain axis. Neurogastroenterol Motil. May 2012;24(5):405-13.
Bermudez-Brito et al., The impact of dietary fibers on dendritic cell responses in vitro is dependent on the differential effects of the fibers on intestinal epithelial cells. Mol Nutr Food Res. Apr. 2015;59(4):698-710.
Bernalier et al., *Ruminococcus hydrogenotrophicus* sp. nov., a new H2/CO2-utilizing acetogenic bacterium isolated from human feces. Arch Microbiol. Sep. 1996;166(3):176-83.
Bernard et al., Dietary pectin-derived acidic oligosaccharides improve the pulmonary bacterial clearance of Pseudomonas aeruginosa lung infection in mice by modulating intestinal microbiota and immunity. J Infect Dis. Jan. 1, 2015;211(1):156-65.
Biagi et al., Gut microbiota trajectory in pediatric patients undergoing hematopoietic SCT. Bone Marrow Transplant. Jul. 2015;50(7):992-8.
Biddle et al., Untangling the Genetic Basis of Fibrolytic Specialization by Lachnospiraceae and Ruminococcaceae in Diverse Gut Communities. Diversity. 2013;5(3):627-640.

(56) References Cited

OTHER PUBLICATIONS

Bischoff et al., Intestinal permeability—a new target for disease prevention and therapy. BMC Gastroenterol. Nov. 18, 2014;14:189, 25 pages.
Blaut, Gut microbiota and energy balance: role in obesity. Conference on 'Carbohydrates in health: friends or foes,' Symposium 3: Non-digestible carbohydrates, gut microbiota and obesity. Proceedings of the Nutrition Society. pp. 1-8, Jul. 14-17, 2014.
Borody et al., Bacteriotherapy using fecal flora: toying with human motions. J Clin Gastroenterol. Jul. 2004;38(6):475-83.
Buffie et al., Precision microbiome reconstitution restores bile acid mediated resistance to Clostridium difficile. Nature. Jan. 8, 2015;517(7533):205-8.
Candon et al., Antibiotics in early life alter the gut microbiome and increase disease incidence in a spontaneous mouse model of autoimmune insulin-dependent diabetes. PLoS One. May 13, 2015;10(5):e0125448, 16 pages.
Cani et al., Gut microbiota, enteroendocrine functions and metabolism. Curr Opin Pharmacol. Dec. 2013;13(6):935-40.
Cassir et al., Clostridium butyricum Strains and Dysbiosis Linked to Necrotizing Enterocolitis in Preterm Neonates. Clin Infect Dis. Oct. 1, 2015 ;61(7):1107-15.
Chambers et al., Control of appetite and energy intake by SCFA: what are the potential underlying mechanisms? Conference on 'Carbohydrates in health: friends or foes,' Symposium 4: Whole grains, dietary fibre, and grain-derived phytochemicals. Proceedings of the Nutrition Society. 9 pages, Jul. 14-17, 2014.
Chen et al., Arabinoxylan in wheat is more responsible than cellulose for promoting intestinal barrier function in weaned male piglets. J Nutr. Jan. 2015;145(1):51-8.
Chen et al., Diet and Parkinson's disease: a potential role of dairy products in men. Ann Neurol. Dec. 2002;52(6):793-801.
Clavel et al., Phylogeny of human intestinal bacteria that activate the dietary lignan secoisolariciresinol diglucoside. FEMS Microbiol Ecol. Mar. 2006;55(3):471-8.
Cobo et al., Colonic MUC2 mucin regulates the expression and antimicrobial activity of β-defensin 2. Mucosal Immunol. Nov. 2015;8(6):1360-72.
Costello et al., Bacterial community variation in human body habitats across space and time. Science. Dec. 18, 2009;326(5960):1694-7.
Crost et al., Utilisation of mucin glycans by the human gut symbiont Ruminococcus gnavus is strain-dependent. PLoS One. Oct. 25, 2013;8(10):e76341, 13 pages.
Cuervo et al., Association of polyphenols from oranges and apples with specific intestinal microorganisms in systemic lupus erythematosus patients. Nutrients. Feb. 16, 2015;7(2):1301-17.
Cuiv et al., Isolation of Genetically Tractable Most-Wanted Bacteria by Metaparental Mating. Sci Rep. Aug. 21, 2015 ;5:13282, 11 pages.
Cuskin et al., Human gut Bacteroidetes can utilize yeast mannan through a selfish mechanism. Nature. Jan. 8, 2015;517(7533):165-169.
Datcu et al., Characterization of the vaginal microflora in health and disease. Dan Med J. Apr. 2014;61 (4):B4830, 24 pages.
David et al., Diet rapidly and reproducibly alters the human gut microbiome. Nature. Jan. 23, 2014;505(7484):559-63.
De Vrese et al., Probiotics, prebiotics, and synbiotics. Adv Biochem Eng Biotechnol. 2008;111:1-66.
Devlin et al., A biosynthetic pathway for a prominent class of microbiota-derived bile acids. Nat Chem Biol. Sep. 2015;11 (9):685-90.
Docampo et al., Emerging Influence of the Intestinal Microbiota during Allogeneic Hematopoietic Cell Transplantation: Control the Gut and the Body Will Follow. Biol Blood Marrow Transplant. Aug. 2015;21(8):1360-6.
Donelli et al., Enteric Toxins from Bacteria Colonizing the Human Gut. Microbial Ecology in Health and Disease. 2000;Suppl. 2:194-208.

Dotan et al., Probiotics in inflammatory bowel disease: possible mechanisms of action. Curr Opin Gastroenterol. Jul. 2005;21 (4):426-30.
Duncan et al., Proposal of a neotype strain (A1-86) for Eubacterium rectale. Request for an opinion. Int J Syst Evol Microbiol. Jul. 2008;58(Pt 7):1735-6.
Edwards et al., Initiation of sporulation in Clostridium difficile: a twist on the classic model. FEMS Microbiol Lett. Sep. 2014;358(2):110-8.
Eren et al., A single genus in the gut microbiome reflects host preference and specificity. ISME J. Jan. 2015;9(1):90-100.
Eriguchi et al., Graft-versus-host disease disrupts intestinal microbial ecology by inhibiting Paneth cell production of a-defensins. Blood. Jul. 5, 2012;120(1):223-31.
Everard et al., Gut microbiota and GLP-1. Rev Endocr Metab Disord. Sep. 2014;15(3):189-96.
Everard et al., Responses of gut microbiota and glucose and lipid metabolism to prebiotics in genetic obese and diet-induced leptin-resistant mice. Diabetes. Nov. 2011;60(11):2775-86. Erratum in: Diabetes. Dec. 2011;60(12):3307.
Finegold et al., Gastrointestinal microflora studies in late-onset autism. Clin Infect Dis. Sep. 1, 2002 ;35(Suppl 1 ):S6-S16.
Flynn et al., Bile diversion to the distal small intestine has comparable metabolic benefits to bariatric surgery. Nat Common. Jul. 21, 2015;6:7715, 14 pages.
Fordtran et al., Intestinal absorption of D-xylose in man. N Engl J Med. Aug. 9, 1962;267:274-9.
Friedl et al., Carbon source dependence and photostimulation of conidiation in Hypocrea atroviridis. Appl Environ Microbiol. Jan. 2008;74(1):245-50.
Furet et al., Comparative assessment of human and farm animal faecal microbiota using real-time quantitative PCR. FEMS Microbiol Ecol. Jun. 2009;68(3):351-62.
Furuya et al., Isolation of a novel bacterium, *Blautia glucerasei* sp. nov., hydrolyzing plant glucosylceramide to ceramide. Arch Microbiol. May 2010;192(5):365-72.
Garcia-Rodenas et al., Nutritional approach to restore impaired intestinal barrier function and growth after neonatal stress in rats. J Pediatr Gastroenterol Nutr. Jul. 2006;43(1):16-24.
Gerbitz et al., Probiotic effects on experimental graft-versus-host disease: let them eat yogurt. Blood. Jun. 1, 2004;103(11):4365-7.
Goodman et al., Identifying genetic determinants needed to establish a human gut symbiont in its habitat. Cell Host Microbe. Sep. 17, 2009;6(3):279-89.
Goto et al., Innate lymphoid cells regulate intestinal epithelial cell glycosylation. Science. Sep. 12, 2014;345(6202):1254009., 12 pages.
Gould, The Bacteria in breast milk. Retrieved online at: https:/lblogs.scientificamerican.com/lab-ratlthe-bacteria-in-breast-milkl?print=true. 2 pages, Dec. 8, 2013.
Grimoud et al., In vitro screening of probiotics and synbiotics according to anti-inflammatory and anti-proliferative effects. Int J Food Microbiol. Nov. 15, 2010;144(1):42-50.
Gu et al., Reconstruction of xylose utilization pathway and regulons in Firmicutes. BMC Genomics. Apr. 21, 2010 ;11:255, 14 pages.
Hansen et al., Two cases of Ruminococcus gnavus bacteremia associated with diverticulitis. J Clin Microbiol. Apr. 2013;51(4):1334-6.
Harnicar et al., Intensified Mycophenolate Mofetil Dosing and Higher Mycophenolic Acid Trough Levels Reduce Severe Acute Graft-versus-Host Disease after Double-Unit Cord Blood Transplantation. Biol Blood Marrow Transplant. May 2015;21(5):920-5.
Hartman et al., Human gut microbiome adopts an alternative state following small bowel transplantation. Proc Natl Acad Sci U S A. Oct. 6, 2009;106(40):17187-92.
Hartvigsen et al., Postprandial effects of test meals including concentrated arabinoxylan and whole grain rye in subjects with the metabolic syndrome: a randomised study. Eur J Clin Nutr. May 2014;68(5):567-74.
Hayashi et al., A single strain of Clostridium butyricum induces intestinal IL-10-producing macrophages to suppress acute experimental colitis in mice. Cell Host Microbe. Jun. 12, 2013;13(6):711-22.

(56) References Cited

OTHER PUBLICATIONS

He et al., Transmissible microbial and metabolomic remodeling by soluble dietary fiber improves metabolic homeostasis. Sci Rep. Jun. 4, 2015;5:10604, 12 pages.

Heimesaat et al., MyD88/TLR9 mediated immunopathology and gut microbiota dynamics in a novel murine model of intestinal graft-versus-host disease. Gut. Aug. 2010;59(8):1079-87.

Hennet et al., Decoding breast milk oligosaccharides. Swiss Med Wkly. Feb. 19, 2014;144:w13927.

Heuvelin et al., Mechanisms involved in alleviation of intestinal inflammation by bifidobacterium breve soluble factors. PLoS One. 2009;4(4):e5184.

Hooper et al., Interactions between the microbiota and the immune system. Science. Jun. 8, 2012;336(6086):1268-73.

Hougee et al., Oral treatment with probiotics reduces allergic symptoms in ovalbumin-sensitized mice: a bacterial strain comparative study. Int Arch Allergy Immunol. 2010;151(2):107-17.

Hu et al., Microbiota-induced activation of epithelial IL-6 signaling links inflammasome-driven inflammation with transmissible cancer. PNAS, 6 pages, Apr. 23, 2013. Pre-publication edition.

Ingerslev et al., Resistant starch and arabinoxylan augment SCFA absorption, but affect postprandial glucose and insulin responses differently. Br J Nutr. May 2014;111(9):1564-76.

Ivanov et al., Induction of intestinal Th17 cells by segmented filamentous bacteria. Cell. Oct. 30, 2009;139(3):485-98.

Jain et al., Influence of synbiotic containing Lactobacillus acidophilus La5, Bifidobacterium lactis Bb 12, *Streptococcus thermophilus*, Lactobacillus bulgaricus and oligofructose on gut barrier function and sepsis in critically ill patients: a randomised controlled trial. Clin Nutr. Aug. 2004;23(4):467-75.

Jenq et al., Identification of Intestinal Commensal Bacteria Protective Against GVHD in Mice and Humans. Biol Blood Marrow Transplant. Feb. 2014;20(2):S22-23.

Jenq et al., Intestinal Blautia Is Associated with Reduced Death from Graft-versus-Host Disease. Biol Blood Marrow Transplant. Aug. 2015;21(8):1373-83.

Jenq et al., Regulation of intestinal inflammation by microbiota following allogeneic bone marrow transplantation. J Exp Med. May 7, 2012;209(5):903-11.

Jenq, Intestinal Microbiota in Bone Marrow Transplantation. Blood, 120(21):SCI-51.

Jeon et al.. Probiotic Bifidobacterium breve induces IL-10-producing Tr1 cells in the colon. PLoS Pathog. 2012;8(5):e1002714.

Johansson et al., Bacteria penetrate the normally impenetrable inner colon mucus layer in both murine colitis models and patients with ulcerative colitis. Gut. Feb. 2014;63(2):281-91.

Johnson et al., Xylose utilization and short-chain fatty acid production by selected components of the intestinal microflora of a rodent pollinator (*Aethomys namaquensis*). J Comp Physiol B. Sep. 2006;176(7):631-41.

Kanai et al., A breakthrough in probiotics: Clostridium butyricum regulates gut homeostasis and anti-inflammatory response in inflammatory bowel disease. J Gastroenterol. Sep. 2015;50(9):928-39.

Kanauchi et al., Eubacterium limosum (probiotic) and its Metabolites Showed Anti-Inflammatory Effects and Increased Mucosal Barrier Function in Colitis. AGA Abstracts, p. A-281, Abstract S1912, Apr. 2005.

Kanauchi et al., Eubacterium limosum ameliorates experimental colitis and metabolite of microbe attenuates colonic inflammatory action with increase of mucosal integrity. World J Gastroenterol. Feb. 21, 2006 ;12(7):1071-7.

Kano et al., Oral administration of milk fermented with *Lactobacillus delbrueckii* ssp. bulgaricus OLL1073R-1 to DBA/1 mice inhibits secretion of proinflammatory cytokines. Cytotechnology. Nov. 2002;40(1-3):67-73.

Keshavarzian et al., Colonic bacterial composition in Parkinson's disease. Mov Disord. Sep. 2015;30(10):1351-60.

Kim et al., Metabolism of Kaempferia parviflora polymethoxyflavones by human intestinal bacterium *Bautia* sp. MRG-PMF1. J Agric Food Chem. Dec. 24, 2014;62(51):12377-83.

Kim et al., Simultaneous consumption of pentose and hexose sugars: an optimal microbial phenotype for efficient fermentation of lignocellulosic biomass. Appl Microbiol Biotechnol. Nov. 2010;88(5):1077-85.

Kinnebrew et al., Early Clostridium difficile infection during allogeneic hematopoietic stem cell transplantation. PLoS One. Mar. 24, 2014;9(3):e90158. 9 pages.

Kong et al., Oral administration of Clostridium butyricum for modulating gastrointestinal microflora in mice. Curr Microbiol. Feb. 2011;62(2):512-7.

Kontiokari et al., Effect of xylitol on growth of nasopharyngeal bacteria in vitro. Antimicrob Agents Chemother. Aug. 1995;39(8):1820-3.

Kreisman et al., Glycoantigens induce human peripheral Tr1 cell differentiation with gut-homing specialization. J Biol Chem. Mar. 18, 2011;286(11):8810-8.

La Scola et al., Aerobic culture of anaerobic bacteria using antioxidants: a preliminary report. Eur J Clin Microbiol Infect Dis. Oct. 2014;33(10):1781-3.

Langlands et al., Prebiotic carbohydrates modify the mucosa associated microflora of the human large bowel. Gut. Nov. 2004;53(11):1610-6.

Lawson et al., Reclassification of Ruminococcus obeum as Blautia obeum comb. nov. Int J Syst Evol Microbiol. Mar. 2015;65(Pt 3):789-93.

Lee et al., Has the microbiota played a critical role in the evolution of the adaptive immune system? Science. Dec. 24, 2010;330(6012):1768-73.

Leffler et al., Clostridium difficile infection. N Engl J Med. Apr. 16, 2015;372(16):1539-48.

Lehar et al., Chemical combination effects predict connectivity in biological systems. Mol Syst Biol. 2007;3:80, 14 pages.

Li et al., Effect of oral feeding with Clostridium leptum on regulatory T-cell responses and allergic airway inflammation in mice. Ann Allergy Asthma Immunol. Sep. 2012;109(3):201-7.

Li et al., Human gut bacterial communities are altered by addition of cruciferous vegetables to a controlled fruit- and vegetable-free diet. J Nutr. Sep. 2009;139(9):1685-91.

Liu et al., Lactobacillus buchneri strain NRRL B-30929 converts a concentrated mixture of xylose and glucose into ethanol and other products. J Ind Microbiol Biotechnol. Feb. 2008;35(2):75-81.

Liu et al., Reclassification of Clostridium coccoides, Ruminococcus hansenii, Ruminococcus hydrogenotrophicus, Ruminococcus luti, Ruminococcus productus and Ruminococcus schinkii as Blautia coccoides gen. nov., comb, nov., Blautia hansenii comb, nov., Blautia hydrogenotrophica comb, nov., Blautia luti comb, nov., Blautia producta comb, nov., Blautia schinkii comb. nov. and description of *Blautia wexlerae* sp. nov., isolated from human faeces. Int J Syst Evol Microbiol. Aug. 2008;58(Pt 8):1896-902.

Lopetuso et al., Commensal Clostridia: leading players in the maintenance of gut homeostasis. Gut Pathog. Aug. 13, 2013;5(1):23.

Lu et al., Arabinoxylan fiber from a by-product of wheat flour processing behaves physiologically like a soluble, fermentable fiber in the large bowel of rats. J Nutr. Aug. 2000;130(8):1984-90.

Macfarlane et al., Review article: prebiotics in the gastrointestinal tract. Aliment Pharmacol Ther. Sep. 1, 2006 ;24(5):701 -14.

Machiels et al., Specific members or the predominant gut microbiota predict pouchitis following colectomy and IPAA in UC. Gut. doi: 10.1136/gutjnl-2015-309398. 11 pages, (2015).

Macpherson et al., Induction of protective IgA by intestinal dendritic cells carrying commensal bacteria. Science. Mar. 12, 2004;303(5664):1662-5.

Maroni et al., Fucosyltransferase 2: a genetic risk factor for primary sclerosing cholangitis and Crohn's disease—a comprehensive review. Clin Rev Allergy Immunol. Jun. 2015;48(2-3):182-91.

Martin et al., Role of commensal and probiotic bacteria in human health: a focus on inflammatory bowel disease. Microb Cell Fact. 2013;12:71, 11 pages.

Mazmanian et al., A microbial symbiosis factor prevents intestinal inflammatory disease. Nature. May 29, 2008;453(7195):620-5.

McDonald et al., Evaluation of microbial community reproducibility, stability and composition in a human distal gut chemostat model. J Microbiol Methods. Nov. 2013;95(2):167-74.

(56) References Cited

OTHER PUBLICATIONS

McLellan et al., Sewage reflects the distribution of human faecal Lachnospiraceae. Environ Microbiol. Aug. 2013;15(8):2213-27.
Meehan et al., A phylogenomic view of ecological specialization in the Lachnospiraceae, a family of digestive tract-associated bacteria. Genome Biol Evol. Mar. 2014;6(3):703-13.
Menard et al., Lactic acid bacteria secrete metabolites retaining anti-inflammatory properties after intestinal transport. Gut. Jun. 2004;53(6):821-8.
Mitchell et al., A multicenter pilot evaluation of the National Institutes of Health chronic graft-versus-host disease (cGVHD) therapeutic response measures: feasibility, interrater reliability, and minimum detectable change. Biol Blood Marrow Transplant. Nov. 2011;17(11):1619-29.
Nagano et al., The induction of Treg cells by gut-indigenous Clostridium. Curr Opin Immunol. Aug. 2012;24(4):392-7.
Natividad et al., Differential induction of antimicrobial REGIII by the intestinal microbiota and Bifidobacterium breve NCC2950. Appl Environ Microbiol. Dec. 2013;79(24):7745-54.
Newton et al., Sewage reflects the microbiomes of human populations. MBio. Feb. 24, 2015;6(2):e02574, 9 pages.
Neyrinck et al., Dietary modulation of clostridial cluster XIVa gut bacteria (*roseburia* spp.) by chitin-glucan fiber improves host metabolic alterations induced by high-fat diet in mice. J Nutr Biochem. Jan. 2012;23(1):51-9.
Neyrinck et al., Prebiotic effects of wheat arabinoxylan related to the increase in bifidobacteria, Roseburia and Bacteroides/Prevotella in diet-induced obese mice. PLoS One. 2011 ;6(6):e20944, 12 pages.
Neyrinck et al., Wheat-derived arabinoxylan oligosaccharides with prebiotic effect increase satietogenic gut peptides and reduce metabolic endotoxemia in diet-induced obese mice. Nutr Diabetes. Jan. 23, 2012;2:e28, 9 pages.
Nielsen et al., Diets high in resistant starch and arabinoxylan modulate digestion processes and SCFA pool size in the large intestine and faecal microbial composition in pigs. Br J Nutr. Dec. 14, 2014;112(11):1837-49.
Noval Rivas et al., A microbiota signature associated with experimental food allergy promotes allergic sensitization and anaphylaxis. J Allergy Clin Immunol. Jan. 2013;131(1):201-12.
Nutsch et al., T cell tolerance and immunity to commensal bacteria. Curr Opin Immunol. Aug. 2012;24(4):385-91.
Ochoa-Reparaz et al., A polysaccharide from the human commensal Bacteroides fragilis protects against CNS demyelinating disease. Mucosal Immunol. Sep. 2010;3(5):487-95.
Ohkohchi et al., Mechanism of D-xylose transport in human small intestine. J Pediatr Gastroenterol Nutr. May-Jun. 1986;5(3):372-8.
Ohtsuka et al., Effects of Bifidobacterium breve on inflammatory gene expression in neonatal and weaning rat intestine. Pediatr Res. Jan. 2012;71(1):46-53.
Okazaki et al., Effect of xylooligosaccharide on the Growth of Bifidobacteria. Bifidobacteria Microflora. 1990;9(2):77-86.
Park et al., *Blautia faecis* sp. nov., isolated from human faeces. Int J Syst Evol Microbiol. Feb. 2013;63(Pt2):599-603.
Park et al., *Blautia stercoris* sp. nov., isolated from human faeces. Int J Syst Evol Microbiol. Apr. 2012;62(Pt 4):776-9.
Parmar et al., Association study of FUT2 (rs601338) with celiac disease and inflammatory bowel disease in the Finnish population. Tissue Antigens. Dec. 2012;80(6):488-93.
Parracho et al., Differences between the gut microflora of children with autistic spectrum disorders and that of healthy children. J Med Microbiol. Oct. 2005;54(Pt 10):987-91.
Penack et al., Graft-versus-host disease: regulation by microbe-associated molecules and innate immune receptors. Blood. Mar. 11, 2010;115(10):1865-72.
Penack et al., Inhibition of neovascularization to simultaneously ameliorate graft-vs-host disease and decrease tumor growth. J Natl Cancer Inst. Jun. 16, 2010;102(12):894-908.

Peran et al., Lactobacillus fermentum, a probiotic capable to release glutathione, prevents colonic inflammation in the TNBS model of rat colitis. Int J Colorectal Dis. Dec. 2006;21(8):737-46.
Petnicki-Ocwieja et al., Nod2 is required for the regulation of commensal microbiota in the intestine. Proc Natl Acad Sci U S A. Sep. 15, 2009;106(37):15813-8.
Petrof et al., Stool substitute transplant therapy for the eradication of Clostridium difficile infection: 'RePOOPulating' the gut. Microbiome. Jan. 9, 2013;1(1):3, 12 pages.
Ponce et al., Graft-versus-host disease after double-unit cord blood transplantation has unique features and an association with engrafting unit-to-recipient HLA match. Biol Blood Marrow Transplant. Jun. 2013;19(6):904-11.
Pourabedin et al., Prebiotics and gut microbiota in chickens. FEMS Microbiol Lett. Aug. 2015;362(15):fnv122, 8 pages.
Puertollano et al., Orally administered Lactobacillus plantarum reduces pro-inflammatory interleukin secretion in sera from Listeria monocytogenes infected mice. Br J Nutr. Apr. 2008;99(4):819-25.
Rashid et al., Determining the Long-term Effect of Antibiotic Administration on the Human Normal Intestinal Microbiota Using Culture and Pyrosequencing Methods. Clin Infect Dis. May 15, 2015;60 Suppl 2:S77-84.
Rayes et al., A Genetic Modifier of the Gut Microbiome Influences the Risk of Graft-versus-Host Disease and Bacteremia After Hematopoietic Stem Cell Transplantation. Biol Blood Marrow Transplant. Mar. 2016;22(3):418-22.
Reid et al., Microbiota restoration: natural and supplemented recovery of human microbial communities. Nat Rev Microbiol. Jan. 2011;9(1):27-38.
Rieu-Lesme et al., A new H2/CO2-using acetogenic bacterium from the rumen: description of *Ruminococcus schinkii* sp. nov. FEMS Microbiol Lett. Jul. 1, 1996 ;140(2-3):281-6.
Roopchand et al., Dietary Polyphenols Promote Growth of the Gut Bacterium Akkermansia muciniphila and Attenuate High-Fat Diet-Induced Metabolic Syndrome. Diabetes. Aug. 2015;64(8):2847-58.
Roux et al., Ruminococcus gnavus total hip arthroplasty infection in a 62-year-old man with ulcerative colitis. J Clin Microbiol. Apr. 2015;53(4):1428-30.
Sagar et al., The combination of Bifidobacterium breve with non-digestible oligosaccharides suppresses airway inflammation in a murine model for chronic asthma. Biochim Biophys Acta. Apr. 2014;1842(4):573-83.
Salminen et al., Gut microflora interactions with xylitol in the mouse, rat and man. Food Chern Toxicol. Nov. 1985;23(11):985-90.
Salvador et al., Sugar composition of dietary fibre and short-chain fatty acid production during in vitro fermentation by human bacteria. Br J Nutr. Jul. 1993;70(1):189-97.
Sandler et al., Short-term benefit from oral vancomycin treatment of regressive-onset autism. J Child Neurol. Jul. 2000;15(7):429-35.
Saujet et al., The regulatory network controlling spore formation in Clostridium difficile. FEMS Microbiol Lett. Sep. 2014;358(1):1-10.
Savaiano et al., Improving lactose digestion and symptoms of lactose intolerance with a novel galacto-oligosaccharide (RP-G28): a randomized, double-blind clinical trial. Nutr J. Dec. 13, 2013;12:160, 9 pages.
Scher et al., Decreased bacterial diversity characterizes the altered gut microbiota in patients with psoriatic arthritis, resembling dysbiosis in inflammatory bowel disease. Arthritis Rheumatol. Jan. 2015;67(1):128-39.
Shankar et al., Species and genus level resolution analysis of gut microbiota in Clostridium difficile patients following fecal microbiota transplantation. Microbiome. Apr. 21, 2014 ;2:13, 10 pages.
Shima et al., Differential effects of two probiotic strains with different bacteriological properties on intestinal gene expression, with special reference to indigenous bacteria. FEMS Immunol Med Microbiol. Jan. 2008;52(1):69-77.
Shono et al., Intestinal microbiota-related effects on graft-versus-host disease. Int J Hematol. May 2015;101(5):428-37.
Smyth et al., FUT2 nonsecretor status links type 1 diabetes susceptibility and resistance to infection. Diabetes. Nov. 2011;60(11):3081-4.

(56) References Cited

OTHER PUBLICATIONS

Sokol et al., Faecalibacterium prausnitzii is an anti-inflammatory commensal bacterium identified by gut microbiota analysis of Crohn disease patients. Proc Natl Acad Sci U S A. Oct. 28, 2008;105(43):16731-6.
Solon-Biet et al., The ratio of macronutrients, not caloric intake, dictates cardiometabolic health, aging, and longevity in ad libitum-fed mice. Cell Metab. Mar. 4, 2014;19(3):418-30.
Sparo et al., Immunomodulatory properties of cell wall extract from Enterococcus faecalis CECT7121. Braz J Infect Dis. Sep.-Oct. 2014;18(5):551-5.
Suez et al.. Artificial sweeteners induce glucose intolerance by altering the gut microbiota. Nature. Oct. 9, 2014;514(7521):181-6.
Sun et al., A novel three-component system-based regulatory model for D-xylose sensing and transport in Clostridium beijerinckii. Mol Microbiol. Feb. 2015;95(4):576-89.
Sun et al., Mature T cell responses are controlled by microRNA-142. J Clin Invest. Jul. 1, 2015;125(7):2825-40.
Tailford et al., Mucin glycan foraging in the human gut microbiome. Front Genet. Mar. 19, 2015;6:81, 18 pages.
Tamura et al., Xylitol affects the intestinal microbiota and metabolism of daidzein in adult male mice. Int J Mol Sci. Dec. 10, 2013;14(12):23993-4007.
Tanoue et al., Immune responses to gut microbiota-commensals and pathogens. Gut Microbes. Jul. 2010;1(4):224-233.
Tap et al., Towards the human intestinal microbiota phylogenetic core. Environ Microbiol. Oct. 2009;11(10):2574-84.
Tapiainen et al., Effect of xylitol on growth of Streptococcus pneumoniae in the presence of fructose and sorbitol. Antimicrob Agents Chemother. Jan. 2001;45(1):166-9.
Tateyama et al., Effect of xylooligosaccharide intake on severe constipation in pregnant women. J Nutr Sci Vitaminol (Tokyo). Dec. 2005;51(6):445-8.
Taur et al., Intestinal domination and the risk of bacteremia in patients undergoing allogeneic hematopoietic stem cell transplantation. Clin Infect Dis. Oct. 2012;55(7):905-14.
Taur et al., The effects of intestinal tract bacterial diversity on mortality following allogeneic hematopoietic stem cell transplantation. Blood. Aug. 14, 2014;124(7):1174-82.
Tawara et al., Influence of donor microbiota on the severity of experimental graft-versus-host-disease. Biol Blood Marrow Transplant. Jan. 2013;19(1):164-8.
Telesford et al., A commensal symbiotic factor derived from Bacteroides fragilis promotes human CD39(+)Foxp3(+) T cells and Treg function. Gut Microbes. Jul. 4, 2015;6(4):234-42.
Telesford et al., Gut commensalism, cytokines, and central nervous system demyelination. J Interferon Cytokine Res. Aug. 2014;34(8):605-14.
Temudo et al., Xylose anaerobic conversion by open-mixed cultures. Appl Microbiol Biotechnol. Feb. 2009;82(2):231-9.
Thaiss et al., Transkingdom control of microbiota diurnal oscillations promotes metabolic homeostasis. Cell. Oct. 23, 2014;159(3):514-29.
Tuovinen et al., Cytokine response of human mononuclear cells induced by intestinal Clostridium species. Anaerobe. Feb. 2013;19:70-6.
Turnbaugh et al., A core gut microbiome in obese and lean twins. Nature. Jan. 22, 2009;457(7228):480-4.
Tvede et al., Bacteriotherapy for chronic relapsing Clostridium difficile diarrhoea in six patients. Lancet. May 27, 1989;1(8648):1156-60.
Ubeda et al., Antibiotics, microbiota, and immune defense. Trends Immunol. Sep. 2012;33(9):459-66.
Vaishnava et al., Paneth cells directly sense gut commensals and maintain homeostasis at the intestinal host-microbial interface. Proc Natl Acad Sci U S A. Dec. 30, 2008;105(52):20858-63.
Valdes et al., Population Dynamics of Some Relevant Intestinal Microbial Groups in Human Fecal Batch Cultures with Added Fermentable Xylooligosaccharides Obtained from Rice Husks. BioResources. 2013;8(2):2429-2441.
Van Den Abbeele et al., Butyrate-producing Clostridium cluster XIVa species specifically colonize mucins in an in vitro gut model. ISME J. May 2013;7(5):949-61.
Van Den Abbeele et al., Different human gut models reveal the distinct fermentation patterns of Arabinoxylan versus inulin. J Agric Food Chem. Oct. 16, 2013;61(41):9819-27.
Van Den Abbeele et al., Microbial community development in a dynamic gut model is reproducible, colon region specific, and selective for Bacteroidetes and Clostridium cluster IX. Appl Environ Microbiol. Aug. 2010;76(15):5237-46.
Vanderhaeghen et al., Methanogen communities in stools of humans of different age and health status and co-occurrence with bacteria. FEMS Microbiol Lett. Jul. 2015;362(13):fnv092, 8 pages.
Vazquez et al., Xylooligosaccharides: manufacture and applications. Trends in Food Science & Technology. Nov. 2000;11(11):387-393.
Veiga et al., *Bifidobacterium animalis* subsp. lactis fermented milk product reduces inflammation by altering a niche for colitogenic microbes. Proc Natl Acad Sci U S A. Oct. 19, 2010;107(42):18132-7.
Weber et al., Low urinary indoxyl sulfate levels early after transplantation reflect a disrupted microbiome and are associated with poor outcome. Blood. Oct. 1, 2015;126(14):1723-8.
Wong et al., Colonic health: fermentation and short chain fatty acids. J Clin Gastroenterol. Mar. 2006;40(3):235-43.
Wu et al., Genetic determinants of in vivo fitness and diet responsiveness in multiple human gut Bacteroides. Science. Oct. 2, 2015;350(6256):aac5992, 8 pages.
Xin et al., Preventing non-alcoholic fatty liver disease through Lactobacillus johnsonii BS15 by attenuating inflammation and mitochondrial injury and improving gut environment in obese mice. Appl Microbiol Biotechnol. Aug. 2014;98(15):6817-29.
Xu et al., Fecal microbiota transplantation broadening its application beyond intestinal disorders. World J Gastroenterol. Jan. 7, 2015;21(1):102-11.
Yadav et al., Peripherally induced tregs—role in immune homeostasis and autoimmunity. Front Immunol. Aug. 7, 2013;4:232, 12 pages.
Yang et al., Xylooligosaccharide supplementation alters gut bacteria in both healthy and prediabetic adults: a pilot study. Front Physiol. Aug. 7, 2015;6:216, 11 pages.
Yaung et al., Improving microbial fitness in the mammalian gut by in vivo temporal functional metagenomics. Mol Syst Biol. Mar. 2015;11(3):788, 16 pages.
Yin et al., Different Dynamic Patterns of β-Lactams, Quinolones, Glycopeptides and Macrolides on Mouse Gut Microbial Diversity. PLoS One. May 13, 2015;10(5):e0126712, 12 pages.
Young et al., Detection of sialic acid-utilising bacteria in a caecal community batch culture using RNA-based stable isotope probing. Nutrients. Mar. 25, 2015;7(4):2109-24.
Youngster et al., Oral, capsulized, frozen fecal microbiota transplantation for relapsing Clostridium difficile infection. JAMA. Nov. 5, 2014;312(17):1772-8.
Yuasa et al., Comparative assessment of D-xylose absorption between small intestine and large intestine. J Pharm Pharmacol. Jan. 1997;49(1):26-9.
Zhang et al., Dynamics of gut microbiota in autoimmune lupus. Appl Environ Microbiol. Dec. 2014;80(24):7551-60.
Zhang et al., Xylan utilization in human gut commensal bacteria is orchestrated by unique modular organization of polysaccharide-degrading enzymes. Proc Natl Acad Sci U S A. Sep. 2, 2014;111(35):E3708-17.
Zoppi et al., Modulation of the intestinal ecosystem by probiotics and lactulose in children during treatment with ceftriaxone. Current Therapeutic Research. May 2001;62(5):418-435.
Bellet et al., "Circadian clock regulates the host response to *Salmonella*," PNAS, 110(24):9897-9902 (2013).
Brown et al., "Extracellular vesicles produced by the gram-positive bacterium bacillus subtilis are disrupted by the lipopeptide surfactin," Molecular Microbiology, 93(1):183-198 (2014).
Emanuelsson et al., "Allergens as eukaryotic proteins lacking bacterial homologues," Molecular Immunology, 44:3256-3260 (2007).

(56) References Cited

OTHER PUBLICATIONS

European Food Safery Authority, "Appendix: The 2013 updated list of QPS status recommended biological agents in support of EFSA risk assessments—3rd revision (new additions)," EFSA Journal, 13(12):4331 (2015).
Extended European Search Report for EP Application No. EP 20171785 dated Nov. 6, 2020.
Hakansson et al., "Gut microbiota and inflammation," Nutrients, 3: 637-682 (2011).
International Search Report and Written Opinion for International Application No. PCT/US2015/062805 dated Jul. 4, 2016.
International Search Report and Written Opinion for International Application No. PCT/US2015/062806 dated Mar. 9, 2016.
International Search Report and Written Opinion for International Application No. PCT/US2015/062808 dated Feb. 24, 2016.
International Search Report and Written Opinion for International Application No. PCT/US2015/062809 dated Mar. 7, 2016.
International Search Report and Written Opinion for International Application No. PCT/US2015/062810 dated May 19, 2016.
Kim et al., "Extracellular vesicle-derived protein from Bifidobacterium longum alleviates food allergy through mast cell suppression," J Allergy Clin Immunol, 137:507-516(2016).
Kohanski et al., "How antibiotics kill bacteria: from targets to networks," Nat Rev Microbiol, 8(6):423-435 (2010).
Lee et al., "Transcription facter oB plays an important role in the production of extracellular membrane-derived vesicles in listeria monocytogenes," Plos One, 8(8):e73196 (2013).
Li et al., "Intestine-derived Clostridium leptum induces murine tolerogenic dentritic cells and regulatory T cells in vitro," Human Immunology, 75:1232-1238 (2014).
McBroom et al., "Outer membrane vesicle production by *Escherichia coli* is independent of membrane instability," Journal of Bacteriology, 188(15): 5385-5392 (2006).

Minikiewicz et al., "The occurrence of sequences identical with epitopes from the allergen pen a 1.0102 among food and non-food proteins," Pol J Food Nutr Sci, 65(1):21-29 (2015).
Penders et al., "The role of the intestinal microbiota in the development of atopic disorders," Allergy, 62:1223-1236 (2007).
Pichler, "Adverse side-effects to biological agents," Allergy, 61:912-920 (2006).
Randhawa et al., "Bioinformatic analysis for allergenicity assessment of bacillus thuringiensis cry proteins expressed in insect-resistant food crops," Food and Chemical Toxicology, 49:356-362 (2011).
Rappazzo et al., "Recombinant M2e outer membrane vesicle vaccines protect against lethal influenza A challenge in BALB/c mice," Vaccine, (2016).
Roier et al., "A novel mechanism for the biogenesis of outer membrane vesicles in gram-negative bacteria," Nature Communications, 1-13 (2015).
Rosenthal et al., "Mechanistic insight into the TH1-biased immune response to recombinant subunit vaccines delivered by probiotic bacteria-derived outer membrane vesicles," Plos One, 9(11):e112802 (2014).
Santiago et al., "Structutal Differences between human proteins and aero- and microbial allergens define allergenicity," Plos One, 7(7):e40552 (2012).
Torres-Maravilla et al., "Identification of bovel anti-inflammatory probiotic strains isolated from pulque," Appl Microbiol Biotechnol, 100:385-396 (2016).
Yeun et al., "Effect of oral probiotics (Bifidobacterium lactis AD011 and Lactobacillus acidophilus AD031) administration on ovalbumin-induced food allergy mouse model," J Microbiol Biotechnol, 18(8):1393-1400 (2008).
Tagirasa., "Tnf-α negatively regulates Th2 differentiation in humans," Canadian Journal of Biotechnology, 1: p. 158 (2017).
Tanabe., "The Effect of Probiotics and Gut Microbiota on Th17 Cells," International Reviews of Immunology, 32: 511 -525 (2013).

\* cited by examiner

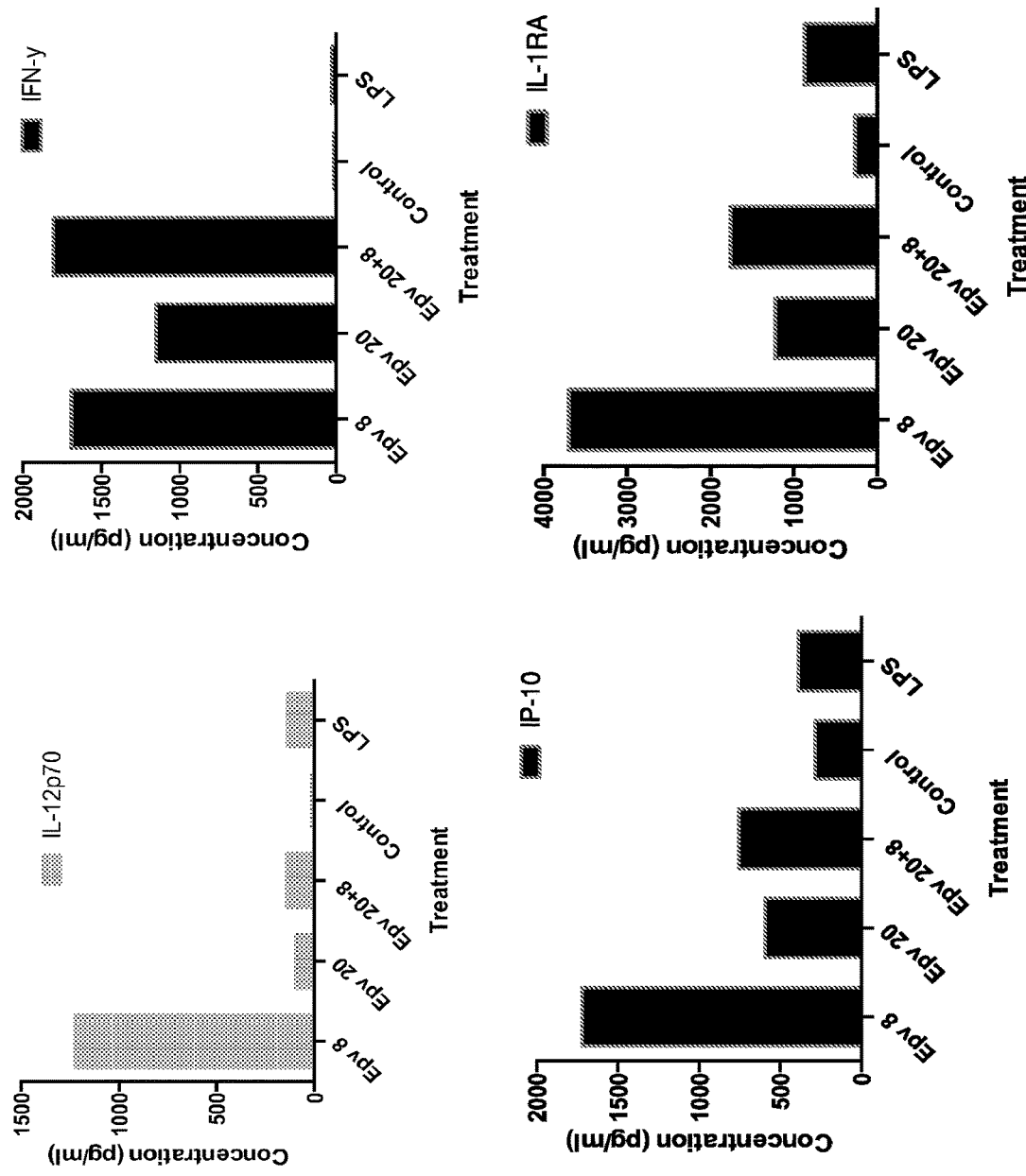
FIG. 14A Epv 20

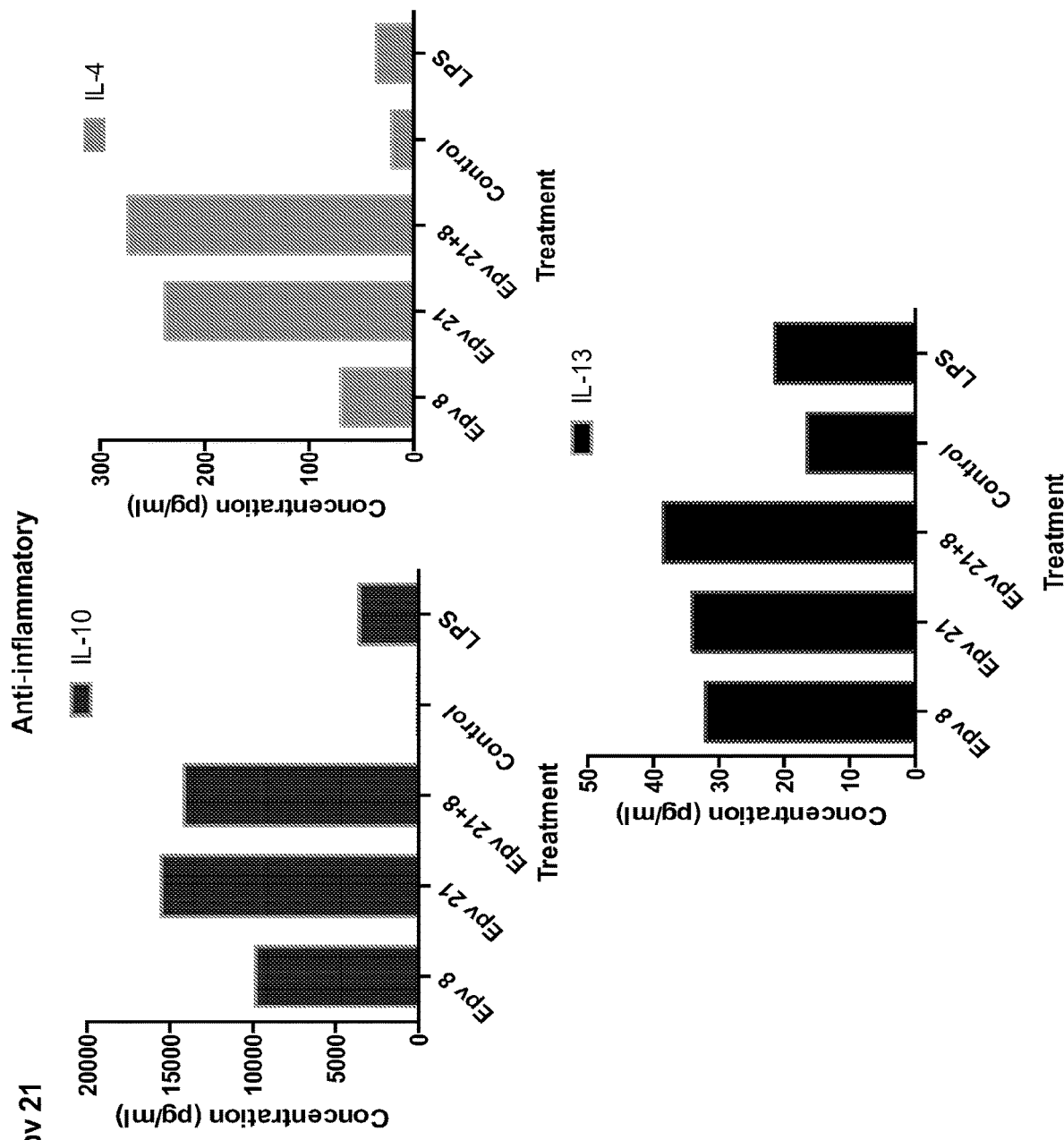
FIG. 15B Epv 21

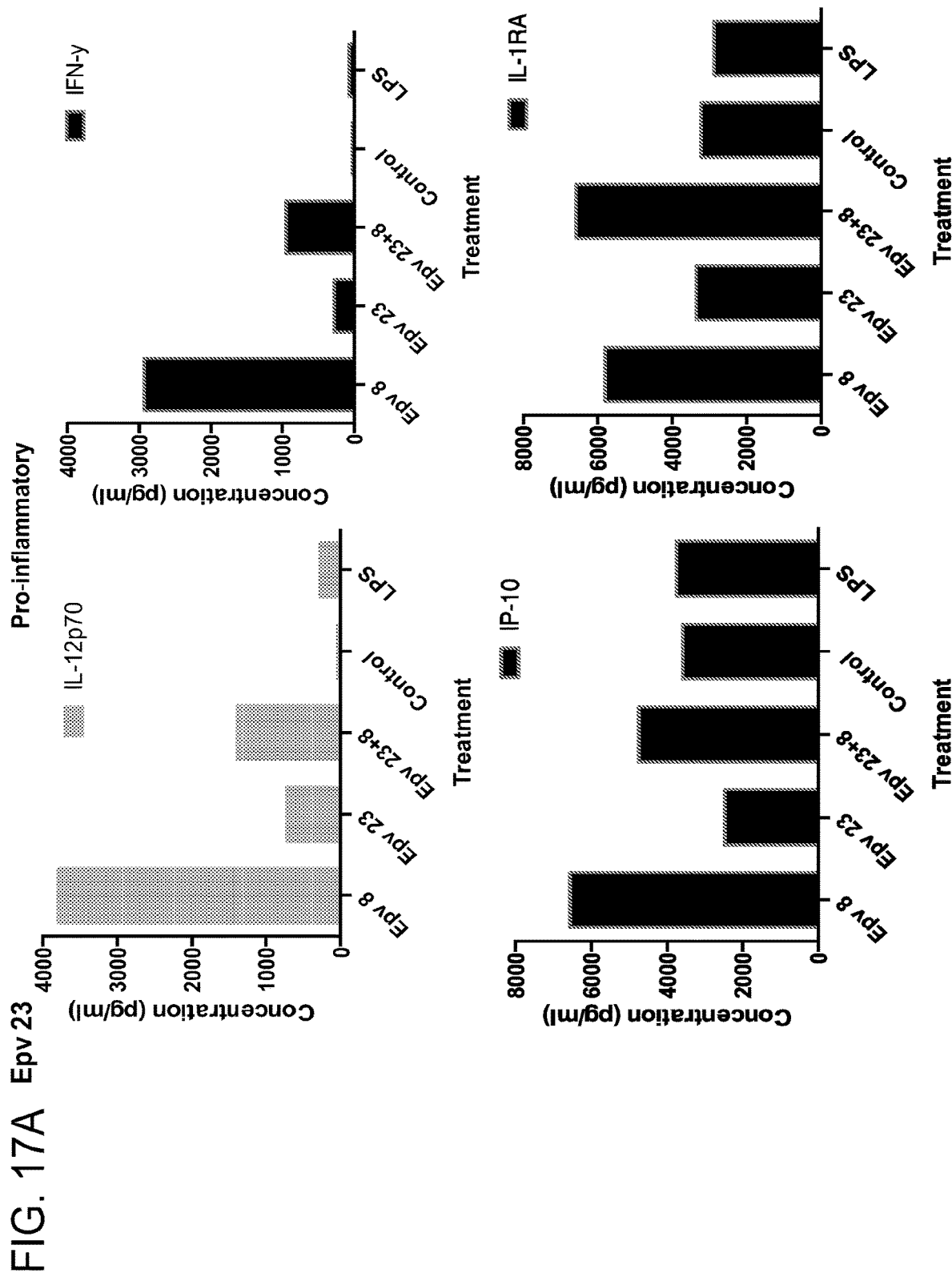

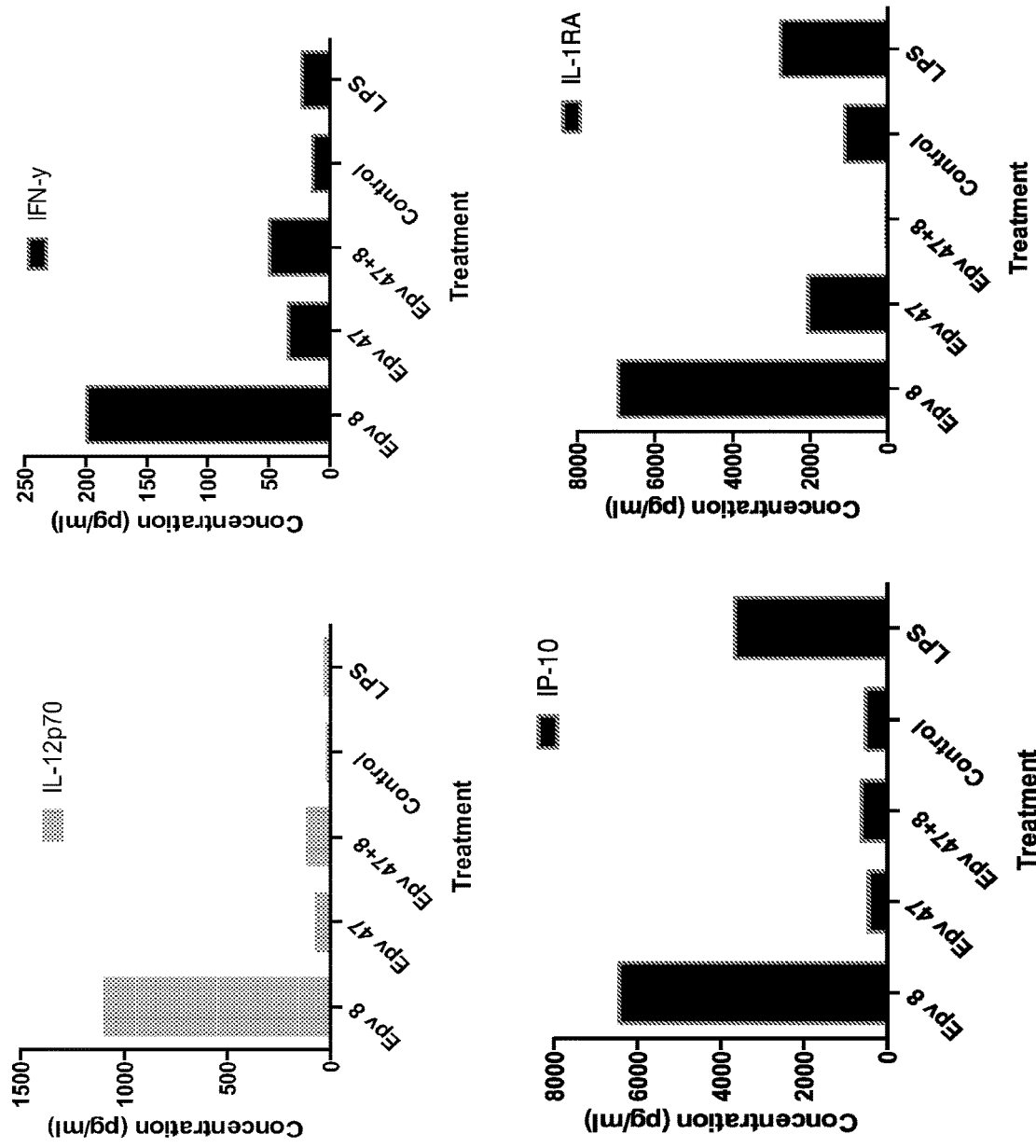
FIG. 20A Epv 47

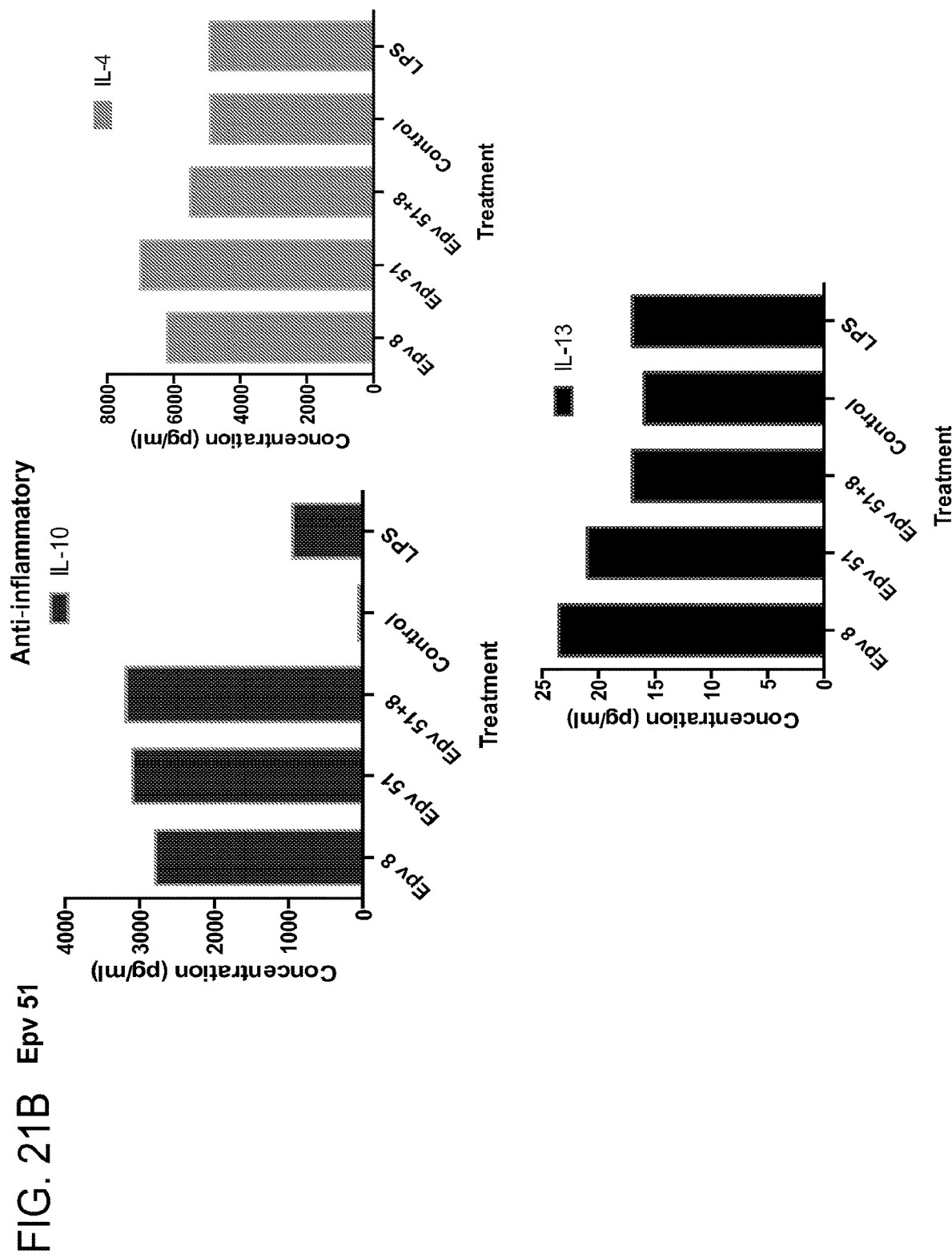
FIG. 21B Epv 51

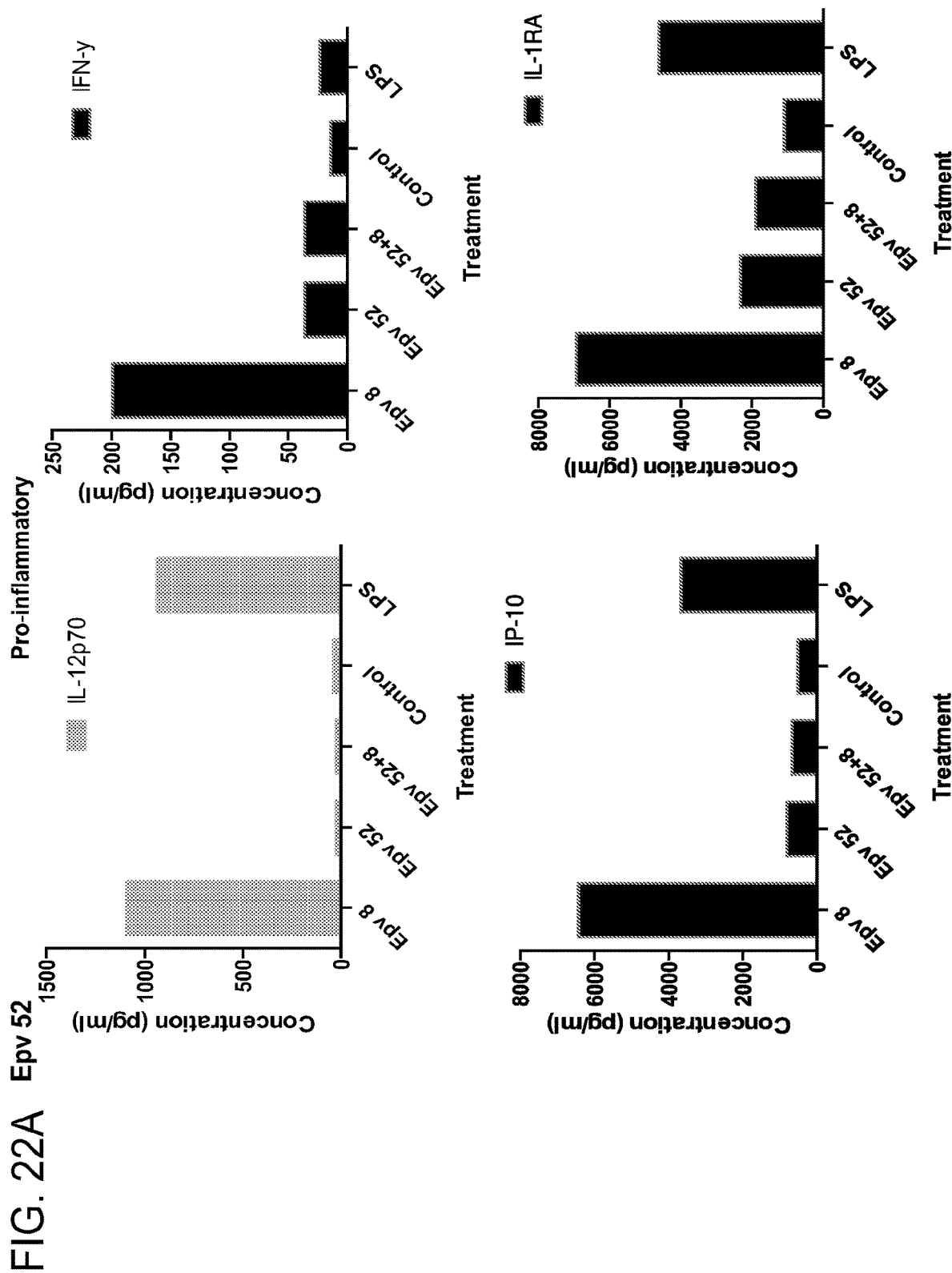
FIG. 22A  Epv 52

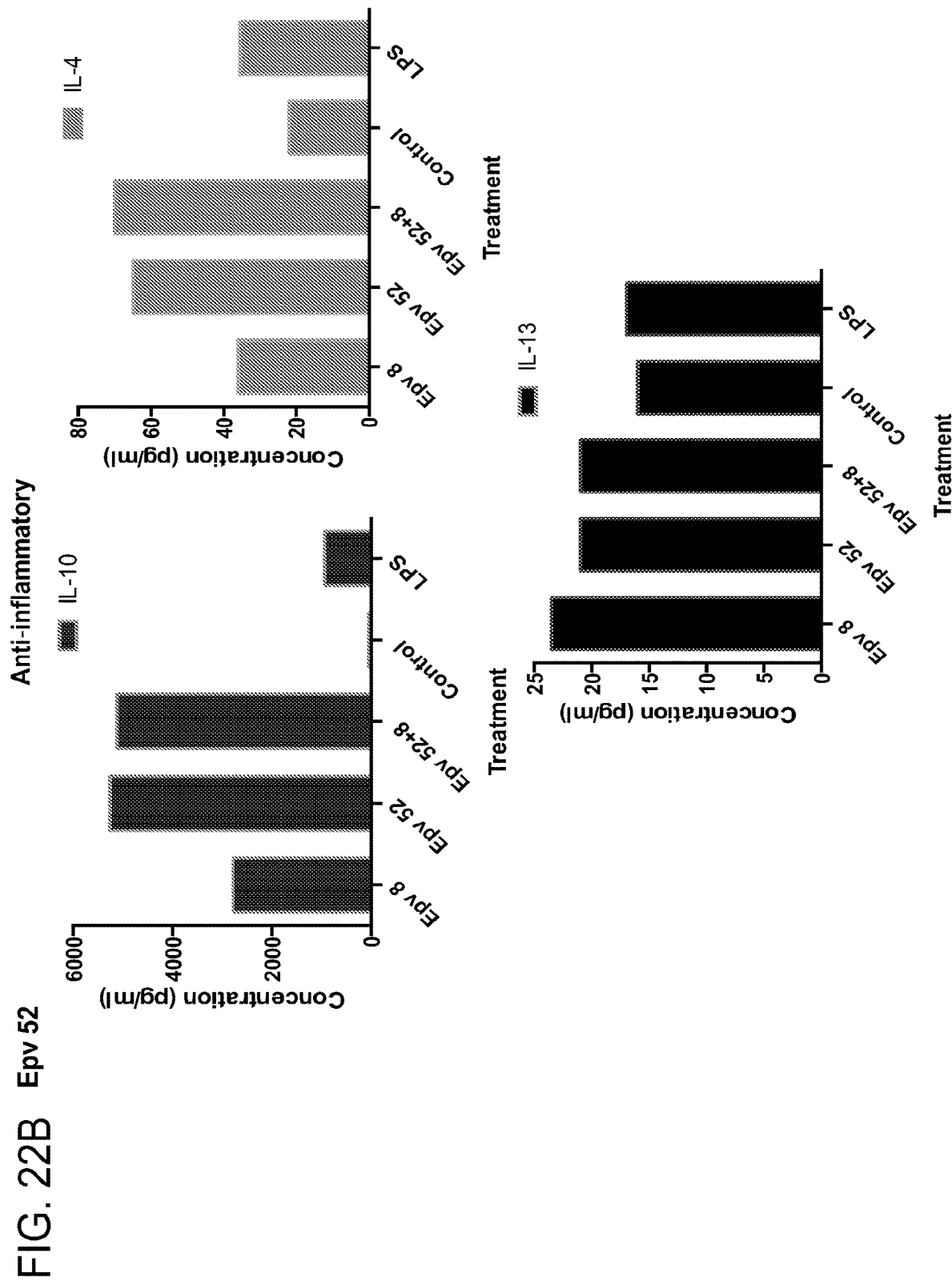
FIG. 22B Epv 52

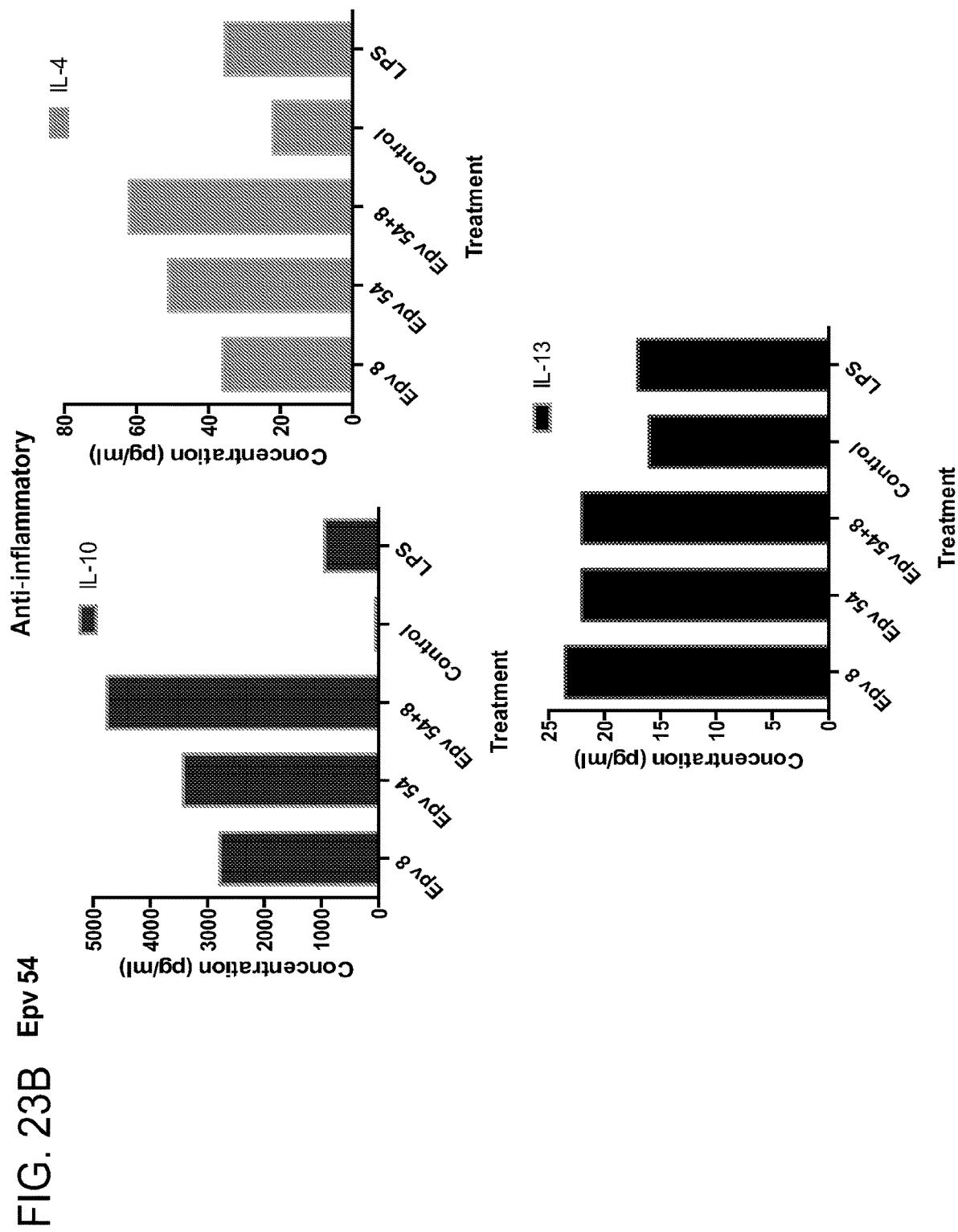
FIG. 23B Epv 54

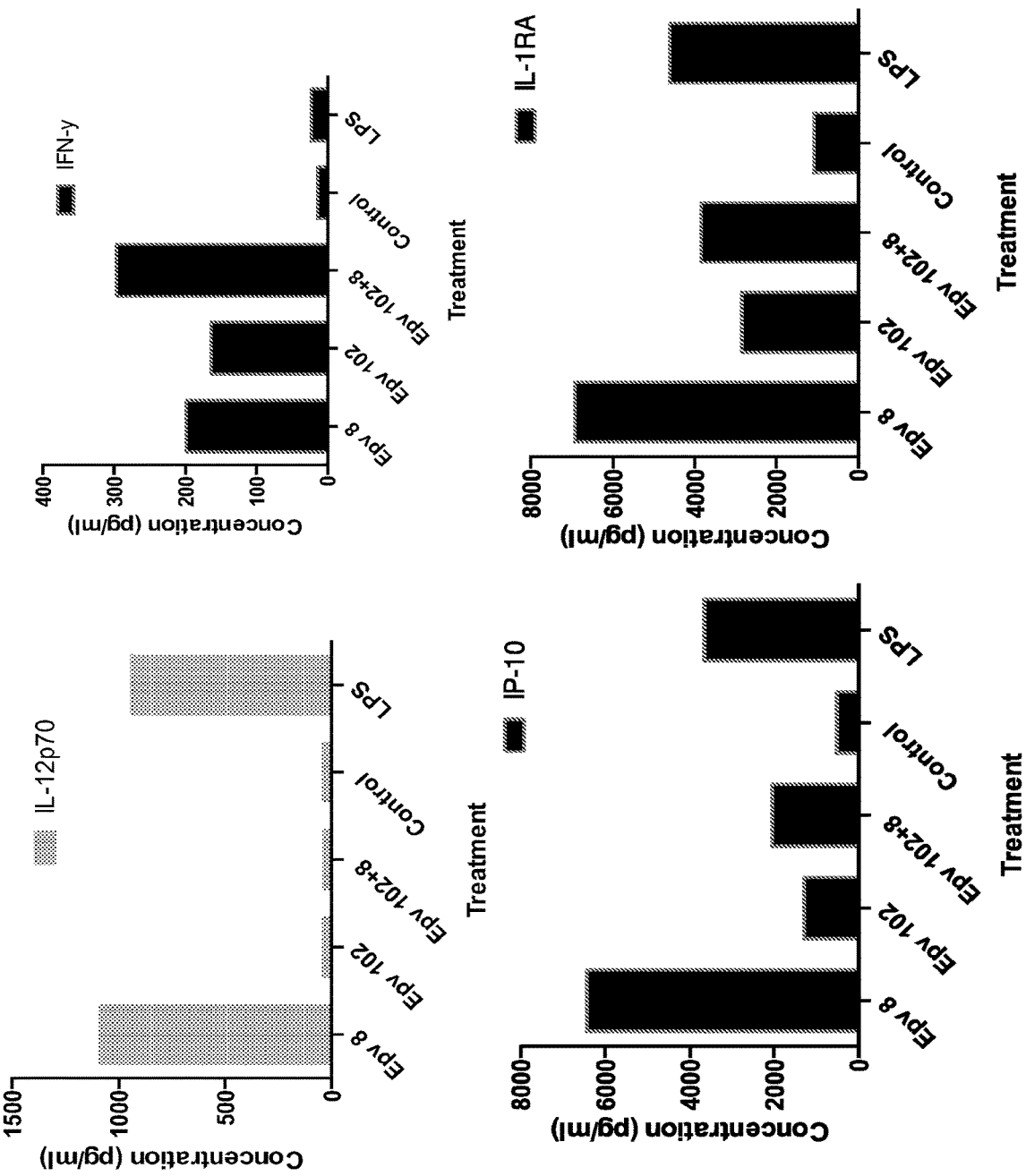

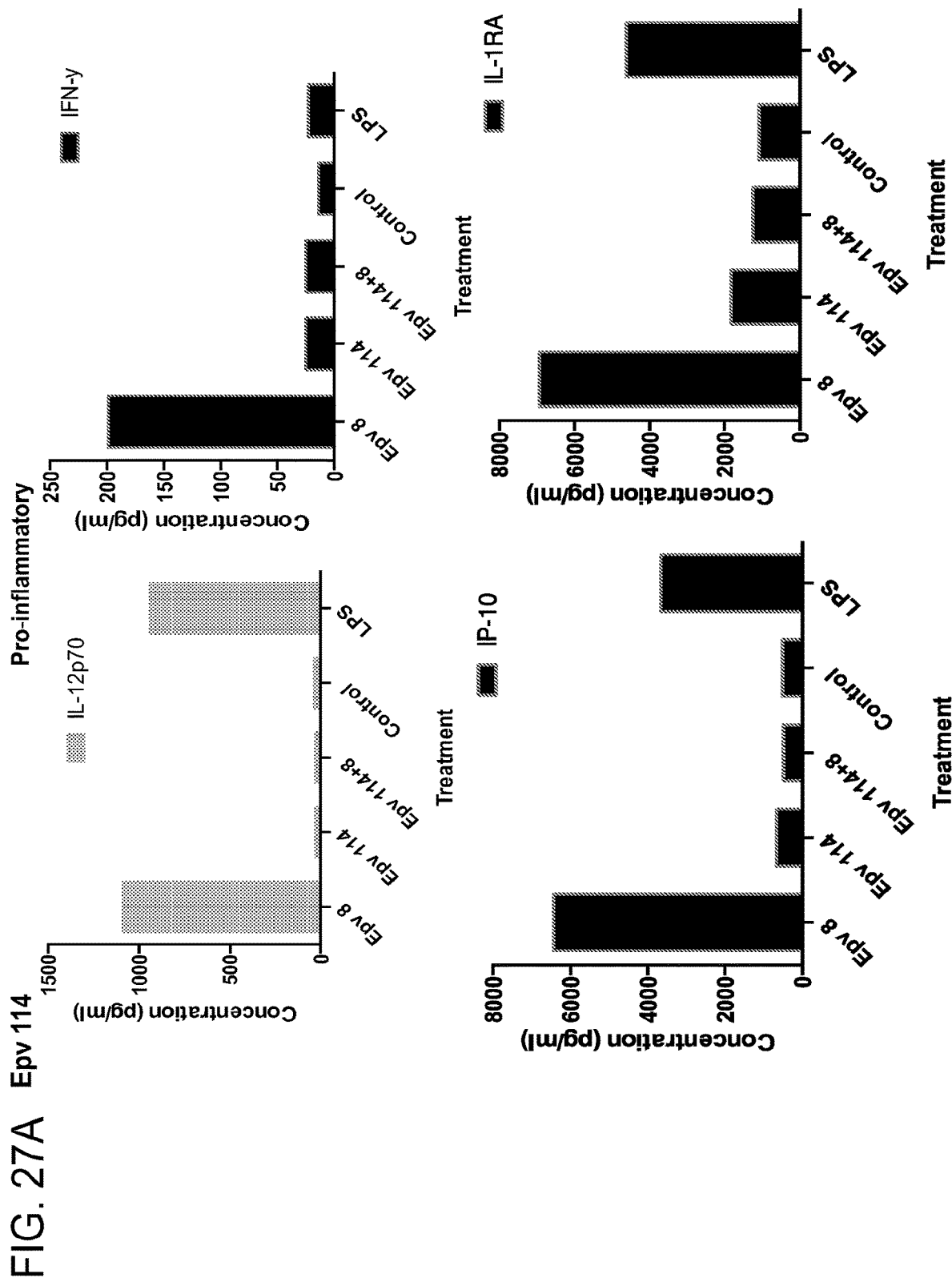
FIG. 27A  Epv 114

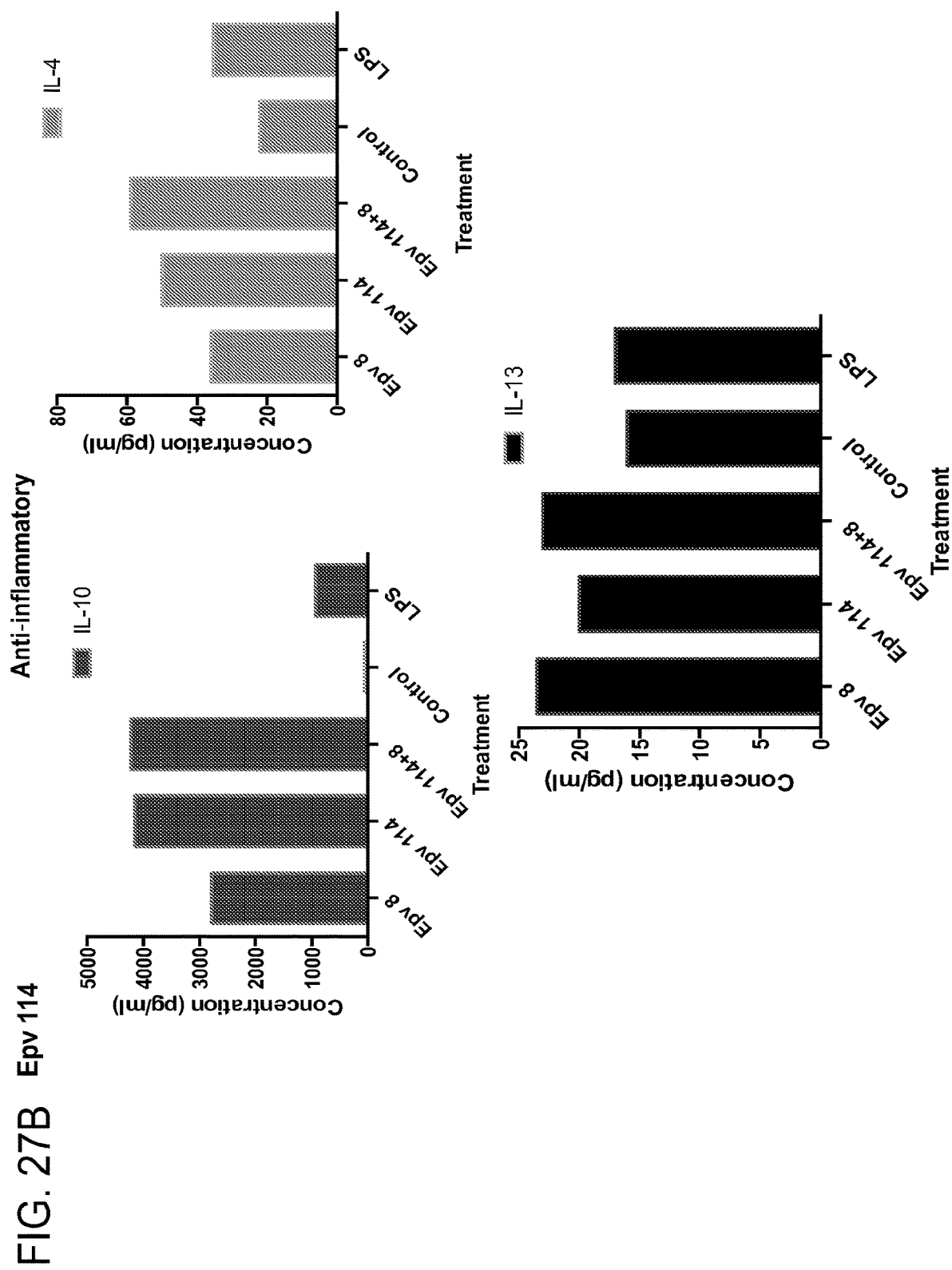
FIG. 27B Epv 114

FIG. 29A
Preferred carbon sources out of 192 different carbon sources tested

| R. gnavus (EPV1) | OD750 |
|---|---|
| Arbutin | 0.525 |
| a-D-Lactose | 0.522 |
| b-Methyl-D-Glucoside | 0.498 |
| Maltose | 0.49 |
| N-Acetyl-D-Glucosamine | 0.49 |
| Maltotriose | 0.478 |
| Gentiobiose | 0.465 |
| Salicin | 0.449 |
| a-D-Glucose | 0.445 |
| D-Fructose | 0.428 |
| L-Fucose | 0.36 |
| D-Galactose | 0.345 |
| L-Arabinose | 0.334 |
| D-Gluconic acid | 0.304 |
| D-Ribose | 0.3 |
| D-Glucosamine | 0.273 |
| D-Arabinose | 0.269 |
| Sucrose | 0.234 |
| D-Xylose | 0.215 |
| Lactulose | 0.143 |
| L-Tartaric acid | 0.141 |
| 3-O-b-D-Galactopyranosyl-D-Arabinose | 0.133 |
| b-Methyl-D-Glucuronic acid | 0.131 |
| D-Mannose | 0.124 |
| L-Rhamnose | 0.101 |
| Uridine | 0.101 |

FIG. 29B
Preferred carbon sources out of 192 different carbon sources tested

| *E. rectale* (EPV2) | OD750 |
|---|---|
| N-Acetyl-D-Glucosamine | 0.174 |
| D-Raffinose | 0.173 |
| Palatinose | 0.157 |
| a-D-Lactose | 0.155 |
| Stachyose | 0.154 |
| g-Cyclodextrin | 0.148 |
| Dextrin | 0.14 |
| Gentiobiose | 0.136 |
| D-Galactose | 0.123 |
| D-Glucosamine | 0.117 |
| D-Melibiose | 0.112 |
| 3-O-b-D-Galactopyranosyl-D-Arabinose | 0.105 |
| b-Methyl-D-Galactoside | 0.103 |

FIG. 29C

| *C. leptum* (EPV6) | OD750 |
|---|---|
| D-Fructose-6-Phosphate | 0.11 |
| D-Trehalose | 0.109 |

FIG. 29D

Preferred carbon sources out of 192 different carbon sources tested

| *B. luti* (EPV3) | OD750 |
|---|---|
| a-D-Glucose | 0.628 |
| Maltotriose | 0.625 |
| Sucrose | 0.592 |
| Palatinose | 0.588 |
| L-Fucose | 0.576 |
| Stachyose | 0.554 |
| a-D-Lactose | 0.549 |
| D-Fructose | 0.544 |
| D-Melibiose | 0.527 |
| Maltose | 0.523 |
| Salicin | 0.493 |
| D-Raffinose | 0.486 |
| Arbutin | 0.435 |
| D-Mannitol | 0.423 |
| Lactulose | 0.381 |
| D-Lactitol | 0.36 |
| D-Gluconic acid | 0.344 |
| m-Inositol | 0.32 |
| Melibionic acid | 0.29 |
| D-Sorbitol | 0.239 |
| D-Arabinose | 0.183 |
| L-Tartaric acid | 0.178 |
| L-Arabinose | 0.133 |
| Bromosuccinic acid | 0.114 |
| D-Ribose | 0.107 |

FIG. 29E

| *B. wexlerae* (EPV5) | OD750 |
|---|---|
| a-D-Glucose | 0.988 |
| D-Fructose | 0.964 |
| Stachyose | 0.96 |
| a-D-Lactose | 0.912 |
| Sucrose | 0.84 |
| D-Lactitol | 0.671 |
| L-Fucose | 0.647 |
| Lactulose | 0.566 |
| D-Melibiose | 0.561 |
| D-Raffinose | 0.522 |
| D-Galactose | 0.428 |
| D-Glucosamine | 0.239 |
| b-Methyl-D-Galactoside | 0.206 |
| D-Cellobiose | 0.163 |
| Pectin | 0.109 |
| Inulin | 0.105 |

FIG. 29F
Preferred carbon sources out of 192 different carbon sources tested

| B. faecis (EPV15) | OD750 |
|---|---|
| Arbutin | 0.525 |
| Gentiobiose | 0.465 |
| Salicin | 0.449 |
| D-Glucosamine | 0.273 |
| D-Arabinose | 0.269 |
| D-Sorbitol | 0.227 |
| D-Fructose | 0.213 |
| D-Cellobiose | 0.212 |
| Sucrose | 0.183 |
| Maltose | 0.183 |
| Lactulose | 0.168 |
| a-D-Lactose | 0.164 |
| a-D-Glucose | 0.164 |
| D-Melibiose | 0.163 |
| D-Mannose | 0.143 |
| L-Tartaric acid | 0.141 |
| Bromosuccinic acid | 0.141 |
| 3-O-b-D-Galactopyranosyl-D-Arabinose | 0.133 |
| b-Methyl-D-Glucuronic acid | 0.131 |
| Maltotriose | 0.127 |
| D-Galactose | 0.125 |
| L-Fucose | 0.123 |
| D-Gluconic acid | 0.121 |
| D-Mannitol | 0.117 |
| Thymidine | 0.105 |
| Inosine | 0.102 |

FIG. 29G

Preferred carbon sources out of 192 different carbon sources tested

| *B. obeum* (EPV20) | OD750 |
|---|---|
| D-Melibiose | 0.588 |
| D-Sorbitol | 0.545 |
| Lactulose | 0.543 |
| D-Lactitol | 0.48 |
| Sucrose | 0.463 |
| L-Arabinose | 0.442 |
| a-D-Glucose | 0.438 |
| D-Galactose | 0.427 |
| D-Mannose | 0.419 |
| D-Fructose | 0.414 |
| Stachyose | 0.405 |
| b-Methyl-D-Galactoside | 0.402 |
| D-Arabinose | 0.395 |
| D-Xylose | 0.377 |
| D-Ribose | 0.376 |
| D-Raffinose | 0.376 |
| D-Fucose | 0.373 |
| Maltose | 0.362 |
| a-D-Lactose | 0.361 |
| Maltotriose | 0.36 |
| 3-O-b-D-Galactopyranosyl-D-Arabinose | 0.352 |
| L-Rhamnose | 0.338 |
| L-Fucose | 0.299 |

FIG. 29H
Preferred carbon sources out of 192 different carbon sources tested

| *B. producta* (EPV21) | OD750 |
|---|---|
| Maltose | 0.199 |
| D-Fructose | 0.193 |
| D-Trehalose | 0.182 |
| a-Methyl-D-Galactoside | 0.179 |
| Stachyose | 0.177 |
| b-Methyl-D-Xyloside | 0.175 |
| Turanose | 0.175 |
| a-D-Glucose | 0.174 |
| Maltotriose | 0.174 |
| D-Galactose | 0.173 |
| b-Methyl-D-Glucoside | 0.17 |
| Maltitol | 0.17 |
| Palatinose | 0.17 |
| D-Arabitol | 0.168 |
| D-Raffinose | 0.167 |
| b-Methyl-D-Galactoside | 0.163 |
| a-D-Lactose | 0.161 |
| Lactulose | 0.156 |
| D-Melibiose | 0.155 |
| Sucrose | 0.153 |
| D-Cellobiose | 0.152 |
| D-Arabinose | 0.148 |
| m-Inositol | 0.146 |

FIG. 29H (cont.)
Preferred carbon sources out of 192 different carbon sources tested

| | |
|---|---|
| 3-O-b-D-Galactopyranosyl-D-Arabinose | 0.146 |
| D-Mannitol | 0.144 |
| a-Methyl-D-Mannoside | 0.142 |
| D-Lactitol | 0.14 |
| Gentiobiose | 0.137 |
| D-Mannose | 0.135 |
| N-Acetyl-Neuraminic acid | 0.134 |
| D-Sorbitol | 0.132 |
| a-Methyl-D-Glucoside | 0.131 |
| L-Rhamnose | 0.129 |
| L-Sorbose | 0.129 |
| L-Arabinose | 0.125 |
| Pyruvic acid | 0.124 |
| Arbutin | 0.118 |
| Salicin | 0.116 |
| Bromosuccinic acid | 0.114 |
| D-Melezitose | 0.113 |
| b-Methyl-D-Glucuronic acid | 0.113 |
| Glucuronamide | 0.107 |
| Amygdalin | 0.107 |
| Pectin | 0.105 |

FIG. 29I

| B. coccoides (EPV22) | OD750 |
|---|---|
| D-Sorbitol | 0.468 |
| Lactulose | 0.442 |
| a-D-Lactose | 0.438 |
| D-Raffinose | 0.423 |
| D-Arabitol | 0.417 |
| Stachyose | 0.407 |
| D-Melibiose | 0.403 |
| Maltotriose | 0.401 |

FIG. 29I (cont.)
Preferred carbon sources out of 192 different carbon sources tested

| Sucrose | 0.398 |
|---|---|
| D-Trehalose | 0.394 |
| Palatinose | 0.392 |
| D-Melezitose | 0.388 |
| Turanose | 0.387 |
| Amygdalin | 0.386 |
| b-Methyl-D-Glucoside | 0.384 |
| D-Galactose | 0.381 |
| Maltose | 0.367 |
| D-Lactitol | 0.363 |
| a-D-Glucose | 0.354 |
| D-Fructose | 0.352 |
| b-Methyl-D-Galactoside | 0.345 |
| 3-O-b-D-Galactopyranosyl-D-Arabinose | 0.335 |
| b-Methyl-D-Glucuronic acid | 0.33 |
| Maltitol | 0.326 |
| D-Cellobiose | 0.324 |
| m-Inositol | 0.323 |
| b-Methyl-D-Xyloside | 0.318 |
| N-Acetyl-Neuraminic acid | 0.315 |
| a-Methyl-D-Galactoside | 0.306 |
| D-Mannitol | 0.286 |
| Gentiobiose | 0.256 |
| Salicin | 0.255 |
| Uridine | 0.215 |
| D-Gluconic acid | 0.213 |
| D-Galacturonic acid | 0.2 |

Preferred carbon sources out of 192 different carbon sources tested

FIG. 29J

| B. hydrogenotrophica (EPV23) | OD750 |
|---|---|
| D-Trehalose | 0.445 |
| Palatinose | 0.418 |
| Salicin | 0.412 |
| D-Fructose | 0.377 |
| Arbutin | 0.35 |
| D-Tagatose | 0.341 |
| L-Arabinose | 0.329 |
| Xylitol | 0.301 |
| Maltotriose | 0.287 |
| a-D-Glucose | 0.282 |
| Maltose | 0.248 |
| D-Ribose | 0.218 |
| a-Keto-Valeric acid | 0.208 |
| D-Aspartic acid | 0.182 |
| a-Ketobutyric acid | 0.16 |
| Dextrin | 0.155 |
| L-Leucine | 0.137 |

FIG. 29K

| Blautia hansenii (EPV24) | OD 750 |
|---|---|
|  |  |
| a-D-Glucose | 0.34 |
| Maltose | 0.317 |
| Maltotriose | 0.311 |
| a-D-Lactose | 0.273 |
| Stachyose | 0.258 |
| D-Galactose | 0.254 |
| N-Acetyl-D-Glucosamine | 0.243 |
| D-Raffinose | 0.232 |
| D-Melibiose | 0.216 |
| Chondroitin Sulfate C | 0.214 |
| Inosine | 0.21 |
| Adenosine | 0.161 |
| 2`-Deoxyadenosine | 0.132 |

FIG. 29L
Preferred carbon sources out of 192 different carbon sources tested

| EPV114 (B. luti BlnlX) | OD750 |
|---|---|
| D-Galactose | 0.195 |
| L-Fucose | 0.221 |
| D-Xylose | 0.252 |
| D-Mannitol | 0.169 |
| L-Rhamnose | 0.205 |
| D-Fructose | 0.253 |
| a-D-Glucose | 0.306 |
| Maltose | 0.338 |
| D-Melibiose | 0.288 |
| a-D-Lactose | 0.296 |
| Lactulose | 0.217 |
| Sucrose | 0.295 |
| Maltotriose | 0.352 |
| m-Inositol | 0.18 |
| D-Cellobiose | 0.143 |
| D-Arabinose | 0.181 |
| Arbutin | 0.256 |
| D-Lactitol | 0.252 |
| b-Methyl-D-Galactoside | 0.214 |
| Palatinose | 0.249 |
| D-Raffinose | 0.314 |
| Salicin | 0.292 |
| Stachyose | 0.658 |
| L-Tartaric acid | 0.14 |

FIG. 29M

Preferred carbon sources out of 192 different carbon sources tested

| EPV54 (B. luti ELU) | OD750 |
|---|---|
| D-Galactose | 0.193 |
| L-Fucose | 0.193 |
| D-Xylose | 0.273 |
| D-Mannitol | 0.168 |
| L-Rhamnose | 0.245 |
| D-Fructose | 0.289 |
| a-D-Glucose | 0.431 |
| Maltose | 0.246 |
| D-Melibiose | 0.193 |
| a-D-Lactose | 0.363 |
| Lactulose | 0.177 |
| Sucrose | 0.305 |
| m-Inositol | 0.263 |
| D-Arabinose | 0.196 |
| Arbutin | 0.195 |
| D-Lactitol | 0.204 |
| b-Methyl-D-Galactoside | 0.198 |
| Palatinose | 0.28 |
| D-Raffinose | 0.399 |
| Salicin | 0.257 |
| Stachyose | 0.88 |
| D-Glucosamine | 0.176 |

FIG. 29N

| EPV102 (R. gnavus) | OD750 |
|---|---|
| L-Arabinose | 0.151 |
| N-Acetyl-D-Glucosamine | 0.205 |
| D-Galactose | 0.212 |
| D-Mannose | 0.134 |
| L-Fucose | 0.324 |
| D-Gluconic acid | 0.203 |
| D-Xylose | 0.14 |
| D-Ribose | 0.13 |
| D-Fructose | 0.194 |
| a-D-Glucose | 0.274 |
| Maltose | 0.263 |
| D-Melibiose | 0.194 |
| Sucrose | 0.298 |
| b-Methyl-D-Glucoside | 0.244 |
| Maltotriose | 0.337 |
| b-Cyclodextrin | 0.192 |
| g-Cyclodextrin | 0.14 |
| D-Arabinose | 0.277 |
| Arbutin | 0.307 |
| Gentiobiose | 0.271 |
| D-Raffinose | 0.265 |
| Salicin | 0.266 |
| Stachyose | 0.318 |
| D-Glucosamine | 0.19 |

FIG. 29O
Preferred carbon sources out of 192 different carbon sources tested

| EPV78 (B. faecis) | OD750 |
|---|---|
| L-Fucose | 0.142 |
| D-Xylose | 0.185 |
| D-Ribose | 0.338 |
| L-Rhamnose | 0.227 |
| a-D-Glucose | 0.138 |
| D-Arabinose | 0.132 |
| D-Raffinose | 0.132 |
| Stachyose | 0.146 |

FIG. 29P

| EPV76 (R. torques) | OD750 |
|---|---|
| D-Galactose | 0.223 |
| D-Gluconic acid | 0.166 |
| D-Fructose | 0.244 |
| a-D-Glucose | 0.257 |
| a-D-Lactose | 0.22 |
| Turanose | 0.129 |

FIG. 29Q
Preferred carbon sources out of 192 different carbon sources tested

| EPV64 (B. wexlerae WAL14507) | OD750 |
|---|---|
| L-Arabinose | 0.47 |
| D-Galactose | 0.536 |
| D-Trehalose | 0.472 |
| D-Sorbitol | 0.148 |
| L-Fucose | 0.679 |
| D-Gluconic acid | 0.436 |
| D-Xylose | 0.478 |
| D-Ribose | 0.133 |
| D-Fructose | 0.679 |
| a-D-Glucose | 0.503 |
| Maltose | 0.719 |
| D-Melibiose | 0.747 |
| a-D-Lactose | 0.732 |
| Lactulose | 0.404 |
| Sucrose | 0.572 |
| Maltotriose | 0.617 |
| D-Cellobiose | 0.163 |
| Dextrin | 0.147 |
| Inulin | 0.127 |
| Mannan | 0.127 |
| Pectin | 0.136 |
| D-Arabinose | 0.591 |
| Gentiobiose | 0.566 |
| D-Lactitol | 0.568 |
| D-Melezitose | 0.691 |
| Maltitol | 0.573 |
| b-Methyl-D-Galactoside | 0.281 |
| Palatinose | 0.648 |
| D-Raffinose | 0.783 |
| Stachyose | 0.537 |
| Turanose | 0.57 |
| D-Glucosamine | 0.204 |
| Oxalic acid | 0.125 |
| Oxalomalic acid | 0.126 |
| Quinic acid | 0.148 |
| L-Tartaric acid | 0.146 |

FIG. 29R
Preferred carbon sources out of 192 different carbon sources tested

| EPV52 (B. wexlerae SJTU) | OD750 |
|---|---|
| L-Arabinose | 0.642 |
| D-Galactose | 0.671 |
| D-Trehalose | 0.69 |
| D-Sorbitol | 0.339 |
| L-Fucose | 0.611 |
| D-Xylose | 0.636 |
| D-Mannitol | 0.127 |
| L-Rhamnose | 0.167 |
| D-Fructose | 0.74 |
| a-D-Glucose | 0.524 |
| Maltose | 0.66 |
| D-Melibiose | 0.704 |
| a-D-Lactose | 0.815 |
| Lactulose | 0.701 |
| Sucrose | 0.739 |
| Maltotriose | 0.676 |
| D-Cellobiose | 0.361 |
| Dextrin | 0.116 |
| Inulin | 0.137 |
| Mannan | 0.123 |
| Pectin | 0.123 |
| N-Acetyl-Neuraminic acid | 0.467 |
| D-Arabinose | 0.534 |
| Arbutin | 0.487 |
| Gentiobiose | 0.506 |
| D-Lactitol | 0.71 |
| D-Melezitose | 0.695 |
| Maltitol | 0.658 |
| b-Methyl-D-Galactoside | 0.321 |
| b-Methyl-D-Xyloside | 0.333 |
| Palatinose | 0.666 |
| D-Raffinose | 0.575 |
| Salicin | 0.591 |
| Stachyose | 0.74 |
| Turanose | 0.581 |
| Oxalic acid | 0.123 |
| L-Tartaric acid | 0.259 |

FIG. 29S

Preferred carbon sources out of 192 different carbon sources tested

| EPV51 (SJTU1416) | OD750 |
|---|---|
| D-Trehalose | 0.136 |
| a-D-Glucose | 0.104 |
| Maltose | 0.165 |
| D-Melibiose | 0.115 |
| a-D-Lactose | 0.171 |
| Lactulose | 0.17 |
| Sucrose | 0.18 |
| b-Methyl-D-Glucoside | 0.113 |
| Maltotriose | 0.207 |
| Amygdalin | 0.12 |
| D-Lactitol | 0.137 |
| D-Melezitose | 0.222 |
| b-Methyl-D-Galactoside | 0.142 |
| D-Raffinose | 0.186 |
| Stachyose | 0.199 |
| Turanose | 0.239 |

FIG. 29T

Preferred carbon sources out of 192 different carbon sources tested

| EPV47 (GQ8980099) | OD750 |
|---|---|
| L-Arabinose | 0.336 |
| N-Acetyl-D-Glucosamine | 0.328 |
| D-Saccharic acid | 0.128 |
| D-Galactose | 0.365 |
| L-Fucose | 0.255 |
| D-Xylose | 0.131 |
| L-Rhamnose | 0.286 |
| D-Fructose | 0.466 |
| a-D-Glucose | 0.421 |
| D-Melibiose | 0.428 |
| a-D-Lactose | 0.468 |
| Lactulose | 0.551 |
| Sucrose | 0.475 |
| Mucic acid | 0.153 |
| D-Arabinose | 0.307 |
| Arbutin | 0.389 |
| 3-O-b-D-Galactopyranosyl-D-Arabinose | 0.16 |
| D-Raffinose | 0.408 |
| Salicin | 0.342 |
| Sedoheptulosan | 0.442 |
| Stachyose | 0.516 |
| D-Glucosamine | 0.247 |

FIG. 29U
Preferred carbon sources out of 192 different carbon sources tested

| EPV35 (E rectale) | OD750 |
|---|---|
| L-Arabinose | 0.216 |
| D-Galactose | 0.208 |
| D-Xylose | 0.14 |
| D-Fructose | 0.178 |
| a-D-Glucose | 0.185 |
| Maltose | 0.113 |
| D-Melibiose | 0.173 |
| a-Methyl-D-Galactoside | 0.14 |
| a-D-Lactose | 0.188 |
| Lactulose | 0.112 |
| b-Methyl-D-Glucoside | 0.171 |
| Maltotriose | 0.151 |
| Dextrin | 0.172 |
| Glycogen | 0.144 |
| Gentiobiose | 0.169 |
| a-Methyl-D-Glucoside | 0.165 |
| b-Methyl-D-Galactoside | 0.119 |
| Stachyose | 0.196 |
| Turanose | 0.22 |
| D-Glucosamine | 0.144 |

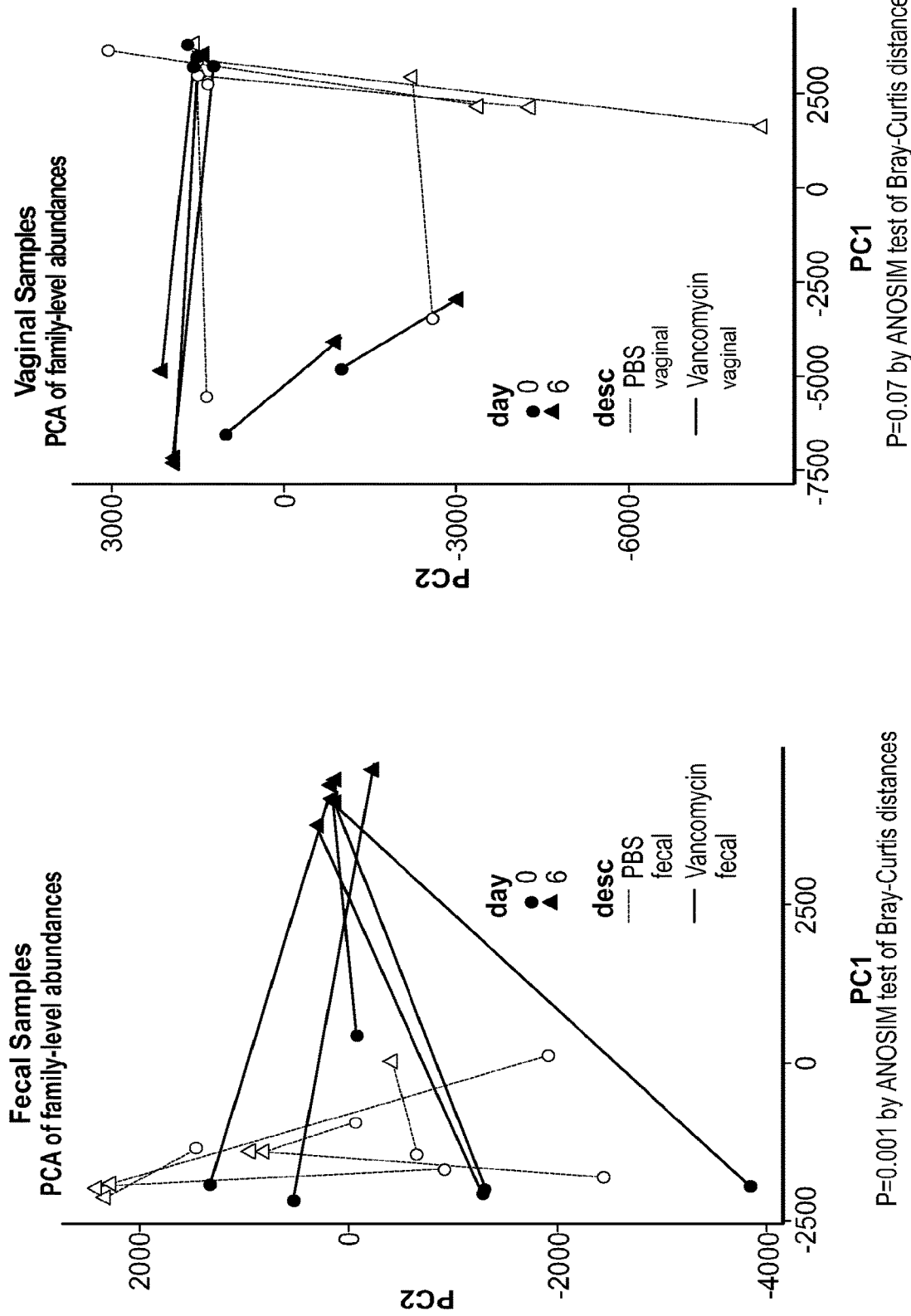
FIG. 32 Shifts in the microbiome of the gut and vagina following treatment with oral vancomycin

PROBIOTIC COMPOSITIONS CONTAINING CLOSTRIDIALES FOR INHIBITING INFLAMMATION

RELATED APPLICATIONS

This application is a continuation of U.S. patent application Ser. No. 16/219,125, filed Dec. 13, 2018 which, in turn, is a continuation of U.S. patent application Ser. No. 15/438,271, filed Feb. 21, 2017 (now abandoned) which, in turn, is a continuation of U.S. patent application Ser. No. 14/952,895, filed Nov. 25, 2015 (U.S. Pat. No. 9,610,307), which, in turn, claims priority to U.S. Provisional Patent Application No. 62/084,536, filed Nov. 25, 2014; U.S. Provisional Patent Application No. 62/084,537, filed Nov. 25, 2014; U.S. Provisional Patent Application No. 62/084,540, filed Nov. 25, 2014; U.S. Provisional Patent Application No. 62/117,632, filed Feb. 18, 2015; U.S. Provisional Patent Application No. 62/117,637, filed Feb. 18, 2015; U.S. Provisional Patent Application No. 62/117,639, filed Feb. 18, 2015; U.S. Provisional Patent Application No. 62/162,562, filed May 15, 2015; and U.S. Provisional Patent Application No. 62/257,714, filed Nov. 19, 2015. The entire contents of each of the foregoing applications are incorporated herein by reference in their entirety.

SEQUENCE LISTING

The instant application contains a Sequence Listing which has been submitted electronically in ASCII format and is hereby incorporated by reference in its entirety. Said ASCII copy, created on Aug. 23, 2019, is named 126383_02105_SL.txt and is 3.96 megabytes in size.

BACKGROUND

Humans and other mammals have numerous microbial niches, and interventions to modulate the microbiota thereof have been focused on antibiotics (which effect largely non-specific eradication of the microbiota in an effort to target a pathogen), probiotics (largely in the form of lactic acid-producing bacteria in food products), prebiotics (stimulatory materials, primarily carbohydrates, that increase bacterial growth and/or activity), and synbiotics (combinations of prebiotics and probiotics) (see. e.g., WO 2011/022542). Autoimmune and inflammatory diseases are characterized by an inappropriate immunological intolerance or an abnormal immune response, and affect up to 50 million Americans. Current treatments for such conditions, such as immunosuppressant drugs, carry a risk of dangerous systemic side effects such as infection, organ damage, and the development of new autoimmunities. There is therefore a need for improved diagnostic and prognostic measures, preventative measures, and treatments for autoimmune and inflammatory diseases.

A healthy microbiota provides the host with multiple benefits, including colonization resistance to a broad spectrum of pathogens, essential nutrient biosynthesis and absorption, and immune stimulation that maintains a healthy gut epithelium and an appropriately controlled systemic immunity. In settings of 'dysbiosis' or disrupted symbiosis, microbiota functions can be lost or deranged, resulting in increased susceptibility to pathogens, altered metabolic profiles, or induction of proinflammatory signals that can result in local or systemic inflammation or autoimmunity. Thus, the intestinal microbiota plays a significant role in the pathogenesis of many diseases and disorders, including a variety of pathogenic infections distal to the gastrointestinal tract. Therefore, in response to the need for durable, efficient, and effective compositions and methods for treatment of immune and inflammatory diseases by way of restoring or enhancing microbiota functions, the present invention provides compositions and methods for treatment and prevention of immune and inflammatory conditions associated with dysbiosis, including dysbiosis distal to the gastrointestinal tract.

SUMMARY OF THE INVENTION

Disclosed herein are therapeutic compositions containing probiotic, non-pathogenic bacterial populations and networks thereof, for the prevention, control, and treatment of diseases, disorders and conditions, in particular immune and inflammatory diseases. In some embodiments, the therapeutic compositions contain prebiotics, e.g., carbohydrates, in conjunction with microbial populations and/or networks thereof. These compositions are advantageous in being suitable for safe administration to humans and other mammalian subjects and are efficacious in numerous dysbiotic diseases, disorders and conditions, such as immune and inflammatory disease.

In one aspect, the invention provides a pharmaceutical composition comprising an isolated population of anti-inflammatory bacterial cells of the order Clostridiales capable of decreasing the secretion of a pro-inflammatory cytokine and/or increasing the secretion of an anti-inflammatory cytokine by a population of human peripheral blood mononuclear cells (PBMCs), and a pharmaceutically acceptable excipient. In one embodiment, the secretion of a pro-inflammatory cytokine by a population of PBMCs is induced by *Enterococcus faecalis*.

In one embodiment, the anti-inflammatory bacterial cells are of the family Lachnospiraceae. In another embodiments, the anti-inflammatory bacterial cells are of the genus *Blautia*, *Clostridium*, *Eubacterium*, or *Ruminococcus*. In one the anti-inflammatory bacterial cells are of the genus *Blautia*. In another embodiment, the anti-inflammatory bacterial cells are of a species selected from the group consisting of *Blautia coccoides*, *Blautia faecis*, *Blautia glucerasea*, *Blautia hansenii*, *Blautia hyrogenotrophica*, *Blautia luti*, *Blautia obeum*, *Blautia producta*, *Blautia schinkii*, *Blautia* sp. M25, *Blautia stercoris*, *Blautia wexlerae*, *Blautia* uncultured bacterium clone BKLE_a03_2, *Blautia* uncultured bacterium clone SJTU_B_14_30, *Blautia* uncultured bacterium clone SJTU_C_14_16, *Blautia* uncultured bacterium clone S1-5, and *Blautia* uncultured PAC000178_s. In one embodiment, the anti-inflammatory bacterial cells are of the species *Ruminococcus gnavus*. In another embodiment, the anti-inflammatory bacterial cells are of the species *Eubacterium rectale*.

In one embodiment, the anti-inflammatory bacterial cells comprise a bacterial cell in vegetative form. In another embodiment, the anti-inflammatory bacterial cells comprise a bacterial cell in spore form.

In one embodiment, the isolated population of anti-inflammatory bacterial cells further comprises a bacterial cell belonging to a bacterial strain set forth in Table 1, Table 1 A, Table 1B, Table 1C, Table 1D, Table 1E, or Table 1F.

In one embodiment, the pharmaceutical composition comprises a prebiotic. In one embodiment, the prebiotic comprises a monomer or polymer selected from the group consisting of arabinoxylan, xylose, soluble fiber dextran, soluble corn fiber, polydextrose, lactose, N-acetyl-lactosamine, glucose, and combinations thereof. In another embodiment, the prebiotic comprises a monomer or polymer selected from the group consisting of galactose, fructose, rhamnose, mannose, uronic acids, 3'-fucosyllactose, 3'-sialylactose, 6'-sialyllactose, lacto-N-neotetraose, 2'-2'-fucosyllactose, and combinations thereof. In one embodiment, the prebiotic comprises a monosaccharide selected from the group consisting of arabinose, fructose, fucose, galactose, glucose, mannose, D-xylose, xylitol, ribose, and combinations thereof. In another embodiment, the prebiotic comprises a disaccharide selected from the group consisting of xylobiose, sucrose, maltose, lactose, lactulose, trehalose, cellobiose, and combinations thereof. In yet another embodiment, the prebiotic comprises a polysaccharide, wherein the polysaccharide is xylooligosaccharide.

In one embodiment, the prebiotic comprises a sugar selected from the group consisting of arabinose, fructose, fucose, lactose, galactose, glucose, mannose, D-xylose, xylitol, ribose, xylobiose, sucrose, maltose, lactose, lactulose, trehalose, cellobiose, xylooligosaccharide, and combinations thereof. In one embodiment, the sugar is xylose.

In one embodiment, the pro-inflammatory cytokine is selected from the group consisting of IFNγ, IL-12p70, IL-1α, IL-6, IL-8, MCP1, MIP1α, MIP1β, TNFα, and combinations thereof.

In one embodiment, the anti-inflammatory cytokine is selected from the group consisting of IL-10, IL-13, IL-4, IL-5, TGFβ, and combinations thereof.

In one embodiment, the pharmaceutical composition is formulated for oral administration. In another embodiment, the pharmaceutical composition is formulated for rectal administration.

In one embodiment, the anti-inflammatory bacterial cells decrease the secretion of a pro-inflammatory cytokine and/or increase the secretion of an anti-inflammatory cytokine by a population of human peripheral blood mononuclear cells (PBMCs) in vitro.

In another aspect, the invention provides a method for reducing inflammation in a subject, the method comprising administering a pharmaceutical composition of the invention to thereby reduce inflammation in the subject.

In one embodiment, the subject has an autoimmune or inflammatory disorder. In one embodiment, the autoimmune or inflammatory disorder is selected from the group consisting of graft-versus-host disease (GVHD), an inflammatory bowel disease (IBD), ulterative colitis, Crohn's disease, multiple sclerosis (MS), systemic lupus erythematosus (SLE), type I diabetes, rheumatoid arthritis, Sjögren's syndrome, and Celiac disease.

In one embodiment, the pharmaceutical composition is administered orally. In another embodiment, the pharmaceutical composition is administered rectally.

In one embodiment, administration of the pharmaceutical composition reduces inflammation in the gastrointestinal tract of the subject. In another embodiment, administration of the pharmaceutical composition reduces inflammation at a site distal to the gastrointestinal tract of the subject. In one embodiment, the distal site is the placenta, the spleen, the skin the liver, the uterus, the blood, an eye/conjunctiva, the mouth an ear, the nose, a lung, the liver, the pancreas, the brain, the embryonic sac, or vagina of the subject. In another embodiment, the distal site is the circulatory system, the reproductive tract, the cardiovascular system, the nervous system, or a combination thereof.

In one embodiment, the subject has a dysbiosis. In one embodiment, the dysbiosis is a gastrointestinal dysbiosis. In another embodiment, the dysbiosis is a distal dysbiosis.

In one embodiment, the anti-inflammatory bacterial cells of the pharmaceutical composition engraft in the gastrointestinal tract of the subject.

In one embodiment, the method further comprises administering a prebiotic to the subject.

BRIEF DESCRIPTION OF THE TABLES

Table 1 provides a list of Operational Taxonomic Units (OTU) with taxonomic assignments made to Genus, Species, and Phylogenetic Clade. Clade membership of bacterial OTUs is based on 16S sequence data. Clades are defined based on the topology of a phylogenetic tree that is constructed from full-length 16S sequences using maximum likelihood methods familiar to individuals with ordinary skill in the art of phylogenetics. Clades are constructed to ensure that all OTUs in a given clade are: (i) within a specified number of bootstrap supported nodes from one another, and (ii) within 5% genetic similarity. OTUs that are within the same clade can be distinguished as genetically and phylogenetically distinct from OTUs in a different clade based on 16S-V4 sequence data, while OTUs falling within the same clade are closely related. OTUs falling within the same clade are evolutionarily closely related and may or may not be distinguishable from one another using 16S-V4 sequence data. Members of the same clade, due to their evolutionary relatedness, play similar functional roles in a microbial ecology such as that found in the human gut. Compositions substituting one species with another from the same clade are likely to have conserved ecological function and therefore are useful in the present invention. All OTUs are denoted as to their putative capacity to form spores and whether they are a Pathogen or Pathobiont (see Definitions for description of "Pathobiont"). NIAID Priority Pathogens are denoted as 'Category-A', 'Category-B', or 'Category-C', and Opportunistic Pathogens are denoted as 'OP'. OTUs that are not pathogenic or for which their ability to exist as a pathogen is unknown are denoted as 'N'. The 'SEQ ID Number' denotes the identifier of the OTU in the Sequence Listing File and 'Public DB Accession' denotes the identifier of the OTU in a public sequence repository. See, e.g., WO 2014/121304.

Table 1A provides a list of exemplary bacteria useful in the present invention.

Table 1B provides a list of exemplary bacteria useful in the present invention.

Table 1C provides a list of exemplary bacteria useful in the present invention.

Table 1D provides a list of exemplary bacteria useful in the present invention.

Table 1E provides a list of exemplary bacteria useful in the present invention. These bacteria are preferably down-modulated in a subject.

Table 1F provides a list of exemplary bacteria that may be used in the invention. These bacteria are preferably up-modulated in a subject.

Table 2A lists species identified as "germinable" and "sporulatable" by colony picking approach.

Table 2B lists species identified as "germinable" using 16S colony picking approach.

Table 2C lists species identified as "sporulatable" using 16s-V4 NGS approach. See, e.g., WO 2014/121304.

Table 3 lists anaerobic bacterial species tested for carbon source usage (Biolog plates).

Table 4 lists exemplary prebiotics/carbon sources.

Table 5 provides bacterial species detected at low frequency in vaginal samples from vancomycin-treated mice (day 6) that were not present in untreated mice (day 0).

IL-13, d) IL-10, e) IL-12p70, f) MCP-1, g) IL-8, h) IL17α, i) IL-α, j) IL-9, k) IL-2, 1) IL-4, m) IL-5, n) MIP-1α, o) MIP-1β, p) TNF-α.

FIG. 11A-11D is a panel of graphs showing that (a-b) EPV3 is capable of inducing a desirable anti-inflammatory cytokine profile for treating or preventing GVHD and (c-d) EPV5 induces a suboptimal profile for GVHD.

Figure 12A:
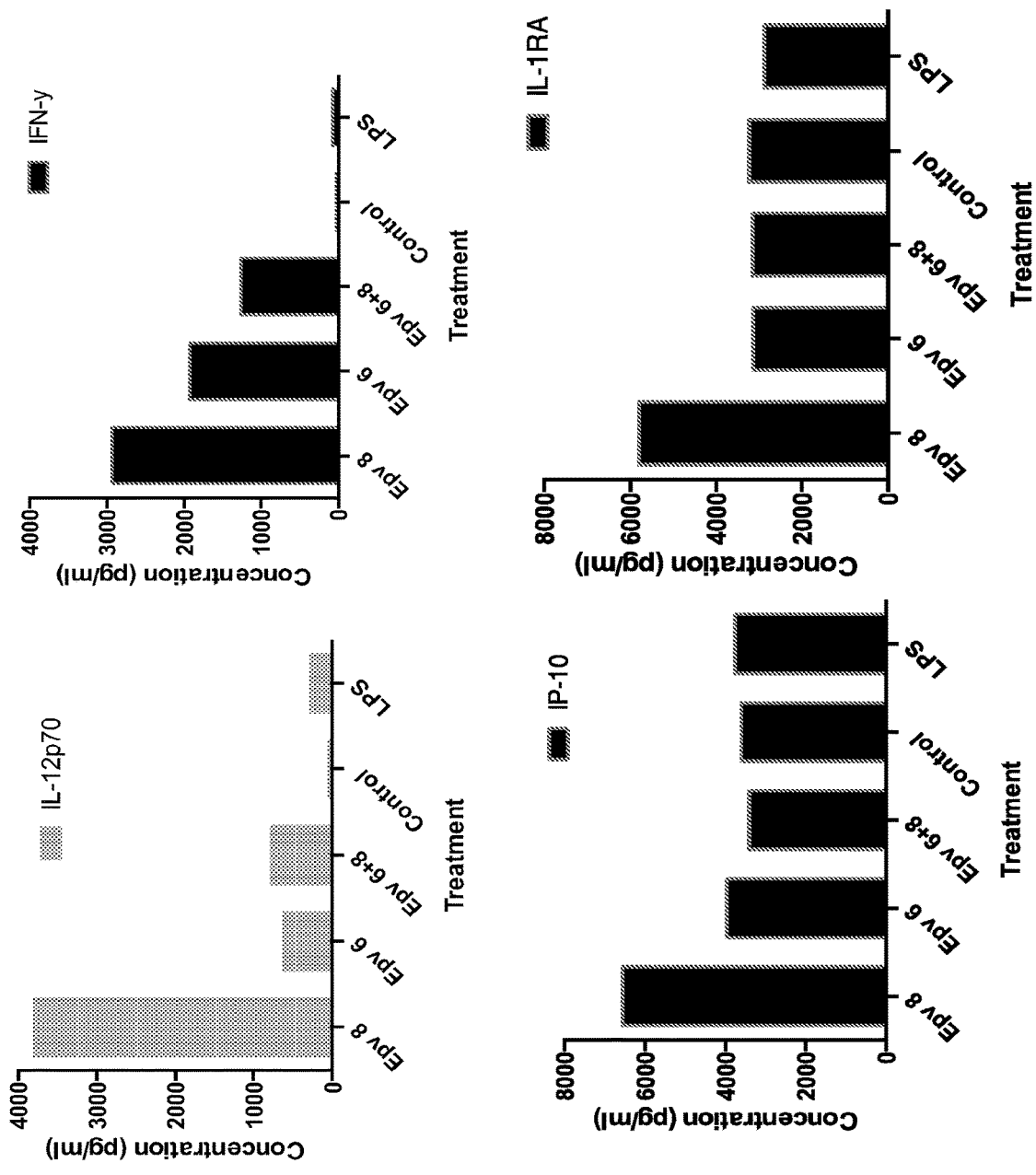
Figure 12B:
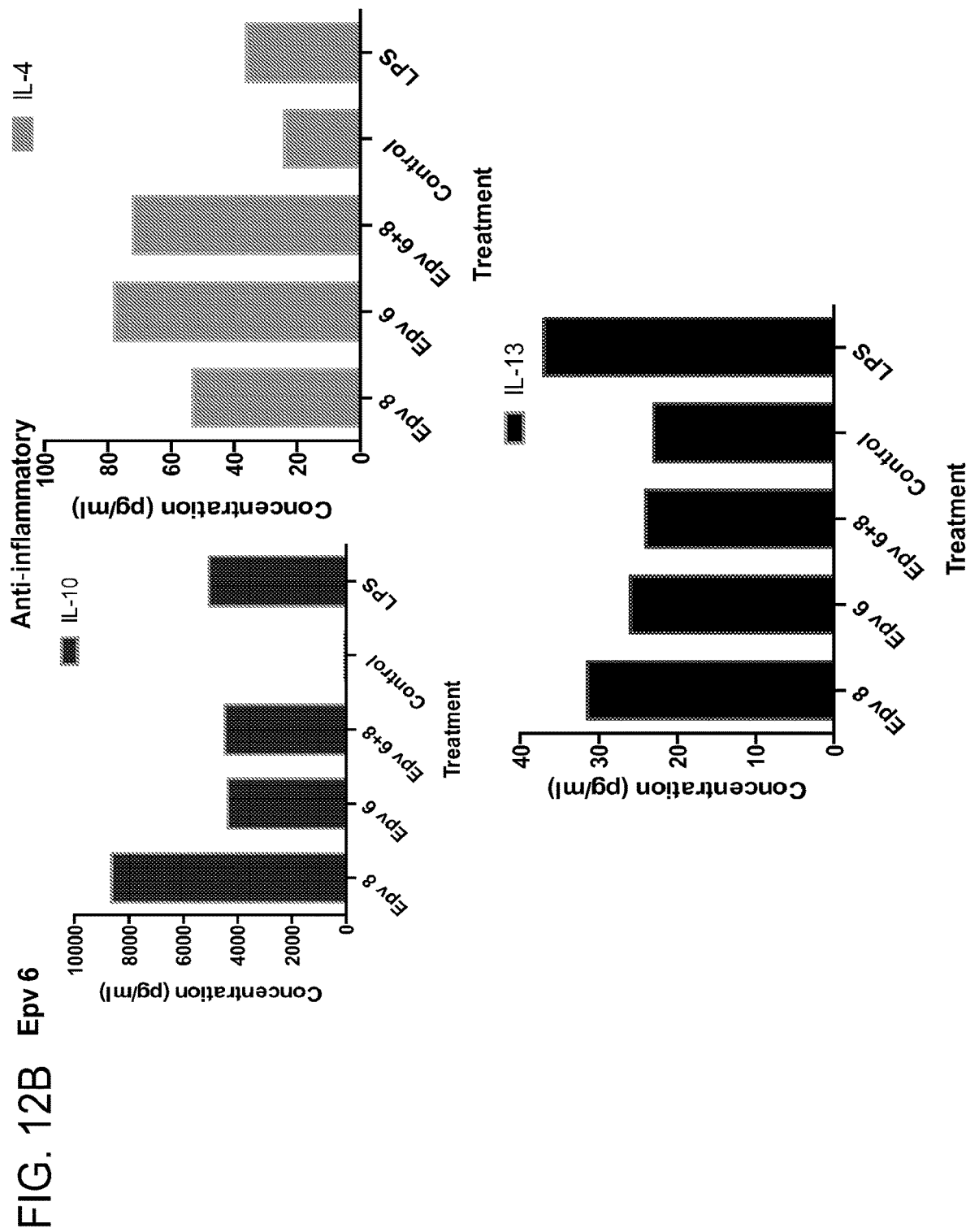

FIG. 12A-12B depicts the production of (a) pro-inflammatory (IL-12p70, IFNγ, IP-10, IL-1RA) and (b) anti-inflammatory (IL-10, IL-4, IL-13) cytokines by human PBMCs following treatment with Epv6 (*Clostridium leptum*).

Figure 13A:
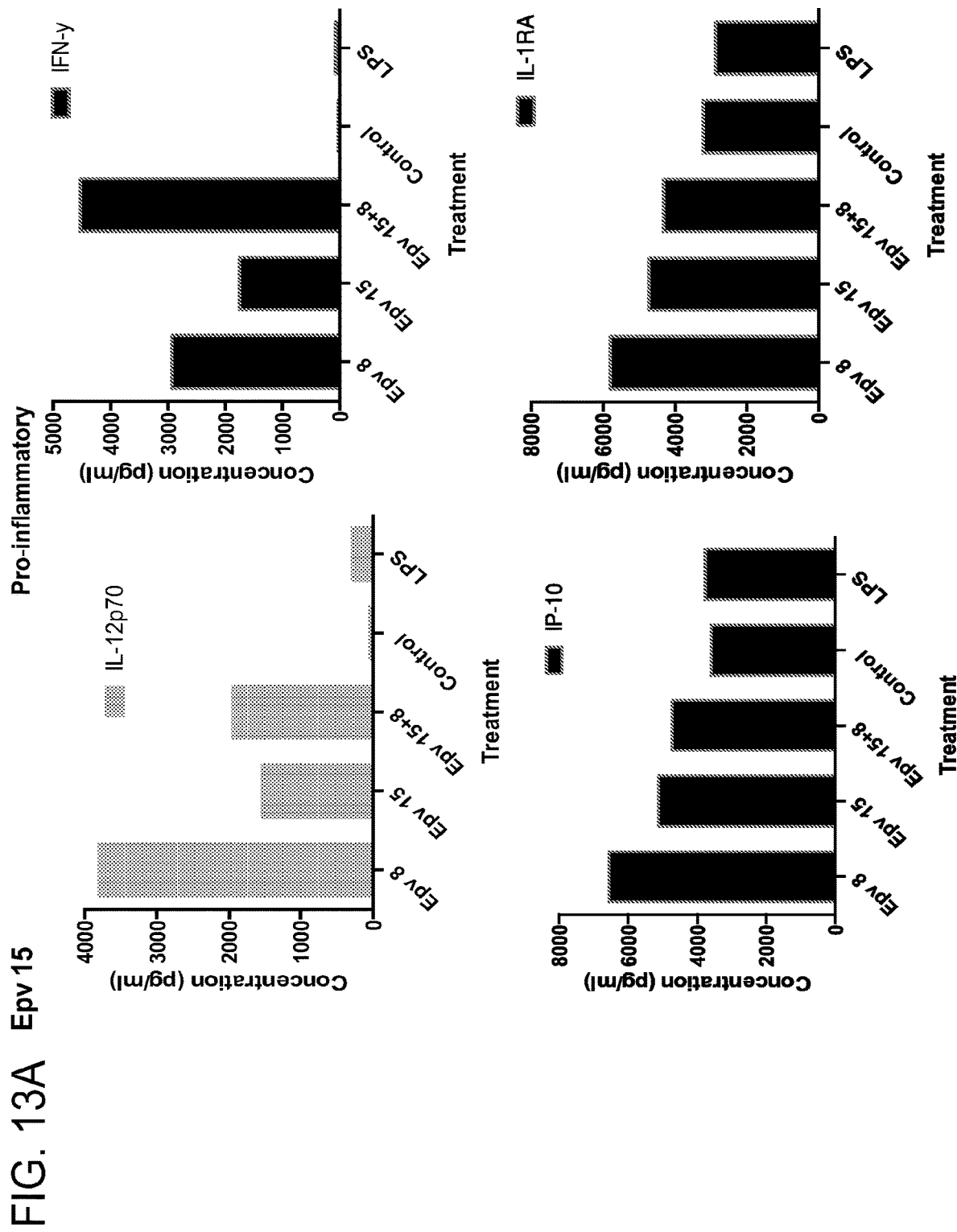
Figure 13B:
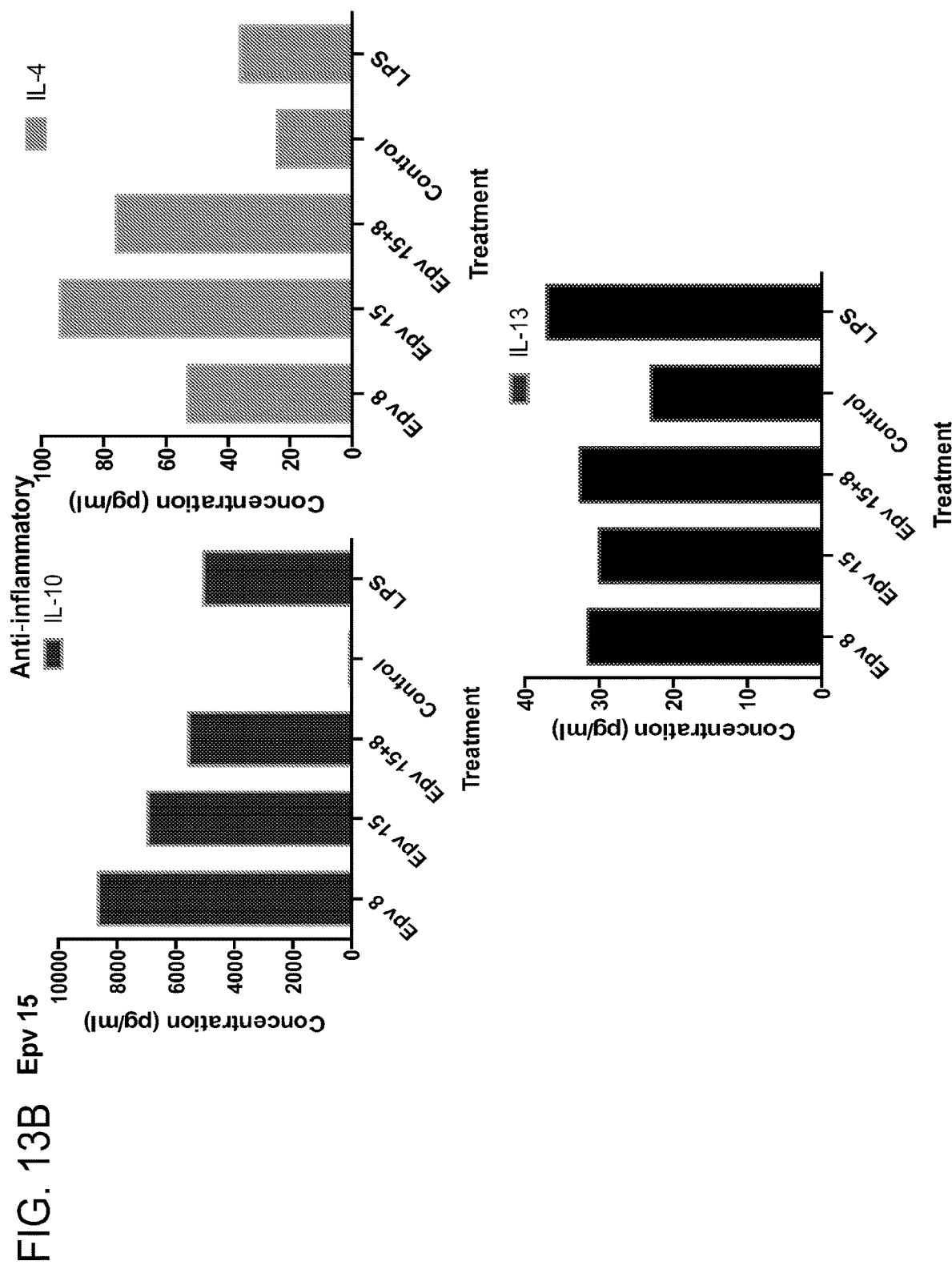

FIG. 13A-13B depicts the production of (a) pro-inflammatory (IL-12p70, IFNγ, IP-10, IL-1RA) and (b) anti-inflammatory (IL-10, IL-4, IL-13) cytokines by human PBMCs following treatment with Epv15 (*Blautia faecis*).

Figure 14B:
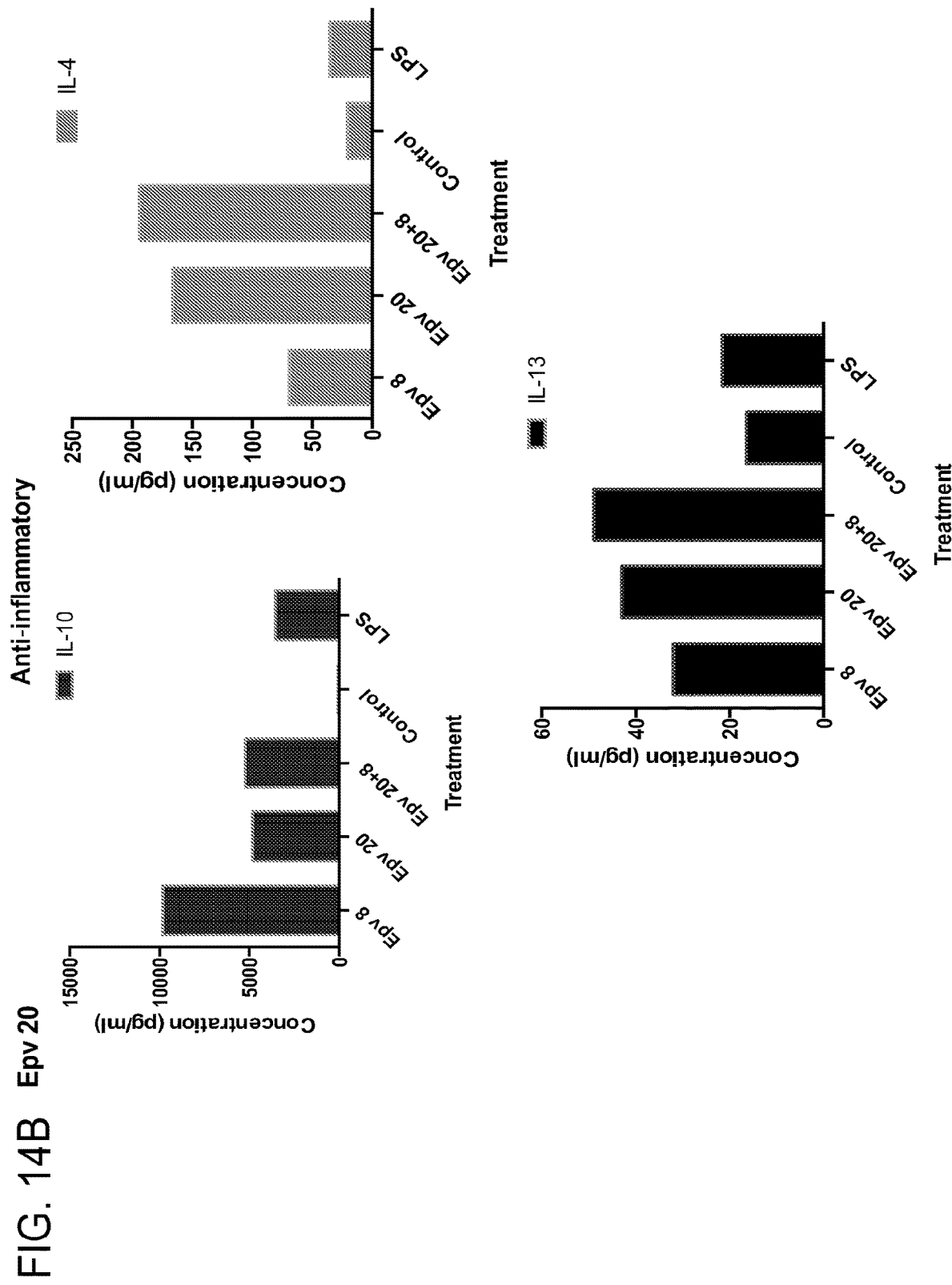

FIG. 14A-14B depicts the production of (a) pro-inflammatory (IL-12p70, IFNγ, IP-10, IL-1RA) and (b) anti-inflammatory (IL-10, IL-4, IL-13) cytokines by human PBMCs following treatment with Epv20 (*Blautia/Ruminococcus* obeum ATCC 29174).

Figure 15A:
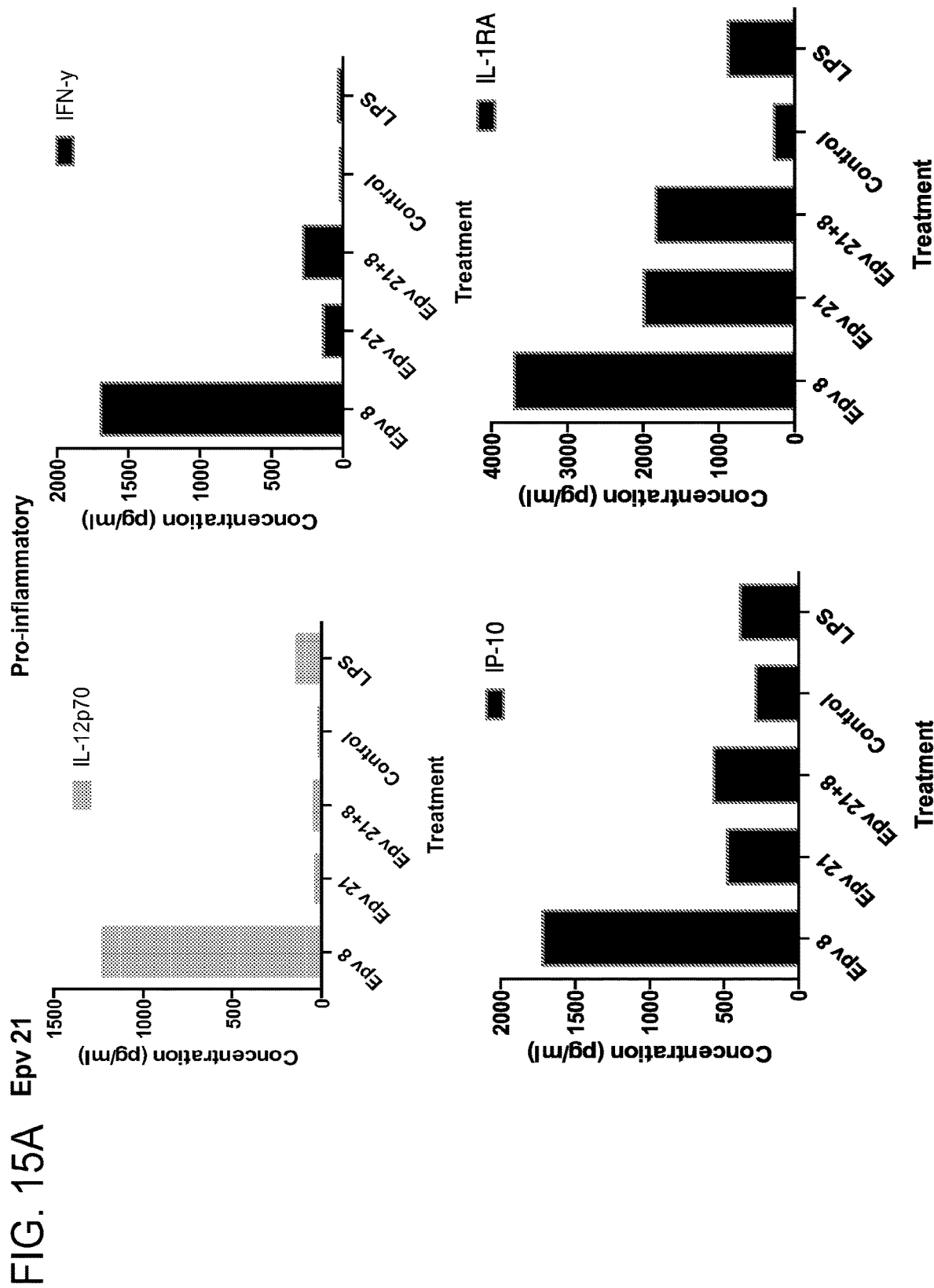

FIG. 15A-15B depicts the production of (a) pro-inflammatory (IL-12p70, IFNγ, IP-10, IL-1RA) and (b) anti-inflammatory (IL-10, IL-4, IL-13) cytokines by human PBMCs following treatment with Epv21 (*Blautia producta* ATCC 27340).

Figure 16A:
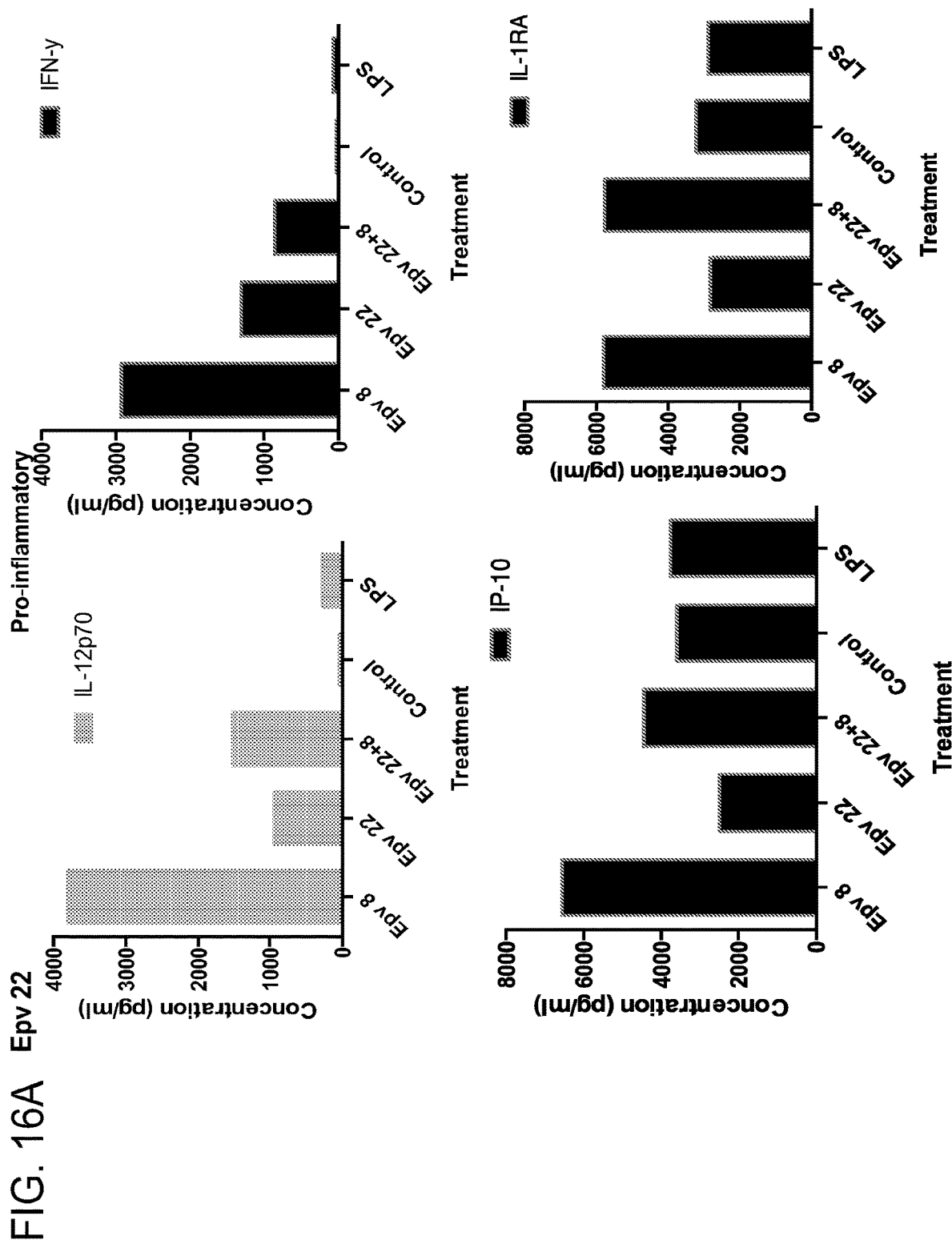
Figure 16B:
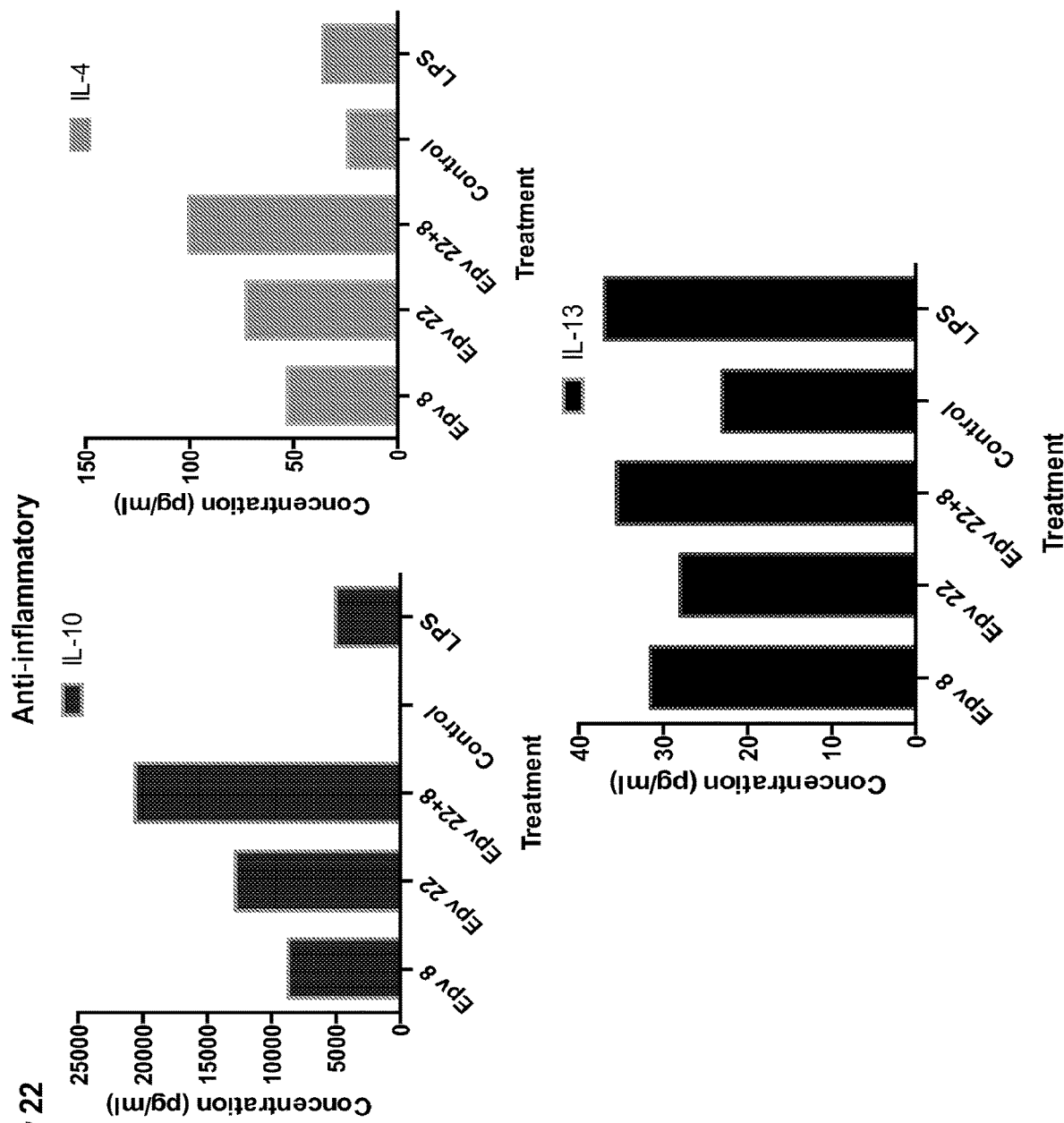

FIG. 16A-16B depicts the production of (a) pro-inflammatory (IL-12p70, IFNγ, IP-10, IL-1RA) and (b) anti-inflammatory (IL-10, IL-4, IL-13) cytokines by human PBMCs following treatment with Epv22 (*Blautia coccoides* ATCC 29236).

Figure 17B:
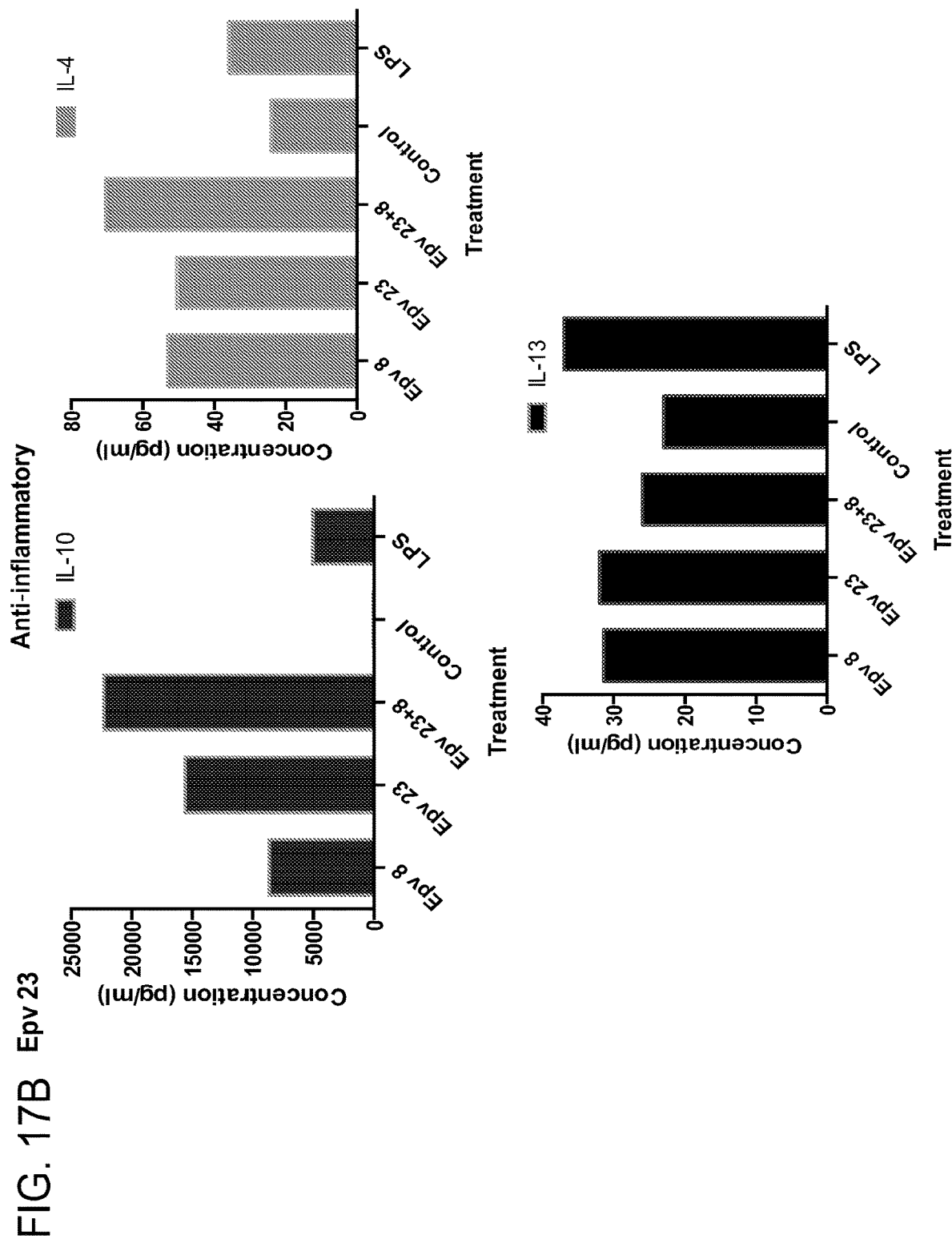

FIG. 17A-17B depicts the production of (a) pro-inflammatory (IL-12p70, IFNγ, IP-10, IL-1RA) and (b) anti-inflammatory (IL-10, IL-4, IL-13) cytokines by human PBMCs following treatment with Epv23 (*Blautia hydrogenotrophica* ATCC BAA-2371).

Figure 18A:
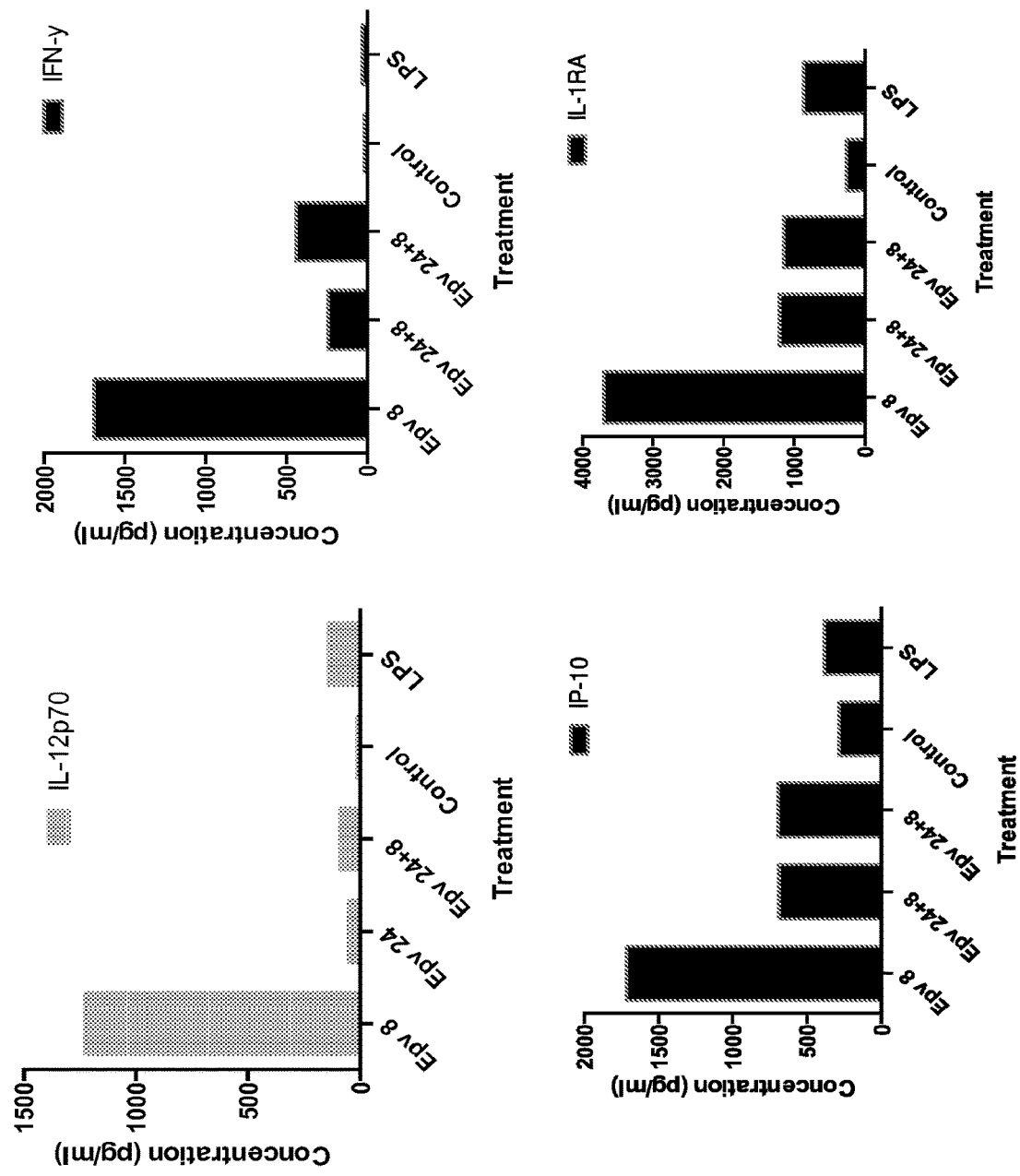
Figure 18B:
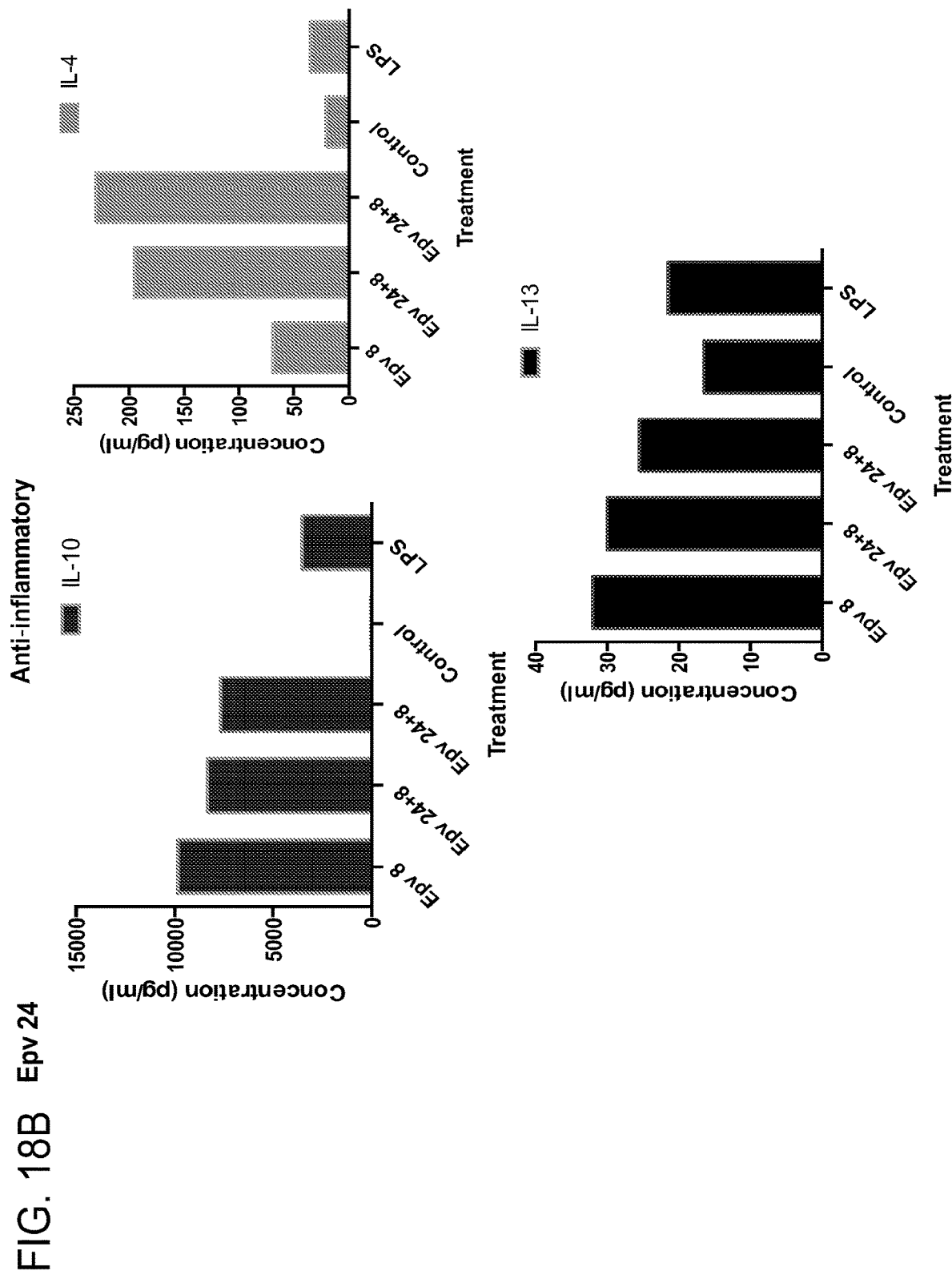

FIG. 18A-18B depicts the production of (a) pro-inflammatory (IL-12p70, IFNγ, IP-10, IL-1RA) and (b) anti-inflammatory (IL-10, IL-4, IL-13) cytokines by human PBMCs following treatment with Epv24 (*Blautia Hansenii* ATCC27752).

Figure 19A:
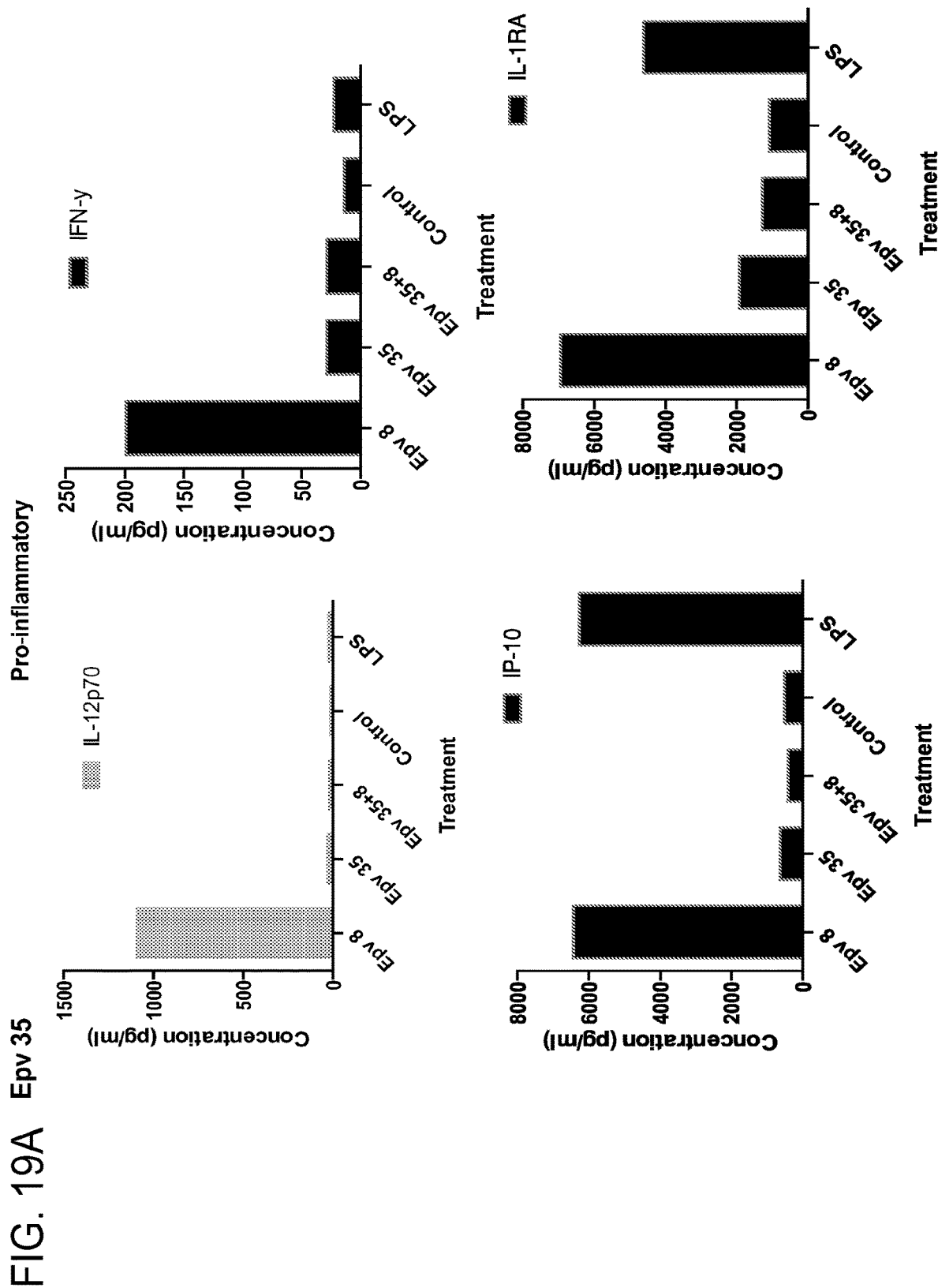
Figure 19B:
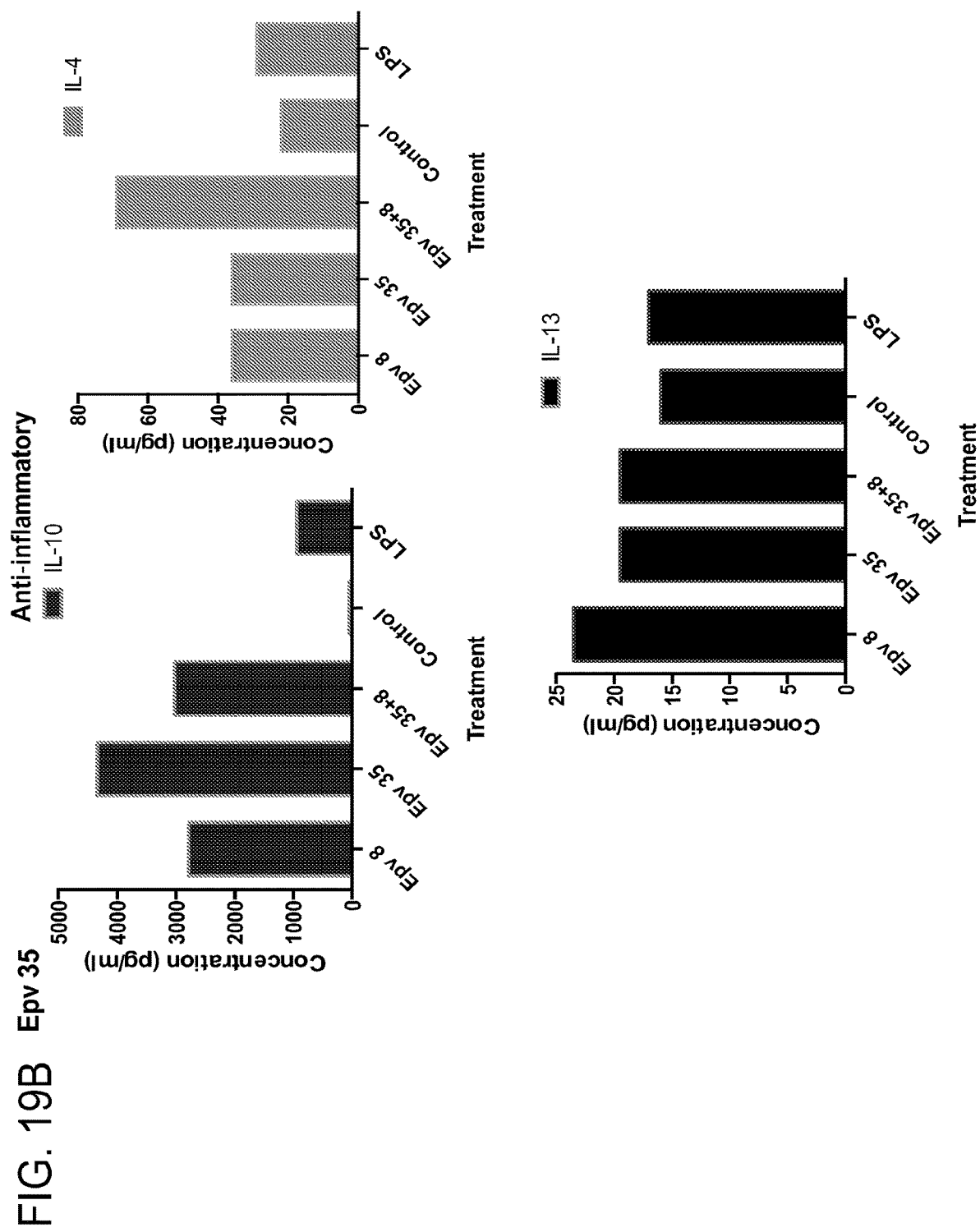

FIG. 19A-19B depicts the production of (a) pro-inflammatory (IL-12p70, IFNγ, IP-10, IL-1RA) and (b) anti-inflammatory (IL-10, IL-4, IL-13) cytokines by human PBMCs following treatment with Epv35 (*Eubacterium rectale*).

Figure 20B:
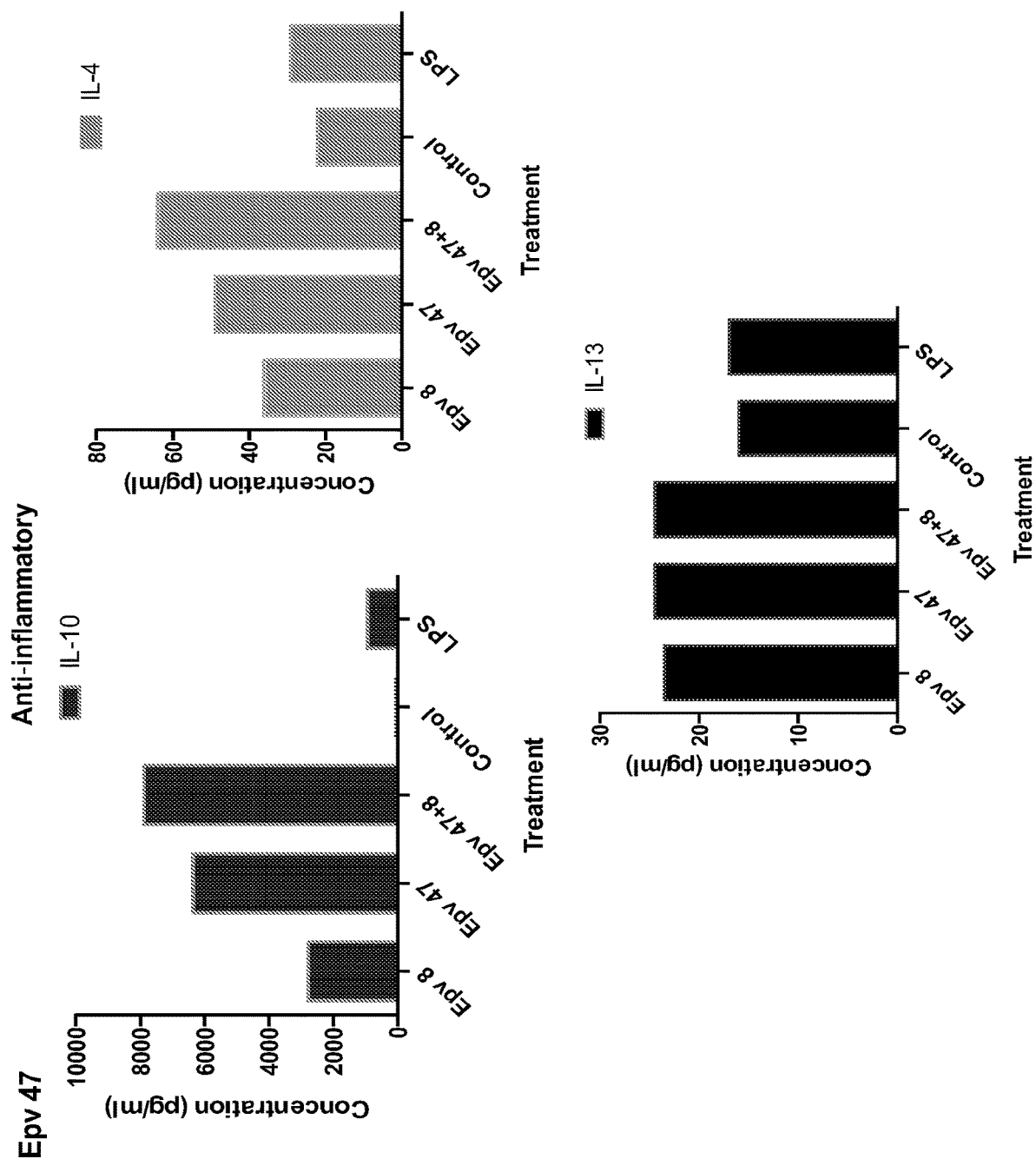

FIG. 20A-20B depicts the production of (a) pro-inflammatory (IL-12p70, IFNγ, IP-10, IL-1RA) and (b) anti-inflammatory (IL-10, IL-4, IL-13) cytokines by human PBMCs following treatment with Epv47 (previously uncultured *Blautia*, similar to GQ898099_s 51-5).

Figure 21A:
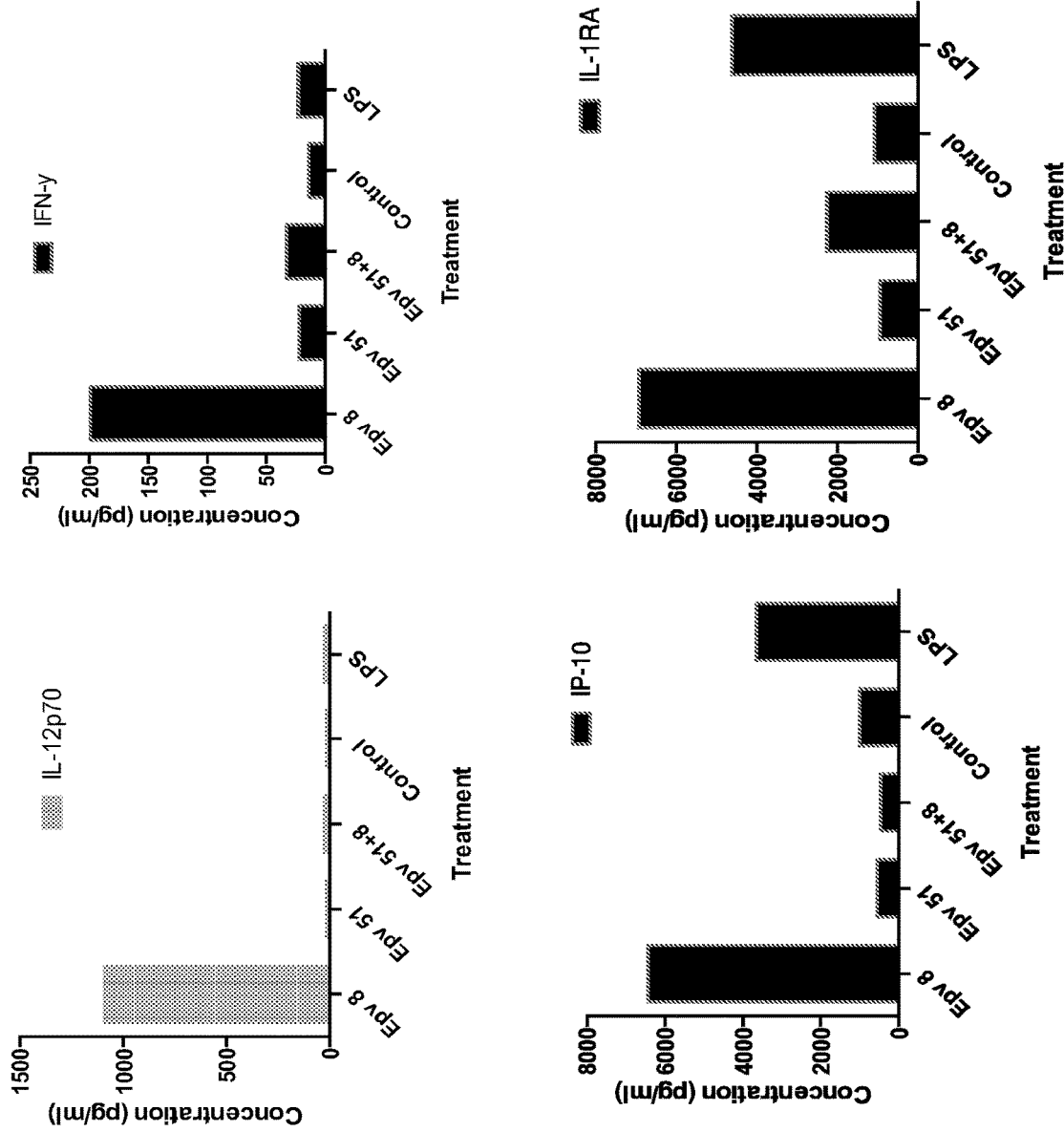

FIG. 21A-21B depicts the production of (a) pro-inflammatory (IL-12p70, IFNγ, IP-10, IL-1RA) and (b) anti-inflammatory (IL-10, IL-4, IL-13) cytokines by human PBMCs following treatment with Epv51 (previously uncultured *Blautia*, similar to SJTU_C_14_16).

FIG. 22A-22B depicts the production of (a) pro-inflammatory (IL-12p70, IFNγ, IP-10, IL-1RA) and (b) anti-inflammatory (IL-10, IL-4, IL-13) cytokines by human PBMCs following treatment with Epv52 (*Blautia wexlerae* (SJTU_B_09_77)).

Figure 23A:
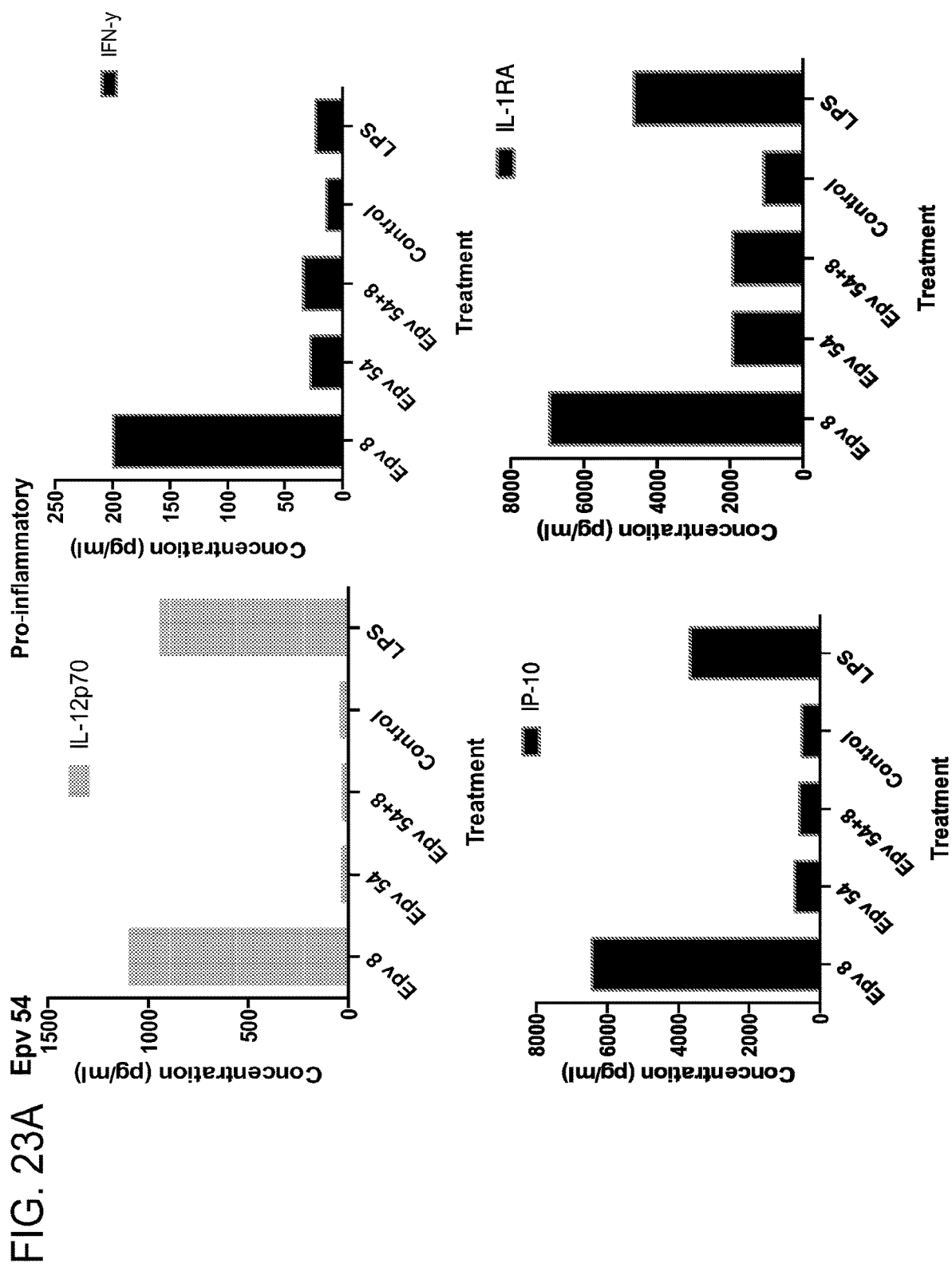

FIG. 23A-23B depicts the production of (a) pro-inflammatory (IL-12p70, IFNγ, IP-10, IL-1RA) and (b) anti-inflammatory (IL-10, IL-4, IL-13) cytokines by human PBMCs following treatment with Epv54 (*Blautia luti* ELU0087-T13-S-NI_000247).

Figure 24A:
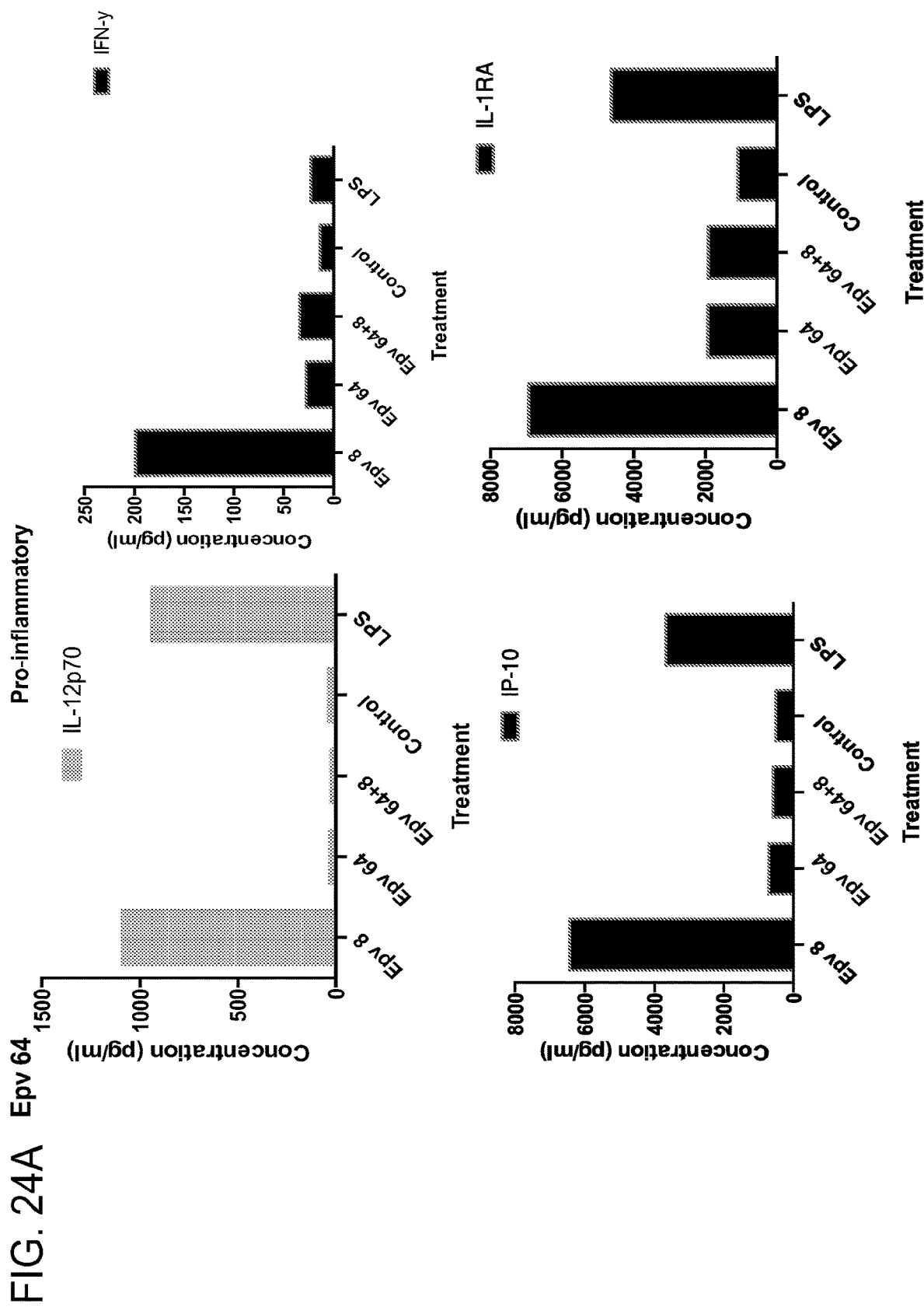
Figure 24B:
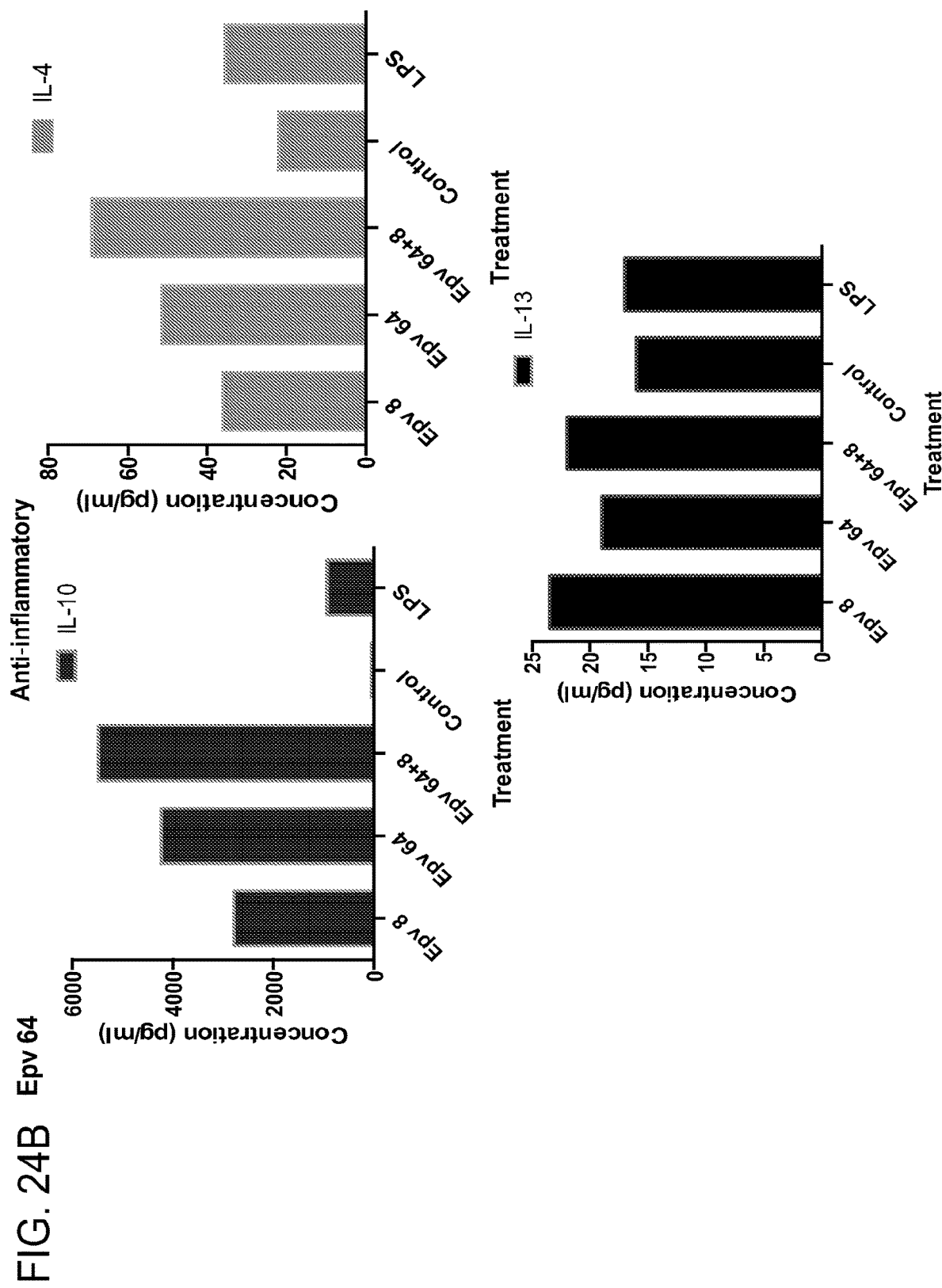

FIG. 24A-24B depicts the production of (a) pro-inflammatory (IL-12p70, IFNγ, IP-10, IL-1RA) and (b) anti-inflammatory (IL-10, IL-4, IL-13) cytokines by human PBMCs following treatment with Epv64 (*Blautia wexlerae* WAL 14507).

Figure 25A:
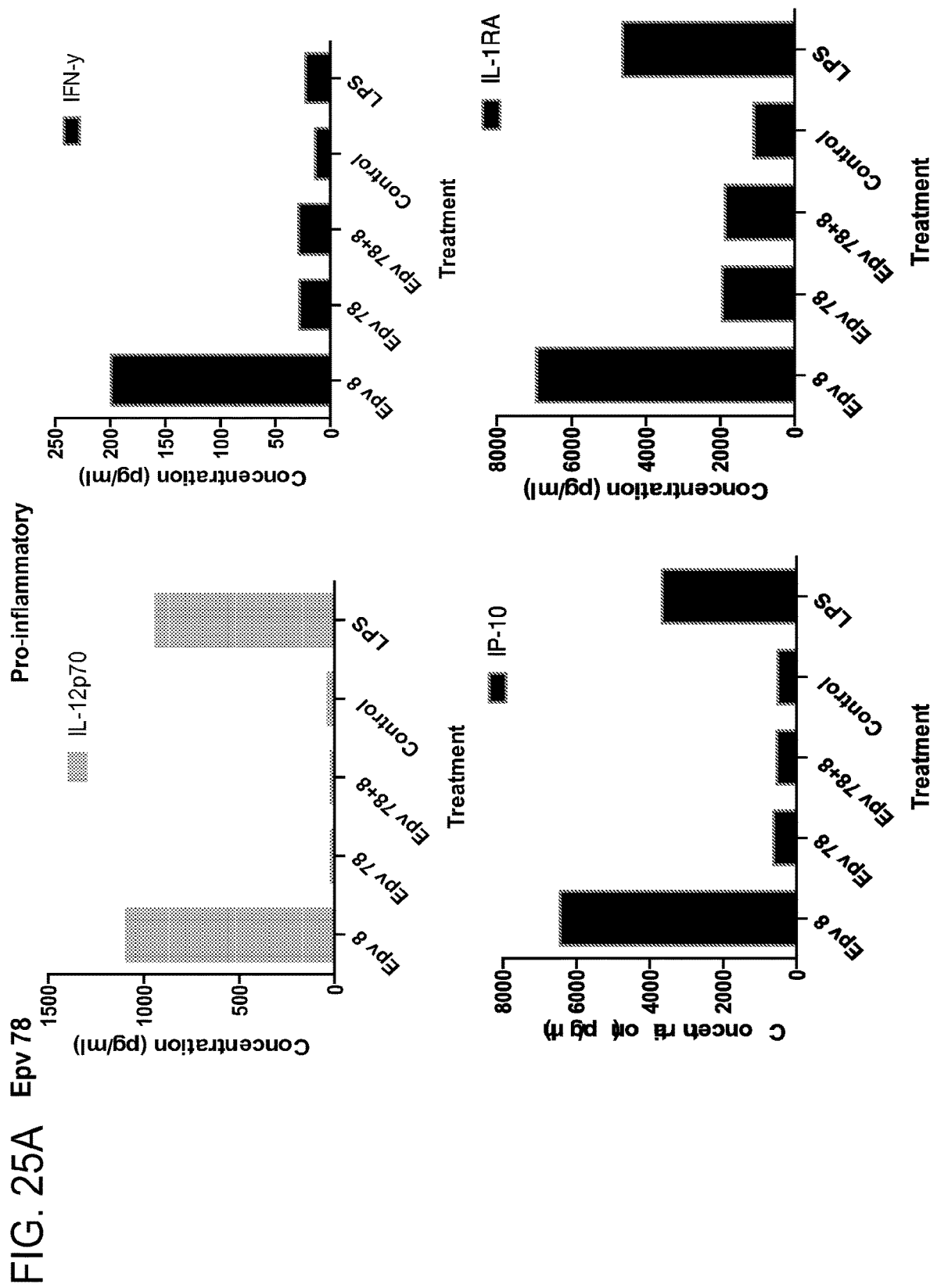
Figure 25B:
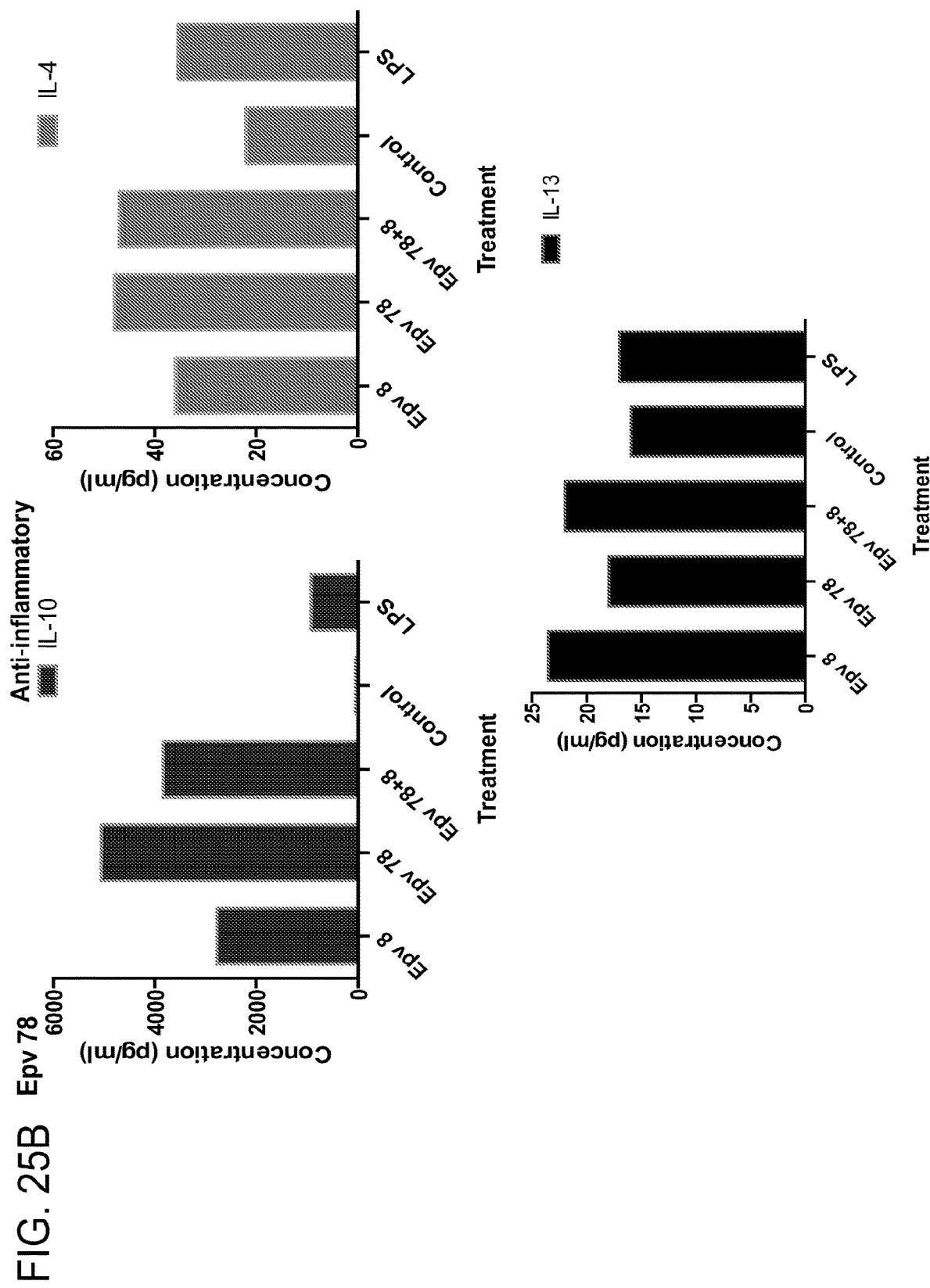

FIG. 25A-25B depicts the production of (a) pro-inflammatory (IL-12p70, IFNγ, IP-10, IL-1RA) and (b) anti-inflammatory (IL-10, IL-4, IL-13) cytokines by human PBMCs following treatment with Epv78 (*Blautia obeum*).

Figure 26B:
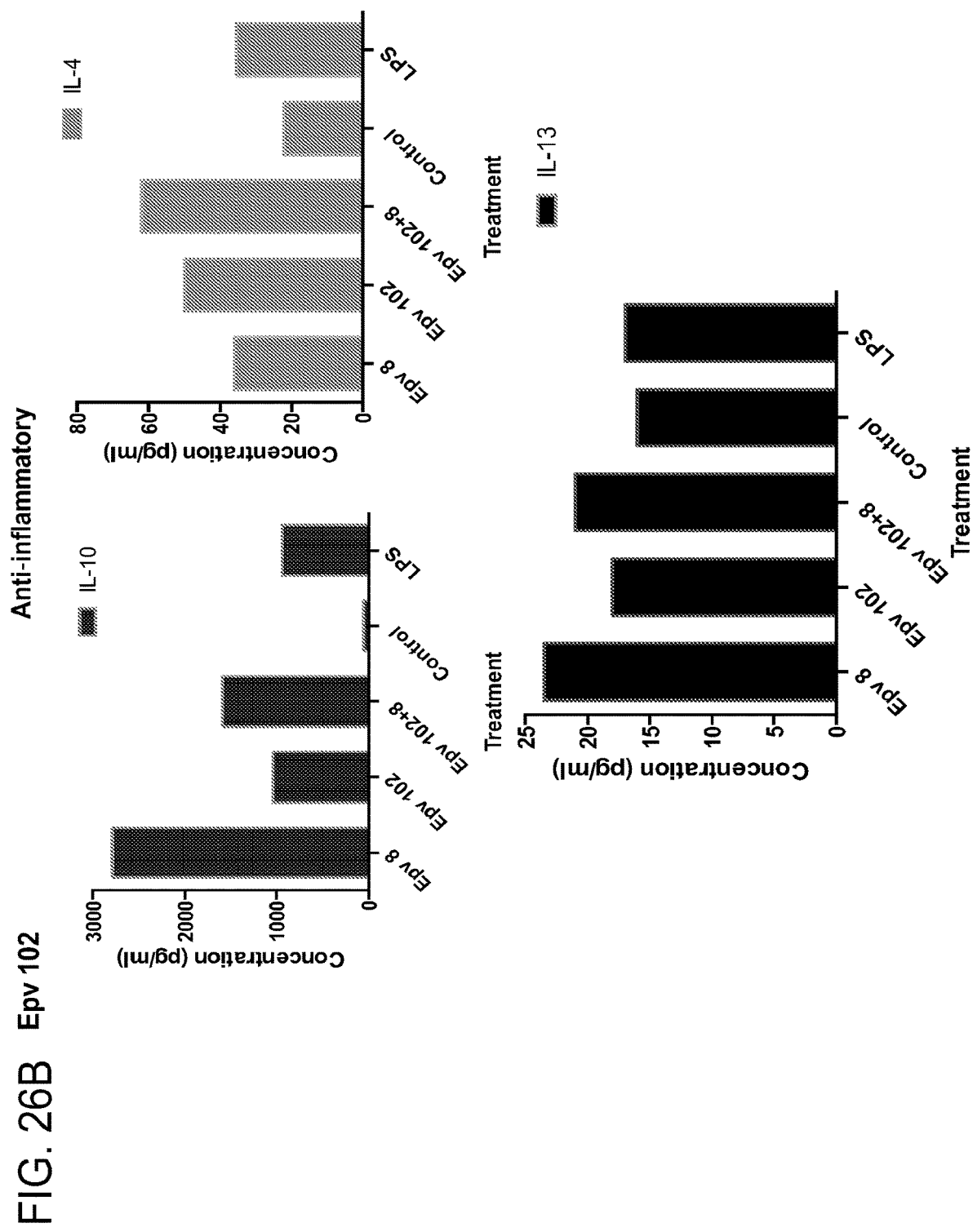

FIG. 26A-26B depicts the production of (a) pro-inflammatory (IL-12p70, IFNγ, IP-10, IL-1RA) and (b) anti-inflammatory (IL-10, IL-4, IL-13) cytokines by human PBMCs following treatment with Epv102 (*Ruminococcus gnavus*).

FIG. 27A-27B depicts the production of (a) pro-inflammatory (IL-12p70, IFNγ, IP-10, IL-1RA) and (b) anti-inflammatory (IL-10, IL-4, IL-13) cytokines by human PBMCs following treatment with Epv114 (*Blautia luti* (BlnIX)).

Figure 28A:
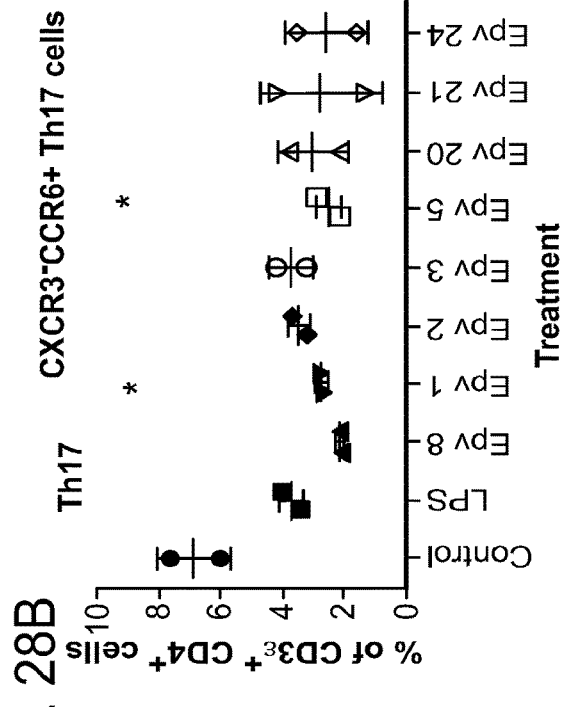
Figure 28B:
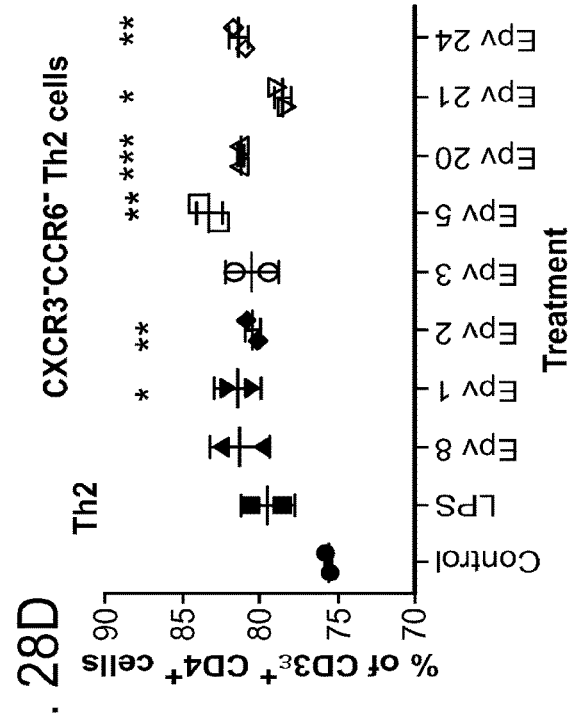
Figure 28C:
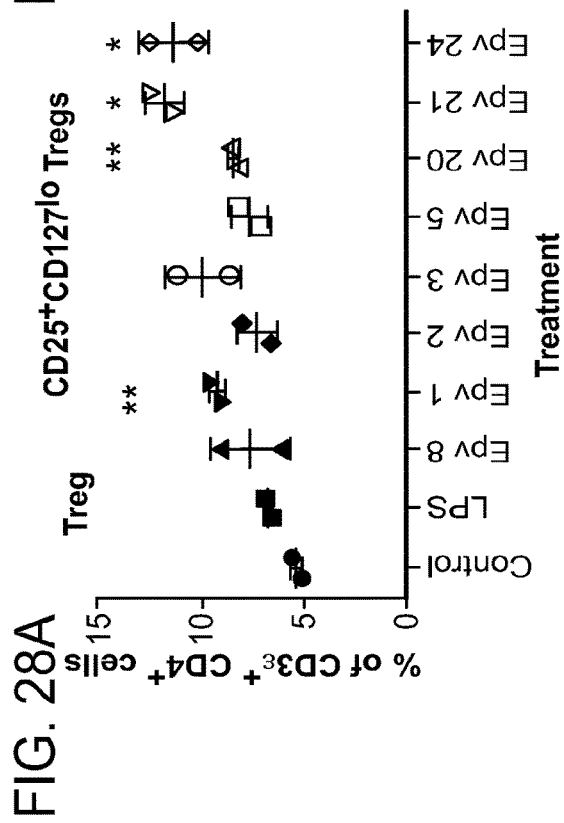
Figure 28D:
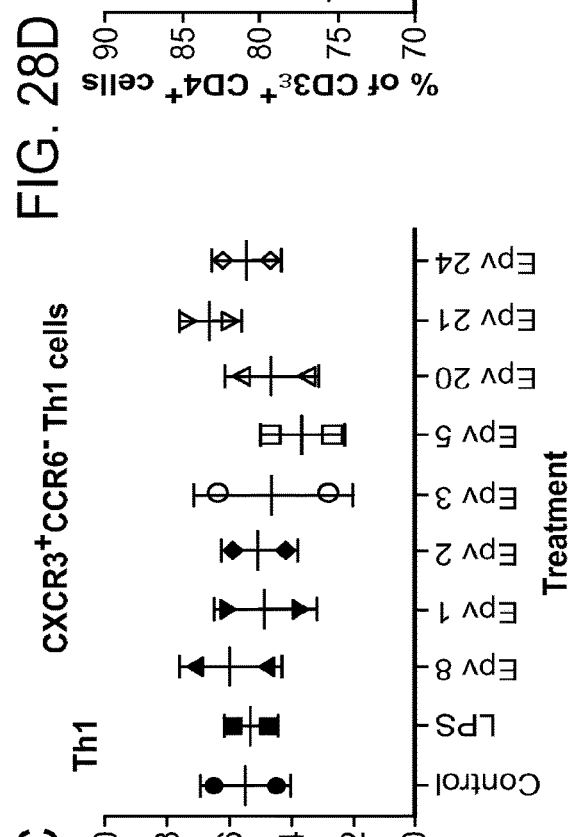

FIG. 28A-28B presents results from flow cytometry analysis of T cell populations in human PBMCs incubated in the presence of various commensal bacteria, determined using flow cytometry. A) Proportion of Treg cells ($CD25^+$ $CD127^{lo}$); B) Proportion of Th17 cells ($CXCR3^-CCR6^+$); C) Proportion of Th1 cells ($CXCR3^+CCR6^-$); D) Proportion of Th2 cells ($CXCR3^-CCR6^-$). Bacterial strains are as follows: Epv 1: *R. gnavus*; Epv 3: *B. luti*; Epv 2: *E. rectale*; Epv 5: *B. wexlerae*; Epv. 8: *E. faecalis*; Epv 20: *B. obeum*; Epv 21: *B. producta*; Epv 24: *B. hansenii*. The results are shown as percent (%) of $CD3\varepsilon^+CD4^+$ cells.

FIG. 29A-29U presents the preferred carbon sources utilized by various commensal bacteria. (a) *R. gnavus*; (b) *E. rectale*; (c) *C. leptum*; (d) *B. luti*; (e) *B. wexlerae*; (f) *B. faecis*; (g) *B. obeum*; (h) *B. producta*; (i) *B. coccoides*; (j) *B. hydrogenotrophica*; (k) *B. hansenii*; (1) *B. luti* BlnI X; (m) *B. luti* ELU; (n) *R. gnavus*; (o) *B. faecis*; (p) *R. torques*; (q) *B. wexlerae* WAL14507; (r) *B. wexlerae* SJTU; (s) SJTU1416; (t) GQ8980099; (u) *E. rectale*.

Figure 30:
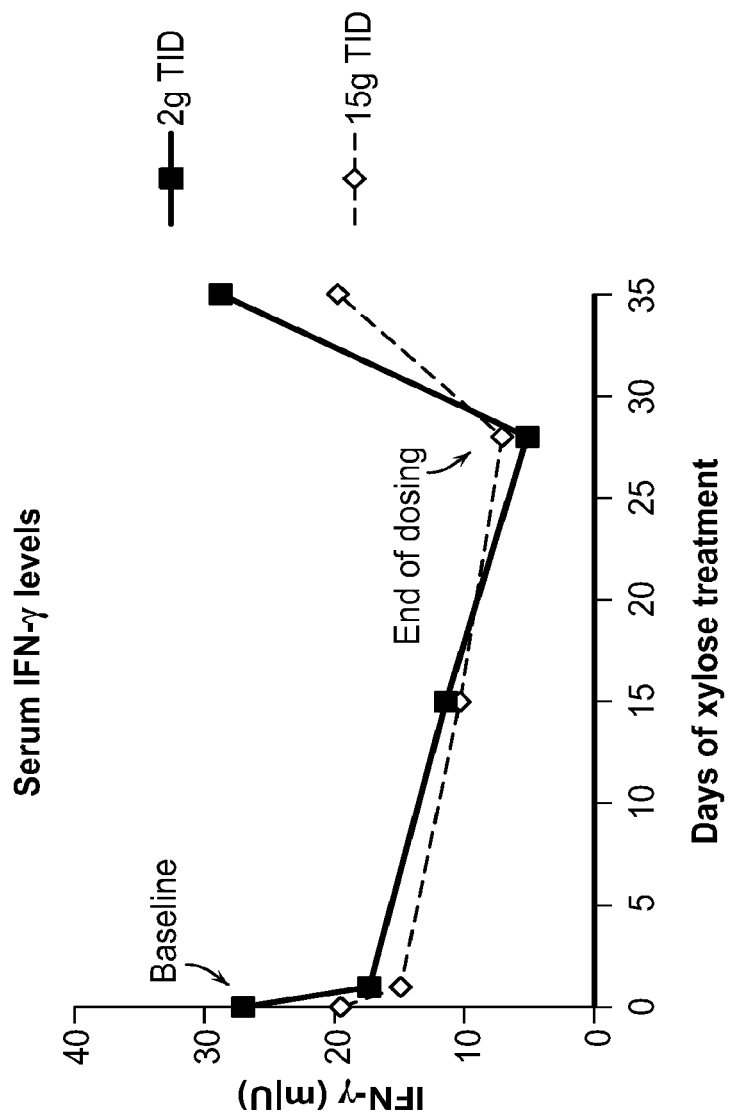

FIG. 30 graphically depicts levels of serum IFNγ before, during, and after treatment with a prebiotic formulation containing xylose.

Figure 31:
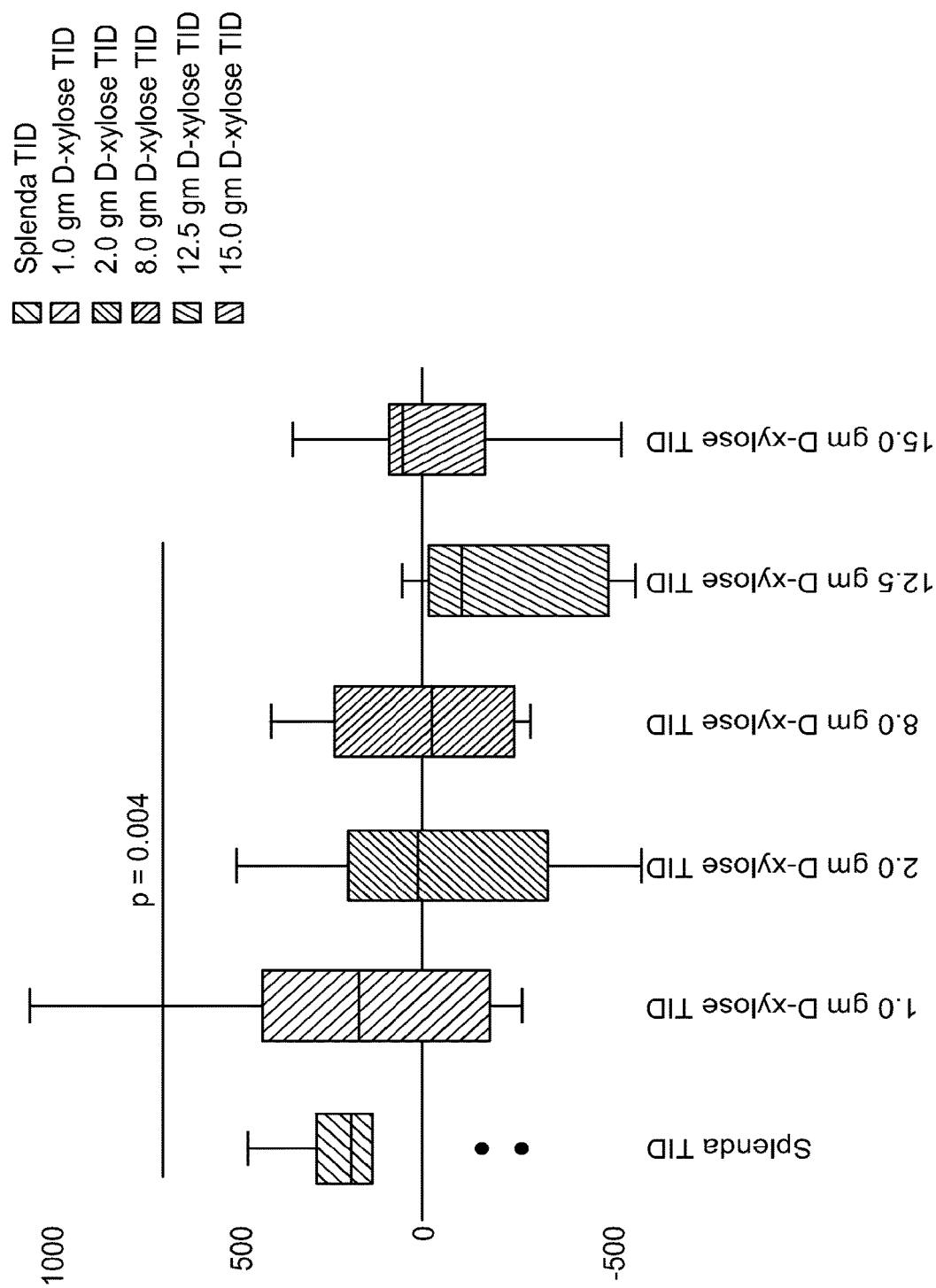

FIG. 31 is a graph that shows the change in Chao 1 diversity (indicator of community richness) over time in subjects administered xylose three times per day (TID) at 1, 2, 8, 12.5 or 15 grams.

FIG. 32 depicts the impact of oral vancomycin on the microbiome of the gut and the vagina, by principal component analysis (PCA).

DETAILED DESCRIPTION

Disclosed herein are therapeutic compositions (e.g., pharmaceutical compositions) containing bacterial entities (e.g., anti-inflammatory bacterial cells) and optionally containing a prebiotic for the prevention, control, and treatment of immune and inflammatory diseases, disorders and conditions. These compositions are advantageous in being suitable for safe administration to humans and other mammalian subjects and are efficacious in treating or preventing numerous immune and inflammatory diseases and gastrointestinal diseases, disorders and conditions associated with a dysbiosis.

The microbes that inhabit the human gastrointestinal tract, skin, lungs, vagina, and other niches are starting to be understood and appreciated for their roles in human health and disease (see, e.g., Human Microbiome Project Consortium (2012) NATURE 486(7402): 207-14). Aspects of the invention are based, in part, on the realization that, although autoimmune and inflammatory diseases are often attributed to genetic mutations, these conditions are also influenced by microbes. It is also appreciated that, because microbes not only interact with the host but with one another, the immunomodulatory behavior of microbes can depend on relationships between microbes. For example, a microbial network in a given niche may comprise diverse microbes that all accomplish one or more of the same functions, or may instead comprise diverse microbes that all individually contribute to accomplish one or more functions. For example, microbes in a given niche may influence and/or regulate the immunomodulatory behavior of other microbes in the same niche, or in a distal niche. In another example, microbes in a given niche may compete with one another for nutrients or space.

Microbes may influence the risk, progression, or treatment efficacy of an autoimmune or inflammatory disease. In certain aspects, microbes play a role in the prevention of an autoimmune or inflammatory disease or in the suppression of an innate or adaptive immune response. Microbes may also stimulate an inflammatory immune response to contribute to, increase the risk of, or worsen the symptoms of an autoimmune or inflammatory disease. Some microbes may be associated with lower disease severity or mortality.

Also disclosed herein are compositions and methods for the prevention and/or treatment of autoimmune and inflammatory diseases in human subjects.

Definitions

As used in the specification and the appended claims, the singular forms "a." "an," and "the" include plural referents unless the context clearly dictates otherwise. Thus, for example. "a compound" includes mixtures of compounds.

The term "about" or "approximately" means within an acceptable error range for the particular value as determined by one of ordinary skill in the art, which will depend in part on how the value is measured or determined, i.e., the limitations of the measurement system. For example, "about" can mean within 3 or more than 3 standard deviations, per the practice in the art. Alternatively. "about" can mean a range of up to 20%. or up to 10%, or up to 5%. or up to 1% of a given value. Alternatively, particularly with respect to biological systems or processes, the term can mean within an order of magnitude, or within 5-fold, or within 2-fold, of a value.

As used herein, the term "purified bacterial preparation" refers to a preparation that includes "isolated" bacteria or bacteria that have been separated from at least one associated substance found in a source material or any material associated with the bacteria in any process used to produce the preparation.

A "bacterial entity" includes one or more bacteria. Generally, a first bacterial entity is distinguishable from a second bacterial entity.

As used herein, the term "formation" refers to synthesis or production.

As used herein, the term "inducing" means increasing the amount or activity of a given material as dictated by context.

As used herein, the term "depletion" refers to reduction in amount of.

As used herein, a "prebiotic" refers to an ingredient that allows specific changes both in the composition and/or activity in the gastrointestinal microbiota that may (or may not) confer benefits upon the host. In some embodiments, a prebiotic can be a comestible food or beverage or ingredient thereof. Prebiotics may include complex carbohydrates, amino acids, peptides, minerals, or other essential nutritional components for the survival of the bacterial composition. Prebiotics include, but are not limited to, amino acids, biotin, fructooligosaccharide, galactooligosaccharides, hemicelluloses (e.g., arabinoxylan, xylan, xyloglucan, and glucomannan), inulin, chitin, lactulose, mannan oligosaccharides, oligofructose-enriched inulin, gums (e.g., guar gum, gum arabic and carregenaan), oligofructose, oligodextrose, tagatose, resistant maltodextrins (e.g., resistant starch), trans-galactooligosaccharide, pectins (e.g., xylogalactouronan, citrus pectin, apple pectin, and rhamnogalacturonan-I), dietary fibers (e.g., soy fiber, sugarbeet fiber, pea fiber, corn bran, and oat fiber) and xylooligosaccharides.

As used herein, "predetermined ratios" refer to ratios determined or selected in advance.

As used herein, "germinable bacterial spores" are spores capable of forming vegetative cells in response to a particular cue (e.g., an environmental condition or a small molecule).

As used herein, "detectably present" refers to presence in an amount that can be detected using assays provided herein or otherwise known in the art that exist as of the filing date.

As used herein. "augmented" refers to an increase in amount and/or localization within to a point where it becomes detectably present.

As used herein. "fecal material" refers to a solid waste product of digested food and includes feces or bowel washes.

As used herein, the phrase "host cell response" refers to a response produced by a cell of a host organism.

As used herein, a "mammalian subject protein" refers to a protein produced by a mammalian subject and encoded by the mammalian subject genome. The term mammalian subject protein includes proteins that have been post-translationally processed and/or modified.

As used herein, the term "food-derived" refers to a protein or carbohydrate found in a consumed food.

As used herein, the term "biological material" refers to a material produced by a biological organism.

As used herein, the term "detection moiety" refers to an assay component that functions to detect an analyte.

As used herein, the term "incomplete network" refers to a partial network that lacks at least one of the entire set of components needed to carry out one or more network functions.

As used herein, the term "supplemental" refers to something that is additional and non-identical.

As used herein, a composition is "substantially free" of microbes when microbes are absent or undetectable as determined by the use of standard genomic and microbiological techniques. A composition is "substantially free" of a prebiotic or immunostimulatory carbohydrate when non-microbial carbohydrates are absent or undetectable as determined by the use of standard biochemical techniques (e.g., dye-based assays).

Microbial agents (individual or populations of microbes, microbial networks or parts of networks, or microbial metabolites) are considered to be "exogenous" to a subject (e.g., a human or non-human animal), a cell, tissue, organ or other environment of a human or non-human animal, if said subject, or said cell, tissue, organ or other environment of the subject, does not contain detectable levels of the microbial agent.

A microbial agent or population thereof is "heterologous" or "heterologously contained" on or in a host environment when, e.g., the microbial agent or population is administered or disposed on, or in the host, or host environment in a number, concentration, form or other modality that is not found in the host prior to administration of the microbial agent or population, or when the microbial agent or population contains an activity or structural component different from a host that does not naturally have the microbial agent within the target environment to which the microbe is administered or thereafter disposed.

As used herein, the term "antioxidant" is understood to include any one or more of various substances such as beta-carotene (a vitamin A precursor), vitamin C, vitamin E, and selenium) that inhibit oxidation or reactions promoted by Reactive Oxygen Species ("ROS") and other radical and non-radical species. Additionally, antioxidants are molecules capable of slowing or preventing the oxidation of other molecules. Non-limiting examples of antioxidants include astaxanthin, carotenoids, coenzyme Q10 ("CoQ10"), flavonoids, glutathione, Goji (wolfberry), hesperidin, lactowolfberry, lignan, lutein, lycopene, polyphenols, selenium, vitamin A, vitamin C, vitamin E, zeaxanthin, or combinations thereof.

"Backbone network ecology" or simply "backbone network" or "backbone" are compositions of microbes that form a foundational composition that can be built upon or subtracted from to optimize a network ecology or functional network ecology to have specific biological characteristics or to comprise desired functional properties, respectively. Microbiome therapeutics can be comprised of these "backbone networks ecologies" in their entirety, or the "backbone networks" can be modified by the addition or subtraction of "R-groups" to give the network ecology desired characteristics and properties. "R-groups" can be defined in multiple terms including, but not limited to: individual OTUs, individual or multiple OTUs derived from a specific phylogenetic clade or a desired phenotype such as the ability to form spores, or functional bacterial compositions that comprise. "Backbone networks" can comprise a computationally derived network ecology in its entirety, or can comprise subsets of the computationally-derived network ecology that represent key nodes in the network that contribute to efficacy such as but not limited to a composition of Keystone OTUs. The number of organisms in a human gastrointestinal tract, is indicative of the functional redundancy of a healthy gut microbiome ecology (see, e.g., The Human Microbiome Consortia (2012). This redundancy makes it highly likely that non-obvious subsets of OTUs or functional pathways (i.e., "backbone networks") are critical to maintaining states of health and/or catalyzing a shift from a dysbiotic state to one of health. One way of exploiting this redundancy is through the substitution of OTUs that share a given clade (see below) or by adding members of a clade not found in the backbone network.

"Bacterial composition" refers to a consortium of microbes comprising two or more OTUs. Backbone network ecologies, functional network ecologies, network classes, and core ecologies are all types of bacterial compositions. As used herein, bacterial composition includes a therapeutic microbial composition, a prophylactic microbial composition, a spore population, a purified spore population, or an ethanol treated spore population.

"Bacterial translocation" refers to the passage of one or more bacteria across the epithelial layer of any organ of a human or non-human animal.

"Network ecology" refers to a consortium of clades or OTUs that co-occur in some number of subjects. As used herein, a "network" is defined mathematically by a graph delineating how specific nodes (i.e., clades or OTUs) and edges (connections between specific clades or OTUs) relate to one another to define the structural ecology of a consortium of clades or OTUs. Any given network ecology will possess inherent phylogenetic diversity and functional properties.

A network ecology can also be defined in terms of its functional capabilities where for example the nodes would be comprised of elements such as, but not limited to, enzymes, clusters of orthologous groups (COGS; http://www.ncbi.nlm.nih.gov books/NBK21090/), or KEGG Orthology Pathways (www.genome.jp/kegg/); these networks are referred to as a "functional network ecology". Functional network ecologies can be reduced to practice by defining the group of OTUs that together comprise the functions defined by the functional network ecology.

The terms "network class". "core network" and "network class ecology" refer to a group of network ecologies that in general are computationally determined to comprise ecologies with similar phylogenetic and/or functional characteristics. A network class therefore contains important biological features, defined either phylogenetically or functionally, of a group (i.e., a cluster) of related network ecologies. One representation of a core network ecology is a designed consortium of microbes, typically non-pathogenic bacteria, that represents core features of a set of phylogenetically or functionally related network ecologies seen in many different subjects. In many occurrences, a core network, while designed as described herein, exists as a network ecology observed in one or more subjects. Core network ecologies are useful for reversing or reducing a dysbiosis in subjects where the underlying, related network ecology has been disrupted.

"Bacterial translocation" refers to the passage of one or more bacteria across the epithelial layer of any organ of a human or non-human animal.

"Clade" refers to the OTUs or members of a phylogenetic tree that are downstream of a statistically valid node in a phylogenetic tree. The clade comprises a set of terminal leaves in the phylogenetic tree (i.e., tips of the tree) that are a distinct monophyletic evolutionary unit and that share some extent of sequence similarity. Clades are hierarchical, in one embodiment, the node in a phylogenetic tree that is selected to define a clade is dependent on the level of resolution suitable for the underlying data used to compute the tree topology.

The "colonization" of a host organism includes the non-transitory residence of a bacterium or other microscopic organism. As used herein, "reducing colonization" of a host subject's gastrointestinal tract or vagina (or any other microbiota niche) by a pathogenic or non-pathogenic bacterium includes a reduction in the residence time of the bacterium in the gastrointestinal tract or vagina, as well as a reduction in the number (or concentration) of the bacterium in the gastrointestinal tract or vagina, or adhered to the luminal surface of the gastrointestinal tract. The reduction in colonization can be permanent or occur during a transient period of time. Measuring reductions of adherent pathogens can be demonstrated directly, e.g., by determining pathogenic burden in a biopsy sample, or reductions may be measured indirectly, e.g., by measuring the pathogenic burden in the stool of a mammalian host.

A "combination" of two or more bacteria includes the physical co-existence of the two bacteria, either in the same material or product or in physically connected products, as well as the temporal co-administration or co-localization of the two bacteria.

"Cytotoxic" activity of bacterium includes the ability of a bacterium kill a cell (e.g., a host cell or a bacterial cell). A "cytostatic" activity of a bacterium includes the ability to inhibit (e.g., partially or fully) the growth, metabolism, and/or proliferation of a cell (e.g., a bacterial cell or a host cell).

"Dysbiosis" refers to a state of the microbiota or microbiome of the gut or other body area, including mucosal or skin surfaces (or any other microbiota niche) in which the normal diversity and/or function of the ecological network is disrupted. Any disruption from the preferred (e.g., ideal) state of the microbiota can be considered a dysbiosis, even if such dysbiosis does not result in a detectable decrease in health. This state of dysbiosis may be unhealthy (e.g., result in a diseased state), it may be unhealthy under only certain conditions, or it may prevent a subject from becoming healthier. Dysbiosis may be due to a decrease in diversity of the microbiota population composition, the overgrowth of one or more population of pathogens (e.g., a population of pathogenic bacteria) or pathobionts, the presence of and/or overgrowth of symbiotic organisms able to cause disease only when certain genetic and/or environmental conditions are present in a patient, or a shift to an ecological network that no longer provides a beneficial function to the host and therefore no longer promotes health. A state of dysbiosis may lead to a disease or disorder (e.g. a gastrointestinal disease, disorder or condition), or the state of dysbiosis may lead to a disease or disorder (e.g., a gastrointestinal disease, disorder or condition) only under certain conditions, or the state of dysbiosis may prevent a subject from responding to treatment or recovering from a disease or disorder (e.g., a gastrointestinal disease, disorder or condition).

The term "distal" generally is used in relation to the gastrointestinal tract, specifically the intestinal lumen, of a human or other mammal. Thus, a "distal dysbiosis" includes a dysbiosis outside of the lumen of the gastrointestinal tract, and a "distal microbiota" includes a microbiota outside of the lumen of the gastrointestinal tract. In specified instances, the term "distal" may be used in relation to the site of administration, engraftment, or colonization of a composition, e.g., a probiotic composition, of the invention. For example, if a probiotic composition is administered vaginally, a "distal" effect of the composition would occur outside the vagina.

"Gastrointestinal dysbiosis" refers to a state of the microbiota or microbiome of the gut in which the normal diversity and/or function of the ecological network or niche is disrupted. The term "gut" as used herein is meant to refer to the entire gastrointestinal or digestive tract (also referred to as the alimentary canal) and it refers to the system of organs within multi-cellular animals which takes in food, digests it to extract energy and nutrients, and expels the remaining waste. As used herein the term "gastrointestinal tract" refers to the entire digestive canal, from the oral cavity to the rectum. The term "gastrointestinal tract" includes, but is not limited to, mouth and proceeds to the esophagus, stomach, small intestine, large intestine, rectum and, finally, the anus.

"Germinant" is a material or composition, or a physical-chemical process, capable of inducing the germination of vegetative bacterial cells from dormant spores, or the proliferation of vegetative bacterial cells, either directly or indirectly in a host organism and/or in vitro.

"Inhibition" of a pathogen or non-pathogen encompasses the inhibition of any desired function or activity of the pathogen or non-pathogen by the probiotic, e.g., bacterial, compositions of the present invention. Demonstrations of inhibition, such as a decrease in the growth of a pathogenic bacterial cell population or a reduction in the level of colonization of a pathogenic bacterial species are provided herein and otherwise recognized by one of ordinary skill in the art. Inhibition of a pathogenic or non-pathogenic bacterial population's "growth" may include inhibiting an increase in the size of a pathogenic or non-pathogenic bacterial cell population and/or inhibiting the proliferation (or multiplication) of a pathogenic or non-pathogenic bacterial cell population. Inhibition of colonization of a pathogenic or non-pathogenic bacterial species may be demonstrated by measuring and comparing the amount or burden of the bacterial species before and after a treatment. An "inhibition" or the act of "inhibiting" includes the total cessation and partial reduction of one or more activities of a pathogen, such as growth, proliferation, colonization, and function. As used herein, inhibition includes cytostatic and/or cytotoxic activities. Inhibition of function includes, for example, the inhibition of expression of a pathogenic gene product (e.g., the genes encoding a toxin and/or toxin biosynthetic pathway, or the genes encoding a structure required for intracellular invasion (e.g., an invasive pilus)) induced by the bacterial composition.

"Isolated" encompasses a bacterium or other entity or substance (e.g., a bacterial population or a prebiotic) that has been (1) separated from at least some of the components with which it was associated when initially produced (whether in nature or in an experimental setting), and/or (2) produced, prepared, purified, and/or manufactured by the hand of man. Isolated bacteria includes, for example, those bacteria that are cultured, even if such cultures are not monocultures. Isolated bacteria may be separated from at least about 10%, about 20%, about 30%, about 40%, about 50%, about 60%, about 70%, about 80%, about 90%. or more of the other components with which they were initially associated. In some embodiments, isolated bacteria are more than about 80%, about 85%, about 90%, about 91%, about 92%, about 93%, about 94%, about 95%, about 96%, about 97%, about 98%, about 99%. or more than about 99% pure. As used herein, a substance is "pure" if it is substantially free of other components. The terms "purify," "purifying" and "purified" refer to a bacterium or other material that has been separated from at least some of the components with which it was associated either when initially produced or generated (e.g., whether in nature or in an experimental setting), or during any time after its initial production. A bacterium or a bacterial population may be considered purified if it is isolated at or after production, such as from a material or environment containing the bacterium or bacterial population, or by passage through culture. A purified bacterium or bacterial population may contain other materials up to about 1%, 2%. 3%, 4%. 5%, 6%, 7%, 8%. 9%, 10%, about 20%, about 30%, about 40%, about 50%, about 60%, about 70%, about 80%, about 90%, or above about 90%, and still be considered "isolated." In some embodiments, purified bacteria and bacterial populations are more than about 80%, about 85%, about 90%, about 91%, about 92%, about 93%, about 94%, about 95%, about 96%, about 97%, about 98%, about 99%. or more than about 99% pure. In the instance of bacterial compositions provided herein, the one or more bacterial types present in the composition can be independently purified from one or more other bacteria produced and/or present in the material or environment containing the bacterial type. In some embodiments, bacterial compositions and the bacterial components thereof are purified from residual habitat products. In some embodiments, pharmaceutical compositions (e.g., bacterial compositions) contain a defined mixture of isolated bacteria. For example, in some embodiments, the pharmaceutical composition (e.g., probiotic composition) contains no more than 100 bacterial species. For example, in some embodiments, the pharmaceutical composition contains no more than 75 bacterial species. In other embodiments, the pharmaceutical composition contains no more than 50 bacterial species, e.g., no more than 40 bacterial species, no more than 30 bacterial species, no more than 25 bacterial species, no more than 20 bacterial species, no more than 15 bacterial species, no more than 10 bacterial species, etc. In other embodiments, the pharmaceutical composition contains no more than 10 bacterial species, e.g., 10 bacterial species, 9 bacterial species, 8 bacterial species, 7 bacterial species, 6 bacterial species, 5 bacterial species, 4 bacterial species, 3 bacterial species, 2 bacterial species, 1 bacterial species. In some embodiments, the pharmaceutical composition contains defined quantities of each bacterial species. In an exemplary embodiment, the pharmaceutical composition contains isolated bacterial populations that are not isolated from fecal matter.

"Keystone OTU" or "keystone function" refers to one or more OTUs or functional pathways (e.g., KEGG or COG pathways) that are common to many network ecologies or functional network ecologies and are members of networks that occur in many subjects (i.e., "are pervasive"). Due to the ubiquitous nature of keystone OTUs and their associated functional pathways, they are central to the function of network ecologies in healthy subjects and are often missing, or at reduced levels, in subjects with disease. Keystone OTUs and their associated functions may exist in low, moderate, or high abundance in subjects. A "non-keystone OTU" or "non-keystone function" refers to an OTU or function that is observed in a network ecology or a functional network ecology, that is not observed in a keystone OTU or function.

"Microbiota" refers to the community of microorganisms that occur (sustainably or transiently) in and/or on a subject, (e.g, a mammal such as a human), including, but not limited to, eukaryotes (e.g., protozoa), archaea, bacteria, and viruses (including bacterial viruses, i.e., a phage).

"Microbiome" refers to the genetic content of the communities of microbes that live in and on the human body, both sustainably and transiently, including eukaryotes, archaea, bacteria, and viruses (including, e.g., bacterial viruses (i.e., phage)), wherein "genetic content" includes genomic DNA, RNA such as ribosomal RNA, the epigenome, plasmids, and all other types of genetic information.

"Microbial carriage" or simply "carriage" refers to the population of microbes inhabiting a niche within or on a subject (e.g., a human subject). Carriage is often defined in terms of relative abundance. For example, OTU1 comprises 60% of the total microbial carriage, meaning that OTU1 has a relative abundance of 60% compared to the other OTUs in the sample from which the measurement is made. Carriage is most often based on genomic sequencing data where the relative abundance or carriage of a single OTU or group of OTUs is defined by the number of sequencing reads that are assigned to that OTU/s relative to the total number of sequencing reads for the sample.

"Microbial augmentation" refers to the establishment or significant increase of a population of microbes that are (i) absent or undetectable (as determined by the use of standard genomic, biochemical and/or microbiological techniques) from the administered therapeutic microbial composition, (ii) absent, undetectable, or present at low frequencies in the host niche (as an example: gastrointestinal tract, skin, anterior-nares, or vagina) before the delivery of the microbial composition, and (iii) are found, i.e., detectable, after the administration of the microbial composition or significantly increase, for instance 2-fold, 5-fold, $1 \times 10^2$, $1 \times 10^3$, $1 \times 10^4$, $1 \times 10^5$, $1 \times 10^6$, $1 \times 10^7$, or greater than $1 \times 10^8$, in cases where they are present at low frequencies. The microbes that comprise an augmented ecology can be derived from exogenous sources, such as food and the environment, or grow out from micro-niches within the host where they reside at low frequency.

The administration of the therapeutic composition (e.g., pharmaceutical composition) can induce an environmental shift in the target niche that promotes favorable conditions for the growth of commensal microbes. In the absence of treatment with a therapeutic microbial composition (e.g., a pharmaceutical composition comprising a bacterial cell population), with or without one or more prebiotics, the host can be constantly exposed to these microbes; however, sustained growth and the positive health effects associated with the stable population of increased levels of the microbes comprising the augmented ecology are not observed.

"Microbial engraftment" or simply "engraftment" refers to the establishment of OTUs comprising a therapeutic microbial composition in a target niche. In one embodiment, the OTUs are absent in the treated host prior to treatment. The microbes that comprise the engrafted ecology are found in the therapeutic microbial composition and establish as constituents of the host microbial ecology upon treatment. Engrafted OTUs can establish for a transient period of time, or demonstrate long-term stability in the microbial ecology that populates the host post-treatment with a therapeutic microbial composition. The engrafted ecology can induce an environmental shift in the target niche that promotes favorable conditions for the growth of commensal microbes capable of catalyzing a shift from a dysbiotic ecology to one representative of a healthy state.

"Ecological niche" or simply "niche" refers to the ecological space that an organism or group of organisms (e.g., a bacterial population) occupies. Niche describes how an organism or population or organisms responds to the distribution of resources, physical parameters (e.g., host tissue space) and competitors (e.g., by growing when resources are abundant, and/or when predators, parasites and pathogens are scarce) and how it in turn alters those same factors (e.g., by limiting access to resources by other organisms, acting as a food source for predators and/or as a consumer of prey).

"Pathobionts" or "opportunistic pathogens" refers to symbiotic organisms able to cause disease only when certain genetic and/or environmental conditions are present in a subject.

"Phylogenetic tree" refers to a graphical representation of the evolutionary relationships of one genetic sequence to another that is generated using a defined set of phylogenetic reconstruction algorithms (e.g., parsimony, maximum likelihood, or Bayesian). Nodes in the tree represent distinct ancestral sequences and the confidence of any node is provided by a bootstrap or Bayesian posterior probability, which measures branch uncertainty.

As used herein, the term "minerals" is understood to include boron, calcium, chromium, copper, iodine, iron, magnesium, manganese, molybdenum, nickel, phosphorus, potassium, selenium, silicon, tin, vanadium, zinc, or combinations thereof.

To be free of "non-comestible products" means that a bacterial composition or other material provided herein does not have a substantial amount of a non-comestible product, e.g., a product or material that is inedible, harmful or otherwise undesired in a product suitable for administration, e.g., oral administration, to a human subject. Non-comestible products are often found in preparations of bacteria from the prior art.

"Operational taxonomic units," "OTU" (or plural "OTUs") refer to a terminal leaf in a phylogenetic tree and is defined by a nucleic acid sequence, e.g., the entire genome, or a specific genetic sequence, and all sequences that share sequence identity to this nucleic acid sequence at the level of species. In some embodiments the specific genetic sequence may be the 16S sequence or a portion of the 16S sequence. In other embodiments, the entire genomes of two entities are sequenced and compared. In another embodiment, select regions such as multilocus sequence tags (MLST), specific genes, or sets of genes may be genetically compared. In 16S embodiments, OTUs that share ≥97% average nucleotide identity across the entire 16S or some variable region of the 16S are considered the same OTU (see, e.g., Claesson et al. (2010) NUCLEIC ACIDS RES. 38: e200; Konstantinidis et al. (2006) PHILOS. TRANS. R. SOC. LOND. B BIOL. SCI. 361: 1929-1940). In embodiments involving the complete genome, MLSTs, specific genes, or sets of genes OTUs that share ≥95% average nucleotide identity are considered the same OTU (see, e.g., Achtman and Wagner (2008) NAT. REV. MICROBIOL. 6: 431-440; Konstantinidis et al. (2006)). OTUs are frequently defined by comparing sequences between organisms. Generally, sequences with less than 95% sequence identity are not considered to form part of the same OTU. OTUs may also be characterized by any combination of nucleotide markers or genes, in particular highly conserved genes (e.g., "house-keeping" genes), or a combination thereof. Such characterization employs, e.g., WGS data or a whole genome sequence.

The term "phylogenetic diversity" refers to the biodiversity present in a given network ecology, core network ecology or network class ecology based on the OTUs that comprise the network. Phylogenetic diversity is a relative term, meaning that a network ecology, core network or network class that is comparatively more phylogenctically diverse than another network contains a greater number of unique species, genera, and taxonomic families. Uniqueness of a species, genera, or taxonomic family is generally defined using a phylogenetic tree that represents the genetic diversity all species, genera, or taxonomic families relative to one another. In another embodiment phylogenetic diversity may be measured using the total branch length or average branch length of a phylogenetic tree.

Phylogenetic diversity may be optimized in a bacterial composition by including a wide range of biodiversity.

"Phylogenetic tree". "rDNA", "rRNA". "16S-rDNA", "16S-rRNA", "16S", "16S sequencing", "16S-NGS". "18S", "18S-rRNA". "18S-rDNA", "18S sequencing", and "18S-NGS" refer to the nucleic acids that encode for the RNA subunits of the ribosome. rDNA refers to the gene that encodes the rRNA that comprises the RNA subunits. There are two RNA subunits in the ribosome termed the small subunit (SSU) and large subunit (LSU); the RNA genetic sequences (rRNA) of these subunits are related to the gene that encodes them (rDNA) by the genetic code. rDNA genes and their complementary RNA sequences are widely used for determination of the evolutionary relationships amount organisms as they are variable, yet sufficiently conserved to allow cross organism molecular comparisons.

Typically 16S rDNA sequence (approximately 1542 nucleotides in length) of the 30S SSU is used for molecular-based taxonomic assignments of prokaryotes and the 18S rDNA sequence (approximately 1869 nucleotides in length) of 40S SSU is used for eukaryotes. The bacterial 16S rDNA is used in reconstructing the evolutionary relationships and sequence similarity of one bacterial isolate to another using phylogenetic approaches. 16S sequences are used for phylogenetic reconstruction as they are in general highly conserved, but contain specific hypervariable regions that harbor sufficient nucleotide diversity to differentiate genera and species of most bacteria.

The "V1-V9 regions" of the 16S rRNA refers to the first through ninth hypervariable regions of the 16S rRNA gene that are used for genetic typing of bacterial samples. These regions in bacteria are defined by nucleotides 69-99, 137-242, 433-497, 576-682, 822-879, 986-1043, 1117-1173, 1243-1294 and 1435-1465 respectively using numbering based on the E. coli system of nomenclature (see, e.g., Brosius et al. (1978) PROC. NAT'L. ACAD. SCI. USA 75(10): 4801-4805). In some embodiments, at least one of the V1, V2, V3, V4, V5, V6, V7, V8, and V9 regions are used to characterize an OTU. In one embodiment, the V1, V2, and V3 regions are used to characterize an OTU. In another embodiment, the V3, V4, and V5 regions are used to characterize an OTU. In another embodiment, the V4 region is used to characterize an OTU. A person of ordinary skill in the art can identify the specific hypervariable regions of a candidate 16S rRNA by comparing the candidate sequence in question to a reference sequence and identifying the hypervariable regions based on similarity to the reference hypervariable regions, or alternatively, one can employ Whole Genome Shotgun (WGS) sequence characterization of microbes or a microbial community.

"Residual habitat products" refers to material derived from the habitat for microbiota within or on a human or animal. For example, microbiota live in feces in the gastrointestinal tract, on the skin itself, in saliva, mucus of the respiratory tract, or secretions of the genitourinary tract (i.e., biological matter associated with the microbial community). Substantially free of residual habitat products means that the bacterial composition no longer contains the biological matter associated with the microbial environment on or in the human or animal subject and is 100% free, 99% free, 98% free, 97% free, 96% free, 95% free, 94% free, 93% free, 92% free, 91% free, 90% free, 85% free, 80% free, 75% free, 70% free, 65% free, or 60% free of any contaminating biological matter associated with the microbial community. Residual habitat products can include abiotic materials (including undigested food) or it can include unwanted microorganisms. Substantially free of residual habitat products may also mean that the bacterial composition contains no detectable cells from a human or animal and that only microbial cells are detectable. In one embodiment, substantially free of residual habitat products may also mean that the bacterial composition contains no detectable viral (e.g., bacterial viruses (i.e., phage)), fungal, or mycoplasmal contaminants. In another embodiment, it means that fewer than $1\times10^{-2}$%, $1\times10^{-3}$%, $1\times10^{-4}$%, $1\times10^{-5}$%, $1\times10^{-6}$%, $1\times10^{-7}$%, $1\times10^{-8}$% of the viable cells in the bacterial composition are human or animal, as compared to microbial cells. There are multiple ways to accomplish this degree of purity, none of which are limiting. For example, contamination may be reduced by isolating desired constituents through multiple steps of streaking to single colonies on solid media until replicate (such as, but not limited to, two) streaks from serial single colonies have shown only a single colony morphology. Alternatively, reduction of contamination can be accomplished by multiple rounds of serial dilutions to single desired cells (e.g., a dilution of $10^{-8}$ or $10^{-9}$), such as through multiple 10-fold serial dilutions. This can further be confirmed by showing that multiple isolated colonies have similar cell shapes and Gram staining behavior. Other methods for confirming adequate purity include genetic analysis (e.g., PCR and DNA sequencing), serology and antigen analysis, enzymatic and metabolic analysis, and methods using instrumentation such as flow cytometry with reagents that distinguish desired constituents from contaminants.

The term "subject" refers to any organism or animal subject that is an object of a method or material, including mammals, e.g., humans, laboratory animals (e.g., primates, rats, mice, rabbits), livestock (e.g., cows, sheep, goats, pigs, turkeys, and chickens), household pets (e.g., dogs, cats, and rodents), horses, kangaroos, and transgenic non-human animals. The subject may be suffering from a dysbiosis, including, but not limited to, an infection due to a gastrointestinal pathogen or may be at risk of developing or transmitting to others an infection due to a gastrointestinal pathogen. Synonyms used herein include "patient" and "animal." In some embodiments, the subject or host may be suffering from a dysbiosis, that contributes to or causes a condition classified as graft-versus-host disease. Crohn's disease. Celiac disease, inflammatory bowel disease, ulcerative colitis, multiple sclerosis, systemic lupus erythematosus. Sjogren's syndrome, or type 1 diabetes. In some embodiments, the host may be suffering from metabolic endotoxemia, altered metabolism of primary bile acids, immune system activation, or an imbalance or reduced production of short chain fatty acids including, for example, butyrate, propionate, acetate, and a branched chain fatty acid.

The term "phenotype" refers to a set of observable characteristics of an individual entity. As example an individual subject may have a phenotype of "health" or "disease". Phenotypes describe the state of an entity and all entities within a phenotype share the same set of characteristics that describe the phenotype. The phenotype of an individual results in part, or in whole, from the interaction of the entities genome and/or microbiome with the environment.

"Spore" or "endospore" refers to an entity, particularly a bacterial entity, which is in a dormant, non-vegetative and non-reproductive stage. Spores are generally resistant to environmental stress such as radiation, desiccation, enzymatic treatment, temperature variation, nutrient deprivation, and chemical disinfectants.

A "spore population" refers to a plurality of spores present in a composition. Synonymous terms used herein include spore composition, spore preparation, ethanol-treated spore fraction and spore ecology. A spore population may be purified from a fecal donation, e.g., via ethanol or heat treatment, or a density gradient separation, or any combination of methods described herein to increase the purity, potency and/or concentration of spores in a sample. Alternatively, a spore population may be derived through culture methods starting from isolated spore former species or spore former OTUs or from a mixture of such species, either in vegetative or spore form.

A "sporulation induction agent" is a material or physical-chemical process that is capable of inducing sporulation in a bacterium, either directly or indirectly, in a host organism and/or in vitro.

To "increase production of bacterial entities" includes an activity or a sporulation induction agent. "Production" includes conversion of vegetative bacterial cells into spores and augmentation of the rate of such conversion, as well as decreasing the germination of bacteria in spore form, decreasing the rate of spore decay in vivo, or ex vivo, or to increasing the total output of spores (e.g., via an increase in volumetric output of fecal material).

"Synergy" or "synergistic interactions" refers to the interaction or cooperation of two or more microbes to produce a combined effect greater than the sum of their separate effects. In one embodiment, "synergy" between two or more microbes can result in the inhibition of a pathogens ability to grow.

As used herein the term "vitamin" is understood to include any of various fat-soluble or water-soluble organic substances (non-limiting examples include vitamin A, Vitamin B1 (thiamine), Vitamin B2 (riboflavin), Vitamin B3 (niacin or niacinamide), Vitamin B5 (pantothenic acid), Vitamin B6 (pyridoxine, pyridoxal, or pyridoxamine, or pyridoxine hydrochloride), Vitamin B7 (biotin), Vitamin B9 (folic acid), and Vitamin B12 (various cobalamins; commonly cyanocobalamin in vitamin supplements), vitamin C, vitamin D, vitamin E, vitamin K, K1 and K2 (i.e., MK-4, MK-7, folic acid and biotin) essential in minute amounts for normal growth and activity of the body and obtained naturally from plant and animal foods, or synthetically made, pro-vitamins, derivatives, and/or analogs.

As used herein, the term "antioxidant" is understood to include any one or more of various substances such as beta-carotene (a vitamin A precursor), vitamin C, vitamin E, and selenium) that inhibit oxidation or reactions promoted by reactive oxygen species ("ROS") and other radical and non-radical species. Additionally, antioxidants are molecules capable of slowing or preventing the oxidation of other molecules. Non-limiting examples of antioxidants include astaxanthin, carotenoids, coenzyme Q10 ("CoQ10"), flavonoids, glutathione, Goji (wolfberry), hesperidin, lactowolfberry, lignan, lutein, lycopene, polyphenols, selenium, vitamin A, vitamin C, vitamin E, zeaxanthin, or combinations thereof.

"Graft versus host disease" as used herein is an immunological disorder in which the immune cells of a transplant attack the tissues of a transplant recipient and may lead to organ dysfunction.

"Acute GVHD" as used herein is GVHD that prevents within the first 100 days of transplant.

"Chronic GVHD" as used herein is GVHD that prevents after the first 100 days of transplant.

"Inhibit," "inhibiting," and "inhibition" mean to decrease an activity, response, condition, disease, or other biological parameter. This can include but is not limited to the complete ablation of the activity, response, condition, or disease. This may also include, for example, a 10% reduction in the activity, response, condition, or disease as compared to the native or control level. Thus, the reduction can be a 10, 20, 30, 40, 50, 60, 70, 80, 90, 100%, or any amount of reduction in between as compared to native or control levels.

"Treatment", "treat", or "treating", mean a method of reducing the effects of a disease or condition. Treatment can also refer to a method of reducing the disease or condition itself rather than just the symptoms. The treatment can be any reduction from native levels and can be but is not limited to the complete ablation of the disease, condition, or the symptoms of the disease or condition. Therefore, in the disclosed methods, treatment" can refer to a 10%, 20%, 30%, 40%, 50%, 60%, 70%, 80%, 90%, or 100% reduction in the severity of an established disease or the disease progression. For example, a disclosed method for reducing the effects of GVHD is considered to be a treatment if there is a 10% reduction in one or more symptoms of the disease in a subject with GVHD when compared to native levels in the same subject or control subjects. Thus, the reduction can be a 10, 20, 30, 40, 50, 60, 70, 80, 90, 100%, or any amount of reduction in between, as compared to native or control levels. It is understood and herein contemplated that "treatment" does not necessarily refer to a cure of the disease or condition, but an improvement in the outlook of a disease or condition (e.g., GVHD).

As used herein "preventing" or "prevention" refers to any methodology where the disease state does not occur due to the actions of the methodology (such as, for example, administration of a pharmaceutical composition as described herein). In one aspect, it is understood that prevention can also mean that the disease is not established to the extent that occurs in untreated controls. For example, there can be a 5%, 10%, 15%, 20%, 25%, 30%, 35%, 40%, 50%, 60%, 70%, 80%, 90%, or 100% reduction in the establishment of disease.

As used herein, the term "recipient" refers to the subject that receives a bone marrow or a solid organ transplantation.

Pharmaceutical Compositions of the Invention

Disclosed herein are pharmaceutical compositions, e.g., probiotic compositions, comprising a population of bacterial cells, e.g., an immunomodulatory bacterial cell population, such as an anti-inflammatory bacterial population, with or without one or more prebiotics, for the prevention, control, and treatment of inflammation, autoimmune and inflammatory disorders, dysbiosis, e.g., gastrointestinal or distal dysbiosis, disorders associated with dysbiosis, and for general nutritional health. These compositions are advantageous in being suitable for safe administration to humans and other mammalian subjects and are efficacious for the treatment, prevention, reduction of onset and amelioration of inflammation, autoimmune and inflammatory disorders, dysbiosis, e.g., gastrointestinal or distal dysbiosis, disorders associated with dysbiosis, and for general nutritional health. These pharmaceutical compositions are formulated as provided herein, and administered to mammalian subjects using the methods as provided herein. In some embodiments, the compositions described herein are formulated for oral administration. In other embodiments, the compositions described herein are formulated for rectal administration.

In one embodiment, therapeutic compositions (e.g., pharmaceutical compositions) are provided for the treatment, prevention, reduction of onset, and amelioration of, inflammation or one or more symptom of an autoimmune or inflammatory disorder, dysbiosis, e.g., gastrointestinal or distal dysbiosis, or a disorder associated with dysbiosis. As used herein, "therapeutic" compositions include compositions that function in a prophylactic (e.g., preventative) manner. Generally, the population is provided in an amount effective to treat (including to prevent) a disease, disorder or condition associated with or characterized by inflammation, dysbiosis, e.g., gastrointestinal or distal dysbiosis, inflammation, or an autoimmune or inflammatory disorder. Such treatment may be effective to reduce the severity of at least one symptom of the dysbiosis, e.g., gastrointestinal or distal dysbiosis, or an autoimmune or inflammatory disorder. Such treatment may be effective to modulate the microbiota diversity present in the mammalian recipient.

In some embodiments, the population of anti-inflammatory bacterial cells is a purified population of bacterial cells. In some embodiments, said purified population of bacterial cells is isolated from a mammalian source. In some embodiments, said purified population of bacterial cells is isolated from a human source. In some embodiments, said purified population of bacterial cells is isolated from the skin of a human source. In some embodiments, said purified population of bacterial cells is isolated from the gastrointestinal tract of a human source. In some embodiments, said purified population of bacterial cells is isolated from the fecal matter of a subject. In some embodiments, said purified population of bacterial cells is isolated from human fecal matter. In other embodiments, said purified population of bacterial cells is not isolated from human fecal matter. In some embodiments, said purified population of bacterial cells is not derived from human fecal matter.

In embodiments, the pharmaceutical compositions (e.g., probiotic compositions) contain immunomodulatory bacterial cells (e.g., anti-inflammatory bacterial cells), which are capable of altering the immune activity of a mammalian subject. In exemplary embodiments, the immunomodulatory bacterial cells are capable of reducing inflammation in a mammalian subject. Such immunomodulatory bacterial cells are referred to herein as "anti-inflammatory bacteria" or "anti-inflammatory bacterial cells". Immunomodulatory bacterial cells can act to alter the immune activity of a subject directly or indirectly. For example, immunomodulatory bacteria can act directly on immune cells through receptors for bacterial components (e.g. Toll-like receptors) or by producing metabolites such as immunomodulatory short chain fatty acids (SCFAs). Such SCFAs can have many positive impacts on the health of the subject, by, for example, reducing inflammation, or improving intestinal barrier integrity. Immunomodulatory bacterial cells can also impact the immune activity of a subject by producing glutathione or gamma-glutamylcysteine.

Pharmaceutical compositions (e.g., probiotic compositions) containing immunomodulatory bacteria (i.e., bacterial cells) can additionally or alternatively impact the immune activity of a subject indirectly by modulating the activity of immune cells in the subject. For example, immunomodulatory bacteria may alter cytokine expression by host immune cells (e.g., macrophages, B lymphocytes, T lymphocytes, mast cells, peripheral blood mononuclear cells (PBMCs), etc.) or other types of host cells capable of cytokine secretion (e.g., endothelial cells, fibroblasts, stromal cells, etc.). In an exemplary embodiment, pharmaceutical compositions (e.g., probiotic compositions) contain a population of anti-inflammatory bacterial cells that are capable of inducing secretion of a anti-inflammatory cytokine by host cells (e.g., host immune cells). For example, anti-inflammatory bacterial cells can induce secretion of one or more anti-inflammatory cytokines such as, but not limited to, IL-10, IL-13, IL-9, IL-4, IL-5, TGFβ, and combinations thereof, by host cells (e.g., host immune cells). In another exemplary embodiment, pharmaceutical compositions (e.g., probiotic compositions) contain anti-inflammatory bacterial cells that are capable of reducing secretion of one or more pro-inflammatory cytokines by a host cell (e.g., by a host immune cell). For example, anti-inflammatory bacterial cells can reduce secretion of one or more pro-inflammatory cytokines, such as, but not limited to, IFNγ, IL-12p70, IL-1α, IL-6, IL-8, MCP1, MIP1α, MIP1β, TNFα, and combinations thereof, by host cells (e.g., host immune cells). In some embodiments, the induction and/or secretion of said pro-inflammatory cytokines may be induced by (e.g., in response to, either directly or indirectly) a bacteria (e.g., *Enterococcus faecalis*). Other cytokines that may be modulated by immunomodulatory bacterial cells include, for example, IL-17A, IL-2, and IL-9.

In some embodiments, immunomodulatory bacteria (i.e., immunomodulatory bacterial cells) are selected for inclusion in a pharmaceutical composition (e.g., probiotic composition) of the invention based on the desired effect of the immunomodulatory bacteria on cytokine secretion by a host cell or a population of host cells (e.g., a host immune cell (e.g., a PBMC)). In some embodiments, said effect of the immunomodulatory bacteria is assessed in vitro using a population of host cells (e.g., a population of isolated host immune cells). For example, in one embodiment, a probiotic composition contains anti-inflammatory bacteria that increase secretion of a anti-inflammatory cytokine, for example, IL-10, IL-13, IL-9, IL-4, IL-5, TGFβ, and combinations thereof, by a host cell (e.g., a host immune cell (e.g., PBMCs, macrophages, B lymphocytes, T lymphocytes, mast cells). In some embodiments, the anti-inflammatory bacteria increase secretion of two or more anti-inflammatory cytokines. In some embodiments, the anti-inflammatory bacteria increase secretion of three or more anti-inflammatory cytokines. In some embodiments, the anti-inflammatory bacteria increase secretion of four or more anti-inflammatory cytokines. In some embodiments, the anti-inflammatory bacteria increase secretion of five or more anti-inflammatory cytokines. In exemplary embodiments, the increase is an increase of at least 5%, 10%, 20%, 30%, 40%, 50%, 60%, 70%, 80%, 80%, 100%, 200%, 300%, 500% or more. In other embodiments, a pharmaceutical composition contains anti-inflammatory bacteria that decrease secretion of a pro-inflammatory cytokine, for example, IFNγ, IL-12p70, IL-1α, IL-6, IL-8, MCP1, MIP1α, MIP1β, TNFα, and combinations thereof, by a host cell. In some embodiments, the anti-inflammatory bacteria decrease secretion of five or more pro-inflammatory cytokines. In exemplary embodiments, the decrease is a decrease of at least 5%, 10%, 20%, 30%, 40%, 50%, 60%, 70%, 80%, 80%, 100%, 200%, 300%, 500% or more. In another embodiment, the pharmaceutical composition contains anti-inflammatory bacterial cells that increase secretion of one or more anti-inflammatory cytokines and reduce secretion of one or more pro-inflammatory cytokines by a host cell (e.g., a host immune cell). Alterations in cytokine expression may occur locally, e.g., in the gastrointestinal tract of a subject, or at a site distal to a microbial niche, e.g., distal to the gastrointestinal tract. In some embodiments, the induction and/or secretion of said pro-inflammatory cytokines may be induced by (e.g., in response to, either directly or indirectly) a bacteria (e.g., *Enterococcus faecalis*).

In some aspects, the pharmaceutical compositions described herein and/or a prebiotic (e.g., a carbohydrate) modulate the release of immune stimulatory cytokines by host cells (e.g., host immune cells). In preferred embodiments, the administered immunomodulatory bacterial cells (e.g., anti-inflammatory bacterial cells) and/or a prebiotic (e.g., a carbohydrate) inhibit or reduce the release of immune stimulatory cytokines. Non-limiting examples of immune modulating cytokines and ligands include B lymphocyte chemoattractant ("BLC"), C—C motif chemokine 11 ("Eotaxin-1"), Eosinophil chemotactic protein 2 ("Eotaxin-2"), Granulocyte colony-stimulating factor ("G-CSF"), Granulocyte macrophage colony-stimulating factor ("GM-CSF"), 1-309, Intercellular Adhesion Molecule 1 ("ICAM-1"), Interferon gamma ("IFN-γ"), Interlukin-1 alpha ("IL-1α"), Interlukin-1β("IL-1β"), Interleukin 1 receptor antagonist ("IL-1 ra"), Interleukin-2 ("IL-2"), Interleukin-4 ("IL-4"), Interleukin-5 ("IL-5"), Interleukin-6 ("IL-6"), Interleukin-6 soluble receptor ("IL-6 sR"), Interleukin-7 ("IL-7"), Interleukin-8 ("IL-8"), Interleukin-10 ("IL-10"), Interleukin-11 ("IL-11"), Subunit β of Interleukin-12 ("IL-12 p40" or "IL-12 p70"), Interleukin-13 ("IL-13"), Interleukin-15 ("IL-15"), Interleukin-16 ("IL-16"), Interleukin-17 ("IL-17"), Chemokine (C—C motif) Ligand 2 ("MCP-1"), Macrophage colony-stimulating factor ("M-CSF"), Monokine induced by gamma interferon ("MIG"), Chemokine (C—C motif) ligand 2 ("MIP-1 alpha"), Chemokine (C—C motif) ligand 4 ("MIP-1β"), Macrophage inflammatory protein-1-5 ("MIP-16"), Platelet-derived growth factor subunit B ("PDGF-BB"), Chemokine (C—C motif) ligand 5, Regulated on Activation, Normal T cell Expressed and Secreted ("RANTES"), TIMP metallopeptidase inhibitor 1 ("TIMP-1"), TIMP metallopeptidase inhibitor 2 ("TIMP-2"), Tumor necrosis factor, lymphotoxin-α ("TNF-α"), Tumor necrosis factor, lymphotoxin-β ("TNF β"), Soluble TNF receptor type 1 ("sTNFRI"), sTNFRIIAR, Brain-derived neurotrophic factor ("BDNF"), Basic fibroblast growth factor ("bFGF"), Bone morphogenetic protein 4 ("BMP-4"), Bone morphogenetic protein 5 ("BMP-5"), Bone morphogenetic protein 7 ("BMP-7"), Nerve growth factor ("b-NGF"), Epidermal growth factor ("EGF"), Epidermal growth factor receptor ("EGFR"), Endocrine-gland-derived vascular endothelial growth factor ("EG-VEGF"), Fibroblast growth factor 4 ("FGF-4"), Keratinocyte growth factor ("FGF-7"), Growth differentiation factor 15 ("GDF-15"), Glial cell-derived neurotrophic factor ("GDNF"), Growth Hormone, Heparin-binding EGF-like growth factor ("HB-EGF"), Hepatocyte growth factor ("HGF"), Insulin-like growth factor binding protein 1 ("IGFBP-1"), Insulin-like growth factor binding protein 2 ("IGFBP-2"), Insulin-like growth factor binding protein 3 ("IGFBP-3"), Insulin-like growth factor binding protein 4 ("IGFBP-4"), Insulin-like growth factor binding protein 6 ("IGFBP-6"), Insulin-like growth factor 1 ("IGF-1"), Insulin, Macrophage colony-stimulating factor ("M-CSF R"), Nerve growth factor receptor ("NGF R"), Neurotrophin-3 ("NT-3"), Neurotrophin-4 ("NT-4"), Osteoclastogenesis inhibitory factor ("Osteoprotegerin"), Platelet-derived growth factor receptors ("PDGF-AA"), Phosphatidylinositol-glycan biosynthesis ("PIGF"), Skp, Cullin, F-box containing complexes ("SCF"), Stem cell factor receptor ("SCF R"), Transforming growth factor α ("TGF-α"), Transforming growth factor β-1 ("TGF β1"), Transforming growth factor β-3 ("TGF β3"), Vascular endothelial growth factor ("VEGF"), Vascular endothelial growth factor receptor 2 ("VEGFR2"), Vascular endothelial growth factor receptor 3 ("VEGFR3"), VEGF-D 6Ckine, Tyrosine-protein kinase receptor UFO ("Axl"), Betacellulin ("BTC"), Mucosae-associated epithelial chemokine ("CCL28"), Chemokine (C—C motif) ligand 27 ("CTACK"), Chemokine (C—X—C motif) ligand 16 ("CXCL16"), C—X—C motif chemokine 5 ("ENA-78"), Chemokine (C—C motif) ligand 26 ("Eotaxin-3"), Granulocyte chemotactic protein 2 ("GCP-2"), GRO, Chemokine (C—C motif) ligand 14 ("HCC-1"), Chemokine (C—C motif) ligand 16 ("HCC-4"), Interleukin-9 ("IL-9"), Interleukin-17 F ("IL-17F"), Interleukin-18-binding protein ("IL-18 BPa"), Interleukin-28 A ("IL-28A"), Interleukin 29 ("IL-29"), Interleukin 31 ("IL-31"), C—X—C motif chemokine 10 ("IP-10"), Chemokine receptor CXCR3 ("I-TAC"), Leukemia inhibitory factor ("LIF"), Light, Chemokine (C motif) ligand ("Lymphotactin"), Monocyte chemoattractant protein 2 ("MCP-2"), Monocyte chemoattractant protein 3 ("MCP-3"), Monocyte chemoattractant protein 4 ("MCP-4"), Macrophage-derived chemokine ("MDC"), Macrophage migration inhibitory factor ("MIF"), Chemokine (C—C motif) ligand 20 ("MIP-3 α"), C—C motif chemokine 19 ("MIP-3 β"), Chemokine (C—C motif) ligand 23 ("MPIF-1"), Macrophage stimulating protein alpha chain ("MSP-α"), Nucleosome assembly protein 1-like 4 ("NAP-2"), Secreted phosphoprotein 1 ("Osteopontin"), Pulmonary and activation-regulated cytokine ("PARC"), Platelet factor 4 ("PF4"), Stroma cell-derived factor-1 α ("SDF-1 α"), Chemokine (C—C motif) ligand 17 ("TARC"), Thymus-expressed chemokine ("TECK"), Thymic stromal lymphopoietin ("TSLP 4-IBB"), CD 166 antigen ("ALCAM"), Cluster of Differentiation 80 ("B7-1"), Tumor necrosis factor receptor superfamily member 17 ("BCMA"), Cluster of Differentiation 14 ("CD14"), Cluster of Differentiation 30 ("CD30"), Cluster of Differentiation 40 ("CD40 Ligand"), Carcinoembryonic antigen-related cell adhesion molecule 1 (biliary glycoprotein) ("CEACAM-1"), Death Receptor 6 ("DR6"), Deoxythymidine kinase ("Dtk"), Type 1 membrane glycoprotein ("Endoglin"), Receptor tyrosine-protein kinase erbB-3 ("ErbB3"), Endothelial-leukocyte adhesion molecule 1 ("E-Selectin"), Apoptosis antigen 1 ("Fas"), Fms-like tyrosine kinase 3 ("Flt-3L"), Tumor necrosis factor receptor superfamily member 1 ("GITR"), Tumor necrosis factor receptor superfamily member 14 ("HVEM"), Intercellular adhesion molecule 3 ("ICAM-3"), IL-1 R4, IL-1 RI, IL-1βR1, IL-17R, IL-2Rγ, IL-21R, Lysosome membrane protein 2 ("LIMPII"), Neutrophil gelatinase-associated lipocalin ("Lipocalin-2"), CD62L ("L-Selectin"), Lymphatic endothelium ("LYVE-1"), MHC class I polypeptide-related sequence A ("MICA"), MHC class I polypeptide-related sequence B ("MICB"), NRG1-β1, Beta-type platelet-derived growth factor receptor ("PDGF Rβ"), Platelet endothelial cell adhesion molecule ("PECAM-1"), RAGE, Hepatitis A virus cellular receptor 1 ("TIM-1"), Tumor necrosis factor receptor superfamily member IOC ("TRAIL R3"), Trappin protein transglutaminase binding domain ("Trappin-2"), Urokinase receptor ("uPAR"), Vascular cell adhesion protein 1 ("VCAM-1"), XEDARActivin A, Agouti-related protein ("AgRP"), Ribonuclease 5 ("Angiogenin"), Angiopoietin 1, Angiostatin, Catheprin S, CD40, Cryptic family protein IB ("Cripto-1"), DAN, Dickkopf-related protein 1 ("DKK-1"), E-Cadherin, Epithelial cell adhesion molecule ("EpCAM"), Fas Ligand (FasL or CD95L), Fcg RIIB/C, FoUistatin, Galectin-7, Intercellular adhesion molecule 2 ("ICAM-2"), IL-13 RI, IL-13R2, IL-17B, IL-2 Ra, IL-2 Rb, IL-23, LAP, Neuronal cell adhesion molecule ("NrCAM"), Plasminogen activator inhibitor-1 ("PAI-1"), Platelet derived growth factor receptors ("PDGF-AB"), Resistin, stromal cell-derived factor 1 ("SDF-1 β"), sgpl30, Secreted frizzled-related protein 2 ("ShhN"), Sialic acid-binding immunoglobulin-type lectins ("Siglec-5"), ST2, Transforming growth factor-β2 ("TGF β2"), Tie-2, Thrombopoietin ("TPO"), Tumor necrosis factor receptor superfamily member 10D ("TRAIL R4"), Triggering receptor expressed on myeloid cells 1 ("TREM-1"), Vascular endothelial growth factor C ("VEGF-C"), VEGFRlAdiponectin, Adipsin ("AND"), α-fetoprotein ("AFP"), Angiopoietin-like 4 ("ANGPTL4"), β-2-microglobulin ("B2M"), Basal cell adhesion molecule ("BCAM"), Carbohydrate antigen 125 ("CA125"), Cancer Antigen 15-3 ("CA15-3"), Carcinoembryonic antigen ("CEA"), cAMP receptor protein ("CRP"), Human Epidermal Growth Factor Receptor 2 ("ErbB2"), Follistatin, Follicle-stimulating hormone ("FSH"), Chemokine (C—X—C motif) ligand 1 ("GRO α"), human chorionic gonadotropin ("β HCG"), Insulin-like growth factor 1 receptor ("IGF-1 sR"), IL-1 sRII, IL-3, IL-18 Rb, IL-21, Leptin, Matrix metalloproteinase-1 ("MMP-1"), Matrix metalloproteinase-2 ("MMP-2"), Matrix metalloproteinase-3 ("MMP-3"), Matrix metalloproteinase-8 ("MMP-8"), Matrix metalloproteinase-9 ("MMP-9"), Matrix metalloproteinase-10 ("MMP-10"), Matrix metalloproteinase-13 ("MMP-13"), Neural Cell Adhesion Molecule ("NCAM-1"), Entactin ("Nidogen-1"), Neuron specific enolase ("NSE"), Oncostatin M ("OSM"), Procalcitonin, Prolactin, Prostate specific antigen ("PSA"), Sialic acid-binding Ig-like lectin 9 ("Siglec-9"), ADAM 17 endopeptidase ("TACE"), Thyroglobulin, Metalloproteinase inhibitor 4 ("TIMP-4"), TSH2B4, Disintegrin and metalloproteinase domain-containing protein 9 ("ADAM-9"), Angiopoietin 2, Tumor necrosis factor ligand superfamily member 13/Acidic leucine-rich nuclear phosphoprotein 32 family member B ("APRIL"), Bone morphogenetic protein 2 ("BMP-2"), Bone morphogenetic protein 9 ("BMP-9"), Complement component 5a ("C5a"), Cathepsin L, CD200, CD97, Chemerin, Tumor necrosis factor receptor superfamily member 6B ("DcR3"), Fatty acid-binding protein 2 ("FABP2"), Fibroblast activation protein, alpha ("FAP"), Fibroblast growth factor 19 ("FGF-19"), Galectin-3, Hepatocyte growth factor receptor ("HGF R"), IFN-γα/β R2, Insulin-like growth factor 2 ("IGF-2"), Insulin-like growth factor 2 receptor ("IGF-2 R"), Interleukin-1 receptor 6 ("IL-1R6"), Interleukin 24 ("IL-24"), Interleukin 33 ("IL-33"), Kallikrein 14, Asparaginyl endopeptidase ("Legumain"), Oxidized low-density lipoprotein receptor 1 ("LOX-"), Mannose-binding lectin ("MBL"), Neprilysin ("NEP"), Notch homolog 1, translocation-associated (Drosophila) ("Notch-1"), Nephroblastoma overexpressed ("NOV"), Osteoactivin, Programmed cell death protein 1 ("PD-1"), N-acetylmuramoyl-L-alanine amidase ("PGRP-5"), Serpin A4, Secreted frizzled related protein 3 ("sFRP-3"), Thrombomodulin, Toll-like receptor 2 ("TLR2"), Tumor necrosis factor receptor superfamily member 10A ("TRAIL R1"), Transferrin ("TRF"), WIF-lACE-2, Albumin, AMICA, Angiopoietin 4, B-cell activating factor ("BAFF"), Carbohydrate antigen 19-9 ("CA19-9"), CD 163, Clusterin, CRT AM, Chemokine (C—X—C motif) ligand 14 ("CXCL14"), Cystatin C, Decorin ("DCN"), Dickkopf-related protein 3 ("Dkk-3"), Delta-like protein 1 ("DLL1"), Fetuin A, Heparin-binding growth factor 1 ("aFGF"), Folate receptor α ("FOLR"), Furin, GPCR-associated sorting protein 1 ("GASP-1"), GPCR-associated sorting protein 2 ("GASP-2"), Granulocyte colony-stimulating factor receptor ("GCSF R"), Serine protease hepsin ("HAI-2"), Interleukin-17B Receptor ("IL-17B R"), Interleukin 27 ("IL-27"), Lymphocyte-activation gene 3 ("LAG-3"), Apolipoprotein A-V ("LDL R"), Pepsinogen I, Retinol binding protein 4 ("RBP4"), SOST, Heparan sulfate proteoglycan ("Syndecan-1"), Tumor necrosis factor receptor superfamily member 13B ("TACI"), Tissue factor pathway inhibitor ("TFPI"), TSP-1, Tumor necrosis factor receptor superfamily, member 10b ("TRAIL R2"), TRANCE, Troponin I, Urokinase Plasminogen Activator ("uPA"), Cadherin 5, type 2 or VE-cadherin (vascular endothelial) also known as CD144 ("VE-Cadherin"), WNTl-inducible-signaling pathway protein 1 ("WISP-1"), and Receptor Activator of Nuclear Factor κ B ("RANK").

In other embodiments, pharmaceutical compositions (e.g., probiotic compositions) containing immunomodulatory bacteria that impact the immune activity of a subject by promoting the differentiation and/or expansion of particular subpopulations of immune cells. For example, immunomodulatory bacteria can increase or decrease the proportion of Treg cells, Th17 cells, Th1 cells, or Th2 cells in a subject. The increase or decrease in the proportion of immune cell subpopulations may be systemic, or it may be localized to a site of action of the probiotic, e.g., in the gastrointestinal tract or at a site of distal dysbiosis. In some embodiments, immunomodulatory bacteria (i.e., anti-inflammatory bacterial cells) are selected for inclusion in a pharmaceutical composition (e.g., a probiotic composition) of the invention based on the desired effect of the pharmaceutical composition on the differentiation and/or expansion of subpopulations of immune cells in the subject.

In one embodiment, a pharmaceutical composition (e.g., a probiotic composition) contains immunomodulatory bacteria (i.e., immunomodulatory bacterial cells) that increase the proportion of Treg cells in a subject (e.g., by inducing expansion of Treg cells in the subject). In another embodiment, a pharmaceutical composition contains immunomodulatory bacteria that decrease the proportion of Treg cells in a subject. In one embodiment, a pharmaceutical composition contains immunomodulatory bacteria that increase the proportion of Th17 cells in a subject (e.g., by inducing expansion of Th17 cells in the subject). In another embodiment, a pharmaceutical composition contains immunomodulatory bacteria that decrease the proportion of Th17 cells in a subject. In one embodiment, a pharmaceutical composition contains immunomodulatory bacteria that increase the proportion of Th1 cells in a subject (e.g., by inducing expansion of Th1 cells in the subject). In another embodiment, a pharmaceutical composition contains immunomodulatory bacteria that decrease the proportion of Th1 cells in a subject. In one embodiment, a pharmaceutical composition contains immunomodulatory bacteria that increase the proportion of Th2 cells in a subject (e.g., by inducing expansion of Th2 cells in the subject). In another embodiment, a pharmaceutical composition contains immunomodulatory bacteria that decrease the proportion of Th2 cells in a subject. The increase or decrease in the proportion of immune cell subpopulations may be systemic, or it may be localized to a site of action of the probiotic, e.g., in the gastrointestinal tract or at a site of distal dysbiosis.

In one embodiment, a pharmaceutical composition (e.g., a probiotic composition) contains immunomodulatory bacteria capable of modulating the proportion of one or more populations of Treg cells, Th17 cells, Th1 cells, Th2 cells, and combinations thereof, in a subject. Certain immune cell profiles may be particularly desirable to treat or prevent particular disorders associated with a dysbiosis. For example, treatment or prevention of an autoimmune or inflammatory disorder (e.g., GVHD) can be promoted by increasing the quantity of Treg cells and Th2 cells, and decreasing the quantity of Th17 cells and Th1 cells. Accordingly, pharmaceutical compositions (e.g., probiotic compositions) for the treatment or prevention of an autoimmune or inflammatory disorder (e.g., GVHD) contain immunomodulatory bacteria capable of promoting the differentiation and/or expansion of Treg cells and Th2 cells, and reducing Th17 and Th1 cells in the subject.

In one embodiment, pharmaceutical compositions (e.g., a therapeutic probiotic compositions) containing a purified population of immunomodulatory microbes, e.g., immunomodulatory bacterial cells, are provided, with or without one or more prebiotics, in an amount effective to: i) treat or prevent dysbiosis, e.g., gastrointestinal or distal dysbiosis, inflammation, or an autoimmune or inflammatory disorder; and/or ii) augment at least one type of microbe, e.g., a bacterium, not present in the therapeutic composition in a mammalian recipient subject to whom the pharmaceutical composition is administered; and/or iii) engraft at least one type of microbe, e.g., an anti-inflammatory bacterial cell, present in the therapeutic composition but not present in a mammalian subject prior to treatment.

In another embodiment, pharmaceutical compositions containing a purified population of immunomodulatory bacteria (e.g., anti-inflammatory bacterial cells) are provided, in an amount effective to i) augment the microbiota diversity present in the mammalian recipient and/or ii) treat or prevent dysbiosis, e.g., gastrointestinal or distal dysbiosis, inflammation, or an autoimmune or inflammatory disorder in a mammalian recipient subject to whom the therapeutic composition is administered, wherein the purified population of immunomodulatory bacteria is obtained by separating the population from at least one residual habitat product in a fecal material obtained from one or a plurality of mammalian donor subjects. In some embodiments, individual bacterial strains can be cultured from fecal material. These strains can then be purified or otherwise isolated and used singly or in combination. In one embodiment, the probiotic composition does not contain a fecal extract.

In one embodiment, the pharmaceutical compositions described herein may be used to treat or correct a dysbiosis in a subject. The dysbiosis may be, for example, a local dysbiosis, or a distal dysbiosis. In another embodiment, the probiotic compositions described herein may be used to prevent a dysbiosis in a subject at risk for developing a dysbiosis.

In another embodiment, pharmaceutical compositions containing a purified population of immunomodulatory bacteria (e.g., anti-inflammatory bacterial cells) are provided, in an amount effective to i) augment the microbiota diversity present in the mammalian recipient and/or ii) treat or prevent dysbiosis, e.g., gastrointestinal or distal dysbiosis, inflammation, or an autoimmune or inflammatory disorder in a mammalian recipient subject to whom the therapeutic composition is administered, wherein the purified population of immunomodulatory bacteria is obtained by separating the population from a non-fecal material source.

In some embodiments, a pharmaceutical composition containing a purified population of immunomodulatory bacterial cells (e.g., anti-inflammatory bacterial cells) described above is co-administered or co-formulated with one or more prebiotics, e.g., carbohydrates. In some embodiments, a pharmaceutical composition is administered before one or more prebiotics is administered to a subject. In some embodiments, the pharmaceutical composition is administered after one or more prebiotics is administered to a subject. In some embodiments, a pharmaceutical composition containing a purified population of immunomodulatory bacterial cells is administered concurrently with one or more prebiotics. In other embodiments, a pharmaceutical composition containing a purified population of immunomodulatory bacterial cells is administered sequentially with one or more prebiotics. In some embodiments, a purified population of immunomodulatory bacterial cells is administered in a pharmaceutical composition formulated to contain one or more pharmaceutical excipients, and optionally one or more prebiotics.

Immunomodulatory bacterial cells (e.g., anti-inflammatory bacterial cells) involved in modulation of the host immune system i) may be human commensals; ii) may be part of an organ's healthy-state microbiome; ii) may be part of a distal organ's healthy-state microbiome; iv) may be exogenous microbes; v) may be innocuous; vi) may be pathobionts; vii) may be pathogens; viii) may be opportunistic pathogens; or ix) any combination thereof. In some aspects, microbes are not required to be actively proliferating (e.g., spores, dormant cells, cells with reduced metabolic rate, or heat-killed cells) to have an immunomodulatory effect. In certain aspects, microbial cell components, rather than whole microbial cells, may have immunomodulatory effects. Non-limiting examples of microbial components are lipids, carbohydrates, proteins, nucleic acids, and small molecules.

The pharmaceutical compositions provided herein, may optionally further comprise a prebiotic, a non-microbial immunomodulatory carbohydrates, or a microbial immunomodulatory cell component, that are effective for the prevention or treatment of an autoimmune or inflammatory disorder such as graft-versus-host disease (GVHD), an inflammatory bowel disease (IBD) including, but not limited to, ulterative colitis and Crohn's disease, multiple sclerosis (MS), systemic lupus erythematosus (SLE), type I diabetes, rheumatoid arthritis, Sjögren's syndrome, and Celiac disease, or dysbiosis.

In certain embodiments, the pharmaceutical compositions comprise at least one type of immunomodulatory bacterial cells (e.g., at least one type of anti-inflammatory bacterial cell) and, optionally, at least one prebiotic (e.g., a carbohydrate), and optionally further comprise a microbial immunomodulatory cell component or substrate for the production of immunomodulatory metabolites, that are effective for the prevention or treatment of an autoimmune or inflammatory disorder. Methods for the prevention and/or treatment of autoimmune and inflammatory diseases in human subjects are also disclosed herein.

In some embodiments, the pharmaceutical compositions, e.g., probiotic compositions, of the invention comprise purified spore populations of anti-inflammatory bacterial cells. In one embodiment, the purified spore populations can engraft in the host and remain present for 1 day, 2 days, 3 days, 4 days, 5 days, 6 days, 7 days, 10 days, 14 days, 21 days, 25 days, 30 days, 60 days, 90 days, or longer than 90 days. Additionally, the purified spore populations can induce other healthy commensal bacteria found in a healthy gut to engraft in the host that are not present in the purified spore populations or present at lesser levels. Therefore, these species are considered to "augment" the delivered spore populations. In this manner, commensal species augmentation of the purified spore population in the recipient's gut leads to a more diverse population of gut microbiota than present initially.

Preferred bacterial cells for use in the present invention include bacterial cells of the genera *Acetanaerobacterium, Acetivibrio, Alicyclobacillus, Alkaliphilus, Anaerofustis, Anaerosporobacter, Anaerostipes, Anaerotruncus, Anoxybacillus, Bacillus, Bacteroides, Blautia, Brachyspira, Brevibacillus, Bryantella, Bulleidia, Butyricicoccus, Butyrivibrio, Catenibacterium, Chlamydiales, Clostridiaceae, Clostridiales, Clostridium, Collinsella, Coprobacillus, Coprococcus, Coxiella, Deferribacteres, Desulfitobacterium, Desulfotomaculum, Dorea, Eggerthella, Erysipelothrix, Erysipelotrichaceae, Ethanoligenens, Eubacterium, Faecalibacterium, Filifactor, Flavonifractor, Flexistipes, Fulvimonas, Fusobacterium, Gemmiger, Geobacillus, Gloeobacter, Holdemania, Hydrogenoanaerobacterium, Kocuria, Lachnobacterium, Lachnospira, Lachnospiraceae, Lactobacillus, Lactonifactor, Leptospira, Lutispora, Lysinibacillus, Mollicutes, Moorella, Nocardia, Oscillibacter, Oscillospira, Paenibacillus, Papillibacter, Pseudoflavonifractor, Robinsoniella, Roseburia, Ruminococcaceae, Ruminococcus, Saccharomonospora, Sarcina, Solobacterium, Sporobacter, Sporolactobacillus, Streptomyces, Subdoligranulum, Sutterella, Syntrophococcus, Thermoanaerobacter, Thermobifida,* and *Turicibacter.*

Preferred bacterial cells also include bacterial cells of the genera *Acetonema, Alkaliphilus, Amphibacillus, Ammonifex, Anaerobacter, Caldicellulosiruptor, Caloramator, Candidatus, Carboxydibrachium, Carboxydothermus, Cohnella, Dendrosporobacter Desulfitobacterium, Desulfosporosinus, Halobacteroides, Heliobacterium, Heliophilum, Heliorestis, Lachnoanaerobaculum, Lysinibacillus, Oceanobacillus, Orenia (S.), Oxalophagus, Oxobacter, Pelospora, Pelotomaculum, Propinispora, Sporohalobacter, Sporomusa, Sporosarcina, Sporotomaculum, Symbiobacterium, Syntrophobotulus, Syntrophospora, Terribacillus, Thermoanaerobacter,* and *Thermosinus.*

In another embodiment, a probiotic composition of the invention consists essentially of *Blautia.*

In one embodiment, a probiotic composition of the invention does not comprise *Blautia* alone.

As provided herein, the pharmaceutical compositions comprise, or in the alternative, modulate, the colonization and/or engraftment, of the following exemplary bacterial entities (e.g., bacterial cells belonging to particular bacterial strains, bacterial species, or bacterial genera): *Lactobacillus gasseri, Lactobacillus fermentum, Lactobacillus reuteri, Enterococcus faecalis, Enterococcus durans, Enterococcus villorum, Blautia luti, Blautia coccoides, Blautia hydrogenotrophica, Blautia hansenii, Blautia wexlerae, Lactobacillus plantarum, Pediococcus acidilactici, Staphylococcus pasteuri, Staphylococcus cohnii, Streptococcus sanguinis, Streptococcus sinensis, Streptococcus mitis, Streptococcus* sp. SCA22, *Streptococcus* sp. CR-3145, *Streptococcus anginosus, Streptococcus mutans, Coprobacillus cateniformis, Clostridium saccharogumia, Eubacterium dolichum* DSM 3991, *Clostridium* sp. PPf35E6, *Clostridium sordelli* ATCC 9714, *Ruminococcus torques, Ruminococcus gnavus, Clostridium clostridioforme, Ruminococcus obeum, Blautia producta, Clostridium* sp. ID5, *Megasphaera micronuciformis, Veillonella parvula, Clostridium methylpentosum, Clostridium islandicum, Faecalibacterium prausnitzii, Bacteroides uniformmis, Eubacterium rectale, Bacteroides thetaiotaomicron, Bacteroides acidifaciens, Bacteroides ovatus, Bacteroides fragilis, Parabacteroides distasonis, Propinionibacteirum propionicum, Actinomycs hyovaginalis, Rothia mucilaginosa, Rothia aeria, Bifidobacterium breve, Scardovia inopinata* and *Eggerthella lenta.*

Preferred bacterial strains are provided in Table 1, Table 1A, Table 1B, Table 1C, Table 1D, Table 1E, and Table 1F. Optionally, in some embodiments, preferred bacterial species are spore formers. The bacterial cells may be in the vegetative form and/or in the spore form. Thus, in some embodiments, the bacterial cell is present in the pharmaceutical composition solely in spore form. In other embodiments, the bacterial cell is present in the pharmaceutical composition solely in vegetative form. Yet, in other embodiments, the bacterial cell may be present in the pharmaceutical composition in a combination of vegetative form and spore form. Where specific strains of a species are provided, one of skill in the art will recognize that other strains of the species can be substituted for the named strain.

In one embodiment, the bacterial entity, e.g., species or strain, useful in the compositions and methods of the invention is *Acidaminococcus intestine.* In one embodiment, the bacterial entity, e.g., species or strain, useful in the compositions and methods of the invention is *Acinetobacter baumannii.* In one embodiment, the bacterial entity, e.g., species or strain, useful in the compositions and methods of the invention is *Acinetobacter Iwoffii.* In one embodiment, the bacterial entity, e.g., species or strain, useful in the compositions and methods of the invention is *Akkermansia muciniphila.* In one embodiment, the bacterial entity, e.g., species or strain, useful in the compositions and methods of the invention is *Alistipes putredinis.* In one embodiment, the bacterial entity, e.g., species or strain, useful in the compositions and methods of the invention is *Alistipes shahii.* In one embodiment, the bacterial entity, e.g., species or strain, useful in the compositions and methods of the invention is *Anaerostipes hadrus.* In one embodiment, the bacterial entity, e.g., species or strain, useful in the compositions and methods of the invention is *Anaerotruncus colihominis*. In one embodiment, the bacterial entity, e.g., species or strain, useful in the compositions and methods of the invention is *Bacteroides caccae*. In one embodiment, the bacterial entity, e.g., species or strain, useful in the compositions and methods of the invention is *Bacteroides cellulosilyticus*. In one embodiment, the bacterial entity, e.g., species or strain, useful in the compositions and methods of the invention is *Bacteroides dorei*. In one embodiment, the bacterial entity, e.g., species or strain, useful in the compositions and methods of the invention is *Bacteroides eggerthii*. In one embodiment, the bacterial entity, e.g., species or strain, useful in the compositions and methods of the invention is *Bacteroides finegoldii*. In one embodiment, the bacterial entity, e.g., species or strain, useful in the compositions and methods of the invention is *Bacteroides fragilis*. In one embodiment, the bacterial entity, e.g., species or strain, useful in the compositions and methods of the invention is *Bacteroides massiliensis*. In one embodiment, the bacterial entity, e.g., species or strain, useful in the compositions and methods of the invention is *Bacteroides ovatus*. In one embodiment, the bacterial entity, e.g., species or strain, useful in the compositions and methods of the invention is *Bacteroides salanitronis*. In one embodiment, the bacterial entity, e.g., species or strain, useful in the compositions and methods of the invention is *Bacteroides salyersiae*. In one embodiment, the bacterial entity, e.g., species or strain, useful in the compositions and methods of the invention is *Bacteroides* sp. 1_1_6. In one embodiment, the bacterial entity, e.g., species or strain, useful in the compositions and methods of the invention is *Bacteroides* sp. 3_1_23. In one embodiment, the bacterial entity, e.g., species or strain, useful in the compositions and methods of the invention is *Bacteroides* sp. D20. In one embodiment, the bacterial entity, e.g., species or strain, useful in the compositions and methods of the invention is *Bacteroides thetaiotaomicrond*. In one embodiment, the bacterial entity, e.g., species or strain, useful in the compositions and methods of the invention is *Bacteroides uniformis*. In one embodiment, the bacterial entity, e.g., species or strain, useful in the compositions and methods of the invention is *Bacteroides vulgatus*. In one embodiment, the bacterial entity, e.g., species or strain, useful in the compositions and methods of the invention is *Bifidobacterium adolescentis*. In one embodiment, the bacterial entity, e.g., species or strain, useful in the compositions and methods of the invention is *Bifidobacterium bifidum*. In one embodiment, the bacterial entity, e.g., species or strain, useful in the compositions and methods of the invention is *Bifidobacterium breve*. In one embodiment, the bacterial entity, e.g., species or strain, useful in the compositions and methods of the invention is *Bifidobacterium faecale*. In one embodiment, the bacterial entity, e.g., species or strain, useful in the compositions and methods of the invention is *Bifidobacterium kashiwanohense*. In one embodiment, the bacterial entity, e.g., species or strain, useful in the compositions and methods of the invention is *Bifidobacterium longum* subsp. *Longum*. In one embodiment, the bacterial entity, e.g., species or strain, useful in the compositions and methods of the invention is *Bifidobacterium pseudocatenulatum*. In one embodiment, the bacterial entity, e.g., species or strain, useful in the compositions and methods of the invention is *Bifidobacterium stercoris*. In one embodiment, the bacterial entity, e.g., species or strain, useful in the compositions and methods of the invention is *Blautia* (*Ruminococcus*) *coccoides*. In one embodiment, the bacterial entity, e.g., species or strain, useful in the compositions and methods of the invention is *Blautia faecis*. In one embodiment, the bacterial entity, e.g., species or strain, useful in the compositions and methods of the invention is *Blautia glucerasea*. In one embodiment, the bacterial entity, e.g., species or strain, useful in the compositions and methods of the invention is *Blautia* (*Ruminococcus*) *hansenii*. In one embodiment, the bacterial entity, e.g., species or strain, useful in the compositions and methods of the invention is *Blautia hydrogenotrophica* (*Ruminococcus hydrogenotrophicus*). In one embodiment, the bacterial entity, e.g., species or strain, useful in the compositions and methods of the invention is *Blautia* (*Ruminococcus*) *luti*. In one embodiment, the bacterial entity, e.g., species or strain, useful in the compositions and methods of the invention is *Blautia* (*Ruminococcus*) *obeum*. In one embodiment, the bacterial entity, e.g., species or strain, useful in the compositions and methods of the invention is *Blautia producta* (*Ruminococcus productus*). In one embodiment, the bacterial entity, e.g., species or strain, useful in the compositions and methods of the invention is *Blautia* (*Ruminococcus*) *schinkii*. In one embodiment, the bacterial entity, e.g., species or strain, useful in the compositions and methods of the invention is *Blautia stercoris*. In one embodiment, the bacterial entity, e.g., species or strain, useful in the compositions and methods of the invention is *Blautia* uncultured bacterium clone BKLE_a03_2 (GenBank: EU469501.1). In one embodiment, the bacterial entity, e.g., species or strain, useful in the compositions and methods of the invention is *Blautia* uncultured bacterium clone SJTU_B_14_30 (GenBank: EF402926.1). In one embodiment, the bacterial entity, e.g., species or strain, useful in the compositions and methods of the invention is *Blautia* uncultured bacterium clone SJTU_C_14_16 (GenBank: EF404657.1). In one embodiment, the bacterial entity, e.g., species or strain, useful in the compositions and methods of the invention is *Blautia* uncultured bacterium clone S1-5 (GenBank: GQ898099.1). In one embodiment, the bacterial entity, e.g., species or strain, useful in the compositions and methods of the invention is *Blautia* uncultured PAC000178_s (www.ezbiocloud.net/ez-taxon/hierarchy?m=browse&k=PAC000178&d=2). In one embodiment, the bacterial entity, e.g., species or strain, useful in the compositions and methods of the invention is *Blautia wexlerae*. In one embodiment, the bacterial entity, e.g., species or strain, useful in the compositions and methods of the invention is *Candidatus Arthromitus* sp. SFB-mouse-Yit. In one embodiment, the bacterial entity, e.g., species or strain, useful in the compositions and methods of the invention is *Catenibacterium mitsuokai*. In one embodiment, the bacterial entity, e.g., species or strain, useful in the compositions and methods of the invention is *Clostridiaceae* bacterium (*Dielma fastidiosa*) JC13. In one embodiment, the bacterial entity, e.g., species or strain, useful in the compositions and methods of the invention is Clostridiales bacterium 1_7_47FAA. In one embodiment, the bacterial entity, e.g., species or strain, useful in the compositions and methods of the invention is *Clostridium asparagiforme*. In one embodiment, the bacterial entity, e.g., species or strain, useful in the compositions and methods of the invention is *Clostridium bolteae*. In one embodiment, the bacterial entity, e.g., species or strain, useful in the compositions and methods of the invention is *Clostridium clostridioforme*. In one embodiment, the bacterial entity, e.g., species or strain, useful in the compositions and methods of the invention is *Clostridium glycyrrhizinilyticum*. In one embodiment, the bacterial entity, e.g., species or strain, useful in the compositions and methods of the invention is *Clostridium* (*Hungatella*) *hathewayi*. In one embodiment, the bacterial entity, e.g., species or strain, useful in the compositions and methods of the invention is *Clostridium histolyticum*. In one embodiment, the bacterial entity, e.g., species or strain, useful in the compositions and methods of the invention is *Clostridium indolis*. In one embodiment, the bacterial entity, e.g., species or strain, useful in the compositions and methods of the invention is *Clostridium leptum*. In one embodiment, the bacterial entity, e.g., species or strain, useful in the compositions and methods of the invention is *Clostridium (Tyzzerella) nexile*. In one embodiment, the bacterial entity, e.g., species or strain, useful in the compositions and methods of the invention is *Clostridium perfringens*. In one embodiment, the bacterial entity, e.g., species or strain, useful in the compositions and methods of the invention is *Clostridium (Erysipelatoclostridium) ramosum*. In one embodiment, the bacterial entity, e.g., species or strain, useful in the compositions and methods of the invention is *Clostridium scindens*. In one embodiment, the bacterial entity, e.g., species or strain, useful in the compositions and methods of the invention is *Clostridium septum*. In one embodiment, the bacterial entity, e.g., species or strain, useful in the compositions and methods of the invention is *Clostridium* sp. 14774. In one embodiment, the bacterial entity, e.g., species or strain, useful in the compositions and methods of the invention is *Clostridium* sp. 7_3_54FAA. In one embodiment, the bacterial entity, e.g., species or strain, useful in the compositions and methods of the invention is *Clostridium* sp. HGF2. In one embodiment, the bacterial entity, e.g., species or strain, useful in the compositions and methods of the invention is *Clostridium symbiosum*. In one embodiment, the bacterial entity, e.g., species or strain, useful in the compositions and methods of the invention is *Collinsella aerofaciens*. In one embodiment, the bacterial entity, e.g., species or strain, useful in the compositions and methods of the invention is *Collinsella intestinalis*. In one embodiment, the bacterial entity, e.g., species or strain, useful in the compositions and methods of the invention is *Coprobacillus* sp. D7. In one embodiment, the bacterial entity, e.g., species or strain, useful in the compositions and methods of the invention is *Coprococcus catus*. In one embodiment, the bacterial entity, e.g., species or strain, useful in the compositions and methods of the invention is *Coprococcus comes*. In one embodiment, the bacterial entity, e.g., species or strain, useful in the compositions and methods of the invention is *Dorea formicigenerans*. In one embodiment, the bacterial entity, e.g., species or strain, useful in the compositions and methods of the invention is *Dorea longicatena*. In one embodiment, the bacterial entity, e.g., species or strain, useful in the compositions and methods of the invention is *Enterococcus faecalis*. In one embodiment, the bacterial entity, e.g., species or strain, useful in the compositions and methods of the invention is *Enterococcus faecium*. In one embodiment, the bacterial entity, e.g., species or strain, useful in the compositions and methods of the invention is *Erysipelotrichaceae* bacterium 3_1_53. In one embodiment, the bacterial entity, e.g., species or strain, useful in the compositions and methods of the invention is *Escherichia coli*. In one embodiment, the bacterial entity, e.g., species or strain, useful in the compositions and methods of the invention is *Escherichia coli* S88. In one embodiment, the bacterial entity, e.g., species or strain, useful in the compositions and methods of the invention is *Eubacterium eligens*. In one embodiment, the bacterial entity, e.g., species or strain, useful in the compositions and methods of the invention is *Eubacterium fissicatena*. In one embodiment, the bacterial entity, e.g., species or strain, useful in the compositions and methods of the invention is *Eubacterium ramulus*. In one embodiment, the bacterial entity, e.g., species or strain, useful in the compositions and methods of the invention is *Eubacterium rectale*. In one embodiment, the bacterial entity, e.g., species or strain, useful in the compositions and methods of the invention is *Faecalibacterium prausnitzii*. In one embodiment, the bacterial entity, e.g., species or strain, useful in the compositions and methods of the invention is *Flavonifractor plautii*. In one embodiment, the bacterial entity, e.g., species or strain, useful in the compositions and methods of the invention is *Fusobacterium mortiferum*. In one embodiment, the bacterial entity, e.g., species or strain, useful in the compositions and methods of the invention is *Fusobacterium nucleatum*. In one embodiment, the bacterial entity, e.g., species or strain, useful in the compositions and methods of the invention is *Holdemania filiformis*. In one embodiment, the bacterial entity, e.g., species or strain, useful in the compositions and methods of the invention is *Hydrogenoanaerobacterium saccharovorans*. In one embodiment, the bacterial entity, e.g., species or strain, useful in the compositions and methods of the invention is *Klebsiella oxytoca*. In one embodiment, the bacterial entity, e.g., species or strain, useful in the compositions and methods of the invention is *Lachnospiraceae* bacterium 3_1_57FAA_CT1. In one embodiment, the bacterial entity, e.g., species or strain, useful in the compositions and methods of the invention is *Lachnospiraceae* bacterium 7_1_58FAA. In one embodiment, the bacterial entity, e.g., species or strain, useful in the compositions and methods of the invention is *Lachnospiraceae* bacterium 5_1_57FAA. In one embodiment, the bacterial entity, e.g., species or strain, useful in the compositions and methods of the invention is *Lactobacillus casei*. In one embodiment, the bacterial entity, e.g., species or strain, useful in the compositions and methods of the invention is *Lactobacillus rhamnosus*. In one embodiment, the bacterial entity, e.g., species or strain, useful in the compositions and methods of the invention is *Lactobacillus ruminis*. In one embodiment, the bacterial entity, e.g., species or strain, useful in the compositions and methods of the invention is *Lactococcus casei*. In one embodiment, the bacterial entity, e.g., species or strain, useful in the compositions and methods of the invention is *Odoribacter splanchnicus*. In one embodiment, the bacterial entity, e.g., species or strain, useful in the compositions and methods of the invention is *Oscillibacter valericigenes*. In one embodiment, the bacterial entity, e.g., species or strain, useful in the compositions and methods of the invention is Parabacteroides *gordonii*. In one embodiment, the bacterial entity, e.g., species or strain, useful in the compositions and methods of the invention is *Parabacteroides johnsonii*. In one embodiment, the bacterial entity, e.g., species or strain, useful in the compositions and methods of the invention is *Parabacteroides merdae*. In one embodiment, the bacterial entity, e.g., species or strain, useful in the compositions and methods of the invention is *Pediococcus acidilactici*. In one embodiment, the bacterial entity, e.g., species or strain, useful in the compositions and methods of the invention is *Peptostreptococcus asaccharolyticus*. In one embodiment, the bacterial entity, e.g., species or strain, useful in the compositions and methods of the invention is *Propionibacterium granulosum*. In one embodiment, the bacterial entity, e.g., species or strain, useful in the compositions and methods of the invention is *Roseburia intestinalis*. In one embodiment, the bacterial entity, e.g., species or strain, useful in the compositions and methods of the invention is *Roseburia inulinivorans*. In one embodiment, the bacterial entity, e.g., species or strain, useful in the compositions and methods of the invention is *Ruminococcus faecis*. In one embodiment, the bacterial entity, e.g., species or strain, useful in the compositions and methods of the invention is *Ruminococcus gnavus*. In one embodiment, the bacterial entity, e.g., species or strain, useful in the compositions and methods of the invention is *Ruminococcus* sp. ID8. In one embodiment, the bacterial entity, e.g., species or strain, useful in the compositions and methods of the invention is *Ruminococcus torques*. In one embodiment, the bacterial entity, e.g., species or strain, useful in the compositions and methods of the invention is *Slackia piriformis*. In one embodiment, the bacterial entity, e.g., species or strain, useful in the compositions and methods of the invention is *Staphylococcus epidermidis*. In one embodiment, the bacterial entity, e.g., species or strain, useful in the compositions and methods of the invention is *Staphylococcus saprophyticus*. In one embodiment, the bacterial entity, e.g., species or strain, useful in the compositions and methods of the invention is *Streptococcus cristatus*. In one embodiment, the bacterial entity, e.g., species or strain, useful in the compositions and methods of the invention is *Streptococcus dysgalactiae* subsp. *Equisimilis*. In one embodiment, the bacterial entity, e.g., species or strain, useful in the compositions and methods of the invention is *Streptococcus infantis*. In one embodiment, the bacterial entity, e.g., species or strain, useful in the compositions and methods of the invention is *Streptococcus oralis*. In one embodiment, the bacterial entity, e.g., species or strain, useful in the compositions and methods of the invention is *Streptococcus sanguinis*. In one embodiment, the bacterial entity, e.g., species or strain, useful in the compositions and methods of the invention is *Streptococcus viridans*. In one embodiment, the bacterial entity, e.g., species or strain, useful in the compositions and methods of the invention is *Streptococcus thermophiles*. In one embodiment, the bacterial entity, e.g., species or strain, useful in the compositions and methods of the invention is *Veillonella dispar.*

In one embodiment, the bacterial population useful in the compositions and methods of the invention comprises *Acidaminococcus intestine*. In one embodiment, the bacterial population useful in the compositions and methods of the invention comprises *Acinetobacter baumannii*. In one embodiment, the bacterial population useful in the compositions and methods of the invention comprises *Acinetobacter Iwoffli*. In one embodiment, the bacterial population useful in the compositions and methods of the invention comprises *Akkermansia muciniphila*. In one embodiment, the bacterial population useful in the compositions and methods of the invention comprises *Alistipes putredinis*. In one embodiment, the bacterial population useful in the compositions and methods of the invention comprises *Alistipes shahii*. In one embodiment, the bacterial population useful in the compositions and methods of the invention comprises *Anaerostipes hadrus*. In one embodiment, the bacterial population useful in the compositions and methods of the invention comprises *Anaerotruncus colihominis*. In one embodiment, the bacterial population useful in the compositions and methods of the invention comprises *Bacteroides caccae*. In one embodiment, the bacterial population useful in the compositions and methods of the invention comprises *Bacteroides cellulosilyticus*. In one embodiment, the bacterial population useful in the compositions and methods of the invention comprises *Bacteroides dorei*. In one embodiment, the bacterial population useful in the compositions and methods of the invention comprises *Bacteroides eggerthii*. In one embodiment, the bacterial population useful in the compositions and methods of the invention comprises *Bacteroides finegoldii*. In one embodiment, the bacterial population useful in the compositions and methods of the invention comprises *Bacteroides fragilis*. In one embodiment, the bacterial population useful in the compositions and methods of the invention comprises *Bacteroides massiliensis*. In one embodiment, the bacterial population useful in the compositions and methods of the invention comprises *Bacteroides ovatus*. In one embodiment, the bacterial population useful in the compositions and methods of the invention comprises *Bacteroides salanitronis*. In one embodiment, the bacterial population useful in the compositions and methods of the invention comprises *Bacteroides salyersiae*. In one embodiment, the bacterial population useful in the compositions and methods of the invention comprises *Bacteroides* sp. 1_1_6. In one embodiment, the bacterial population useful in the compositions and methods of the invention comprises *Bacteroides* sp. 3_1_23. In one embodiment, the bacterial population useful in the compositions and methods of the invention comprises *Bacteroides* sp. D20. In one embodiment, the bacterial population useful in the compositions and methods of the invention comprises *Bacteroides thetaiotaomicrond*. In one embodiment, the bacterial population useful in the compositions and methods of the invention comprises *Bacteroides uniformis*. In one embodiment, the bacterial population useful in the compositions and methods of the invention comprises *Bacteroides vulgatus*. In one embodiment, the bacterial population useful in the compositions and methods of the invention comprises *Bifidobacterium adolescentis*. In one embodiment, the bacterial population useful in the compositions and methods of the invention comprises *Bifidobacterium bifidum*. In one embodiment, the bacterial population useful in the compositions and methods of the invention comprises *Bifidobacterium breve*. In one embodiment, the bacterial population useful in the compositions and methods of the invention comprises *Bifidobacterium faecale*. In one embodiment, the bacterial population useful in the compositions and methods of the invention comprises *Bifidobacterium kashiwanohense*. In one embodiment, the bacterial population useful in the compositions and methods of the invention comprises *Bifidobacterium Iongum* subsp. *Longum*. In one embodiment, the bacterial population useful in the compositions and methods of the invention comprises *Bifidobacterium pseudocatenulatum*. In one embodiment, the bacterial population useful in the compositions and methods of the invention comprises *Bifidobacterium stercoris*. In one embodiment, the bacterial population useful in the compositions and methods of the invention comprises *Blautia (Ruminococcus) coccoides*. In one embodiment, the bacterial population useful in the compositions and methods of the invention comprises *Blautia faecis*. In one embodiment, the bacterial population useful in the compositions and methods of the invention comprises *Blautia glucerasea*. In one embodiment, the bacterial population useful in the compositions and methods of the invention comprises *Blautia (Ruminococcus) hansenii*. In one embodiment, the bacterial population useful in the compositions and methods of the invention comprises *Blautia hydrogenotrophica (Ruminococcus hydrogenotrophicus)*. In one embodiment, the bacterial population useful in the compositions and methods of the invention comprises *Blautia (Ruminococcus) luti*. In one embodiment, the bacterial population useful in the compositions and methods of the invention comprises *Blautia (Ruminococcus) obeum*. In one embodiment, the bacterial population useful in the compositions and methods of the invention comprises *Blautia producta (Ruminococcus productus)*. In one embodiment, the bacterial population useful in the compositions and methods of the invention comprises *Blautia (Ruminococcus) schinkii*. In one embodiment, the bacterial population useful in the compositions and methods of the invention comprises *Blautia stercoris*. In one embodiment, the bacterial population useful in the compositions and methods of the invention comprises *Blautia* uncultured bacterium clone BKLE_a03_2 (GenBank: EU469501.1). In one embodiment, the bacterial population useful in the compositions and methods of the invention comprises *Blautia* uncultured bacterium clone SJTU_B_14_30 (GenBank: EF402926.1). In one embodiment, the bacterial population useful in the compositions and methods of the invention comprises *Blautia* uncultured bacterium clone SJTU_C_14_16 (GenBank: EF404657.1). In one embodiment, the bacterial population useful in the compositions and methods of the invention comprises *Blautia* uncultured bacterium clone S1-5 (GenBank: GQ898099.1). In one embodiment, the bacterial population useful in the compositions and methods of the invention comprises *Blautia* uncultured PAC000178_s (www.ezbiocloud.net/eztaxon/hierarchy?m=browse&k=PAC000178&d=2). In one embodiment, the bacterial population useful in the compositions and methods of the invention comprises *Blautia wexlerae*. In one embodiment, the bacterial population useful in the compositions and methods of the invention comprises *Candidatus Arthromitus* sp. SFB-mouse-Yit. In one embodiment, the bacterial population useful in the compositions and methods of the invention comprises *Catenibacterium mitsuokai*. In one embodiment, the bacterial population useful in the compositions and methods of the invention comprises *Clostridiaceae* bacterium (*Dielma fastidiosa*) JC13. In one embodiment, the bacterial population useful in the compositions and methods of the invention comprises Clostridiales bacterium 1_7_47FAA. In one embodiment, the bacterial population useful in the compositions and methods of the invention comprises *Clostridium asparagiforme*. In one embodiment, the bacterial population useful in the compositions and methods of the invention comprises *Clostridium bolteae*. In one embodiment, the bacterial population useful in the compositions and methods of the invention comprises *Clostridium clostridioforme*. In one embodiment, the bacterial population useful in the compositions and methods of the invention comprises *Clostridium glycyrrhizinilyticum*. In one embodiment, the bacterial population useful in the compositions and methods of the invention comprises *Clostridium* (*Hungatella*) *hathewayi*. In one embodiment, the bacterial population useful in the compositions and methods of the invention comprises *Clostridium histolyticum*. In one embodiment, the bacterial population useful in the compositions and methods of the invention comprises *Clostridium indolis*. In one embodiment, the bacterial population useful in the compositions and methods of the invention comprises *Clostridium leptum*. In one embodiment, the bacterial population useful in the compositions and methods of the invention comprises *Clostridium* (*Tyzzerella*) *nexile*. In one embodiment, the bacterial population useful in the compositions and methods of the invention comprises *Clostridium perfringens*. In one embodiment, the bacterial population useful in the compositions and methods of the invention comprises *Clostridium* (*Erysipelatoclostridium*) *ramosum*. In one embodiment, the bacterial population useful in the compositions and methods of the invention comprises *Clostridium scindens*. In one embodiment, the bacterial entity, e.g., species or strain, useful in the compositions and methods of the invention is *Clostridium septum*. In one embodiment, the bacterial population useful in the compositions and methods of the invention comprises *Clostridium* sp. 14774. In one embodiment, the bacterial population useful in the compositions and methods of the invention comprises *Clostridium* sp. 7_3_54FAA. In one embodiment, the bacterial population useful in the compositions and methods of the invention comprises *Clostridium* sp. HGF2. In one embodiment, the bacterial population useful in the compositions and methods of the invention comprises *Clostridium symbiosum*. In one embodiment, the bacterial population useful in the compositions and methods of the invention comprises *Collinsella aerofaciens*. In one embodiment, the bacterial population useful in the compositions and methods of the invention comprises *Collinsella intestinalis*. In one embodiment, the bacterial population useful in the compositions and methods of the invention comprises *Coprobacillus* sp. D7. In one embodiment, the bacterial population useful in the compositions and methods of the invention comprises *Coprococcus catus*. In one embodiment, the bacterial population useful in the compositions and methods of the invention comprises *Coprococcus comes*. In one embodiment, the bacterial population useful in the compositions and methods of the invention comprises *Dorea formicigenerans*. In one embodiment, the bacterial population useful in the compositions and methods of the invention comprises *Dorea longicatena*. In one embodiment, the bacterial population useful in the compositions and methods of the invention comprises *Enterococcus faecalis*. In one embodiment, the bacterial population useful in the compositions and methods of the invention comprises *Enterococcus faecium*. In one embodiment, the bacterial population useful in the compositions and methods of the invention comprises *Erysipelotrichaceae* bacterium 3_1_53. In one embodiment, the bacterial population useful in the compositions and methods of the invention comprises *Escherichia coli*. In one embodiment, the bacterial population useful in the compositions and methods of the invention comprises *Escherichia coli* S88. In one embodiment, the bacterial population useful in the compositions and methods of the invention comprises *Eubacterium eligens*. In one embodiment, the bacterial population useful in the compositions and methods of the invention comprises *Eubacterium fissicatena*. In one embodiment, the bacterial population useful in the compositions and methods of the invention comprises *Eubacterium ramulus*. In one embodiment, the bacterial population useful in the compositions and methods of the invention comprises *Eubacterium rectale*. In one embodiment, the bacterial population useful in the compositions and methods of the invention comprises *Faecalibacterium prausnitzii*. In one embodiment, the bacterial population useful in the compositions and methods of the invention comprises *Flavonifractor plautii*. In one embodiment, the bacterial population useful in the compositions and methods of the invention comprises *Fusobacterium mortiferum*. In one embodiment, the bacterial population useful in the compositions and methods of the invention comprises *Fusobacterium nucleatum*. In one embodiment, the bacterial population useful in the compositions and methods of the invention comprises *Holdemania filiformis*. In one embodiment, the bacterial population useful in the compositions and methods of the invention comprises *Hydrogenoanaerobacterium saccharovorans*. In one embodiment, the bacterial population useful in the compositions and methods of the invention comprises *Klebsiella oxytoca*. In one embodiment, the bacterial population useful in the compositions and methods of the invention comprises *Lachnospiraceae* bacterium 3_1_57FAA_CT1. In one embodiment, the bacterial population useful in the compositions and methods of the invention comprises *Lachnospiraceae* bacterium 7_1_58FAA. In one embodiment, the bacterial population useful in the compositions and methods of the invention comprises *Lachnospiraceae* bacterium 5_1_57FAA. In one embodiment, the bacterial population useful in the compositions and methods of the invention comprises *Lactobacillus casei*. In one embodiment, the bacterial population useful in the compositions and methods of the invention comprises *Lactobacillus rhamnosus*. In one embodiment, the bacterial population useful in the compositions and methods of the invention comprises *Lactobacillus ruminis*. In one embodiment, the bacterial population useful in the compositions and methods of the invention comprises *Lactococcus casei*. In one embodiment, the bacterial population useful in the compositions and methods of the invention comprises *Odoribacter splanchnicus*. In one embodiment, the bacterial population useful in the compositions and methods of the invention comprises *Oscillibacter valericigenes*. In one embodiment, the bacterial population useful in the compositions and methods of the invention comprises *Parabacteroides gordonii*. In one embodiment, the bacterial population useful in the compositions and methods of the invention comprises *Parabacteroides johnsonii*. In one embodiment, the bacterial population useful in the compositions and methods of the invention comprises *Parabacteroides merdae*. In one embodiment, the bacterial population useful in the compositions and methods of the invention comprises *Pediococcus acidilactici*. In one embodiment, the bacterial population useful in the compositions and methods of the invention comprises *Peptostreptococcus asaccharolyticus*. In one embodiment, the bacterial population useful in the compositions and methods of the invention comprises *Propionibacterium granulosum*. In one embodiment, the bacterial population useful in the compositions and methods of the invention comprises *Roseburia intestinalis*. In one embodiment, the bacterial population useful in the compositions and methods of the invention comprises *Roseburia inulinivorans*. In one embodiment, the bacterial population useful in the compositions and methods of the invention comprises *Ruminococcus faecis*. In one embodiment, the bacterial population useful in the compositions and methods of the invention comprises *Ruminococcus gnavus*. In one embodiment, the bacterial population useful in the compositions and methods of the invention comprises *Ruminococcus* sp. ID8. In one embodiment, the bacterial population useful in the compositions and methods of the invention comprises *Ruminococcus torques*. In one embodiment, the bacterial population useful in the compositions and methods of the invention comprises *Slackia piriformis*. In one embodiment, the bacterial population useful in the compositions and methods of the invention comprises *Staphylococcus epidermidis*. In one embodiment, the bacterial population useful in the compositions and methods of the invention comprises *Staphylococcus saprophyticus*. In one embodiment, the bacterial population useful in the compositions and methods of the invention comprises *Streptococcus cristatus*. In one embodiment, the bacterial population useful in the compositions and methods of the invention comprises *Streptococcus dysgalactiae* subsp. *Equisimilis*. In one embodiment, the bacterial population useful in the compositions and methods of the invention comprises *Streptococcus infantis*. In one embodiment, the bacterial population useful in the compositions and methods of the invention comprises *Streptococcus oralis*. In one embodiment, the bacterial population useful in the compositions and methods of the invention comprises *Streptococcus sanguinis*. In one embodiment, the bacterial population useful in the compositions and methods of the invention comprises *Streptococcus viridans*. In one embodiment, the bacterial population useful in the compositions and methods of the invention comprises *Streptococcus thermophiles*. In one embodiment, the bacterial population useful in the compositions and methods of the invention comprises *Veillonella dispar*.

In some embodiments, the pharmaceutical composition comprises engineered bacteria. For example, engineered bacteria include bacteria harboring i) one or more genetic changes, such change being an insertion, deletion, translocation, or substitution, or any combination thereof, of one or more nucleotides contained on the bacterial chromosome or on an endogenous plasmid, wherein the genetic change may result in the alteration, disruption, removal, or addition of one or more protein-coding genes, non-protein-coding genes, gene regulatory regions, or any combination thereof, and wherein such change may be a fusion of two or more separate genomic regions or may be synthetically derived; ii) one or more foreign plasmids containing a mutant copy of an endogenous gene, such mutation being an insertion, deletion, or substitution, or any combination thereof, of one or more nucleotides; and iii) one or more foreign plasmids containing a mutant or non-mutant exogenous gene or a fusion of two or more endogenous, exogenous, or mixed genes. The engineered bacteria may be produced using techniques including but not limited to site-directed mutagenesis, transposon mutagenesis, knock-outs, knock-ins, polymerase chain reaction mutagenesis, chemical mutagenesis, ultraviolet light mutagenesis, transformation (chemically or by electroporation), phage transduction, or any combination thereof. Suitable bacteria for engineering are known in the art. For example, as described in PCT Publications Nos. WO 93/18163, DELIVERY AND EXPRESSION OF A HYBRID SURFACE PROTEIN ON THE SURFACE OF GRAM POSITIVE BACTERIA; WO 03/06593, METHODS FOR TREATING CANCER BY ADMINISTERING TUMOR-TARGETED BACTERIA AND AN IMMUNOMODULATORY AGENT; and WO 2010/141143, ENGINEERED AVIRULENT BACTERIA STRAINS AND USE IN MEDICAL TREATMENTS.

In some embodiments, the engineered bacteria are natural human commensals. In other embodiments, the engineered bacteria are attenuated strains of pathogens, and may include, but are not limited to, *Pseudomonas aeruginosa*, *Salmonella* species, *Listeria monocytogenes*, *Mycoplasma hominis*, *Escherichia coli*, *Shigella* species, and *Streptococcus* species, see, e.g. PCT Publications No. WO 03/06593, METHODS FOR TREATING CANCER BY ADMINISTERING TUMOR-TARGETTED BACTERIA AND AN IMMUNOMODULATORY AGENT. Attenuated strains of pathogens will lack all or parts of virulence operons, may lack immune-stimulatory surface moieties (e.g., lipopolysaccharide for Gram-negative bacteria), or may contain one or more nutrient auxotrophies. In specific embodiments, the engineered bacteria are attenuated intracellular pathogens, such as avirulent strains of *Listeria monocytogenes*.

In some embodiments, the composition of the invention comprises one or more types of bacteria (e.g., one or more bacterial species or more than one strain of a particular bacterial species) capable of producing butyrate in a mammalian subject. Butyrate-producing bacteria may be identified experimentally, such as by NMR or gas chromatography analyses of microbial products or colorimetric assays (Rose (1955) METHODS ENZYMOL. 1: 591-5). Butyrate-producing bacteria may also be identified computationally, such as by the identification of one or more enzymes involved in butyrate synthesis. Non-limiting examples of enzymes found in butyrate-producing bacteria include butyrate kinase, phosphotransbutyrylase, and butyryl CoA:acetate CoA transferase (Louis et al. (2004) J. BACT. 186(7): 2099-2106). Butyrate-producing strains include, but are not limited to, *Faecalibacterium prausnitzii, Eubacterium* spp., *Butyrivibrio fibrisolvens, Roseburia intestinalis, Clostridium* spp., *Anaerostipes caccae*, and *Ruminococcus* spp. In some embodiments, a pharmaceutical composition comprises two or more types of bacteria (e.g., two or more bacterial species or two or more strains of a particular bacterial species), wherein at least two types of bacteria are capable of producing butyrate in a mammalian subject. In other embodiments, the pharmaceutical composition comprises two or more types of bacteria, wherein two or more types of bacteria cooperate (i.e., cross-feed) to produce an immunomodulatory SCFA (e.g., butyrate) in a mammalian subject. In a preferred embodiment, the pharmaceutical composition comprises at least one type of bacteria (e.g., *Bifidobacterium* spp.) capable of metabolizing a prebiotic, including but not limited to, inulin, inulin-type fructans, or oligofructose, such that the resulting metabolic product may be converted by a second type of bacteria (e.g., a butyrate-producing bacteria such as *Roseburia* spp.) to an immunomodulatory SCFA such as butyrate (see, e.g., Falony et al. (2006) APPL. ENVIRON. MICROBIOL. 72(12): 7835-7841). In other aspects, the composition comprises at least one acetate-producing bacteria (e.g., *Bacteroides thetaiotaomicron*) and at least one acetate-consuming, butyrate-producing bacteria (e.g., *Faecalibacterium prausnitzii*).

In some embodiments, the pharmaceutical composition comprises one or more types of bacteria (e.g., one or more bacterial species or more than one strain of a particular bacterial species) capable of producing propionate in a mammalian subject, optionally further comprising a prebiotic or substrate appropriate for proprionate biosynthesis. Examples of prebiotics or substrates used for the production of propionate include, but are not limited to, L-rhamnose, D-tagalose, resistant starch, inulin, polydextrose, arabinoxylans, arabinoxylan oligosaccharides, mannooligosaccharides, and laminarans (Hosseini et al. (2011) NUTRITION REVIEWS 69(5): 245-258). Propionate-producing bacteria may be identified experimentally, such as by NMR or gas chromatography analyses of microbial products or colorimetric assays (Rose (1955)). Propionate-producing bacteria may also be identified computationally, such as by the identification of one or more enzymes involved in propionate biosynthesis. Non-limiting examples of enzymes found in propionate-producing bacteria include enzymes of the succinate pathway, including but not limited to phophoenylpyrvate carboxykinase, pyruvate kinase, pyruvate carboxylase, malate dehydrogenase, fumarate hydratase, succinate dehydrogenase, succinyl CoA synthetase, methylmalonyl Coa decarboxylase, and propionate CoA transferase, as well as enzymes of the acrylate pathway, including but not limited to L-lactate dehydrogenase, propionate CoA transferase, lactoyl CoA dehydratase, acyl CoA dehydrogenase, phosphate acetyltransferase, and propionate kinase. Non-limiting examples of bacteria that utilize the succinate pathway are *Bacteroides fragilis* and other species (including *Bacteroides vulgatus*), *Propionibacterium* spp. (including *freudenrichii* and *acidipropionici*), *Veillonella* spp. (including *gazogenes*), *Micrococcus lactilyticus, Selenomonas ruminantium, Escherichia coli*, and *Prevotella ruminocola*. Non-limiting examples of bacteria that utilize the acrylate pathway are *Clostridium neopropionicum* X4, and *Megasphaera elsdenii*.

In preferred embodiments, the combination of a bacteria and a prebiotic is selected based on the fermentation or metabolic preferences of one or more bacteria capable of producing immunomodulatory SCFAs (e.g., preference for complex versus simple sugar or preference for a fermentation product versus a prebiotic). For example, *M. eldsenii* prefers lactate fermentation to glucose fermentation, and maximization of propionate production by *M. eldsenii* in a mammalian subject may therefore be achieved by administering along with *M. eldsenii* a favored substrate (e.g., lactate) or one or more bacteria capable of fermenting glucose into lactate (e.g., *Streptococcus bovis*) (see, e.g., Hosseini et al. (2011)). Thus, in some embodiments, the composition comprises at least one type of SCFA-producing bacteria and a sugar fermentation product (e.g., lactate). In other embodiments, the composition comprises at least one type of SCFA-producing bacteria and at least one type of sugar-fermenting bacteria, wherein the fermentation product of the second, sugar-fermenting bacteria is the preferred substrate of the SCFA-producing bacteria.

Immunomodulation can also be achieved by the bacterial production of glutathione or gamma-glutamylcysteine. Thus, in certain embodiments, the pharmaceutical composition, dosage form, or kit comprises at least one type of bacteria (e.g., one or more bacterial species or more than one strain of a particular bacterial species) capable of producing glutathione and/or gamma-glutamylcysteine in a mammalian subject. In some aspects, the composition comprises one or more bacteria selected for the presence of glutamate cysteine ligase (e.g., *Lactobacillus fermentum*) and/or L-proline biosynthesis enzymes (e.g., *E. coli*) (Peran et al. (2006) INT. J. COLORECTAL DIS. 21(8): 737-746; Veeravalli et al. (2011) NAT. CHEM. BIO. 7(2): 101-105). In a preferred embodiment, at least one bacteria in the composition is *L. fermentum*.

Para-cresol (p-cresol) is a microbial product, via the fermentation of tyrosine or phenylalanine. Sulfated in the liver or colon to p-cresyl sulfate, this molecule reduces Th1-mediated responses (Shiba et al. (2014) TOXICOL. APPL. PHARMACOL. 274(2): 191-9). In some embodiments, the composition comprises at least one type of bacteria (e.g., one or more bacterial species or more than one strain of a particular bacterial species) capable of fermenting tyrosine and/or phenylalanine to p-cresol in a mammalian subject. Non-limiting examples of such bacteria include *Bacteroides fragilis, Clostridium difficile*, and *Lactobacillus* sp. Strain #11198-(see, e.g., Yokoyama and Carlson (1981) APPL. ENVIRON. MICROBIOL. 41(1): 71-76), and other bacteria with p-hydroxylphenyl acetate decarboxylase activity.

In one aspect, provided herein are therapeutic compositions (e.g., pharmaceutical compositions) containing a purified population of bacterial cells. As used herein, the terms "purify", "purified" and "purifying" refer to the state of a population (e.g., a plurality of known or unknown amount and/or concentration) of desired bacterial cells, that have undergone one or more processes of purification, e.g., a selection or an enrichment of the desired bacteria, or alternatively a removal or reduction of residual habitat products as described herein. In some embodiments, a purified population has no detectable undesired activity or, alternatively, the level or amount of the undesired activity is at or below an acceptable level or amount. In other embodiments, a purified population has an amount and/or concentration of desired bacterial cells at or above an acceptable amount and/or concentration. In other embodiments, the purified population of bacterial cells is enriched as compared to the starting material (e.g., a fecal material) from which the population is obtained. This enrichment may be by 10%, 20%, 30%, 40%, 50%, 60%, 70%, 80%, 85%, 90%, 91%, 92%, 93%, 94%, 95%, 96%, 97%, 98%, 99%, 99.9%, 99.99%, 99.999%, 99.9999%, 99.9999%, or greater than 99.999999%, as compared to the starting material.

In certain embodiments, the purified populations of bacterial cells have reduced or undetectable levels of one or more pathogenic activities, such as toxicity, an ability to cause infection of the mammalian recipient subject, an undesired immunomodulatory activity, an autoimmune response, a metabolic response, or an inflammatory response or a neurological response. Such a reduction in a pathogenic activity may be by 10%, 20%, 30%, 40%, 50%, 60%, 70%, 80%, 85%, 90%, 91%, 92%, 93%, 94%, 95%, 96%, 97%, 98%, 99%, 99.9%, 99.99%, 99.999%, 99.9999%, or greater than 99.9999%, as compared to the starting material. In other embodiments, the purified populations of bacterial cells have reduced sensory components as compared to fecal material, such as reduced odor, taste, appearance, and umami.

In another embodiment, the invention provides purified populations of bacterial cells that are substantially free of residual habitat products. In certain embodiments, this means that the bacterial composition no longer contains a substantial amount of the biological matter associated with the microbial community while living on or in the human or animal subject, and the purified population of bacterial cells (e.g., bacterial spores or vegetative cells) may be 100% free, 99% free, 98% free, 97% free, 96% free, 95% free, 94% free, 93% free, 92% free, 91% free, 90% free, 85% free, 80% free, 75% free, 70% free, 60% free, or 50% free, of any contamination of the biological matter associated with the microbial community. Substantially free of residual habitat products may also mean that the bacterial composition contains no detectable cells from a human or animal, and that only microbial cells are detectable, in particular, only desired microbial cells are detectable. In another embodiment, it means that fewer than $1\times10^{-2}$%, $1\times10^{-3}$%, $1\times10^{-4}$%, $1\times10^{-5}$%, $1\times10^{-6}$%, $1\times10^{-7}$%, $1\times10^{-8}$% of the cells in the bacterial composition are human or animal, as compared to microbial cells. In another embodiment, the residual habitat product present in the purified population is reduced at least a certain level from the fecal material obtained from the mammalian donor subject, e.g., reduced by at least about 10%, 20%, 30%, 40%, 50%, 60%, 70%, 80%, 90%, 91%, 92%, 93%, 94%, 95%, 96%, 97%, 98%, 99%, 99.9%, 99.99%, 99.999%, 99.9999%, or greater than 99.9999%.

In one embodiment, substantially free of residual habitat products or substantially free of a detectable level of a pathogenic material means that the bacterial composition contains no detectable viral (including bacterial viruses (i.e., phage)), fungal, or mycoplasmal or toxoplasmal contaminants, or a eukaryotic parasite such as a helminth. Alternatively, the purified population of bacterial cells (e.g., bacterial spores and/or vegetative cells) is substantially free of an acellular material, e.g., DNA, viral coat material, or non-viable bacterial material. Alternatively, the purified population of bacterial cells may processed by a method that kills, inactivates, or removes one or more specific undesirable viruses, such as an enteric virus, including norovirus, poliovirus or hepatitis A virus.

As described herein, purified populations of bacterial cells can be demonstrated by, for example, genetic analysis (e.g., PCR, DNA sequencing), serology and antigen analysis, microscopic analysis, microbial analysis including germination and culturing, or methods using instrumentation such as flow cytometry with reagents that distinguish desired bacterial entities and/or fungal entities from non-desired, contaminating materials. In yet another embodiment, the spores in a purified population of bacterial cells undergo partial germination during processing and formulation such that the final composition comprises spores and vegetative bacteria.

In another embodiment, provided herein are methods for production of a pharmaceutical composition, e.g., a probiotic composition, comprising a population of bacterial cells (e.g., a population of anti-inflammatory bacterial cells), with or without one or more prebiotics, suitable for therapeutic administration to a mammalian subject in need thereof. In one embodiment, the composition can be produced by generally following the steps of: (a) providing a fecal material obtained from a mammalian donor subject; and (b) subjecting the fecal material to at least one purification treatment or step under conditions such that a population of bacterial cells is produced from the fecal material.

Individual bacterial strains can also be isolated from stool samples using culture methods. For example, 5 mls of phosphate-buffered saline (PBS) is added to 1 mg of frozen stool sample and homogenized by vortexing in an anaerobic chamber for isolation of anaerobic bacteria. The suspension is then serially diluted ten-fold (e.g., $10^{-1}$ to $10^{-9}$ dilutions) and 100 µl aliquots of each dilution are spread evenly over the surface of agar plates containing different formulations e.g., anaerobic blood agar plates, *Bacteroides* bile esculin plates, laked kanamycin vancomycin plates, egg yolk agar plates and de Man Rogosa and Sharpe agar plates. Inverted plates are incubated in an anaerobic chamber for 48 hr+/−4 hours. Colonies with different morphologies are picked and replated on anaerobic blood agar plates for further testing, PCR analysis and 16 S sequencing. Selected bacterial strains can be grown for therapeutic use singly or in combination.

In one embodiment, a probiotic composition of the invention is not a fecal transplant. In some embodiments all or essentially all of the bacterial entities present in a purified population are originally obtained from a fecal material and subsequently, e.g., for production of pharmaceutical compositions, are grown in culture as described herein or otherwise known in the art. In some embodiments all or essentially all of the bacterial entities and/or fungal entities present in a purified population are obtained from a fecal material and subsequently are grown in culture as described herein or otherwise known in the art. In one embodiment, the bacterial cells are cultured from a bacterial stock and purified as described herein. In one embodiment, each of the populations of bacterial cells are independently cultured and purified, e.g., each population is cultured separately and subsequently mixed together. In one embodiment, one or more of the populations of bacterial cells in the composition are co-cultured.

Identification of Immunomodulatory Bacteria.

In some embodiments, immunomodulatory bacteria are identified by screening bacteria to determine whether the bacteria induce secretion of a pro-inflammatory or a anti-inflammatory cytokines by a host cell (e.g., a host immune cell). In some embodiments, the immunomodulatory bacteria are screened in vitro. For example, human or mammalian cells capable of cytokine secretion, such as immune cells (e.g., PBMCs, macrophages, T cells, etc.) can be exposed to candidate immunomodulatory bacteria, or supernatants obtained from cultures of candidate immunomodulatory bacteria, and changes in cytokine expression or secretion can be measured using standard techniques, such as ELISA, immunoblot, Luminex, antibody array, quantitative PCR, microarray, etc. Bacteria for inclusion in a pharmaceutical composition (e.g., a probiotic composition) can be selected based on the ability to induce a desired cytokine profile in human or mammalian cells (e.g., immune cells). For example, anti-inflammatory bacteria can be selected for inclusion in a pharmaceutical composition based on the ability to induce secretion of one or more anti-inflammatory cytokines, and/or the ability to reduce secretion of one or more pro-inflammatory cytokines. Anti-inflammatory cytokines include, for example, IL-10, IL-13, IL-9, IL-4, IL-5, TGFβ, and combinations thereof. Pro-inflammatory cytokines include, for example, IFNγ, IL-12p70, IL-1α, IL-6, IL-8, MCP1, MIP1α, MIP1β, TNFα, and combinations thereof. In some embodiments, anti-inflammatory bacteria may be selected for inclusion in a pharmaceutical compositions based on the ability to modulate the secretion of one or more anti-inflammatory cytokines and/or that ability to reduce secretion of one or pro-inflammatory cytokines that have been induced by a bacterial cell of a different bacteria type. In some embodiments, the different bacterial cell is of a different bacterial genus. In some embodiments, the different bacterial cell is of a different bacterial species. In some embodiments, the different bacterial cell is of a different bacterial strain.

In other embodiments, immunomodulatory bacteria are identified by screening bacteria to determine whether the bacteria impact the differentiation and/or expansion of particular subpopulations of immune cells. For example, candidate bacteria can be screened for the ability to promote differentiation and/or expansion of Treg cells, Th17 cells, Th1 cells and/or Th2 cells from precursor cells, e.g., naive T cells. By way of example, naïve T cells can be cultured in the presence of candidate bacteria or supernatants obtained from cultures of candidate bacteria, and the quantity of Treg cells, Th17 cells, Th1 cells and/or Th2 cells can be determined using standard techniques, such as FACS analysis. Markers indicative of Treg cells include, for example, $CD25^+CD127^{lo}$. Markers indicative of Th17 cells include, for example, $CXCR3^-$ $CCR6^+$. Markers indicative of Th1 cells include, for example, $CXCR3^+CCR6^-$. Markers indicative of Th2 cells include, for example, $CXCR3^+CCR6^-$. Other markers indicative of particular T cell subpopulations are known in the art, and may be used in the assays described herein, e.g., to identify populations of immune cells impacted by candidate immunomodulatory bacteria. Bacteria can be selected for inclusion in a pharmaceutical composition based on the ability to promote differentiation and/or expansion of a desired immune cell subpopulation.

In other embodiments, immunomodulatory bacteria are identified by screening bacteria to determine whether the bacteria secrete short chain fatty acids (SCFA), such as, for example, butyrate, acetate, propionate, or valerate, or combinations thereof. For example, secretion of short chain fatty acids into bacterial supernatants can be measured using standard techniques. In one embodiment, bacterial supernatants can be screened to measure the level of one or more short chain fatty acids using NMR, mass spectrometry (e.g., GC-MS, tandem mass spectrometry, matrix-assisted laser desorption/ionization, etc.), ELISA, or immunoblot. Expression of bacterial genes responsible for production of short chain fatty acids can also be determined by standard techniques, such as Northern blot, microarray, or quantitative PCR.

In some embodiments, provided herein are pharmaceutical compositions comprising a population of bacterial cells (e.g., bacterial cells of the order Clostridiales) containing one type of bacteria. In some embodiments, provided herein are pharmaceutical compositions comprising a population of bacterial cells (e.g., bacterial cells of the Order Clostridiales) containing more than one type of bacteria. As used herein, a "type" or more than one "types" of bacteria may be differentiated at the genus level, the species level, the sub-species level, the strain level or by any other taxonomic method, as described herein and otherwise known in the art.

In some embodiment, the pharmaceutical composition may contain one or more types of bacteria, including bacterial strains of the same species or of different species. For instance, a pharmaceutical composition may comprise bacterial cells of 1, at least 2, at least 3, or at least 4 types of bacteria. In another embodiment, a bacterial composition may comprise at least 5, at least 6, at least 7, at least 8, at least 9, at least 10, at least 11, at least 12, at least 13, at least 14, at least 15, at least 16, at least 17, at least 18, at least 19, or at least 20, at least 30, at least 40, at least 50, or more than 50 types of bacteria, as defined by species or operational taxonomic unit (OTU) encompassing such species. In a preferred embodiment, a pharmaceutical composition comprises from 2 to no more than 40, from 2 to no more than 30, from 2 to no more than 20, from 2 to no more than 15, from 2 to no more than 10, from 2 to no more than 5, types of bacteria. In another preferred embodiment, a bacterial composition comprises a single type of bacteria.

In a preferred embodiment, the composition comprises about 20 or fewer isolated populations of bacterial cells. In another embodiment, the composition comprises about 15 or fewer isolated populations of bacterial cells. In another embodiment, the composition comprises about 10 or fewer isolated populations of bacterial cells. In another embodiment, the composition comprises about 5 or fewer isolated populations of bacterial cells. In another embodiment, the composition comprises about 4 or fewer isolated populations of bacterial cells. In another embodiment, the composition comprises about 3 or fewer isolated populations of bacterial cells. In another embodiment, the composition comprises about 2 isolated populations of bacterial cells. In another embodiment, the composition comprises between about 12 and 20 isolated populations of bacterial cells. In another embodiment, the composition comprises a single isolated population of bacterial cells. In another embodiment, the composition comprises at least two isolated populations of bacterial cells. In yet another embodiment, the composition comprises about 1, 2, 3, 4, 5, 6, 7, 8, 9, 10, 11, 12, 13, 14, 15, 16, 17, 18, 19, or 20 isolated populations of bacterial cells.

In some embodiments, the pharmaceutical composition contains a defined mixture of isolated bacteria. For example, in some embodiments, the pharmaceutical composition contains no more than 100 types of bacteria. In other embodiments, the pharmaceutical composition contains no more than 75 types of bacteria. In some embodiments, the pharmaceutical composition contains no more than 60 types of bacteria. In other embodiments, the pharmaceutical composition contains no more than 50 types of bacteria. In some embodiments, the pharmaceutical composition contains no more than 45 types of bacteria. In other embodiments, the pharmaceutical composition contains no more than 40 types of bacteria. In some embodiments, the pharmaceutical composition contains no more than 35 types of bacteria. In other embodiments, the pharmaceutical composition contains no more than 30 types of bacteria. In some embodiments, the pharmaceutical composition contains no more than 25 types of bacteria. In other embodiments, the pharmaceutical composition contains no more than 20 types of bacteria. In some embodiments, the pharmaceutical composition contains no more than 15 types of bacteria. In other embodiments, the pharmaceutical composition contains no more than 14 types of bacteria. In some embodiments, the pharmaceutical composition contains no more than 13 types of bacteria. In other embodiments, the pharmaceutical composition contains no more than 12 types of bacteria. In some embodiments, the pharmaceutical composition contains no more than 11 types of bacteria. In other embodiments, the pharmaceutical composition contains no more than 10 types of bacteria. In some embodiments, the pharmaceutical composition contains no more than 9 types of bacteria. In other embodiments, the pharmaceutical composition contains no more than 8 types of bacteria. In some embodiments, the pharmaceutical composition contains no more than 7 types of bacteria. In other embodiments, the pharmaceutical composition contains no more than 6 types of bacteria. In some embodiments, the pharmaceutical composition contains no more than 5 types of bacteria. In other embodiments, the pharmaceutical composition contains no more than 4 types of bacteria. In some embodiments, the pharmaceutical composition contains no more than 3 types of bacteria. In other embodiments, the pharmaceutical composition contains no more than 2 types of bacteria. In some embodiments, the pharmaceutical composition contains no more than 1 type of bacteria. In some embodiments, the pharmaceutical composition contains defined quantities of each bacterial species. In an exemplary embodiment, the bacteria incorporated into the pharmaceutical composition are not isolated from fecal matter Provided herein are pharmaceutical compositions comprising at least one, at least two or at least three types of bacteria that are not identical and that are capable of decreasing the risk and/or severity of an autoimmune or inflammatory disease, symptom, condition, or disorder, or dysbiosis. In an embodiment, the pharmaceutical composition comprises at least about 2, 3, 4, 5, 6, 7, 8, 9, or 10 types of isolated bacteria. In one embodiment, the pharmaceutical composition comprises at least about 4 types of isolated bacteria or at least about 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50 or more types of isolated bacteria. In some embodiments, the above invention relates to pharmaceutical compositions further comprising one or more prebiotics.

In some embodiments, the pharmaceutical composition of the invention includes at least one type of bacteria, wherein said bacteria is a bacterial strain (e.g., strain of anti-inflammatory bacterial cells), and the composition includes at least $1 \times 10^3$ colony forming units (CFU) per dose of said bacterial strain. In other embodiments, the pharmaceutical composition of the invention includes at least one type of bacteria, wherein said bacteria is a bacterial strain, and the composition includes at least about $1 \times 10^3$, $1 \times 10^4$, $1 \times 10^5$, $1 \times 10^6$, $1 \times 10^7$, $1 \times 10^8$, $1 \times 10^9$, $1 \times 10^{10}$, $1 \times 10^{11}$, $1 \times 10^{12}$, $1 \times 10^{13}$, $1 \times 10^{14}$, $1 \times 10^{15}$, or greater than $1 \times 10^{15}$ CFU per dose of each bacterial strain present in the composition.

In some embodiments, the pharmaceutical compositions of the invention are formulated for oral or gastric administration, typically to a mammalian subject (e.g., a human). In some embodiments, the composition is formulated for oral administration as a solid, semi-solid, gel, or liquid form, such as in the form of a pill, tablet, capsule, or lozenge. In another embodiment, the pharmaceutical composition is formulated as a skin patch. In another embodiment, the pharmaceutical composition is formulated for topical administration. In one embodiment, the pharmaceutical composition is formulated as a food product. In some embodiments, such formulations contain or are coated by an enteric coating to protect the bacterial strain through the stomach and small intestine, although spores are generally resistant to the stomach and small intestines. In other embodiments, the pharmaceutical compositions may be formulated with a germinant to enhance engraftment, or efficacy. In yet other embodiments, the pharmaceutical compositions may be co-formulated or co-administered with prebiotic substances, to enhance engraftment or efficacy.

The composition(s) may include different types of carriers depending on whether it is to be administered in solid, liquid or aerosol form, and whether it needs to be sterile for such routes of administration such as injection. The present invention can be administered intravenously, intradermally, intraarterially, intraperitoneally, intralesionally, intracranially, intraarticularly, intraprostaticaly, intrapleurally, intratracheally, intranasally, intravitreally, intravaginally, intrarectally, topically, intratumorally, intramuscularly, intraperitoneally, subcutaneously, subconjunctival, intravesicularlly, mucosally, intlrapericardially, intraumbilically, intraocularally, orally, topically, locally, as an injection, infusion, continuous infusion, localized perfusion bathing target cells directly, via a catheter, via a lavage, in lipid compositions (e.g., liposomes), as an aerosol, or by other method or any combination of the fore going as would be known to one of ordinary skill in the art (see, for example, Remington's Pharmaceutical Sciences, 18th Ed. Mack Printing Company, 1990, incorporated herein by reference).

In some embodiments, the composition comprises at least one lipid. As used herein, a "lipid" includes fats, oils, triglycerides, cholesterol, phospholipids, fatty acids in any form including free fatty acids. Fats, oils and fatty acids can be saturated, unsaturated (cis or trans) or partially unsaturated (cis or trans). In some embodiments, the lipid comprises at least one fatty acid selected from lauric acid (12:0), myristic acid (14:0), palmitic acid (16:0), palmitoleic acid (16:1), margaric acid (17:0), heptadecenoic acid (17:1), stearic acid (18:0), oleic acid (18:1), linoleic acid (18:2), linolenic acid (18:3), octadecatetraenoic acid (18:4), arachidic acid (20:0), eicosenoic acid (20:1), eicosadienoic acid (20:2), eicosatetraenoic acid (20:4), eicosapentaenoic acid (20:5) (EPA), docosanoic acid (22:0), docosenoic acid (22:1), docosapentaenoic acid (22:5), docosahexaenoic acid (22:6) (DHA), and tetracosanoic acid (24:0). In other embodiments, the composition comprises at least one modified lipid, for example, a lipid that has been modified by cooking.

In some embodiments, the composition comprises at least one supplemental mineral or mineral source. Examples of minerals include, without limitation: chloride, sodium, calcium, iron, chromium, copper, iodine, zinc, magnesium, manganese, molybdenum, phosphorus, potassium, and selenium. Suitable forms of any of the foregoing minerals include soluble mineral salts, slightly soluble mineral salts, insoluble mineral salts, chelated minerals, mineral complexes, non-reactive minerals such as carbonyl minerals, and reduced minerals, and combinations thereof.

In certain embodiments, the composition comprises at least one supplemental vitamin. The at least one vitamin can be fat-soluble or water soluble vitamins. Suitable vitamins include but are not limited to vitamin C, vitamin A, vitamin E, vitamin B12, vitamin K, riboflavin, niacin, vitamin D, vitamin B6, folic acid, pyridoxine, thiamine, pantothenic acid, and biotin. Suitable forms of any of the foregoing are salts of the vitamin, derivatives of the vitamin, compounds having the same or similar activity of the vitamin, and metabolites of the vitamin.

In other embodiments, the pharmaceutical composition comprises an excipient. Non-limiting examples of suitable excipients include a buffering agent, a preservative, a stabilizer, a binder, a compaction agent, a lubricant, a dispersion enhancer, a disintegration agent, a flavoring agent, a sweetener, and a coloring agent.

In another embodiment, the excipient is a buffering agent. Non-limiting examples of suitable buffering agents include sodium citrate, magnesium carbonate, magnesium bicarbonate, calcium carbonate, and calcium bicarbonate.

In some embodiments, the excipient comprises a preservative. Non-limiting examples of suitable preservatives include antioxidants, such as alpha-tocopherol and ascorbate, and antimicrobials, such as parabens, chlorobutanol, and phenol.

In cases where a pharmaceutical composition contains a anaerobic bacterial strain, the pharmaceutical formulation and excipients can be selected to prevent exposure of the bacterial strains to oxygen.

In other embodiments, the composition comprises a binder as an excipient. Non-limiting examples of suitable binders include starches, pregelatinized starches, gelatin, polyvinylpyrolidone, cellulose, methylcellulose, sodium carboxymethylcellulose, ethylcellulose, polyacrylamides, polyvinyloxoazolidone, polyvinylalcohols, $C_{12}$-$C_{18}$ fatty acid alcohol, polyethylene glycol, polyols, saccharides, oligosaccharides, and combinations thereof.

In another embodiment, the composition comprises a lubricant as an excipient. Non-limiting examples of suitable lubricants include magnesium stearate, calcium stearate, zinc stearate, hydrogenated vegetable oils, sterotex, polyoxyethylene monostearate, talc, polyethyleneglycol, sodium benzoate, sodium lauryl sulfate, magnesium lauryl sulfate, and light mineral oil.

In other embodiments, the composition comprises a dispersion enhancer as an excipient. Non-limiting examples of suitable dispersants include starch, alginic acid, polyvinylpyrrolidones, guar gum, kaolin, bentonite, purified wood cellulose, sodium starch glycolate, isoamorphous silicate, and microcrystalline cellulose as high HLB emulsifier surfactants.

In some embodiments, the pharmaceutical composition comprises a disintegrant as an excipient. In other embodiments, the disintegrant is a non-effervescent disintegrant. Non-limiting examples of suitable non-effervescent disintegrants include starches such as corn starch, potato starch, pregelatinized and modified starches thereof, sweeteners, clays, such as bentonite, micro-crystalline cellulose, alginates, sodium starch glycolate, gums such as agar, guar, locust bean, karaya, pecitin, and tragacanth. In another embodiment, the disintegrant is an effervescent disintegrant. Non-limiting examples of suitable effervescent disintegrants include sodium bicarbonate in combination with citric acid, and sodium bicarbonate in combination with tartaric acid.

In another embodiment, the excipient comprises a flavoring agent. Flavoring agents can be chosen from synthetic flavor oils and flavoring aromatics; natural oils; extracts from plants, leaves, flowers, and fruits; and combinations thereof. In some embodiments the flavoring agent is selected from cinnamon oils; oil of wintergreen; peppermint oils; clover oil; hay oil; anise oil; eucalyptus; vanilla; citrus oil such as lemon oil, orange oil, grape and grapefruit oil; and fruit essences including apple, peach, pear, strawberry, raspberry, cherry, plum, pineapple, and apricot.

In other embodiments, the excipient comprises a sweetener. Non-limiting examples of suitable sweeteners include glucose (corn syrup), dextrose, invert sugar, fructose, and mixtures thereof (when not used as a carrier); saccharin and its various salts such as the sodium salt; dipeptide sweeteners such as aspartame; dihydrochalcone compounds, glycyrrhizin; *Stevia Rebaudiana* (Stevioside); chloro derivatives of sucrose such as sucralose; and sugar alcohols such as sorbitol, mannitol, sylitol, and the like. Also contemplated are hydrogenated starch hydrolysates and the synthetic sweetener 3,6-dihydro-6-methyl-1,2,3-oxathiazin-4-one-2, 2-dioxide, particularly the potassium salt (acesulfame-K), and sodium and calcium salts thereof.

In yet other embodiments, the composition comprises a coloring agent. Non-limiting examples of suitable color agents include food, drug and cosmetic colors (FD&C), drug and cosmetic colors (D&C), and external drug and cosmetic colors (Ext. D&C). The coloring agents can be used as dyes or their corresponding lakes.

The weight fraction of the excipient or combination of excipients in the formulation of the pharmaceutical composition is usually about 99% or less, such as about 95% or less, about 90% or less, about 85% or less, about 80% or less, about 75% or less, about 70% or less, about 65% or less, about 60% or less, about 55% or less, 50% or less, about 45% or less, about 40% or less, about 35% or less, about 30% or less, about 25% or less, about 20% or less, about 15% or less, about 10% or less, about 5% or less, about 2% or less, or about 1% or less of the total weight of the composition.

The compositions disclosed herein can be formulated into a variety of forms and administered by a number of different means. The compositions can be administered orally, rectally, or parenterally, in formulations containing conventionally acceptable carriers, adjuvants, and vehicles as desired. The term "parenteral" as used herein includes subcutaneous, intravenous, intramuscular, or intrasternal injection and infusion techniques. In an exemplary embodiment, the composition is administered orally.

Solid dosage forms for oral administration include capsules, tablets, caplets, pills, troches, lozenges, powders, and granules. A capsule typically comprises a core material comprising a bacterial composition and a shell wall that encapsulates the core material. In some embodiments, the core material comprises at least one of a solid, a liquid, and an emulsion. In other embodiments, the shell wall material comprises at least one of a soft gelatin, a hard gelatin, and a polymer. Suitable polymers include, but are not limited to: cellulosic polymers such as hydroxypropyl cellulose, hydroxyethyl cellulose, hydroxypropyl methyl cellulose (HPMC), methyl cellulose, ethyl cellulose, cellulose acetate, cellulose acetate phthalate, cellulose acetate trimellitate, hydroxypropylmethyl cellulose phthalate, hydroxypropylmethyl cellulose succinate and carboxymethylcellulose sodium; acrylic acid polymers and copolymers, such as those formed from acrylic acid, methacrylic acid, methyl acrylate, ammonio methylacrylate, ethyl acrylate, methyl methacrylate and/or ethyl methacrylate (e.g., those copolymers sold under the trade name "Eudragit"); vinyl polymers and copolymers such as polyvinyl pyrrolidone, polyvinyl acetate, polyvinylacetate phthalate, vinylacetate crotonic acid copolymer, and ethylene-vinyl acetate copolymers; and shellac (purified lac). In yet other embodiments, at least one polymer functions as taste-masking agents.

Tablets, pills, and the like can be compressed, multiply compressed, multiply layered, and/or coated. The coating can be single or multiple. In one embodiment, the coating material comprises at least one of a saccharide, a polysaccharide, and glycoproteins extracted from at least one of a plant, a fungus, and a microbe. Non-limiting examples include corn starch, wheat starch, potato starch, tapioca starch, cellulose, hemicellulose, dextrans, maltodextrin, cyclodextrins, inulins, pectin, mannans, gum arabic, locust bean gum, mesquite gum, guar gum, gum karaya, gum ghatti, tragacanth gum, funori, carrageenans, agar, alginates, chitosans, or gellan gum. In some embodiments the coating material comprises a protein. In another embodiment, the coating material comprises at least one of a fat and an oil. In other embodiments, the at least one of a fat and an oil is high temperature melting. In yet another embodiment, the at least one of a fat and an oil is hydrogenated or partially hydrogenated. In one embodiment, the at least one of a fat and an oil is derived from a plant. In other embodiments, the at least one of a fat and an oil comprises at least one of glycerides, free fatty acids, and fatty acid esters. In some embodiments, the coating material comprises at least one edible wax. The edible wax can be derived from animals, insects, or plants. Non-limiting examples include beeswax, lanolin, bayberry wax, carnauba wax, and rice bran wax. Tablets and pills can additionally be prepared with enteric coatings.

Alternatively, powders or granules embodying the bacterial compositions disclosed herein can be incorporated into a food product. In some embodiments, the food product is a drink for oral administration. Non-limiting examples of a suitable drink include fruit juice, a fruit drink, an artificially flavored drink, an artificially sweetened drink, a carbonated beverage, a sports drink, a liquid diary product, a shake, an alcoholic beverage, a caffeinated beverage, infant formula and so forth. Other suitable means for oral administration include aqueous and nonaqueous solutions, emulsions, suspensions and solutions and/or suspensions reconstituted from non-effervescent granules, containing at least one of suitable solvents, preservatives, emulsifying agents, suspending agents, diluents, sweeteners, coloring agents, and flavoring agents.

In some embodiments, the food product can be a solid foodstuff. Suitable examples of a solid foodstuff include without limitation a food bar, a snack bar, a cookie, a brownie, a muffin, a cracker, an ice cream bar, a frozen yogurt bar, and the like.

In other embodiments, the pharmaceutical compositions disclosed herein are incorporated into a therapeutic food. In some embodiments, the therapeutic food is a ready-to-use food that optionally contains some or all essential macronutrients and micronutrients. In another embodiment, the compositions disclosed herein are incorporated into a supplementary food that is designed to be blended into an existing meal. In one embodiment, the supplemental food contains some or all essential macronutrients and micronutrients. In another embodiment, the bacterial compositions disclosed herein are blended with or added to an existing food to fortify the food's protein nutrition. Examples include food staples (grain, salt, sugar, cooking oil, margarine), beverages (coffee, tea, soda, beer, liquor, sports drinks), snacks, sweets and other foods.

In one embodiment, the formulations are filled into gelatin capsules for oral administration. An example of an appropriate capsule is a 250 mg gelatin capsule containing from 10 mg (up to 100 mg) of lyophilized powder ($10^8$ to $10^{11}$ CFUs), 160 mg microcrystalline cellulose, 77.5 mg gelatin, and 2.5 mg magnesium stearate. In an alternative embodiment, from $10^5$ to $10^{12}$, $10^5$ to $10^7$, $10^6$ to $10^7$, or $10^8$ to $10^{10}$ CFUs may be used, with attendant adjustments of the excipients if necessary. In an alternative embodiment, an enteric-coated capsule or tablet or with a buffering or protective composition can be used.

The pharmaceutical compositions, with or without one or more prebiotics, are generally formulated for oral or gastric administration, typically to a mammalian subject. In particular embodiments, the composition is formulated for oral administration as a solid, semi-solid, gel, or liquid form, such as in the form of a pill, tablet, capsule, or lozenge. In some embodiments, such formulations contain or are coated by an enteric coating to protect the bacteria through the stomach and small intestine, although spores are generally resistant to the stomach and small intestines. In other embodiments, the pharmaceutical compositions, with or without one or more prebiotics, may be formulated with a germinant to enhance engraftment, or efficacy. In yet other embodiments, the pharmaceutical compositions may be co-formulated or co-administered with prebiotic substances, to enhance engraftment or efficacy. In some embodiments, bacterial compositions may be co-formulated or co-administered with prebiotic substances, to enhance engraftment or efficacy.

In some formulations, the pharmaceutical composition contains at least about 0.5%, 1%, 2%, 5%, 10%, 20%, 30%, 40%, 50%, 60%, 70%, 80%, 90% or greater than 90% spores on a mass basis. In some formulations, the administered dose does not exceed 200, 300, 400, 500, 600, 700, 800, 900 milligrams or 1, 1.1, 1.2, 1.3, 1.4, 1.5, 1.6, 1.7, 1.8, or 1.9 grams in mass.

The pharmaceutical compositions of the invention may include live microbes, dead microbes, microbes that are lyophilized, freeze-dried, and/or substantially dehydrated, or the composition may include bacterial or fungal spores or virions.

Bacterial compositions for use in the pharmaceutical compositions can be described by operational taxonomic units (OTUs). Bacterial compositions may be prepared comprising one or at least two types of isolated bacteria, wherein a first type and a second type are independently chosen from the species or OTUs listed in Table 1. Additionally, a bacterial composition may be prepared comprising at least two types of isolated bacteria, wherein a first OTU and a second OTU are independently characterized by, i.e., at least 95%, 96%, 97%. 98%, 99% or including 100% sequence identity to, sequences listed.

Pharmaceutical compositions may be prepared comprising one or at least two types of isolated bacteria, chosen from the species in Table 1, Table 1A, Table 1B, Table 1C, Table 1D, Table 1E, or Table 1F. Generally, the first bacteria and the second bacteria are not the same. The sequences provided in the sequencing listing file for OTUs in Table 1 are full 16S sequences. Therefore, in one embodiment, the first and/or second OTUs may be characterized by the full 16S sequences of OTUs listed in Table 1. In another embodiment, the first and/or second OTUs may be characterized by one or more of the variable regions of the 16S sequence (V1-V9). In some embodiments, at least one of the V1, V2, V3, V4, V5, V6, V7, V8, and V9 regions are used to characterize an OTU. In one embodiment, the V1, V2, and V3 regions are used to characterize an OTU. In another embodiment, the V3, V4, and V5 regions are used to characterize an OTU. In another embodiment, the V4 region is used to characterize an OTU.

Using well known techniques, in order to determine the full 16S sequence or the sequence of any hypervariable region of the 16S sequence, genomic DNA is extracted from a bacterial sample, the 16S rDNA (full region or specific hypervariable regions) amplified using polymerase chain reaction (PCR), the PCR products cleaned, and nucleotide sequences delineated to determine the genetic composition of 16S gene or subdomain of the gene. If full 16S sequencing is performed, the sequencing method used may be, but is not limited to, Sanger sequencing. If one or more hypervariable regions are used, such as the V4 region, the sequencing may be, but is not limited to being, performed using the Sanger method or using a next-generation sequencing method, such as an Illumina (sequencing by synthesis) method using barcoded primers allowing for multiplex reactions.

OTUs can be defined by a combination of nucleotide markers or genes, in particular highly conserved genes (e.g., "house-keeping" genes), or a combination thereof, full-genome sequence, or partial genome sequence generated using amplified genetic products, or whole genome sequence (WGS). Using well defined methods DNA extracted from a bacterial sample will have specific genomic regions amplified using PCR and sequenced to determine the nucleotide sequence of the amplified products. In the whole genome shotgun (WGS) method, extracted DNA will be directly sequenced without amplification. Sequence data can be generated using any sequencing technology including, but not limited to Sanger, Illumina, 454 Life Sciences, Ion Torrent, ABI, Pacific Biosciences, and/or Oxford Nanopore.

Prebiotics

In one aspect, the pharmaceutical compositions described herein contain a prebiotic. In another aspect, the pharmaceutical compositions are co-administered with a prebiotic (e.g., sequentially or concurrently). A prebiotic is a selectively fermented ingredient that allows specific changes, both in the composition and/or activity in the gastrointestinal microbiota, that confers benefits upon host well-being and health. Prebiotics can include complex carbohydrates, amino acids, peptides, or other nutritional components useful for the survival of the bacterial composition. Prebiotics include, but are not limited to, amino acids, biotin, fructooligosaccharide, galactooligosaccharides, inulin, lactulose, mannan oligosaccharides, oligofructose-enriched inulin, oligofructose, oligodextrose, tagatose, trans-galactooligosaccharide, and xylooligosaccharides.

Suitable prebiotics are usually plant-derived complex carbohydrates, oligosaccharides or polysaccharides. Generally, prebiotics are indigestible or poorly digested by humans and serve as a food source for bacteria. Prebiotics which can be used in the pharmaceutical dosage forms, pharmaceutical compositions, and kits provided herein include, without limitation, galactooligosaccharides (GOS), trans-galactooligosaccharides, fructooligosaccharides or oligofructose (FOS), inulin, oligofructose-enriched inulin, lactulose, arabinoxylan, xylooligosaccharides (XOS), mannooligosaccharides, gum guar, gum arabic, tagatose, amylose, amylopectin, xylan, pectin, and the like and combinations of thereof. Prebiotics can be found in certain foods, e.g. chicory root, Jerusalem artichoke, Dandelion greens, garlic, leek, onion, asparagus, wheat bran, wheat flour, banana, milk, yogurt, sorghum, burdock, broccoli, Brussels sprouts, cabbage, cauliflower, collard greens, kale, radish and rutabaga, and miso. Alternatively, prebiotics can be purified or chemically or enzymatically synthesized.

In some embodiments, the composition comprises at least one prebiotic. In some embodiment, the prebiotic is a carbohydrate. In some embodiments, the composition of the present invention comprises a prebiotic mixture, which comprises at least one carbohydrate. A "carbohydrate" refers to a sugar or polymer of sugars. The terms "saccharide," "polysaccharide," "carbohydrate," and "oligosaccharide" may be used interchangeably. Most carbohydrates are aldehydes or ketones with many hydroxyl groups, usually one on each carbon atom of the molecule. Carbohydrates generally have the molecular formula $(CH_2O)_n$. A carbohydrate can be a monosaccharide, a disaccharide, trisaccharide, oligosaccharide, or polysaccharide. The most basic carbohydrate is a monosaccharide, such as glucose, sucrose, galactose, mannose, ribose, arabinose, xylose, and fructose. Disaccharides are two joined monosaccharides. Exemplary disaccharides include sucrose, maltose, cellobiose, and lactose. Typically, an oligosaccharide includes between three and six monosaccharide units (e.g., raffinose, stachyose), and polysaccharides include six or more monosaccharide units. Exemplary polysaccharides include starch, glycogen, and cellulose. Carbohydrates can contain modified saccharide units, such as 2'-deoxyribose wherein a hydroxyl group is removed, 2'-fluororibose wherein a hydroxyl group is replace with a fluorine, or N-acetylglucosamine, a nitrogen-containing form of glucose (e.g., 2'-fluororibose, deoxyribose, and hexose). Carbohydrates can exist in many different forms, for example, conformers, cyclic forms, acyclic forms, stereoisomers, tautomers, anomers, and isomers. Carbohydrates may be purified from natural (e.g., plant or microbial) sources (i.e., they are enzymatically synthetized), or they may be chemically synthesized or modified.

Suitable prebiotic carbohydrates can include one or more of a carbohydrate, carbohydrate monomer, carbohydrate oligomer, or carbohydrate polymer. In certain embodiments, the pharmaceutical composition, dosage form, or kit comprises at least one type of microbe and at least one type of non-digestible saccharide, which includes non-digestible monosaccharides, non-digestible oligosaccharides, or non-digestible polysaccharides. In one embodiment, the sugar units of an oligosaccharide or polysaccharide can be linked in a single straight chain or can be a chain with one or more side branches. The length of the oligosaccharide or polysaccharide can vary from source to source. In one embodiment, small amounts of glucose can also be contained in the chain. In another embodiment, the prebiotic composition can be partially hydrolyzed or contain individual sugar moieties that are components of the primary oligosaccharide (see, e.g., U.S. Pat. No. 8,486,668, PREBIOTIC FORMULATIONS AND METHODS OF USE).

Prebiotic carbohydrates may include, but are not limited to monosaccharaides (e.g., trioses, tetroses, pentoses, aldopentoses, ketopentoses, hexoses, cyclic hemiacetals, ketohexoses, heptoses) and multimers thereof, as well as epimers, cyclic isomers, stereoisomers, and anomers thereof. Nonlimiting examples of monosaccharides include (in either the L- or D-conformation) glyceraldehyde, threose, ribose, altrose, glucose, mannose, talose, galactose, gulose, idose, lyxose, arabinose, xylose, allose, erythrose, erythrulose, tagalose, sorbose, ribulose, psicose, xylulose, fructose, dihydroxyacetone, and cyclic (alpha or beta) forms thereof. Multimers (disaccharides, trisaccharides, oligosaccharides, polysaccharides) thereof include but are not limited to sucrose, lactose, maltose, lactulose, trehalose, cellobiose, kojibiose, nigerose, isomaltose, sophorose, laminaribiose, gentioboise, turanose, maltulose, palatinose, gentiobiulose, mannobiose, melibiulose, rutinose, rutinulose, xylobiose, primeverose, amylose, amylopectin, starch (including resistant starch), chitin, cellulose, agar, agarose, xylan, glycogen, bacterial polysaccharides such as capsular polysaccharides, LPS, and peptodglycan, and biofilm exopolysaccharide (e.g., alginate, EPS), N-linked glycans, and O-linked glycans. Prebiotic sugars may be modified and carbohydrate derivatives include amino sugars (e.g., sialic acid, N-acetylglucosamine, galactosamine), deoxy sugars (e.g., rhamnose, fucose, deoxyribose), sugar phosphates, glycosylamines, sugar alcohols, and acidic sugars (e.g., glucuronic acid, ascorbic acid).

In some embodiments, the prebiotic carbohydrate component of the pharmaceutical composition, dosage form, or kit consists essentially of one or more non-digestible saccharides. In one embodiment, non-digestible oligosaccharides the non-digestible oligosaccharides are galactooligosaccharides (GOS). In another embodiment, the non-digestible oligosaccharides are fructooligosaccharides (FOS).

In some embodiments, the prebiotic composition of the invention comprises one or more of GOS, lactulose, raffinose, stachyose, lactosucrose, FOS (i.e., oligofructose or oligofructan), inulin, isomalto-oligosaccharide, xylo-oligosaccharide, paratinose oligosaccharide, transgalactosylated oligosaccharides (i.e., transgalacto-oligosaccharides), trans-galactosylate disaccharides, soybean oligosaccharides (i.e., soyoligosaccharides), gentiooligosaccharides, glucooligosaccharides, pecticoligosaccharides, palatinose polycondensates, difructose anhydride III, sorbitol, maltitol, lactitol, polyols, polydextrose, reduced paratinose, cellulose, β-glucose, β-galactose, β-fructose, verbascose, galactinol, and β-glucan, guar gum, pectin, high, sodium alginate, and lambda carrageenan, or mixtures thereof. The GOS may be a short-chain GOS, a long-chain GOS, or any combination thereof. The FOS may be a short-chain FOS, a long-chain FOS, or any combination thereof.

In some embodiments, the prebiotic composition comprises two carbohydrate species (nonlimiting examples being a GOS and FOS) in a mixture of at least 1:1, at least 2:1, at least 5:1, at least 9:1, at least 10:1, about 20:1, or at least 20:1.

In some embodiments, the prebiotic composition of the invention comprises a mixture of one or more non-digestible oligosaccharides, non-digestible polysaccharides, free monosaccharides, non-digestible saccharides, starch, or non-starch polysaccharides. In one embodiment, a prebiotic component of a prebiotic composition is a GOS composition. In one embodiment, a prebiotic composition is a pharmaceutical composition. In one embodiment, a pharmaceutical composition is a GOS composition.

Oligosaccharides are generally considered to have a reducing end and a non-reducing end, whether or not the saccharide at the reducing end is in fact a reducing sugar. Most oligosaccharides described herein are described with the name or abbreviation for the non-reducing saccharide (e.g., Gal or D-Gal), preceded or followed by the configuration of the glycosidic bond (α or β), the ring bond, the ring position of the reducing saccharide involved in the bond, and then the name or abbreviation of the reducing saccharide (e.g., Glc or D-Glc). The linkage (e.g., glycosidic linkage, galactosidic linkage, glucosidic linkage) between two sugar units can be expressed, for example, as 1,4, 1→4, or (1-4).

Both FOS and GOS are non-digestible saccharides. β glycosidic linkages of saccharides, such as those found in, but not limited to, FOS and GOS, make these prebiotics mainly non-digestible and unabsorbable in the stomach and small intestine α-linked GOS (α-GOS) is also not hydrolyzed by human salivary amylase, but can be used by *Bifidobacterium bifidum* and *Clostridium butyricum* (Yamashita et al. (2004) J. APPL. GLYCOSCI. 51: 115-122). FOS and GOS can pass through the small intestine and into the large intestine (colon) mostly intact, except where commensal microbes and microbes administered as part of a pharmaceutical composition are able to metabolize the oligosaccharides.

GOS (also known as galacto-oligosaccharides, galactooligosaccharides, trans-oligosaccharide (TOS), trans-galactooligosaccharide (TGOS), and trans-galactooligosaccharide) are oligomers or polymers of galactose molecules ending mainly with a glucose or sometimes ending with a galactose molecule and have varying degree of polymerization (generally the DP is between 2-20) and type of linkages. In one embodiment, GOS comprises galactose and glucose molecules. In another embodiment, GOS comprises only galactose molecules. In a further embodiment, GOS are galactose-containing oligosaccharides of the form of [β-D-Gal-(1-6)]$_n$-β-D-Gal-(1-4)-D-Glc wherein n is 2-20. In another embodiment, GOS are galactose-containing oligosaccharides of the form Glc α1-4-[β Gal 1-6)]$_n$ where n=2-20. In another embodiment, GOS are in the form of α-D-Glc (1-4)-[β-D-Gal-(1-6)-]$_n$ where n=2-20. Gal is a galactopyranose unit and Glc (or Glu) is a glucopyranose unit.

In one embodiment, a prebiotic composition comprises a GOS-related compound. A GOS-related compound can have the following properties: a) a "lactose" moiety; e.g., GOS with a gal-glu moiety and any polymerization value or type of linkage; or b) be stimulatory to "lactose fermenting" microbes in the human GI tract; for example, raffinose (gal-fru-glu) is a "related" GOS compound that is stimulatory to both lactobacilli and bifidobacteria.

In one embodiment, a prebiotic composition comprises GOS with a low degree of polymerization. In one embodiment a prebiotic composition comprising GOS with a low degree of polymerization increases growth of probiotic and select commensal bacteria to a greater extent than an equivalent amount of a prebiotic composition comprising GOS with a high degree of polymerization. In one embodiment, a prebiotic composition comprising a high percentage of GOS with a low degree of polymerization increases growth of probiotic and beneficial commensal bacteria to a greater extent than an equivalent amount of a prebiotic composition comprising a low percentage of GOS with a low degree of polymerization (DP). In one embodiment a prebiotic composition comprises GOS with a DP less than 20, such as less than 10, less than 9, less than 8, less than 7, less than 6, less than 5, less than 4, or less than 3. In another embodiment a prebiotic composition comprising GOS with a low DP increases growth of co-formulated or co-administered microbes and/or beneficial commensal microbes in the GI tract of a subject.

Linkages between the individual sugar units found in GOS and other oligosaccharides include β-(1-6), β-(1-4), β-(1-3) and β-(1-2) linkages. In one embodiment, the administered oligosaccharides (e.g., GOS) are branched saccharides. In another embodiment, the administered oligosacchardies (e.g, GOS) are linear saccharides.

In some embodiments, the GOS comprises a disaccharide Gal α (1-6) Gal, at least one trisaccharide selected from Gal β (1-6)-Gal β (1-4)-Glc and Gal β (1-3)-Gal β (1-4)-Glc, the tetrasaccharide Gal β(1-6)-Gal β (1-6)-Gal β (1-4)-Glc and the pentasaccharide Gal β (1-6)-Gal β (1-6)-Gal β (1-6)-Gal β (1-4)-Glc.

In one embodiment, a GOS composition is a mixture of 10 to 45% w/v disaccharide, 10 to 45% w/v trisaccharide, 10 to 45% w/v tetrasaccharide and 10 to 45% w/v pentasaccharide. In another embodiment, a GOS composition is a mixture of oligosaccharides comprising 20-28% by weight of β (1-3) linkages, 20-25% by weight of β (1-4) linkages, and 45-55% by weight of β (1-6) linkages. In one embodiment, a GOS composition is a mixture of oligosaccharides comprising 26% by weight of β (1-3) linkages, 23% by weight of β (1-4) linkages, and 51% by weight of β (1-6) linkages.

Alpha-GOS (also called alpha-bond GOS or alpha-linked GOS) are oligosaccharides having an alpha-galactopyranosyl group. Alpha-GOS comprises at least one alpha glycosidic linkage between the saccharide units. Alpha-GOS are generally represented by α-(Gal)$_n$ (n usually represents an integer of 2 to 10) or α-(Gal)$_n$ Glc (n usually represents an integer of 1 to 9). Examples include a mixture of α-galactosylglucose, α-galactobiose, α-galactotriose, α-galactotetraose, and higher oligosaccharides. Additional non-limiting examples include melibiose, manninootriose, raffinose, stachyose, and the like, which can be produced from beat, soybean oligosaccharide, and the like.

Commercially available and enzyme synthesized alpha-GOS products are also useful for the compositions described herein. Synthesis of alpha-GOS with an enzyme is conducted utilizing the dehydration condensation reaction of α-galactosidase with the use of galactose, galactose-containing substance, or glucose as a substrate. The galactose-containing substance includes hydrolysates of galactose-containing substances, for example, a mixture of galactose and glucose obtained by allowing beta-galactosidase to act on lactose, and the like. Glucose can be mixed separately with galactose and be used as a substrate with α-galactosidase (see e.g., WO 02/18614). Methods of preparing alpha-GOS have been described (see, e.g., EP 1514551 and EP 2027863).

In one embodiment, a GOS composition comprises a mixture of saccharides that are alpha-GOS and saccharides that are produced by transgalactosylation using β-galactosidase. In another embodiment, GOS comprises alpha-GOS. In another embodiment, alpha-GOS comprises α-$(Gal)_2$ from 10% to 100% by weight. In one embodiment, GOS comprises only saccharides that are produced by transgalactosylation using β-galactosidase.

In one embodiment, a GOS composition can comprise GOS with alpha linkages and beta linkages.

In one embodiment, the pharmaceutical composition, dosage form, or kit comprises, in addition to one or more microbes, an oligosaccharide composition that is a mixture of oligosaccharides comprising 1-20% by weight of di-saccharides, 1-20% by weight tri-saccharides, 1-20% by weight tetra-saccharides, and 1-20% by weight penta-saccharides. In another embodiment, an oligosaccharide composition is a mixture of oligosaccharides consisting essentially of 1-20% by weight of di-saccharides, 1-20% by weight tri-saccharides, 1-20% by weight tetra-saccharides, and 1-20% by weight penta-saccharides.

In one embodiment, a prebiotic composition is a mixture of oligosaccharides comprising 1-20% by weight of saccharides with a degree of polymerization (DP) of 1-3, 1-20% by weight of saccharides with DP of 4-6, 1-20% by weight of saccharides with DP of 7-9, and 1-20% by weight of saccharides with DP of 10-12, 1-20% by weight of saccharides with DP of 13-15.

In another embodiment, a prebiotic composition comprises a mixture of oligosaccharides comprising 50-55% by weight of di-saccharides, 20-30% by weight tri-saccharides, 10-20% by weight tetra-saccharide, and 1-10% by weight penta-saccharides. In one embodiment, a GOS composition is a mixture of oligosaccharides comprising 52% by weight of di-saccharides, 26% by weight tri-saccharides, 14% by weight tetra-saccharide, and 5% by weight penta-saccharides. In another embodiment, a prebiotic composition comprises a mixture of oligosaccharides comprising 45-55% by weight tri-saccharides, 15-25% by weight tetra-saccharides, 1-10% by weight penta-saccharides.

In certain embodiments, the composition according to the invention comprises a mixture of neutral and acid oligosaccharides as disclosed in PCT Application WO 2005/039597 (N. V. Nutricia) and US Patent Application 2015/0004130, which are hereby incorporated by reference. In one embodiment, the acid oligosaccharide has a degree of polymerization (DP) between 1 and 5000. In another embodiment, the DP is between 1 and 1000. In another embodiment, the DP is between 2 and 250. If a mixture of acid oligosaccharides with different degrees of polymerization is used, the average DP of the acid oligosaccharide mixture is preferably between 2 and 1000. The acid oligosaccharide may be a homogeneous or heterogeneous carbohydrate. The acid oligosaccharides may be prepared from pectin, pectate, alginate, chondroitine, hyaluronic acids, heparin, heparane, bacterial carbohydrates, sialoglycans, fucoidan, fucooligosaccharides or carrageenan, and are preferably prepared from pectin or alginate. The acid oligosaccharides may be prepared by the methods described in PCT Application WO 01/60378, which is hereby incorporated by reference. The acid oligosaccharide is preferably prepared from high methoxylated pectin, which is characterized by a degree of methoxylation above 50%. As used herein, "degree of methoxylation" (also referred to as DE or "degree of esterification") is intended to mean the extent to which free carboxylic acid groups contained in the polygalacturonic acid chain have been esterified (e.g. by methylation). In some embodiments, the acid oligosaccharides have a degree of methoxylation above about 10%, above about 20%, above about 50%, above about 70%. In some embodiments, the acid oligosaccharides have a degree of methylation above about 10%, above about 20%, above about 50%, above about 70%.

The term neutral oligosaccharides as used in the present invention refers to saccharides which have a degree of polymerization of monose units exceeding 2, exceeding 3, exceeding 4, or exceeding 10, which are not or only partially digested in the intestine by the action of acids or digestive enzymes present in the human upper digestive tract (small intestine and stomach) but which are fermented by the human intestinal flora and preferably lack acidic groups. The neutral oligosaccharide is structurally (chemically) different from the acid oligosaccharide. The term "neutral oligosaccharides", as used herein, preferably refers to saccharides which have a degree of polymerization of the oligosaccharide below 60 monose units. The term "monose units" refers to units having a closed ring structure, e.g., the pyranose or furanose forms. In some embodiments, the neutral oligosaccharide comprises at least 90% or at least 95% monose units selected from the group consisting of mannose, arabinose, fructose, fucose, rhamnose, galactose, -D-galactopyranose, ribose, glucose, xylose and derivatives thereof, calculated on the total number of monose units contained therein. Suitable neutral oligosaccharides are preferably fermented by the gut flora. Nonlimiting examples of suitable neutral oligosaccharides are cellobiose (4-O-β-D-glucopyranosyl-D-glucose), cellodextrins ((4-O-β-D-glucopyranosyl)n-D-glucose), B-cyclo-dextrins (cyclic molecules of α-1-4-linked D-glucose; α-cyclodextrin-hexamer, β-cyclodextrin-heptamer and γ-cyclodextrin-octamer), indigestible dextrin, gentiooligosaccharides (mixture of β-1-6 linked glucose residues, some 1-4 linkages), glucooligosaccharides (mixture of α-D-glucose), isomaltooligosaccharides (linear α-1-6 linked glucose residues with some 1-4 linkages), isomaltose (6-O-α-D-glucopyranosyl-D-glucose); isomaltriose (6-O-α-D-glucopyranosyl-(1-6)-α-D-glucopyranosyl-D-glucose), panose (6-O-α-D-glucopyranosyl-(1-6)-α-D-glucopyranosyl-(1-4)-D-glucose), leucrose (5-O-α-D-glucopyranosyl-D-fructopyranoside), palatinose or isomaltulose (6-O-α-D-glucopyranosyl-D-fructose), theanderose (O-α-D-glucopyranosyl-(1-6)-O-α-D-glucopyranosyl-(1-2)-B-D-fructo furanoside), D-agatose, D-lyxo-hexylose, lactosucrose (O-α-D-galactopyranosyl-(1-4)-O-α-D-glucopyranosyl-(1-2)-β-D-fructofuranoside), α-galactooligosaccharides including raffinose, stachyose and other soy oligosaccharides (O-α-D-galactopyranosyl-(1-6)-α-D-glucopyranosyl-β-D-fructofuranoside), -galactooligosaccharides or transgalacto-oligosaccharides β-D-galactopyranosyl-(1-6)-[β-D-glucopyranosyl]n-(1-4) α-D glucose), lactulose (4-O-β-D-galactopyranosyl-D-fructose), 4'-galatosyllactose (O-D-galactopyranosyl-(1-4)-O-β-D-glucopyranosyl-(1-4)-D-glucopyranose), synthetic galactooligosaccharide (neogalactobiose, isogalactobiose, galsucrose, isolactose I, II and III), fructans-Levan-type (β-D-(2→6)-fructofuranosyl)$_n$ α-D-glucopyranoside), fructans-Inulin-type (β-D-((2-1)-fructofuranosyl)$_n$ α-D-glucopyranoside), 1 f-β-fructofuranosylnystose (β-D-((2→1)-fructofuranosyl)n B-D-fructofuranoside), xylooligo-saccharides (B-D-((1→4)-xylose)$_n$, lafinose, lactosucrose and arabinooligosaccharides.

In some embodiments, the neutral oligosaccharide is selected from the group consisting of fructans, fructooligosaccharides, indigestible dextrins galactooligo-saccharides (including transgalactooligosaccharides), xylooligosaccharides, arabinooligo-saccharides, glucooligosaccharides, mannooligosaccharides, fucooligosaccharides and mixtures thereof.

Suitable oligosaccharides and their production methods are further described in Laere K. J. M. (Laere, K. J. M., Degradation of structurally different non-digestible oligosaccharides by intestinal bacteria: glycosylhydrolases of Bi. *adolescentis*. PhD-thesis (2000), Wageningen Agricultural University, Wageningen, The Netherlands), the entire content of which is hereby incorporated by reference. Transgalactooligosaccharides (TOS) are for example sold under the trademark Vivinal™ (Borculo Domo Ingredients, Netherlands). Indigestible dextrin, which may be produced by pyrolysis of corn starch, comprises α(1→4) and α(1→6) glucosidic bonds, as are present in the native starch, and contains 1→2 and 1→3 linkages and levoglucosan. Due to these structural characteristics, indigestible dextrin contains well-developed, branched particles that are partially hydrolysed by human digestive enzymes. Numerous other commercial sources of indigestible oligosaccharides are readily available and known to skilled persons in the art. For example, transgalactooligosaccharide is available from Yakult Honsha Co., Tokyo, Japan. Soybean oligosaccharide is available from Calpis Corporation distributed by Ajinomoto U.S.A. Inc., Teaneck, N.J.

In a further preferred embodiment, the pharmaceutical composition contains a prebiotic mixture of an acid oligosaccharide with a DP between 1 and 5000, prepared from pectin, alginate, and mixtures thereof; and a neutral oligosaccharide, selected from the group of fructans, fructooligosaccharides, indigestible dextrins, galactooligosaccharides including transgalacto-oligosaccharides, xylooligosaccharides, arabinooligosaccharides, glucooligosaccharides, manno-oligosaccharides, fucooligosaccharides, and mixtures thereof.

In certain embodiments, the prebiotic mixture comprises xylose. In other embodiments, the prebiotic mixture comprises a xylose polymer (i.e. xylan). In some embodiments, the prebiotic comprises xylose derivatives, such as xylitol, a sugar alcohol generated by reduction of xylose by catalytic hydrogenation of xylose, and also xylose oligomers (e.g., xylooligosaccharide). While xylose can be digested by humans, via xylosyltransferase activity, most xylose ingested by humans is excreted in urine. In contrast, some microorganisms are efficient at xylose metabolism or may be selected for enhanced xylose metabolism. Microbial xylose metabolism may occur by at least four pathways, including the isomerase pathway, the Weimburg pathway, the Dahms pathway, and, for eukaryotic microorganisms, the oxidoreductase pathway.

The xylose isomerase pathway involves the direct conversion of D-xylose into D-xylulose by xylose isomerase, after which D-xylulose is phosphorylated by xylulose kinase to yield D-xylolose-5-phosphate, an intermediate of the pentose phosphate pathway.

In the Weimberg pathway, D-xylose is oxidized to D-xylono-lactone by a D-xylose dehydrogenase. Then D-xylose dehydrogenase is hydrolyzed by a lactonase to yield D-xylonic acid, and xylonate dehydratase acitivity then yields 2-keto-3-deoxy-xylonate. The final steps of the Weimberg pathway are a dehydratase reaction to form 2-keto glutarate semialdehyde and an oxidizing reaction to form 2-ketoglutarate, an intermediate of the Krebs cycle.

The Dahms pathway follows the same mechanism as the Weimberg pathway but diverges once it has yielded 2-keto-3-deoxy-xylonate. In the Dahms pathway, an aldolase splits 2-keto-3-deoxy-xylonate into pyruvate and glycolaldehyde.

The xylose oxido-reductase pathway, also known as the xylose reductase-xylitol dehydrogenase pathway, begins by the reduction of D-xylose to xylitol by xylose reductase followed by the oxidation of xylitol to D-xylulose by xylitol dehydrogenase. As in the isomerase pathway, the next step in the oxido-reductase pathway is the phosphorylation of D-xylulose by xylulose kinase to yield D-xylolose-5-phosphate.

Xylose is present in foods like fruits and vegetables and other plants such as trees for wood and pulp production. Thus, xylose can be obtained in the extracts of such plants. Xylose can be obtained from various plant sources using known processes including acid hydrolysis followed by various types of chromatography. Examples of such methods to produce xylose include those described in Maurelli, L. et al. (2013), Appl. Biochem. Biotechnol. 170:1104-1118; Hooi H. T et al. (2013), Appl. Biochem. Biotechnol. 170: 1602-1613; Zhang H-J. et al. (2014), Bioprocess Biosyst. Eng. 37:2425-2436.

Preferably, the metabolism of xylose and/or the shift in microbiota due to the metabolism of the xylose provided in a pharmaceutical composition of the invention confers a benefit to a host, e.g. immunological tolerance. For example, in aspects in which the patient is at risk or suffering from GVHD, the immunological tolerance may reduce graft-versus-host activity while maintaining graft-versus-leukemia activity. In another example, in aspects in which the patient suffers from Celiac disease, the immunological tolerance prevents an inappropriate immune response to gluten. The xylose may be, e.g. i) cytotoxic for an autoimmune disease- and/or inflammatory disease-associated associated pathogen or pathobiont, ii) cytostatic for an autoimmune disease- and/or inflammatory disease-associated pathogen or pathobiont, iii) capable of decreasing the growth of autoimmune disease- and/or inflammatory disease-associated pathogen or pathobiont, iv) capable of inhibiting the growth of an autoimmune disease- and/or inflammatory disease-associated pathogen or pathobiont, v) capable of decreasing the colonization of an autoimmune disease- and/or inflammatory disease-associated pathogen or pathobiont, vi) capable of inhibiting the colonization of an autoimmune disease- and/or inflammatory disease-associated pathogen or pathobiont, vii) capable of eliciting an immunomodulatory response in the host that reduces the risk of an autoimmune and/or inflammatory disorder, viii), capable of eliciting an immunomodulatory response in the host that reduces the severity of an autoimmune and/or inflammatory disorder, ix)

capable of promoting barrier integrity directly or indirectly through its impact on microbiota, or x) any combination of i)-ix).

In some embodiments, the pharmaceutical composition or dosage form comprises a bacterial population and xylose in an amount effective to promote the growth of select bacteria of the family Clostridiacea, including members of the genus *Clostridium, Ruminococcus,* or *Blautia* or relatives thereof in a host. In some embodiments, the pharmaceutical composition or dosage form is further effective to promote the proliferation of select bacteria of the family Clostridiacea, including members of the genus *Clostridium, Ruminococcus,* or *Blautia* or relatives thereof in a host. In certain embodiments, the pharmaceutical composition or dosage form comprises a bacterial population and xylose in an amount effective to promote the colonization and/or engraftment of select bacteria of the family Clostridiacea, including members of the genus *Clostridium, Ruminococcus,* or *Blautia* or relatives thereof in a host. In preferred embodiments, the pharmaceutical composition or dosage form is further capable of altering a dysbiotic state such that the growth, proliferation, colonization, and/or engraftment of a host by a pathogen, pathobiont, disease-associated microbe, or a combination thereof such that the population of at least one pathogen, pathobiont, or disease-associated microbe is decreased 2-fold, 5-fold, 10-fold, 50-fold, 100-fold, 200-fold, 500-fold, 1000-fold, 10000-fold, or over 10000-fold. In one embodiment, the pharmaceutical composition or dosage form is capable of locally or systemically eliminating at least one pathogen, pathobiont, or disease-associated microbe from a host.

In some embodiments, the prebiotic comprises a carbohydrate monomer or polymer that has been modified i.e., substituted with other substituents (e.g., acetyl group, glucuronic acid residue, arabinose residue, or the like) (see US Patent Application 20090148573, hereby incorporated by reference). The term "modified", as used herein, refers to a molecule modified from a reference molecule, and includes not only artificially produced molecules but also naturally occurring molecules. In preferred embodiments, the modification occurs at one or more hydroxyl groups of the reference carbohydrate. In some embodiments, the modification occurs at carbon-2 (C2), the modification occurs at carbon-6 (C6), or a combination thereof.

In some embodiments, a carbohydrate (a monomer, or, preferably, a polymer) is modified with one or more hydrophilic groups. Nonlimiting examples of the hydrophilic groups include an acetyl group, a 4-O-methyl-α-D-glucuronic acid residue, an L-arabinofuranose residue, an L-arabinose residue, and an α-D-glucuronic acid residue. In some embodiments, the modification is the replacement of one or more hydroxyl groups with —H, —CH$_2$OH, —CH$_3$, or —NH$_2$.

In some embodiments, the composition comprises at least one carbohydrate that elicits an immunomodulatory response. Exemplary immunomodulary carbohydrates include (but are not limited to) fructo-oligosaccharides, glycosaminoglycans (e.g., heparin sulfate, chondroitin sulfate A, hyaluronan), O-glycans, and carrageenan oligosaccharides, and galacto-oligosaccharides. Immunomodulatory carbohydrates may be purified from plants or microbes or may be synthetically derived. Immunomodulatory carbohydrates may be effective to, for example, prevent disease, suppress symptoms, treat disease, or any combination thereof.

In some embodiments, immunomodulatory carbohydrates are C-type lectin receptor ligands. In preferred embodiments, the C-type lectin receptor ligands are produced by one or more fungal species. In other embodiments, the immunomodulatory carbohydrates are bacterial exopolysaccharides, such as (but not limited to) the exopolysaccharides (EPS) produced by *Bacillus subtilis, Bifidobacterium breve,* or *Bacteroides fragilis.* In some aspects, immunomodulatory carbohydrates are zwitterionic polysaccharides. In some aspects, immunomodulatory carbohydrates modulate toll-like receptor 2 (TLR2) and/or toll-like receptor 4 (TLR4) responses in a host. For example, autoimmune or inflammatory diseases characterized by intestinal inflammation may be prevented by a TLR4 agonist such as but not limited to *B. subtilis* EPS (see, e.g., Jones et al. (2014) J. IMMUNOL. 192: 4813-4820). Immunomodulatory carbohydrates may also activate CD4+ T cells and/or lead to an upregulation of the anti-inflammatory cytokine interleukin-10 (Mazmanian and Kasper (2006) NAT. REV. IMMUNOL. 6: 849-858). Immunomodulatory carbohydrates may be selected for administration to a patient based on the presence, abundance, distribution, modification and/or linkages of sugar residues. For example, immunomodulatory carbohydrates used in the prevention of intestinal disorders or autoimmune conditions that manifest in the gut (non-limiting examples being IBD and GVHD) may be selected based on i) a high abundance of mannose residues; ii) the presence of terminal mannopyranosyl (t-Man) residues and/or 2,6 linked mannopyranosyl residues (2,6-Man), iii) a ratio of mannose to glucose residues in the approximate range of 8:2 to 9:1, iv) the presence of galactose residues, v) areas of positive charge, or vi) a combination thereof.

Carbohydrates may be selected according to the fermentation or metabolic preferences of a microbe (e.g., an anti-inflammatory bacterial cell) selected for administration to a mammalian subject. Selection criteria include but are not limited to sugar complexity (e.g., monosaccharides, including but not limited to glucose, versus oligosaccharides or starches) as well as by desired end-product. Non-liming examples include the fermentation products ethanol and carbon dioxide (CO$_2$) (e.g., via ethanol fermentation by *Saccharomyces* sp. *Zymomonas* sp.), lactate (e.g., via homolactic acid fermentation by *Lactococcus* sp., *Streptococcus* sp., *Enterococcus* sp., *Pediococcus* sp. and some species *Lactobacillus*), lactate, ethanol, and CO$_2$ (e.g., via heterolactic acid fermentation (which includes the phosphoketolase pathway) by some species of *Lactobacillus* as well as *Leuconostoc* sp., *Oenococcus* sp., and *Weissella* sp.), butanol, acetone, CO$_2$ and H$_2$ (via acetone-butanol fermentation by some *Clostridium* sp.), and short chain fatty acids (with or without the production of other products) (see, e.g., Muller (2011) Bacterial Fermentation. Encyclopedia of Life Sciences). Examples of fermentation leading to short chain fatty acid production include homoacetic acid fermentation (e.g., by *Acetobacterium* sp., and resulting in acetate), propionic acid fermentation (e.g., by *Propionibacterium* sp., and resulting in propionate, acetate and CO$_2$) mixed acid fermentation (e.g., by *Escherichia* sp., and resulting in ethanol, lactate, acetate, succinate, formate, CO$_2$, and H$_2$), butyrate fermentation (e.g., by some *Clostridium* sp., resulting in butyrate, CO$_2$, and H$_2$), and 2,3-butanediol fermentation (e.g., by *Enterobacter* sp., resulting in ethanol, butanediol, lactate, formate, CO$_2$, and H$_2$). In some embodiments, selection of carbohydrates for co-formulation of co-administration with a type of microbe or types of microbe may be achieved by computational analysis of microbial enzymatic pathways, including but not limited to the presence of metabolic/fermentation pathway enzymes.

Other prebiotics include molecules capable of selective or semi-selective utilization by microbes (e.g., bacterial cells) of the compositions contained herein. The ability of a microbe to utilize a metabolite of interest is determined by the genomic capacity of that microbe. Public databases have characterized many microbes and automate the annotation of the genome to allow a computational analysis of the metabolites a microbe is potentially able to utilize. Databases such as the Cluster of Orthologous Groups (COGs) database characterize genomes from a variety of species in this manner and are capable of characterizing newly sequenced genomes as well (e.g. see in this fashion (Tatusov et al. (2000) NUCL. ACID RES. 28(1): 33-36). Furthermore, pathway analysis classifies COGs into different categories with associated one letter codes including J, translation; L replication, recombination, and repair, K transcription; O molecular chaperones and related functions, M, cell wall structure and biogenesis and outer membrane, N secretion motility and chemotaxis; T signal Transduction; P inorganic ion transport and metabolism; C energy production and conversion; G, carbohydrate metabolism and transport; E amino acid metabolism and transport; F, nueclotide metabolism and transport; D cell Division and chromosome partitioning; R general functional prediction. In preferred embodiments, COGs of the categories, N, M, P, C, G, E, and F are selected as preferred COGs to both provide enhanced growth on specific substrates and modified behaviors relevant for antitumor properties.

COGs are selected to be specific or semi enriched in the host or other microbes within a host by searching for specific functions present in the microbe of interest but absent from a large set of other competition organisms. Tissue specific analysis of the host for enzymes expressed within a tissue is performed to identify tissue specific enzymatic activities in the host. Specific functions are absent from at least 90%, at least 80%, at least 70%, at least 60%, at least 50%, at least 40%, at least 30% at least 20% or at least 10% of the other organisms selected from the group of the host, the host tissue, the disease-associated microbiota, the host gut microbiota, the host niche specific to the engraftment of the microbial composition (e.g., GI tract, skin).

Once these COGs are identified, databases like KEGG are used to link the enzymatic functions to identify the metabolites that are substrates for these selective COGs. Furthermore, the selective analysis to generate selective metabolites is repeated on the set of substrate of COGs to validate that the pathways and metabolites are selective to the desired microbial composition.

Methods of the Invention

In one aspect, the invention provides methods for modulating an immune response in a subject in need thereof, the method comprising administering a pharmaceutical composition of the invention to thereby modulate the immune response in the subject. In some embodiments, the immune response is against a microorganism. In some embodiments, the immune response is against self (e.g., an auto-immune response). In some embodiments, the immune response is a pro-inflammatory immune response.

In another aspect, the invention provides methods for reducing inflammation in a subject in need thereof, the method comprising administering a pharmaceutical composition of the invention to thereby reduce inflammation in the subject. In some embodiments, the immune response is against a microorganism. In some embodiments, the subject has an autoimmune or inflammatory disorder. In some embodiments, the autoimmune or inflammatory disorder is selected from the group consisting of graft-versus-host disease (GVHD), an inflammatory bowel disease (IBD), ulterative colitis, Crohn's disease, multiple sclerosis (MS), systemic lupus erythematosus (SLE), type I diabetes, rheumatoid arthritis, Sjögren's syndrome, and Celiac disease. In an exemplary embodiments, the autoimmune or inflammatory disorder is GVHD. In another exemplary embodiment, the autoimmune or inflammatory disorder is IBD. In yet another exemplary embodiment, the autoimmune or inflammatory disorder is ulcerative colitis. In an exemplary embodiment, the autoimmune or inflammatory disorder is Crohn's disease. In another exemplary embodiment, the autoimmune or inflammatory disorder is multiple sclerosis (MS). In yet another embodiment, the autoimmune or inflammatory disorder is systemic lupus erythematosus. In an exemplary embodiment, the autoimmune or inflammatory disorder is type I diabetes. In another exemplary embodiment, the autoimmune or inflammatory disorder is rheumatoid arthritis. In yet another exemplary embodiment, the autoimmune or inflammatory disorder is rheumatoid arthritis. In an exemplary embodiment, the autoimmune or inflammatory disorder is Sjögren's syndrome. In another exemplary embodiment, the autoimmune or inflammatory disorder is Celiac disease.

Autoimmune and inflammatory diseases that may be treated with the pharmaceutical compositions of the present invention, include, but are not limited to: Acute Disseminated Encephalomyelitis, Acute necrotizing hemorrhagic leukoencephalitis, Addison's disease, adhesive capsulitis, Agammaglobulinemia, Alopecia areata, Amyloidosis, Ankylosing spondylitis, Anti-GBM nephritis, Anti-TBM nephritis, Antiphospholipid syndrome, arthofibrosis, atrial fibrosis, autoimmune angioedema, autoimmune aplastic anemia, autoimmune dusautonomia, autoimmune hepatitis, autoimmune hyperlipidemia, autoimmune immunodeficiency, autoimmune inner ear disease, autoimmune myocarditis, autoimmune oophoritis, autoimmune pancreatitis, autoimmune retinopathy, autoimmune thrombocytopenic purpura, autoimmune thyroid disease, autoimmune urticaria, axonal and neuronal neuropathies, Balo disease, Behçet's disease, benign mucosal pemphigold, Bullous pemphigold, cardiomyopathy, Castleman disease, Celiac Disease, Chagas disease, chronic fatigue syndrome, chronic inflammatory demyelinating polyneuropathy, chronic Lyme disease, chronic recurrent multifocal osteomyelitis, Churg-Strauss syndrome, cicatricial pemphigold, cirrhosis, Cogans syndrome, cold agglutinin disease, congenital heart block, Coxsackle myocarditis, CREST disease, Crohn's disease, Cystic Fibrosis, essential mixed cryoglobulinemia, deficiency of the interleukin-1 receptor antagonist, demyelinating neuropathies, dermatitis herpetiformis, dermatomyosis, Devic's disease, discoid lupus, Dressler's syndrome, Dupuytren's contracture, endometriosis, endomyocardial fibrosis, eosinophilic esophagitis, eosinophilic facsciitis, erythema nodosum, experimental allergic encephalomyelitis, Evans syndrome, Familial Mediterranean Fever, fibromyalgia, fibrosing alveolitis, giant cell arteritis, giant cell myocarditis, glomerulonephritis, Goodpasture's syndrome, Graft-versus-host disease (GVHD), granulomatosus with polyanglitis, Graves' disease, Guillain-Bare syndrome, Hashimoto's encephalitis, Hashimoto's thyroiditis, hemolytic anemia, Henoch-Schonlein purpura, hepatitis, herpes gestationis, hypogammaglobulinemia, idiopathic thrombocytopenic purpura, IgA nephropathy, IgG4-related sclerosing disease, immunoregulatory lipoproteins, inclusion body myositis, inflammatory bowel disorders, interstitial cystitis, juvenile arthritis, juvenile myositis, Kawasaki syndrome, keloid, Lambert-Eaton syndrome, leukocytoclastic vasculitis, lichen planus, lichen sclerosus, ligneous conjunctivitis, linear IgA disease, mediastinal fibrosis, Meniere's disease, microscopic polyanglitis, mixed connective tissue disease, Mooren's ulcer, Mucha-Hamermann disease, Multiple Sclerosis (MS), Myasthenia gravis, myelofibrosis, Myositis, narcolepsy, Neonatal Onset Multisystem Inflammatory Disease, nephrogenic systemic fibrosis, neutropenia, nonalcoholic fatty liver disease, nonalcoholic steatohepatitis (NASH), ocular-cicatricial pemphigold, optic neuritis, palindromic rheumatism, Pediatric Autoimmune Neuropsychiatric Disorders Associated with *Streptococcus* (PANDAS), paraneoplastic cerebellar degeneration, paroxysmal nocturnal nemoglobinuria, Parry Romberg syndrome, Parsonnage-Turner syndrome, Pars planitis, Pemphigus, Peripheral neuropathy, perivenous encephalomyelitis, pernicious anemia, Peyronie's disease, POEMS syndrome, polyarteritis *nodosa*, progressive massive fibrosis, Tumor Necrosis Factor Receptor-assoicated Periodic Syndrome, Type I autoimmune polyglandular syndrome, Type II autoimmune polyglandular syndrome, Type III autoimmune polyglandular syndrome, polymyalgia rhematica, polymyositis, postmyocardial infarction syndrome, postpericardiotomy syndrome, progesterone dermatitis, primary biliary cirrhosis, primary sclerosing cholangitis, psoriasis, psoriatic arthritis, idiopathic pulmonary fibrosis, pyoderma gangrenosum, pure red cell aplasia, Raynauds phenomenon, reactic arthritis, reflex sympathetic dystrophy, Reiter's syndrome, relapsing polychondritis, restless legs syndrome, retroperitoneal fibrosis, rheumatic fever, rheumatoid arthritis, sarcoidosis, Schmidt syndrome, scleritis, scleroderma, Sjögren's syndrome, sperm and testicular autoimmunity, stiff person syndrome, subacute bacterial endocarditis, Susac's syndrome, sympathetic ophthalmia, systemic lupus erythematosus (SLE), Takayasu's arthritis, temporal arteritis, thrombocytopenic purpura, Tolosa-Hunt syndrome, transverse myelitis, Type 1 diabetes, ulcerative colitis, undifferentiated connective tissue disease, uveitis, vasculitis, vesiculobullous dermatosis, and Vitiligo.

The microbes described herein may additively or synergistically reduce the number of types of autoimmune disease- or inflammatory disease-associated pathogens or pathobionts either distally—e.g., orally-administered microbes reduce the total microbial burden in an organ not in the gastrointestinal tract, or intravaginally-administered microbes reduce the total microbial burden in an organ that is not the vagina—or locally, e.g., the intestines or vagina, respectively. Distal sites include but are not limited to the liver, spleen, fallopian tubes and uterus.

Similarly, the microbes described herein may additively or synergistically elicit an immunomodulatory response either distally, e.g., in which enteral administration of microbes results in altering the immune response at the skin or liver, or locally, e.g., the enteral administration of microbes results in altering the immune response in the intestines.

In some situations, the recipient subject is immunocompromised or immunosuppressed, or is at risk of developing an immune or inflammatory disorder.

In embodiments, the microbial composition is administered enterically, with or without prebiotics. This preferentially includes oral administration, or by an oral or nasal tube (including nasogastric, nasojejunal, oral gastric, or oral jejunal). In other embodiments, administration includes rectal administration (including enema, suppository, or colonoscopy). The pharmaceutical composition may be administered to at least one region of the gastrointestinal tract, including the mouth, esophagus, stomach, small intestine, large intestine, and rectum. In some embodiments, the pharmaceutical composition is administered to all regions of the gastrointestinal tract. The pharmaceutical compositions may be administered orally in the form of medicaments such as powders, capsules, tablets, gels or liquids. The pharmaceutical compositions may also be administered in gel or liquid form by the oral route or through a nasogastric tube, or by the rectal route in a gel or liquid form, by enema or instillation through a colonoscope or by a suppository. In some embodiments, the pharmaceutical composition of the invention is administered enterically with one ore more prebiotics.

If the composition is administered colonoscopically and, optionally, if the microbial composition, with or without one or more prebiotics, is administered by other rectal routes (such as an enema or suppository) or even if the subject has an oral administration, the subject may have a colonic-cleansing preparation. The colon-cleansing preparation can facilitate proper use of the colonoscope or other administration devices, but even when it does not serve a mechanical purpose it can also maximize the proportion of bacteria from the pharmaceutical composition relative to the other organisms previously residing in the gastrointestinal tract of the subject. Any ordinarily acceptable colonic-cleansing preparation may be used such as those typically provided when a subject undergoes a colonoscopy.

Pretreatment Protocols.

Prior to administration of the pharmaceutical composition, with or without one or more prebiotics, the subject can optionally have a pretreatment protocol to prepare the gastrointestinal tract or vagina to receive the pharmaceutical composition. In these instances, the pretreatment protocol can enhance the ability of the pharmaceutical composition to affect the patient's microbiome.

As one way of preparing the patient for administration of the microbial ecosystem, at least one antibiotic can be administered to alter the bacteria in the patient. As another way of preparing the patient for administration of the microbial ecosystem, a standard colon-cleansing preparation can be administered to the patient to substantially empty the contents of the colon, such as used to prepare a patient for a colonscopy. By "substantially emptying the contents of the colon," this application means removing at least 75%, at least 80%, at least 90%, at least 95%, or about 100% of the contents of the ordinary volume of colon contents. Antibiotic treatment can precede the colon-cleansing protocol.

If a patient has received an antibiotic for treatment of an infection, or if a patient has received an antibiotic as part of a specific pretreatment protocol, in one embodiment, the antibiotic can be stopped in sufficient time to allow the antibiotic to be substantially reduced in concentration in the gut or vagina before the pharmaceutical composition is administered. In one embodiment, the antibiotic can be discontinued 1, 2, or 3 days before the administration of the pharmaceutical composition. In another embodiment, the antibiotic can be discontinued 3, 4, 5, 6, or 7 antibiotic half-lives before administration of the pharmaceutical composition. In another embodiment, the antibiotic can be chosen so the bacterial constituents in the pharmaceutical composition have an MIC50 that is higher than the concentration of the antibiotic in the gut or vagina.

MIC50 of the bacterial constituents in the pharmaceutical composition can be determined by methods well known in the art (see, e.g., Reller et al. (2009) CLINICAL INFECTIOUS DISEASES 49(11):1749-1755). In such an embodiment, the additional time between antibiotic administration and administration of the pharmaceutical composition is not necessary. If the pretreatment protocol is part of treatment of an acute infection, the antibiotic can be chosen so that the infection is sensitive to the antibiotic, but the bacterial constituents in the pharmaceutical composition are not sensitive to the antibiotic.

Routes of Administration.

Compositions can be administered by any route suitable for the delivery of disclosed compositions for treating, inhibiting, or preventing a dysbiosis, or an diseases and disorders associated with a dysbiosis, include, but are not limited to orally, sublingually, rectally, parentally (e.g., intravenous injection (i.v.), intracranial injection (i.e.); intramuscular injection (i.m.), intraperitoneal injection (i.p.), and subcutaneous injection (s.c.) and intraosseous infusion (i.o.)), transdermally, extracorporeally, inhalation, topically or the like, including topical intranasal administration or administration by inhalant.

In some embodiments, the subject is fed a meal within one hour of administration of the pharmaceutical composition. In another embodiment, the subject is fed a meal concurrently with administration of the pharmaceutical composition.

In some embodiments, the therapeutic composition is administered at intervals greater than two days, such as once every three, four, five or six days, or every week or less frequently than every week. In other embodiments, the preparation is administered intermittently according to a set schedule, e.g., once a day, once weekly, or once monthly, or when the subject relapses from the primary illness.

In certain embodiments, the pharmaceutical composition is administered enterically. This preferentially includes oral administration, or by an oral or nasal tube (including nasogastric, nasojejunal, oral gastric, or oral jejunal). In other embodiments, administration includes rectal administration (including enema, suppository, or colonoscopy). The pharmaceutical composition can be administered to at least one region of the gastrointestinal tract, including the mouth, esophagus, stomach, small intestine, large intestine, and rectum. In some embodiments, it is administered to all regions of the gastrointestinal tract. The pharmaceutical compositions can be administered orally in the form of medicaments such as powders, capsules, tablets, gels or liquids. The bacterial compositions can also be administered in gel or liquid form by the oral route or through a nasogastric tube, or by the rectal route in a gel or liquid form, by enema or instillation through a colonoscope or by a suppository. In certain embodiments of the above invention, the microbial composition is administered enterically with one or more prebiotics.

If the composition is administered colonoscopically and, optionally, if the composition is administered by other rectal routes (such as an enema or suppository) or even if the subject has an oral administration, the subject can have a colon-cleansing preparation. The colon-cleansing preparation can facilitate proper use of the colonoscope or other administration devices, but even when it does not serve a mechanical purpose, it can also maximize the proportion of the bacterial cells in the pharmaceutical composition relative to the other organisms previously residing in the gastrointestinal tract of the subject. For example, the colon cleansing preparation may maximize the amount of bacterial entities of the bacterial composition that reach and/or engraft in the gastrointestinal tract of the subject.

Dosages and Schedule for Administration.

In some embodiments, the pharmaceutical compositions are provided in a dosage form. In certain embodiments, the dosage form is designed for administration of at least one OTU or combinations thereof disclosed herein, wherein the total amount of pharmaceutical composition administered is selected from 0.1 ng to 10 g, 10 ng to 1 g, 100 ng to 0.1 g, 0.1 mg to 500 mg, 1 mg to 100 mg, or from 10-15 mg. In other embodiments, the pharmaceutical composition is consumed at a rate of from 0.1 ng to 10 g a day, 10 ng to 1 g a day, 100 ng to 0.1 g a day, 0.1 mg to 500 mg a day, 1 mg to 100 mg a day, or from 10-15 mg a day, or more.

In certain embodiments, the treatment period is at least 1 day, at least 2 days, at least 3 days, at least 4 days, at least 5 days, at least 6 days, at least 1 week, at least 2 weeks, at least 3 weeks, at least 4 weeks, at least 1 month, at least 2 months, at least 3 months, at least 4 months, at least 5 months, at least 6 months, or at least 1 year. In some embodiments the treatment period is from 1 day to 1 week, from 1 week to 4 weeks, from 1 month, to 3 months, from 3 months to 6 months, from 6 months to 1 year, or for over a year.

In one embodiment, between about $10^5$ and about $10^{12}$ CFUs total can be administered to the patient in a given dosage form. In another embodiment, an effective amount can be provided in from 1 to 500 ml or from 1 to 500 grams of the pharmaceutical composition having from $10^7$ to $10^{11}$ bacteria per ml or per gram, or, for example, a capsule, tablet or suppository may contain from 1 mg to 1000 mg lyophilized powder having from $10^7$ to $10^{11}$ CFUs. Those receiving acute treatment can receive higher doses than those who are receiving chronic administration (such as hospital workers or those admitted into long-term care facilities).

Any of the pharmaceutical compositions described herein can be administered once on a single occasion or on multiple occasions, such as once a day for several days or more than once a day on the day of administration (including twice daily, three times daily, or up to five times daily). In another embodiment, the preparation can be administered intermittently according to a set schedule, e.g., once weekly, once monthly, or when the patient relapses from the primary illness.

Combination Therapy.

The pharmaceutical compositions, with or without one or more prebiotics, can be administered with other agents in a combination therapy mode, including anti-microbial agents. Administration can be sequential, over a period of hours or days, or simultaneous.

In one embodiment, the microbial compositions, with or without one or more prebiotics, are included in combination therapy with one or more anti-microbial agents, which include anti-bacterial agents, anti-fungal agents, anti-viral agents and anti-parasitic agents.

Anti-bacterial agents can include cephalosporin antibiotics (cephalexin, cefuroxime, cefadroxil, cefazolin, cephalothin, cefaclor, cefamandole, cefoxitin, cefprozil, and cefobiprole); fluoroquinolone antibiotics (cipro, levaquin, floxin, tequin, avelox, and norflox); tetracycline antibiotics (tetracycline, minocycline, oxytetracycline, and doxycycline); penicillin antibiotics (amoxicillin, ampicillin, penicillin V, dicloxacillin, carbenicillin, vancomycin, and methicillin); and carbapenem antibiotics (ertapenem, doripenem, imipenem/cilastatin, and meropenem).

Anti-viral agents can include Abacavir, Acyclovir, Adefovir, Amprenavir, Atazanavir, Cidofovir, Darunavir, Delavirdine, Didanosine, Docosanol, Efavirenz, Elvitegravir, Emtricitabine, Enfuvirtide, Etravirine, Famciclovir, Foscarnet, Fomivirsen, Ganciclovir, Indinavir, Idoxuridine, Lamivudine, Lopinavir Maraviroc, MK-2048, Nelfmavir, Nevirapine, Penciclovir, Raltegravir, Rilpivirine, Ritonavir, Saquinavir, Stavudine, Tenofovir Trifluridine, Valaciclovir, Valganciclovir, Vidarabine, Ibacitabine, Amantadine, Oseltamivir, Rimantidine, Tipranavir, Zalcitabine, Zanamivir and Zidovudine.

Anti-fungal agents include, but are not limited, to polyene antifungals such as natamycin, rimocidin, filipin, nystatin, amphotericin B, candicin, and hamycin; imidazole antifungals such as miconazole, ketoconazole, clotrimazole, econazole, omoconazole, bifonazole, butoconazole, fenticonazole, isoconazole, oxiconazole, sertaconazole, sulconazole, and tioconazole; triazole antifungals such as fluconazole, itraconazole, isavuconazole, ravuconazole, posaconazole, voriconazole, terconazole, and albaconazole; thiazole antifungals such as abafungin; allylamine antifungals such as terbinafine, naftifine, and butenafine; and echinocandin antifungals such as anidulafungin, caspofungin, and micafungin. Other compounds that have antifungal properties include, but are not limited to polygodial, benzoic acid, ciclopirox, tolnaftate, undecylenic acid, flucytosine or 5-fluorocytosine, griseofulvin, and haloprogin.

In one embodiment, the pharmaceutical compositions are administered in combination with one or more corticosteroids, mesalazine, mesalamine, sulfasalazine, sulfasalazine derivatives, immunosuppressive drugs, cyclosporin A, mercaptopurine, azathiopurine, prednisone, methotrexate, antihistamines, glucocorticoids, epinephrine, theophylline, cromolyn sodium, anti-leukotrienes, anti-cholinergic drugs for rhinitis, anti-cholinergic decongestants, mast-cell stabilizers, monoclonal anti-IgE antibodies, vaccines, and combinations thereof.

The pharmaceutical compositions described herein have beneficial effects for the subject locally, at the site of administration (e.g., in the gastrointestinal tract for compositions administered orally, or in the vagina for compositions administered vaginally), as previously described. Surprisingly, the pharmaceutical compositions described herein may also be used to correct or prevent a dysbiosis at a site distal to the site of administration, intended engraftment, or intended colonization of a composition, e.g., a probiotic composition, of the invention. For example, if a probiotic composition is administered vaginally, a distal effect of the composition would occur outside the vagina. Similarly, if a probiotic composition is administered to the skin, e.g., through a skin patch, transdermal lotion, etc., a distal effect of the composition would occur in a niche other than the skin. If a probiotic composition is administered to the lungs, e.g., in an inhalable formulation, a distal effect of the composition would occur outside the lungs. If a probiotic composition is administered to the ear, eye, nose, etc., a distal effect of the composition would occur at a site other than the site of administration, engraftment, or colonization of the composition (i.e., distal to the ear, distal to the eye, distal to the nose, etc.).

Distal sites include but are not limited to the liver, spleen, fallopian tubes and uterus. Other distal sites include skin, blood and lymph nodes. In other embodiments, the distal site is placenta, spleen, liver, uterus, blood, eyes, ears, lungs, liver, pancreas, brain, embryonic sac, or vagina. In another embodiment, the distal site is vagina, skin, lungs, brain, nose, ear, eyes/conjunctiva, mouth, circulatory system, e.g., blood, placenta, reproductive tract, cardiovascular system, and/or nervous system. A probiotic composition may have an effect on the microbiota of more than one distal site in a subject. For example, in some embodiments, a probiotic composition modulates the microbiota of one or more sites distal to the site of administration, engraftment, or colonization, e.g., one or more of placenta, spleen, liver, uterus, blood, eyes, ears, lungs, liver, pancreas, brain, embryonic sac, vagina, skin, brain, nose, mouth, reproductive tract, cardiovascular system, and/or nervous system. In preferred embodiments, the probiotic composition contains a immunomodulatory bacteria, e.g., a anti-inflammatory bacteria.

Without wishing to be bound by theory, the probiotic compositions of the invention may impact sites distal sites in several ways.

Pharmaceutical compositions described herein can correct or treat a distal dysbiosis by correcting the imbalance in microbial diversity that is present at the distal site. Bacteria contained in the pharmaceutical composition can correct the distal dysbiosis directly, by translocating to the distal site. Bacteria contained in the pharmaceutical composition can also correct the distal dysbiosis indirectly, by promoting translocation of other gut commensals to the distal site, or by modifying the microenvironment of the distal site to create conditions that restore a healthy microbiome, e.g., by reducing inflammation.

A distal dysbiosis includes disruptions in the normal diversity and/or function of the microbial network in a subject at a site other than the gastrointestinal tract, which is generally the site of administration of probiotics provided orally. In cases where a probiotic composition is administered vaginally to a subject, a distal dysbiosis can include disruptions in the normal diversity and/or function of the microbial network in a subject at a site other than the vagina.

In order to characterize a distal dysbiosis, provided are methods of detecting, quantifying and characterizing 16S, 18S and ITS signatures in immune organs, such as the lymph nodes, spleen, etc. Moreover, provided are methods of detecting bacterial and fungal components typically associated with one microbiota in a distal site, often associating (in a physiological or pathological manner) with the microbiota of that distal site. For example, bacteria normally detected in the GI tract or vagina are detected in distal sites, for example, the blood.

In one embodiment, a bacterial strain present in the pharmaceutical composition engrafts in the gastrointestinal tract of a subject, and translocates to a distal site, thereby augmenting the bacterial strain present in the pharmaceutical composition at the distal site. In one embodiment, the bacterial strain present in the pharmaceutical composition is not detectably present at the distal site prior to administration of the pharmaceutical composition.

In another embodiment, a bacterial strain present in the pharmaceutical composition is augmented in the gastrointestinal tract of a subject without engraftment, and translocates to a distal site, thereby augmenting the bacterial strain present in the pharmaceutical composition at the distal site. In one embodiment, the bacterial strain present in the pharmaceutical composition is not detectably present at the distal site prior to administration of the pharmaceutical composition.

In another embodiment, a bacterial strain present in the pharmaceutical composition modulates the microenvironment of the gut, augmenting a second bacterial strain present within the gut microbiota. The second bacterial strain augmented in the gut translocates to a distal site, thereby augmenting the second bacterial strain at the distal site. In embodiments, the second bacterial strain is not present in the pharmaceutical composition. In some embodiments, the bacterial strain present in the pharmaceutical composition is an immunomodulatory bacteria, e.g., an anti-inflammatory bacteria. Modulation of the microenvironment of the gut may include, for example, alteration of cytokines secreted by host cells in and around the gut, reducing inflammation in the gut, increasing secretion of short chain fatty acids in the gut, or altering the proportion of immune cell subpopulations in the gut, each of which impacts the gut microbiome. Modulation of the microenvironment of the gut can include increasing or decreasing overall microbial diversity.

In another embodiment, a bacterial strain present in the pharmaceutical composition modulates the microenvironment at a distal site in a subject, thereby augmenting a second bacterial strain at the distal site. In embodiments, the second bacterial strain is not present in the pharmaceutical composition. In some embodiments, the bacterial strain present in the pharmaceutical composition is an immunomodulatory bacteria, e.g., an anti-inflammatory bacteria. Immunomodulatory bacteria can modulate the microenvironment at a distal site in a subject by, for example, reducing systemic inflammation. This can be achieved by altering the profile of cytokine expression by immune cells which circulate throughout the body, or altering the proportion of immune cell subpopulations which circulate throughout the body. Bacterial strains present in the pharmaceutical composition can also modulate intestinal permeability, e.g., by secretion of short chain fatty acids, which impacts the microenvironment of distal sites. In addition or alternatively, bacterial strains present in the pharmaceutical composition can increase or decrease overall microbial diversity.

Accordingly, the pharmaceutical compositions described herein may additively or synergistically elicit an immunomodulatory response either distally, e.g., in which enteral administration of microbes results in altering the immune response at a site outside the gastrointestinal tract such as the skin or liver, or locally, e.g. the enteral administration of microbes results in altering the immune response in the gastrointestinal tract, e.g., in the intestines.

The immune system of a subject and the microbiome of the subject are closely linked, and interact systemically. Disruptions to the microbiome, both in the gastrointestinal tract and at distal sites, can have profound effects throughout the body of the subject. In particular, disruptions to the microbiome increase systemic inflammation and intestinal barrier dysfunction in a subject. Increased inflammation and intestinal barrier dysfunction negatively impact the health of the subject in many ways, by contributing to a wide range of inflammatory and autoimmune conditions distal to the gastrointestinal tract. Conversely, increased inflammation in a subject leads to disruptions in the subject's microbiome, and disruptions to the microbiome lead in turn to further increases in inflammation. Administration of a pharmaceutical composition containing immunomodulatory bacteria can reduce inflammation in the gastrointestinal tract and restore intestinal barrier integrity, resulting in a reduction in inflammation at sites distal to the gastrointestinal tract, and improvement in the symptoms of autoimmune or inflammatory disorders associated with systemic inflammation. Administration of a pharmaceutical composition containing bacterial strains that secrete short chain fatty acids are also capable of reducing inflammation restoring intestinal barrier integrity.

The pharmaceutical compositions and methods described herein can prevent or treat the loss or reduction of barrier function recognized to occur during dysbiosis or in the shift in one or more microbiotal populations that give rise to the dysbiosis. The loss of barrier function results in systemic seeding of bacterial populations resulting in dysbiotic activity, and in some events, the loss of barrier function results in a local reseeding of the bacterial populations. In both situations, the resulting immune activation leads to pathogenic inflammatory and immune responses. In response, provided are compositions that are capable of restoring barrier function, restoring the normal microbiotal components, and reducing (e.g., suppressing) immune/inflammatory response. In some compositions, provided are antibiotic agents that remove the existing microflora in a target niche, while newly administered or recruited bacteria populate (or re-populate) the target niche. Co-administration or co-formulation with a carbohydrate may synergistically affect this population/repopulation technique.

Disorders associated with a dysbiosis, i.e., a gastrointestinal dysbiosis or a distal dysbiosis, which increases systemic inflammation and/or reduces intestinal barrier integrity include, for example, autoimmune or inflammatory disorders, Crohn's Disease, vaginal dysbiosis, and transplant disorders such as graft-versus-host disease. These disorders can be treated by administration (e.g., oral administration) of pharmaceutical compositions containing immunomodulatory (e.g., anti-inflammatory) bacterial strains.

The pharmaceutical compositions described herein may additively or synergistically reduce the number of types of autoimmune disease- or inflammatory disease-associated pathogens or pathobionts either distally—e.g., orally-administered microbes reduce the total microbial burden in an organ not in the gastrointestinal tract, or intravaginally-administered microbes reduce the total microbial burden in an organ that is not the vagina—or locally, e.g., the intestines or vagina, respectively.

Accordingly, in one aspect, the invention provides a method of reducing inflammation in a subject, comprising administering to the subject a probiotic composition comprising an isolated, anti-inflammatory bacterial population, such that inflammation in the subject is reduced. A systemic reduction in inflammation can modulate the microbiome of niches distal to the site of administration, intended engraftment, or intended colonization of the bacterial population. The probiotic composition can contain an excipient useful for formulation as a pharmaceutical composition. In instances where the bacterial population includes anaerobic bacteria, the excipient can, in one embodiment, reduce exposure of the bacterial population to oxygen.

In a preferred embodiment, administration of the probiotic composition can reduce inflammation at a site distal to the site of administration, engraftment, or colonization, such as, for example, vagina, skin, lungs, brain, nose, ear, eyes/conjunctiva, mouth, circulatory system, e.g., blood, placenta, embryonic sac, reproductive tract, cardiovascular system, and/or nervous system. In one embodiment, administration of the probiotic composition can reduce inflammation at a site selected from blood, skin, vagina, liver, spleen, fallopian tubes, uterus, or a combination thereof. In one embodiment, administration of the probiotic composition modulates the microbiome at a distal site.

The anti-inflammatory bacterial population can induce a decrease in secretion of pro-inflammatory cytokines and/or an increase in secretion of anti-inflammatory cytokines by host cells. The anti-inflammatory properties of the bacterial population can be determined by methods described herein or known in the art, for example, by measuring alterations in cytokine secretion by peripheral blood mononuclear cells (PBMCs) exposed to the bacterial population. Anti-inflammatory bacteria can be selected for inclusion in the probiotic formulation based on modulation of particular cytokines of interest. For example, anti-inflammatory bacteria can be selected based on the ability to decrease secretion of one or more pro-inflammatory cytokines, e.g., IFNγ, IL-12p70, IL-1α, IL-6, IL-8, MCP1, MIP1α, MIP1β, TNFα, and combinations thereof, and/or the ability to increase secretion of one or more anti-inflammatory cytokines, e.g., IL-10, IL-13, IL-4, IL-5, TGFβ, and combinations thereof.

In another aspect, the invention provides methods of treating or preventing a distal dysbiosis in a subject, by administering to the subject a probiotic composition comprising an isolated bacterial population in an amount sufficient to alter the microbiome at a site distal to the site of administration, engraftment, or colonization of the bacterial population, such that the distal dysbiosis is treated. For example, administration of the probiotic composition may modulate a first microbiome at the site of administration, engraftment or colonization of the bacterial population, causing subsequent modulation of a second microbiome at a site that is distinct from the first microbiome, e.g., a distal site.

In one embodiment, the invention provides methods of treating or preventing a distal dysbiosis, by orally administering a probiotic composition which alters the microbiome at a site distal to the gastrointestinal tract.

In another aspect, the invention provides a method of treating or preventing a disorder associated with a distal dysbiosis in a subject in need thereof, comprising administering to the subject a probiotic composition comprising an isolated bacterial population in an amount sufficient to alter the microbiome at a site of the distal dysbiosis, such that the disorder associated with the distal dysbiosis is treated. Disorders associated with distal dysbiosis, including disruptions to the systemic microbiome, are described herein and include, for example, autoimmune or inflammatory disorders such as graft-versus-host disease (GVHD), an inflammatory bowel disease (IBD), ulterative colitis, Crohn's disease, multiple sclerosis (MS), systemic lupus erythematosus (SLE), type I diabetes, rheumatoid arthritis, Sjögren's syndrome, and Celiac disease; transplant disorders such as graft-versus-host disease; and vaginal dysbiosis. In one embodiment, the disorder associated with distal dysbiosis occurs in the respiratory tract (e.g., lung), including but not limited to Cystic Fibrosis and chronic obstructive pulmonary disorder (COPD).

In one embodiment, the probiotic composition contains a species of bacteria that is deficient at the site of the distal dysbiosis. Administration of the probiotic composition can increase the quantity of the deficient species in the distal microbiome. In one embodiment, the deficient species is not detectably present at the site of the distal dysbiosis prior to administration of the probiotic composition. In one embodiment, the species of bacteria in the probiotic composition translocates to the site of the distal dysbiosis.

In another embodiment, the probiotic composition results in augmentation of a species of bacteria not present in the probiotic composition at a distal site. This augmentation can result from, for example, translocation of a species of bacteria not present in the probiotic composition to the distal site, and/or modulation of the microenvironment of the distal site in a manner that alters the microbiome.

In preferred embodiments, the probiotic composition contains immunomodulatory bacteria, e.g., anti-inflammatory bacteria.

In another aspect, the invention provides a method of reducing intestinal permeability in a subject, by administering a probiotic composition comprising an isolated bacterial population, wherein administration of the probiotic composition augments a species of bacteria that produces short chain fatty acids, such that the intestinal permeability of the subject is reduced. In other embodiments, intestinal permeability and disorders associated therewith is improved by administering a probiotic composition containing mucin-containing bacteria, and/or anti-inflammatory bacteria.

Pharmaceutical compositions useful for correcting or treating a distal dysbiosis, or for treating a disorder distal to the site of administration (e.g., the gastrointestinal tract) associated with a dysbiosis, can include any of the pharmaceutical compositions described herein. In exemplary embodiments, a pharmaceutical composition useful for correcting or treating a distal dysbiosis includes one or more bacterial strains from Table 1. In other embodiments, the pharmaceutical composition useful for correcting or treating a distal dysbiosis includes one or more bacterial strains from Table 1 A. In other embodiments, the pharmaceutical composition useful for correcting or treating a distal dysbiosis includes one or more bacterial strains from Table 1B. In other embodiments, the pharmaceutical composition useful for correcting or treating a distal dysbiosis includes one or more bacterial strains from Table 1C. In other embodiments, the pharmaceutical composition useful for correcting or treating a distal dysbiosis includes one or more bacterial strains from Table 1D. In other embodiments, the pharmaceutical composition useful for correcting or treating a distal dysbiosis includes one or more bacterial strains from Table 1E. In other embodiments, the pharmaceutical composition useful for correcting or treating a distal dysbiosis includes one or more bacterial strains from Table 1F. In some embodiments, the pharmaceutical composition contains a single strain of bacteria. In other embodiments, the pharmaceutical composition contains two or more strains of bacteria, e.g., 2, 3, 4, 5, 6, 7, 8, 9, 10, 15, 20, 30, 40, 50, 60, 70, 80, 90, 100, 500, 1000 or more strains of bacteria. In other embodiments, the pharmaceutical composition contains or is administered in conjunction with a prebiotic, as described herein.

Exemplary pharmaceutical compositions useful for treatment of disorders associated with a dysbiosis distal to the site of administration (e.g., the gastrointestinal tract) contain bacterial strains capable of reducing inflammation in a subject. As described herein, such immunomodulatory (anti-inflammatory) bacteria can modulate cytokine expression by host immune cells, resulting in an overall increase in secretion of anti-inflammatory cytokines and/or an overall decrease in secretion of pro-inflammatory cytokines, systemically reducing inflammation in the subject. In exemplary embodiments, pharmaceutical compositions useful for treatment of disorders associated with a distal dysbiosis stimulate secretion of one or more anti-inflammatory cytokines by host immune cells, such as PBMCs. Anti-inflammatory cytokines include, but are not limited to, IL-10, IL-13, IL-9, IL-4, IL-5, TGFβ, and combinations thereof. In other exemplary embodiments, pharmaceutical compositions useful for treatment of disorders associated with a distal dysbiosis inhibit secretion of one or more pro-inflammatory cytokines by host immune cells, such as PBMCs. Pro-inflammatory cytokines include, but are not limited to, IFNγ, IL-12p70, IL-1α, IL-6, IL-8, MCP1, MIP1α, MIP1β, TNFα, and combinations thereof. Other exemplary cytokines are known in the art and are described herein. Pharmaceutical compositions containing anti-inflammatory bacteria reduce inflammation at the site of administration, e.g., in the gastrointestinal tract, as well as at distal sites throughout the body of the subject.

Other exemplary pharmaceutical compositions useful for treatment of disorders associated with a dysbiosis distal to the site of administration (e.g., the gastrointestinal tract)

contain bacterial strains capable of altering the proportion of immune subpopulations, e.g., T cell subpopulations, in the subject.

For example, immunomodulatory bacteria can increase or decrease the proportion of Treg cells, Th17 cells, Th1 cells, or Th2 cells in a subject. The increase or decrease in the proportion of immune cell subpopulations may be systemic, or it may be localized to a site of action of the pharmaceutical, e.g., in the gastrointestinal tract or at the site of a distal dysbiosis. In some embodiments, a pharmaceutical composition comprising immunomodulatory bacteria is used for treatment of disorders associated with a dysbiosis distal to the site of administration (e.g., the gastrointestinal tract) based on the desired effect of the pharmaceutical composition on the differentiation and/or expansion of subpopulations of immune cells in the subject.

In one embodiment, a pharmaceutical composition contains immunomodulatory bacteria that increase the proportion of Treg cells in a subject. In another embodiment, a pharmaceutical composition contains immunomodulatory bacteria that decrease the proportion of Treg cells in a subject. In one embodiment, a pharmaceutical composition contains immunomodulatory bacteria that increase the proportion of Th17 cells in a subject. In another embodiment, a pharmaceutical composition contains immunomodulatory bacteria that decrease the proportion of Th17 cells in a subject. In one embodiment, a pharmaceutical composition contains immunomodulatory bacteria that increase the proportion of Th1 cells in a subject. In another embodiment, a pharmaceutical composition contains immunomodulatory bacteria that decrease the proportion of Th1 cells in a subject. In one embodiment, a pharmaceutical composition contains immunomodulatory bacteria that increase the proportion of Th2 cells in a subject. In another embodiment, a pharmaceutical composition contains immunomodulatory bacteria that decrease the proportion of Th2 cells in a subject.

In one embodiment, a pharmaceutical composition contains immunomodulatory bacteria capable of modulating the proportion of one or more of Treg cells, Th17 cells, Th1 cells, and combinations thereof in a subject. Certain immune cell profiles may be particularly desirable to treat or prevent particular disorders associated with a dysbiosis. For example, treatment or prevention of autoimmune or inflammatory disorders can be promoted by increasing numbers of Treg cells and Th2 cells, and decreasing numbers of Th17 cells and Th1 cells. Accordingly, pharmaceutical compositions for the treatment or prevention of autoimmune or inflammatory disorders may contain pharmaceuticals capable of promoting Treg cells and Th2 cells, and reducing Th17 and Th1 cells.

Distal disorders associated with loss of intestinal barrier function can be treated or improved by administration of pharmaceutical compositions containing bacterial strains that produce short chain fatty acids (SCFAs), such as, for example, butyrate, acetate, propionate, or valerate, or combinations thereof. Distal disorders associated with loss of intestinal barrier function can be treated or improved by administration of probiotic compositions containing bacterial strains that reduce inflammation, as described herein.

In other embodiments, the distal dysbiosis is caused by a deficiency in microbes that produce lactic acid. Accordingly, in one embodiment, the probiotic composition can contain a species of bacteria that produce lactic acid.

EXAMPLES

The invention is further illustrated by the following examples. The examples are offered for illustrative purposes only, and are not intended to limit the scope of the present invention in any way. The entire contents of all references, patents, and published patent applications cited throughout this application are hereby incorporated by reference in their entirety.

The practice of the present invention will employ, unless otherwise indicated, conventional methods of protein chemistry, biochemistry, recombinant DNA techniques and pharmacology, within the skill of the art. Such techniques are explained fully in the literature. See, e.g., T. E. Creighton, *Proteins: Structures and Molecular Properties* (W.H. Freeman and Company, 1993); A. L. Lehninger, *Biochemistry* (Worth Publishers, Inc., current addition); Sambrook, et al., *Molecular Cloning: A Laboratory Manual* (2nd Edition, 1989); *Methods In Enzymology* (S. Colowick and N. Kaplan eds., Academic Press, Inc.); *Remington's Pharmaceutical Sciences*, 18th Edition (Easton, Pa.: Mack Publishing Company, 1990); Carey and Sundberg *Advanced Organic Chemistry* $3^{rd}$ Ed. (Plenum Press, Vols A and B, 1992). Enzyme Linked Immunosorbent Assays (ELISAs) and Western blots described below are performed using kits according to the manufacturers' (e.g., Life Technologies, Thermo Fisher Scientific, New York, USA) instructions.

EXAMPLES

The invention is further illustrated by the following examples. The examples are offered for illustrative purposes only, and are not intended to limit the scope of the present invention in any way. The entire contents of all references, patents, and published patent applications cited throughout this application are hereby incorporated by reference in their entirety.

The practice of the present invention will employ, unless otherwise indicated, conventional methods of protein chemistry, biochemistry, recombinant DNA techniques and pharmacology, within the skill of the art. Such techniques are explained fully in the literature. See, e.g., T. E. Creighton, *Proteins: Structures and Molecular Properties* (W.H. Freeman and Company, 1993); A. L. Lehninger, *Biochemistry* (Worth Publishers, Inc., current addition); Sambrook, et al., *Molecular Cloning: A Laboratory Manual* (2nd Edition, 1989); *Methods In Enzymology* (S. Colowick and N. Kaplan eds., Academic Press, Inc.); *Remington's Pharmaceutical Sciences*, 18th Edition (Easton, Pa.: Mack Publishing Company, 1990); Carey and Sundberg *Advanced Organic Chemistry* $3^{rd}$ Ed. (Plenum Press, Vols A and B, 1992). Enzyme Linked Immunosorbent Assays (ELISAs) and Western blots described below are performed using kits according to the manufacturers' (e.g., Life Technologies, Thermo Fisher Scientific, New York, USA) instructions.

Example 1. Assessment of Intestinal Permeability after Administration of Bacteria, Prebiotic or Combinations Thereof The main function of the gastrointestinal (GI) tract is to digest and absorb nutrients from food. The mucosa of the GI tract forms a selective barrier between the host and the environment of the gut lumen. The mucosa allows transport of nutrients while restricting passage of larger molecules and bacteria. Impaired barrier integrity is believed to contribute to the pathogenesis of many disorders including autoimmune diseases, including transplant disorders such as graft-versus-host-disease (GVHD), and neurological disorders. Disruption of the intestinal barrier due to toxins, dysbiosis, inflammation or other factors is believed to result in the passage and presentation of environmental antigens to the immune system leading to aberrant immune responses. Similarly, the leakage of bacterial endotoxin or other toxic metabolites into the circulation can lead to systemic inflammation promoting the development of autoimmunity and neuroinflammation.

Restoration of GI barrier integrity through the administration of selected prebiotics and/or probiotics represents an approach to correct a basic defect underlying multiple pathological conditions.

In a first set of experiments, intestinal permeability was assessed using serum endotoxin levels as a marker of gut permeability in mice treated with xylose and/or antibiotics. Basal levels of intestinal permeability can be measured under disease or normal conditions. Intestinal permeability can be induced in mice through administration of inflammatory stimuli such as cholera toxin (3 oral gavages of 10 pg cholera toxin, 5 days apart), Poly I:C (3 intraperioneal injections of 1 mg/kg, 3 days apart) or dextran sulfate (3% dextran sulfate sodium salt in drinking water for 7 days). Quantitation of intestinal permeability was carried out by quantitatively measuring plasma levels of endotoxin originating from gut bacteria using a commercially available chromogenic assay (Lonza, Rockland, Me.). The results of these experiments are shown in FIG. 1.

Quantitation of intestinal permeability can also be conducted using a number of alternative methods (reviewed in Bischoff et al, 2014) for example, by quantifying leakage of fluorescently-labeled high molecular weight dextran (FITC-dextran) into the plasma following oral administration (oral gavage with 0.6 g/kg 4 kDa FITC-dextran, serum samples collected 4 hours later and read for fluorescence intensity at 521 nm; Hsiao et al, 2013). To study the effect of bacterial strains on intestinal permeability, mice are gavaged orally with $10^7$-$10^{10}$ bacterial cells for an average of 5 administrations, typically daily or 2 days apart. Bacteria can be administred as single strains or combinations of strains. The bacteria can be administered alone or in combination with a pre-biotic(s). The pre-biotic can be xylose or xylose-containing molecules as a preferred carbon source for anaerobic bacteria. Other prebiotics that can be used include, for example, those described in Table 4. After administration of bacteria+/−pre-biotic, intestinal permability is assessed using the preferred method at the desired time point(s) starting on day 1 post-treatment.

Figure 1:
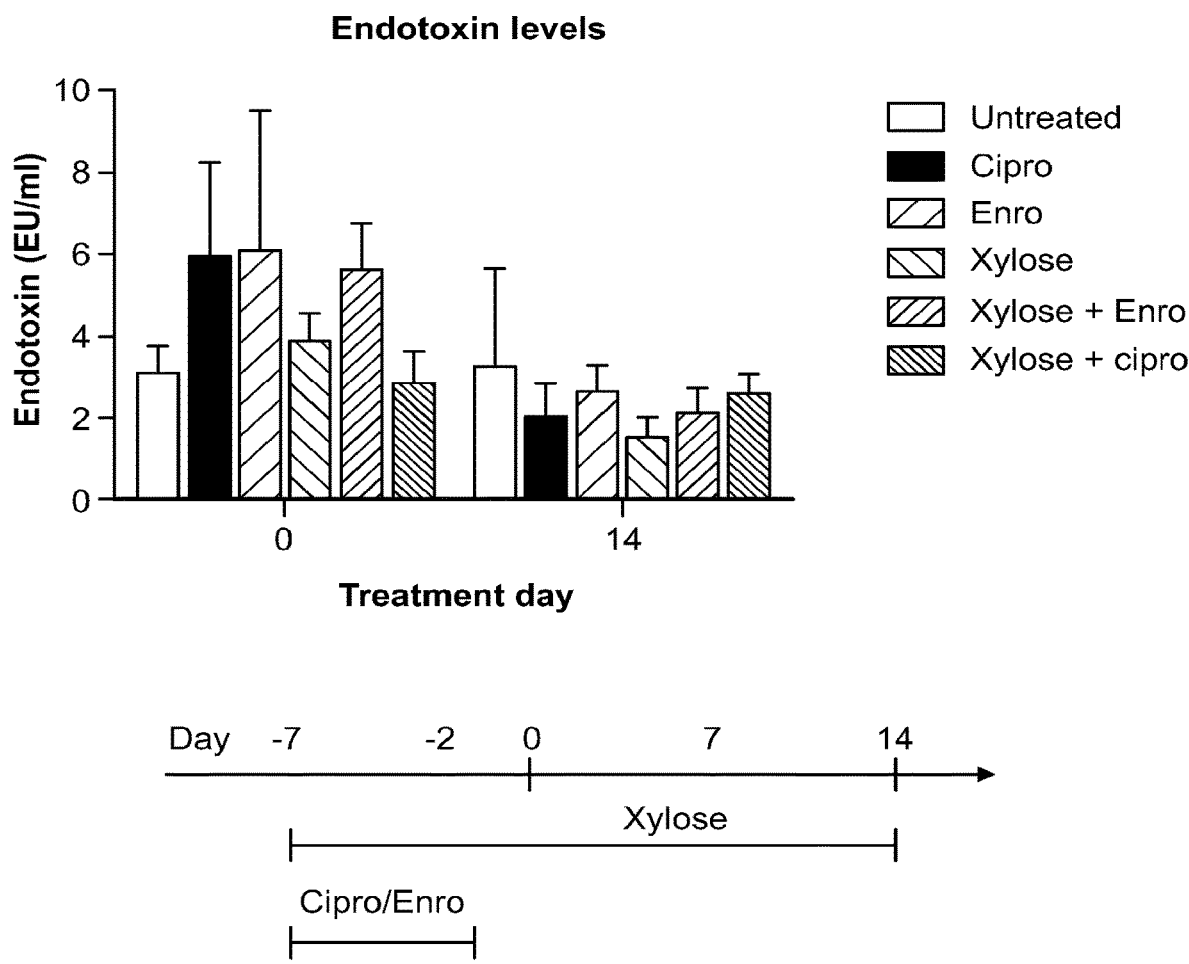
FIG. 1 is a graph depicting serum endotoxin levels (EU/ml) over time following treatment with xylose. Treatment of mice with xylose alone reduces basal levels of serum endotoxin (day 14 vs day 0). Antibiotic treatment (Ciprofloxacin (cipro) or enrofloxacin (enro)) leads to an increase in serum endotoxin levels (measured 2 days after a 5 day course, at day 0) with a return to baseline by day 14. Xylose counteracts the endotoxin increase caused by cipro but not enro antibiotic treatment.
Figure 2A:
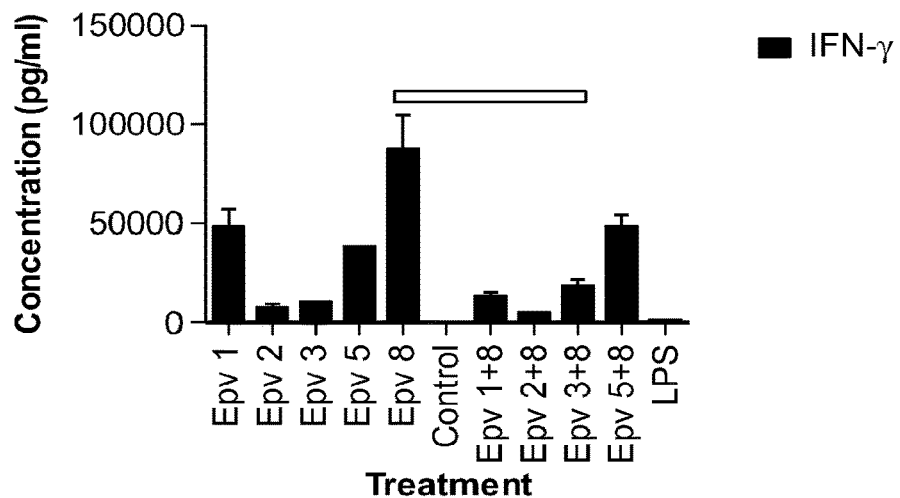
FIG. 2A-2O is a panel of graphs showing the time course of Th1 related cytokines that were released by human peripheral mononuclear cells (PBMCs) incubated with *Ruminococcus gnavus* (Epv 1), *Eubacterium rectale* (Epv 2), *Blautia luti* (Epv 3), *Blautia wexlerae* (Epv 5) and *Enterococcus faecalis* (Epv 8), or combinations of each bacterium with *E. faecalis*. Amounts of interferon gamma (IFN-γ), IL-12p70, IL-6, IL-2 and TNFα that were released in culture supernatants by PBMCs were measured after 24, 48 and 72 hours. a) IFN-γ concentration (pg/ml) after 24 hours. b) IFN-γ concentration (pg/ml) after 48 hours. c) IFN-γ concentration (pg/ml) after 72 hours. d) IL-12p70 concentration (pg/ml) after 24 hours. e) IL-12p70 concentration (pg/ml) after 48 hours. f) IL-12p70 concentration (pg/ml) after 72 hours. g) IL-6 concentration (pg/ml) after 24 hours. h) IL-6 concentration (pg/ml) after 48 hours. i) IL-6 concentration (pg/ml) after 72 hours. j) IL-2 concentration (pg/ml) after 24 hours. k) IL-2 concentration (pg/ml) after 48 hours. l) IL-2 concentration (pg/ml) after 72 hours. m) TNFα concentration (pg/ml) after 24 hours. n) TNFα concentration (pg/ml) after 48 hours. o) TNFα concentration (pg/ml) after 72 hours.
Figure 2B:
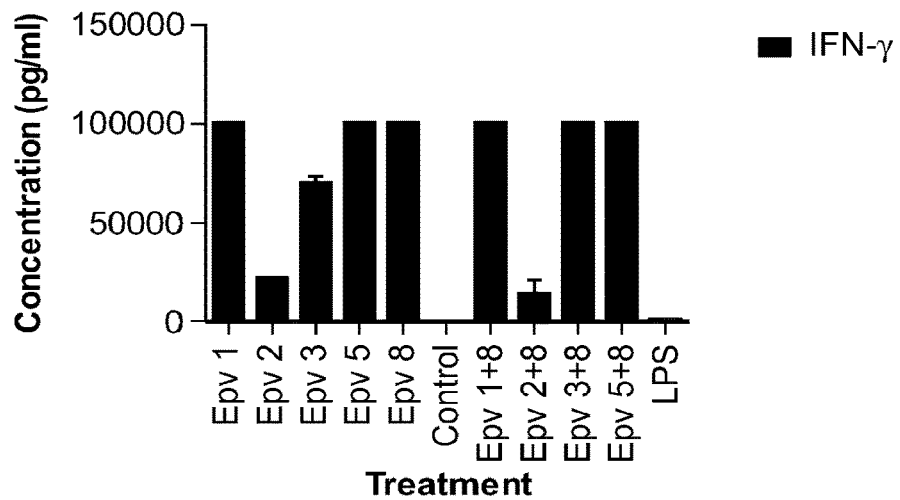
Figure 2C:
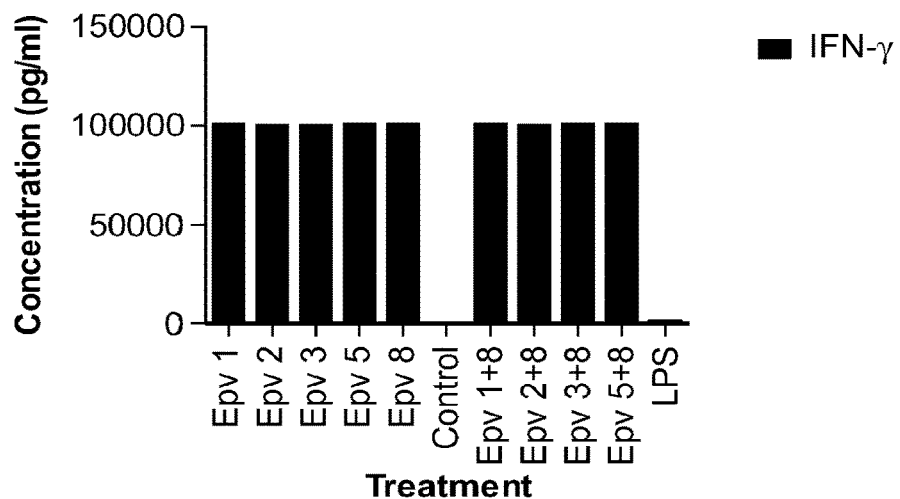
Figure 2D:
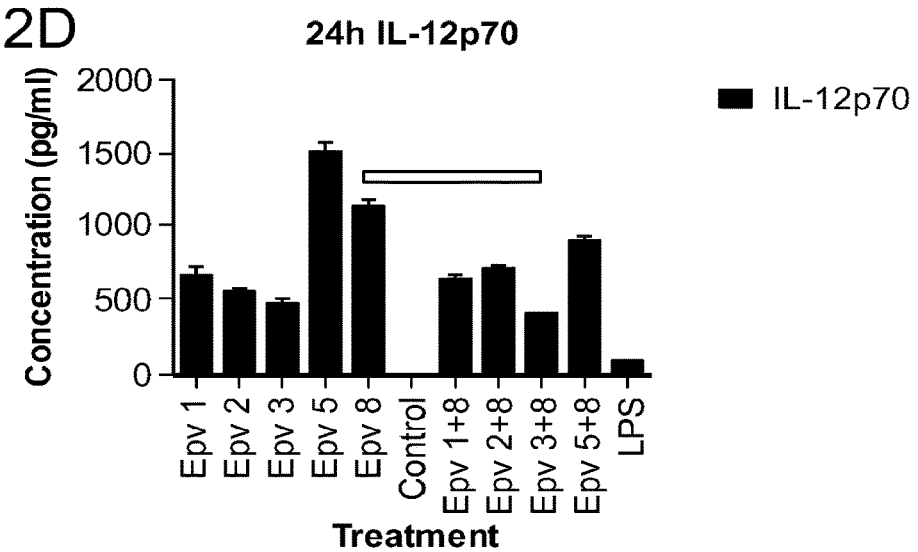
Figure 2E:
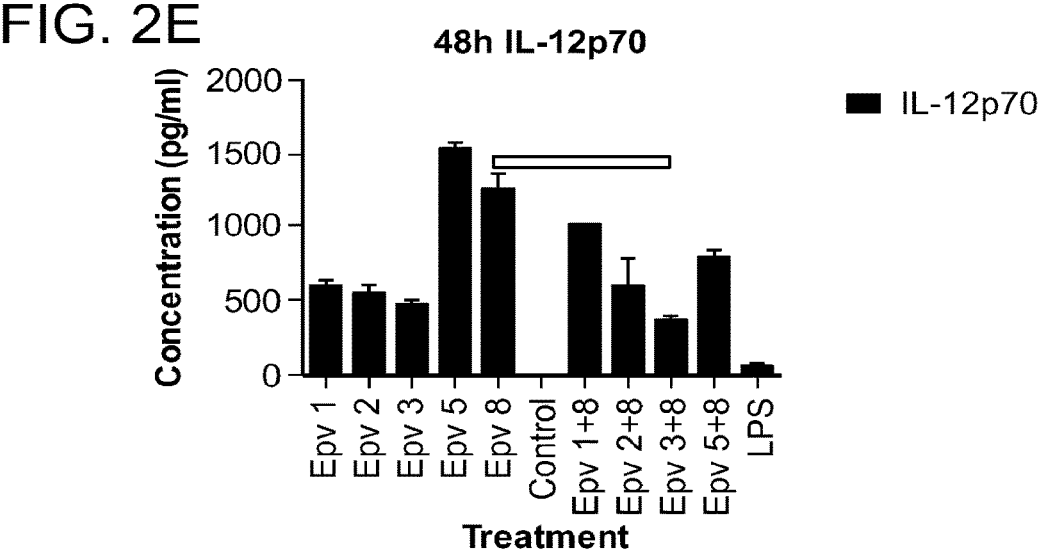
Figure 2F:
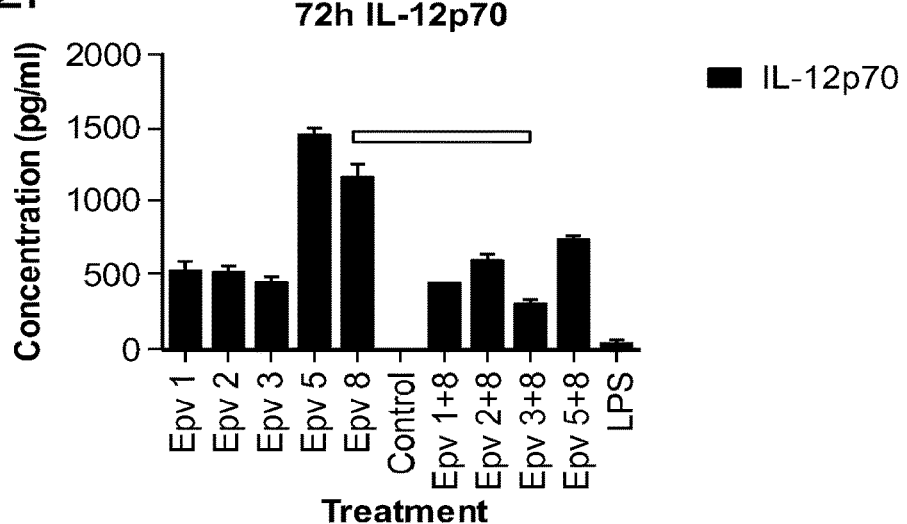
Figure 2G:
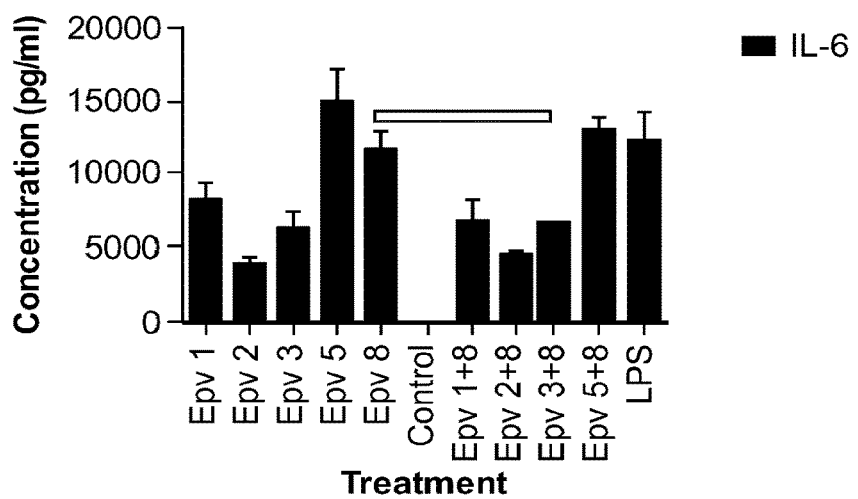
Figure 2H:
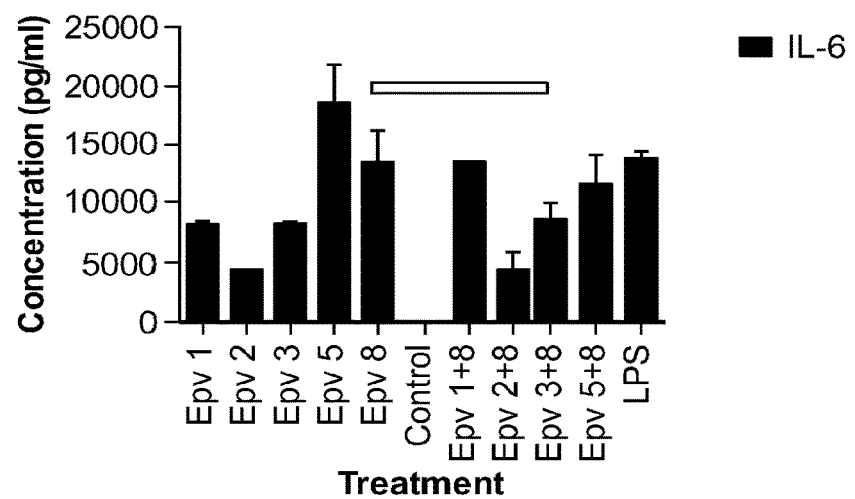
Figure 2I:
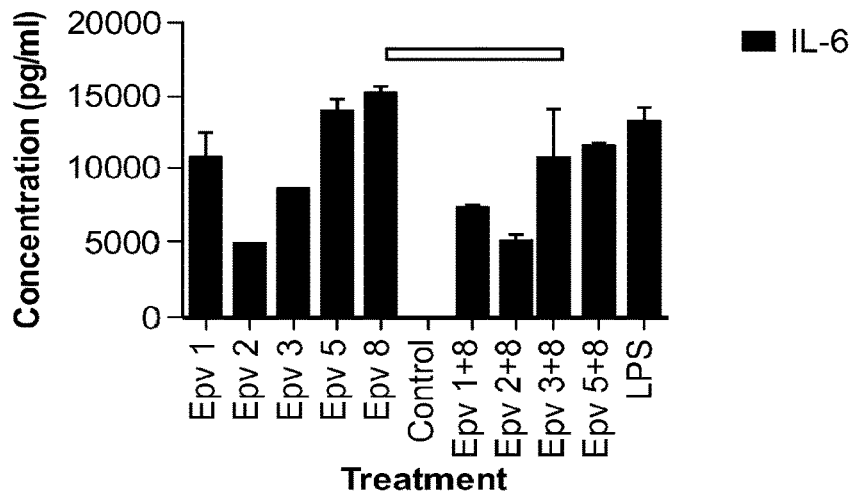
Figure 2J:
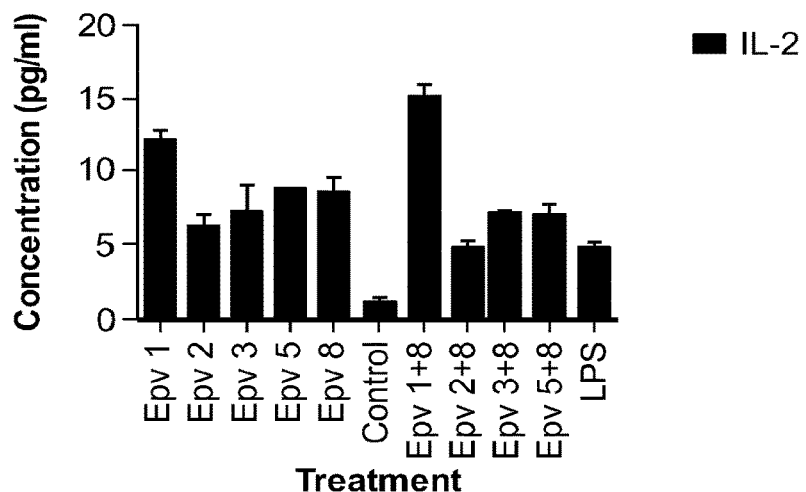
Figure 2K:
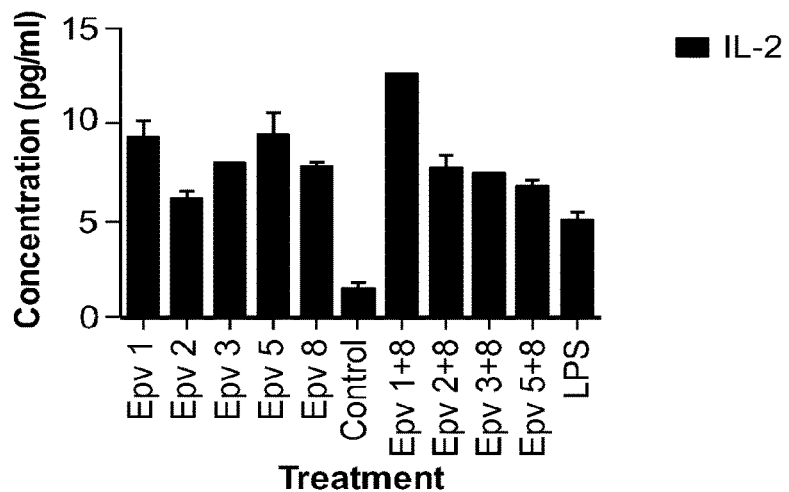
Figure 2L:
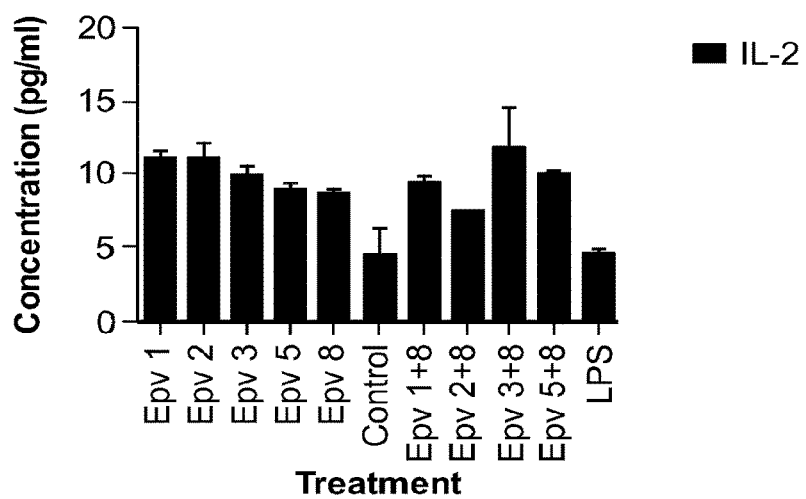
Figure 2M:
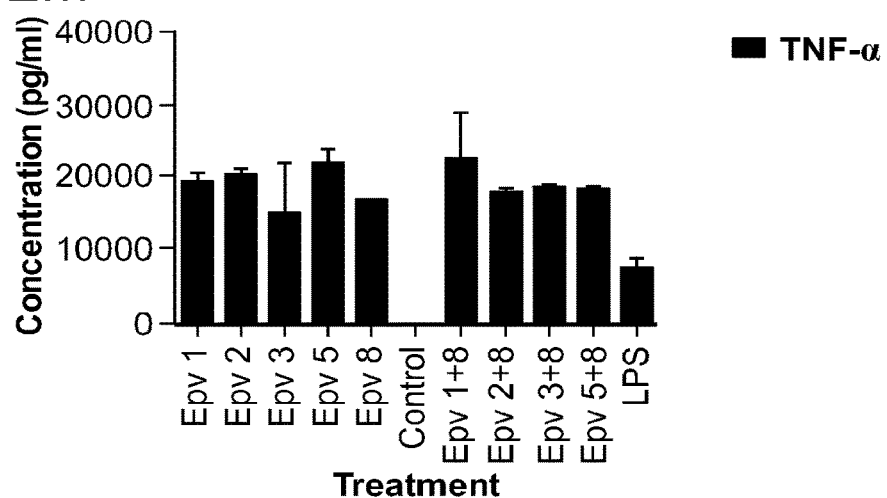
Figure 2N:
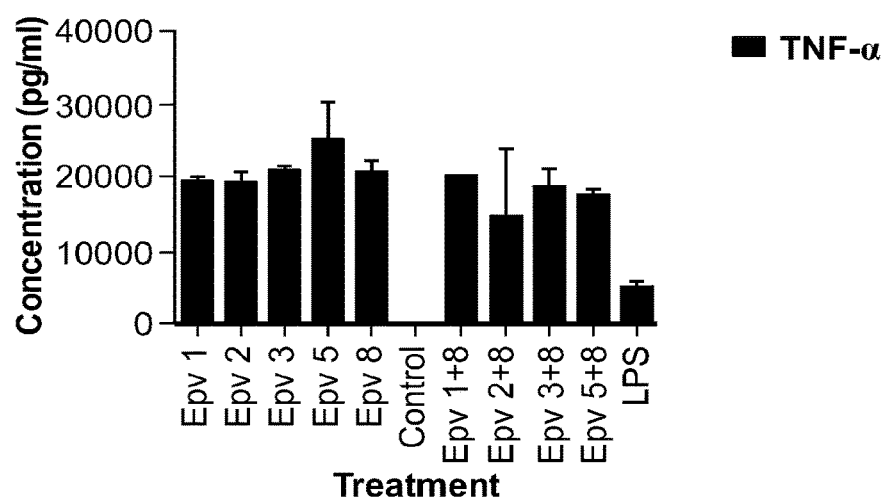
Figure 2O:
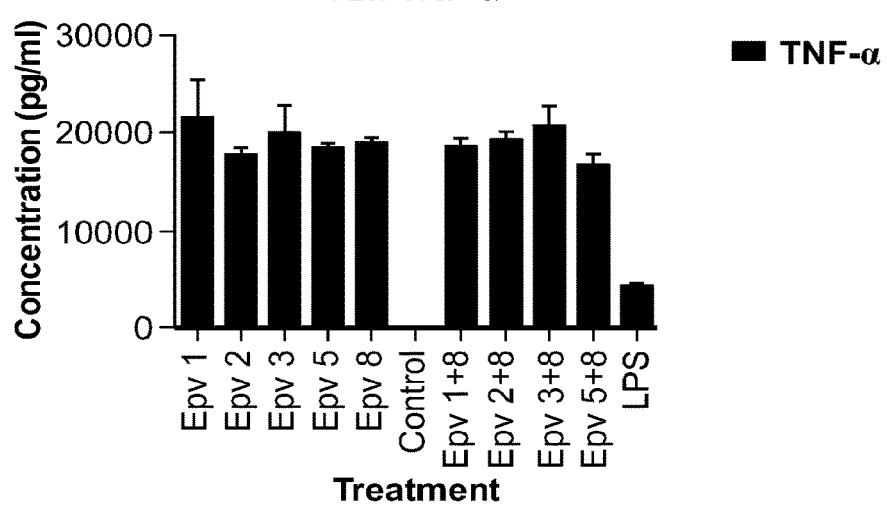
Figure 3A:
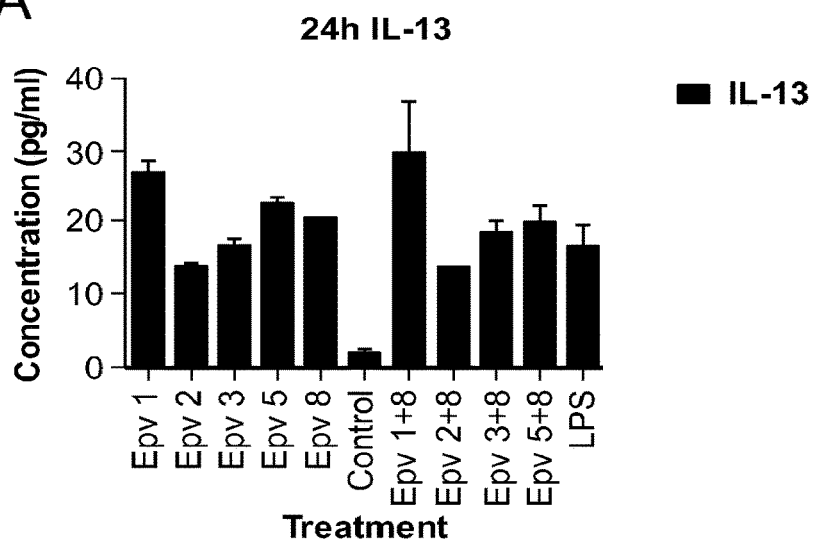
FIG. 3A-3I is a panel of graphs showing the time course of Th2 related cytokines that were released by human PBMCs incubated with *R. gnavus* (Epv 1), *E. rectale* (Epv 2), *B. luti* (Epv 3), *B. wexlerae* (Epv 5) and *E. faecalis* (Epv 8), or combinations of each bacterium with *E. faecalis*. Amounts of IL-13, IL-4 and IL-5 that were released in culture supernatants by PBMCs were measured after 24, 48 and 72 hours. a) IL-13 concentration (pg/ml) after 24 hours. b) IL-13 concentration (pg/ml) after 48 hours. c) IL-13 concentration (pg/ml) after 72 hours. d) IL-4 concentration (pg/ml) after 24 hours. e) IL-4 concentration (pg/ml) after 48 hours. f) IL-4 concentration (pg/ml) after 72 hours. g) IL-5 concentration (pg/ml) after 24 hours. h) IL-5 concentration (pg/ml) after 48 hours. i) IL-5 concentration (pg/ml) after 72 hours.
Figure 3B:
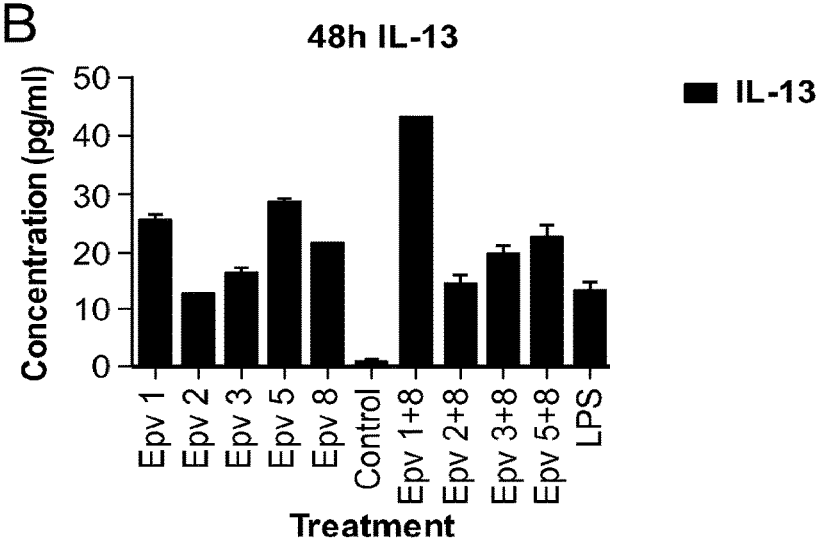
Figure 3C:
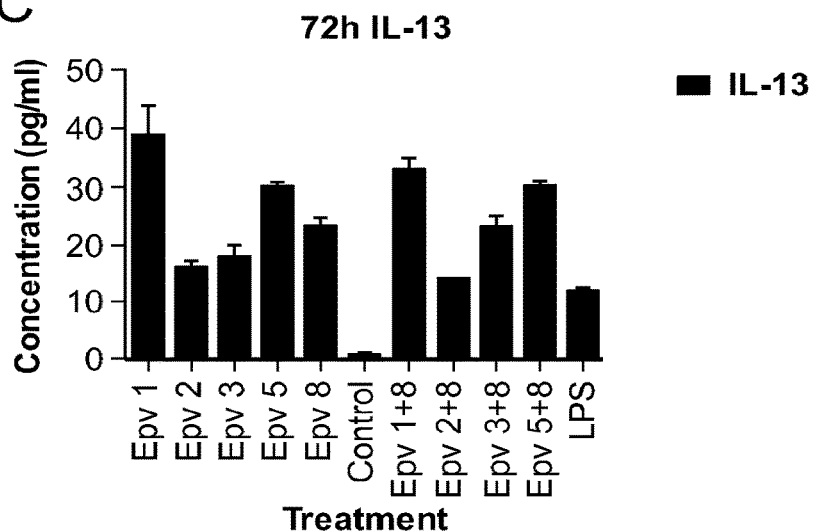
Figure 3D:
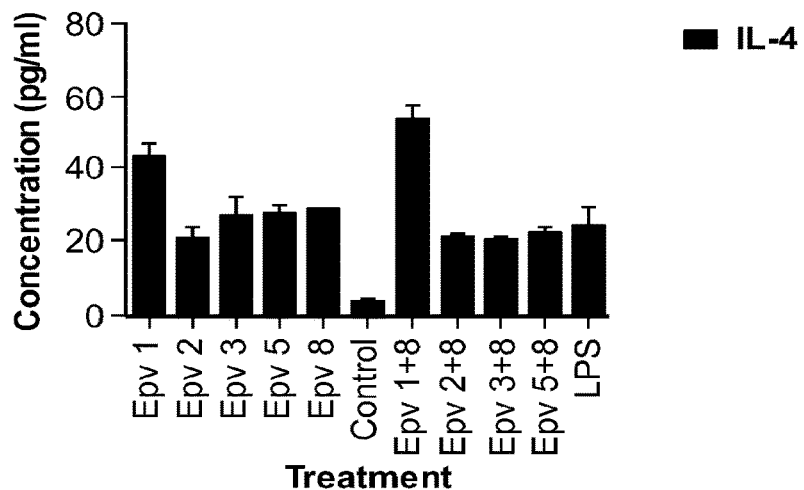
Figure 3E:
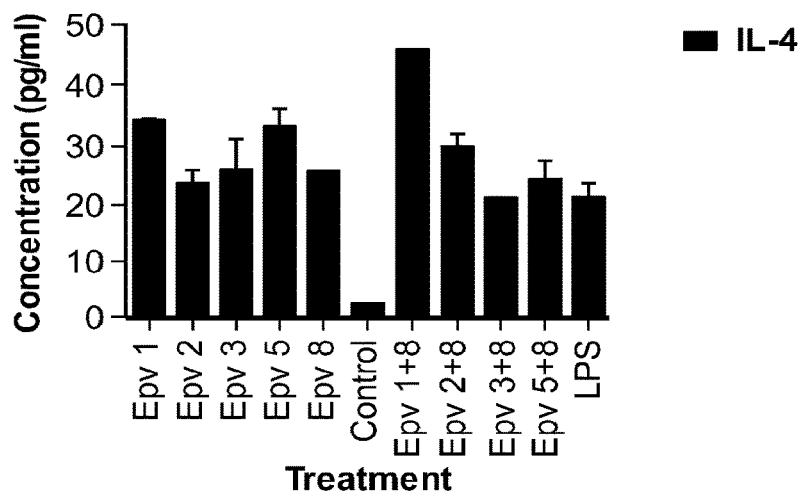
Figure 3F:
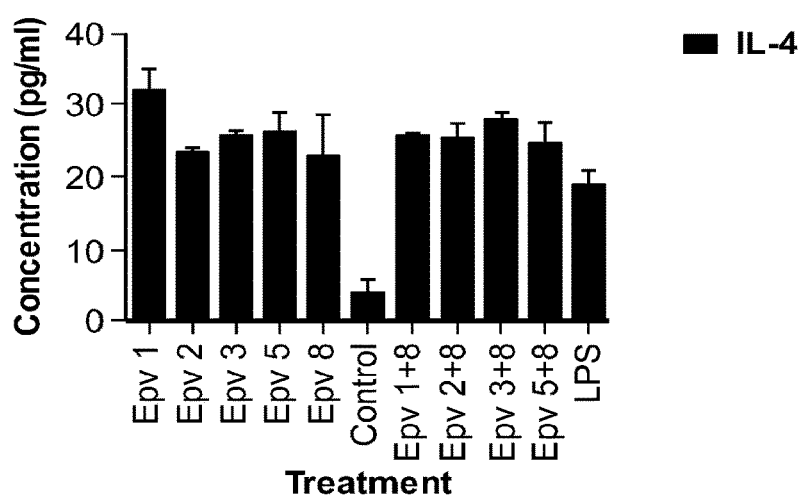
Figure 3G:
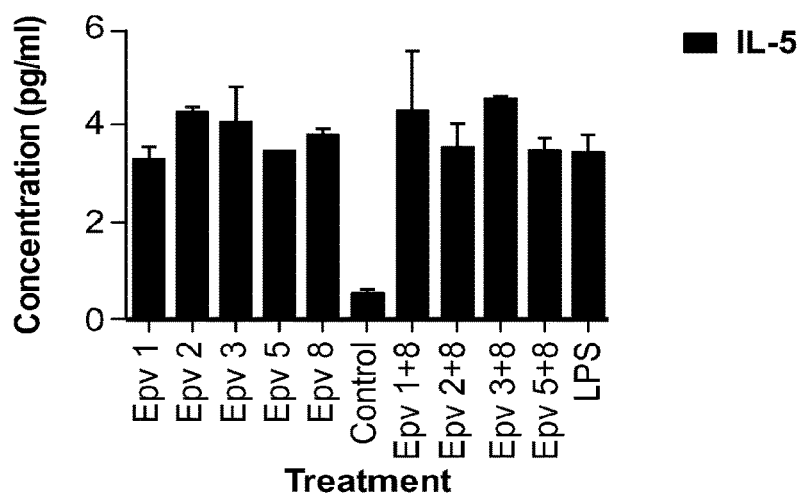
Figure 3H:
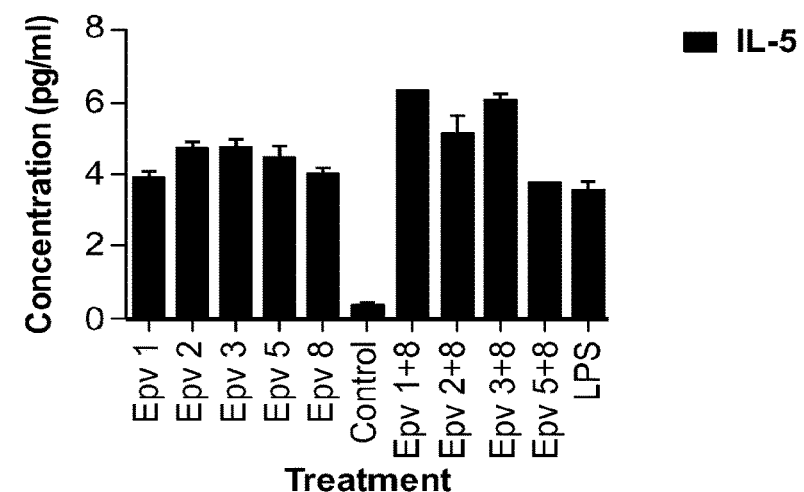
Figure 3I:
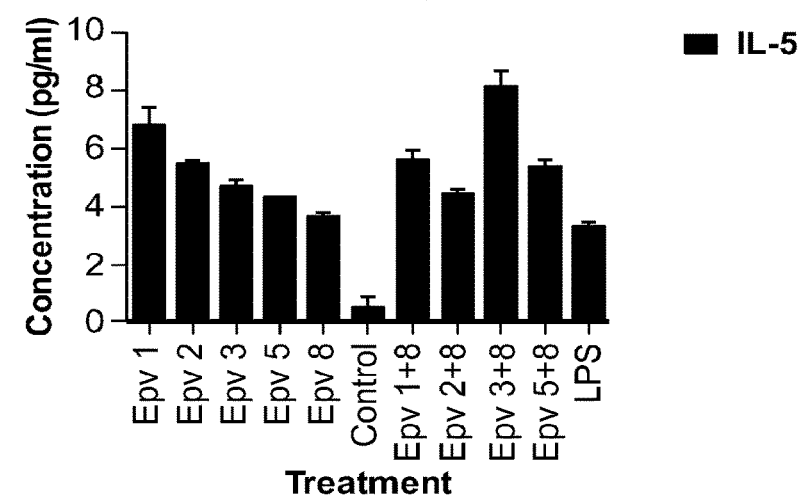
Figure 4A:
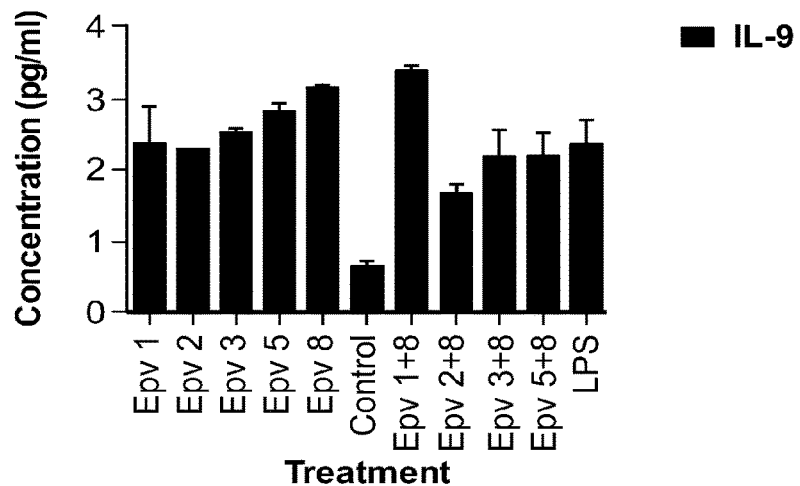
FIG. 4A-4I is a panel of graphs showing the time course of Th9, Th17 and Treg cytokines that were released by human PBMCs incubated with *R. gnavus* (Epv 1), *E. rectale* (Epv 2), *B. luti* (Epv 3), *B. wexlerae* (Epv 5) and *E. faecalis* (Epv 8), or combinations of each bacterium with *E. faecalis*. Amounts of IL-9, IL-17 and IL-10 that were released in culture supernatants by PBMCs were measured after 24, 48 and 72 hours. a) IL-9 concentration (pg/ml) after 24 hours. b) IL-9 concentration (pg/ml) after 48 hours. c) IL-9 concentration (pg/ml) after 72 hours. d) IL-17 concentration (pg/ml) after 24 hours. e) IL-17 concentration (pg/ml) after 48 hours. f) IL-17 concentration (pg/ml) after 72 hours. g) IL-10 concentration (pg/ml) after 24 hours. h) IL-10 concentration (pg/ml) after 48 hours. i) IL-10 concentration (pg/ml) after 72 hours.
Figure 4B:
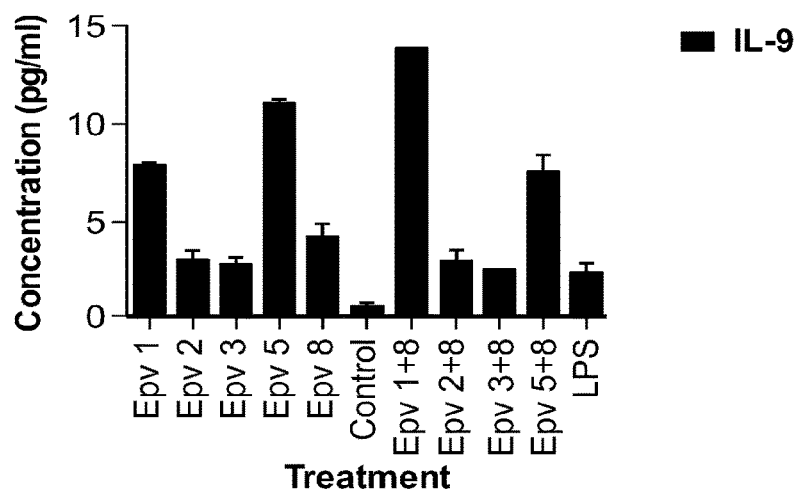
Figure 4C:
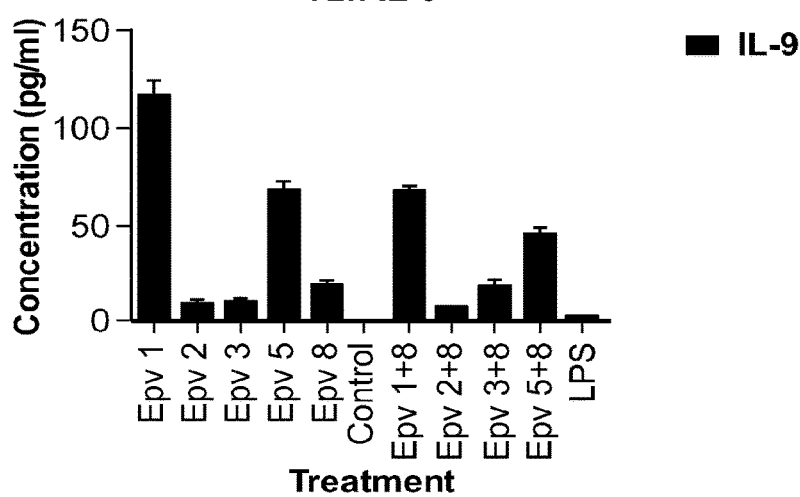
Figure 4D:
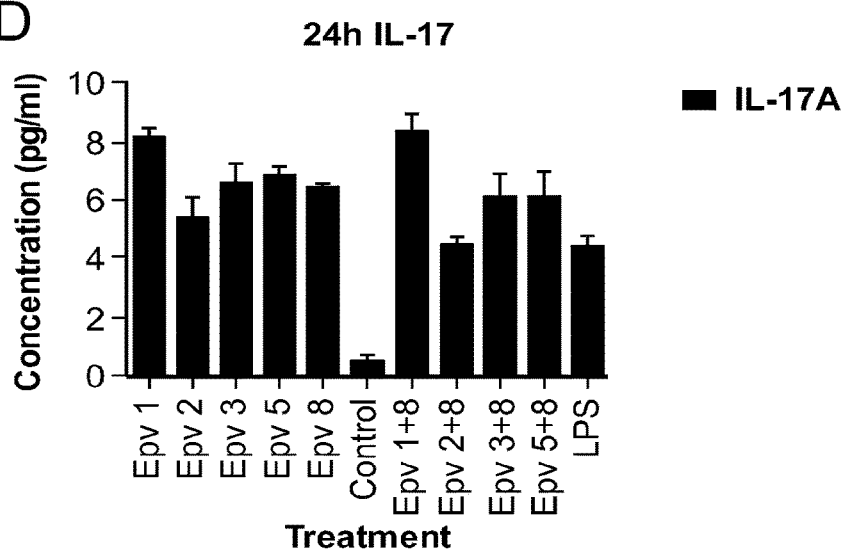
Figure 4E:
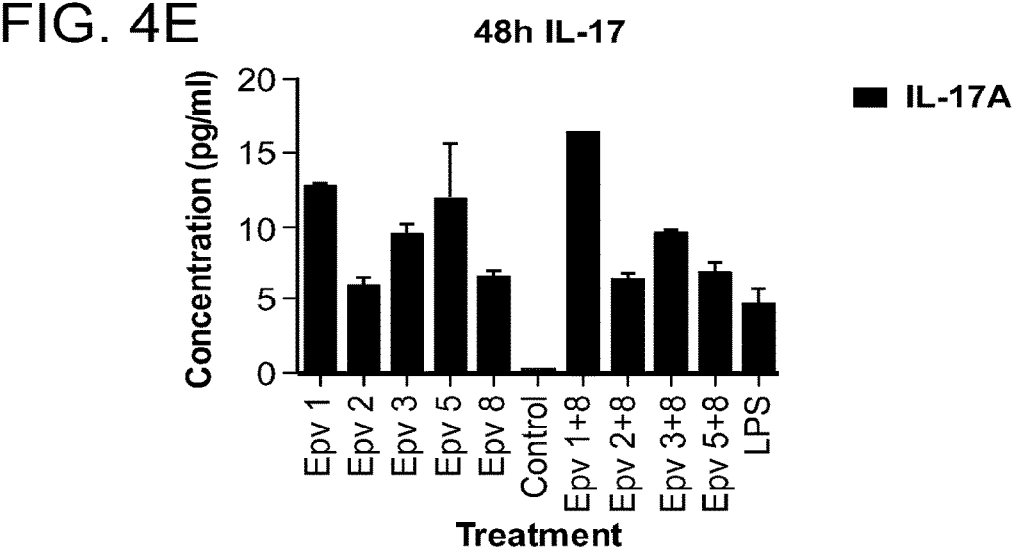
Figure 4F:
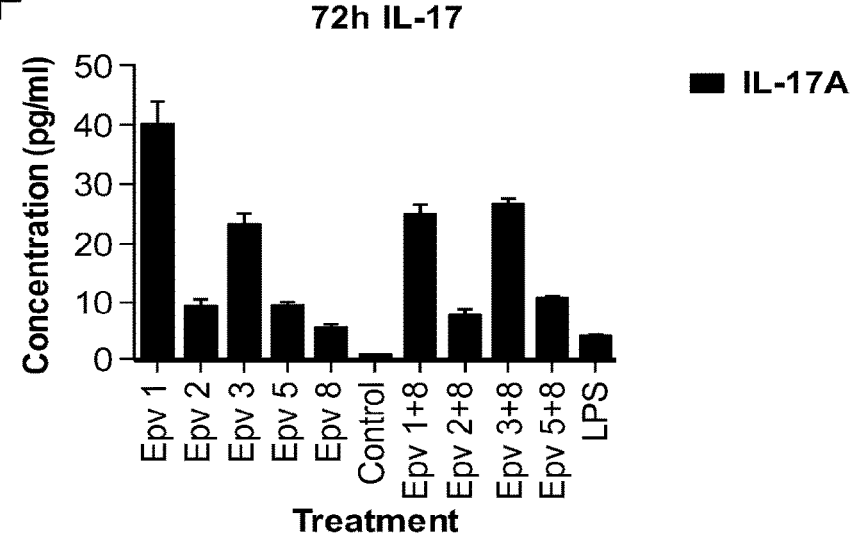
Figure 4G:
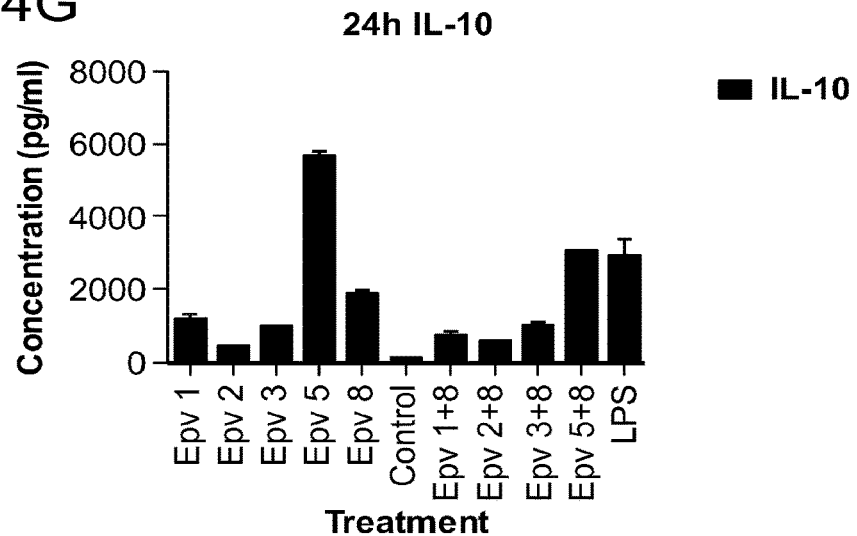
Figure 4H:
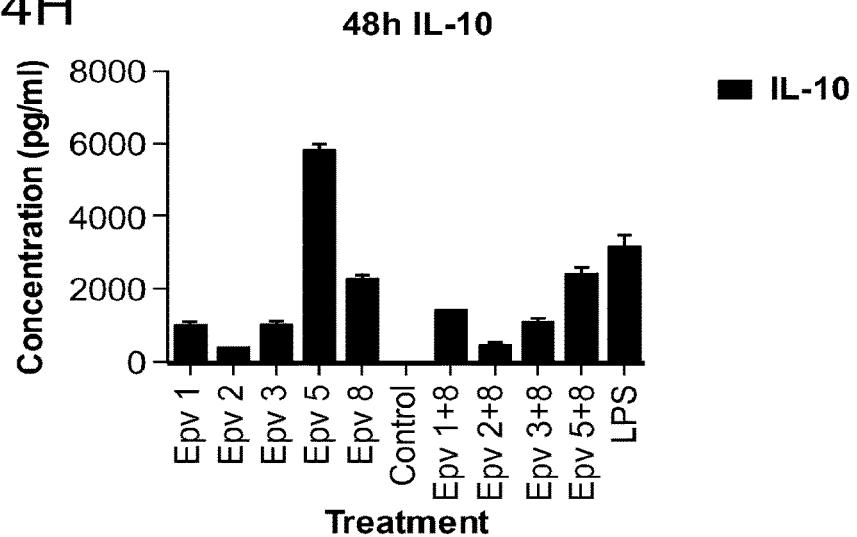
Figure 4I:
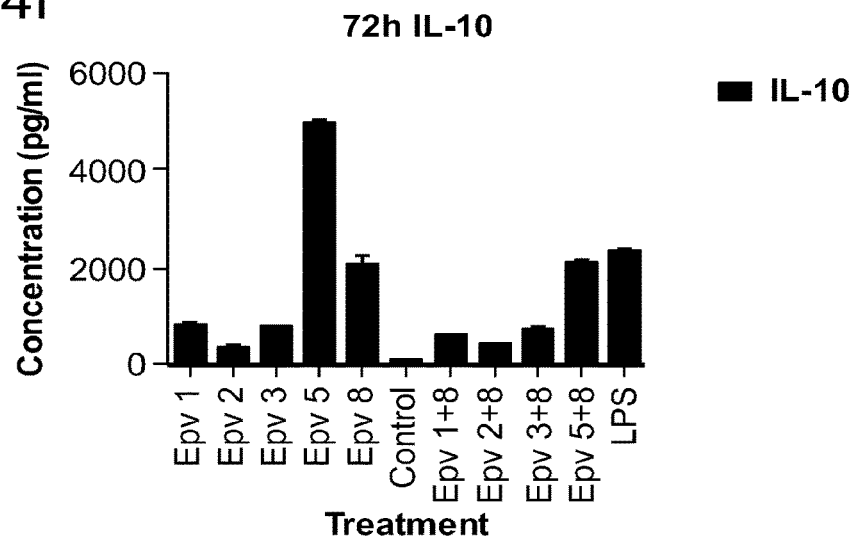
Figure 5A:
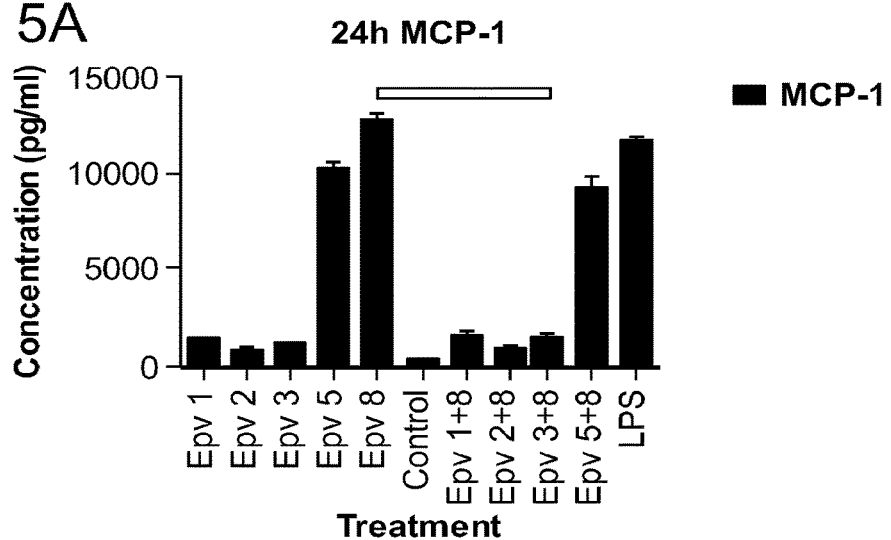
FIG. 5A-5X is a panel of graphs showing the time course of monocyte, macrophage and neutrophil-derived inflammatory cytokines that were released by human PBMCs incubated with *R. gnavus* (Epv 1), *E. rectale* (Epv 2), *B. luti* (Epv 3), *B. wexlerae* (Epv 5) and *E. faecalis* (Epv 8), or combinations of each bacterium with *E. faecalis*. Amounts of monocyte chemotactic protein 1 (MCP-1), macrophage inflammatory protein 10 (MIP1), macrophage inflammatory protein 1α (MIP1α), regulated on activation, normal T expressed and secreted protein (RANTES), interleukin-1α (IL-1α), interleukin-1β (IL1β), interferon α2 (IFN-α2) and interleukin-8 (IL-8) that were released in culture supernatants by PBMCs were measured after 24, 48 and 72 hours. a) MCP-1 concentration (pg/ml) after 24 hours. b) MCP-1 concentration (pg/ml) after 48 hours. c) MCP-1 concentration (pg/ml) after 72 hours. d) MIP1β concentration (pg/ml) after 24 hours. e) MIP1β concentration (pg/ml) after 48 hours. f) MIP1β concentration (pg/ml) after 72 hours. g) MIP1α concentration (pg/ml) after 24 hours. h) MIP1α concentration (pg/ml) after 48 hours. i) MIP1a concentration (pg/ml) after 72 hours. j) RANTES concentration (pg/ml) after 24 hours. k) RANTES concentration (pg/ml) after 48 hours. l) RANTES concentration (pg/ml) after 72 hours. m) IL-1α concentration (pg/ml) after 24 hours. n) IL-1α concentration (pg/ml) after 48 hours. o) IL-1α concentration (pg/ml) after 72 hours. p) IL1β concentration (pg/ml) after 24 hours. q) IL1β concentration (pg/ml) after 48 hours. r) IL1β concentration (pg/ml) after 72 hours. s) IFN-α2 concentration (pg/ml) after 24 hours. t) IFN-α2 concentration (pg/ml) after 48 hours. u) IFN-α2 concentration (pg/ml) after 72 hours. v) IL-8 concentration (pg/ml) after 24 hours. w) IL-8 concentration (pg/ml) after 48 hours. x) IL-8 concentration (pg/ml) after 72 hours.
Figure 5B:
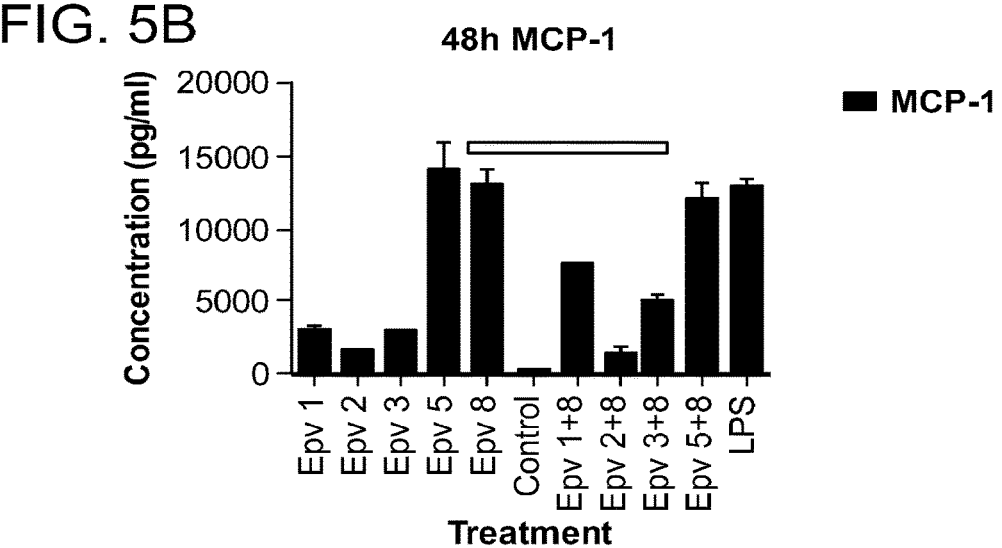
Figure 5C:
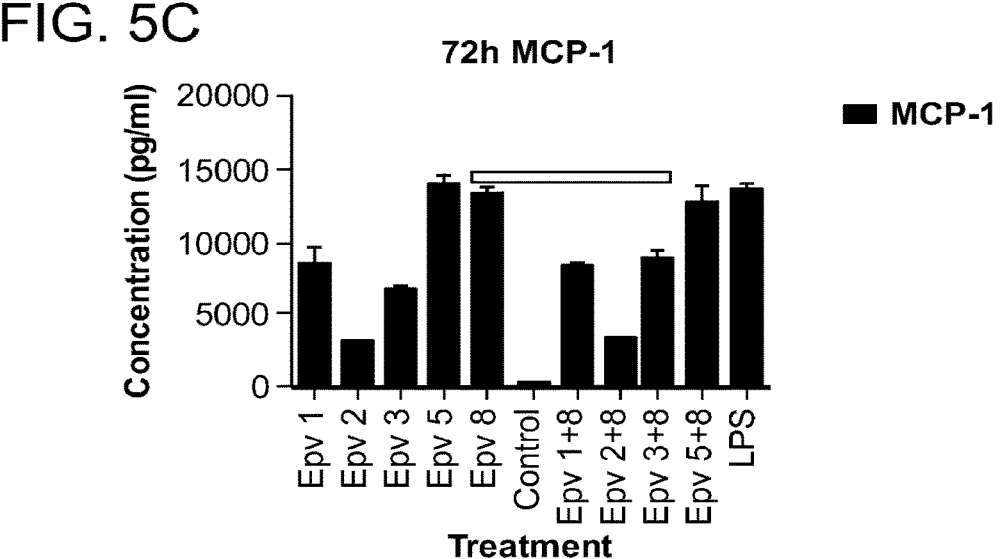
Figure 5D:
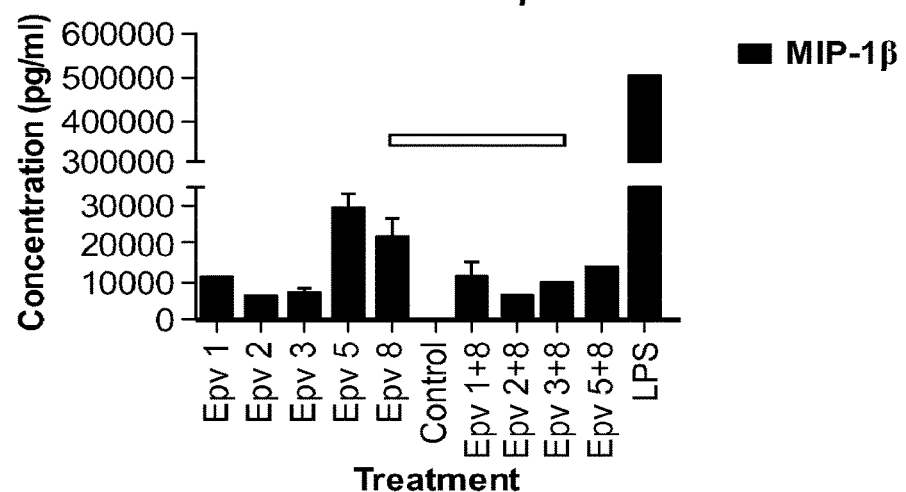
Figure 5E:
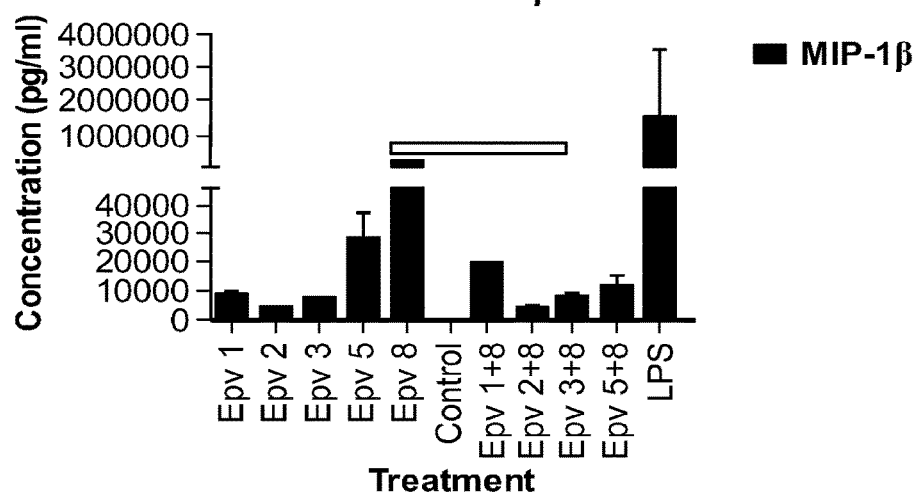
Figure 5F:
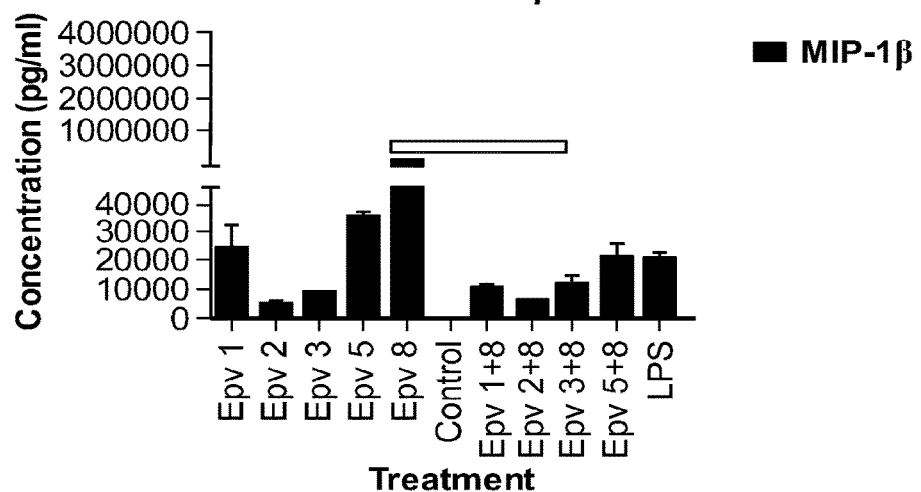
Figure 5G:
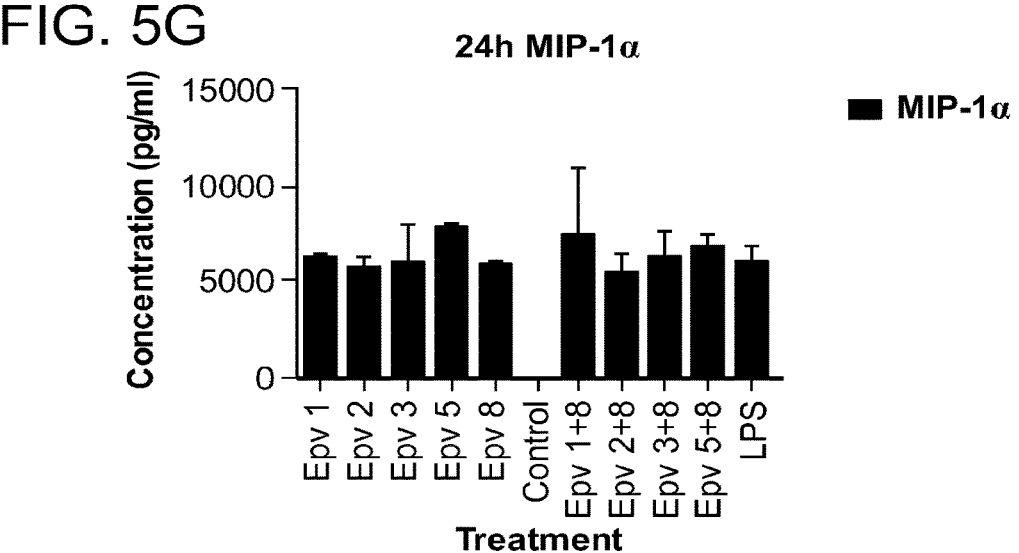
Figure 5H:
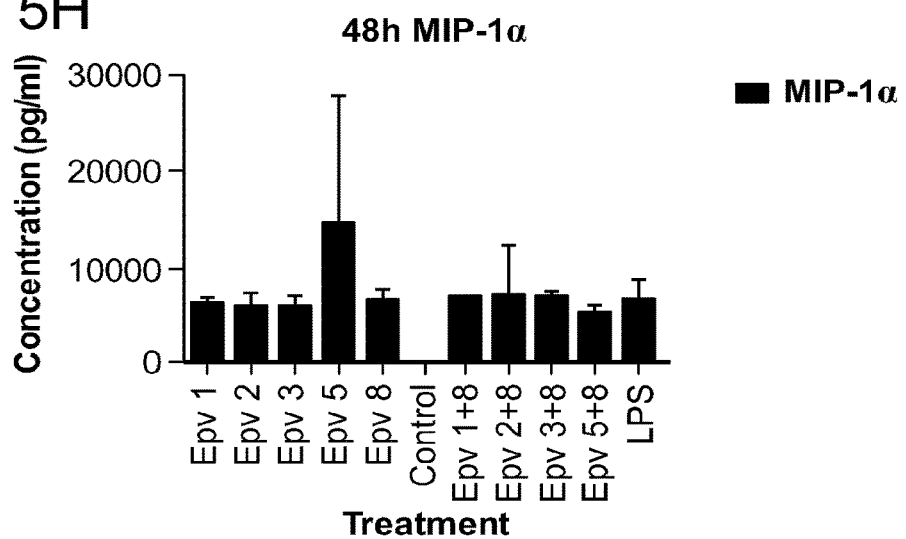
Figure 5I:
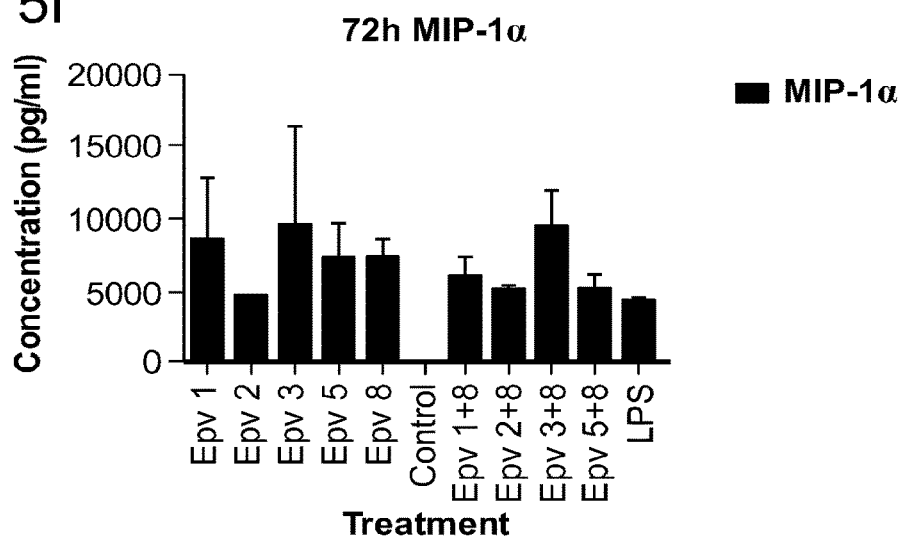
Figure 5J:
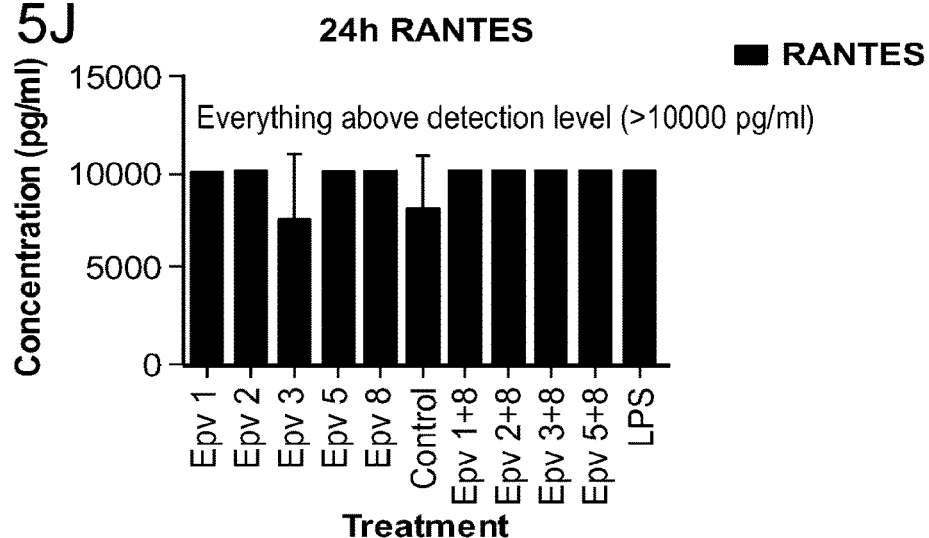
Figure 5K:
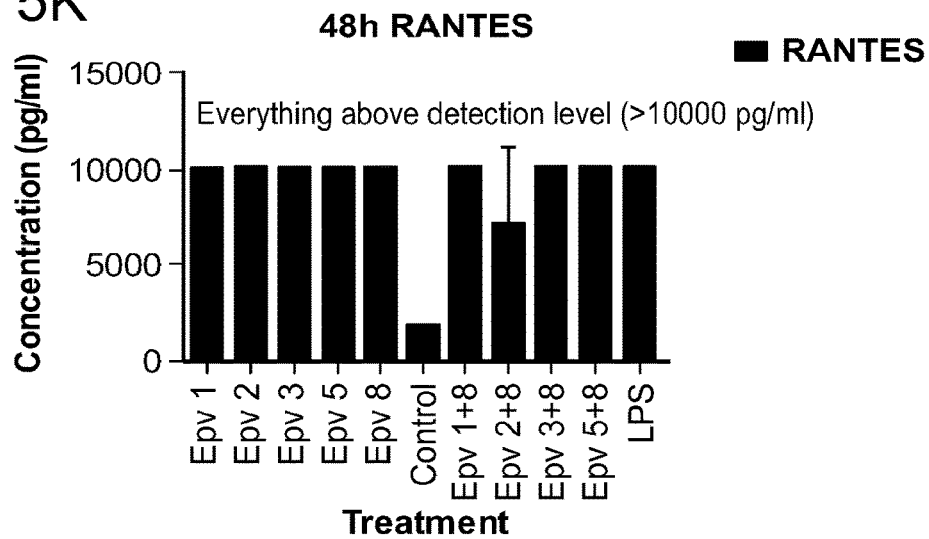
Figure 5L:
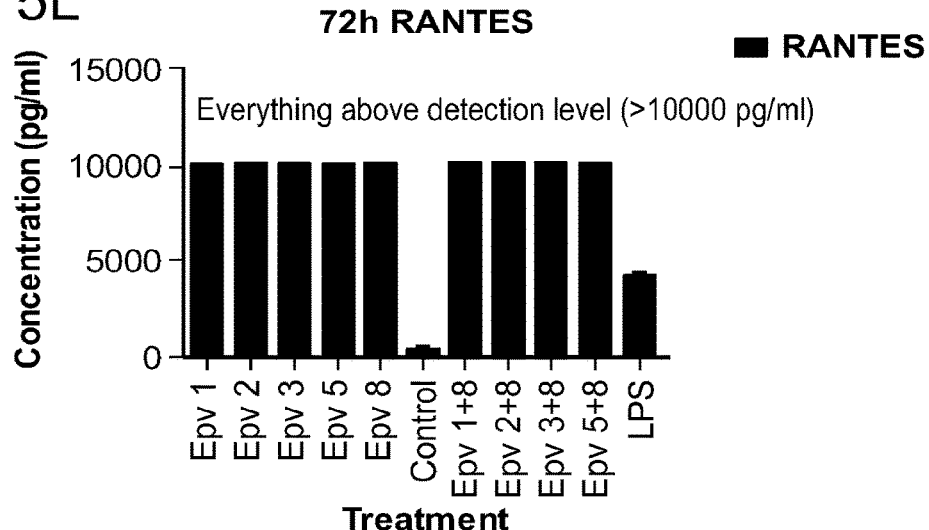
Figure 5M:
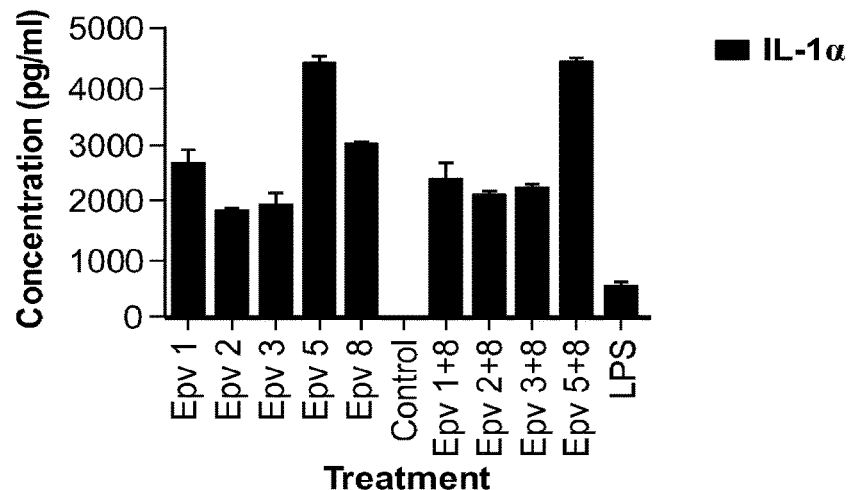
Figure 5N:
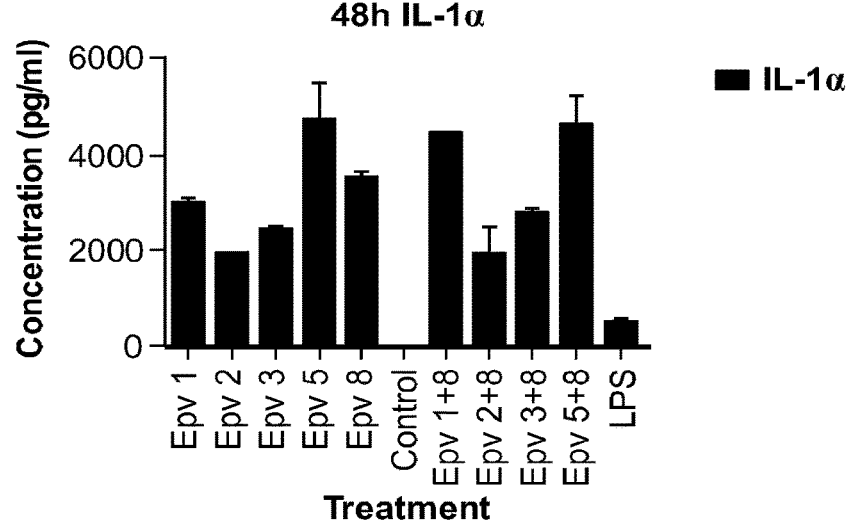
Figure 5O:
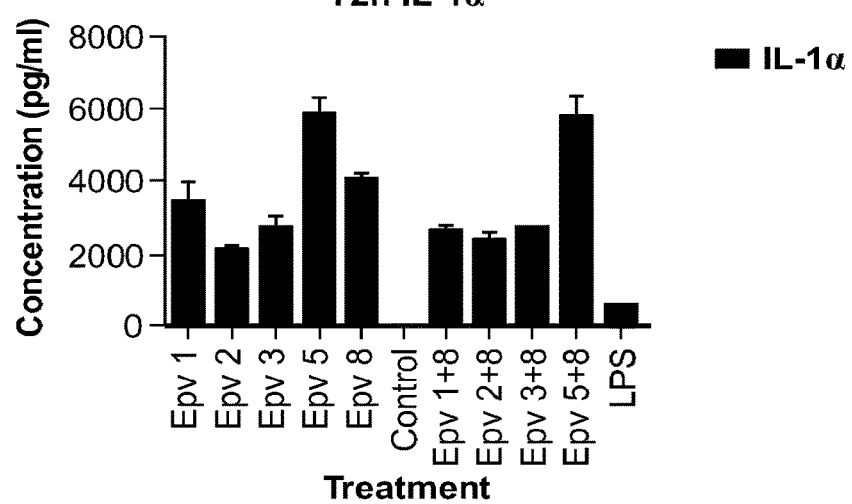
Figure 5P:
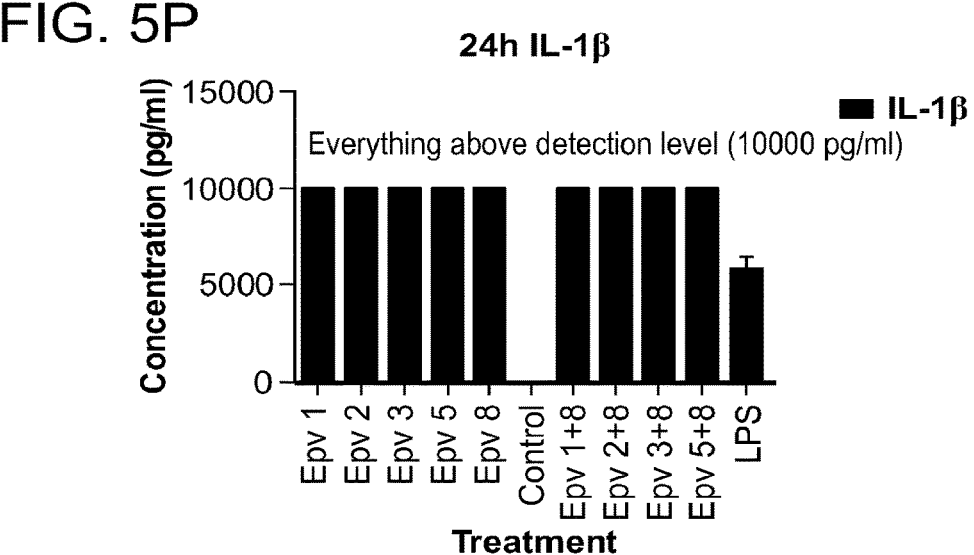
Figure 5Q:
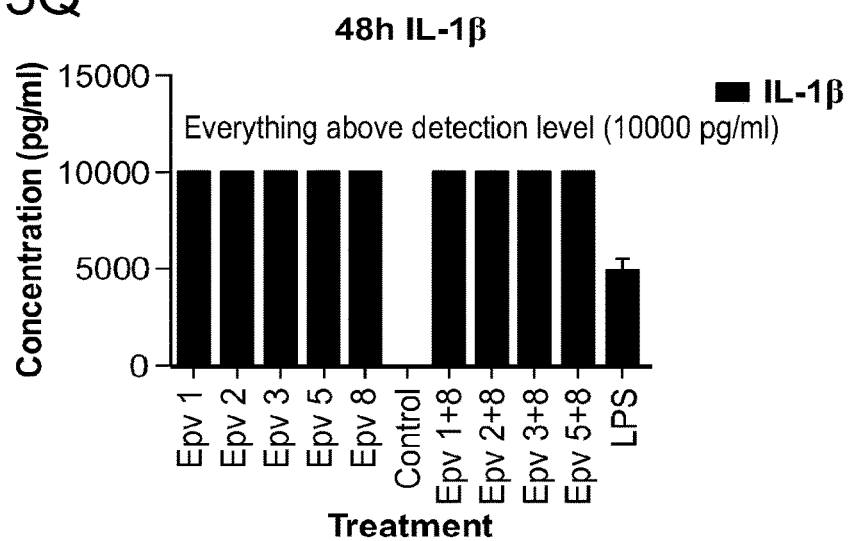
Figure 5R:
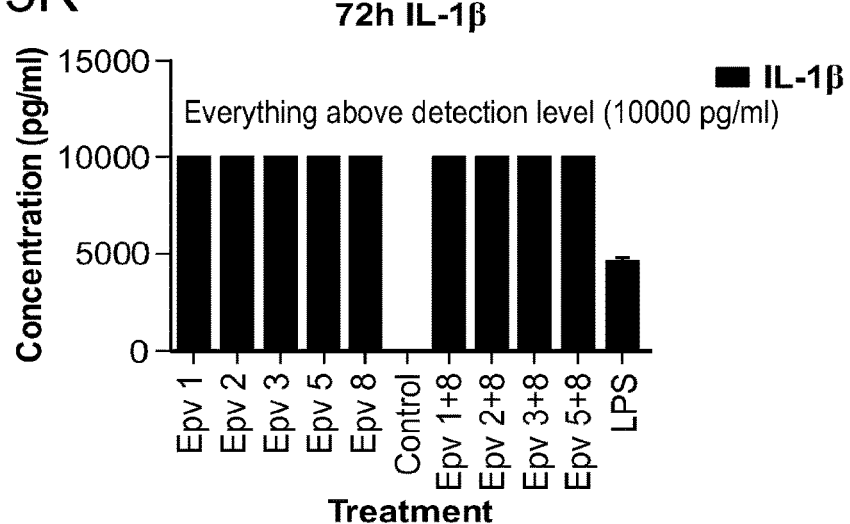
Figure 5S:
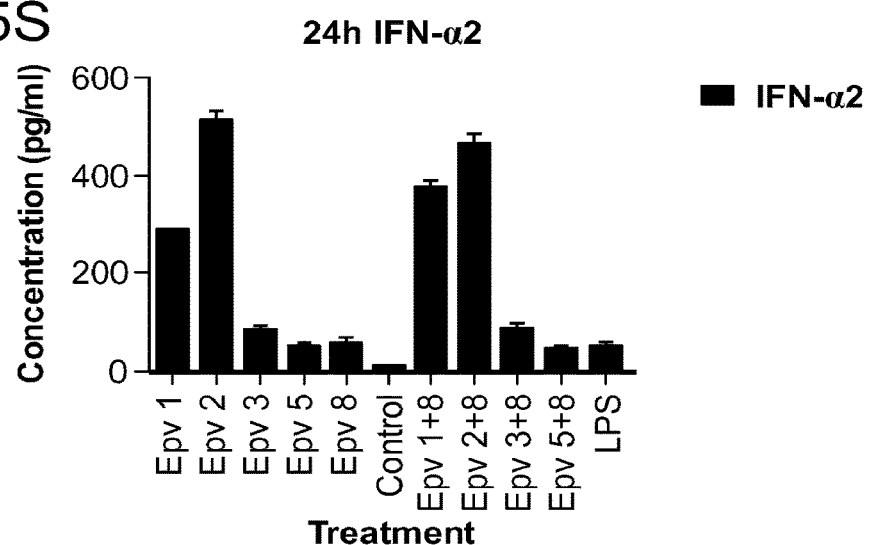
Figure 5T:
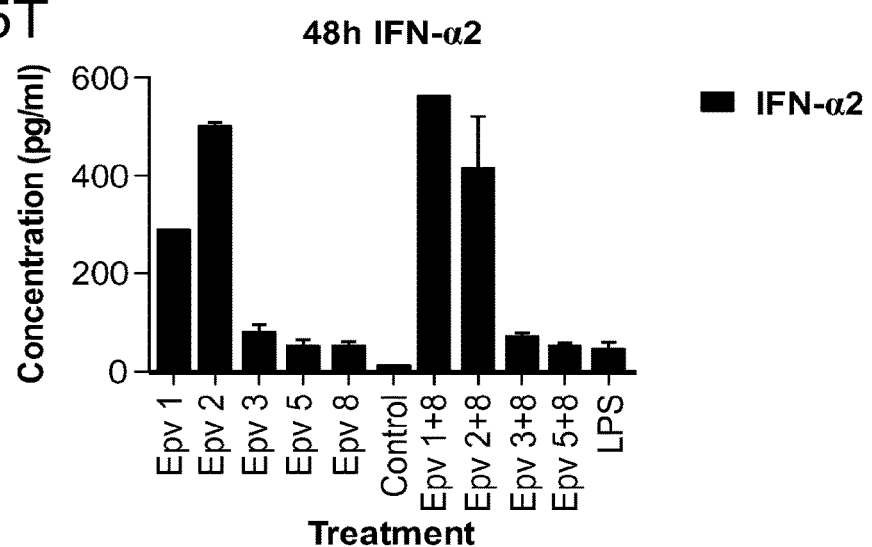
Figure 5U:
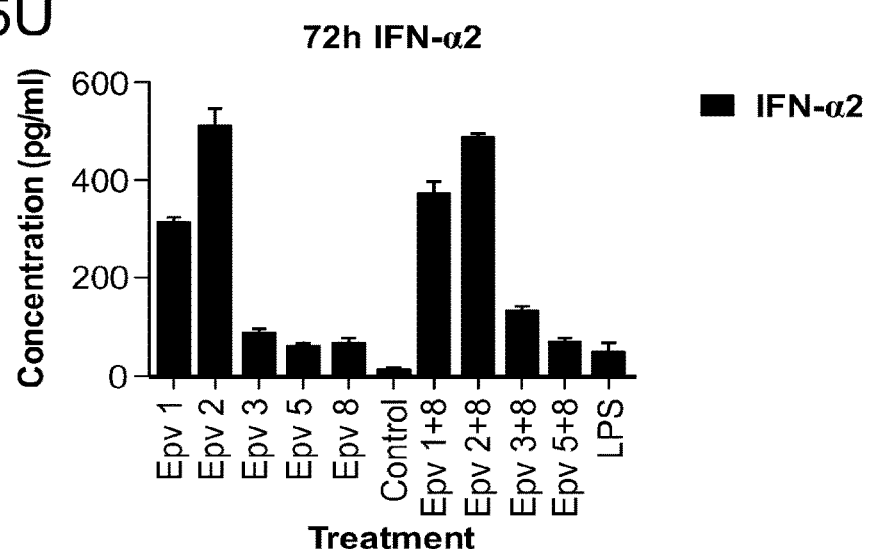
Figure 5V:
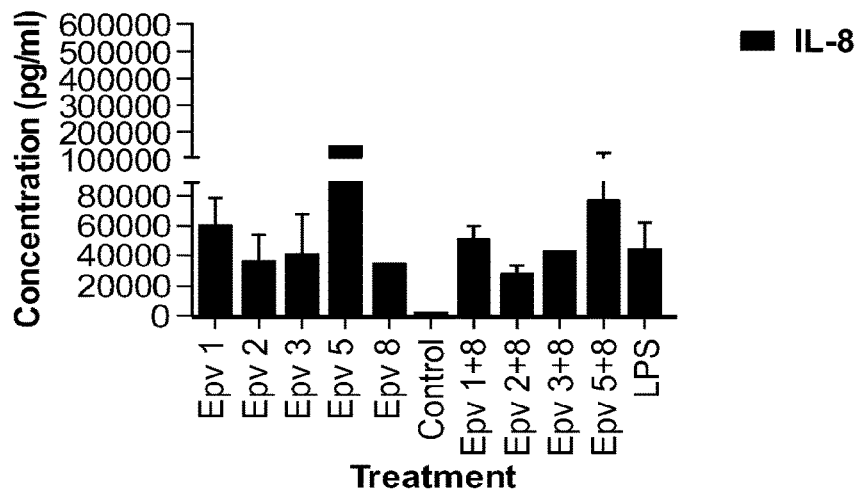
Figure 5W:
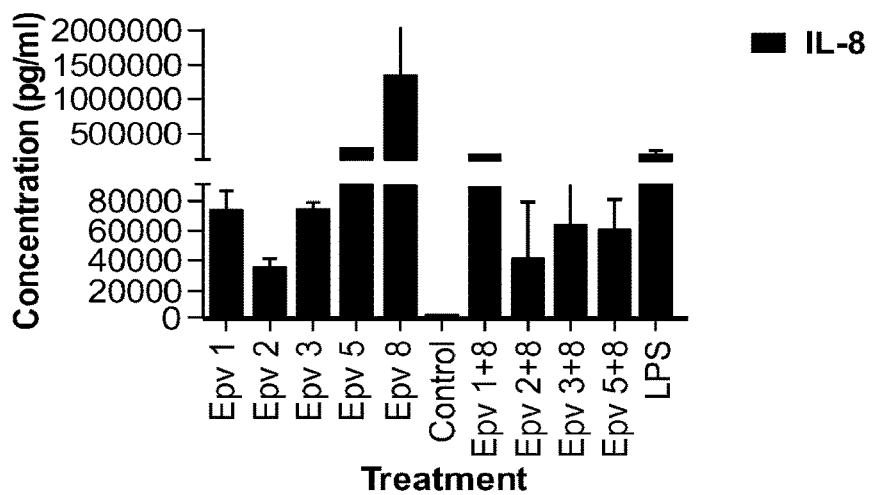
Figure 5X:
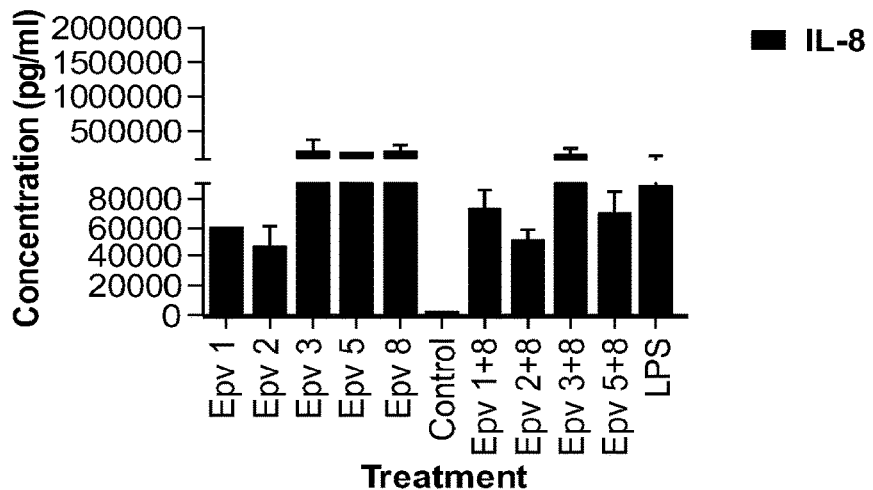
Figure 6A:
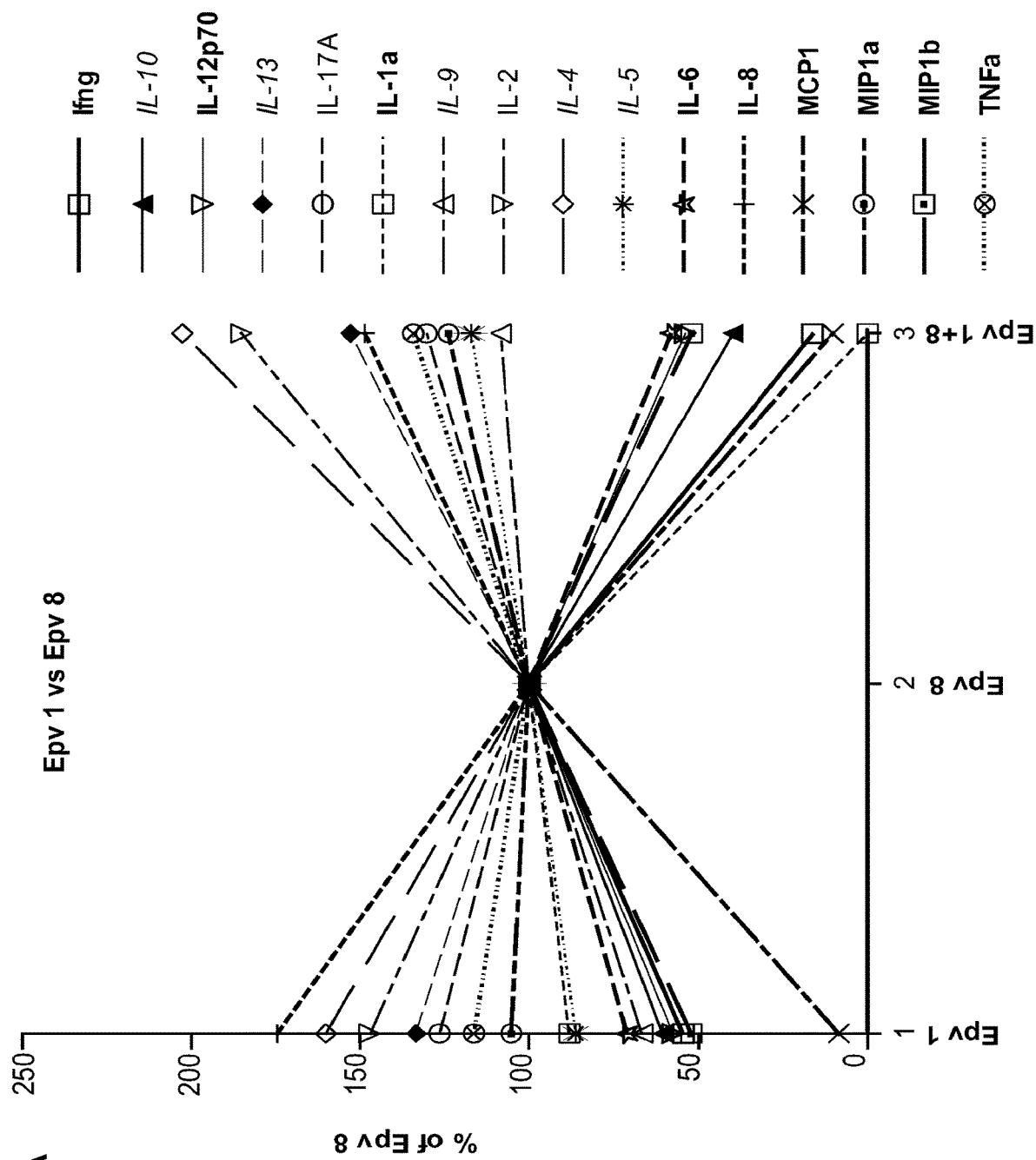
FIG. 6A-6D is a panel of graphs showing the secreted levels of cytokines IFNγ (Ifng), IL-12p70, IL-1α (IL-1a), IL-6, IL-8, MCP1, MIP1α (MIP1a), MIP1β (MIP1b), TNFα (TNFa), IL-10, IL-13, IL-9, IL-4, IL-5, IL-17α (IL-17A) and IL-2 produced by PBMCs in the presence of a) *R. gnavus*, b) *B. wexlerae*, c) *E. rectale* and d) *B. luti*, alone or in combination with *E. faecalis* (Epv 8), relative to levels secreted following treatment with *E. faecalis* alone for 24 hours (*E. faecalis*=100%).
Figure 6B:
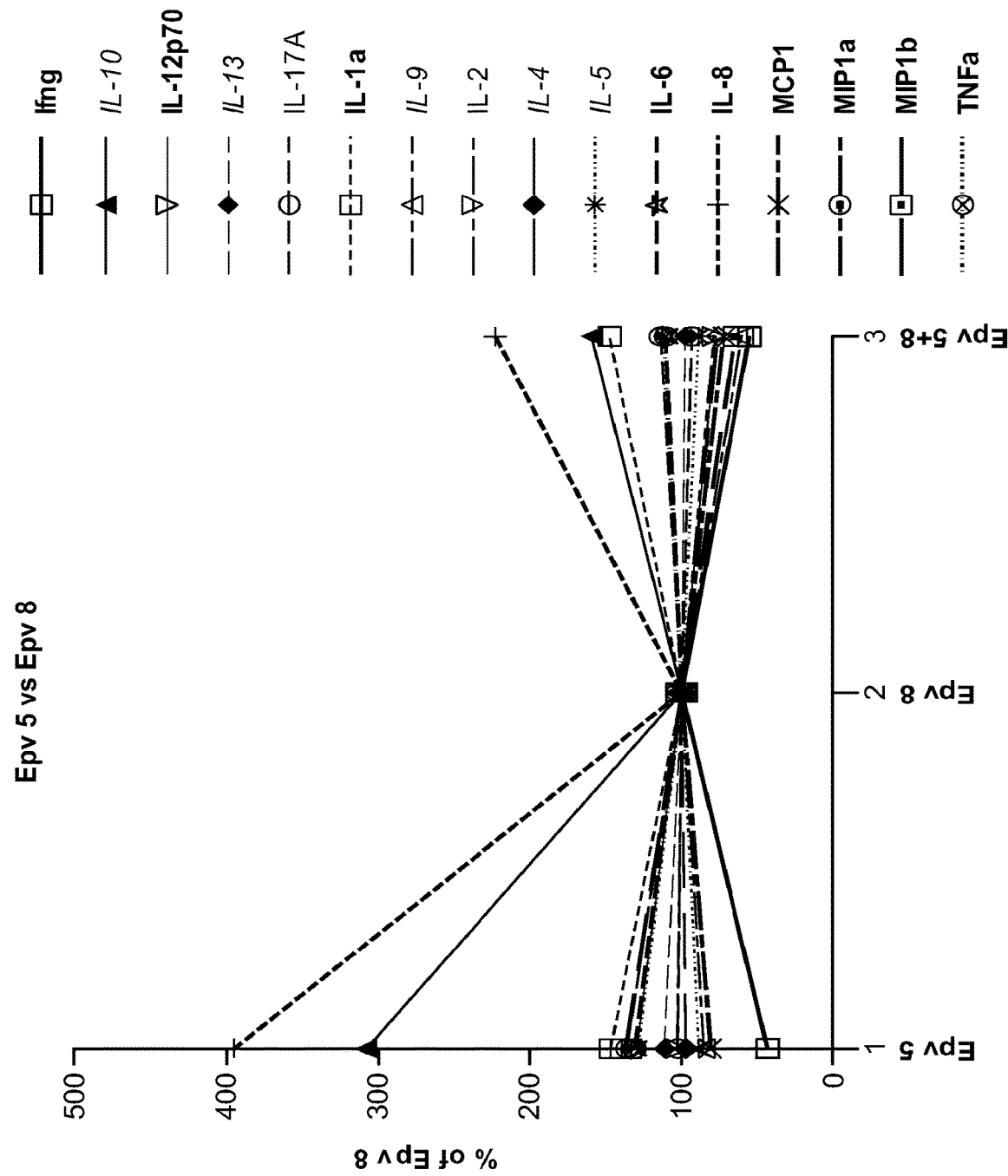
Figure 6C:
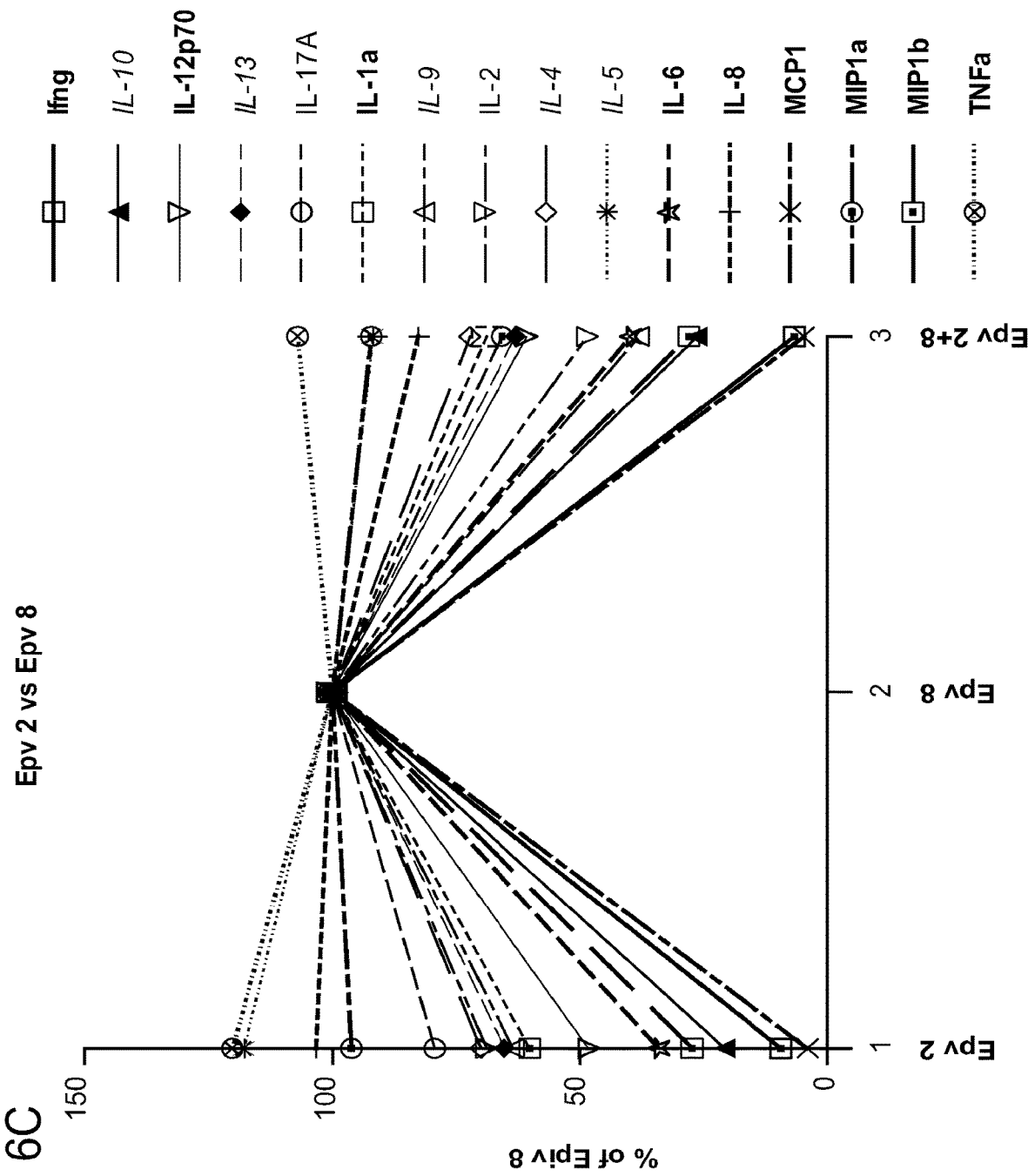
Figure 6D:
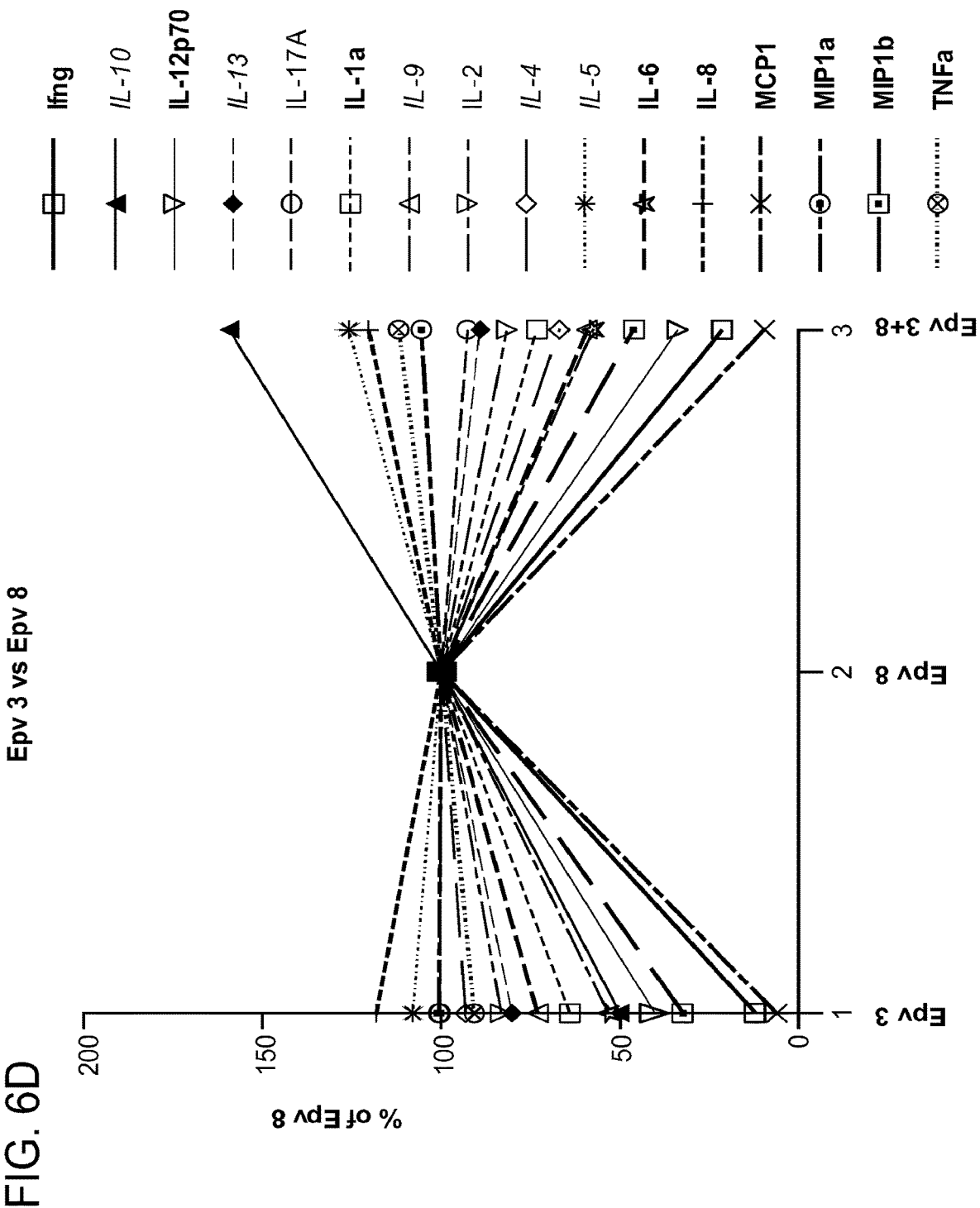
Figure 7A:
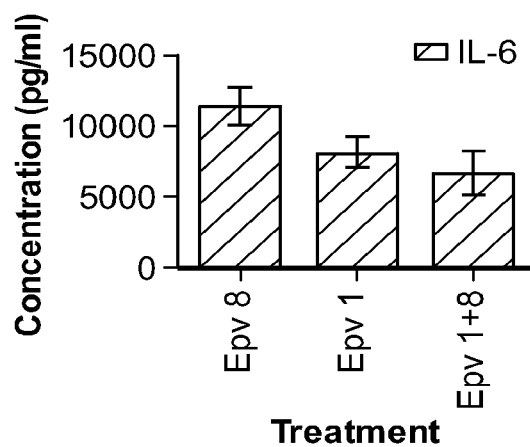
FIG. 7A-7P is a panel of graphs that show the effect of *R. gnavus* (Epv1) on cytokine concentration (pg/ml) either alone or in combination with Epv 8 (*E. faecalis*) on cytokine production by human PBMCs (pg/ml). a) IL-6, b) IFN-γ, c) IL-13, d) IL-10, e) IL-12p70, f) MCP-1, g) IL-8, h) IL17A, i) IL-α, j) IL-9, k) IL-2, l) IL-4, m) IL-5, n) MIP-1α, o) MIP-1β, p) TNF-α.
Figure 7B:
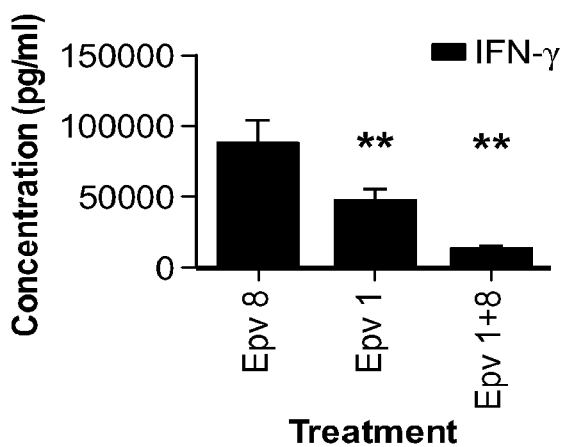
Figure 7C:
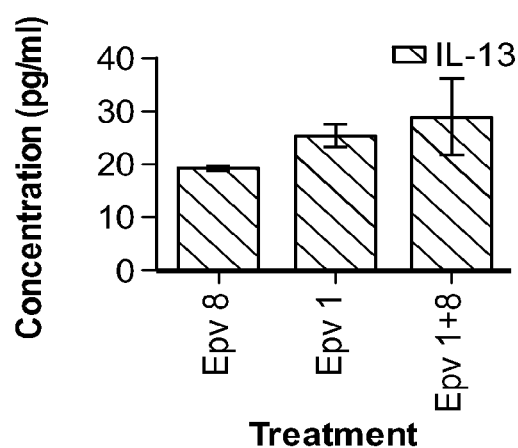
Figure 7D:
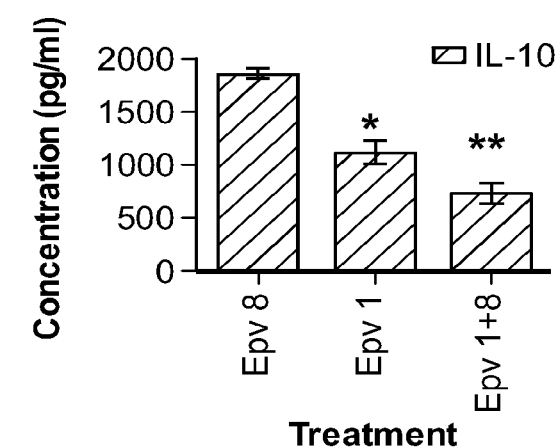
Figure 7E:
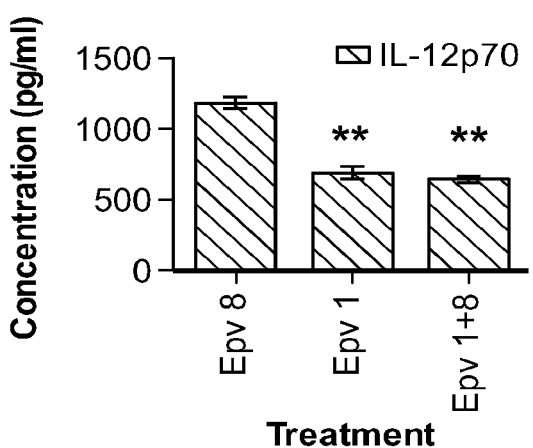
Figure 7F:
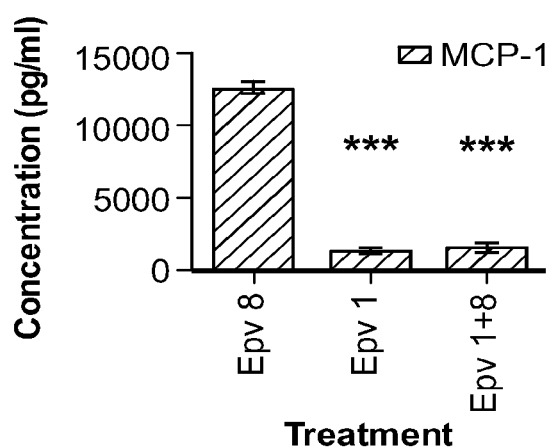
Figure 7G:
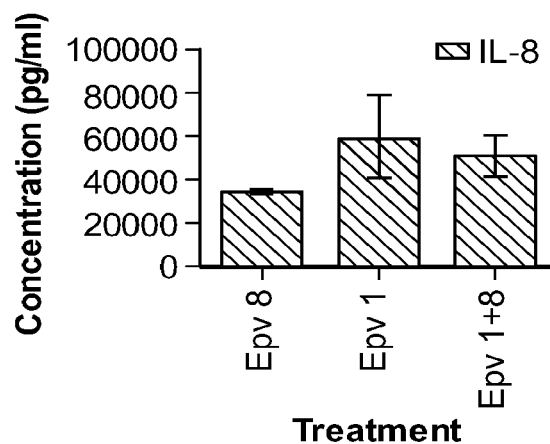
Figure 7H:
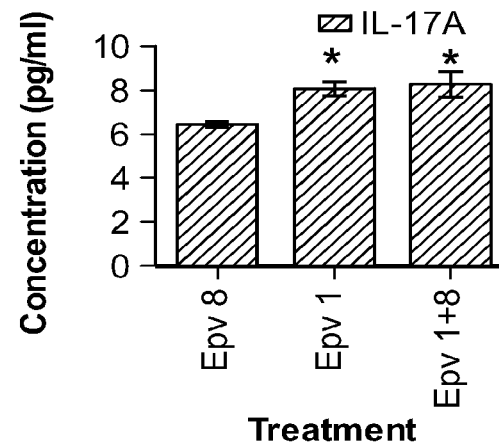
Figure 7I:
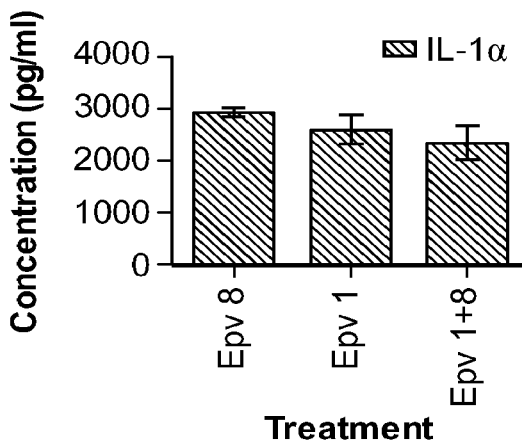
Figure 7J:
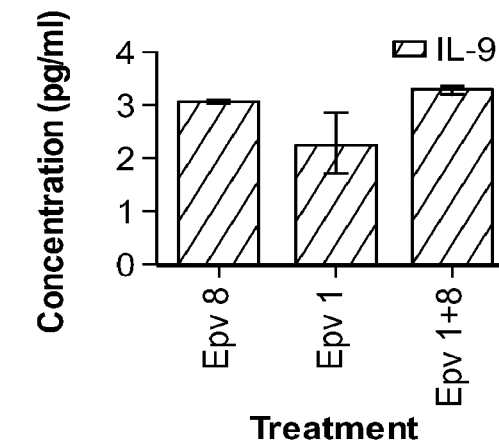
Figure 7K:
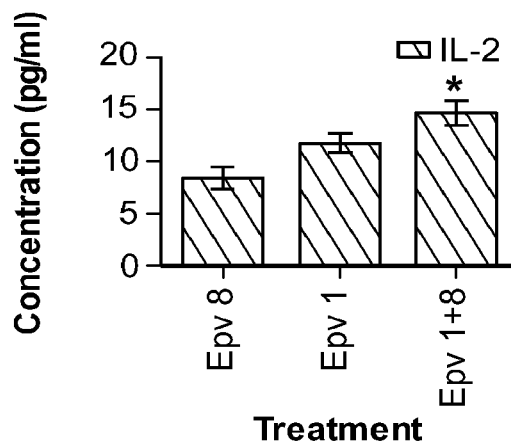
Figure 7L:
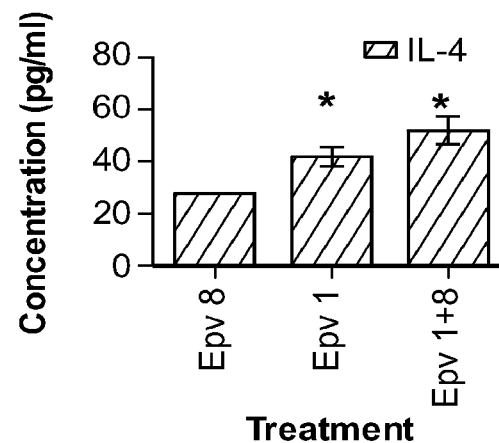
Figure 7M:
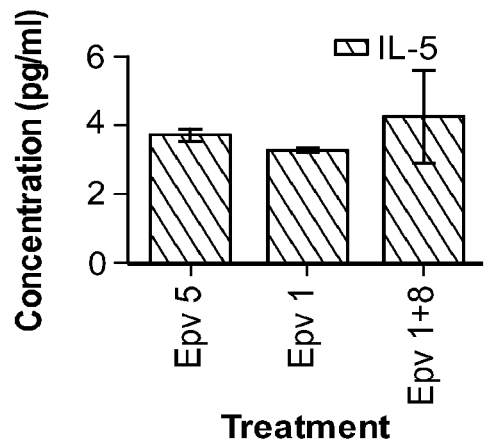
Figure 7N:
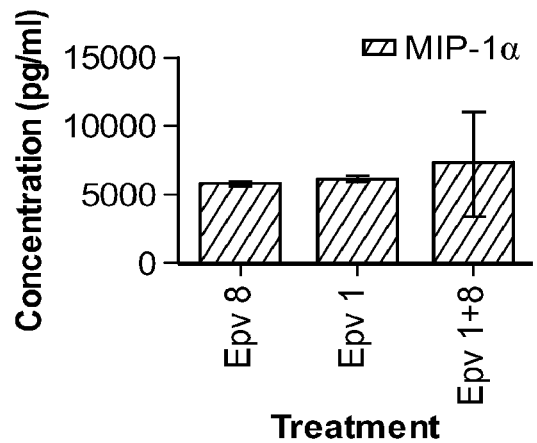
Figure 7O:
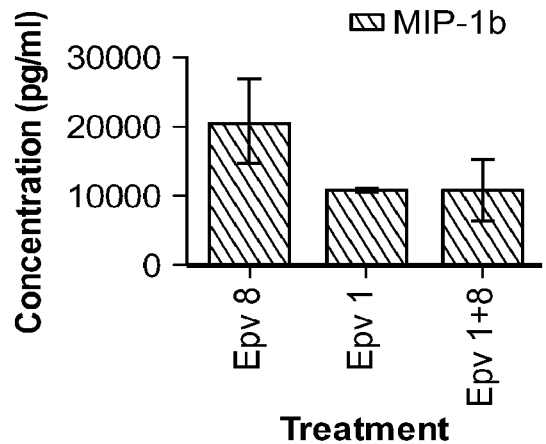
Figure 7P:
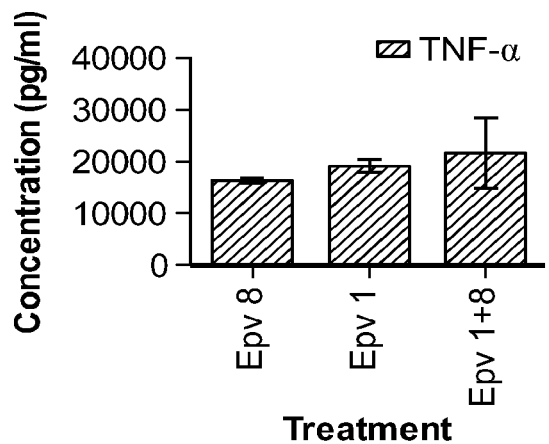
Figure 8A:
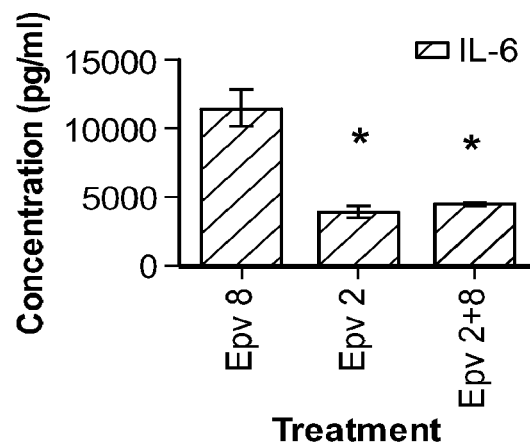
FIG. 8A-8P is a panel of graphs that show the effect of *E. rectale* (Epv2) on cytokine concentration (pg/ml) either alone or in combination with Epv 8 (*E. faecalis*) on cytokine production by human PBMCs (pg/ml). a) IL-6, b) IFN-γ, c) IL-13, d) IL-10, e) IL-12p70, f) MCP-1, g) IL-8, h) IL17A, i) IL-α, j) IL-9, k) IL-2, l) IL-4, m) IL-5, n) MIP-1α, o) MIP-1β, p) TNF-α.
Figure 8B:
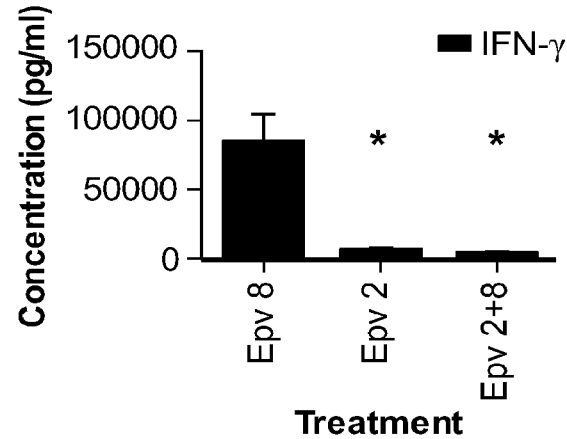
Figure 8C:
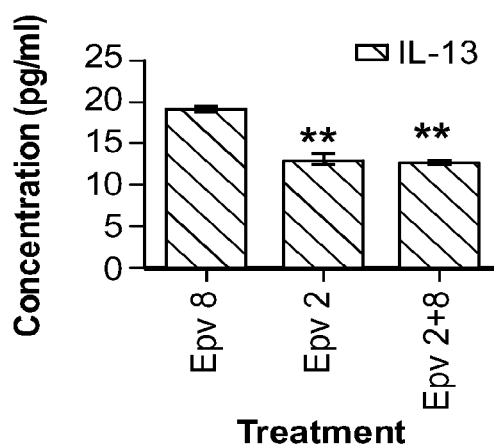
Figure 8D:
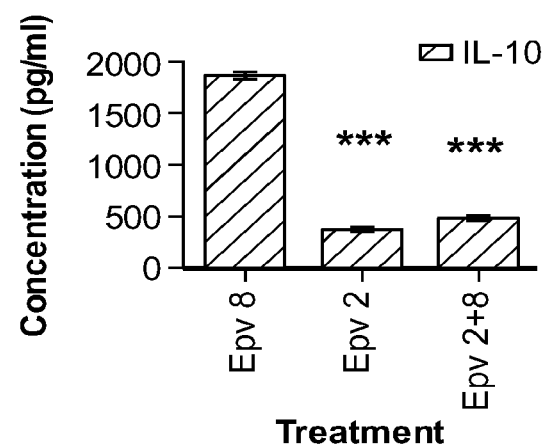
Figure 8E:
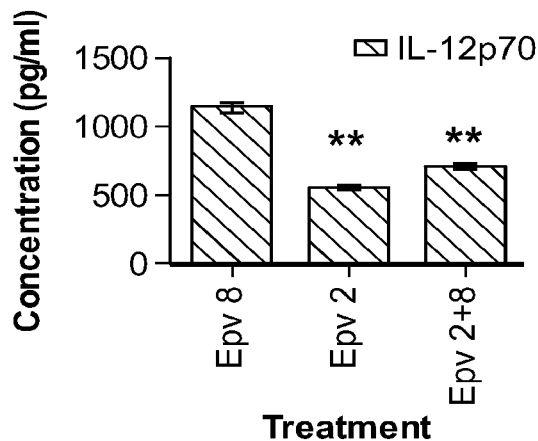
Figure 8F:
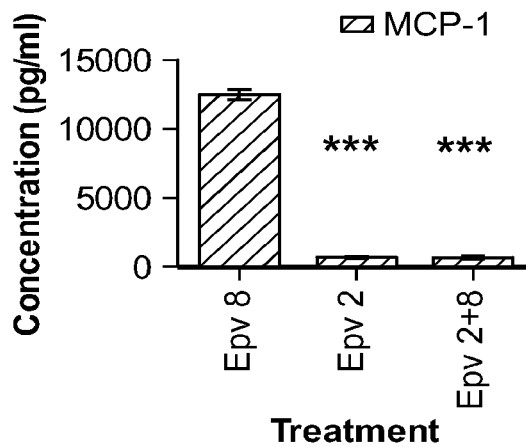
Figure 8G:
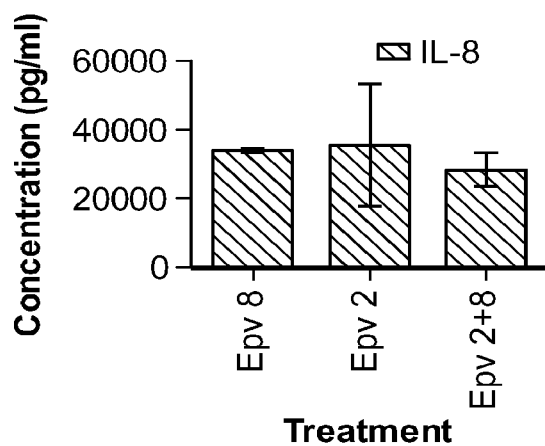
Figure 8H:
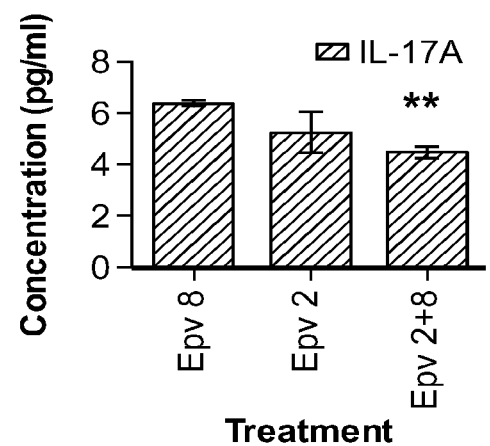
Figure 8I:
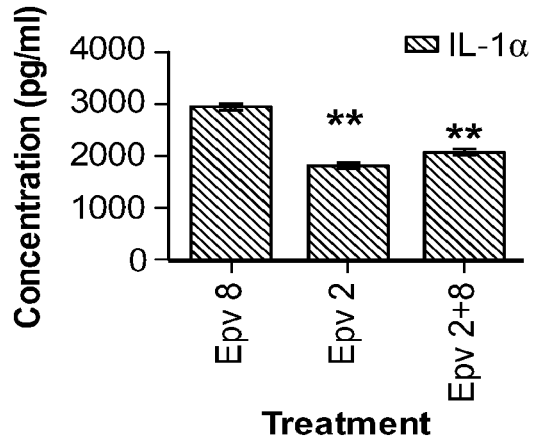
Figure 8J:
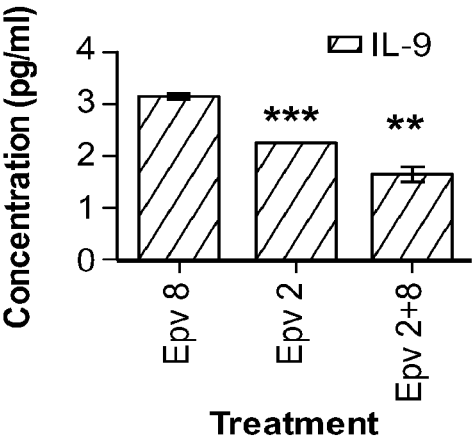
Figure 8K:
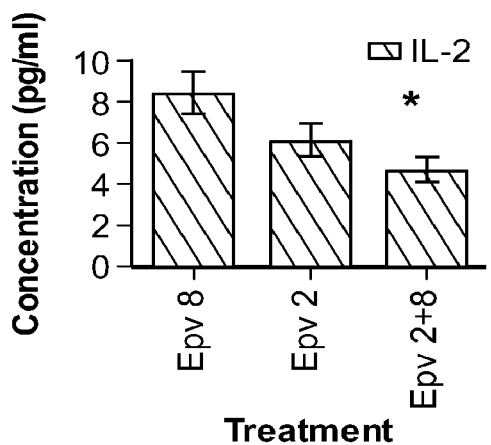
Figure 8L:
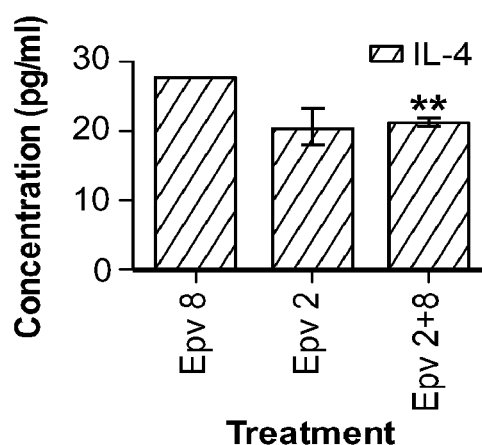
Figure 8M:
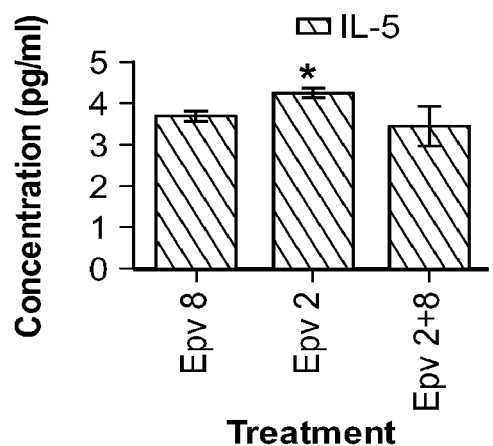
Figure 8N:
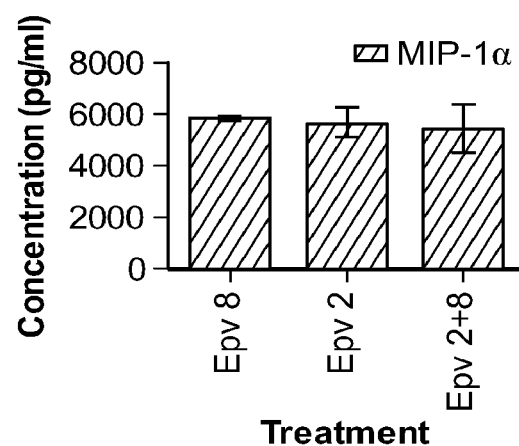
Figure 8O:
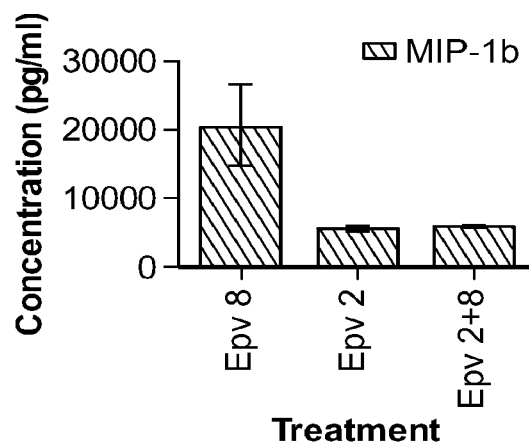
Figure 8P:
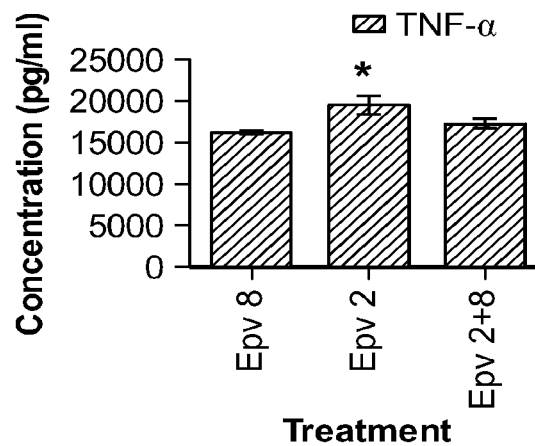
Figure 9A:
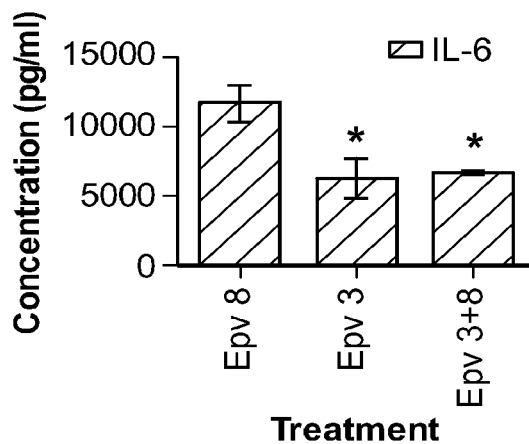
FIG. 9A-9P is a panel of graphs that show the effect of *B. luti* (Epv3) on cytokine concentration (pg/ml) either alone or in combination with Epv 8 (*E. faecalis*) on cytokine production by human PBMCs (pg/ml). a) IL-6, b) IFN-γ, c) IL-13, d) IL-10, e) IL-12p70, f) MCP-1, g) IL-8, h) IL17α, i) IL-α, j) IL-9, k) IL-2, l) IL-4, m) IL-5, n) MIP-1α, o) MIP-1β, p) TNF-α.
Figure 9B:
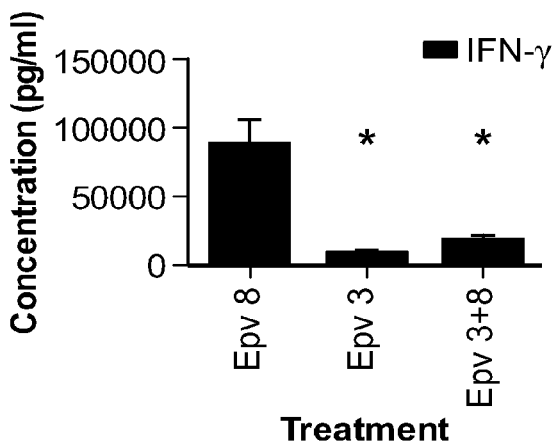
Figure 9C:
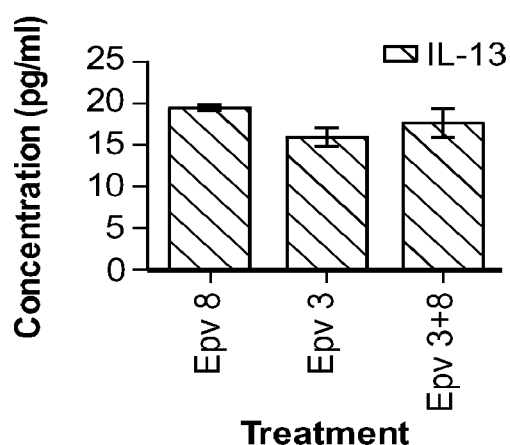
Figure 9D:
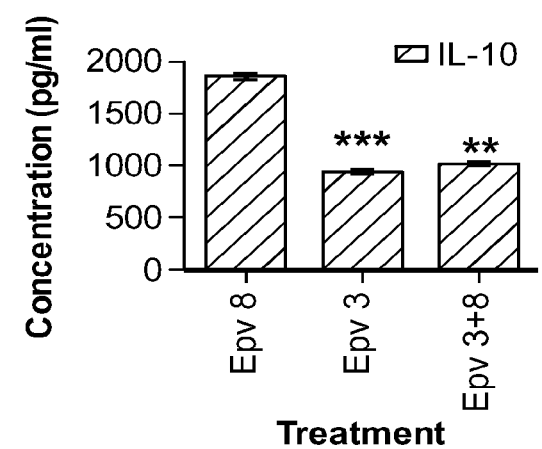
Figure 9E:
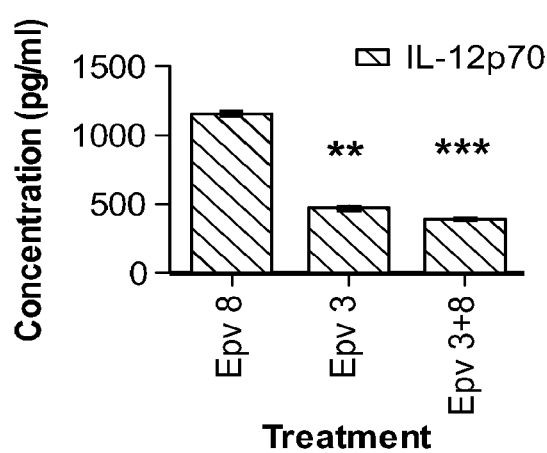
Figure 9F:
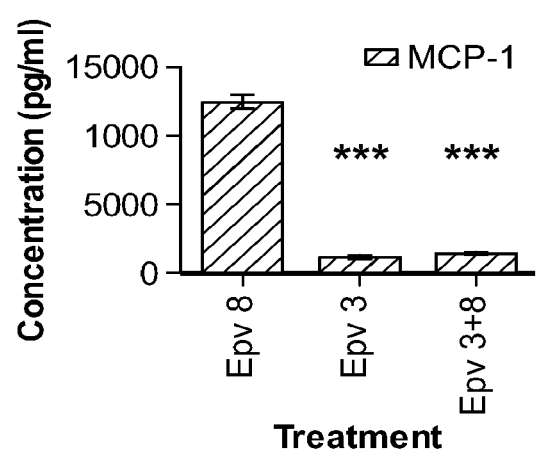
Figure 9G:
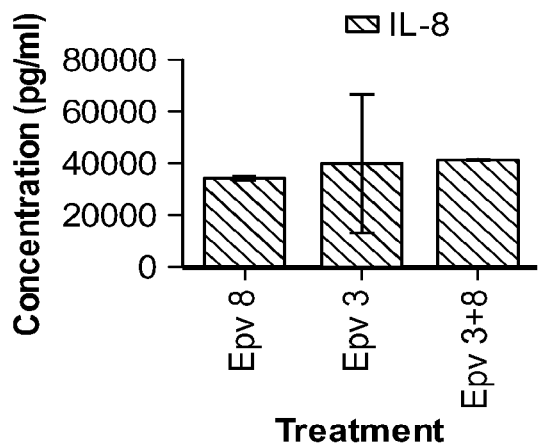
Figure 9H:
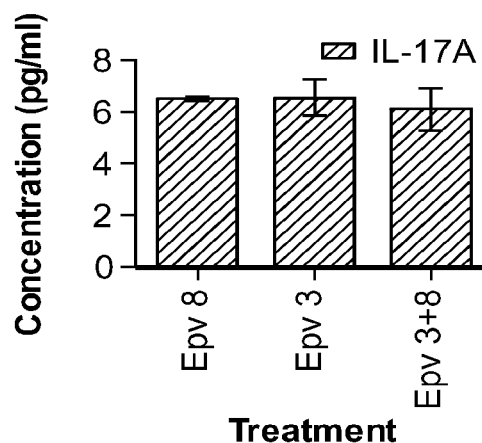
Figure 9I:
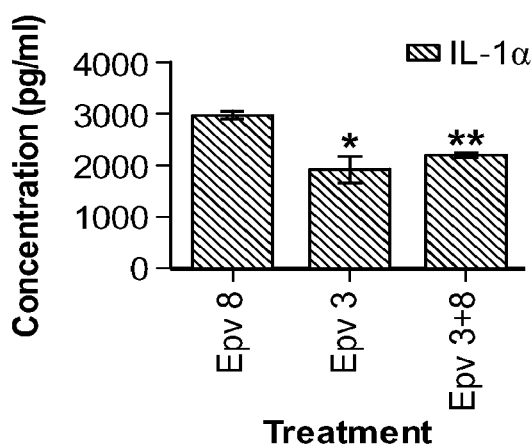
Figure 9J:
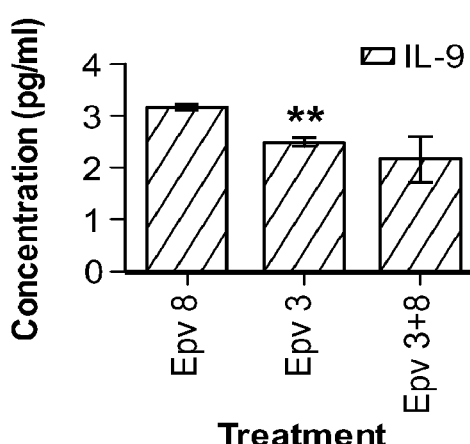
Figure 9K:
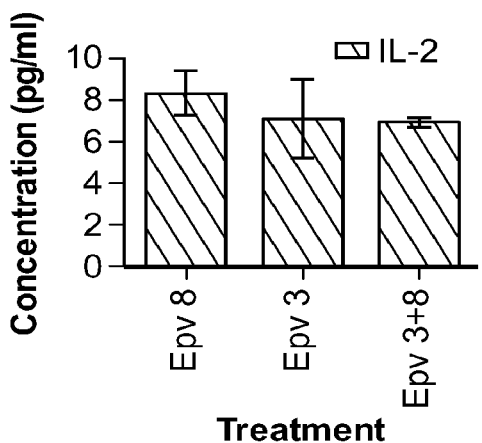
Figure 9L:
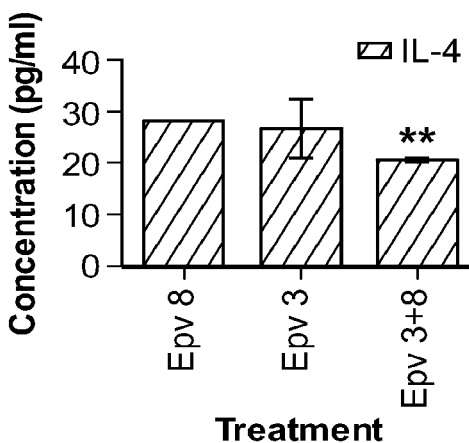
Figure 9M:
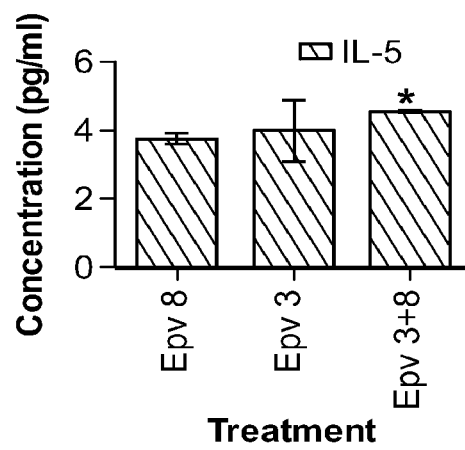
Figure 9N:
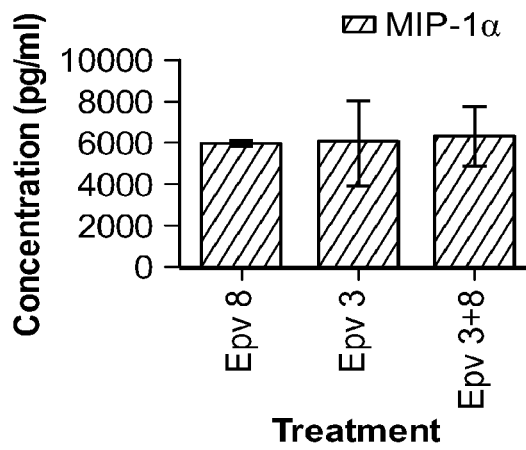
Figure 9O:
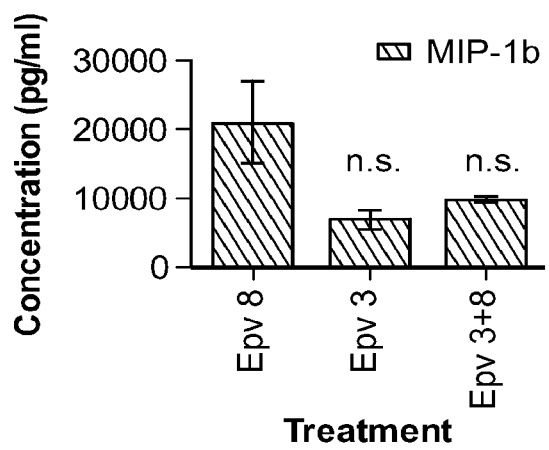
Figure 9P:
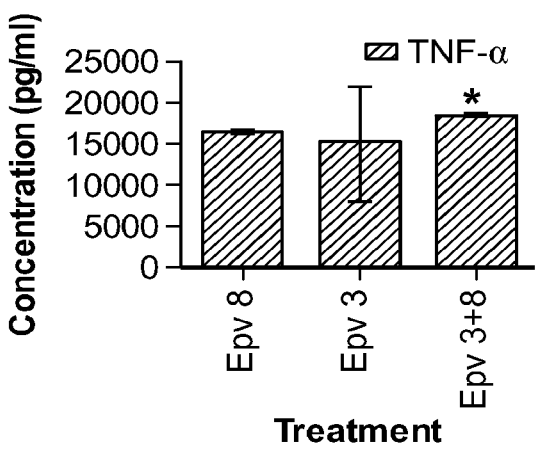
Figure 10A:
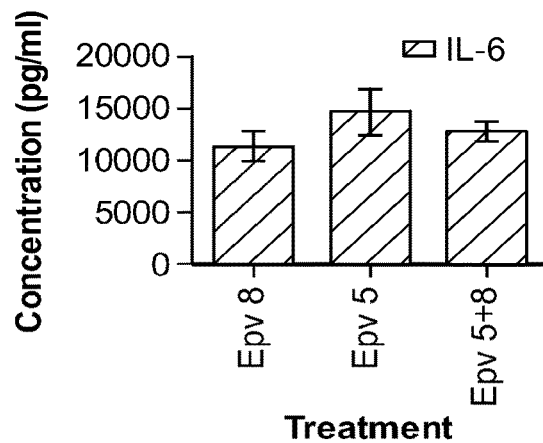
FIG. 10A-10P is a panel of graphs that show the effect of *B. wexlarae*) on cytokine concentration (pg/ml) either alone or in combination with Epv 8 (*E. faecalis*) on cytokine production by human PBMCs (pg/ml). a) IL-6, b) IFN-γ, c)
Figure 10B:
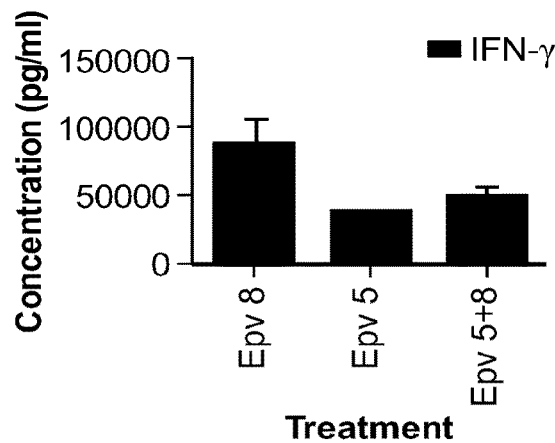
Figure 10C:
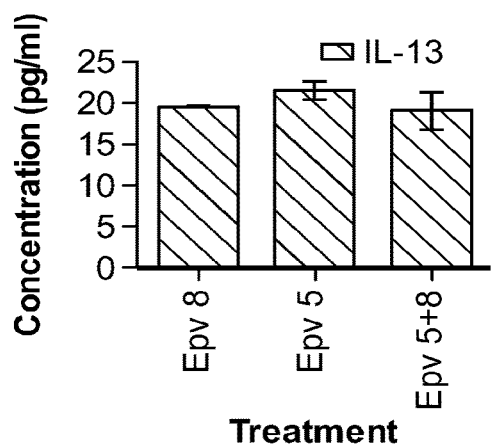
Figure 10D:
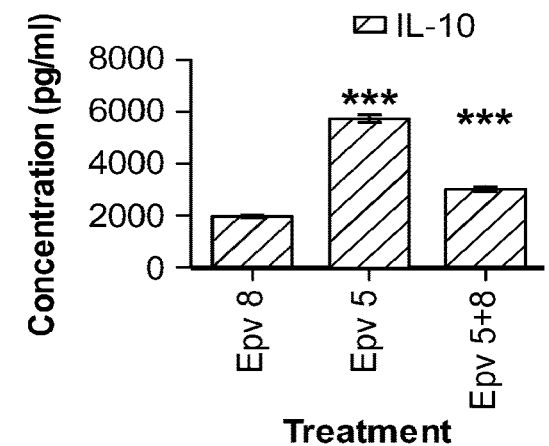
Figure 10E:
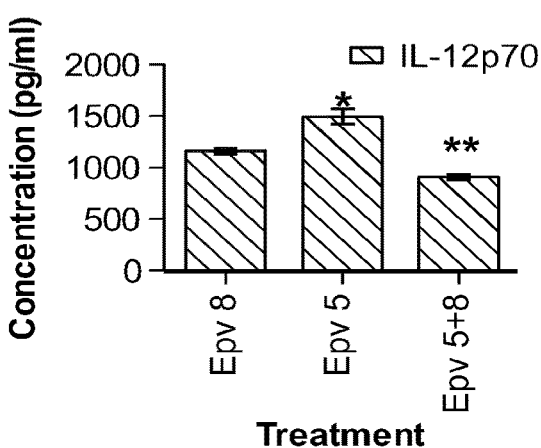
Figure 10F:
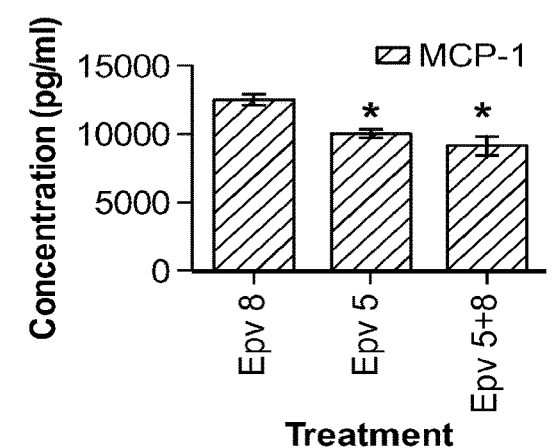
Figure 10G:
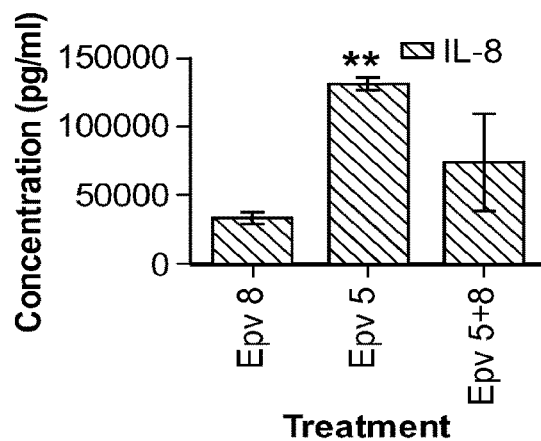
Figure 10H:
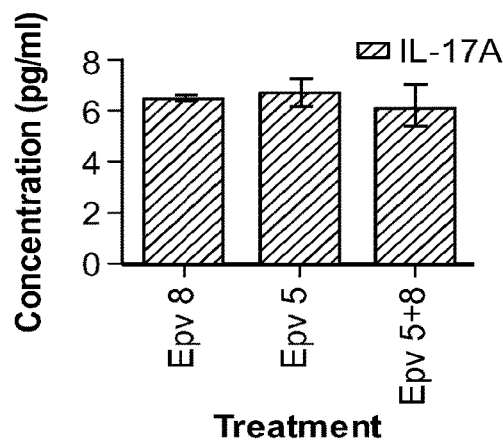
Figure 10I:
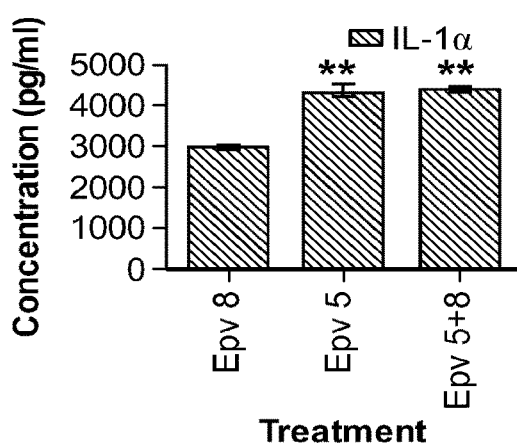
Figure 10J:
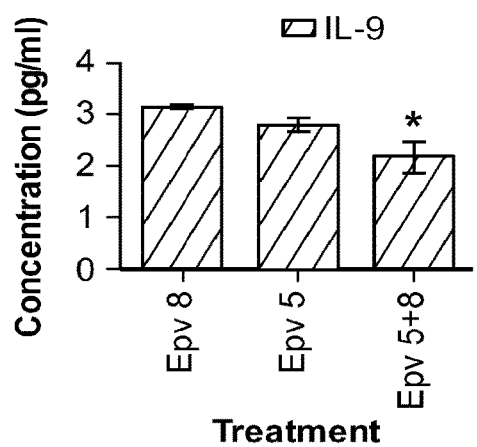
Figure 10K:
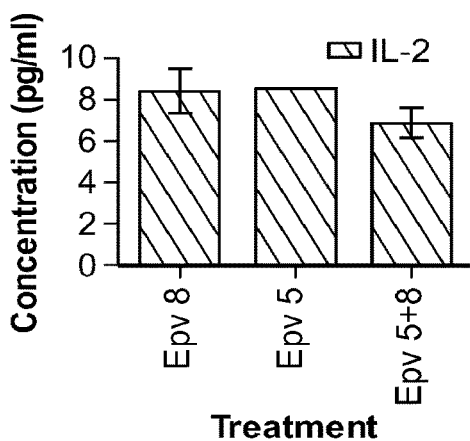
Figure 10L:
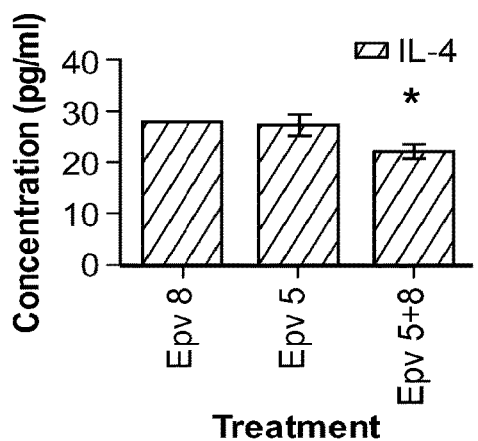
Figure 10M:
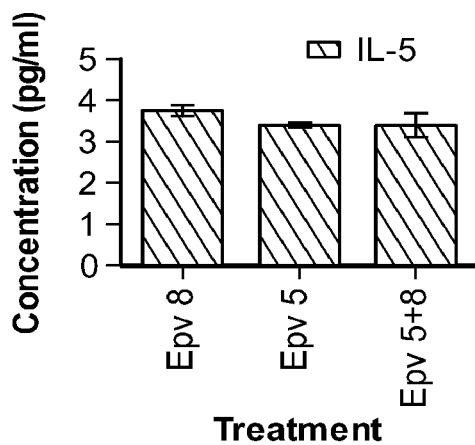
Figure 10N:
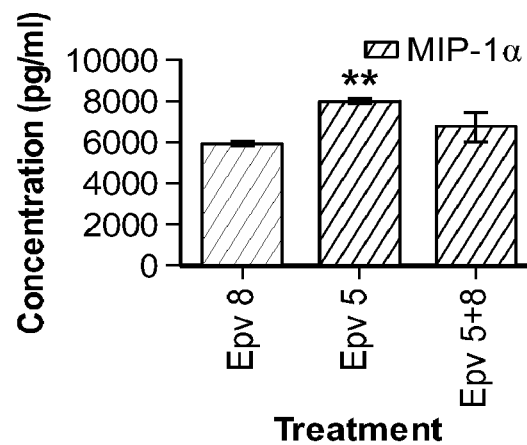
Figure 10O:
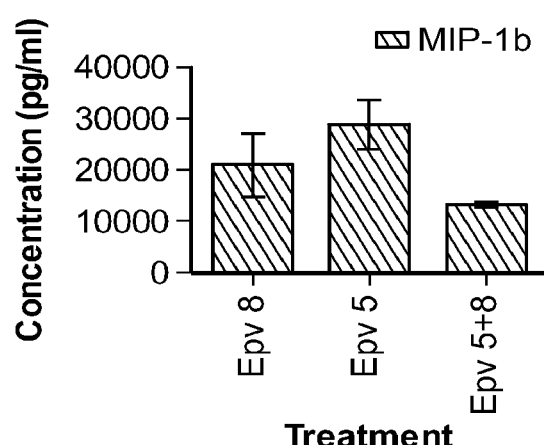
Figure 10P:
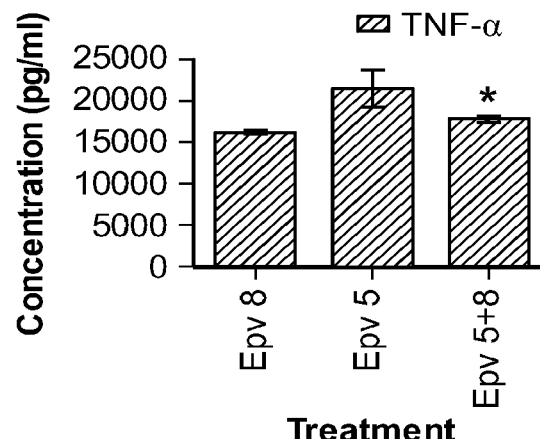
Figure 11A:
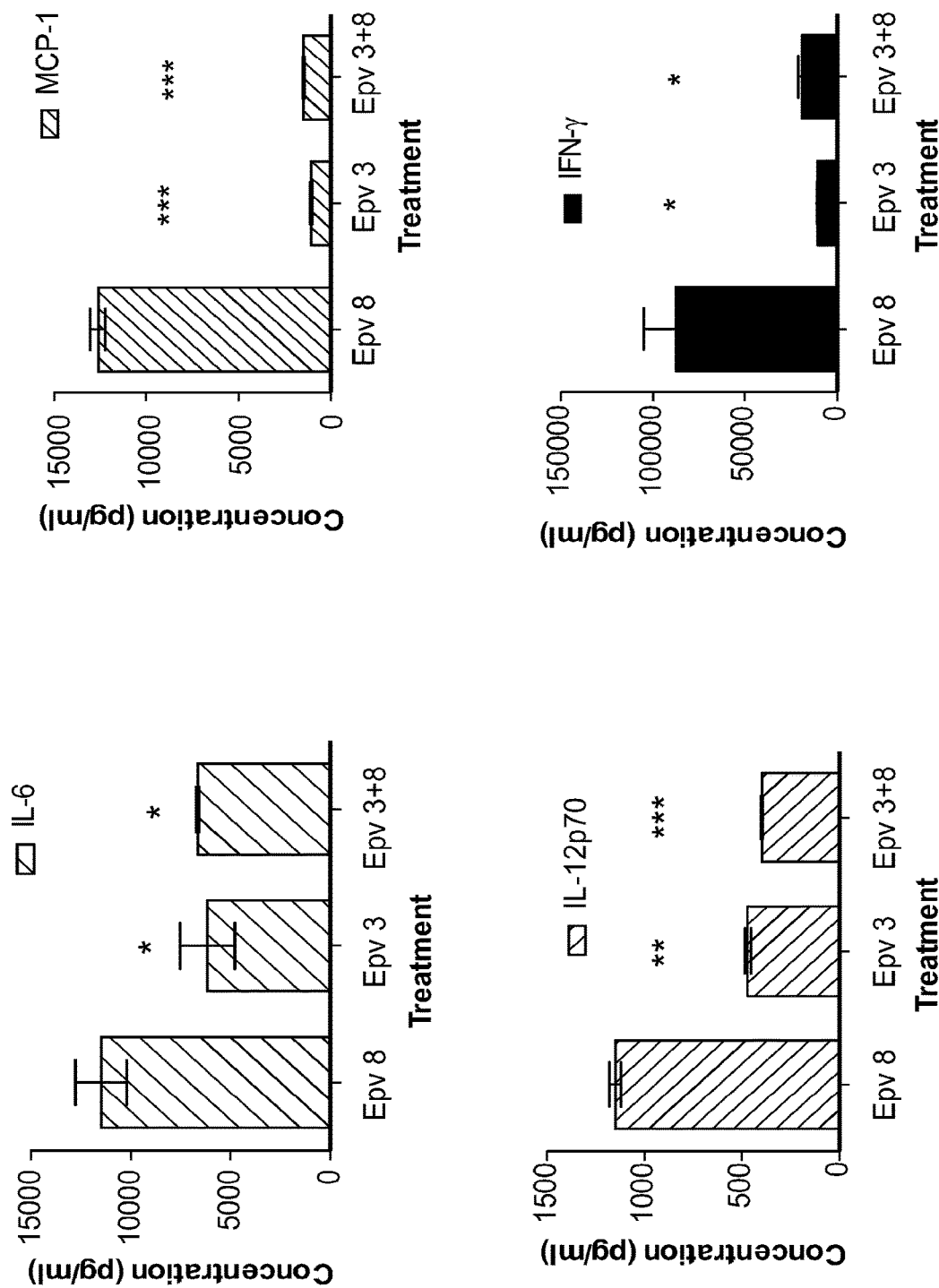
Figure 11B:
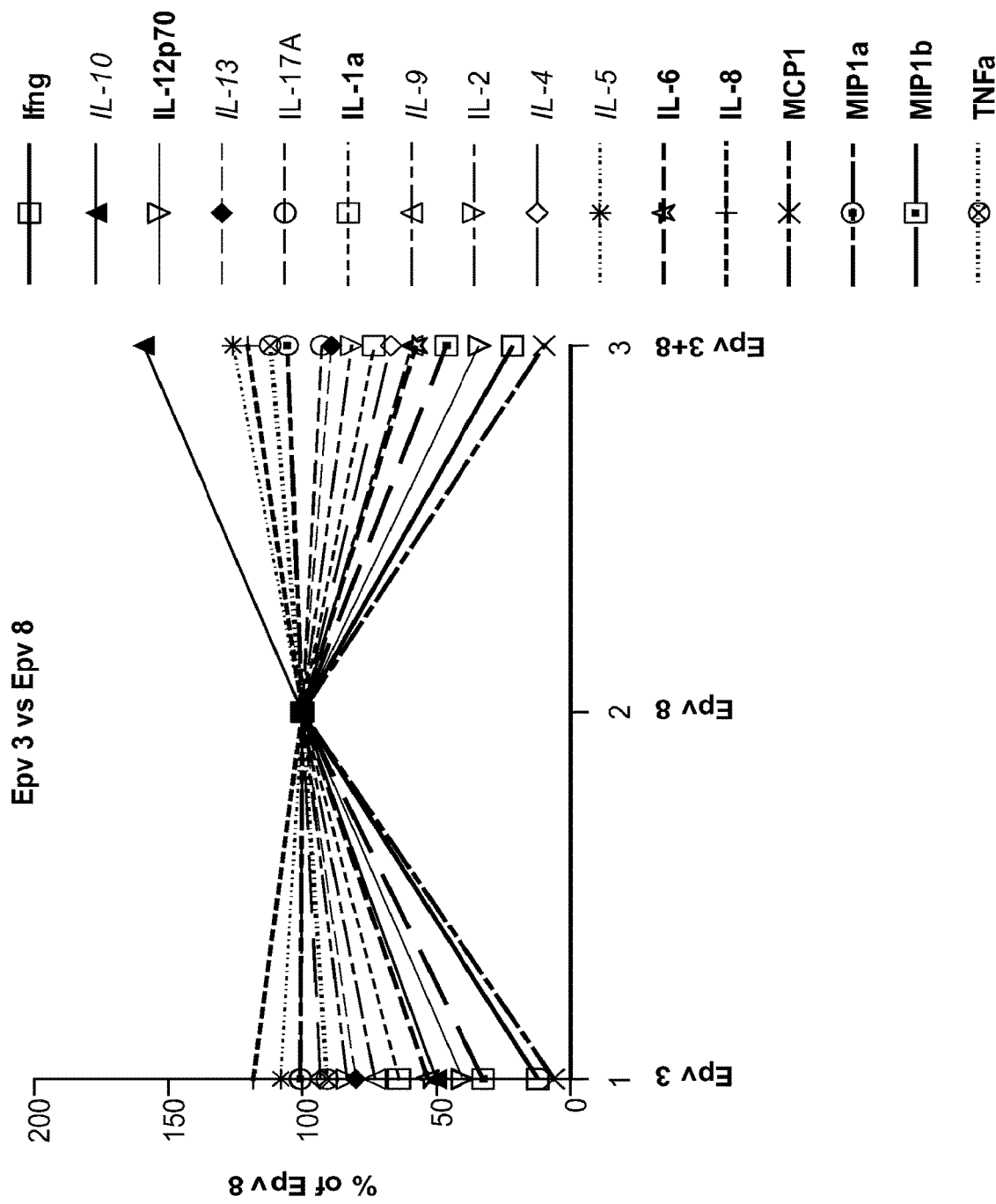
Figure 11C:
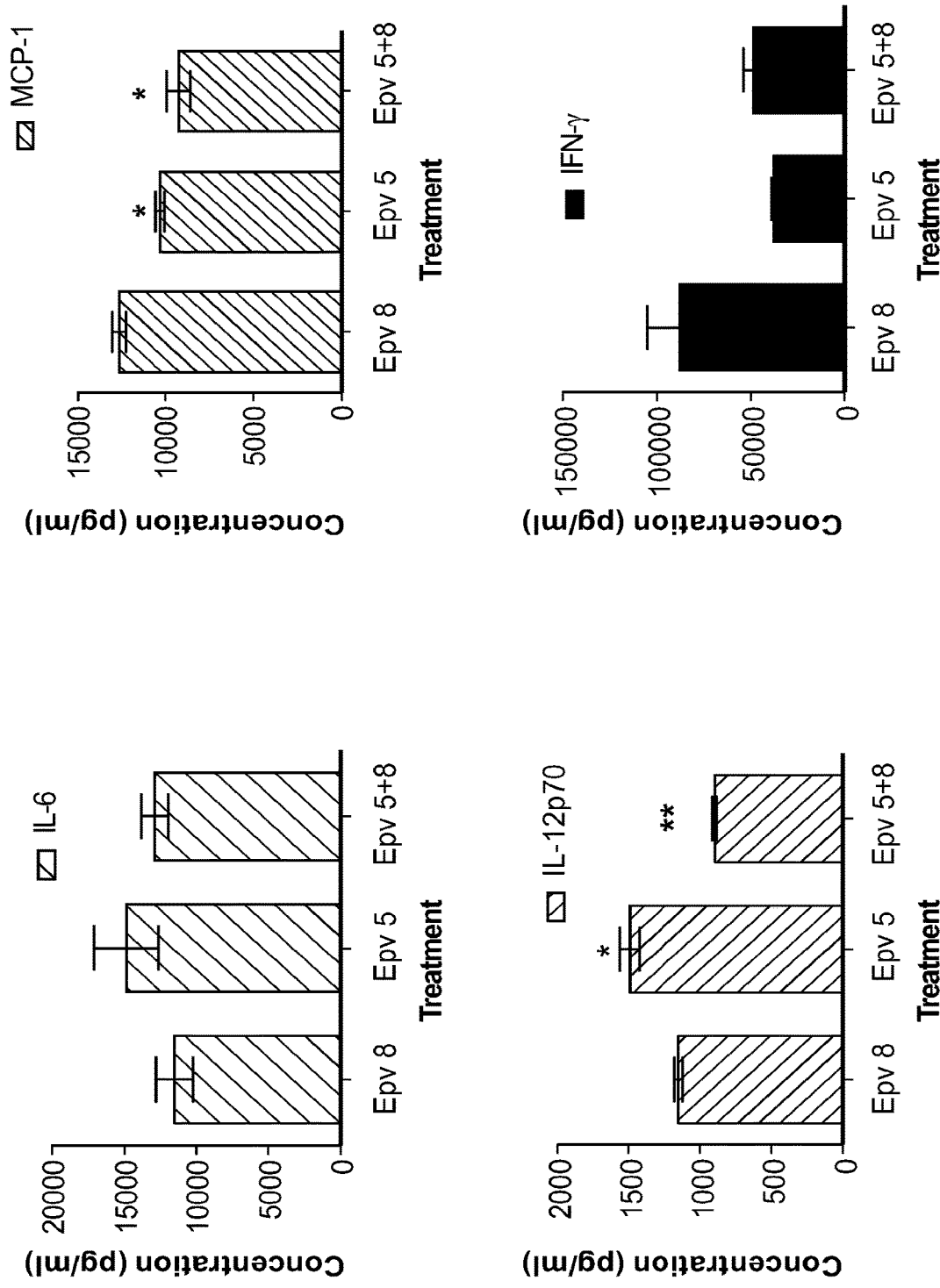
Figure 11D:
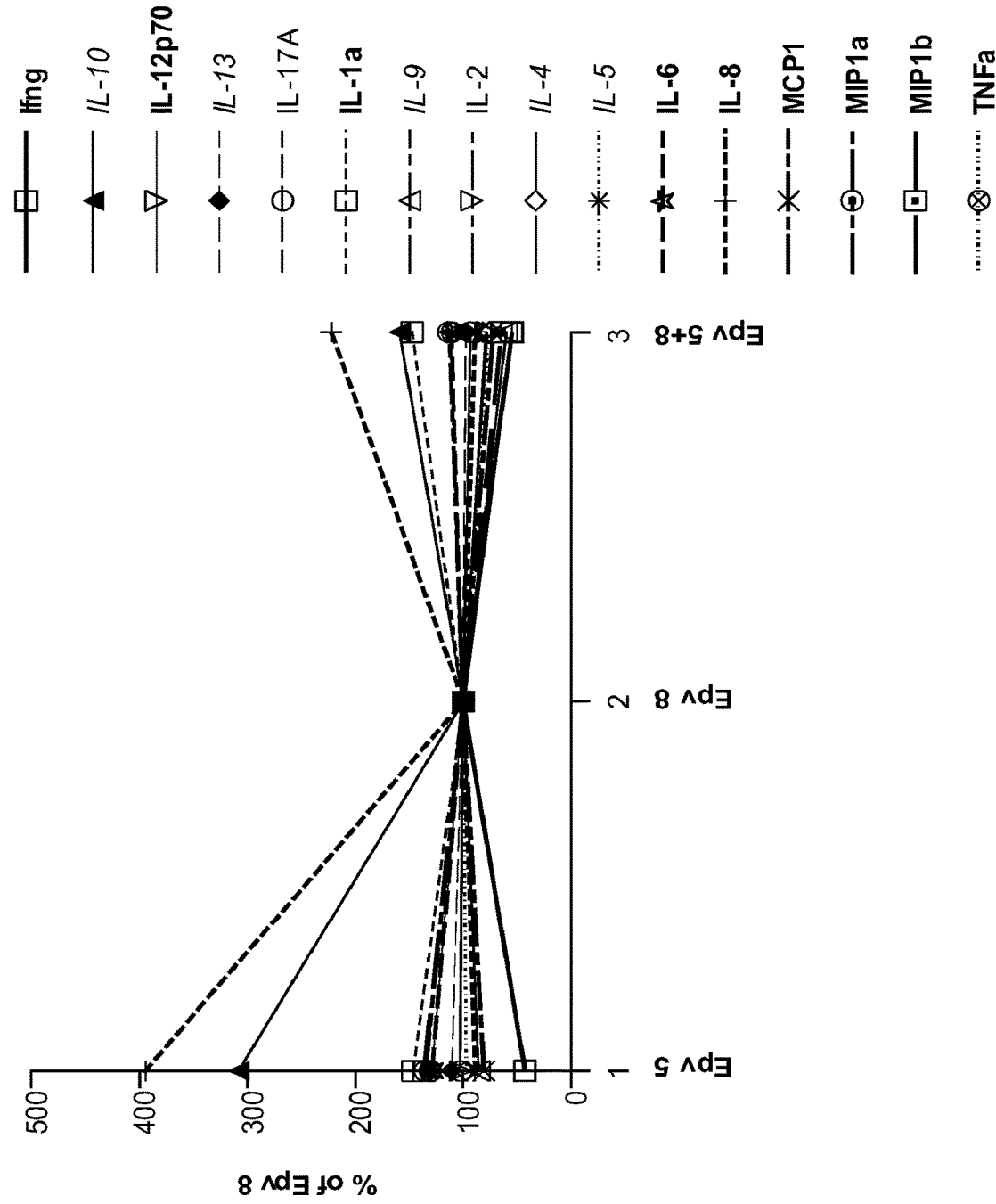

As shown in FIG. 1, C57BU6 mice were either left untreated or were treated with xylose at 10 g/L in drinking water from day −7 to day 14; ciprofloxacin (cipro) at 0.25 g/L in drinking water from day −7 to day −2; enrofloxacin (enro) at 0.25 g/L in drinking water from day −7 to day −2; xylose+cipro or xylose+enro. Analysis of serum samples collected on days 0 and 14 showed that basal levels of serum endotoxin are present in normal mice that remained unchanged in untreated mice. Xylose treatment reduced these basal levels over time, suggesting an increase in gut barrier integrity even in normal animals. Antibiotic treatment with cipro, a broad spectrum quinolone antibiotic, or enro, an anaerobe-sparing antibiotic, led to an increase in serum endotoxin levels (measured 2 days after a 5 day course), likely due to disruption of the microbiota. Serum endotoxin levels returned to baseline over time. As shown in FIG. 1, xylose appeared to counteract the increase in serum endotoxin level caused by cipro, but not enro. The differential effect of xylose on these 2 antibiotics may relate to its ability to preserve/promote expansion of anaerobic bacteria, which are killed by cipro but not enro.

Example 2. Immunomodulatory Properties of Different Human Commensal Bacteria on Human Peripheral Blood Mononuclear Cells The microbiota of mammalian hosts is composed of bacterial species that possess both pro- and anti-inflammatory properties. In healthy individuals, a balance or state of eubiosis is maintained that supports gut barrier integrity, immune containment of commensal bacteria and promotion of a tolerogenic environment. Under disease conditions, dysbiosis characterized by an imbalance in pro- and anti-inflammatory bacteria results in local inflammation and compromised gut barrier integrity, leading to systemic inflammation and aberrant immune responses. Administration of selected probiotic bacterial strains (+/−prebiotics) that possess anti-inflammatory activity and promote immune tolerance represents an approach to correct a basic defect underlying multiple pathological conditions.

An in vitro system was developed to efficiently test the inflammatory and immunomodulatory properties of different human commensal bacteria on human peripheral blood mononuclear cells (PBMCs). Experiments were carried out with 21 bacterial candidates to profile their anti-inflammatory properties against human PBMCs. The innate properties of bacteria alone on human PBMCs were tested as well as their ability to counteract the pro-inflammatory activity of *Enterococcus feacalis*.

Human PBMCs were isolated from fresh blood by density-gradient centrifugation using Ficoll (1-4). Freshly isolated PBMCs were plated at $1.5 \times 10^6$ cells per ml per well of a 24-well plate in a total volume of 2 mls RPMI-1640 medium+5% human serum, and incubated at 37° C./5% $CO_2$ with the following:

(1) 500 µl of different commensal bacteria suspensions at OD 0.8
(2) *E. faecalis* at $10^7$ colony-forming units (cfu)
(3) A combination of commensal bacteria (OD 0.8)+*E. faecalis* ($10^7$ cfu)
(4) Complete medium alone as a negative control
(5) Bacterial lipopolysaccharide (LPS; 100 ng/ml) as an immunomodulatory "positive" control Culture supernatants were collected at 24, 48 and 72 h, and the cytokine profile was analyzed by Luminex technology according to manufacturer's instruction (EMD Millipore, Danvers, Mass.). Cytokine production was detectable in culture supernatants by 24 h with levels increasing over 48-72 h and sometimes exceeding the range of quantitation. The results are presented in FIGS. 2-5 for all time points. The 24 h time point was chosen as the optimal time point for further analysis. The 24 h results are shown as a composite in FIG. 6 and with statistical analysis on individual cytokines in FIGS. 7-10. The results represent the properties of each bacterial species against human PBMCs and their ability to counteract inflammatory stimulation with *E. faecalis* in vitro. It was found that the commensal bacteria tested have distinct immunomodulatory properties, and most appear to counteract the inflammatory activity of *E. Faecalis* for at least one cytokine.

FIG. 2 shows the time course of Th1 related cytokines that were released by human PBMCs incubated with *Ruminococcus gnavus* (Epv 1), *Eubacterium rectale* (Epv 2), *Blautia luti* (Epv 3), *Blautia wexlerae* (Epv 5) and *Enterococcus faecalis* (Epv 8), or combinations of each bacterium with *E. faecalis*. Amounts of Th1-related pro-inflammatory cytokines interferon gamma (IFN-γ), interleukin-12 p70 (IL-12p70), interleukin-6 (IL-6), interleukin-2 (IL-2) and tumor necrosis factor alpha (TNFα) released by PBMCs were measured after 24, 48 and 72 hours. As shown in FIG. 2, all commensals have unique immunomodulatory properties. As expected, E. faecalis induced high levels of these pro-inflammatory cytokines. By comparison, most of the other bacterial candidates induced lower levels of Th1-related cytokines and were able to counteract the induction of one or more inflammatory cytokines by E. faecalis. In particular, Blautia luti (Epv 3), showed minimal induction of Th1-related cytokines on its own and was most effective in counteracting induction of these cytokines by E. faecalis (Epv 8). This profile is desirable for disease indications which are primarily driven by Th1 immune responses, such as GVHD.

FIG. 3 shows the time course of Th2 related cytokines that were released in cells treated with R. gnavus (Epv 1), E. rectale (Epv 2), B. luti (Epv 3), B. wexlerae (Epv 5) and E. faecalis (Epv 8), or combinations thereof. Amounts of anti-inflammatory cytokines interleukin-13 (IL-13), interleukin-4 (IL-4) and interleukin-5 (IL-5) released by PBMCs were measured after 24, 48 and 72 hours. Each bacterium displayed detectable pattern of cytokine induction and ability to modulate the effect of E. faecalis. Th2-related cytokines are beneficial in counteracting Th1 reponses. Bacteria capable of promoting Th2 cytokine release are therefore of interest in Th1-driven diseases. R. gnavus appeared the most active in terms of elicitng Th2 cytokine on its own or in the presence of E. faecalis.

FIG. 4 shows the time course of Th9, Th17 and Treg cytokines that were released in cells treated with R. gnavus (Epv 1), E. rectale (Epv 2), B. luti (Epv 3), B. wexlerae (Epv 5) and E. faecalis (Epv 8), or combinations thereof. Amounts of interleukin-9 (IL-9), interleukin-17 (IL-17) and interleukin-10 (IL-10) released by PBMCs were measured after 24, 48 and 72 hours. The activity of IL-9 and IL-17 is context-dependent in that these cytokines can be beneficial under some conditions but detrimental under other conditions depending on the mechanisms responsible for disease pathogenesis. For example, IL-17 is expected to contribute to disease pathogenesis in GVHD but could provide a benefit in Th2-driven disorders. IL-10 produced by regulatory T cells (Treg) is generally immunosuppressive and is expected to provide a benefit in most inflammatory disorders whether Th1- or Th2-driven. As shown in FIG. 4, all bacterial candidates elicited IL-9 and IL-17 to varying degrees and B. wexlerae (Epv 5) was the most potent in inducing IL-10.

FIG. 5 shows the time course of monocyte, macrophage and neutrophil-related inflammatory cytokines that were released by PBMCs treated with R. gnavus (Epv 1), E. rectale (Epv 2), B. luti (Epv 3), B. wexlerae (Epv 5) and E. faecalis (Epv 8), or combinations thereof. Amounts of monocyte chemotactic protein 1 (MCP-1), macrophage inflammatory protein 1β (MIP1β), macrophage inflammatory protein 1α (MIP1α), regulated on activation, normal T expressed and secreted protein (RANTES), interleukin-1α (IL-1α), interleukin-1β (IL1β), interferon α2 (IFN-α2) and interleukin-8 (IL-8) that were released were measured after 24, 48 and 72 hours. In general, these cytokines contribute to inflammation by innate immune effector cells. The bacteria tested showed different degrees of induction and effects on E. faecalis. Overall, E. rectale (Epv 2) and B. luti (Epv 3) were the least inflammatory and the most effective at countering the effect of E. faecalis (Epv 8).

A composite illustration of the secretion of each of the pro-inflammatory and anti-inflammatory cytokines described above in the presence of each commensal alone or in combination with EPV8 is graphed relative to the pro-inflammatory bacterial strain E. faecalis (Epv 8) in FIG. 6. In the context of GVHD, IFNγ (IFNg), IL-12p70, IL-1α (IL-1α), IL-6, IL-8, MCP1, MIP1α (MIP1α), MIP1β (MIP1b) and TNFα (TNFa) are considered pro-inflammatory cytokines. IL-10, IL-13, IL-9, IL-4 and IL-5 are considered anti-inflammatory cytokines. IL-17 (IL-17A), IL-9 and IL-2 have context dependent activity. The results are shown as a percentage of Epv 8, where cytokine levels in the presence of E. faecalis after 24 hours is set at 100%. Each commensal has a unique signature and each one added alone to human PBMCs appeared to be less inflammatory than E. fecalis (below 100% for pro-inflammatory cytokines), except for B. wexlerae (Epv 5). When added to PBMCs in combination with E. faecalis, most commensals tested (except for Epv 5) also counteracted the pro-inflamamtory activity of E. faecalis (below 100% for pro-inflammatory cytokines).

FIGS. 7-10 detail individual cytokine profiles of PBMCs following exposure to various commensals, alone or in combination with the pro-inflammatory bacterium E. faecalis (Epv8). In particular, FIG. 7 shows the effect of R. gnavus (EPV1) on cytokine concentration (pg/ml) either alone or in combination with Epv 8 (E. faecalis).

FIG. 8 shows the effect of E. rectale (EPV 2) on cytokine concentration (pg/ml) either alone or in combination with Epv 8 (E. faecalis). FIG. 9 shows the effect of B. luti (EPV 3) on cytokine concentration (pg/ml) either alone or in combination with Epv 8 (E. faecalis). FIG. 10 shows the effect of B. wexlerae (EPV 5) on cytokine concentration (pg/ml) either alone or in combination with Epv 8 (E. faecalis).

Overall, the foregoing data indicate that, among the bacteria tested, EPV3 has a significantly desirable anti-inflammatory profile for a Th-1-driven condition, such as GVHD while EPV5 has a suboptimal anti-inflammatory profile for GVHD. As shown in FIG. 11, EPV3 has relatively low intrinsic inflammatory activity compared to EPV 8 and is able to reduce the induction of pro-inflammatory cytokines by EPV 8, including IL-6, MCP-1, IL-12p70, and IFNγ which are believed to contribute to the pathogenesis of GVHD. By comparison, EPV 5 is similar to EPV 8 in terms of induction of pro-inflammatory cytokines and shows little ability to counteract the induction of pro-inflammatory cytokines by EPV 8.

Additional bacteria were profiled using this methodology including: Clostridium leptum (EPV 6), Blautia faecis (EPV15), Blautia/Ruminococcus obeum ATCC 29174 (EPV 20), Blautia product ATCC 27340 (EPV 21), Blautia coccoides ATCC 29236 (EPV 22), Blautia hydrogenotrophica ATCC BAA-2371 (EPV-23) and Blautia Hansenii ATCC27752 (EPV 24). Strains freshly isolated by Epiva from the stool of a normal healthy volunteer were also profiled and included: Eubacterium rectale (EPV 35), a previously uncultured Blautia, similar to GQ898099_s S1-5 (EPV 47), a previously uncultured Blautia, similar to SJTU_C_14_16 (EPV 51), Blautia wexlerae (SJ-TU_B_09_77) (EPV 52), Blautia luti ELU0087-T13-S—NI_000247 (EPV 54), Blautia wexlerae WAL 14507 (EPV 64), Blautia obeum (EPV 78), Ruminococcus gnavus (EPV 102) and Blautia luti (BlnIX) (EPV 114). Results focusing on key pro-inflammatory (IL-12p70, IFNγ, IP-10, IL-1RA) and anti-inflammatory (IL-10, IL-4, IL-13) cytokines are shown in FIGS. 12-27. As observed with the initial set of bacterial candidates, each isolate displayed a defined signature. Candidates for treatment of autoimmune or inflammatory disorders, such as GVHD, displayed low induction of pro-inflammatory cytokines and/or positive induction of anti-inflammatory cytokines, and had ability to counteract the inflammatory activity of *E. faecalis*. Bacterial candidates meeting these criteria include, for example, EPV 35, 51, 78 and 114.

Taken together, these results show that commensals have distinct immunomodulatory properties and display a definable signature in terms of their ability to induce cytokines in human host cells, or counteract the pro-inflammatory activity of another bacterium (*E. faecalis*). Accordingly, bacterial compositions may be selected in order to achieve a desired modulation of pro- and anti-inflammatory cytokines. For example, anti-inflammatory bacterial strains may be selected based on their ability to reduce key pro-inflammatory cytokines such as interferon gamma, IL-12p70, IP-10 and IL-1RA and/or increase anti-inflammatory cytokines such as IL-13, IL-10 and IL-4.

Example 3. Effect of Commensal Human Bacteria on T-Cell Polarization

In order to determine whether exposure to commensal bacteria may polarize T cells toward a particular phenotype, flow cytometry analysis was performed on human PBMCs cultured with various commensal bacteria as described above. The cells recovered from culture were washed in phosphate-buffered saline and stained with a cocktail of fluorescently labeled antibodies against specific cell surface protein markers to allow for the detection of Th1 cells (CXCR3$^+$CCR6$^-$), Th2 cells (CXCR3$^-$CCR6$^-$), Th17 cells (CXCR3$^+$CCR6$^+$) and Tregs (CD25$^+$CD127$^{lo}$). Negative control wells contained PBMCs in culture medium alone and positive control wells contained PBMCs+LPS (100 ng/ml) as a known immune stimulus. The commensal bacteria examined inluded: Epv 1: *R. gnavus*; Epv 3: *B. luti*; Epv 2: *E. rectale*; Epv 5: *B. wexlerae*; Epv. 8: *E. faecalis*; Epv 20: *B. obeum*, ATCC 29174; Epv 21: B. product, ATCC 27340; Epv 24: *B. hansenii*, ATCC 27752. As shown in FIG. 28, exposure of human PBMCs to bacteria did result in a shift in the relative proportion of T cell populations compared to the PBMCs alone (control) although statistical significance was not achieved in every case. Overall, most bacteria tested caused an increase in the proportion of T cells with a regulatory phenotype (Tregs) with EPV 21 and EPV 24 having the greatest impact and EPV8 (*E. faecalis*) causing little or no increase in Tregs. Most bacteria also caused a decrease in the proportion of Th17 cells, an increase in Th2 cells and had little or no effect on the proportion of Th1 cells. This type of analysis indicates that commensal bacteria can modulate the proportions of effector T cell types and can be used to select the desired phenotype for a given disease application. For example, the optimal T cell profile to address pro-inflammatory disorders such as GVHD would consist of ↑Treg, ↓Th17, ↓ or unchanged Th1, and ↑Th2. This phenotype was induced by many of the bacteria tested.

Example 4. Pattern of Carbon Source Utilization by Commensal Bacteria

Modulation of the microbiota to correct a dysbiosis associated with pathological conditions can potentially be achieved through administration of bacteria (or bacterial combinations) and prebiotic(s) as a carbon source to promote endogenous expansion of beneficial bacteria. Alternatively, prebiotics can be administered in combination with bacteria to promote their growth or create a favorable environment for their growth. Profiling of carbon source usage by bacterial isolates can be used to customize and optimize selection of prebiotics for particular bacterial strains. Profiling of carbon source usage was conducted on 21 anaerobic commensal bacteria (Table 3) using 96 well plates from Biolog (Hayward, Calif.) where each well contains a different carbon source for a total of 192 different carbon sources (PM01 and PM02A plates). The carbon sources tested are listed in Table 4. The assay was conducted according to manufacturer's instructions. Briefly, pre-cultured bacteria were suspended in Biolog assay medium at a 750 nm optical density (OD) of 0.3-0.4 and 100 µl of the suspension was transferred to each well of the 96 well PM01 and PM02 assay plates. The plates were then incubated at 37° C. in an anaerobic chamber for 24 hr or longer. The amount of growth on each carbon source was evaluated by measuring the optical density (OD) of each well at 750 nm. The results are summarized in FIG. 29, and indicate that each individual strain displays a unique pattern of carbon source usage. Interestingly, different isolates of the same species (e.g. *B. luti* and *B. wexlerae*) show related (albeit distinct) patterns. Overall, these results indicate that characterization of carbon source usage for profiling of bacterial candidates allows optimal selection of prebiotics. Preferred prebiotics can be selected which increase the growth (indicated by an increase in optical density) of bacterial species contained in probiotic compositions.

Example 5. Normal Human Volunteer Study of a Prebiotic Formulation Containing Xylose D-xylose is a carbon source generally preferred by anaerobic bacteria. Preliminary results in the mouse indicate that it may act to promote gut barrier integrity (FIG. 1). It is also used as a carbon source by several bacterial strains (FIG. 29) that were determined to possess a desirable immunological profile for target indications such as GVHD (FIG. 19, 25, 27). A parallel, double-blind, 5 cohort escalation food safety study was conducted to examine D-xylose in normal human volunteers. The study was a double-blind, single-center, parallel group study designed to evaluate the tolerability and potential microbiome changes induced by ingestion of D-xylose at 5 different amounts in healthy, adult volunteers enrolled at 1 study center in the United States (US).

Subjects were screened for eligibility within 21 days prior to the first planned ingestion of study sweetener on Day 1 (Baseline). Within each of 5 cohorts, eligible subjects were randomly assigned in a double-blinded, 6:2 ratio to ingest either D-xylose or the GRAS sweetener Splenda® (control), dissolved into 2 to 6 oz of sterile water and ingested TID with meals for a total of 82 ingestions taken over 28 consecutive days. D-xylose ingestion amounts ranged from 1 to 15 g TID (total daily amount of 3 to 45 g), and all subjects randomized to Splenda® ingested 1 dissolved, commercially available packet TID (3 packets total per day).

Subjects returned to the study center weekly on Days 8, 15, 22, and 28 for ingestion, tolerability, and compliance evaluations. Safety was evaluated on a continual basis through adverse events (AE) monitoring, clinical laboratory measurements, vital sign monitoring, physical examinations, electrocardiograms (ECGs), telephone follow-up, and electronic subject ingestion diaries. Stool was collected pre-ingestion and at pre-specified time points, and post-ingestion samples were evaluated for changes in the gut microbiome compared with Baseline for all subjects. For subjects who consented to further sampling, additional stool specimens were used to potentially isolate living bacteria that could be categorized for research and potential commercialization purposes. Serum and urine were collected for measurement of D-xylose levels and pharmacokinetic (PK) assessments and PK/pharmacodynamics (PD) correlations. Telephone follow-up was conducted as needed, but minimally once per week. The total duration for each participant was up to 60 days, including the Screening period (Day −21 to 0), the ingestion period (Day 1 to 28), and an End-of-Study (EOS) follow-up visit conducted 7 (+3) days after the last ingestion of study sweetener.

Criteria for Evaluation
Safety

Safety was evaluated on a continual basis through AE monitoring, clinical laboratory measurements, vital sign monitoring, physical examinations, ECGs, telephone follow-up, and electronic subject ingestion diaries.

Immunology and Other Assessments

Stool was collected at pre-specified pre- and post-ingestion time points and post-ingestion samples were evaluated for changes in the gut microbiome compared with Baseline. Additional optional specimens were collected to potentially isolate living bacteria that could be categorized for research and potential commercialization purposes.

Blood was collected at pre-specified pre- and post-ingestion time points to evaluate C-reactive protein (CRP), serum cytokines (tumor necrosis factor alpha [TNF-α], interleukin [IL]-2, IL-6, interferon gamma [IFN-γ], and IL-10), and T-cell markers CD3, CD4, CD8, CD25, and FOXP3. Plasma was also stored and may be tested for biomarkers and/or metabolic markers for up to 7 years.

Pharmacokinetics

Blood and urine were collected at pre-specified pre- and post-ingestion time points to measure D-xylose levels and to characterize the systemic absorption profiles of D-xylose.

Statistical Methods

Statistical analyses were conducted using SAS®, Version 9.2 (SAS Institute, Inc., Cary, N.C., USA). The sample size calculations were empiric and based on an estimation of normal healthy volunteer variability in reported symptoms and side effects and not on a statistical method. A weighted randomization scheme was implemented such that more subjects were enrolled at the higher D-xylose ingestion amounts to account for potential toxicity-related effects that could have resulted in withdrawal and/or analysis ineligibility, and to enable collection of more data at ingestion amounts for which limited data were available.

Analysis Populations

The safety population comprised all subjects who ingested any amount of study sweetener.

Safety

AEs were coded using the Medical Dictionary for Regulatory Activities (MedDRA), Version 18.0 (Northrup Grumman Corporation, Chantilly, Va., USA), and summarized by cohort. Laboratory, vital sign, and physical examination data were summarized by cohort using descriptive statistics over time, including statistics for changes from Baseline. ECG findings were also summarized by cohort over time as well as using frequency counts and percentages, as normal or abnormal, with the relevance of abnormalities categorized by clinical significance.

Immunology and Other Assessments

Stool sample compliance was summarized by cohort, using the following calculation for each subject:

$$\text{Percentage compliance} = \frac{\text{Total number of stool samples collected}}{\text{Total number of stool samples expected}} \times 100$$

A total of 7 stool samples were expected to be collected for each subject. Evaluation of changes in the gut microbiome were evaluated in stool samples through taxonomic classification, relative and statistical differential abundance analyses by cohort and time point, an alpha diversity analysis calculated using the Shannon diversity index by cohort and time point, a beta diversity analysis using Bray-Curtis dissimilarity and Unifrac distance by subject and time point, and a principal coordinates analysis using the beta diversity data.

Summary statistics (n, mean, standard deviation, median, minimum, and maximum) were presented for serum concentrations of CRP, flow cytometry T-cell markers (CD3, CD4, CD8, CD25, and FOXP3), and cytokines (TNF-α, IL-2, IL-6, IFN-γ, and IL-10) as per their nominal time points.

Pharmacokinetics

Phoenix® WinNonLin®, Version 6.2.1, was used for PK analyses.

Serum D-xylose concentrations were summarized by cohort using nominal sample times according to actual amount received using summary statistics (n, coefficient of variation [CV], mean, standard deviation [SD], median, minimum, and maximum). Evidence for the occurrence of steady-state was assessed graphically by comparing the time course of either trough or 2-hour post-ingestion serum concentrations of D-xylose as different levels of D-xylose. Accumulation was assessed by comparing the 2-hour post-first-ingestion serum levels with those observed at Week 2 (Day 15) and Week 4 (Day 28).

The total amount of D-xylose excreted in urine was analyzed for all subjects over 5 hours post-ingestion and pooled for analysis; the pooling for analysis reflected the subject mean within a given time of collection (e.g., Day 15 and then Day 28) sorted by ingested amount. Urine PK parameters for D-xylose levels included $Ae_{(0-t)}$ (cumulative amount of sweetener recovered in urine) and percent sweetener amount excreted over a 5-hour period.

Summary of Results

Forty-eight subjects were randomized to ingest either 1 packet of commercially-available Splenda® TID (n=12) or D-xylose TID at the following ingestion amounts (n=36 total):
1 g: 6 subjects
2 g: 6 subjects
8 g: 7 subjects
12.5 g: 8 subjects
15 g: 9 subjects Over the 28-day ingestion period, study sweetener ingestion compliance was >90% for all subjects. Two subjects (4.2%) discontinued from the study prematurely; primary reasons for discontinuation were a protocol violation (positive urine drug screen) and withdrawal of consent. The proportion of males (47.9%) and females (52.1%) was balanced, and the majority of subjects were White (89.6%) and not Hispanic or Latino (77.1%). Subject ages spanned a wide range, with a median of 38.3 (range 22.5 to 60.5) years for the combined D-xylose cohorts and 43.6 (range 24.9 to 64.3) years for the Splenda® cohort.

Safety

D-xylose and Splenda® were both well tolerated, with no new safety concerns identified. One subject required a D-xylose reduction from 15 g to 12.5 g TID at the Week 1 (Day 8) visit due to AEs of moderate abdominal distension, diarrhea, and GI pain; no other modifications to sweetener ingestion amounts were implemented.

Overall, 17 subjects (35.4%) experienced at least 1 AE, including a higher proportion of subjects who ingested any amount of D-xylose (14 subjects [38.9%]) than Splenda® (3 subjects [25.0%]). Reported AE rates increased with increasing D-xylose ingestion amounts, with incidences ranging from 16.7% in subjects who ingested the 2 lowest amounts (1 and 2 g TID) to 66.7% in subjects who ingested the highest amount (15 g TID). AEs reported for more than 1 subject in the D-xylose cohorts included diarrhea (3 subjects [8.3%]) and flatulence and GI pain (2 subjects [5.6%] each). AEs in the Splenda® cohort included abdominal distension, flatulence, increased blood creatinine, infrequent bowel movements, and rhinitis. The incidence of AEs was highest during Weeks 1 and 2 (Days 2 through 15), regardless of sweetener type or ingestion amount. During this 2-week period, 18 subjects overall (37.5%) experienced AEs, compared with 7 subjects (14.6%) overall who experienced AEs either on Day 1 or after Week 2.

All AEs were mild in severity with the exception of moderate AEs reported for 4 subjects (11.1%) in the D-xylose cohorts. These moderate AEs included abdominal distension, concussion/post-concussion syndrome, diarrhea, GI pain, increased blood bilirubin, and neutropenia.

No SAEs, severe AEs, or subject deaths were reported. One subject in the 8 g TID D-xylose cohort experienced non-serious, moderate AEs of concussion and post-concussion syndrome that were noted to have contributed to study discontinuation; however, this subject's primary reason for discontinuation was withdrawal of consent.

GI-related AEs, which were of special interest, were reported for 7 subjects (19.4%) in the D-xylose cohorts and 2 subjects (16.7%) in the Splenda® cohort. GI-related events were mild for all but 1 subject in the 15 g TID D-xylose cohort who experienced moderate GI-related AEs of abdominal distension, diarrhea, and GI pain that required reduction of the D-xylose ingestion amount to 12.5 g TID.

Eleven subjects (22.9%) experienced at least 1 AE that was considered by the Investigator to be related to study sweetener, including 9 subjects (25.0%) in the D-xylose cohorts and 2 subjects (16.7%) in the Splenda® cohort. The incidence of sweetener-related AEs appeared to increase with increasing D-xylose ingestion amounts. Sweetener-related AEs reported for more than 1 subject in the D-xylose cohorts included diarrhea (3 subjects [8.3%]) and flatulence and GI pain (2 subjects [5.6%] each). Sweetener-related AEs reported in the Splenda® cohort were abdominal distension, flatulence, and infrequent bowel movements.

No fluctuations in clinical laboratory measurements over time were considered to be clinically meaningful. Categorical shifts from Baseline that occurred in >10% of subjects in either the combined D-xylose or Splenda® cohorts included decreased or increased glucose (27.7% D-xylose and 16.7% Splenda®) and decreased absolute neutrophil count (ANC) (13.9% and 8.3%); these shifts were not associated with sweetener type or ingestion amount.

Immunology and Other Assessments

To assess the effect of D-xylose on the gut microbiome, this study incorporated an analysis of alpha diversity, beta diversity, and differentially abundant taxa. These factors were assessed both across cohorts and over time. Regardless of sweetener ingestion amount, no apparent significant impact on the intra-sample alpha diversity of the gut microbiome was observed, and no significant changes in community composition were observed over time on study. Numerous taxa were identified as differentially abundant, but these findings may reflect the relatively small sample sizes in each cohort.

Across all D-xylose cohorts, 8.3% of subjects with normal serum CRP at Baseline experienced at least 1 post-ingestion CRP value >2.9 mg/L. A substantially higher proportion of subjects in the Splenda® cohort (41.7%) had normal serum CRP at Baseline and experienced at least 1 post-ingestion CRP value >2.9 mg/L. None of the post-ingestion CRP values for any subject were deemed clinically significant.

Because most individual cytokine data points were below the limit of quantitation (BLQ) and therefore set to zero, cytokine summary statistics were limited and did not indicate any consistent or clinically meaningful changes over time for either sweetener or any D-xylose ingestion amount. There was a trend for reduced levels of serum interferon gamma over time in the 2 g and 15 g D-xylose cohorts (FIG. 30). No consistent or clinically meaningful changes over time in total T-cells or any T-cell subsets were observed for either sweetener or any D-xylose ingestion amount.

Pharmacokinetics

Serum D-xylose concentrations increased linearly with increasing ingestion amounts. Little to no accumulation of serum D-xylose occurred at Day 15 following 1 g to 12.5 g TID ingestion, while an approximately 1.9-fold accumulation ratio was observed in the 15 mg TID cohort (although variability was high). On Day 28, the accumulation ratio ranged from 1.08 to 1.31 following 1 g to 12.5 g TID ingestion and 1.68 following 15 g TID ingestion, although variability was moderate to high in all but the 8 g TID cohort.

In the 1 g TID cohort, approximately 40% of the ingested amount of D-xylose was recovered in urine within 5 hours post-ingestion on Days 1, 15, and 28. In the 2 g through 15 g TID cohorts, between 23% and 32% of the ingested amount of D-xylose was recovered in urine within 5 hours post-ingestion on Days 1, 15, and 28. The fraction excreted in urine was similar among Days 1, 15, and 28.

A review of the time course of serum D-xylose concentrations and the corresponding urinary excretion profiles indicated high ingestion compliance.

Changes in the Gut Microbiome

A total of 344 stool samples were collected in OMNIgene. GUT collection kits and shipped to the GenoFIND laboratory for DNA extraction and V3-V4 16S amplicon sequencing. There were no major shifts in the microbiome alpha diversity between the different treatment groups (absolute number of OTUs, abundance of OTUs) or over time on study. There was an overall decrease in the Chao diversity index over time (indicator of community richness—#of singleton, doubleton OTUs), as shown in FIG. 31. Numerous taxa were identified as differentially abundant, but this finding may be attributable to the relatively small sample sizes of each cohort. Similar observations were made in the mouse study, e.g., xylose treatment did not cause major shifts in the gut microbiome but showed some differences at the family level. Overall, these results suggest that, under the conditions tested in normal individuals and normal mice, ingestion of xylose exerts subtle changes in the gut microbiome. The impact of xylose on the microbiome under disease conditions remains to be determined.

Taken together, the results of this trial show that D-xylose is safe and well-tolerated, and indicate that prebiotic formulations containing xylose may reduce inflammation in a subject, resulting in reduction of serum levels of pro-inflammatory cytokines.

Example 6. Distal Augmentation

The trillions of organisms forming the microbiome function as an organ system interconnected throughout the body. The possibility that modification of the microbiome in a given physical location may influence the microbiome at other sites in the body (distal augmentation) was investigated. Seven week old C57Bl/6 female mice were acclimatized for 7 days prior to the start of the study by daily handling and shuffling between cages. All mice were housed at three mice per cage in individually vented cages (Thoren, Hazleton, Pa.). At day 0, baseline fresh fecal pellets, and vaginal lavages with 100 µL of sterile double-distilled water were collected and immediately frozen at −80° C. for microbiome analysis. After baseline collection, mice were given to drink either autoclaved water (N=6) or 0.5 mg/L of the antibiotic vancomycin in autoclaved water (N=6) ad libitum. Water alone is not expected to influence the microbiome and acted as a negative control. Oral vancomycin is poorly absorbed from the gut and its ingestion does not result in significant levels of drug in the body (Rao et al, 2011). The impact of oral vancomycin is therefore expected to be limited to the gastrointestinal tract such that microbiome changes elsewhere in the body (e.g. vagina) would be attributable to distal augmentation. At day 6, fresh fecal pellets and vaginal lavages with 100 µL of sterile double-distilled water were collected and immediately stored at −80° C. for microbiome analysis.

Isolation and sequencing of microbial DNA from the stool and vaginal samples was performed by DNA Genotek (Ottawa, ON, Canada). The V3-V4 region of the 16S ribosomal subunit was amplified with custom PCR primers and sequenced on an Illumina MiSeq to a minimum acceptable read depth of 25,000 sequences per sample. The widely accepted read depth requirement for accurate taxonomic profiling is 15,000-100,000 reads (Illumina, 2014). A closed-reference taxonomic classification was performed, where each sequence was aligned to the SILVA reference database, version 123. Sequences were aligned using the UCLUST algorithm included in QIIME version 1.9.1 (Caporaso et al., 2010). A minimum threshold of 97% sequence identity was used to classify sequences according to representative sequences in the database. At 97% sequence identity, each OTU represents a genetically unique group of biological organisms. These OTU's were then assigned a curated taxonomic label based on the seven level SILVA taxonomy.

As expected, oral vancomycin treatment had a strong impact on the microbiome of the gut. As shown by principal component analysis (PCA) at the family level, the day 0 to day 6 pattern in fecal samples was clearly different in the control vs oral vancomycin group (FIG. 32). Interestingly, the day 0 to day 6 pattern in the vaginal samples also showed an overall difference between the PBS and oral vancomycin groups even though the vaginal environment is not exposed to vancomycin following oral administration of the antibiotic (FIG. 32). In addition, some bacterial species were detected at low frequency in vaginal samples of the vancomycin-treated group at day 6 (median abundance of approximately 0.00002%) that were not present at day 0 (Table 5). These results support the concept of distal augmentation whereby modification of the microbiome at one site also has an impact at a distal site(s). This finding opens the possibility of modulating the microbiome, for example at the level of the gut, to effect therapeutic changes in the microbiome at other sites, for example the lung.

Example 7. Co-Culture of Bacteria Plus Prebiotic and Host-Cells and Analysis of Host Cell Cytokine Response The following work is done in the presence and absence (as a control) of one or more selected prebiotic carbohydrates. This assay may be used to test or confirm the ability of a prebiotic-bacterium pair to elicit an immunomodulatory response such that the production or release of proinflammatory cytokines decreases and/or the production or release of anti-inflammatory cytokines increases, may be used to evaluate the difference in cytokine response in the presence or absence of a prebiotic mixture, and/or may be used to evaluate an array of prebiotic candidates. Clostridales bacteria are obtained from the ATCC or purified from a human donor and cultured in brain-heart infusion broth at 37° C. The bacteria are harvested by centrifugation (3000 g, 15 minutes) after 24 hours of stationary growth. To test the effects of spores on human intestinal cells and/or human peripheral blood mononuclear cells (huPBMC), bacteria are first heat killed (95° C., 30 minutes) before the centrifugation step. Bacteria (or spores) are washed three times with 1×PBS (pH 7.2, Gibco BRL) and subsequently diluted to obtain final cell densities of $10^6$ and 107 colony forming units (cfu)/ml in RPMI 1640 medium (Gibco BRL).

Human enterocyte-like CaCO-2 cells (passage 60-65) are seeded at a density of $2.5×10^5$ cells/ml on 25 mm cell culture inserts (0.4 µm nucleopore size; Becton Dickinson). The inserts are placed into six well tissue culture plates (Nunc) and cultured 18-22 days at 370C/10% $CO_2$ in DMEM (glutamine, high glucose; Amimed) supplemented with 20% decomplemented fetal calf serum (56° C., 30 minutes; Amimed), 1% MEM non-essential amino acids (Gibco BRL), 10 µg/ml gentamycin (Gibco BRL), and 0.1% penicillin/streptomycin (10 000 IU/ml/10 000 UG/ml; Gibco BRL). The cell culture medium is changed every second day until the cells are fully differentiated. Transepithelial electrical resistance (TEER) is determined continuously in confluent CaCO-2 monolayers using a MultiCell-ERS voltmeter/ohmmeter or as described in Example 44.

Tissue culture inserts covered with CaCO-2 cell monolayers are washed twice with prewarmed RPMI 1640 medium and transferred to six well tissue culture plates. 2 mL culture medium is added to the apical and basolateral compartments of the transwell cell culture system.

Next, the apical surface of CaCO-2 monolayers is challenged by addition of $10^6$ or $10^7$ cfu/ml of Clostridiales bacteria or spores, in the absence of gentamicin. After four hours, gentamicin is added (at 150 µg/mL) to stop bacterial growth and metabolite secretion. CaCO-2 cells are stimulated with the bacteria or spores for 6-36 hours in a 37° C., 10% $CO_2$ incubator. Then the CaCO-2 cells are collected, washed once with cold 1×PBS (pH 7.2), and lysed in denaturation solution for RNA extraction (Micro RNA Isolation Kit, Stratagene). Cellular lysates are stored at −20° C. and cell culture supernatants are collected from the apical compartment and frozen at −20° C. The immune response of CaCO-2 cells is monitored by analysis of cytokine gene transcription (TNF-α, IL-8, monocyte chemoattracting protein 1 (MCP-1), TGF-β, IL-12, IFN-γ, IL-4, IL-10) using a reverse transcription-polymerase chain reaction (RT-PCR) technique and determination of cytokine secretion in cell culture supernatants using an ELISA (Haller D, Bode C, Hammes W P, Pfeifer A M A, Schiffrin E J, Blum S, 2000. Non-pathogenic bacteria elicit a differential cytokine response by intestinal epithelial cell/leucocyte co-cultures. Gut. 47:79-97).

REFERENCES

1. Bischoff, S C, Giovanni, B, Buuman, W, Ockhuizen, T, Schulzke, J-D, Serino, M, Tilg, H, Watson, A and Wells, J M. (2014) Intestinal permeability—a new target for disease prevention and therapy. BMC GASTROENTEROLOGY 14: 189.
2. Boyum, A. (1968) Isolation of mononuclear cells and granulocytes from human blood. Scand. J. CLIN. LAB. INVEST. 21, Suppl 97 (Paper IV), 77-89.
3. Boyum A. (1976) Isolation of lymphocytes, granulocytes and macrophages. SCAND J IMMUNOL. (Suppl 5):9-15.
4. Bach M K, Brashler J R. (1970) Isolation of subpopulations of lymphocytic cells by the use of isotonically balanced solutions of Ficoll. I. Development of methods and demonstration of the existence of a large but finite number of subpopulations. EXP CELL RES. 61:387-96.
5. Fotino, M., Merson, E. J. and Allen, F. H. (1971) Micromethod for rapid separation of lymphocytes from peripheral blood. ANN. CLIN. LAB. SCI. 1:131-133.
6. Hsiao, E Y, McBride, S W, Hsien, S, Sharon G, Hyde, E R, McCue T, Codelli, J A, Chow, J, Reisman, S E, Petrosino, J F, Patterson, P H and Mazmanian, SK (2013) Microbiota modulate behavioral and physiological abnormalities associated with neurodevelopmental disorders. CELL 155: 1451-1463.
7. Caporaso, J. G., Kuczynski, J., Stombaugh, J., Bittinger, K., Bushman, F. D., Costello, E. K., Knight, R. (2010). QIIME allows analysis of high-throughput community sequencing data. NATURE METHODS 7 (5): 335-336. doi: 10.1038/nmeth.f.303
8. Illumina. (2014). Frequently Asked Questions: 16S Metagenomic Sequencing. Retrieved from http://www.illumina.com/content/dam/illuminamarketing/documents/products/other/16smetagen omics-faq-1270-2014-003.pdf
9. Rao S, Kupfer Y, Pagala M, Chapnick E and Tessler S. (2011) Systemic absorption of oral vancomycin in patients with *Clostridium difficile* infection. SCAND J INFECT DIS 5: 386-388.

TABLE 1

| | | See, e.g., WO 2014/121304 | | | |
|---|---|---|---|---|---|
| OTU | SEQ ID Number | Public DB Accession | Clade | Spore Former | Pathogen Status |
| *Eubacterium saburreum* | 858 | AB525414 | clade_178 | Y | N |
| *Eubacterium* sp. oral clone IR009 | 866 | AY349376 | clade_178 | Y | N |
| *Lachnospiraceae bacterium* ICM62 | 1061 | HQ616401 | clade_178 | Y | N |
| *Lachnospiraceae bacterium* MSX33 | 1062 | HQ616384 | clade_178 | Y | N |
| *Lachnospiraceae bacterium* oral taxon 107 | 1063 | ADDS01000069 | clade_178 | Y | N |
| *Alicyclobacillus acidocaldarius* | 122 | NR_074721 | clade_179 | Y | N |
| *Clostridium baratii* | 555 | NR_029229 | clade_223 | Y | N |
| *Clostridium colicanis* | 576 | FJ957863 | clade_223 | Y | N |
| *Clostridium paraputrificum* | 611 | AB536771 | clade_223 | Y | N |
| *Clostridium sardiniense* | 621 | NR_041006 | clade_223 | Y | N |
| *Eubacterium budayi* | 837 | NR_024682 | clade_223 | Y | N |
| *Eubacterium moniliforme* | 851 | HF558373 | clade_223 | Y | N |
| *Eubacterium multiforme* | 852 | NR_024683 | clade_223 | Y | N |
| *Eubacterium nitritogenes* | 853 | NR_024684 | clade_223 | Y | N |
| *Anoxybacillus flavithermus* | 173 | NR_074667 | clade_238 | Y | N |
| *Bacillus aerophilus* | 196 | NR_042339 | clade_238 | Y | N |
| *Bacillus aestuarii* | 197 | GQ980243 | clade_238 | Y | N |
| *Bacillus amyloliquefaciens* | 199 | NR_075005 | clade_238 | Y | N |
| *Bacillus anthracis* | 200 | AAEN01000020 | clade_238 | Y | Category-A |
| *Bacillus atrophaeus* | 201 | NR_075016 | clade_238 | Y | OP |
| *Bacillus badius* | 202 | NR_036893 | clade_238 | Y | OP |
| *Bacillus cereus* | 203 | ABDJ01000015 | clade_238 | Y | OP |
| *Bacillus circulans* | 204 | AB271747 | clade_238 | Y | OP |
| *Bacillus firmus* | 207 | NR_025842 | clade_238 | Y | OP |
| *Bacillus flexus* | 208 | NR_024691 | clade_238 | Y | OP |
| *Bacillus fordii* | 209 | NR_025786 | clade_238 | Y | OP |
| *Bacillus halmapalus* | 211 | NR_026144 | clade_238 | Y | OP |
| *Bacillus herbersteinensis* | 213 | NR_042286 | clade_238 | Y | OP |
| *Bacillus idriensis* | 215 | NR_043268 | clade_238 | Y | OP |
| *Bacillus lentus* | 216 | NR_040792 | clade_238 | Y | OP |
| *Bacillus licheniformis* | 217 | NC_006270 | clade_238 | Y | OP |
| *Bacillus megaterium* | 218 | GU252124 | clade_238 | Y | OP |
| *Bacillus nealsonii* | 219 | NR_044546 | clade_238 | Y | OP |
| *Bacillus niabensis* | 220 | NR_043334 | clade_238 | Y | OP |
| *Bacillus niacini* | 221 | NR_024695 | clade_238 | Y | OP |
| *Bacillus pocheonensis* | 222 | NR_041377 | clade_238 | Y | OP |
| *Bacillus pumilus* | 223 | NR_074977 | clade_238 | Y | OP |
| *Bacillus safensis* | 224 | JQ624766 | clade_238 | Y | OP |
| *Bacillus simplex* | 225 | NR_042136 | clade_238 | Y | OP |
| *Bacillus sonorensis* | 226 | NR_025130 | clade_238 | Y | OP |
| *Bacillus* sp. 10403023 MM10403188 | 227 | CAET01000089 | clade_238 | Y | OP |
| *Bacillus* sp. 2_A_57_CT2 | 230 | ACWD01000095 | clade_238 | Y | OP |
| *Bacillus* sp. 2008724126 | 228 | GU252108 | clade_238 | Y | OP |

TABLE 1-continued

See, e.g., WO 2014/121304

| OTU | SEQ ID Number | Public DB Accession | Clade | Spore Former | Pathogen Status |
|---|---|---|---|---|---|
| *Bacillus* sp. 2008724139 | 229 | GU252111 | clade_238 | Y | OP |
| *Bacillus* sp. 7_16AIA | 231 | FN397518 | clade_238 | Y | OP |
| *Bacillus* sp. AP8 | 233 | JX101689 | clade_238 | Y | OP |
| *Bacillus* sp. B27(2008) | 234 | EU362173 | clade_238 | Y | OP |
| *Bacillus* sp. BT1B_CT2 | 235 | ACWC01000034 | clade_238 | Y | OP |
| *Bacillus* sp. GB1.1 | 236 | FJ897765 | clade_238 | Y | OP |
| *Bacillus* sp. GB9 | 237 | FJ897766 | clade_238 | Y | OP |
| *Bacillus* sp. HU19.1 | 238 | FJ897769 | clade_238 | Y | OP |
| *Bacillus* sp. HU29 | 239 | FJ897771 | clade_238 | Y | OP |
| *Bacillus* sp. HU33.1 | 240 | FJ897772 | clade_238 | Y | OP |
| *Bacillus* sp. JC6 | 241 | JF824800 | clade_238 | Y | OP |
| *Bacillus* sp. oral taxon F79 | 248 | HM099654 | clade_238 | Y | OP |
| *Bacillus* sp. SRC_DSF1 | 243 | GU797283 | clade_238 | Y | OP |
| *Bacillus* sp. SRC_DSF10 | 242 | GU797292 | clade_238 | Y | OP |
| *Bacillus* sp. SRC_DSF2 | 244 | GU797284 | clade_238 | Y | OP |
| *Bacillus* sp. SRC_DSF6 | 245 | GU797288 | clade_238 | Y | OP |
| *Bacillus* sp. tc09 | 249 | HQ844242 | clade_238 | Y | OP |
| *Bacillus* sp. zh168 | 250 | FJ851424 | clade_238 | Y | OP |
| *Bacillus sphaericus* | 251 | DQ286318 | clade_238 | Y | OP |
| *Bacillus sporothermodurans* | 252 | NR_026010 | clade_238 | Y | OP |
| *Bacillus subtilis* | 253 | EU627588 | clade_238 | Y | OP |
| *Bacillus thermoamylovorans* | 254 | NR_029151 | clade_238 | Y | OP |
| *Bacillus thuringiensis* | 255 | NC_008600 | clade_238 | Y | OP |
| *Bacillus weihenstephanensis* | 256 | NR_074926 | clade_238 | Y | OP |
| *Geobacillus kaustophilus* | 933 | NR_074989 | clade_238 | Y | N |
| *Geobacillus stearothermophilus* | 936 | NR_040794 | clade_238 | Y | N |
| *Geobacillus thermodenitrificans* | 938 | NR_074976 | clade_238 | Y | N |
| *Geobacillus thermoglucosidasius* | 939 | NR_043022 | clade_238 | Y | N |
| *Lysinibacillus sphaericus* | 1193 | NR_074883 | clade_238 | Y | N |
| *Clostridiales* sp. SS3_4 | 543 | AY305316 | clade_246 | Y | N |
| *Clostridium beijerinckii* | 557 | NR_074434 | clade_252 | Y | N |
| *Clostridium botulinum* | 560 | NC_010723 | clade_252 | Y | Category-A |
| *Clostridium butyricum* | 561 | ABDT01000017 | clade_252 | Y | N |
| *Clostridium chauvoei* | 568 | EU106372 | clade_252 | Y | N |
| *Clostridium favososporum* | 582 | X76749 | clade_252 | Y | N |
| *Clostridium histolyticum* | 592 | HF558362 | clade_252 | Y | N |
| *Clostridium isatidis* | 597 | NR_026347 | clade_252 | Y | N |
| *Clostridium limosum* | 602 | FR870444 | clade_252 | Y | N |
| *Clostridium sartagoforme* | 622 | NR_026490 | clade_252 | Y | N |
| *Clostridium septicum* | 624 | NR_026020 | clade_252 | Y | N |
| *Clostridium* sp. 7_2_43FAA | 626 | ACDK01000101 | clade_252 | Y | N |
| *Clostridium sporogenes* | 645 | ABKW02000003 | clade_252 | Y | N |
| *Clostridium tertium* | 653 | Y18174 | clade_252 | Y | N |
| *Clostridium carnis* | 564 | NR_044716 | clade_253 | Y | N |
| *Clostridium celatum* | 565 | X77844 | clade_253 | Y | N |
| *Clostridium disporicum* | 579 | NR_026491 | clade_253 | Y | N |
| *Clostridium gasigenes* | 585 | NR_024945 | clade_253 | Y | N |
| *Clostridium quinii* | 616 | NR_026149 | clade_253 | Y | N |
| *Clostridium hylemonae* | 593 | AB023973 | clade_260 | Y | N |
| *Clostridium scindens* | 623 | AF262238 | clade_260 | Y | N |
| *Lachnospiraceae* bacterium 5_1_57FAA | 1054 | ACTR01000020 | clade_260 | Y | N |
| *Clostridium glycyrrhizinilyticum* | 588 | AB233029 | clade_262 | Y | N |
| *Clostridium nexile* | 607 | X73443 | clade_262 | Y | N |
| *Coprococcus comes* | 674 | ABVR01000038 | clade_262 | Y | N |
| *Lachnospiraceae* bacterium 1_1_57FAA | 1048 | ACTM01000065 | clade_262 | Y | N |
| *Lachnospiraceae* bacterium 1_4_56FAA | 1049 | ACTN01000028 | clade_262 | Y | N |
| *Lachnospiraceae* bacterium 8_1_57FAA | 1057 | ACWQ01000079 | clade_262 | Y | N |
| *Ruminococcus lactaris* | 1663 | ABOU02000049 | clade_262 | Y | N |
| *Ruminococcus torques* | 1670 | AAVP02000002 | clade_262 | Y | N |
| *Paenibacillus lautus* | 1397 | NR_040882 | clade_270 | Y | N |
| *Paenibacillus polymyxa* | 1399 | NR_037006 | clade_270 | Y | N |
| *Paenibacillus* sp. HGF5 | 1402 | AEXS01000095 | clade_270 | Y | N |
| *Paenibacillus* sp. HGF7 | 1403 | AFDH01000147 | clade_270 | Y | N |
| *Eubacterium* sp. oral clone JI012 | 868 | AY349379 | clade_298 | Y | N |
| *Alicyclobacillus contaminans* | 124 | NR_041475 | clade_301 | Y | N |

TABLE 1-continued

See, e.g., WO 2014/121304

| OTU | SEQ ID Number | Public DB Accession | Clade | Spore Former | Pathogen Status |
|---|---|---|---|---|---|
| *Alicyclobacillus herbarius* | 126 | NR_024753 | clade_301 | Y | N |
| *Alicyclobacillus pomorum* | 127 | NR_024801 | clade_301 | Y | N |
| *Blautia coccoides* | 373 | AB571656 | clade_309 | Y | N |
| *Blautia glucerasea* | 374 | AB588023 | clade_309 | Y | N |
| *Blautia glucerasei* | 375 | AB439724 | clade_309 | Y | N |
| *Blautia hansenii* | 376 | ABYU02000037 | clade_309 | Y | N |
| *Blautia luti* | 378 | AB691576 | clade_309 | Y | N |
| *Blautia producta* | 379 | AB600998 | clade_309 | Y | N |
| *Blautia schinkii* | 380 | NR_026312 | clade_309 | Y | N |
| *Blautia* sp. M25 | 381 | HM626178 | clade_309 | Y | N |
| *Blautia stercoris* | 382 | HM626177 | clade_309 | Y | N |
| *Blautia wexlerae* | 383 | EF036467 | clade_309 | Y | N |
| *Bryantella formatexigens* | 439 | ACCL02000018 | clade_309 | Y | N |
| *Clostridium coccoides* | 573 | EF025906 | clade_309 | Y | N |
| *Eubacterium cellulosolvens* | 839 | AY178842 | clade_309 | Y | N |
| *Lachnospiraceae bacterium* 6_1_63FAA | 1056 | ACTV01000014 | clade_309 | Y | N |
| *Ruminococcus hansenii* | 1662 | M59114 | clade_309 | Y | N |
| *Ruminococcus obeum* | 1664 | AY169419 | clade_309 | Y | N |
| *Ruminococcus* sp. 5_1_39BFAA | 1666 | ACII01000172 | clade_309 | Y | N |
| *Ruminococcus* sp. K_1 | 1669 | AB222208 | clade_309 | Y | N |
| *Syntrophococcus sucromutans* | 1911 | NR_036869 | clade_309 | Y | N |
| *Bacillus alcalophilus* | 198 | X76436 | clade_327 | Y | N |
| *Bacillus clausii* | 205 | FN397477 | clade_327 | Y | OP |
| *Bacillus gelatini* | 210 | NR_025595 | clade_327 | Y | OP |
| *Bacillus halodurans* | 212 | AY144582 | clade_327 | Y | OP |
| *Bacillus* sp. oral taxon F26 | 246 | HM099642 | clade_327 | Y | OP |
| *Clostridium innocuum* | 595 | M23732 | clade_351 | Y | N |
| *Clostridium* sp. HGF2 | 628 | AENW01000022 | clade_351 | Y | N |
| *Clostridium perfringens* | 612 | ABDW01000023 | clade_353 | Y | Category-B |
| *Sarcina ventriculi* | 1687 | NR_026146 | clade_353 | Y | N |
| *Clostridium bartlettii* | 556 | ABEZ02000012 | clade_354 | Y | N |
| *Clostridium bifermentans* | 558 | X73437 | clade_354 | Y | N |
| *Clostridium ghonii* | 586 | AB542933 | clade_354 | Y | N |
| *Clostridium glycolicum* | 587 | FJ384385 | clade_354 | Y | N |
| *Clostridium mayombei* | 605 | FR733682 | clade_354 | Y | N |
| *Clostridium sordellii* | 625 | AB448946 | clade_354 | Y | N |
| *Clostridium* sp. MT4 E | 635 | FJ159523 | clade_354 | Y | N |
| *Eubacterium tenue* | 872 | M59118 | clade_354 | Y | N |
| *Clostridium argentinense* | 553 | NR_029232 | clade_355 | Y | N |
| *Clostridium* sp. JC122 | 630 | CAEV01000127 | clade_355 | Y | N |
| *Clostridium* sp. NMBHI_1 | 636 | JN093130 | clade_355 | Y | N |
| *Clostridium subterminale* | 650 | NR_041795 | clade_355 | Y | N |
| *Clostridium sulfidigenes* | 651 | NR_044161 | clade_355 | Y | N |
| *Dorea formicigenerans* | 773 | AAXA02000006 | clade_360 | Y | N |
| *Dorea longicatena* | 774 | AJ132842 | clade_360 | Y | N |
| *Lachnospiraceae bacterium* 2_1_46FAA | 1050 | ADLB01000035 | clade_360 | Y | N |
| *Lachnospiraceae bacterium* 2_1_58FAA | 1051 | ACTO01000052 | clade_360 | Y | N |
| *Lachnospiraceae bacterium* 4_1_37FAA | 1053 | ADCR01000030 | clade_360 | Y | N |
| *Lachnospiraceae bacterium* 9_1_43BFAA | 1058 | ACTX01000023 | clade_360 | Y | N |
| *Ruminococcus gnavus* | 1661 | X94967 | clade_360 | Y | N |
| *Ruminococcus* sp. ID8 | 1668 | AY960564 | clade_360 | Y | N |
| *Blautia hydrogenotrophica* | 377 | ACBZ01000217 | clade_368 | Y | N |
| *Lactonifactor longoviformis* | 1147 | DQ100449 | clade_368 | Y | N |
| *Robinsoniella peoriensis* | 1633 | AF445258 | clade_368 | Y | N |
| *Eubacterium infirmum* | 849 | U13039 | clade_384 | Y | N |
| *Eubacterium* sp. WAL 14571 | 864 | FJ687606 | clade_384 | Y | N |
| Erysipelotrichaceae bacterium 5_2_54FAA | 823 | ACZW01000054 | clade_385 | Y | N |
| *Eubacterium biforme* | 835 | ABYT01000002 | clade_385 | Y | N |
| *Eubacterium cylindroides* | 842 | FP929041 | clade_385 | Y | N |
| *Eubacterium dolichum* | 844 | L34682 | clade_385 | Y | N |
| *Eubacterium* sp. 3_1_31 | 861 | ACTL01000045 | clade_385 | Y | N |
| *Eubacterium tortuosum* | 873 | NR_044648 | clade_385 | Y | N |
| *Bulleidia extructa* | 441 | ADFR01000011 | clade_388 | Y | N |
| *Solobacterium moorei* | 1739 | AECQ01000039 | clade_388 | Y | N |
| *Coprococcus catus* | 673 | EU266552 | clade_393 | Y | N |
| *Lachnospiraceae bacterium* | 1064 | HM099641 | clade_393 | Y | N |

TABLE 1-continued

See, e.g., WO 2014/121304

| OTU | SEQ ID Number | Public DB Accession | Clade | Spore Former | Pathogen Status |
|---|---|---|---|---|---|
| oral taxon F15 | | | | | |
| *Clostridium cochlearium* | 574 | NR_044717 | clade_395 | Y | N |
| *Clostridium malenominatum* | 604 | FR749893 | clade_395 | Y | N |
| *Clostridium tetani* | 654 | NC_004557 | clade_395 | Y | N |
| *Acetivibrio ethanolgignens* | 6 | FR749897 | clade_396 | Y | N |
| *Anaerosporobacter mobilis* | 161 | NR_042953 | clade_396 | Y | N |
| *Bacteroides pectinophilus* | 288 | ABVQ01000036 | clade_396 | Y | N |
| *Clostridium aminovalericum* | 551 | NR_029245 | clade_396 | Y | N |
| *Clostridium phytofermentans* | 613 | NR_074652 | clade_396 | Y | N |
| *Eubacterium hallii* | 848 | L34621 | clade_396 | Y | N |
| *Eubacterium xylanophilum* | 875 | L34628 | clade_396 | Y | N |
| *Ruminococcus callidus* | 1658 | NR_029160 | clade_406 | Y | N |
| *Ruminococcus champanellensis* | 1659 | FP929052 | clade_406 | Y | N |
| *Ruminococcus* sp. 18P13 | 1665 | AJ515913 | clade_406 | Y | N |
| *Ruminococcus* sp. 9SE51 | 1667 | FM954974 | clade_406 | Y | N |
| *Anaerostipes caccae* | 162 | ABAX03000023 | clade_408 | Y | N |
| *Anaerostipes* sp. 3_2_56FAA | 163 | ACWB01000002 | clade_408 | Y | N |
| Clostridiales bacterium 1_7_47FAA | 541 | ABQR01000074 | clade_408 | Y | N |
| Clostridiales sp. SM4_1 | 542 | FP929060 | clade_408 | Y | N |
| Clostridiales sp. SSC_2 | 544 | FP929061 | clade_408 | Y | N |
| *Clostridium aerotolerans* | 546 | X76163 | clade_408 | Y | N |
| *Clostridium aldenense* | 547 | NR_043680 | clade_408 | Y | N |
| *Clostridium algidixylanolyticum* | 550 | NR_028726 | clade_408 | Y | N |
| *Clostridium amygdalinum* | 552 | AY353957 | clade_408 | Y | N |
| *Clostridium asparagiforme* | 554 | ACCJ01000522 | clade_408 | Y | N |
| *Clostridium bolteae* | 559 | ABCC02000039 | clade_408 | Y | N |
| *Clostridium celerecrescens* | 566 | JQ246092 | clade_408 | Y | N |
| *Clostridium citroniae* | 569 | ADLJ01000059 | clade_408 | Y | N |
| *Clostridium clostridiiformes* | 571 | M59089 | clade_408 | Y | N |
| *Clostridium clostridioforme* | 572 | NR_044715 | clade_408 | Y | N |
| *Clostridium hathewayi* | 590 | AY552788 | clade_408 | Y | N |
| *Clostridium indolis* | 594 | AF028351 | clade_408 | Y | N |
| *Clostridium lavalense* | 600 | EF564277 | clade_408 | Y | N |
| *Clostridium saccharolyticum* | 620 | CP002109 | clade_408 | Y | N |
| *Clostridium* sp. M62_1 | 633 | ACFX02000046 | clade_408 | Y | N |
| *Clostridium* sp. SS2_1 | 638 | ABGC03000041 | clade_408 | Y | N |
| *Clostridium sphenoides* | 643 | X73449 | clade_408 | Y | N |
| *Clostridium symbiosum* | 652 | ADLQ01000114 | clade_408 | Y | N |
| *Clostridium xylanolyticum* | 658 | NR_037068 | clade_408 | Y | N |
| *Eubacterium hadrum* | 847 | FR749933 | clade_408 | Y | N |
| Lachnospiraceae bacterium 3_1_57FAA_CT1 | 1052 | ACTP01000124 | clade_408 | Y | N |
| Lachnospiraceae bacterium 5_1_63FAA | 1055 | ACTS01000081 | clade_408 | Y | N |
| Lachnospiraceae bacterium A4 | 1059 | DQ789118 | clade_408 | Y | N |
| Lachnospiraceae bacterium DJF VP30 | 1060 | EU728771 | clade_408 | Y | N |
| Lachnospiraceae genomosp. C1 | 1065 | AY278618 | clade_408 | Y | N |
| *Clostridium difficile* | 578 | NC_013315 | clade_409 | Y | OP |
| *Eubacterium* sp. AS15b | 862 | HQ616364 | clade_428 | Y | N |
| *Eubacterium* sp. OBRC9 | 863 | HQ616354 | clade_428 | Y | N |
| *Eubacterium* sp. oral clone OH3A | 871 | AY947497 | clade_428 | Y | N |
| *Eubacterium yurii* | 876 | AEES01000073 | clade_428 | Y | N |
| *Clostridium acetobutylicum* | 545 | NR_074511 | clade_430 | Y | N |
| *Clostridium algidicarnis* | 549 | NR_041746 | clade_430 | Y | N |
| *Clostridium cadaveris* | 562 | AB542932 | clade_430 | Y | N |
| *Clostridium carboxidivorans* | 563 | FR733710 | clade_430 | Y | N |
| *Clostridium estertheticum* | 580 | NR_042153 | clade_430 | Y | N |
| *Clostridium fallax* | 581 | NR_044714 | clade_430 | Y | N |
| *Clostridium felsineum* | 583 | AF270502 | clade_430 | Y | N |
| *Clostridium frigidicarnis* | 584 | NR_024919 | clade_430 | Y | N |
| *Clostridium kluyveri* | 598 | NR_074165 | clade_430 | Y | N |
| *Clostridium magnum* | 603 | X77835 | clade_430 | Y | N |
| *Clostridium putrefaciens* | 615 | NR_024995 | clade_430 | Y | N |
| *Clostridium* sp. HPB_46 | 629 | AY862516 | clade_430 | Y | N |
| *Clostridium tyrobutyricum* | 656 | NR_044718 | clade_430 | Y | N |

TABLE 1-continued

See, e.g., WO 2014/121304

| OTU | SEQ ID Number | Public DB Accession | Clade | Spore Former | Pathogen Status |
|---|---|---|---|---|---|
| *Sutterella parvirubra* | 1899 | AB300989 | clade_432 | Y | N |
| *Acetanaerobacterium elongatum* | 4 | NR_042930 | clade_439 | Y | N |
| *Clostridium cellulosi* | 567 | NR_044624 | clade_439 | Y | N |
| *Ethanoligenens harbinense* | 832 | AY675965 | clade_439 | Y | N |
| *Eubacterium rectale* | 856 | FP929042 | clade_444 | Y | N |
| *Eubacterium* sp. oral clone GI038 | 865 | AY349374 | clade_444 | Y | N |
| *Lachnobacterium bovis* | 1045 | GU324407 | clade_444 | Y | N |
| *Roseburia cecicola* | 1634 | GU233441 | clade_444 | Y | N |
| *Roseburia faecalis* | 1635 | AY804149 | clade_444 | Y | N |
| *Roseburia faecis* | 1636 | AY305310 | clade_444 | Y | N |
| *Roseburia hominis* | 1637 | AJ270482 | clade_444 | Y | N |
| *Roseburia intestinalis* | 1638 | FP929050 | clade_444 | Y | N |
| *Roseburia inulinivorans* | 1639 | AJ270473 | clade_444 | Y | N |
| *Brevibacillus brevis* | 410 | NR_041524 | clade_448 | Y | N |
| *Brevibacillus laterosporus* | 414 | NR_037005 | clade_448 | Y | N |
| *Bacillus coagulans* | 206 | DQ297928 | clade_451 | Y | OP |
| *Sporolactobacillus inulinus* | 1752 | NR_040962 | clade_451 | Y | N |
| *Kocuria palustris* | 1041 | EU333884 | clade_453 | Y | N |
| *Nocardia farcinica* | 1353 | NC_006361 | clade_455 | Y | N |
| *Bacillus* sp. oral taxon F28 | 247 | HM099650 | clade_456 | Y | OP |
| *Catenibacterium mitsuokai* | 495 | AB030224 | clade_469 | Y | N |
| *Clostridium* sp. TM_40 | 640 | AB249652 | clade_469 | Y | N |
| *Coprobacillus cateniformis* | 670 | AB030218 | clade_469 | Y | N |
| *Coprobacillus* sp. 29_1 | 671 | ADKX01000057 | clade_469 | Y | N |
| *Clostridium rectum* | 618 | NR_029271 | clade_470 | Y | N |
| *Eubacterium nodatum* | 854 | U13041 | clade_476 | Y | N |
| *Eubacterium saphenum* | 859 | NR_026031 | clade_476 | Y | N |
| *Eubacterium* sp. oral clone JH012 | 867 | AY349373 | clade_476 | Y | N |
| *Eubacterium* sp. oral clone JS001 | 870 | AY349378 | clade_476 | Y | N |
| *Faecalibacterium prausnitzii* | 880 | ACOP02000011 | clade_478 | Y | N |
| *Gemmiger formicilis* | 932 | GU562446 | clade_478 | Y | N |
| *Subdoligranulum variabile* | 1896 | AJ518869 | clade_478 | Y | N |
| Clostridiaceae bacterium JC13 | 532 | JF824807 | clade_479 | Y | N |
| *Clostridium* sp. MLG055 | 634 | AF304435 | clade_479 | Y | N |
| Erysipelotrichaceae bacterium 3_1_53 | 822 | ACTJ01000113 | clade_479 | Y | N |
| *Clostridium cocleatum* | 575 | NR_026495 | clade_481 | Y | N |
| *Clostridium ramosum* | 617 | M23731 | clade_481 | Y | N |
| *Clostridium saccharogumia* | 619 | DQ100445 | clade_481 | Y | N |
| *Clostridium spiroforme* | 644 | X73441 | clade_481 | Y | N |
| *Coprobacillus* sp. D7 | 672 | ACDT01000199 | clade_481 | Y | N |
| Clostridiales bacterium SY8519 | 535 | AB477431 | clade_482 | Y | N |
| *Clostridium* sp. SY8519 | 639 | AP012212 | clade_482 | Y | N |
| *Eubacterium ramulus* | 855 | AJ011522 | clade_482 | Y | N |
| *Erysipelothrix inopinata* | 819 | NR_025594 | clade_485 | Y | N |
| *Erysipelothrix rhusiopathiae* | 820 | ACLK01000021 | clade_485 | Y | N |
| *Erysipelothrix tonsillarum* | 821 | NR_040871 | clade_485 | Y | N |
| *Holdemania filiformis* | 1004 | Y11466 | clade_485 | Y | N |
| *Mollicutes* bacterium pACH93 | 1258 | AY297808 | clade_485 | Y | N |
| *Coxiella burnetii* | 736 | CP000890 | clade_486 | Y | Category-B |
| *Clostridium hiranonis* | 591 | AB023970 | clade_487 | Y | N |
| *Clostridium irregulare* | 596 | NR_029249 | clade_487 | Y | N |
| *Clostridium orbiscindens* | 609 | Y18187 | clade_494 | Y | N |
| *Clostridium* sp. NML 04A032 | 637 | EU815224 | clade_494 | Y | N |
| *Flavonifractor plautii* | 886 | AY724678 | clade_494 | Y | N |
| *Pseudoflavonifractor capillosus* | 1591 | AY136666 | clade_494 | Y | N |
| Ruminococcaceae bacterium D16 | 1655 | ADDX01000083 | clade_494 | Y | N |
| *Acetivibrio cellulolyticus* | 5 | NR_025917 | clade_495 | Y | N |
| *Clostridium aldrichii* | 548 | NR_026099 | clade_495 | Y | N |
| *Clostridium clariflavum* | 570 | NR_041235 | clade_495 | Y | N |
| *Clostridium stercorarium* | 647 | NR_025100 | clade_495 | Y | N |
| *Clostridium straminisolvens* | 649 | NR_024829 | clade_495 | Y | N |
| *Clostridium thermocellum* | 655 | NR_074629 | clade_495 | Y | N |
| *Fusobacterium nucleatum* | 901 | ADVK01000034 | clade_497 | Y | N |
| *Eubacterium barkeri* | 834 | NR_044661 | clade_512 | Y | N |

TABLE 1-continued

See, e.g., WO 2014/121304

| OTU | SEQ ID Number | Public DB Accession | Clade | Spore Former | Pathogen Status |
|---|---|---|---|---|---|
| *Eubacterium callanderi* | 838 | NR_026330 | clade_512 | Y | N |
| *Eubacterium limosum* | 850 | CP002273 | clade_512 | Y | N |
| *Anaerotruncus colihominis* | 164 | ABGD02000021 | clade_516 | Y | N |
| *Clostridium methylpentosum* | 606 | ACEC01000059 | clade_516 | Y | N |
| *Clostridium* sp. YIT 12070 | 642 | AB491208 | clade_516 | Y | N |
| *Hydrogenoanaerobacterium saccharovorans* | 1005 | NR_044425 | clade_516 | Y | N |
| *Ruminococcus albus* | 1656 | AY445600 | clade_516 | Y | N |
| *Ruminococcus flavefaciens* | 1660 | NR_025931 | clade_516 | Y | N |
| *Clostridium haemolyticum* | 589 | NR_024749 | clade_517 | Y | N |
| *Clostridium novyi* | 608 | NR_074343 | clade_517 | Y | N |
| *Clostridium* sp. LMG 16094 | 632 | X95274 | clade_517 | Y | N |
| *Eubacterium ventriosum* | 874 | L34421 | clade_519 | Y | N |
| *Bacteroides galacturonicus* | 280 | DQ497994 | clade_522 | Y | N |
| *Eubacterium eligens* | 845 | CP001104 | clade_522 | Y | N |
| *Lachnospira multipara* | 1046 | FR733699 | clade_522 | Y | N |
| *Lachnospira pectinoschiza* | 1047 | L14675 | clade_522 | Y | N |
| *Lactobacillus rogosae* | 1114 | GU269544 | clade_522 | Y | N |
| *Bacillus horti* | 214 | NR_036860 | clade_527 | Y | OP |
| *Bacillus* sp. 9_3AIA | 232 | FN397519 | clade_527 | Y | OP |
| *Eubacterium brachy* | 836 | U13038 | clade_533 | Y | N |
| *Filifactor alocis* | 881 | CP002390 | clade_533 | Y | N |
| *Filifactor villosus* | 882 | NR_041928 | clade_533 | Y | N |
| *Clostridium leptum* | 601 | AJ305238 | clade_537 | Y | N |
| *Clostridium* sp. YIT 12069 | 641 | AB491207 | clade_537 | Y | N |
| *Clostridium sporosphaeroides* | 646 | NR_044835 | clade_537 | Y | N |
| *Eubacterium coprostanoligenes* | 841 | HM037995 | clade_537 | Y | N |
| *Ruminococcus bromii* | 1657 | EU266549 | clade_537 | Y | N |
| *Eubacterium siraeum* | 860 | ABCA03000054 | clade_538 | Y | N |
| *Clostridium viride* | 657 | NR_026204 | clade_540 | Y | N |
| *Oscillibacter* sp. G2 | 1386 | HM626173 | clade_540 | Y | N |
| *Oscillibacter valericigenes* | 1387 | NR_074793 | clade_540 | Y | N |
| *Oscillospira guilliermondii* | 1388 | AB040495 | clade_540 | Y | N |
| *Butyrivibrio crossotus* | 455 | ABWN01000012 | clade_543 | Y | N |
| *Clostridium* sp. L2_50 | 631 | AAYW02000018 | clade_543 | Y | N |
| *Coprococcus eutactus* | 675 | EF031543 | clade_543 | Y | N |
| *Coprococcus* sp. ART55_1 | 676 | AY350746 | clade_543 | Y | N |
| *Eubacterium ruminantium* | 857 | NR_024661 | clade_543 | Y | N |
| *Collinsella aerofaciens* | 659 | AAVN02000007 | clade_553 | Y | N |
| *Alkaliphilus metalliredigenes* | 137 | AY137848 | clade_554 | Y | N |
| *Alkaliphilus oremlandii* | 138 | NR_043674 | clade_554 | Y | N |
| *Clostridium sticklandii* | 648 | L04167 | clade_554 | Y | N |
| *Turicibacter sanguinis* | 1965 | AF349724 | clade_555 | Y | N |
| *Fulvimonas* sp. NML 060897 | 892 | EF589680 | clade_557 | Y | N |
| *Desulfitobacterium frappieri* | 753 | AJ276701 | clade_560 | Y | N |
| *Desulfitobacterium hafniense* | 754 | NR_074996 | clade_560 | Y | N |
| *Desulfotomaculum nigrificans* | 756 | NR_044832 | clade_560 | Y | N |
| *Lutispora thermophila* | 1191 | NR_041236 | clade_564 | Y | N |
| *Brachyspira pilosicoli* | 405 | NR_075069 | clade_565 | Y | N |
| *Eggerthella lenta* | 778 | AF292375 | clade_566 | Y | N |
| *Streptomyces albus* | 1888 | AJ697941 | clade_566 | Y | N |
| Chlamydiales bacterium NS11 | 505 | JN606074 | clade_567 | Y | N |
| *Anaerofustis stercorihominis* | 159 | ABIL02000005 | clade_570 | Y | N |
| *Butyricicoccus pullicaecorum* | 453 | HH793440 | clade_572 | Y | N |
| *Eubacterium desmolans* | 843 | NR_044644 | clade_572 | Y | N |
| *Papillibacter cinnamivorans* | 1415 | NR_025025 | clade_572 | Y | N |
| *Sporobacter termitidis* | 1751 | NR_044972 | clade_572 | Y | N |
| *Deferribacteres* sp. oral clone JV006 | 744 | AY349371 | clade_575 | Y | N |
| *Clostridium colinum* | 577 | NR_026151 | clade_576 | Y | N |
| *Clostridium lactatifermentans* | 599 | NR_025651 | clade_576 | Y | N |
| *Clostridium piliforme* | 614 | D14639 | clade_576 | Y | N |
| *Saccharomonospora viridis* | 1671 | X54286 | clade_579 | Y | N |
| *Thermobifida fusca* | 1921 | NC_007333 | clade_579 | Y | N |

TABLE 1-continued

See, e.g., WO 2014/121304

| OTU | SEQ ID Number | Public DB Accession | Clade | Spore Former | Pathogen Status |
|---|---|---|---|---|---|
| *Leptospira licerasiae* | 1164 | EF612284 | clade__585 | Y | OP |
| *Moorella thermoacetica* | 1259 | NR_075001 | clade__590 | Y | N |
| *Thermoanaerobacter pseudethanolicus* | 1920 | CP000924 | clade__590 | Y | N |
| *Flexistipes sinusarabici* | 888 | NR_074881 | clade__591 | Y | N |
| *Gloeobacter violaceus* | 942 | NR_074282 | clade__596 | Y | N |
| *Eubacterium* sp. oral clone JN088 | 869 | AY349377 | clade__90 | Y | N |
| *Clostridium oroticum* | 610 | FR749922 | clade__96 | Y | N |
| *Clostridium* sp. D5 | 627 | ADBG01000142 | clade__96 | Y | N |
| *Eubacterium contortum* | 840 | FR749946 | clade__96 | Y | N |
| *Eubacterium fissicatena* | 846 | FR749935 | clade__96 | Y | N |
| *Corynebacterium coyleae* | 692 | X96497 | clade__100 | N | N |
| *Corynebacterium mucifaciens* | 711 | NR_026396 | clade__100 | N | N |
| *Corynebacterium ureicelerivorans* | 733 | AM397636 | clade__100 | N | N |
| *Corynebacterium appendicis* | 684 | NR_028951 | clade__102 | N | N |
| *Corynebacterium genitalium* | 698 | ACLJ01000031 | clade__102 | N | N |
| *Corynebacterium glaucum* | 699 | NR_028971 | clade__102 | N | N |
| *Corynebacterium imitans* | 703 | AF537597 | clade__102 | N | N |
| *Corynebacterium riegelii* | 719 | EU848548 | clade__102 | N | N |
| *Corynebacterium* sp. L_2012475 | 723 | HE575405 | clade__102 | N | N |
| *Corynebacterium* sp. NML 93_0481 | 724 | GU238409 | clade__102 | N | N |
| *Corynebacterium sundsvallense* | 728 | Y09655 | clade__102 | N | N |
| *Corynebacterium tuscaniae* | 730 | AY677186 | clade__102 | N | N |
| *Prevotella maculosa* | 1504 | AGEK01000035 | clade__104 | N | N |
| *Prevotella oris* | 1513 | ADDV01000091 | clade__104 | N | N |
| *Prevotella salivae* | 1517 | AB108826 | clade__104 | N | N |
| *Prevotella* sp. ICM55 | 1521 | HQ616399 | clade__104 | N | N |
| *Prevotella* sp. oral clone AA020 | 1528 | AY005057 | clade__104 | N | N |
| *Prevotella* sp. oral clone GI032 | 1538 | AY349396 | clade__104 | N | N |
| *Prevotella* sp. oral taxon G70 | 1558 | GU432179 | clade__104 | N | N |
| *Prevotella corporis* | 1491 | L16465 | clade__105 | N | N |
| *Bacteroides* sp. 4_1_36 | 312 | ACTC01000133 | clade__110 | N | N |
| *Bacteroides* sp. AR20 | 315 | AF139524 | clade__110 | N | N |
| *Bacteroides* sp. D20 | 319 | ACPT01000052 | clade__110 | N | N |
| *Bacteroides* sp. F_4 | 322 | AB470322 | clade__110 | N | N |
| *Bacteroides uniformis* | 329 | AB050110 | clade__110 | N | N |
| *Prevotella nanceiensis* | 1510 | JN867228 | clade__127 | N | N |
| *Prevotella* sp. oral taxon 299 | 1548 | ACWZ01000026 | clade__127 | N | N |
| *Prevotella bergensis* | 1485 | ACKS01000100 | clade__128 | N | N |
| *Prevotella buccalis* | 1489 | JN867261 | clade__129 | N | N |
| *Prevotella timonensis* | 1564 | ADEF01000012 | clade__129 | N | N |
| *Prevotella oralis* | 1512 | AEPE01000021 | clade__130 | N | N |
| *Prevotella* sp. SEQ072 | 1525 | JN867238 | clade__130 | N | N |
| *Leuconostoc carnosum* | 1177 | NR_040811 | clade__135 | N | N |
| *Leuconostoc gasicomitatum* | 1179 | FN822744 | clade__135 | N | OP |
| *Leuconostoc inhae* | 1180 | NR_025204 | clade__135 | N | N |
| *Leuconostoc kimchii* | 1181 | NR_075014 | clade__135 | N | N |
| *Edwardsiella tarda* | 777 | CP002154 | clade__139 | N | N |
| *Photorhabdus asymbiotica* | 1466 | Z76752 | clade__139 | N | N |
| *Psychrobacter arcticus* | 1607 | CP000082 | clade__141 | N | N |
| *Psychrobacter cibarius* | 1608 | HQ698586 | clade__141 | N | N |
| *Psychrobacter cryohalolentis* | 1609 | CP000323 | clade__141 | N | N |
| *Psychrobacter faecalis* | 1610 | HQ698566 | clade__141 | N | N |
| *Psychrobacter nivimaris* | 1611 | HQ698587 | clade__141 | N | N |
| *Psychrobacter pulmonis* | 1612 | HQ698582 | clade__141 | N | N |
| *Pseudomonas aeruginosa* | 1592 | AABQ07000001 | clade__154 | N | N |
| *Pseudomonas* sp. 2_1_26 | 1600 | ACWU01000257 | clade__154 | N | N |
| *Corynebacterium confusum* | 691 | Y15886 | clade__158 | N | N |
| *Corynebacterium propinquum* | 712 | NR_037038 | clade__158 | N | N |
| *Corynebacterium pseudodiphtheriticum* | 713 | X84258 | clade__158 | N | N |
| *Bartonella bacilliformis* | 338 | NC_008783 | clade__159 | N | N |
| *Bartonella grahamii* | 339 | CP001562 | clade__159 | N | N |
| *Bartonella henselae* | 340 | NC_005956 | clade__159 | N | N |

TABLE 1-continued

See, e.g., WO 2014/121304

| OTU | SEQ ID Number | Public DB Accession | Clade | Spore Former | Pathogen Status |
|---|---|---|---|---|---|
| *Bartonella quintana* | 341 | BX897700 | clade_159 | N | N |
| *Bartonella tamiae* | 342 | EF672728 | clade_159 | N | N |
| *Bartonella washoensis* | 343 | FJ719017 | clade_159 | N | N |
| *Brucella abortus* | 430 | ACBJ01000075 | clade_159 | N | Category-B |
| *Brucella canis* | 431 | NR_044652 | clade_159 | N | Category-B |
| *Brucella ceti* | 432 | ACJD01000006 | clade_159 | N | Category-B |
| *Brucella melitensis* | 433 | AE009462 | clade_159 | N | Category-B |
| *Brucella microti* | 434 | NR_042549 | clade_159 | N | Category-B |
| *Brucella ovis* | 435 | NC_009504 | clade_159 | N | Category-B |
| *Brucella sp. 83_13* | 436 | ACBQ01000040 | clade_159 | N | Category-B |
| *Brucella sp. BO1* | 437 | EU053207 | clade_159 | N | Category-B |
| *Brucella suis* | 438 | ACBK01000034 | clade_159 | N | Category-B |
| *Ochrobactrum anthropi* | 1360 | NC_009667 | clade_159 | N | N |
| *Ochrobactrum intermedium* | 1361 | ACQA01000001 | clade_159 | N | N |
| *Ochrobactrum pseudintermedium* | 1362 | DQ365921 | clade_159 | N | N |
| *Prevotella* genomosp. C2 | 1496 | AY278625 | clade_164 | N | N |
| *Prevotella multisaccharivorax* | 1509 | AFJE01000016 | clade_164 | N | N |
| *Prevotella* sp. oral clone IDR_CEC_0055 | 1543 | AY550997 | clade_164 | N | N |
| *Prevotella* sp. oral taxon 292 | 1547 | GQ422735 | clade_164 | N | N |
| *Prevotella* sp. oral taxon 300 | 1549 | GU409549 | clade_164 | N | N |
| *Prevotella marshii* | 1505 | AEEI01000070 | clade_166 | N | N |
| *Prevotella* sp. oral clone IK053 | 1544 | AY349401 | clade_166 | N | N |
| *Prevotella* sp. oral taxon 781 | 1554 | GQ422744 | clade_166 | N | N |
| *Prevotella stercorea* | 1562 | AB244774 | clade_166 | N | N |
| *Prevotella brevis* | 1487 | NR_041954 | clade_167 | N | N |
| *Prevotella ruminicola* | 1516 | CP002006 | clade_167 | N | N |
| *Prevotella* sp. sp24 | 1560 | AB003384 | clade_167 | N | N |
| *Prevotella* sp. sp34 | 1561 | AB003385 | clade_167 | N | N |
| *Prevotella albensis* | 1483 | NR_025300 | clade_168 | N | N |
| *Prevotella copri* | 1490 | ACBX02000014 | clade_168 | N | N |
| *Prevotella oulorum* | 1514 | L16472 | clade_168 | N | N |
| *Prevotella* sp. BI_42 | 1518 | AJ581354 | clade_168 | N | N |
| *Prevotella* sp. oral clone P4PB_83 P2 | 1546 | AY207050 | clade_168 | N | N |
| *Prevotella* sp. oral taxon G60 | 1557 | GU432133 | clade_168 | N | N |
| *Prevotella amnii* | 1484 | AB547670 | clade_169 | N | N |
| *Bacteroides caccae* | 268 | EU136686 | clade_170 | N | N |
| *Bacteroides finegoldii* | 277 | AB222699 | clade_170 | N | N |
| *Bacteroides intestinalis* | 283 | ABJL02000006 | clade_171 | N | N |
| *Bacteroides* sp. XB44A | 326 | AM230649 | clade_171 | N | N |
| Bifidobacteriaceae genomosp. C1 | 345 | AY278612 | clade_172 | N | N |
| *Bifidobacterium adolescentis* | 346 | AAXD02000018 | clade_172 | N | N |
| *Bifidobacterium angulatum* | 347 | ABYS02000004 | clade_172 | N | N |
| *Bifidobacterium animalis* | 348 | CP001606 | clade_172 | N | N |
| *Bifidobacterium breve* | 350 | CP002743 | clade_172 | N | N |
| *Bifidobacterium catenulatum* | 351 | ABXY01000019 | clade_172 | N | N |
| *Bifidobacterium dentium* | 352 | CP001750 | clade_172 | N | OP |
| *Bifidobacterium gallicum* | 353 | ABXB03000004 | clade_172 | N | N |
| *Bifidobacterium infantis* | 354 | AY151398 | clade_172 | N | N |
| *Bifidobacterium kashiwanohense* | 355 | AB491757 | clade_172 | N | N |
| *Bifidobacterium longum* | 356 | ABQQ01000041 | clade_172 | N | N |
| *Bifidobacterium pseudocatenulatum* | 357 | ABXX02000002 | clade_172 | N | N |
| *Bifidobacterium pseudolongum* | 358 | NR_043442 | clade_172 | N | N |
| *Bifidobacterium scardovii* | 359 | AJ307005 | clade_172 | N | N |
| *Bifidobacterium* sp. HM2 | 360 | AB425276 | clade_172 | N | N |
| *Bifidobacterium* sp. HMLN12 | 361 | JF519685 | clade_172 | N | N |
| *Bifidobacterium* sp. M45 | 362 | HM626176 | clade_172 | N | N |
| *Bifidobacterium* sp. MSX5B | 363 | HQ616382 | clade_172 | N | N |
| *Bifidobacterium* sp. TM_7 | 364 | AB218972 | clade_172 | N | N |
| *Bifidobacterium thermophilum* | 365 | DQ340557 | clade_172 | N | N |
| *Leuconostoc citreum* | 1178 | AM157444 | clade_175 | N | N |
| *Leuconostoc lactis* | 1182 | NR_040823 | clade_175 | N | N |

TABLE 1-continued

See, e.g., WO 2014/121304

| OTU | SEQ ID Number | Public DB Accession | Clade | Spore Former | Pathogen Status |
|---|---|---|---|---|---|
| *Alicyclobacillus acidoterrestris* | 123 | NR_040844 | clade_179 | N | N |
| *Alicyclobacillus cycloheptanicus* | 125 | NR_024754 | clade_179 | N | N |
| *Acinetobacter baumannii* | 27 | ACYQ01000014 | clade_181 | N | N |
| *Acinetobacter calcoaceticus* | 28 | AM157426 | clade_181 | N | N |
| *Acinetobacter* genomosp. C1 | 29 | AY278636 | clade_181 | N | N |
| *Acinetobacter haemolyticus* | 30 | ADMT01000017 | clade_181 | N | N |
| *Acinetobacter johnsonii* | 31 | ACPL01000162 | clade_181 | N | N |
| *Acinetobacter junii* | 32 | ACPM01000135 | clade_181 | N | N |
| *Acinetobacter lwoffii* | 33 | ACPN01000204 | clade_181 | N | N |
| *Acinetobacter parvus* | 34 | AIEB01000124 | clade_181 | N | N |
| *Acinetobacter schindleri* | 36 | NR_025412 | clade_181 | N | N |
| *Acinetobacter* sp. 56A1 | 37 | GQ178049 | clade_181 | N | N |
| *Acinetobacter* sp. CIP 101934 | 38 | JQ638573 | clade_181 | N | N |
| *Acinetobacter* sp. CIP 102143 | 39 | JQ638578 | clade_181 | N | N |
| *Acinetobacter* sp. M16_22 | 41 | HM366447 | clade_181 | N | N |
| *Acinetobacter* sp. RUH2624 | 42 | ACQF01000094 | clade_181 | N | N |
| *Acinetobacter* sp. SH024 | 43 | ADCH01000068 | clade_181 | N | N |
| *Lactobacillus jensenii* | 1092 | ACQD01000066 | clade_182 | N | N |
| *Alcaligenes faecalis* | 119 | AB680368 | clade_183 | N | N |
| *Alcaligenes* sp. CO14 | 120 | DQ643040 | clade_183 | N | N |
| *Alcaligenes* sp. S3 | 121 | HQ262549 | clade_183 | N | N |
| *Oligella ureolytica* | 1366 | NR_041998 | clade_183 | N | N |
| *Oligella urethralis* | 1367 | NR_041753 | clade_183 | N | N |
| *Eikenella corrodens* | 784 | ACEA01000028 | clade_185 | N | N |
| *Kingella denitrificans* | 1019 | AEWV01000047 | clade_185 | N | N |
| *Kingella* genomosp. P1 oral cone MB2_C20 | 1020 | DQ003616 | clade_185 | N | N |
| *Kingella kingae* | 1021 | AFHS01000073 | clade_185 | N | N |
| *Kingella oralis* | 1022 | ACJW02000005 | clade_185 | N | N |
| *Kingella* sp. oral clone ID059 | 1023 | AY349381 | clade_185 | N | N |
| *Neisseria elongata* | 1330 | ADBF01000003 | clade_185 | N | N |
| *Neisseria* genomosp. P2 oral clone MB5_P15 | 1332 | DQ003630 | clade_185 | N | N |
| *Neisseria* sp. oral clone JC012 | 1345 | AY349388 | clade_185 | N | N |
| *Neisseria* sp. SMC_A9199 | 1342 | FJ763637 | clade_185 | N | N |
| *Simonsiella muelleri* | 1731 | ADCY01000105 | clade_185 | N | N |
| *Corynebacterium glucuronolyticum* | 700 | ABYP01000081 | clade_193 | N | N |
| *Corynebacterium pyruviciproducens* | 716 | FJ185225 | clade_193 | N | N |
| *Rothia aeria* | 1649 | DQ673320 | clade_194 | N | N |
| *Rothia dentocariosa* | 1650 | ADDW01000024 | clade_194 | N | N |
| *Rothia* sp. oral taxon 188 | 1653 | GU470892 | clade_194 | N | N |
| *Corynebacterium accolens* | 681 | ACGD01000048 | clade_195 | N | N |
| *Corynebacterium macginleyi* | 707 | AB359393 | clade_195 | N | N |
| *Corynebacterium pseudogenitalium* | 714 | ABYQ01000237 | clade_195 | N | N |
| *Corynebacterium tuberculostearicum* | 729 | ACVP01000009 | clade_195 | N | N |
| *Lactobacillus casei* | 1074 | CP000423 | clade_198 | N | N |
| *Lactobacillus paracasei* | 1106 | ABQV01000067 | clade_198 | N | N |
| *Lactobacillus zeae* | 1143 | NR_037122 | clade_198 | N | N |
| *Prevotella dentalis* | 1492 | AB547678 | clade_205 | N | N |
| *Prevotella* sp. oral clone ASCG10 | 1529 | AY923148 | clade_206 | N | N |
| *Prevotella* sp. oral clone HF050 | 1541 | AY349399 | clade_206 | N | N |
| *Prevotella* sp. oral clone ID019 | 1542 | AY349400 | clade_206 | N | N |
| *Prevotella* sp. oral clone IK062 | 1545 | AY349402 | clade_206 | N | N |
| *Prevotella* genomosp. P9 oral clone MB7_G16 | 1499 | DQ003633 | clade_207 | N | N |
| *Prevotella* sp. oral clone AU069 | 1531 | AY005062 | clade_207 | N | N |
| *Prevotella* sp. oral clone CY006 | 1532 | AY005063 | clade_207 | N | N |

TABLE 1-continued

See, e.g., WO 2014/121304

| OTU | SEQ ID Number | Public DB Accession | Clade | Spore Former | Pathogen Status |
|---|---|---|---|---|---|
| *Prevotella* sp. oral clone FL019 | 1534 | AY349392 | clade_207 | N | N |
| *Actinomyces* genomosp. C1 | 56 | AY278610 | clade_212 | N | N |
| *Actinomyces* genomosp. C2 | 57 | AY278611 | clade_212 | N | N |
| *Actinomyces* genomosp. P1 oral clone MB6_C03 | 58 | DQ003632 | clade_212 | N | N |
| *Actinomyces georgiae* | 59 | GU561319 | clade_212 | N | N |
| *Actinomyces israelii* | 60 | AF479270 | clade_212 | N | N |
| *Actinomyces massiliensis* | 61 | AB545934 | clade_212 | N | N |
| *Actinomyces meyeri* | 62 | GU561321 | clade_212 | N | N |
| *Actinomyces odontolyticus* | 66 | ACYT01000123 | clade_212 | N | N |
| *Actinomyces orihominis* | 68 | AJ575186 | clade_212 | N | N |
| *Actinomyces* sp. CCUG 37290 | 71 | AJ234058 | clade_212 | N | N |
| *Actinomyces* sp. ICM34 | 75 | HQ616391 | clade_212 | N | N |
| *Actinomyces* sp. ICM41 | 76 | HQ616392 | clade_212 | N | N |
| *Actinomyces* sp. ICM47 | 77 | HQ616395 | clade_212 | N | N |
| *Actinomyces* sp. ICM54 | 78 | HQ616398 | clade_212 | N | N |
| *Actinomyces* sp. oral clone IP081 | 87 | AY349366 | clade_212 | N | N |
| *Actinomyces* sp. oral taxon 178 | 91 | AEUH01000060 | clade_212 | N | N |
| *Actinomyces* sp. oral taxon 180 | 92 | AEPP01000041 | clade_212 | N | N |
| *Actinomyces* sp. TeJ5 | 80 | GU561315 | clade_212 | N | N |
| *Haematobacter* sp. BC14248 | 968 | GU396991 | clade_213 | N | N |
| *Paracoccus denitrificans* | 1424 | CP000490 | clade_213 | N | N |
| *Paracoccus marcusii* | 1425 | NR_044922 | clade_213 | N | N |
| *Grimontia hollisae* | 967 | ADAQ01000013 | clade_216 | N | N |
| *Shewanella putrefaciens* | 1723 | CP002457 | clade_216 | N | N |
| *Afipia* genomosp. 4 | 111 | EU117385 | clade_217 | N | N |
| *Rhodopseudomonas palustris* | 1626 | CP000301 | clade_217 | N | N |
| *Methylobacterium extorquens* | 1223 | NC_010172 | clade_218 | N | N |
| *Methylobacterium podarium* | 1224 | AY468363 | clade_218 | N | N |
| *Methylobacterium radiotolerans* | 1225 | GU294320 | clade_218 | N | N |
| *Methylobacterium* sp. 1sub | 1226 | AY468371 | clade_218 | N | N |
| *Methylobacterium* sp. MM4 | 1227 | AY468370 | clade_218 | N | N |
| *Achromobacter denitrificans* | 18 | NR_042021 | clade_224 | N | N |
| *Achromobacter piechaudii* | 19 | ADMS01000149 | clade_224 | N | N |
| *Achromobacter xylosoxidans* | 20 | ACRC01000072 | clade_224 | N | N |
| *Bordetella bronchiseptica* | 384 | NR_025949 | clade_224 | N | OP |
| *Bordetella holmesii* | 385 | AB683187 | clade_224 | N | OP |
| *Bordetella parapertussis* | 386 | NR_025950 | clade_224 | N | OP |
| *Bordetella pertussis* | 387 | BX640418 | clade_224 | N | OP |
| *Microbacterium chocolatum* | 1230 | NR_037045 | clade_225 | N | N |
| *Microbacterium flavescens* | 1231 | EU714363 | clade_225 | N | N |
| *Microbacterium lacticum* | 1233 | EU714351 | clade_225 | N | N |
| *Microbacterium oleivorans* | 1234 | EU714381 | clade_225 | N | N |
| *Microbacterium oxydans* | 1235 | EU714348 | clade_225 | N | N |
| *Microbacterium paraoxydans* | 1236 | AJ491806 | clade_225 | N | N |
| *Microbacterium phyllosphaerae* | 1237 | EU714359 | clade_225 | N | N |
| *Microbacterium schleiferi* | 1238 | NR_044936 | clade_225 | N | N |
| *Microbacterium* sp. 768 | 1239 | EU714378 | clade_225 | N | N |
| *Microbacterium* sp. oral strain C24KA | 1240 | AF287752 | clade_225 | N | N |
| *Microbacterium testaceum* | 1241 | EU714365 | clade_225 | N | N |
| *Corynebacterium atypicum* | 686 | NR_025540 | clade_229 | N | N |
| *Corynebacterium mastitidis* | 708 | AB359395 | clade_229 | N | N |
| *Corynebacterium* sp. NML 97_0186 | 725 | GU238411 | clade_229 | N | N |
| *Mycobacterium elephantis* | 1275 | AF385898 | clade_237 | N | OP |
| *Mycobacterium paraterrae* | 1288 | EU919229 | clade_237 | N | OP |
| *Mycobacterium phlei* | 1289 | GU142920 | clade_237 | N | OP |
| *Mycobacterium* sp. 1776 | 1293 | EU703152 | clade_237 | N | N |
| *Mycobacterium* sp. 1781 | 1294 | EU703147 | clade_237 | N | N |
| *Mycobacterium* sp. AQ1GA4 | 1297 | HM210417 | clade_237 | N | N |
| *Mycobacterium* sp. GN_10546 | 1299 | FJ497243 | clade_237 | N | N |

TABLE 1-continued

See, e.g., WO 2014/121304

| OTU | SEQ ID Number | Public DB Accession | Clade | Spore Former | Pathogen Status |
|---|---|---|---|---|---|
| Mycobacterium sp. GN_10827 | 1300 | FJ497247 | clade_237 | N | N |
| Mycobacterium sp. GN_11124 | 1301 | FJ652846 | clade_237 | N | N |
| Mycobacterium sp. GN_9188 | 1302 | FJ497240 | clade_237 | N | N |
| Mycobacterium sp. GR_2007_210 | 1303 | FJ555538 | clade_237 | N | N |
| Anoxybacillus contaminans | 172 | NR_029006 | clade_238 | N | N |
| Bacillus aeolius | 195 | NR_025557 | clade_238 | N | N |
| Brevibacterium frigoritolerans | 422 | NR_042639 | clade_238 | N | N |
| Geobacillus sp. E263 | 934 | DQ647387 | clade_238 | N | N |
| Geobacillus sp. WCH70 | 935 | CP001638 | clade_238 | N | N |
| Geobacillus thermocatenulatus | 937 | NR_043020 | clade_238 | N | N |
| Geobacillus thermoleovorans | 940 | NR_074931 | clade_238 | N | N |
| Lysinibacillus fusiformis | 1192 | FN397522 | clade_238 | N | N |
| Planomicrobium koreense | 1468 | NR_025011 | clade_238 | N | N |
| Sporosarcina newyorkensis | 1754 | AFPZ01000142 | clade_238 | N | N |
| Sporosarcina sp. 2681 | 1755 | GU994081 | clade_238 | N | N |
| Ureibacillus composti | 1968 | NR_043746 | clade_238 | N | N |
| Ureibacillus suwonensis | 1969 | NR_043232 | clade_238 | N | N |
| Ureibacillus terrenus | 1970 | NR_025394 | clade_238 | N | N |
| Ureibacillus thermophilus | 1971 | NR_043747 | clade_238 | N | N |
| Ureibacillus thermosphaericus | 1972 | NR_040961 | clade_238 | N | N |
| Prevotella micans | 1507 | AGWK01000061 | clade_239 | N | N |
| Prevotella sp. oral clone DA058 | 1533 | AY005065 | clade_239 | N | N |
| Prevotella sp. SEQ053 | 1523 | JN867222 | clade_239 | N | N |
| Treponema socranskii | 1937 | NR_024868 | clade_240 | N | OP |
| Treponema sp. 6:H:D15A_4 | 1938 | AY005083 | clade_240 | N | N |
| Treponema sp. oral taxon 265 | 1953 | GU408850 | clade_240 | N | N |
| Treponema sp. oral taxon G85 | 1958 | GU432215 | clade_240 | N | N |
| Porphyromonas endodontalis | 1472 | ACNN01000021 | clade_241 | N | N |
| Porphyromonas sp. oral clone BB134 | 1478 | AY005068 | clade_241 | N | N |
| Porphyromonas sp. oral clone F016 | 1479 | AY005069 | clade_241 | N | N |
| Porphyromonas sp. oral clone P2PB_52 P1 | 1480 | AY207054 | clade_241 | N | N |
| Porphyromonas sp. oral clone P4GB_100 P2 | 1481 | AY207057 | clade_241 | N | N |
| Acidovorax sp. 98_63833 | 26 | AY258065 | clade_245 | N | N |
| Comamonadaceae bacterium NML000135 | 663 | JN585335 | clade_245 | N | N |
| Comamonadaceae bacterium NML790751 | 664 | JN585331 | clade_245 | N | N |
| Comamonadaceae bacterium NML910035 | 665 | JN585332 | clade_245 | N | N |
| Comamonadaceae bacterium NML910036 | 666 | JN585333 | clade_245 | N | N |
| Comamonas sp. NSP5 | 668 | AB076850 | clade_245 | N | N |
| Delftia acidovorans | 748 | CP000884 | clade_245 | N | N |
| Xenophilus aerolatus | 2018 | JN585329 | clade_245 | N | N |
| Oribacterium sp. oral taxon 078 | 1380 | ACIQ02000009 | clade_246 | N | N |
| Oribacterium sp. oral taxon 102 | 1381 | GQ422713 | clade_246 | N | N |
| Weissella cibaria | 2007 | NR_036924 | clade_247 | N | N |
| Weissella confusa | 2008 | NR_040816 | clade_247 | N | N |
| Weissella hellenica | 2009 | AB680902 | clade_247 | N | N |
| Weissella kandleri | 2010 | NR_044659 | clade_247 | N | N |
| Weissella koreensis | 2011 | NR_075058 | clade_247 | N | N |
| Weissella paramesenteroides | 2012 | ACKU01000017 | clade_247 | N | N |
| Weissella sp. KLDS 7.0701 | 2013 | EU600924 | clade_247 | N | N |
| Mobiluncus curtisii | 1251 | AEPZ01000013 | clade_249 | N | N |
| Enhydrobacter aerosaccus | 785 | ACYI01000081 | clade_256 | N | N |
| Moraxella osloensis | 1262 | JN175341 | clade_256 | N | N |

TABLE 1-continued

See, e.g., WO 2014/121304

| OTU | SEQ ID Number | Public DB Accession | Clade | Spore Former | Pathogen Status |
|---|---|---|---|---|---|
| *Moraxella* sp. GM2 | 1264 | JF837191 | clade_256 | N | N |
| *Brevibacterium casei* | 420 | JF951998 | clade_257 | N | N |
| *Brevibacterium epidermidis* | 421 | NR_029262 | clade_257 | N | N |
| *Brevibacterium sanguinis* | 426 | NR_028016 | clade_257 | N | N |
| *Brevibacterium* sp. H15 | 427 | AB177640 | clade_257 | N | N |
| *Acinetobacter radioresistens* | 35 | ACVR01000010 | clade_261 | N | N |
| *Lactobacillus alimentarius* | 1068 | NR_044701 | clade_263 | N | N |
| *Lactobacillus farciminis* | 1082 | NR_044707 | clade_263 | N | N |
| *Lactobacillus kimchii* | 1097 | NR_025045 | clade_263 | N | N |
| *Lactobacillus nodensis* | 1101 | NR_041629 | clade_263 | N | N |
| *Lactobacillus tucceti* | 1138 | NR_042194 | clade_263 | N | N |
| *Pseudomonas mendocina* | 1595 | AAUL01000021 | clade_265 | N | N |
| *Pseudomonas pseudoalcaligenes* | 1598 | NR_037000 | clade_265 | N | N |
| *Pseudomonas* sp. NP522b | 1602 | EU723211 | clade_265 | N | N |
| *Pseudomonas stutzeri* | 1603 | AM905854 | clade_265 | N | N |
| *Paenibacillus barcinonensis* | 1390 | NR_042272 | clade_270 | N | N |
| *Paenibacillus barengoltzii* | 1391 | NR_042756 | clade_270 | N | N |
| *Paenibacillus chibensis* | 1392 | NR_040885 | clade_270 | N | N |
| *Paenibacillus cookii* | 1393 | NR_025372 | clade_270 | N | N |
| *Paenibacillus durus* | 1394 | NR_037017 | clade_270 | N | N |
| *Paenibacillus glucanolyticus* | 1395 | D78470 | clade_270 | N | N |
| *Paenibacillus lactis* | 1396 | NR_025739 | clade_270 | N | N |
| *Paenibacillus pabuli* | 1398 | NR_040853 | clade_270 | N | N |
| *Paenibacillus popilliae* | 1400 | NR_040888 | clade_270 | N | N |
| *Paenibacillus* sp. CIP 101062 | 1401 | HM212646 | clade_270 | N | N |
| *Paenibacillus* sp. JC66 | 1404 | JF824808 | clade_270 | N | N |
| *Paenibacillus* sp. R_27413 | 1405 | HE586333 | clade_270 | N | N |
| *Paenibacillus* sp. R_27422 | 1406 | HE586338 | clade_270 | N | N |
| *Paenibacillus timonensis* | 1408 | NR_042844 | clade_270 | N | N |
| *Rothia mucilaginosa* | 1651 | ACVO01000020 | clade_271 | N | N |
| *Rothia nasimurium* | 1652 | NR_025310 | clade_271 | N | N |
| *Prevotella* sp. oral taxon 302 | 1550 | ACZK01000043 | clade_280 | N | N |
| *Prevotella* sp. oral taxon F68 | 1556 | HM099652 | clade_280 | N | N |
| *Prevotella tannerae* | 1563 | ACIJ02000018 | clade_280 | N | N |
| Prevotellaceae bacterium P4P_62 P1 | 1566 | AY207061 | clade_280 | N | N |
| *Porphyromonas asaccharolytica* | 1471 | AENO01000048 | clade_281 | N | N |
| *Porphyromonas gingivalis* | 1473 | AE015924 | clade_281 | N | N |
| *Porphyromonas macacae* | 1475 | NR_025908 | clade_281 | N | N |
| *Porphyromonas* sp. UQD 301 | 1477 | EU012301 | clade_281 | N | N |
| *Porphyromonas uenonis* | 1482 | ACLR01000152 | clade_281 | N | N |
| *Leptotrichia buccalis* | 1165 | CP001685 | clade_282 | N | N |
| *Leptotrichia hofstadii* | 1168 | ACVB02000032 | clade_282 | N | N |
| *Leptotrichia* sp. oral clone HE012 | 1173 | AY349386 | clade_282 | N | N |
| *Leptotrichia* sp. oral taxon 223 | 1176 | GU408547 | clade_282 | N | N |
| *Bacteroides fluxus* | 278 | AFBN01000029 | clade_285 | N | N |
| *Bacteroides helcogenes* | 281 | CP002352 | clade_285 | N | N |
| *Parabacteroides johnsonii* | 1419 | ABYH01000014 | clade_286 | N | N |
| *Parabacteroides merdae* | 1420 | EU136685 | clade_286 | N | N |
| *Treponema denticola* | 1926 | ADEC01000002 | clade_288 | N | OP |
| *Treponema genomosp.* P5 oral clone MB3_P23 | 1929 | DQ003624 | clade_288 | N | N |
| *Treponema putidum* | 1935 | AJ543428 | clade_288 | N | OP |
| *Treponema* sp. oral clone P2PB_53 P3 | 1942 | AY207055 | clade_288 | N | N |
| *Treponema* sp. oral taxon 247 | 1949 | GU408748 | clade_288 | N | N |
| *Treponema* sp. oral taxon 250 | 1950 | GU408776 | clade_288 | N | N |
| *Treponema* sp. oral taxon 251 | 1951 | GU408781 | clade_288 | N | N |
| *Anaerococcus hydrogenalis* | 144 | ABXA01000039 | clade_289 | N | N |
| *Anaerococcus* sp. 8404299 | 148 | HM587318 | clade_289 | N | N |
| *Anaerococcus* sp. gpac215 | 156 | AM176540 | clade_289 | N | N |
| *Anaerococcus vaginalis* | 158 | ACXU01000016 | clade_289 | N | N |
| *Propionibacterium acidipropionici* | 1569 | NC_019395 | clade_290 | N | N |
| *Propionibacterium avidum* | 1571 | AJ003055 | clade_290 | N | N |
| *Propionibacterium* | 1573 | FJ785716 | clade_290 | N | N |

TABLE 1-continued

See, e.g., WO 2014/121304

| OTU | SEQ ID Number | Public DB Accession | Clade | Spore Former | Pathogen Status |
|---|---|---|---|---|---|
| granulosum | | | | | |
| Propionibacterium jensenii | 1574 | NR_042269 | clade_290 | N | N |
| Propionibacterium propionicum | 1575 | NR_025277 | clade_290 | N | N |
| Propionibacterium sp. H456 | 1577 | AB177643 | clade_290 | N | N |
| Propionibacterium thoenii | 1581 | NR_042270 | clade_290 | N | N |
| Bifidobacterium bifidum | 349 | ABQP01000027 | clade_293 | N | N |
| Leuconostoc mesenteroides | 1183 | ACKV01000113 | clade_295 | N | N |
| Leuconostoc pseudomesenteroides | 1184 | NR_040814 | clade_295 | N | N |
| Johnsonella ignava | 1016 | X87152 | clade_298 | N | N |
| Propionibacterium acnes | 1570 | ADJM01000010 | clade_299 | N | N |
| Propionibacterium sp. 434_HC2 | 1576 | AFIL01000035 | clade_299 | N | N |
| Propionibacterium sp. LG | 1578 | AY354921 | clade_299 | N | N |
| Propionibacterium sp. S555a | 1579 | AB264622 | clade_299 | N | N |
| Alicyclobacillus sp. CCUG 53762 | 128 | HE613268 | clade_301 | N | N |
| Actinomyces cardiffensis | 53 | GU470888 | clade_303 | N | N |
| Actinomyces funkei | 55 | HQ906497 | clade_303 | N | N |
| Actinomyces sp. HKU31 | 74 | HQ335393 | clade_303 | N | N |
| Actinomyces sp. oral taxon C55 | 94 | HM099646 | clade_303 | N | N |
| Kerstersia gyiorum | 1018 | NR_025669 | clade_307 | N | N |
| Pigmentiphaga daeguensis | 1467 | JN585327 | clade_307 | N | N |
| Aeromonas allosaccharophila | 104 | S39232 | clade_308 | N | N |
| Aeromonas enteropelogenes | 105 | X71121 | clade_308 | N | N |
| Aeromonas hydrophila | 106 | NC_008570 | clade_308 | N | N |
| Aeromonas jandaei | 107 | X60413 | clade_308 | N | N |
| Aeromonas salmonicida | 108 | NC_009348 | clade_308 | N | N |
| Aeromonas trota | 109 | X60415 | clade_308 | N | N |
| Aeromonas veronii | 110 | NR_044845 | clade_308 | N | N |
| Marvinbryantia formatexigens | 1196 | AJ505973 | clade_309 | N | N |
| Rhodobacter sp. oral taxon C30 | 1620 | HM099648 | clade_310 | N | N |
| Rhodobacter sphaeroides | 1621 | CP000144 | clade_310 | N | N |
| Lactobacillus antri | 1071 | ACLL01000037 | clade_313 | N | N |
| Lactobacillus coleohominis | 1076 | ACOH01000030 | clade_313 | N | N |
| Lactobacillus fermentum | 1083 | CP002033 | clade_313 | N | N |
| Lactobacillus gastricus | 1085 | AICN01000060 | clade_313 | N | N |
| Lactobacillus mucosae | 1099 | FR693800 | clade_313 | N | N |
| Lactobacillus oris | 1103 | AEKL01000077 | clade_313 | N | N |
| Lactobacillus pontis | 1111 | HM218420 | clade_313 | N | N |
| Lactobacillus reuteri | 1112 | ACGW02000012 | clade_313 | N | N |
| Lactobacillus sp. KLDS 1.0707 | 1127 | EU600911 | clade_313 | N | N |
| Lactobacillus sp. KLDS 1.0709 | 1128 | EU600913 | clade_313 | N | N |
| Lactobacillus sp. KLDS 1.0711 | 1129 | EU600915 | clade_313 | N | N |
| Lactobacillus sp. KLDS 1.0713 | 1131 | EU600917 | clade_313 | N | N |
| Lactobacillus sp. KLDS 1.0716 | 1132 | EU600921 | clade_313 | N | N |
| Lactobacillus sp. KLDS 1.0718 | 1133 | EU600922 | clade_313 | N | N |
| Lactobacillus sp. oral taxon 052 | 1137 | GQ422710 | clade_313 | N | N |
| Lactobacillus vaginalis | 1140 | ACGV01000168 | clade_313 | N | N |
| Brevibacterium aurantiacum | 419 | NR_044854 | clade_314 | N | N |
| Brevibacterium linens | 423 | AJ315491 | clade_314 | N | N |
| Lactobacillus pentosus | 1108 | JN813103 | clade_315 | N | N |
| Lactobacillus plantarum | 1110 | ACGZ02000033 | clade_315 | N | N |
| Lactobacillus sp. KLDS 1.0702 | 1123 | EU600906 | clade_315 | N | N |
| Lactobacillus sp. KLDS 1.0703 | 1124 | EU600907 | clade_315 | N | N |
| Lactobacillus sp. KLDS 1.0704 | 1125 | EU600908 | clade_315 | N | N |
| Lactobacillus sp. KLDS 1.0705 | 1126 | EU600909 | clade_315 | N | N |
| Agrobacterium radiobacter | 115 | CP000628 | clade_316 | N | N |

TABLE 1-continued

See, e.g., WO 2014/121304

| OTU | SEQ ID Number | Public DB Accession | Clade | Spore Former | Pathogen Status |
|---|---|---|---|---|---|
| *Agrobacterium tumefaciens* | 116 | AJ389893 | clade_316 | N | N |
| *Corynebacterium argentoratense* | 685 | EF463055 | clade_317 | N | N |
| *Corynebacterium diphtheriae* | 693 | NC_002935 | clade_317 | N | OP |
| *Corynebacterium pseudotuberculosis* | 715 | NR_037070 | clade_317 | N | N |
| *Corynebacterium renale* | 717 | NR_037069 | clade_317 | N | N |
| *Corynebacterium ulcerans* | 731 | NR_074467 | clade_317 | N | N |
| *Aurantimonas coralicida* | 191 | AY065627 | clade_318 | N | N |
| *Aureimonas altamirensis* | 192 | FN658986 | clade_318 | N | N |
| *Lactobacillus acidipiscis* | 1066 | NR_024718 | clade_320 | N | N |
| *Lactobacillus salivarius* | 1117 | AEBA01000145 | clade_320 | N | N |
| *Lactobacillus* sp. KLDS 1.0719 | 1134 | EU600923 | clade_320 | N | N |
| *Lactobacillus buchneri* | 1073 | ACGH01000101 | clade_321 | N | N |
| *Lactobacillus* genomosp. C1 | 1086 | AY278619 | clade_321 | N | N |
| *Lactobacillus* genomosp. C2 | 1087 | AY278620 | clade_321 | N | N |
| *Lactobacillus hilgardii* | 1089 | ACGP01000200 | clade_321 | N | N |
| *Lactobacillus kefiri* | 1096 | NR_042230 | clade_321 | N | N |
| *Lactobacillus parabuchneri* | 1105 | NR_041294 | clade_321 | N | N |
| *Lactobacillus parakefiri* | 1107 | NR_029039 | clade_321 | N | N |
| *Lactobacillus curvatus* | 1079 | NR_042437 | clade_322 | N | N |
| *Lactobacillus sakei* | 1116 | DQ989236 | clade_322 | N | N |
| *Aneurinibacillus aneurinilyticus* | 167 | AB101592 | clade_323 | N | N |
| *Aneurinibacillus danicus* | 168 | NR_028657 | clade_323 | N | N |
| *Aneurinibacillus migulanus* | 169 | NR_036799 | clade_323 | N | N |
| *Aneurinibacillus terranovensis* | 170 | NR_042271 | clade_323 | N | N |
| *Staphylococcus aureus* | 1757 | CP002643 | clade_325 | N | Category-B |
| *Staphylococcus auricularis* | 1758 | JQ624774 | clade_325 | N | N |
| *Staphylococcus capitis* | 1759 | ACFR01000029 | clade_325 | N | N |
| *Staphylococcus caprae* | 1760 | ACRH01000033 | clade_325 | N | N |
| *Staphylococcus carnosus* | 1761 | NR_075003 | clade_325 | N | N |
| *Staphylococcus cohnii* | 1762 | JN175375 | clade_325 | N | N |
| *Staphylococcus condimenti* | 1763 | NR_029345 | clade_325 | N | N |
| *Staphylococcus epidermidis* | 1764 | ACHE01000056 | clade_325 | N | N |
| *Staphylococcus equorum* | 1765 | NR_027520 | clade_325 | N | N |
| *Staphylococcus haemolyticus* | 1767 | NC_007168 | clade_325 | N | N |
| *Staphylococcus hominis* | 1768 | AM157418 | clade_325 | N | N |
| *Staphylococcus lugdunensis* | 1769 | AEQA01000024 | clade_325 | N | N |
| *Staphylococcus pasteuri* | 1770 | FJ189773 | clade_325 | N | N |
| *Staphylococcus pseudintermedius* | 1771 | CP002439 | clade_325 | N | N |
| *Staphylococcus saccharolyticus* | 1772 | NR_029158 | clade_325 | N | N |
| *Staphylococcus saprophyticus* | 1773 | NC_007350 | clade_325 | N | N |
| *Staphylococcus* sp. clone bottae7 | 1777 | AF467424 | clade_325 | N | N |
| *Staphylococcus* sp. H292 | 1775 | AB177642 | clade_325 | N | N |
| *Staphylococcus* sp. H780 | 1776 | AB177644 | clade_325 | N | N |
| *Staphylococcus succinus* | 1778 | NR_028667 | clade_325 | N | N |
| *Staphylococcus warneri* | 1780 | ACPZ01000009 | clade_325 | N | N |
| *Staphylococcus xylosus* | 1781 | AY395016 | clade_325 | N | N |
| *Cardiobacterium hominis* | 490 | ACKY01000036 | clade_326 | N | N |
| *Cardiobacterium valvarum* | 491 | NR_028847 | clade_326 | N | N |
| *Pseudomonas fluorescens* | 1593 | AY622220 | clade_326 | N | N |
| *Pseudomonas gessardii* | 1594 | FJ943496 | clade_326 | N | N |
| *Pseudomonas monteilii* | 1596 | NR_024910 | clade_326 | N | N |
| *Pseudomonas poae* | 1597 | GU188951 | clade_326 | N | N |
| *Pseudomonas putida* | 1599 | AF094741 | clade_326 | N | N |
| *Pseudomonas* sp. G1229 | 1601 | DQ910482 | clade_326 | N | N |
| *Pseudomonas tolaasii* | 1604 | AF320988 | clade_326 | N | N |
| *Pseudomonas viridiflava* | 1605 | NR_042764 | clade_326 | N | N |
| *Listeria grayi* | 1185 | ACCR02000003 | clade_328 | N | OP |
| *Listeria innocua* | 1186 | JF967625 | clade_328 | N | N |
| *Listeria ivanovii* | 1187 | X56151 | clade_328 | N | N |
| *Listeria monocytogenes* | 1188 | CP002003 | clade_328 | N | Category-B |
| *Listeria welshimeri* | 1189 | AM263198 | clade_328 | N | OP |
| *Capnocytophaga* sp. oral clone ASCH05 | 484 | AY923149 | clade_333 | N | N |
| *Capnocytophaga sputigena* | 489 | ABZV01000054 | clade_333 | N | N |

TABLE 1-continued

See, e.g., WO 2014/121304

| OTU | SEQ ID Number | Public DB Accession | Clade | Spore Former | Pathogen Status |
|---|---|---|---|---|---|
| *Leptotrichia* genomosp. C1 | 1166 | AY278621 | clade_334 | N | N |
| *Leptotrichia shahii* | 1169 | AY029806 | clade_334 | N | N |
| *Leptotrichia* sp. neutropenic Patient | 1170 | AF189244 | clade_334 | N | N |
| *Leptotrichia* sp. oral clone GT018 | 1171 | AY349384 | clade_334 | N | N |
| *Leptotrichia* sp. oral clone GT020 | 1172 | AY349385 | clade_334 | N | N |
| *Bacteroides* sp. 20_3 | 296 | ACRQ01000064 | clade_335 | N | N |
| *Bacteroides* sp. 3_1_19 | 307 | ADCJ01000062 | clade_335 | N | N |
| *Bacteroides* sp. 3_2_5 | 311 | ACIB01000079 | clade_335 | N | N |
| *Parabacteroides distasonis* | 1416 | CP000140 | clade_335 | N | N |
| *Parabacteroides goldsteinii* | 1417 | AY974070 | clade_335 | N | N |
| *Parabacteroides gordonii* | 1418 | AB470344 | clade_335 | N | N |
| *Parabacteroides* sp. D13 | 1421 | ACPW01000017 | clade_335 | N | N |
| *Capnocytophaga* genomosp. C1 | 477 | AY278613 | clade_336 | N | N |
| *Capnocytophaga ochracea* | 480 | AEOH01000054 | clade_336 | N | N |
| *Capnocytophaga* sp. GEJ8 | 481 | GU561335 | clade_336 | N | N |
| *Capnocytophaga* sp. oral strain A47ROY | 486 | AY005077 | clade_336 | N | N |
| *Capnocytophaga* sp. S1b | 482 | U42009 | clade_336 | N | N |
| *Paraprevotella clara* | 1426 | AFFY01000068 | clade_336 | N | N |
| *Bacteroides heparinolyticus* | 282 | JN867284 | clade_338 | N | N |
| *Prevotella heparinolytica* | 1500 | GQ422742 | clade_338 | N | N |
| *Treponema* genomosp. P4 oral clone MB2_G19 | 1928 | DQ003618 | clade_339 | N | N |
| *Treponema* genomosp. P6 oral clone MB4_G11 | 1930 | DQ003625 | clade_339 | N | N |
| *Treponema* sp. oral taxon 254 | 1952 | GU408803 | clade_339 | N | N |
| *Treponema* sp. oral taxon 508 | 1956 | GU413616 | clade_339 | N | N |
| *Treponema* sp. oral taxon 518 | 1957 | GU413640 | clade_339 | N | N |
| *Chlamydia muridarum* | 502 | AE002160 | clade_341 | N | OP |
| *Chlamydia trachomatis* | 504 | U68443 | clade_341 | N | OP |
| *Chlamydia psittaci* | 503 | NR_036864 | clade_342 | N | Category-B |
| *Chlamydophila pneumoniae* | 509 | NC_002179 | clade_342 | N | OP |
| *Chlamydophila psittaci* | 510 | D85712 | clade_342 | N | OP |
| *Anaerococcus octavius* | 146 | NR_026360 | clade_343 | N | N |
| *Anaerococcus* sp. 8405254 | 149 | HM587319 | clade_343 | N | N |
| *Anaerococcus* sp. 9401487 | 150 | HM587322 | clade_343 | N | N |
| *Anaerococcus* sp. 9403502 | 151 | HM587325 | clade_343 | N | N |
| *Gardnerella vaginalis* | 923 | CP001849 | clade_344 | N | N |
| *Campylobacter lari* | 466 | CP000932 | clade_346 | N | OP |
| *Anaerobiospirillum succiniciproducens* | 142 | NR_026075 | clade_347 | N | N |
| *Anaerobiospirillum thomasii* | 143 | AJ420985 | clade_347 | N | N |
| *Ruminobacter amylophilus* | 1654 | NR_026450 | clade_347 | N | N |
| *Succinatimonas hippei* | 1897 | AEVO01000027 | clade_347 | N | N |
| *Actinomyces europaeus* | 54 | NR_026363 | clade_348 | N | N |
| *Actinomyces* sp. oral clone GU009 | 82 | AY349361 | clade_348 | N | N |
| *Moraxella catarrhalis* | 1260 | CP002005 | clade_349 | N | N |
| *Moraxella lincolnii* | 1261 | FR822735 | clade_349 | N | N |
| *Moraxella* sp. 16285 | 1263 | JF682466 | clade_349 | N | N |
| *Psychrobacter* sp. 13983 | 1613 | HM212668 | clade_349 | N | N |
| *Actinobaculum massiliae* | 49 | AF487679 | clade_350 | N | N |
| *Actinobaculum schaalii* | 50 | AY957507 | clade_350 | N | N |
| *Actinobaculum* sp. BM#101342 | 51 | AY282578 | clade_350 | N | N |
| *Actinobaculum* sp. P2P_19 P1 | 52 | AY207066 | clade_350 | N | N |
| *Actinomyces* sp. oral clone IO076 | 84 | AY349363 | clade_350 | N | N |
| *Actinomyces* sp. oral taxon 848 | 93 | ACUY01000072 | clade_350 | N | N |
| *Actinomyces neuii* | 65 | X71862 | clade_352 | N | N |
| *Mobiluncus mulieris* | 1252 | ACKW01000035 | clade_352 | N | N |
| *Blastomonas natatoria* | 372 | NR_040824 | clade_356 | N | N |
| *Novosphingobium aromaticivorans* | 1357 | AAAV03000008 | clade_356 | N | N |
| *Sphingomonas* sp. oral clone FI012 | 1745 | AY349411 | clade_356 | N | N |

TABLE 1-continued

See, e.g., WO 2014/121304

| OTU | SEQ ID Number | Public DB Accession | Clade | Spore Former | Pathogen Status |
|---|---|---|---|---|---|
| *Sphingopyxis alaskensis* | 1749 | CP000356 | clade_356 | N | N |
| *Oxalobacter formigenes* | 1389 | ACDQ01000020 | clade_357 | N | N |
| *Veillonella atypica* | 1974 | AEDS01000059 | clade_358 | N | N |
| *Veillonella dispar* | 1975 | ACIK02000021 | clade_358 | N | N |
| *Veillonella* genomosp. P1 oral clone MB5_P17 | 1976 | DQ003631 | clade_358 | N | N |
| *Veillonella parvula* | 1978 | ADFU01000009 | clade_358 | N | N |
| *Veillonella* sp. 3_1_44 | 1979 | ADCV01000019 | clade_358 | N | N |
| *Veillonella* sp. 6_1_27 | 1980 | ADCW01000016 | clade_358 | N | N |
| *Veillonella* sp. ACP1 | 1981 | HQ616359 | clade_358 | N | N |
| *Veillonella* sp. AS16 | 1982 | HQ616365 | clade_358 | N | N |
| *Veillonella* sp. BS32b | 1983 | HQ616368 | clade_358 | N | N |
| *Veillonella* sp. ICM51a | 1984 | HQ616396 | clade_358 | N | N |
| *Veillonella* sp. MSA12 | 1985 | HQ616381 | clade_358 | N | N |
| *Veillonella* sp. NVG 100cf | 1986 | EF108443 | clade_358 | N | N |
| *Veillonella* sp. OK11 | 1987 | JN695650 | clade_358 | N | N |
| *Veillonella* sp. oral clone ASCG01 | 1990 | AY923144 | clade_358 | N | N |
| *Veillonella* sp. oral clone ASCG02 | 1991 | AY953257 | clade_358 | N | N |
| *Veillonella* sp. oral clone OH1A | 1992 | AY947495 | clade_358 | N | N |
| *Veillonella* sp. oral taxon 158 | 1993 | AENU01000007 | clade_358 | N | N |
| *Kocuria marina* | 1040 | GQ260086 | clade_365 | N | N |
| *Kocuria rhizophila* | 1042 | AY030315 | clade_365 | N | N |
| *Kocuria rosea* | 1043 | X87756 | clade_365 | N | N |
| *Kocuria varians* | 1044 | AF542074 | clade_365 | N | N |
| *Clostridiaceae bacterium* END_2 | 531 | EF451053 | clade_368 | N | N |
| *Micrococcus antarcticus* | 1242 | NR_025285 | clade_371 | N | N |
| *Micrococcus luteus* | 1243 | NR_075062 | clade_371 | N | N |
| *Micrococcus lylae* | 1244 | NR_026200 | clade_371 | N | N |
| *Micrococcus* sp. 185 | 1245 | EU714334 | clade_371 | N | N |
| *Lactobacillus brevis* | 1072 | EU194349 | clade_372 | N | N |
| *Lactobacillus parabrevis* | 1104 | NR_042456 | clade_372 | N | N |
| *Pediococcus acidilactici* | 1436 | ACXB01000026 | clade_372 | N | N |
| *Pediococcus pentosaceus* | 1437 | NR_075052 | clade_372 | N | N |
| *Lactobacillus dextrinicus* | 1081 | NR_036861 | clade_373 | N | N |
| *Lactobacillus perolens* | 1109 | NR_029360 | clade_373 | N | N |
| *Lactobacillus rhamnosus* | 1113 | ABWJ01000068 | clade_373 | N | N |
| *Lactobacillus saniviri* | 1118 | AB602569 | clade_373 | N | N |
| *Lactobacillus* sp. BT6 | 1121 | HQ616370 | clade_373 | N | N |
| *Mycobacterium mageritense* | 1282 | FR798914 | clade_374 | N | OP |
| *Mycobacterium neoaurum* | 1286 | AF268445 | clade_374 | N | OP |
| *Mycobacterium smegmatis* | 1291 | CP000480 | clade_374 | N | OP |
| *Mycobacterium* sp. HE5 | 1304 | AJ012738 | clade_374 | N | N |
| *Dysgonomonas gadei* | 775 | ADLV01000001 | clade_377 | N | N |
| *Dysgonomonas mossii* | 776 | ADLW01000023 | clade_377 | N | N |
| *Porphyromonas levii* | 1474 | NR_025907 | clade_377 | N | N |
| *Porphyromonas somerae* | 1476 | AB547667 | clade_377 | N | N |
| *Bacteroides barnesiae* | 267 | NR_041446 | clade_378 | N | N |
| *Bacteroides coprocola* | 272 | ABIY02000050 | clade_378 | N | N |
| *Bacteroides coprophilus* | 273 | ACBW01000012 | clade_378 | N | N |
| *Bacteroides dorei* | 274 | ABWZ01000093 | clade_378 | N | N |
| *Bacteroides massiliensis* | 284 | AB200226 | clade_378 | N | N |
| *Bacteroides plebeius* | 289 | AB200218 | clade_378 | N | N |
| *Bacteroides* sp. 3_1_33FAA | 309 | ACPS01000085 | clade_378 | N | N |
| *Bacteroides* sp. 3_1_40A | 310 | ACRT01000136 | clade_378 | N | N |
| *Bacteroides* sp. 4_3_47FAA | 313 | ACDR02000029 | clade_378 | N | N |
| *Bacteroides* sp. 9_1_42FAA | 314 | ACAA01000096 | clade_378 | N | N |
| *Bacteroides* sp. NB_8 | 323 | AB117565 | clade_378 | N | N |
| *Bacteroides vulgatus* | 331 | CP000139 | clade_378 | N | N |
| *Bacteroides ovatus* | 287 | ACWH01000036 | clade_38 | N | N |
| *Bacteroides* sp. 1_1_30 | 294 | ADCL01000128 | clade_38 | N | N |
| *Bacteroides* sp. 2_1_22 | 297 | ACPQ01000117 | clade_38 | N | N |
| *Bacteroides* sp. 2_2_4 | 299 | ABZZ01000168 | clade_38 | N | N |
| *Bacteroides* sp. 3_1_23 | 308 | ACRS01000081 | clade_38 | N | N |
| *Bacteroides* sp. D1 | 318 | ACAB02000030 | clade_38 | N | N |
| *Bacteroides* sp. D2 | 321 | ACGA01000077 | clade_38 | N | N |
| *Bacteroides* sp. D22 | 320 | ADCK01000151 | clade_38 | N | N |
| *Bacteroides xylanisolvens* | 332 | ADKP01000087 | clade_38 | N | N |
| *Treponema lecithinolyticum* | 1931 | NR_026247 | clade_380 | N | OP |
| *Treponema parvum* | 1933 | AF302937 | clade_380 | N | OP |
| *Treponema* sp. oral clone | 1940 | AY349417 | clade_380 | N | N |

TABLE 1-continued

See, e.g., WO 2014/121304

| OTU | SEQ ID Number | Public DB Accession | Clade | Spore Former | Pathogen Status |
|---|---|---|---|---|---|
| JU025 | | | | | |
| *Treponema* sp. oral taxon 270 | 1954 | GQ422733 | clade_380 | N | N |
| *Parascardovia denticolens* | 1428 | ADEB01000020 | clade_381 | N | N |
| *Scardovia inopinata* | 1688 | AB029087 | clade_381 | N | N |
| *Scardovia wiggsiae* | 1689 | AY278626 | clade_381 | N | N |
| Clostridiales bacterium 9400853 | 533 | HM587320 | clade_384 | N | N |
| *Mogibacterium diversum* | 1254 | NR_027191 | clade_384 | N | N |
| *Mogibacterium neglectum* | 1255 | NR_027203 | clade_384 | N | N |
| *Mogibacterium pumilum* | 1256 | NR_028608 | clade_384 | N | N |
| *Mogibacterium timidum* | 1257 | Z36296 | clade_384 | N | N |
| *Borrelia burgdorferi* | 389 | ABGI01000001 | clade_386 | N | OP |
| *Borrelia garinii* | 392 | ABJV01000001 | clade_386 | N | OP |
| *Borrelia* sp. NE49 | 397 | AJ224142 | clade_386 | N | OP |
| *Caldimonas manganoxidans* | 457 | NR_040787 | clade_387 | N | N |
| Comamonadaceae bacterium oral taxon F47 | 667 | HM099651 | clade_387 | N | N |
| *Lautropia mirabilis* | 1149 | AEQP01000026 | clade_387 | N | N |
| *Lautropia* sp. oral clone AP009 | 1150 | AY005030 | clade_387 | N | N |
| *Peptoniphilus asaccharolyticus* | 1441 | D14145 | clade_389 | N | N |
| *Peptoniphilus duerdenii* | 1442 | EU526290 | clade_389 | N | N |
| *Peptoniphilus harei* | 1443 | NR_026358 | clade_389 | N | N |
| *Peptoniphilus indolicus* | 1444 | AY153431 | clade_389 | N | N |
| *Peptoniphilus lacrimalis* | 1446 | ADDO01000050 | clade_389 | N | N |
| *Peptoniphilus* sp. gpac077 | 1450 | AM176527 | clade_389 | N | N |
| *Peptoniphilus* sp. JC140 | 1447 | JF824803 | clade_389 | N | N |
| *Peptoniphilus* sp. oral taxon 386 | 1452 | ADCS01000031 | clade_389 | N | N |
| *Peptoniphilus* sp. oral taxon 836 | 1453 | AEAA01000090 | clade_389 | N | N |
| Peptostreptococcaceae bacterium ph1 | 1454 | JN837495 | clade_389 | N | N |
| *Dialister pneumosintes* | 765 | HM596297 | clade_390 | N | N |
| *Dialister* sp. oral taxon 502 | 767 | GQ422739 | clade_390 | N | N |
| *Cupriavidus metallidurans* | 741 | GU230889 | clade_391 | N | N |
| *Herbaspirillum seropedicae* | 1001 | CP002039 | clade_391 | N | N |
| *Herbaspirillum* sp. JC206 | 1002 | JN657219 | clade_391 | N | N |
| *Janthinobacterium* sp. SY12 | 1015 | EF455530 | clade_391 | N | N |
| *Massilia* sp. CCUG 43427A | 1197 | FR773700 | clade_391 | N | N |
| *Ralstonia pickettii* | 1615 | NC_010682 | clade_391 | N | N |
| *Ralstonia* sp. 5_7_47FAA | 1616 | ACUF01000076 | clade_391 | N | N |
| *Francisella novicida* | 889 | ABSS01000002 | clade_392 | N | N |
| *Francisella philomiragia* | 890 | AY928394 | clade_392 | N | N |
| *Francisella tularensis* | 891 | ABAZ01000082 | clade_392 | N | Category-A |
| *Ignatzschineria indica* | 1009 | HQ823562 | clade_392 | N | N |
| *Ignatzschineria* sp. NML 95_0260 | 1010 | HQ823559 | clade_392 | N | N |
| *Streptococcus mutans* | 1814 | AP010655 | clade_394 | N | N |
| *Lactobacillus gasseri* | 1084 | ACOZ01000018 | clade_398 | N | N |
| *Lactobacillus hominis* | 1090 | FR681902 | clade_398 | N | N |
| *Lactobacillus iners* | 1091 | AEKJ01000002 | clade_398 | N | N |
| *Lactobacillus johnsonii* | 1093 | AE017198 | clade_398 | N | N |
| *Lactobacillus senioris* | 1119 | AB602570 | clade_398 | N | N |
| *Lactobacillus* sp. oral clone HT002 | 1135 | AY349382 | clade_398 | N | N |
| *Weissella beninensis* | 2006 | EU439435 | clade_398 | N | N |
| *Sphingomonas echinoides* | 1744 | NR_024700 | clade_399 | N | N |
| *Sphingomonas* sp. oral taxon A09 | 1747 | HM099639 | clade_399 | N | N |
| *Sphingomonas* sp. oral taxon F71 | 1748 | HM099645 | clade_399 | N | N |
| *Zymomonas mobilis* | 2032 | NR_074274 | clade_399 | N | N |
| *Arcanobacterium haemolyticum* | 174 | NR_025347 | clade_400 | N | N |
| *Arcanobacterium pyogenes* | 175 | GU585578 | clade_400 | N | N |
| *Trueperella pyogenes* | 1962 | NR_044858 | clade_400 | N | N |
| *Lactococcus garvieae* | 1144 | AF061005 | clade_401 | N | N |
| *Lactococcus lactis* | 1145 | CP002365 | clade_401 | N | N |
| *Brevibacterium mcbrellneri* | 424 | ADNU01000076 | clade_402 | N | N |
| *Brevibacterium paucivorans* | 425 | EU086796 | clade_402 | N | N |
| *Brevibacterium* sp. JC43 | 428 | JF824806 | clade_402 | N | N |
| *Selenomonas artemidis* | 1692 | HM596274 | clade_403 | N | N |

TABLE 1-continued

See, e.g., WO 2014/121304

| OTU | SEQ ID Number | Public DB Accession | Clade | Spore Former | Pathogen Status |
|---|---|---|---|---|---|
| *Selenomonas* sp. FOBRC9 | 1704 | HQ616378 | clade_403 | N | N |
| *Selenomonas* sp. oral taxon 137 | 1715 | AENV01000007 | clade_403 | N | N |
| *Desmospora activa* | 751 | AM940019 | clade_404 | N | N |
| *Desmospora* sp. 8437 | 752 | AFHT01000143 | clade_404 | N | N |
| *Paenibacillus* sp. oral taxon F45 | 1407 | HM099647 | clade_404 | N | N |
| *Corynebacterium ammoniagenes* | 682 | ADNS01000011 | clade_405 | N | N |
| *Corynebacterium aurimucosum* | 687 | ACLH01000041 | clade_405 | N | N |
| *Corynebacterium bovis* | 688 | AF537590 | clade_405 | N | N |
| *Corynebacterium canis* | 689 | GQ871934 | clade_405 | N | N |
| *Corynebacterium casei* | 690 | NR_025101 | clade_405 | N | N |
| *Corynebacterium durum* | 694 | Z97069 | clade_405 | N | N |
| *Corynebacterium efficiens* | 695 | ACLI01000121 | clade_405 | N | N |
| *Corynebacterium falsenii* | 696 | Y13024 | clade_405 | N | N |
| *Corynebacterium flavescens* | 697 | NR_037040 | clade_405 | N | N |
| *Corynebacterium glutamicum* | 701 | BA000036 | clade_405 | N | N |
| *Corynebacterium jeikeium* | 704 | ACYW01000001 | clade_405 | N | OP |
| *Corynebacterium kroppenstedtii* | 705 | NR_026380 | clade_405 | N | N |
| *Corynebacterium lipophiloflavum* | 706 | ACHJ01000075 | clade_405 | N | N |
| *Corynebacterium matruchotii* | 709 | ACSH02000003 | clade_405 | N | N |
| *Corynebacterium minutissimum* | 710 | X82064 | clade_405 | N | N |
| *Corynebacterium resistens* | 718 | ADGN01000058 | clade_405 | N | N |
| *Corynebacterium simulans* | 720 | AF537604 | clade_405 | N | N |
| *Corynebacterium singulare* | 721 | NR_026394 | clade_405 | N | N |
| *Corynebacterium* sp. 1 ex sheep | 722 | Y13427 | clade_405 | N | N |
| *Corynebacterium* sp. NML 99_0018 | 726 | GU238413 | clade_405 | N | N |
| *Corynebacterium striatum* | 727 | ACGE01000001 | clade_405 | N | OP |
| *Corynebacterium urealyticum* | 732 | X81913 | clade_405 | N | OP |
| *Corynebacterium variabile* | 734 | NR_025314 | clade_405 | N | N |
| *Aerococcus sanguinicola* | 98 | AY837833 | clade_407 | N | N |
| *Aerococcus urinae* | 99 | CP002512 | clade_407 | N | N |
| *Aerococcus urinaeequi* | 100 | NR_043443 | clade_407 | N | N |
| *Aerococcus viridans* | 101 | ADNT01000041 | clade_407 | N | N |
| *Fusobacterium naviforme* | 898 | HQ223106 | clade_408 | N | N |
| *Moryella indoligenes* | 1268 | AF527773 | clade_408 | N | N |
| *Selenomonas* genomosp. P5 | 1697 | AY341820 | clade_410 | N | N |
| *Selenomonas* sp. oral clone IQ048 | 1710 | AY349408 | clade_410 | N | N |
| *Selenomonas sputigena* | 1717 | ACKP02000033 | clade_410 | N | N |
| *Hyphomicrobium sulfonivorans* | 1007 | AY468372 | clade_411 | N | N |
| *Methylocella silvestris* | 1228 | NR_074237 | clade_411 | N | N |
| *Legionella pneumophila* | 1153 | NC_002942 | clade_412 | N | OP |
| *Lactobacillus coryniformis* | 1077 | NR_044705 | clade_413 | N | N |
| *Arthrobacter agilis* | 178 | NR_026198 | clade_414 | N | N |
| *Arthrobacter arilaitensis* | 179 | NR_074608 | clade_414 | N | N |
| *Arthrobacter bergerei* | 180 | NR_025612 | clade_414 | N | N |
| *Arthrobacter globiformis* | 181 | NR_026187 | clade_414 | N | N |
| *Arthrobacter nicotianae* | 182 | NR_026190 | clade_414 | N | N |
| *Mycobacterium abscessus* | 1269 | AGQU01000002 | clade_418 | N | OP |
| *Mycobacterium chelonae* | 1273 | AB548610 | clade_418 | N | OP |
| *Bacteroides salanitronis* | 291 | CP002530 | clade_419 | N | N |
| *Paraprevotella xylaniphila* | 1427 | AFBR01000011 | clade_419 | N | N |
| *Barnesiella intestinihominis* | 336 | AB370251 | clade_420 | N | N |
| *Barnesiella viscericola* | 337 | NR_041508 | clade_420 | N | N |
| *Parabacteroides* sp. NS31_3 | 1422 | JN029805 | clade_420 | N | N |
| Porphyromonadaceae bacterium NML 060648 | 1470 | EF184292 | clade_420 | N | N |
| *Tannerella forsythia* | 1913 | CP003191 | clade_420 | N | N |
| *Tannerella* sp. 6_1_58FAA_CT1 | 1914 | ACWX01000068 | clade_420 | N | N |
| *Mycoplasma amphoriforme* | 1311 | AY531656 | clade_421 | N | N |
| *Mycoplasma genitalium* | 1317 | L43967 | clade_421 | N | N |
| *Mycoplasma pneumoniae* | 1322 | NC_000912 | clade_421 | N | N |

TABLE 1-continued

See, e.g., WO 2014/121304

| OTU | SEQ ID Number | Public DB Accession | Clade | Spore Former | Pathogen Status |
|---|---|---|---|---|---|
| *Mycoplasma penetrans* | 1321 | NC_004432 | clade_422 | N | N |
| *Ureaplasma parvum* | 1966 | AE002127 | clade_422 | N | N |
| *Ureaplasma urealyticum* | 1967 | AAYN01000002 | clade_422 | N | N |
| *Treponema* genomosp. P1 | 1927 | AY341822 | clade_425 | N | N |
| *Treponema* sp. oral taxon 228 | 1943 | GU408580 | clade_425 | N | N |
| *Treponema* sp. oral taxon 230 | 1944 | GU408603 | clade_425 | N | N |
| *Treponema* sp. oral taxon 231 | 1945 | GU408631 | clade_425 | N | N |
| *Treponema* sp. oral taxon 232 | 1946 | GU408646 | clade_425 | N | N |
| *Treponema* sp. oral taxon 235 | 1947 | GU408673 | clade_425 | N | N |
| *Treponema* sp. ovine footrot | 1959 | AJ010951 | clade_425 | N | N |
| *Treponema vincentii* | 1960 | ACYH01000036 | clade_425 | N | OP |
| Burkholderiales bacterium 1_1_47 | 452 | ADCQ01000066 | clade_432 | N | OP |
| *Parasutterella excrementihominis* | 1429 | AFBP01000029 | clade_432 | N | N |
| *Parasutterella secunda* | 1430 | AB491209 | clade_432 | N | N |
| *Sutterella morbirenis* | 1898 | AJ832129 | clade_432 | N | N |
| *Sutterella sanguinus* | 1900 | AJ748647 | clade_432 | N | N |
| *Sutterella* sp. YIT 12072 | 1901 | AB491210 | clade_432 | N | N |
| *Sutterella stercoricanis* | 1902 | NR_025600 | clade_432 | N | N |
| *Sutterella wadsworthensis* | 1903 | ADMF01000048 | clade_432 | N | N |
| *Propionibacterium freudenreichii* | 1572 | NR_036972 | clade_433 | N | N |
| *Propionibacterium* sp. oral taxon 192 | 1580 | GQ422728 | clade_433 | N | N |
| *Tessaracoccus* sp. oral taxon F04 | 1917 | HM099640 | clade_433 | N | N |
| *Peptoniphilus ivorii* | 1445 | Y07840 | clade_434 | N | N |
| *Peptoniphilus* sp. gpac007 | 1448 | AM176517 | clade_434 | N | N |
| *Peptoniphilus* sp. gpac018A | 1449 | AM176519 | clade_434 | N | N |
| *Peptoniphilus* sp. gpac148 | 1451 | AM176535 | clade_434 | N | N |
| *Flexispira rappini* | 887 | AY126479 | clade_436 | N | N |
| *Helicobacter bilis* | 993 | ACDN01000023 | clade_436 | N | N |
| *Helicobacter cinaedi* | 995 | ABQT01000054 | clade_436 | N | N |
| *Helicobacter* sp. None | 998 | U44756 | clade_436 | N | N |
| *Brevundimonas subvibrioides* | 429 | CP002102 | clade_438 | N | N |
| *Hyphomonas neptunium* | 1008 | NR_074092 | clade_438 | N | N |
| *Phenylobacterium zucineum* | 1465 | AY628697 | clade_438 | N | N |
| *Streptococcus downei* | 1793 | AEKN01000002 | clade_441 | N | N |
| *Streptococcus* sp. SHV515 | 1848 | Y07601 | clade_441 | N | N |
| *Acinetobacter* sp. CIP 53.82 | 40 | JQ638584 | clade_443 | N | N |
| *Halomonas elongata* | 990 | NR_074782 | clade_443 | N | N |
| *Halomonas johnsoniae* | 991 | FR775979 | clade_443 | N | N |
| *Butyrivibrio fibrisolvens* | 456 | U41172 | clade_444 | N | N |
| *Roseburia* sp. 11SE37 | 1640 | FM954975 | clade_444 | N | N |
| *Roseburia* sp. 11SE38 | 1641 | FM954976 | clade_444 | N | N |
| *Shuttleworthia satelles* | 1728 | ACIP02000004 | clade_444 | N | N |
| *Shuttleworthia* sp. MSX8B | 1729 | HQ616383 | clade_444 | N | N |
| *Shuttleworthia* sp. oral taxon G69 | 1730 | GU432167 | clade_444 | N | N |
| *Bdellovibrio* sp. MPA | 344 | AY294215 | clade_445 | N | N |
| *Desulfobulbus* sp. oral clone CH031 | 755 | AY005036 | clade_445 | N | N |
| *Desulfovibrio desulfuricans* | 757 | DQ092636 | clade_445 | N | N |
| *Desulfovibrio fairfieldensis* | 758 | U42221 | clade_445 | N | N |
| *Desulfovibrio piger* | 759 | AF192152 | clade_445 | N | N |
| *Desulfovibrio* sp. 3_1_syn3 | 760 | ADDR01000239 | clade_445 | N | N |
| *Geobacter bemidjiensis* | 941 | CP001124 | clade_445 | N | N |
| *Brachybacterium alimentarium* | 401 | NR_026269 | clade_446 | N | N |
| *Brachybacterium conglomeratum* | 402 | AB537169 | clade_446 | N | N |
| *Brachybacterium tyrofermentans* | 403 | NR_026272 | clade_446 | N | N |
| *Dermabacter hominis* | 749 | FJ263375 | clade_446 | N | N |
| *Aneurinibacillus thermoaerophilus* | 171 | NR_029303 | clade_448 | N | N |
| *Brevibacillus agri* | 409 | NR_040983 | clade_448 | N | N |
| *Brevibacillus centrosporus* | 411 | NR_043414 | clade_448 | N | N |

TABLE 1-continued

See, e.g., WO 2014/121304

| OTU | SEQ ID Number | Public DB Accession | Clade | Spore Former | Pathogen Status |
|---|---|---|---|---|---|
| *Brevibacillus choshinensis* | 412 | NR_040980 | clade_448 | N | N |
| *Brevibacillus invocatus* | 413 | NR_041836 | clade_448 | N | N |
| *Brevibacillus parabrevis* | 415 | NR_040981 | clade_448 | N | N |
| *Brevibacillus reuszeri* | 416 | NR_040982 | clade_448 | N | N |
| *Brevibacillus* sp. phR | 417 | JN837488 | clade_448 | N | N |
| *Brevibacillus thermoruber* | 418 | NR_026514 | clade_448 | N | N |
| *Lactobacillus murinus* | 1100 | NR_042231 | clade_449 | N | N |
| *Lactobacillus oeni* | 1102 | NR_043095 | clade_449 | N | N |
| *Lactobacillus ruminis* | 1115 | ACGS02000043 | clade_449 | N | N |
| *Lactobacillus vini* | 1141 | NR_042196 | clade_449 | N | N |
| *Gemella haemolysans* | 924 | ACDZ02000012 | clade_450 | N | N |
| *Gemella morbillorum* | 925 | NR_025904 | clade_450 | N | N |
| *Gemella morbillorum* | 926 | ACRX01000010 | clade_450 | N | N |
| *Gemella sanguinis* | 927 | ACRY01000057 | clade_450 | N | N |
| *Gemella* sp. oral clone ASCE02 | 929 | AY923133 | clade_450 | N | N |
| *Gemella* sp. oral clone ASCF04 | 930 | AY923139 | clade_450 | N | N |
| *Gemella* sp. oral clone ASCF12 | 931 | AY923143 | clade_450 | N | N |
| *Gemella* sp. WAL 1945J | 928 | EU427463 | clade_450 | N | N |
| *Sporolactobacillus nakayamae* | 1753 | NR_042247 | clade_451 | N | N |
| *Gluconacetobacter entanii* | 945 | NR_028909 | clade_452 | N | N |
| *Gluconacetobacter europaeus* | 946 | NR_026513 | clade_452 | N | N |
| *Gluconacetobacter hansenii* | 947 | NR_026133 | clade_452 | N | N |
| *Gluconacetobacter oboediens* | 949 | NR_041295 | clade_452 | N | N |
| *Gluconacetobacter xylinus* | 950 | NR_074338 | clade_452 | N | N |
| *Auritibacter ignavus* | 193 | FN554542 | clade_453 | N | N |
| *Dermacoccus* sp. Ellin185 | 750 | AEIQ01000090 | clade_453 | N | N |
| *Janibacter limosus* | 1013 | NR_026362 | clade_453 | N | N |
| *Janibacter melonis* | 1014 | EF063716 | clade_453 | N | N |
| *Acetobacter aceti* | 7 | NR_026121 | clade_454 | N | N |
| *Acetobacter fabarum* | 8 | NR_042678 | clade_454 | N | N |
| *Acetobacter lovaniensis* | 9 | NR_040832 | clade_454 | N | N |
| *Acetobacter malorum* | 10 | NR_025513 | clade_454 | N | N |
| *Acetobacter orientalis* | 11 | NR_028625 | clade_454 | N | N |
| *Acetobacter pasteurianus* | 12 | NR_026107 | clade_454 | N | N |
| *Acetobacter pomorum* | 13 | NR_042112 | clade_454 | N | N |
| *Acetobacter syzygii* | 14 | NR_040868 | clade_454 | N | N |
| *Acetobacter tropicalis* | 15 | NR_036881 | clade_454 | N | N |
| *Gluconacetobacter azotocaptans* | 943 | NR_028767 | clade_454 | N | N |
| *Gluconacetobacter diazotrophicus* | 944 | NR_074292 | clade_454 | N | N |
| *Gluconacetobacter johannae* | 948 | NR_024959 | clade_454 | N | N |
| *Nocardia brasiliensis* | 1351 | AIHV01000038 | clade_455 | N | N |
| *Nocardia cyriacigeorgica* | 1352 | HQ009486 | clade_455 | N | N |
| *Nocardia puris* | 1354 | NR_028994 | clade_455 | N | N |
| *Nocardia* sp. 01_Je_025 | 1355 | GU574059 | clade_455 | N | N |
| *Rhodococcus equi* | 1623 | ADNW01000058 | clade_455 | N | N |
| *Oceanobacillus caeni* | 1358 | NR_041533 | clade_456 | N | N |
| *Oceanobacillus* sp. Ndiop | 1359 | CAER01000083 | clade_456 | N | N |
| *Ornithinibacillus bavariensis* | 1384 | NR_044923 | clade_456 | N | N |
| *Ornithinibacillus* sp. 7_10AIA | 1385 | FN397526 | clade_456 | N | N |
| *Virgibacillus proomii* | 2005 | NR_025308 | clade_456 | N | N |
| *Corynebacterium amycolatum* | 683 | ABZU01000033 | clade_457 | N | OP |
| *Corynebacterium hansenii* | 702 | AM946639 | clade_457 | N | N |
| *Corynebacterium xerosis* | 735 | FN179330 | clade_457 | N | OP |
| Staphylococcaceae bacterium NML 92_0017 | 1756 | AY841362 | clade_458 | N | N |
| *Staphylococcus fleurettii* | 1766 | NR_041326 | clade_458 | N | N |
| *Staphylococcus sciuri* | 1774 | NR_025520 | clade_458 | N | N |
| *Staphylococcus vitulinus* | 1779 | NR_024670 | clade_458 | N | N |
| *Stenotrophomonas maltophilia* | 1782 | AAVZ01000005 | clade_459 | N | N |
| *Stenotrophomonas* sp. FG_6 | 1783 | EF017810 | clade_459 | N | N |
| *Mycobacterium africanum* | 1270 | AF480605 | clade_46 | N | OP |
| *Mycobacterium alsiensis* | 1271 | AJ938169 | clade_46 | N | OP |
| *Mycobacterium avium* | 1272 | CP000479 | clade_46 | N | OP |
| *Mycobacterium* | 1274 | AM062764 | clade_46 | N | OP |

TABLE 1-continued

See, e.g., WO 2014/121304

| OTU | SEQ ID Number | Public DB Accession | Clade | Spore Former | Pathogen Status |
|---|---|---|---|---|---|
| colombiense | | | | | |
| Mycobacterium gordonae | 1276 | GU142930 | clade_46 | N | OP |
| Mycobacterium intracellulare | 1277 | GQ153276 | clade_46 | N | OP |
| Mycobacterium kansasii | 1278 | AF480601 | clade_46 | N | OP |
| Mycobacterium lacus | 1279 | NR_025175 | clade_46 | N | OP |
| Mycobacterium leprae | 1280 | FM211192 | clade_46 | N | OP |
| Mycobacterium lepromatosis | 1281 | EU203590 | clade_46 | N | OP |
| Mycobacterium mantenii | 1283 | FJ042897 | clade_46 | N | OP |
| Mycobacterium marinum | 1284 | NC_010612 | clade_46 | N | OP |
| Mycobacterium microti | 1285 | NR_025234 | clade_46 | N | OP |
| Mycobacterium parascrofulaceum | 1287 | ADNV01000350 | clade_46 | N | OP |
| Mycobacterium seoulense | 1290 | DQ536403 | clade_46 | N | OP |
| Mycobacterium sp. 1761 | 1292 | EU703150 | clade_46 | N | N |
| Mycobacterium sp. 1791 | 1295 | EU703148 | clade_46 | N | N |
| Mycobacterium sp. 1797 | 1296 | EU703149 | clade_46 | N | N |
| Mycobacterium sp. B10_07.09.0206 | 1298 | HQ174245 | clade_46 | N | N |
| Mycobacterium sp. NLA001000736 | 1305 | HM627011 | clade_46 | N | N |
| Mycobacterium sp. W | 1306 | DQ437715 | clade_46 | N | N |
| Mycobacterium tuberculosis | 1307 | CP001658 | clade_46 | N | Category-C |
| Mycobacterium ulcerans | 1308 | AB548725 | clade_46 | N | OP |
| Mycobacterium vulneris | 1309 | EU834055 | clade_46 | N | OP |
| Xanthomonas campestris | 2016 | EF101975 | clade_461 | N | N |
| Xanthomonas sp. kmd_489 | 2017 | EU723184 | clade_461 | N | N |
| Dietzia natronolimnaea | 769 | GQ870426 | clade_462 | N | N |
| Dietzia sp. BBDP51 | 770 | DQ337512 | clade_462 | N | N |
| Dietzia sp. CA149 | 771 | GQ870422 | clade_462 | N | N |
| Dietzia timorensis | 772 | GQ870424 | clade_462 | N | N |
| Gordonia bronchialis | 951 | NR_027594 | clade_463 | N | N |
| Gordonia polyisoprenivorans | 952 | DQ385609 | clade_463 | N | N |
| Gordonia sp. KTR9 | 953 | DQ068383 | clade_463 | N | N |
| Gordonia sputi | 954 | FJ536304 | clade_463 | N | N |
| Gordonia terrae | 955 | GQ848239 | clade_463 | N | N |
| Leptotrichia goodfellowii | 1167 | ADAD01000110 | clade_465 | N | N |
| Leptotrichia sp. oral clone IK040 | 1174 | AY349387 | clade_465 | N | N |
| Leptotrichia sp. oral clone P2PB_51 P1 | 1175 | AY207053 | clade_465 | N | N |
| Bacteroidales genomosp. P7 oral clone MB3_P19 | 264 | DQ003623 | clade_466 | N | N |
| Butyricimonas virosa | 454 | AB443949 | clade_466 | N | N |
| Odoribacter laneus | 1363 | AB490805 | clade_466 | N | N |
| Odoribacter splanchnicus | 1364 | CP002544 | clade_466 | N | N |
| Capnocytophaga gingivalis | 478 | ACLQ01000011 | clade_467 | N | N |
| Capnocytophaga granulosa | 479 | X97248 | clade_467 | N | N |
| Capnocytophaga sp. oral clone AH015 | 483 | AY005074 | clade_467 | N | N |
| Capnocytophaga sp. oral strain S3 | 487 | AY005073 | clade_467 | N | N |
| Capnocytophaga sp. oral taxon 338 | 488 | AEXX01000050 | clade_467 | N | N |
| Capnocytophaga canimorsus | 476 | CP002113 | clade_468 | N | N |
| Capnocytophaga sp. oral clone ID062 | 485 | AY349368 | clade_468 | N | N |
| Lactobacillus catenaformis | 1075 | M23729 | clade_469 | N | N |
| Lactobacillus vitulinus | 1142 | NR_041305 | clade_469 | N | N |
| Cetobacterium somerae | 501 | AJ438155 | clade_470 | N | N |
| Fusobacterium gonidiaformans | 896 | ACET01000043 | clade_470 | N | N |
| Fusobacterium mortiferum | 897 | ACDB02000034 | clade_470 | N | N |
| Fusobacterium necrogenes | 899 | X55408 | clade_470 | N | N |
| Fusobacterium necrophorum | 900 | AM905356 | clade_470 | N | N |
| Fusobacterium sp. 12_1B | 905 | AGWJ01000070 | clade_470 | N | N |
| Fusobacterium sp. 3_1_5R | 911 | ACDD01000078 | clade_470 | N | N |
| Fusobacterium sp. D12 | 918 | ACDG02000036 | clade_470 | N | N |
| Fusobacterium ulcerans | 921 | ACDH01000090 | clade_470 | N | N |
| Fusobacterium varium | 922 | ACIE01000009 | clade_470 | N | N |
| Mycoplasma arthritidis | 1312 | NC_011025 | clade_473 | N | N |
| Mycoplasma faucium | 1314 | NR_024983 | clade_473 | N | N |
| Mycoplasma hominis | 1318 | AF443616 | clade_473 | N | N |

TABLE 1-continued

See, e.g., WO 2014/121304

| OTU | SEQ ID Number | Public DB Accession | Clade | Spore Former | Pathogen Status |
|---|---|---|---|---|---|
| *Mycoplasma orale* | 1319 | AY796060 | clade_473 | N | N |
| *Mycoplasma salivarium* | 1324 | M24661 | clade_473 | N | N |
| *Mitsuokella jalaludinii* | 1247 | NR_028840 | clade_474 | N | N |
| *Mitsuokella multacida* | 1248 | ABWK02000005 | clade_474 | N | N |
| *Mitsuokella* sp. oral taxon 521 | 1249 | GU413658 | clade_474 | N | N |
| *Mitsuokella* sp. oral taxon G68 | 1250 | GU432166 | clade_474 | N | N |
| *Selenomonas* genomosp. C1 | 1695 | AY278627 | clade_474 | N | N |
| *Selenomonas* genomosp. P8 oral clone MB5_P06 | 1700 | DQ003628 | clade_474 | N | N |
| *Selenomonas ruminantium* | 1703 | NR_075026 | clade_474 | N | N |
| *Veillonellaceae* bacterium oral taxon 131 | 1994 | GU402916 | clade_474 | N | N |
| *Alloscardovia omnicolens* | 139 | NR_042583 | clade_475 | N | N |
| *Alloscardovia* sp. OB7196 | 140 | AB425070 | clade_475 | N | N |
| *Bifidobacterium urinalis* | 366 | AJ278695 | clade_475 | N | N |
| *Prevotella loescheii* | 1503 | JN867231 | clade_48 | N | N |
| *Prevotella* sp. oral clone ASCG12 | 1530 | DQ272511 | clade_48 | N | N |
| *Prevotella* sp. oral clone GU027 | 1540 | AY349398 | clade_48 | N | N |
| *Prevotella* sp. oral taxon 472 | 1553 | ACZS01000106 | clade_48 | N | N |
| *Selenomonas dianae* | 1693 | GQ422719 | clade_480 | N | N |
| *Selenomonas flueggei* | 1694 | AF287803 | clade_480 | N | N |
| *Selenomonas* genomosp. C2 | 1696 | AY278628 | clade_480 | N | N |
| *Selenomonas* genomosp. P6 oral clone MB3_C41 | 1698 | DQ003636 | clade_480 | N | N |
| *Selenomonas* genomosp. P7 oral clone MB5_C08 | 1699 | DQ003627 | clade_480 | N | N |
| *Selenomonas infelix* | 1701 | AF287802 | clade_480 | N | N |
| *Selenomonas noxia* | 1702 | GU470909 | clade_480 | N | N |
| *Selenomonas* sp. oral clone FT050 | 1705 | AY349403 | clade_480 | N | N |
| *Selenomonas* sp. oral clone GI064 | 1706 | AY349404 | clade_480 | N | N |
| *Selenomonas* sp. oral clone GT010 | 1707 | AY349405 | clade_480 | N | N |
| *Selenomonas* sp. oral clone HU051 | 1708 | AY349406 | clade_480 | N | N |
| *Selenomonas* sp. oral clone IK004 | 1709 | AY349407 | clade_480 | N | N |
| *Selenomonas* sp. oral clone JI021 | 1711 | AY349409 | clade_480 | N | N |
| *Selenomonas* sp. oral clone JS031 | 1712 | AY349410 | clade_480 | N | N |
| *Selenomonas* sp. oral clone OH4A | 1713 | AY947498 | clade_480 | N | N |
| *Selenomonas* sp. oral clone P2PA_80 P4 | 1714 | AY207052 | clade_480 | N | N |
| *Selenomonas* sp. oral taxon 149 | 1716 | AEEJ01000007 | clade_480 | N | N |
| *Veillonellaceae* bacterium oral taxon 155 | 1995 | GU470897 | clade_480 | N | N |
| *Agrococcus jenensis* | 117 | NR_026275 | clade_484 | N | N |
| *Microbacterium gubbeenense* | 1232 | NR_025098 | clade_484 | N | N |
| *Pseudoclavibacter* sp. Timone | 1590 | FJ375951 | clade_484 | N | N |
| *Tropheryma whipplei* | 1961 | BX251412 | clade_484 | N | N |
| *Zimmermannella bifida* | 2031 | AB012592 | clade_484 | N | N |
| *Legionella hackeliae* | 1151 | M36028 | clade_486 | N | OP |
| *Legionella longbeachae* | 1152 | M36029 | clade_486 | N | OP |
| *Legionella* sp. D3923 | 1154 | JN380999 | clade_486 | N | OP |
| *Legionella* sp. D4088 | 1155 | JN381012 | clade_486 | N | OP |
| *Legionella* sp. H63 | 1156 | JF831047 | clade_486 | N | OP |
| *Legionella* sp. NML 93L054 | 1157 | GU062706 | clade_486 | N | OP |
| *Legionella steelei* | 1158 | HQ398202 | clade_486 | N | OP |
| *Tatlockia micdadei* | 1915 | M36032 | clade_486 | N | N |
| *Helicobacter pullorum* | 996 | ABQU01000097 | clade_489 | N | N |
| *Acetobacteraceae* bacterium AT_5844 | 16 | AGEZ01000040 | clade_490 | N | N |
| *Roseomonas cervicalis* | 1643 | ADVL01000363 | clade_490 | N | N |
| *Roseomonas mucosa* | 1644 | NR_028857 | clade_490 | N | N |
| *Roseomonas* sp. | 1645 | AF533357 | clade_490 | N | N |

TABLE 1-continued

See, e.g., WO 2014/121304

| OTU | SEQ ID Number | Public DB Accession | Clade | Spore Former | Pathogen Status |
|---|---|---|---|---|---|
| Roseomonas sp. NML94_0193 | 1646 | AF533359 | clade_490 | N | N |
| Roseomonas sp. NML97_0121 | 1647 | AF533358 | clade_490 | N | N |
| Roseomonas sp. NML98_0009 | 1648 | AF533360 | clade_490 | N | N |
| Rickettsia akari NML98_0157 | 1627 | CP000847 | clade_492 | N | OP |
| Rickettsia conorii | 1628 | AE008647 | clade_492 | N | OP |
| Rickettsia prowazekii | 1629 | M21789 | clade_492 | N | Category-B |
| Rickettsia rickettsii | 1630 | NC_010263 | clade_492 | N | OP |
| Rickettsia slovaca | 1631 | L36224 | clade_492 | N | OP |
| Rickettsia typhi | 1632 | AE017197 | clade_492 | N | OP |
| Anaeroglobus geminatus | 160 | AGCJ01000054 | clade_493 | N | N |
| Megasphaera genomosp. C1 | 1201 | AY278622 | clade_493 | N | N |
| Megasphaera micronuciformis | 1203 | AECS01000020 | clade_493 | N | N |
| Clostridiales genomosp. BVAB3 | 540 | CP001850 | clade_495 | N | N |
| Tsukamurella paurometabola | 1963 | X80628 | clade_496 | N | N |
| Tsukamurella tyrosinosolvens | 1964 | AB478958 | clade_496 | N | N |
| Abiotrophia para_adiacens | 2 | AB022027 | clade_497 | N | N |
| Carnobacterium divergens | 492 | NR_044706 | clade_497 | N | N |
| Carnobacterium maltaromaticum | 493 | NC_019425 | clade_497 | N | N |
| Enterococcus avium | 800 | AF133535 | clade_497 | N | N |
| Enterococcus caccae | 801 | AY943820 | clade_497 | N | N |
| Enterococcus casseliflavus | 802 | AEWT01000047 | clade_497 | N | N |
| Enterococcus durans | 803 | AJ276354 | clade_497 | N | N |
| Enterococcus faecalis | 804 | AE016830 | clade_497 | N | N |
| Enterococcus faecium | 805 | AM157434 | clade_497 | N | N |
| Enterococcus gallinarum | 806 | AB269767 | clade_497 | N | N |
| Enterococcus gilvus | 807 | AY033814 | clade_497 | N | N |
| Enterococcus hawaiiensis | 808 | AY321377 | clade_497 | N | N |
| Enterococcus hirae | 809 | AF061011 | clade_497 | N | N |
| Enterococcus italicus | 810 | AEPV01000109 | clade_497 | N | N |
| Enterococcus mundtii | 811 | NR_024906 | clade_497 | N | N |
| Enterococcus raffinosus | 812 | FN600541 | clade_497 | N | N |
| Enterococcus sp. BV2CASA2 | 813 | JN809766 | clade_497 | N | N |
| Enterococcus sp. CCRI_16620 | 814 | GU457263 | clade_497 | N | N |
| Enterococcus sp. F95 | 815 | FJ463817 | clade_497 | N | N |
| Enterococcus sp. RfL6 | 816 | AJ133478 | clade_497 | N | N |
| Enterococcus thailandicus | 817 | AY321376 | clade_497 | N | N |
| Fusobacterium canifelinum | 893 | AY162222 | clade_497 | N | N |
| Fusobacterium genomosp. C1 | 894 | AY278616 | clade_497 | N | N |
| Fusobacterium genomosp. C2 | 895 | AY278617 | clade_497 | N | N |
| Fusobacterium periodonticum | 902 | ACJY01000002 | clade_497 | N | N |
| Fusobacterium sp. 1_1_41FAA | 906 | ADGG01000053 | clade_497 | N | N |
| Fusobacterium sp. 11_3_2 | 904 | ACUO01000052 | clade_497 | N | N |
| Fusobacterium sp. 2_1_31 | 907 | ACDC02000018 | clade_497 | N | N |
| Fusobacterium sp. 3_1_27 | 908 | ADGF01000045 | clade_497 | N | N |
| Fusobacterium sp. 3_1_33 | 909 | ACQE01000178 | clade_497 | N | N |
| Fusobacterium sp. 3_1_36A2 | 910 | ACPU01000044 | clade_497 | N | N |
| Fusobacterium sp. AC18 | 912 | HQ616357 | clade_497 | N | N |
| Fusobacterium sp. ACB2 | 913 | HQ616358 | clade_497 | N | N |
| Fusobacterium sp. AS2 | 914 | HQ616361 | clade_497 | N | N |
| Fusobacterium sp. CM1 | 915 | HQ616371 | clade_497 | N | N |
| Fusobacterium sp. CM21 | 916 | HQ616375 | clade_497 | N | N |
| Fusobacterium sp. CM22 | 917 | HQ616376 | clade_497 | N | N |
| Fusobacterium sp. oral clone ASCF06 | 919 | AY923141 | clade_497 | N | N |
| Fusobacterium sp. oral clone ASCF11 | 920 | AY953256 | clade_497 | N | N |
| Granulicatella adiacens | 959 | ACKZ01000002 | clade_497 | N | N |
| Granulicatella elegans | 960 | AB252689 | clade_497 | N | N |
| Granulicatella paradiacens | 961 | AY879298 | clade_497 | N | N |

TABLE 1-continued

See, e.g., WO 2014/121304

| OTU | SEQ ID Number | Public DB Accession | Clade | Spore Former | Pathogen Status |
|---|---|---|---|---|---|
| *Granulicatella* sp. oral clone ASC02 | 963 | AY923126 | clade_497 | N | N |
| *Granulicatella* sp. oral clone ASCA05 | 964 | DQ341469 | clade_497 | N | N |
| *Granulicatella* sp. oral clone ASCB09 | 965 | AY953251 | clade_497 | N | N |
| *Granulicatella* sp. oral clone ASCG05 | 966 | AY923146 | clade_497 | N | N |
| *Tetragenococcus halophilus* | 1918 | NR_075020 | clade_497 | N | N |
| *Tetragenococcus koreensis* | 1919 | NR_043113 | clade_497 | N | N |
| *Vagococcus fluvialis* | 1973 | NR_026489 | clade_497 | N | N |
| *Chryseobacterium anthropi* | 514 | AM982793 | clade_498 | N | N |
| *Chryseobacterium gleum* | 515 | ACKQ02000003 | clade_498 | N | N |
| *Chryseobacterium hominis* | 516 | NR_042517 | clade_498 | N | N |
| *Treponema refringens* | 1936 | AF426101 | clade_499 | N | OP |
| *Treponema* sp. oral clone JU031 | 1941 | AY349416 | clade_499 | N | N |
| *Treponema* sp. oral taxon 239 | 1948 | GU408738 | clade_499 | N | N |
| *Treponema* sp. oral taxon 271 | 1955 | GU408871 | clade_499 | N | N |
| *Alistipes finegoldii* | 129 | NR_043064 | clade_500 | N | N |
| *Alistipes onderdonkii* | 131 | NR_043318 | clade_500 | N | N |
| *Alistipes putredinis* | 132 | ABFK02000017 | clade_500 | N | N |
| *Alistipes shahii* | 133 | FP929032 | clade_500 | N | N |
| *Alistipes* sp. HGB5 | 134 | AENZ01000082 | clade_500 | N | N |
| *Alistipes* sp. JC50 | 135 | JF824804 | clade_500 | N | N |
| *Alistipes* sp. RMA 9912 | 136 | GQ140629 | clade_500 | N | N |
| *Mycoplasma agalactiae* | 1310 | AF010477 | clade_501 | N | N |
| *Mycoplasma bovoculi* | 1313 | NR_025987 | clade_501 | N | N |
| *Mycoplasma fermentans* | 1315 | CP002458 | clade_501 | N | N |
| *Mycoplasma flocculare* | 1316 | X62699 | clade_501 | N | N |
| *Mycoplasma ovipneumoniae* | 1320 | NR_025989 | clade_501 | N | N |
| *Arcobacter butzleri* | 176 | AEPT01000071 | clade_502 | N | N |
| *Arcobacter cryaerophilus* | 177 | NR_025905 | clade_502 | N | N |
| *Campylobacter curvus* | 461 | NC_009715 | clade_502 | N | OP |
| *Campylobacter rectus* | 467 | ACFU01000050 | clade_502 | N | OP |
| *Campylobacter showae* | 468 | ACVQ01000030 | clade_502 | N | OP |
| *Campylobacter* sp. FOBRC14 | 469 | HQ616379 | clade_502 | N | OP |
| *Campylobacter* sp. FOBRC15 | 470 | HQ616380 | clade_502 | N | OP |
| *Campylobacter* sp. oral clone BB120 | 471 | AY005038 | clade_502 | N | OP |
| *Campylobacter sputorum* | 472 | NR_044839 | clade_502 | N | OP |
| *Bacteroides ureolyticus* | 330 | GQ167666 | clade_504 | N | N |
| *Campylobacter gracilis* | 463 | ACYG01000026 | clade_504 | N | OP |
| *Campylobacter hominis* | 464 | NC_009714 | clade_504 | N | OP |
| *Dialister invisus* | 762 | ACIM02000001 | clade_506 | N | N |
| *Dialister micraerophilus* | 763 | AFBB01000028 | clade_506 | N | N |
| *Dialister microaerophilus* | 764 | AENT01000008 | clade_506 | N | N |
| *Dialister propionicifaciens* | 766 | NR_043231 | clade_506 | N | N |
| *Dialister succinatiphilus* | 768 | AB370249 | clade_506 | N | N |
| *Megasphaera elsdenii* | 1200 | AY038996 | clade_506 | N | N |
| *Megasphaera* genomosp. type_1 | 1202 | ADGP01000010 | clade_506 | N | N |
| *Megasphaera* sp. BLPYG_07 | 1204 | HM990964 | clade_506 | N | N |
| *Megasphaera* sp. UPII 199_6 | 1205 | AFIJ01000040 | clade_506 | N | N |
| *Chromobacterium violaceum* | 513 | NC_005085 | clade_507 | N | N |
| *Laribacter hongkongensis* | 1148 | CP001154 | clade_507 | N | N |
| *Methylophilus* sp. ECd5 | 1229 | AY436794 | clade_507 | N | N |
| *Finegoldia magna* | 883 | ACHM02000001 | clade_509 | N | N |
| *Parvimonas micra* | 1431 | AB729072 | clade_509 | N | N |
| *Parvimonas* sp. oral taxon 110 | 1432 | AFII01000002 | clade_509 | N | N |
| *Peptostreptococcus micros* | 1456 | AM176538 | clade_509 | N | N |
| *Peptostreptococcus* sp. oral clone FJ023 | 1460 | AY349390 | clade_509 | N | N |
| *Peptostreptococcus* sp. P4P_31 P3 | 1458 | AY207059 | clade_509 | N | N |
| *Helicobacter pylori* | 997 | CP000012 | clade_510 | N | OP |

TABLE 1-continued

See, e.g., WO 2014/121304

| OTU | SEQ ID Number | Public DB Accession | Clade | Spore Former | Pathogen Status |
|---|---|---|---|---|---|
| *Anaplasma marginale* | 165 | ABOR01000019 | clade_511 | N | N |
| *Anaplasma phagocytophilum* | 166 | NC_007797 | clade_511 | N | N |
| *Ehrlichia chaffeensis* | 783 | AAIF01000035 | clade_511 | N | OP |
| *Neorickettsia risticii* | 1349 | CP001431 | clade_511 | N | N |
| *Neorickettsia sennetsu* | 1350 | NC_007798 | clade_511 | N | N |
| *Pseudoramibacter alactolyticus* | 1606 | AB036759 | clade_512 | N | N |
| *Veillonella montpellierensis* | 1977 | AF473836 | clade_513 | N | N |
| *Veillonella* sp. oral clone ASCA08 | 1988 | AY923118 | clade_513 | N | N |
| *Veillonella* sp. oral clone ASCB03 | 1989 | AY923122 | clade_513 | N | N |
| *Inquilinus limosus* | 1012 | NR_029046 | clade_514 | N | N |
| *Sphingomonas* sp. oral clone FZ016 | 1746 | AY349412 | clade_514 | N | N |
| *Anaerococcus lactolyticus* | 145 | ABYO01000217 | clade_515 | N | N |
| *Anaerococcus prevotii* | 147 | CP001708 | clade_515 | N | N |
| *Anaerococcus* sp. gpac104 | 152 | AM176528 | clade_515 | N | N |
| *Anaerococcus* sp. gpac126 | 153 | AM176530 | clade_515 | N | N |
| *Anaerococcus* sp. gpac155 | 154 | AM176536 | clade_515 | N | N |
| *Anaerococcus* sp. gpac199 | 155 | AM176539 | clade_515 | N | N |
| *Anaerococcus tetradius* | 157 | ACGC01000107 | clade_515 | N | N |
| *Bacteroides coagulans* | 271 | AB547639 | clade_515 | N | N |
| Clostridiales bacterium 9403326 | 534 | HM587324 | clade_515 | N | N |
| Clostridiales bacterium ph2 | 539 | JN837487 | clade_515 | N | N |
| *Peptostreptococcus* sp. 9succ1 | 1457 | X90471 | clade_515 | N | N |
| *Peptostreptococcus* sp. oral clone AP24 | 1459 | AB175072 | clade_515 | N | N |
| *Tissierella praeacuta* | 1924 | NR_044860 | clade_515 | N | N |
| *Helicobacter canadensis* | 994 | ABQS01000108 | clade_518 | N | N |
| *Peptostreptococcus anaerobius* | 1455 | AY326462 | clade_520 | N | N |
| *Peptostreptococcus stomatis* | 1461 | ADGQ01000048 | clade_520 | N | N |
| *Bilophila wadsworthia* | 367 | ADCP01000166 | clade_521 | N | N |
| *Desulfovibrio vulgaris* | 761 | NR_074897 | clade_521 | N | N |
| *Actinomyces nasicola* | 64 | AJ508455 | clade_523 | N | N |
| *Cellulosimicrobium funkei* | 500 | AY501364 | clade_523 | N | N |
| *Lactococcus raffinolactis* | 1146 | NR_044359 | clade_524 | N | N |
| Bacteroidales genomosp. P1 | 258 | AY341819 | clade_529 | N | N |
| Bacteroidales genomosp. P2 oral clone MB1_G13 | 259 | DQ003613 | clade_529 | N | N |
| Bacteroidales genomosp. P3 oral clone MB1_G34 | 260 | DQ003615 | clade_529 | N | N |
| Bacteroidales genomosp. P4 oral clone MB2_G17 | 261 | DQ003617 | clade_529 | N | N |
| Bacteroidales genomosp. P5 oral clone MB2_P04 | 262 | DQ003619 | clade_529 | N | N |
| Bacteroidales genomosp. P6 oral clone MB3_C19 | 263 | DQ003634 | clade_529 | N | N |
| Bacteroidales genomosp. P8 oral clone MB4_G15 | 265 | DQ003626 | clade_529 | N | N |
| Bacteroidetes bacterium oral taxon D27 | 333 | HM099638 | clade_530 | N | N |
| Bacteroidetes bacterium oral taxon F31 | 334 | HM099643 | clade_530 | N | N |
| Bacteroidetes bacterium oral taxon F44 | 335 | HM099649 | clade_530 | N | N |
| *Flavobacterium* sp. NF2_1 | 885 | FJ195988 | clade_530 | N | N |
| *Myroides odoratimimus* | 1326 | NR_042354 | clade_530 | N | N |
| *Myroides* sp. MY15 | 1327 | GU253339 | clade_530 | N | N |
| Chlamydiales bacterium NS16 | 507 | JN606076 | clade_531 | N | N |
| *Chlamydophila pecorum* | 508 | D88317 | clade_531 | N | OP |
| *Parachlamydia* sp. UWE25 | 1423 | BX908798 | clade_531 | N | N |
| *Fusobacterium russii* | 903 | NR_044687 | clade_532 | N | N |
| *Streptobacillus moniliformis* | 1784 | NR_027615 | clade_532 | N | N |
| Eubacteriaceae bacterium P4P_50 P4 | 833 | AY207060 | clade_533 | N | N |
| *Abiotrophia defectiva* | 1 | ACIN02000016 | clade_534 | N | N |
| *Abiotrophia* sp. oral clone P4PA_155 P1 | 3 | AY207063 | clade_534 | N | N |
| *Catonella* genomosp. P1 | 496 | DQ003629 | clade_534 | N | N |

TABLE 1-continued

See, e.g., WO 2014/121304

| OTU | SEQ ID Number | Public DB Accession | Clade | Spore Former | Pathogen Status |
|---|---|---|---|---|---|
| oral clone MB5_P12 | | | | | |
| *Catonella morbi* | 497 | ACIL02000016 | clade_534 | N | N |
| *Catonella* sp. oral clone FL037 | 498 | AY349369 | clade_534 | N | N |
| *Eremococcus coleocola* | 818 | AENN01000008 | clade_534 | N | N |
| *Facklamia hominis* | 879 | Y10772 | clade_534 | N | N |
| *Granulicatella* sp. M658_99_3 | 962 | AJ271861 | clade_534 | N | N |
| *Campylobacter coli* | 459 | AAFL01000004 | clade_535 | N | OP |
| *Campylobacter concisus* | 460 | CP000792 | clade_535 | N | OP |
| *Campylobacter fetus* | 462 | ACLG01001177 | clade_535 | N | OP |
| *Campylobacter jejuni* | 465 | AL139074 | clade_535 | N | Category-B |
| *Campylobacter upsaliensis* | 473 | AEPU01000040 | clade_535 | N | OP |
| *Atopobium minutum* | 183 | HM007583 | clade_539 | N | N |
| *Atopobium parvulum* | 184 | CP001721 | clade_539 | N | N |
| *Atopobium rimae* | 185 | ACFE01000007 | clade_539 | N | N |
| *Atopobium* sp. BS2 | 186 | HQ616367 | clade_539 | N | N |
| *Atopobium* sp. F0209 | 187 | EU592966 | clade_539 | N | N |
| *Atopobium* sp. ICM42b10 | 188 | HQ616393 | clade_539 | N | N |
| *Atopobium* sp. ICM57 | 189 | HQ616400 | clade_539 | N | N |
| *Atopobium vaginae* | 190 | AEDQ01000024 | clade_539 | N | N |
| Coriobacteriaceae bacterium BV3Ac1 | 677 | JN809768 | clade_539 | N | N |
| *Actinomyces naeslundii* | 63 | X81062 | clade_54 | N | N |
| *Actinomyces oricola* | 67 | NR_025559 | clade_54 | N | N |
| *Actinomyces oris* | 69 | BABV01000070 | clade_54 | N | N |
| *Actinomyces* sp. 7400942 | 70 | EU484334 | clade_54 | N | N |
| *Actinomyces* sp. ChDC B197 | 72 | AF543275 | clade_54 | N | N |
| *Actinomyces* sp. GEJ15 | 73 | GU561313 | clade_54 | N | N |
| *Actinomyces* sp. M2231_94_1 | 79 | AJ234063 | clade_54 | N | N |
| *Actinomyces* sp. oral clone GU067 | 83 | AY349362 | clade_54 | N | N |
| *Actinomyces* sp. oral clone IO077 | 85 | AY349364 | clade_54 | N | N |
| *Actinomyces* sp. oral clone IP073 | 86 | AY349365 | clade_54 | N | N |
| *Actinomyces* sp. oral clone JA063 | 88 | AY349367 | clade_54 | N | N |
| *Actinomyces* sp. oral taxon 170 | 89 | AFBL01000010 | clade_54 | N | N |
| *Actinomyces* sp. oral taxon 171 | 90 | AECW01000034 | clade_54 | N | N |
| *Actinomyces urogenitalis* | 95 | ACFH01000038 | clade_54 | N | N |
| *Actinomyces viscosus* | 96 | ACRE01000096 | clade_54 | N | N |
| *Orientia tsutsugamushi* | 1383 | AP008981 | clade_541 | N | OP |
| *Megamonas funiformis* | 1198 | AB300988 | clade_542 | N | N |
| *Megamonas hypermegale* | 1199 | AJ420107 | clade_542 | N | N |
| *Aeromicrobium marinum* | 102 | NR_025681 | clade_544 | N | N |
| *Aeromicrobium* sp. JC14 | 103 | JF824798 | clade_544 | N | N |
| *Luteococcus sanguinis* | 1190 | NR_025507 | clade_544 | N | N |
| Propionibacteriaceae bacterium NML 02_0265 | 1568 | EF599122 | clade_544 | N | N |
| *Rhodococcus corynebacterioides* | 1622 | X80615 | clade_546 | N | N |
| *Rhodococcus erythropolis* | 1624 | ACNO01000030 | clade_546 | N | N |
| *Rhodococcus fascians* | 1625 | NR_037021 | clade_546 | N | N |
| *Segniliparus rotundus* | 1690 | CP001958 | clade_546 | N | N |
| *Segniliparus rugosus* | 1691 | ACZI01000025 | clade_546 | N | N |
| *Exiguobacterium acetylicum* | 878 | FJ970034 | clade_547 | N | N |
| *Macrococcus caseolyticus* | 1194 | NR_074941 | clade_547 | N | N |
| *Streptomyces* sp. 1 AIP_2009 | 1890 | FJ176782 | clade_548 | N | N |
| *Streptomyces* sp. SD 524 | 1892 | EU544234 | clade_548 | N | N |
| *Streptomyces* sp. SD 528 | 1893 | EU544233 | clade_548 | N | N |
| *Streptomyces thermoviolaceus* | 1895 | NR_027616 | clade_548 | N | N |
| *Borrelia afzelii* | 388 | ABCU01000001 | clade_549 | N | OP |
| *Borrelia crocidurae* | 390 | DQ057990 | clade_549 | N | OP |
| *Borrelia duttonii* | 391 | NC_011229 | clade_549 | N | OP |
| *Borrelia hermsii* | 393 | AY597657 | clade_549 | N | OP |
| *Borrelia hispanica* | 394 | DQ057988 | clade_549 | N | OP |
| *Borrelia persica* | 395 | HM161645 | clade_549 | N | OP |
| *Borrelia recurrentis* | 396 | AF107367 | clade_549 | N | OP |

TABLE 1-continued

See, e.g., WO 2014/121304

| OTU | SEQ ID Number | Public DB Accession | Clade | Spore Former | Pathogen Status |
|---|---|---|---|---|---|
| *Borrelia spielmanii* | 398 | ABKB01000002 | clade_549 | N | OP |
| *Borrelia turicatae* | 399 | NC_008710 | clade_549 | N | OP |
| *Borrelia valaisiana* | 400 | ABCY01000002 | clade_549 | N | OP |
| *Providencia alcalifaciens* | 1586 | ABXW01000071 | clade_55 | N | N |
| *Providencia rettgeri* | 1587 | AM040492 | clade_55 | N | N |
| *Providencia rustigianii* | 1588 | AM040489 | clade_55 | N | N |
| *Providencia stuartii* | 1589 | AF008581 | clade_55 | N | N |
| *Treponema pallidum* | 1932 | CP001752 | clade_550 | N | OP |
| *Treponema phagedenis* | 1934 | AEFH01000172 | clade_550 | N | N |
| *Treponema* sp. clone DDKL_4 | 1939 | Y08894 | clade_550 | N | N |
| *Acholeplasma laidlawii* | 17 | NR_074448 | clade_551 | N | N |
| *Mycoplasma putrefaciens* | 1323 | U26055 | clade_551 | N | N |
| Mycoplasmataceae genomosp. P1 oral clone MB1_G23 | 1325 | DQ003614 | clade_551 | N | N |
| *Spiroplasma insolitum* | 1750 | NR_025705 | clade_551 | N | N |
| *Collinsella intestinalis* | 660 | ABXH02000037 | clade_553 | N | N |
| *Collinsella stercoris* | 661 | ABXJ01000150 | clade_553 | N | N |
| *Collinsella tanakaei* | 662 | AB490807 | clade_553 | N | N |
| *Caminicella sporogenes* | 458 | NR_025485 | clade_554 | N | N |
| *Acidaminococcus fermentans* | 21 | CP001859 | clade_556 | N | N |
| *Acidaminococcus intestini* | 22 | CP003058 | clade_556 | N | N |
| *Acidaminococcus* sp. D21 | 23 | ACGB01000071 | clade_556 | N | N |
| *Phascolarctobacterium faecium* | 1462 | NR_026111 | clade_556 | N | N |
| *Phascolarctobacterium* sp. YIT 12068 | 1463 | AB490812 | clade_556 | N | N |
| *Phascolarctobacterium succinatutens* | 1464 | AB490811 | clade_556 | N | N |
| *Acidithiobacillus ferrivorans* | 25 | NR_074660 | clade_557 | N | N |
| Xanthomonadaceae bacterium NML 03_0222 | 2015 | EU313791 | clade_557 | N | N |
| *Catabacter hongkongensis* | 494 | AB671763 | clade_558 | N | N |
| *Christensenella minuta* | 512 | AB490809 | clade_558 | N | N |
| Clostridiales bacterium oral clone P4PA_66 P1 | 536 | AY207065 | clade_558 | N | N |
| Clostridiales bacterium oral taxon 093 | 537 | GQ422712 | clade_558 | N | N |
| *Heliobacterium modesticaldum* | 1000 | NR_074517 | clade_560 | N | N |
| *Alistipes indistinctus* | 130 | AB490804 | clade_561 | N | N |
| Bacteroidales bacterium ph8 | 257 | JN837494 | clade_561 | N | N |
| *Candidatus Sulcia muelleri* | 475 | CP002163 | clade_561 | N | N |
| *Cytophaga xylanolytica* | 742 | FR733683 | clade_561 | N | N |
| Flavobacteriaceae genomosp. C1 | 884 | AY278614 | clade_561 | N | N |
| *Gramella forsetii* | 958 | NR_074707 | clade_561 | N | N |
| *Sphingobacterium faecium* | 1740 | NR_025537 | clade_562 | N | N |
| *Sphingobacterium mizutaii* | 1741 | JF708889 | clade_562 | N | N |
| *Sphingobacterium multivorum* | 1742 | NR_040953 | clade_562 | N | N |
| *Sphingobacterium spiritivorum* | 1743 | ACHA02000013 | clade_562 | N | N |
| *Jonquetella anthropi* | 1017 | ACOO02000004 | clade_563 | N | N |
| *Pyramidobacter piscolens* | 1614 | AY207056 | clade_563 | N | N |
| *Synergistes* genomosp. C1 | 1904 | AY278615 | clade_563 | N | N |
| *Synergistes* sp. RMA 14551 | 1905 | DQ412722 | clade_563 | N | N |
| Synergistetes bacterium ADV897 | 1906 | GQ258968 | clade_563 | N | N |
| *Candidatus Arthromitus* sp. SFB_mouse_Yit | 474 | NR_074460 | clade_564 | N | N |
| *Gracilibacter thermotolerans* | 957 | NR_043559 | clade_564 | N | N |
| *Brachyspira aalborgi* | 404 | FM178386 | clade_565 | N | N |
| *Brachyspira* sp. HIS3 | 406 | FM178387 | clade_565 | N | N |
| *Brachyspira* sp. HIS4 | 407 | FM178388 | clade_565 | N | N |
| *Brachyspira* sp. HIS5 | 408 | FM178389 | clade_565 | N | N |
| *Adlercreutzia equolifaciens* | 97 | AB306661 | clade_566 | N | N |
| Coriobacteriaceae bacterium JC110 | 678 | CAEM01000062 | clade_566 | N | N |
| Coriobacteriaceae bacterium phI | 679 | JN837493 | clade_566 | N | N |
| *Cryptobacterium curtum* | 740 | GQ422741 | clade_566 | N | N |
| *Eggerthella sinensis* | 779 | AY321958 | clade_566 | N | N |

TABLE 1-continued

See, e.g., WO 2014/121304

| OTU | SEQ ID Number | Public DB Accession | Clade | Spore Former | Pathogen Status |
|---|---|---|---|---|---|
| *Eggerthella* sp. 1_3_56FAA | 780 | ACWN01000099 | clade_566 | N | N |
| *Eggerthella* sp. HGA1 | 781 | AEXR01000021 | clade_566 | N | N |
| *Eggerthella* sp. YY7918 | 782 | AP012211 | clade_566 | N | N |
| *Gordonibacter pamelaeae* | 680 | AM886059 | clade_566 | N | N |
| *Gordonibacter pamelaeae* | 956 | FP929047 | clade_566 | N | N |
| *Slackia equolifaciens* | 1732 | EU377663 | clade_566 | N | N |
| *Slackia exigua* | 1733 | ACUX01000029 | clade_566 | N | N |
| *Slackia faecicanis* | 1734 | NR_042220 | clade_566 | N | N |
| *Slackia heliotrinireducens* | 1735 | NR_074439 | clade_566 | N | N |
| *Slackia isoflavoniconvertens* | 1736 | AB566418 | clade_566 | N | N |
| *Slackia piriformis* | 1737 | AB490806 | clade_566 | N | N |
| *Slackia* sp. NATTS | 1738 | AB505075 | clade_566 | N | N |
| Chlamydiales bacterium NS13 | 506 | JN606075 | clade_567 | N | N |
| Victivallaceae bacterium NML 080035 | 2003 | FJ394915 | clade_567 | N | N |
| *Victivallis vadensis* | 2004 | ABDE02000010 | clade_567 | N | N |
| *Streptomyces griseus* | 1889 | NR_074787 | clade_573 | N | N |
| *Streptomyces* sp. SD 511 | 1891 | EU544231 | clade_573 | N | N |
| *Streptomyces* sp. SD 534 | 1894 | EU544232 | clade_573 | N | N |
| *Cloacibacillus evryensis* | 530 | GQ258966 | clade_575 | N | N |
| *Deferribacteres* sp. oral clone JV001 | 743 | AY349370 | clade_575 | N | N |
| *Deferribacteres* sp. oral clone JV023 | 745 | AY349372 | clade_575 | N | N |
| Synergistetes bacterium LBVCM1157 | 1907 | GQ258969 | clade_575 | N | N |
| Synergistetes bacterium oral taxon 362 | 1909 | GU410752 | clade_575 | N | N |
| Synergistetes bacterium oral taxon D48 | 1910 | GU430992 | clade_575 | N | N |
| *Peptococcus* sp. oral clone JM048 | 1439 | AY349389 | clade_576 | N | N |
| *Helicobacter winghamensis* | 999 | ACDO01000013 | clade_577 | N | N |
| *Wolinella succinogenes* | 2014 | BX571657 | clade_577 | N | N |
| *Olsenella* genomosp. C1 | 1368 | AY278623 | clade_578 | N | N |
| *Olsenella profusa* | 1369 | FN178466 | clade_578 | N | N |
| *Olsenella* sp. F0004 | 1370 | EU592964 | clade_578 | N | N |
| *Olsenella* sp. oral taxon 809 | 1371 | ACVE01000002 | clade_578 | N | N |
| *Olsenella uli* | 1372 | CP002106 | clade_578 | N | N |
| *Nocardiopsis dassonvillei* | 1356 | CP002041 | clade_579 | N | N |
| *Peptococcus niger* | 1438 | NR_029221 | clade_580 | N | N |
| *Peptococcus* sp. oral taxon 167 | 1440 | GQ422727 | clade_580 | N | N |
| *Akkermansia muciniphila* | 118 | CP001071 | clade_583 | N | N |
| *Opitutus terrae* | 1373 | NR_074978 | clade_583 | N | N |
| Clostridiales bacterium oral taxon F32 | 538 | HM099644 | clade_584 | N | N |
| *Leptospira borgpetersenii* | 1161 | NC_008508 | clade_585 | N | OP |
| *Leptospira broomii* | 1162 | NR_043200 | clade_585 | N | OP |
| *Leptospira interrogans* | 1163 | NC_005823 | clade_585 | N | OP |
| *Methanobrevibacter gottschalkii* | 1213 | NR_044789 | clade_587 | N | N |
| *Methanobrevibacter millerae* | 1214 | NR_042785 | clade_587 | N | N |
| *Methanobrevibacter oralis* | 1216 | HE654003 | clade_587 | N | N |
| *Methanobrevibacter thaueri* | 1219 | NR_044787 | clade_587 | N | N |
| *Methanobrevibacter smithii* | 1218 | ABYV02000002 | clade_588 | N | N |
| *Deinococcus radiodurans* | 746 | AE000513 | clade_589 | N | N |
| *Deinococcus* sp. R_43890 | 747 | FR682752 | clade_589 | N | N |
| *Thermus aquaticus* | 1923 | NR_025900 | clade_589 | N | N |
| *Actinomyces* sp. c109 | 81 | AB167239 | clade_590 | N | N |
| Syntrophomonadaceae genomosp. P1 | 1912 | AY341821 | clade_590 | N | N |
| *Anaerobaculum hydrogeniformans* | 141 | ACJX02000009 | clade_591 | N | N |
| *Microcystis aeruginosa* | 1246 | NC_010296 | clade_592 | N | N |
| *Prochlorococcus marinus* | 1567 | CP000551 | clade_592 | N | N |
| *Methanobrevibacter acididurans* | 1208 | NR_028779 | clade_593 | N | N |
| *Methanobrevibacter arboriphilus* | 1209 | NR_042783 | clade_593 | N | N |
| *Methanobrevibacter curvatus* | 1210 | NR_044796 | clade_593 | N | N |
| *Methanobrevibacter* | 1211 | NR_044776 | clade_593 | N | N |

TABLE 1-continued

See, e.g., WO 2014/121304

| OTU | SEQ ID Number | Public DB Accession | Clade | Spore Former | Pathogen Status |
|---|---|---|---|---|---|
| cuticularis | | | | | |
| Methanobrevibacter filiformis | 1212 | NR_044801 | clade_593 | N | N |
| Methanobrevibacter woesei | 1220 | NR_044788 | clade_593 | N | N |
| Roseiflexus castenholzii | 1642 | CP000804 | clade_594 | N | N |
| Methanobrevibacter olleyae | 1215 | NR_043024 | clade_595 | N | N |
| Methanobrevibacter ruminantium | 1217 | NR_042784 | clade_595 | N | N |
| Methanobrevibacter wolinii | 1221 | NR_044790 | clade_595 | N | N |
| Methanosphaera stadtmanae | 1222 | AY196684 | clade_595 | N | N |
| Chloroflexi genomosp. P1 | 511 | AY331414 | clade_596 | N | N |
| Halorubrum lipolyticum | 992 | AB477978 | clade_597 | N | N |
| Methanobacterium formicicum | 1207 | NR_025028 | clade_597 | N | N |
| Acidilobus saccharovorans | 24 | AY350586 | clade_598 | N | N |
| Hyperthermus butylicus | 1006 | CP000493 | clade_598 | N | N |
| Ignicoccus islandicus | 1011 | X99562 | clade_598 | N | N |
| Metallosphaera sedula | 1206 | D26491 | clade_598 | N | N |
| Thermofilum pendens | 1922 | X14835 | clade_598 | N | N |
| Prevotella melaninogenica | 1506 | CP002122 | clade_6 | N | N |
| Prevotella sp. ICM1 | 1520 | HQ616385 | clade_6 | N | N |
| Prevotella sp. oral clone FU048 | 1535 | AY349393 | clade_6 | N | N |
| Prevotella sp. oral clone GI030 | 1537 | AY349395 | clade_6 | N | N |
| Prevotella sp. SEQ116 | 1526 | JN867246 | clade_6 | N | N |
| Streptococcus anginosus | 1787 | AECT01000011 | clade_60 | N | N |
| Streptococcus milleri | 1812 | X81023 | clade_60 | N | N |
| Streptococcus sp. 16362 | 1829 | JN590019 | clade_60 | N | N |
| Streptococcus sp. 69130 | 1832 | X78825 | clade_60 | N | N |
| Streptococcus sp. AC15 | 1833 | HQ616356 | clade_60 | N | N |
| Streptococcus sp. CM7 | 1839 | HQ616373 | clade_60 | N | N |
| Streptococcus sp. OBRC6 | 1847 | HQ616352 | clade_60 | N | N |
| Burkholderia ambifaria | 442 | AAUZ01000009 | clade_61 | N | OP |
| Burkholderia cenocepacia | 443 | AAHI01000060 | clade_61 | N | OP |
| Burkholderia cepacia | 444 | NR_041719 | clade_61 | N | OP |
| Burkholderia mallei | 445 | CP000547 | clade_61 | N | Category-B |
| Burkholderia multivorans | 446 | NC_010086 | clade_61 | N | OP |
| Burkholderia oklahomensis | 447 | DQ108388 | clade_61 | N | OP |
| Burkholderia pseudomallei | 448 | CP001408 | clade_61 | N | Category-B |
| Burkholderia rhizoxinica | 449 | HQ005410 | clade_61 | N | OP |
| Burkholderia sp. 383 | 450 | CP000151 | clade_61 | N | OP |
| Burkholderia xenovorans | 451 | U86373 | clade_61 | N | OP |
| Prevotella buccae | 1488 | ACRB01000001 | clade_62 | N | N |
| Prevotella genomosp. P8 oral clone MB3_P13 | 1498 | DQ003622 | clade_62 | N | N |
| Prevotella sp. oral clone FW035 | 1536 | AY349394 | clade_62 | N | N |
| Prevotella bivia | 1486 | ADFO01000096 | clade_63 | N | N |
| Prevotella disiens | 1494 | AEDO01000026 | clade_64 | N | N |
| Bacteroides faecis | 276 | GQ496624 | clade_65 | N | N |
| Bacteroides fragilis | 279 | AP006841 | clade_65 | N | N |
| Bacteroides nordii | 285 | NR_043017 | clade_65 | N | N |
| Bacteroides salyersiae | 292 | EU136690 | clade_65 | N | N |
| Bacteroides sp. 1_1_14 | 293 | ACRP01000155 | clade_65 | N | N |
| Bacteroides sp. 1_1_6 | 295 | ACIC01000215 | clade_65 | N | N |
| Bacteroides sp. 2_1_56FAA | 298 | ACWI01000065 | clade_65 | N | N |
| Bacteroides sp. AR29 | 316 | AF139525 | clade_65 | N | N |
| Bacteroides sp. B2 | 317 | EU722733 | clade_65 | N | N |
| Bacteroides thetaiotaomicron | 328 | NR_074277 | clade_65 | N | N |
| Actinobacillus minor | 45 | ACFT01000025 | clade_69 | N | N |
| Haemophilus parasuis | 978 | GU226366 | clade_69 | N | N |
| Vibrio cholerae | 1996 | AAUR01000095 | clade_71 | N | Category-B |
| Vibrio fluvialis | 1997 | X76335 | clade_71 | N | Category-B |
| Vibrio furnissii | 1998 | CP002377 | clade_71 | N | Category-B |
| Vibrio mimicus | 1999 | ADAF01000001 | clade_71 | N | Category-B |
| Vibrio parahaemolyticus | 2000 | AAWQ01000116 | clade_71 | N | Category-B |
| Vibrio sp. RC341 | 2001 | ACZT01000024 | clade_71 | N | Category-B |
| Vibrio vulnificus | 2002 | AE016796 | clade_71 | N | Category-B |
| Lactobacillus acidophilus | 1067 | CP000033 | clade_72 | N | N |
| Lactobacillus amylolyticus | 1069 | ADNY01000006 | clade_72 | N | N |
| Lactobacillus amylovorus | 1070 | CP002338 | clade_72 | N | N |
| Lactobacillus crispatus | 1078 | ACOG01000151 | clade_72 | N | N |
| Lactobacillus delbrueckii | 1080 | CP002341 | clade_72 | N | N |

TABLE 1-continued

See, e.g., WO 2014/121304

| OTU | SEQ ID Number | Public DB Accession | Clade | Spore Former | Pathogen Status |
|---|---|---|---|---|---|
| *Lactobacillus helveticus* | 1088 | ACLM01000202 | clade_72 | N | N |
| *Lactobacillus kalixensis* | 1094 | NR_029083 | clade_72 | N | N |
| *Lactobacillus kefiranofaciens* | 1095 | NR_042440 | clade_72 | N | N |
| *Lactobacillus leichmannii* | 1098 | JX986966 | clade_72 | N | N |
| *Lactobacillus* sp. 66c | 1120 | FR681900 | clade_72 | N | N |
| *Lactobacillus* sp. KLDS 1.0701 | 1122 | EU600905 | clade_72 | N | N |
| *Lactobacillus* sp. KLDS 1.0712 | 1130 | EU600916 | clade_72 | N | N |
| *Lactobacillus* sp. oral clone HT070 | 1136 | AY349383 | clade_72 | N | N |
| *Lactobacillus ultunensis* | 1139 | ACGU01000081 | clade_72 | N | N |
| *Prevotella intermedia* | 1502 | AF414829 | clade_81 | N | N |
| *Prevotella nigrescens* | 1511 | AFPX01000069 | clade_81 | N | N |
| *Prevotella pallens* | 1515 | AFPY01000135 | clade_81 | N | N |
| *Prevotella* sp. oral taxon 310 | 1551 | GQ422737 | clade_81 | N | N |
| *Prevotella* genomosp. C1 | 1495 | AY278624 | clade_82 | N | N |
| *Prevotella* sp. CM38 | 1519 | HQ610181 | clade_82 | N | N |
| *Prevotella* sp. oral taxon 317 | 1552 | ACQH01000158 | clade_82 | N | N |
| *Prevotella* sp. SG12 | 1527 | GU561343 | clade_82 | N | N |
| *Prevotella denticola* | 1493 | CP002589 | clade_83 | N | N |
| *Prevotella* genomosp. P7 oral clone MB2_P31 | 1497 | DQ003620 | clade_83 | N | N |
| *Prevotella histicola* | 1501 | JN867315 | clade_83 | N | N |
| *Prevotella multiformis* | 1508 | AEWX01000054 | clade_83 | N | N |
| *Prevotella* sp. JCM 6330 | 1522 | AB547699 | clade_83 | N | N |
| *Prevotella* sp. oral clone GI059 | 1539 | AY349397 | clade_83 | N | N |
| *Prevotella* sp. oral taxon 782 | 1555 | GQ422745 | clade_83 | N | N |
| *Prevotella* sp. oral taxon G71 | 1559 | GU432180 | clade_83 | N | N |
| *Prevotella* sp. SEQ065 | 1524 | JN867234 | clade_83 | N | N |
| *Prevotella veroralis* | 1565 | ACVA01000027 | clade_83 | N | N |
| *Bacteroides acidifaciens* | 266 | NR_028607 | clade_85 | N | N |
| *Bacteroides cellulosilyticus* | 269 | ACCH01000108 | clade_85 | N | N |
| *Bacteroides clarus* | 270 | AFBM01000011 | clade_85 | N | N |
| *Bacteroides eggerthii* | 275 | ACWG01000065 | clade_85 | N | N |
| *Bacteroides oleiciplenus* | 286 | AB547644 | clade_85 | N | N |
| *Bacteroides pyogenes* | 290 | NR_041280 | clade_85 | N | N |
| *Bacteroides* sp. 315_5 | 300 | FJ848547 | clade_85 | N | N |
| *Bacteroides* sp. 31SF15 | 301 | AJ583248 | clade_85 | N | N |
| *Bacteroides* sp. 31SF18 | 302 | AJ583249 | clade_85 | N | N |
| *Bacteroides* sp. 35AE31 | 303 | AJ583244 | clade_85 | N | N |
| *Bacteroides* sp. 35AE37 | 304 | AJ583245 | clade_85 | N | N |
| *Bacteroides* sp. 35BE34 | 305 | AJ583246 | clade_85 | N | N |
| *Bacteroides* sp. 35BE35 | 306 | AJ583247 | clade_85 | N | N |
| *Bacteroides* sp. WH2 | 324 | AY895180 | clade_85 | N | N |
| *Bacteroides* sp. XB12B | 325 | AM230648 | clade_85 | N | N |
| *Bacteroides stercoris* | 327 | ABFZ02000022 | clade_85 | N | N |
| *Actinobacillus pleuropneumoniae* | 46 | NR_074857 | clade_88 | N | N |
| *Actinobacillus ureae* | 48 | AEVG01000167 | clade_88 | N | N |
| *Haemophilus aegyptius* | 969 | AFBC01000053 | clade_88 | N | N |
| *Haemophilus ducreyi* | 970 | AE017143 | clade_88 | N | OP |
| *Haemophilus haemolyticus* | 973 | JN175335 | clade_88 | N | N |
| *Haemophilus influenzae* | 974 | AADP01000001 | clade_88 | N | OP |
| *Haemophilus parahaemolyticus* | 975 | GU561425 | clade_88 | N | N |
| *Haemophilus parainfluenzae* | 976 | AEWU01000024 | clade_88 | N | N |
| *Haemophilus paraphrophaemolyticus* | 977 | M75076 | clade_88 | N | N |
| *Haemophilus somnus* | 979 | NC_008309 | clade_88 | N | N |
| *Haemophilus* sp. 70334 | 980 | HQ680854 | clade_88 | N | N |
| *Haemophilus* sp. HK445 | 981 | FJ685624 | clade_88 | N | N |
| *Haemophilus* sp. oral clone ASCA07 | 982 | AY923117 | clade_88 | N | N |
| *Haemophilus* sp. oral clone ASCG06 | 983 | AY923147 | clade_88 | N | N |
| *Haemophilus* sp. oral clone BJ021 | 984 | AY005034 | clade_88 | N | N |
| *Haemophilus* sp. oral clone BJ095 | 985 | AY005033 | clade_88 | N | N |
| *Haemophilus* sp. oral taxon 851 | 987 | AGRK01000004 | clade_88 | N | N |

TABLE 1-continued

See, e.g., WO 2014/121304

| OTU | SEQ ID Number | Public DB Accession | Clade | Spore Former | Pathogen Status |
|---|---|---|---|---|---|
| *Haemophilus sputorum* | 988 | AFNK01000005 | clade_88 | N | N |
| *Histophilus somni* | 1003 | AF549387 | clade_88 | N | N |
| *Mannheimia haemolytica* | 1195 | ACZX01000102 | clade_88 | N | N |
| *Pasteurella bettyae* | 1433 | L06088 | clade_88 | N | N |
| *Moellerella wisconsensis* | 1253 | JN175344 | clade_89 | N | N |
| *Morganella morganii* | 1265 | AJ301681 | clade_89 | N | N |
| *Morganella* sp. JB_T16 | 1266 | AJ781005 | clade_89 | N | N |
| *Proteus mirabilis* | 1582 | ACLE01000013 | clade_89 | N | N |
| *Proteus penneri* | 1583 | ABVP01000020 | clade_89 | N | N |
| *Proteus* sp. HS7514 | 1584 | DQ512963 | clade_89 | N | N |
| *Proteus vulgaris* | 1585 | AJ233425 | clade_89 | N | N |
| *Oribacterium sinus* | 1374 | ACKX01000142 | clade_90 | N | N |
| *Oribacterium* sp. ACB1 | 1375 | HM120210 | clade_90 | N | N |
| *Oribacterium* sp. ACB7 | 1376 | HM120211 | clade_90 | N | N |
| *Oribacterium* sp. CM12 | 1377 | HQ616374 | clade_90 | N | N |
| *Oribacterium* sp. ICM51 | 1378 | HQ616397 | clade_90 | N | N |
| *Oribacterium* sp. OBRC12 | 1379 | HQ616355 | clade_90 | N | N |
| *Oribacterium* sp. oral taxon 108 | 1382 | AFIH01000001 | clade_90 | N | N |
| *Actinobacillus actinomycetemcomitans* | 44 | AY362885 | clade_92 | N | N |
| *Actinobacillus succinogenes* | 47 | CP000746 | clade_92 | N | N |
| *Aggregatibacter actinomycetemcomitans* | 112 | CP001733 | clade_92 | N | N |
| *Aggregatibacter aphrophilus* | 113 | CP001607 | clade_92 | N | N |
| *Aggregatibacter segnis* | 114 | AEPS01000017 | clade_92 | N | N |
| *Averyella dalhousiensis* | 194 | DQ481464 | clade_92 | N | N |
| *Bisgaard Taxon* | 368 | AY683487 | clade_92 | N | N |
| *Bisgaard Taxon* | 369 | AY683489 | clade_92 | N | N |
| *Bisgaard Taxon* | 370 | AY683491 | clade_92 | N | N |
| *Bisgaard Taxon* | 371 | AY683492 | clade_92 | N | N |
| *Buchnera aphidicola* | 440 | NR_074609 | clade_92 | N | N |
| *Cedecea davisae* | 499 | AF493976 | clade_92 | N | N |
| *Citrobacter amalonaticus* | 517 | FR870441 | clade_92 | N | N |
| *Citrobacter braakii* | 518 | NR_028687 | clade_92 | N | N |
| *Citrobacter farmeri* | 519 | AF025371 | clade_92 | N | N |
| *Citrobacter freundii* | 520 | NR_028894 | clade_92 | N | N |
| *Citrobacter gillenii* | 521 | AF025367 | clade_92 | N | N |
| *Citrobacter koseri* | 522 | NC_009792 | clade_92 | N | N |
| *Citrobacter murliniae* | 523 | AF025369 | clade_92 | N | N |
| *Citrobacter rodentium* | 524 | NR_074903 | clade_92 | N | N |
| *Citrobacter sedlakii* | 525 | AF025364 | clade_92 | N | N |
| *Citrobacter* sp. 30_2 | 526 | ACDJ01000053 | clade_92 | N | N |
| *Citrobacter* sp. KMSI_3 | 527 | GQ468398 | clade_92 | N | N |
| *Citrobacter werkmanii* | 528 | AF025373 | clade_92 | N | N |
| *Citrobacter youngae* | 529 | ABWL02000011 | clade_92 | N | N |
| *Cronobacter malonaticus* | 737 | GU122174 | clade_92 | N | N |
| *Cronobacter sakazakii* | 738 | NC_009778 | clade_92 | N | N |
| *Cronobacter turicensis* | 739 | FN543093 | clade_92 | N | N |
| *Enterobacter aerogenes* | 786 | AJ251468 | clade_92 | N | N |
| *Enterobacter asburiae* | 787 | NR_024640 | clade_92 | N | N |
| *Enterobacter cancerogenus* | 788 | Z96078 | clade_92 | N | N |
| *Enterobacter cloacae* | 789 | FP929040 | clade_92 | N | N |
| *Enterobacter cowanii* | 790 | NR_025566 | clade_92 | N | N |
| *Enterobacter hormaechei* | 791 | AFHR01000079 | clade_92 | N | N |
| *Enterobacter* sp. 247BMC | 792 | HQ122932 | clade_92 | N | N |
| *Enterobacter* sp. 638 | 793 | NR_074777 | clade_92 | N | N |
| *Enterobacter* sp. JC163 | 794 | JN657217 | clade_92 | N | N |
| *Enterobacter* sp. SCSS | 795 | HM007811 | clade_92 | N | N |
| *Enterobacter* sp. TSE38 | 796 | HM156134 | clade_92 | N | N |
| Enterobacteriaceae bacterium 9_2_54FAA | 797 | ADCU01000033 | clade_92 | N | N |
| Enterobacteriaceae bacterium CF01Ent_1 | 798 | AJ489826 | clade_92 | N | N |
| Enterobacteriaceae bacterium Smarlab 3302238 | 799 | AY538694 | clade_92 | N | N |
| *Escherichia albertii* | 824 | ABKX01000012 | clade_92 | N | N |
| *Escherichia coli* | 825 | NC_008563 | clade_92 | N | Category-B |
| *Escherichia fergusonii* | 826 | CU928158 | clade_92 | N | N |
| *Escherichia hermannii* | 827 | HQ407266 | clade_92 | N | N |
| *Escherichia* sp. 1_1_43 | 828 | ACID01000033 | clade_92 | N | N |
| *Escherichia* sp. 4_1_40B | 829 | ACDM02000056 | clade_92 | N | N |
| *Escherichia* sp. B4 | 830 | EU722735 | clade_92 | N | N |
| *Escherichia vulneris* | 831 | NR_041927 | clade_92 | N | N |
| *Ewingella americana* | 877 | JN175329 | clade_92 | N | N |

TABLE 1-continued

See, e.g., WO 2014/121304

| OTU | SEQ ID Number | Public DB Accession | Clade | Spore Former | Pathogen Status |
|---|---|---|---|---|---|
| *Haemophilus* genomosp. P2 oral clone MB3_C24 | 971 | DQ003621 | clade_92 | N | N |
| *Haemophilus* genomosp. P3 oral clone MB3_C38 | 972 | DQ003635 | clade_92 | N | N |
| *Haemophilus* sp. oral clone JM053 | 986 | AY349380 | clade_92 | N | N |
| *Hafnia alvei* | 989 | DQ412565 | clade_92 | N | N |
| *Klebsiella oxytoca* | 1024 | AY292871 | clade_92 | N | OP |
| *Klebsiella pneumoniae* | 1025 | CP000647 | clade_92 | N | OP |
| *Klebsiella* sp. AS10 | 1026 | HQ616362 | clade_92 | N | N |
| *Klebsiella* sp. Co9935 | 1027 | DQ068764 | clade_92 | N | N |
| *Klebsiella* sp. enrichment culture clone SRC_DSD25 | 1036 | HM195210 | clade_92 | N | N |
| *Klebsiella* sp. OBRC7 | 1028 | HQ616353 | clade_92 | N | N |
| *Klebsiella* sp. SP_BA | 1029 | FJ999767 | clade_92 | N | N |
| *Klebsiella* sp. SRC_DSD1 | 1033 | GU797254 | clade_92 | N | N |
| *Klebsiella* sp. SRC_DSD11 | 1030 | GU797263 | clade_92 | N | N |
| *Klebsiella* sp. SRC_DSD12 | 1031 | GU797264 | clade_92 | N | N |
| *Klebsiella* sp. SRC_DSD15 | 1032 | GU797267 | clade_92 | N | N |
| *Klebsiella* sp. SRC_DSD2 | 1034 | GU797253 | clade_92 | N | N |
| *Klebsiella* sp. SRC_DSD6 | 1035 | GU797258 | clade_92 | N | N |
| *Klebsiella variicola* | 1037 | CP001891 | clade_92 | N | N |
| *Kluyvera ascorbata* | 1038 | NR_028677 | clade_92 | N | N |
| *Kluyvera cryocrescens* | 1039 | NR_028803 | clade_92 | N | N |
| *Leminorella grimontii* | 1159 | AJ233421 | clade_92 | N | N |
| *Leminorella richardii* | 1160 | HF558368 | clade_92 | N | N |
| *Pantoea agglomerans* | 1409 | AY335552 | clade_92 | N | N |
| *Pantoea ananatis* | 1410 | CP001875 | clade_92 | N | N |
| *Pantoea brenneri* | 1411 | EU216735 | clade_92 | N | N |
| *Pantoea citrea* | 1412 | EF688008 | clade_92 | N | N |
| *Pantoea conspicua* | 1413 | EU216737 | clade_92 | N | N |
| *Pantoea septica* | 1414 | EU216734 | clade_92 | N | N |
| *Pasteurella dagmatis* | 1434 | ACZR01000003 | clade_92 | N | N |
| *Pasteurella multocida* | 1435 | NC_002663 | clade_92 | N | N |
| *Plesiomonas shigelloides* | 1469 | X60418 | clade_92 | N | N |
| *Raoultella ornithinolytica* | 1617 | AB364958 | clade_92 | N | N |
| *Raoultella planticola* | 1618 | AF129443 | clade_92 | N | N |
| *Raoultella terrigena* | 1619 | NR_037085 | clade_92 | N | N |
| *Salmonella bongori* | 1683 | NR_041699 | clade_92 | N | Category-B |
| *Salmonella enterica* | 1672 | NC_011149 | clade_92 | N | Category-B |
| *Salmonella enterica* | 1673 | NC_011205 | clade_92 | N | Category-B |
| *Salmonella enterica* | 1674 | DQ344532 | clade_92 | N | Category-B |
| *Salmonella enterica* | 1675 | ABEH02000004 | clade_92 | N | Category-B |
| *Salmonella enterica* | 1676 | ABAK02000001 | clade_92 | N | Category-B |
| *Salmonella enterica* | 1677 | NC_011080 | clade_92 | N | Category-B |
| *Salmonella enterica* | 1678 | EU118094 | clade_92 | N | Category-B |
| *Salmonella enterica* | 1679 | NC_011094 | clade_92 | N | Category-B |
| *Salmonella enterica* | 1680 | AE014613 | clade_92 | N | Category-B |
| *Salmonella enterica* | 1682 | ABFH02000001 | clade_92 | N | Category-B |
| *Salmonella enterica* | 1684 | ABEM01000001 | clade_92 | N | Category-B |
| *Salmonella enterica* | 1685 | ABAM02000001 | clade_92 | N | Category-B |
| *Salmonella typhimurium* | 1681 | DQ344533 | clade_92 | N | Category-B |
| *Salmonella typhimurium* | 1686 | AF170176 | clade_92 | N | Category-B |
| *Serratia fonticola* | 1718 | NR_025339 | clade_92 | N | N |
| *Serratia liquefaciens* | 1719 | NR_042062 | clade_92 | N | N |
| *Serratia marcescens* | 1720 | GU826157 | clade_92 | N | N |
| *Serratia odorifera* | 1721 | ADBY01000001 | clade_92 | N | N |
| *Serratia proteamaculans* | 1722 | AAUN01000015 | clade_92 | N | N |
| *Shigella boydii* | 1724 | AAKA01000007 | clade_92 | N | Category-B |
| *Shigella dysenteriae* | 1725 | NC_007606 | clade_92 | N | Category-B |
| *Shigella flexneri* | 1726 | AE005674 | clade_92 | N | Category-B |
| *Shigella sonnei* | 1727 | NC_007384 | clade_92 | N | Category-B |
| *Tatumella ptyseos* | 1916 | NR_025342 | clade_92 | N | N |
| *Trabulsiella guamensis* | 1925 | AY373830 | clade_92 | N | N |
| *Yersinia aldovae* | 2019 | AJ871363 | clade_92 | N | OP |
| *Yersinia aleksiciae* | 2020 | AJ627597 | clade_92 | N | OP |
| *Yersinia bercovieri* | 2021 | AF366377 | clade_92 | N | OP |
| *Yersinia enterocolitica* | 2022 | FR729477 | clade_92 | N | Category-B |
| *Yersinia frederiksenii* | 2023 | AF366379 | clade_92 | N | OP |
| *Yersinia intermedia* | 2024 | AF366380 | clade_92 | N | OP |
| *Yersinia kristensenii* | 2025 | ACCA01000078 | clade_92 | N | OP |
| *Yersinia mollaretii* | 2026 | NR_027546 | clade_92 | N | OP |
| *Yersinia pestis* | 2027 | AE013632 | clade_92 | N | Category-A |
| *Yersinia pseudotuberculosis* | 2028 | NC_009708 | clade_92 | N | OP |
| *Yersinia rohdei* | 2029 | ACCD01000071 | clade_92 | N | OP |

TABLE 1-continued

See, e.g., WO 2014/121304

| OTU | SEQ ID Number | Public DB Accession | Clade | Spore Former | Pathogen Status |
|---|---|---|---|---|---|
| *Yokenella regensburgei* | 2030 | AB273739 | clade_92 | N | N |
| *Conchiformibius kuhniae* | 669 | NR_041821 | clade_94 | N | N |
| *Morococcus cerebrosus* | 1267 | JN175352 | clade_94 | N | N |
| *Neisseria bacilliformis* | 1328 | AFAY01000058 | clade_94 | N | N |
| *Neisseria cinerea* | 1329 | ACDY01000037 | clade_94 | N | N |
| *Neisseria flavescens* | 1331 | ACQV01000025 | clade_94 | N | N |
| *Neisseria gonorrhoeae* | 1333 | CP002440 | clade_94 | N | OP |
| *Neisseria lactamica* | 1334 | ACEQ01000095 | clade_94 | N | N |
| *Neisseria macacae* | 1335 | AFQE01000146 | clade_94 | N | N |
| *Neisseria meningitidis* | 1336 | NC_003112 | clade_94 | N | OP |
| *Neisseria mucosa* | 1337 | ACDX01000110 | clade_94 | N | N |
| *Neisseria pharyngis* | 1338 | AJ239281 | clade_94 | N | N |
| *Neisseria polysaccharea* | 1339 | ADBE01000137 | clade_94 | N | N |
| *Neisseria sicca* | 1340 | ACKO02000016 | clade_94 | N | N |
| *Neisseria sp.* KEM232 | 1341 | GQ203291 | clade_94 | N | N |
| *Neisseria sp.* oral clone AP132 | 1344 | AY005027 | clade_94 | N | N |
| *Neisseria sp.* oral strain B33KA | 1346 | AY005028 | clade_94 | N | N |
| *Neisseria sp.* oral taxon 014 | 1347 | ADEA01000039 | clade_94 | N | N |
| *Neisseria sp.* TM10_1 | 1343 | DQ279352 | clade_94 | N | N |
| *Neisseria subflava* | 1348 | ACEO01000067 | clade_94 | N | N |
| *Okadaella gastrococcus* | 1365 | HQ699465 | clade_98 | N | N |
| *Streptococcus agalactiae* | 1785 | AAJO01000130 | clade_98 | N | N |
| *Streptococcus alactolyticus* | 1786 | NR_041781 | clade_98 | N | N |
| *Streptococcus australis* | 1788 | AEQR01000024 | clade_98 | N | N |
| *Streptococcus bovis* | 1789 | AEEL01000030 | clade_98 | N | N |
| *Streptococcus canis* | 1790 | AJ413203 | clade_98 | N | N |
| *Streptococcus constellatus* | 1791 | AY277942 | clade_98 | N | N |
| *Streptococcus cristatus* | 1792 | AEVC01000028 | clade_98 | N | N |
| *Streptococcus dysgalactiae* | 1794 | AP010935 | clade_98 | N | N |
| *Streptococcus equi* | 1795 | CP001129 | clade_98 | N | N |
| *Streptococcus equinus* | 1796 | AEVB01000043 | clade_98 | N | N |
| *Streptococcus gallolyticus* | 1797 | FR824043 | clade_98 | N | N |
| *Streptococcus genomosp.* C1 | 1798 | AY278629 | clade_98 | N | N |
| *Streptococcus genomosp.* C2 | 1799 | AY278630 | clade_98 | N | N |
| *Streptococcus genomosp.* C3 | 1800 | AY278631 | clade_98 | N | N |
| *Streptococcus genomosp.* C4 | 1801 | AY278632 | clade_98 | N | N |
| *Streptococcus genomosp.* C5 | 1802 | AY278633 | clade_98 | N | N |
| *Streptococcus genomosp.* C6 | 1803 | AY278634 | clade_98 | N | N |
| *Streptococcus genomosp.* C7 | 1804 | AY278635 | clade_98 | N | N |
| *Streptococcus genomosp.* C8 | 1805 | AY278609 | clade_98 | N | N |
| *Streptococcus gordonii* | 1806 | NC_009785 | clade_98 | N | N |
| *Streptococcus infantarius* | 1807 | ABJK02000017 | clade_98 | N | N |
| *Streptococcus infantis* | 1808 | AFNN01000024 | clade_98 | N | N |
| *Streptococcus intermedius* | 1809 | NR_028736 | clade_98 | N | N |
| *Streptococcus lutetiensis* | 1810 | NR_037096 | clade_98 | N | N |
| *Streptococcus massiliensis* | 1811 | AY769997 | clade_98 | N | N |
| *Streptococcus mitis* | 1813 | AM157420 | clade_98 | N | N |
| *Streptococcus oligofermentans* | 1815 | AY099095 | clade_98 | N | N |
| *Streptococcus oralis* | 1816 | ADMV01000001 | clade_98 | N | N |
| *Streptococcus parasanguinis* | 1817 | AEKM01000012 | clade_98 | N | N |
| *Streptococcus pasteurianus* | 1818 | AP012054 | clade_98 | N | N |
| *Streptococcus peroris* | 1819 | AEVF01000016 | clade_98 | N | N |
| *Streptococcus pneumoniae* | 1820 | AE008537 | clade_98 | N | N |
| *Streptococcus porcinus* | 1821 | EF121439 | clade_98 | N | N |
| *Streptococcus pseudopneumoniae* | 1822 | FJ827123 | clade_98 | N | N |
| *Streptococcus pseudoporcinus* | 1823 | AENS01000003 | clade_98 | N | N |
| *Streptococcus pyogenes* | 1824 | AE006496 | clade_98 | N | OP |
| *Streptococcus ratti* | 1825 | X58304 | clade_98 | N | N |
| *Streptococcus sanguinis* | 1827 | NR_074974 | clade_98 | N | N |
| *Streptococcus sinensis* | 1828 | AF432857 | clade_98 | N | N |
| *Streptococcus sp.* 2_1_36FAA | 1831 | ACOI01000028 | clade_98 | N | N |

TABLE 1-continued

See, e.g., WO 2014/121304

| OTU | SEQ ID Number | Public DB Accession | Clade | Spore Former | Pathogen Status |
|---|---|---|---|---|---|
| *Streptococcus* sp. 2285_97 | 1830 | AJ131965 | clade_98 | N | N |
| *Streptococcus* sp. ACS2 | 1834 | HQ616360 | clade_98 | N | N |
| *Streptococcus* sp. AS20 | 1835 | HQ616366 | clade_98 | N | N |
| *Streptococcus* sp. BS35a | 1836 | HQ616369 | clade_98 | N | N |
| *Streptococcus* sp. C150 | 1837 | ACRI01000045 | clade_98 | N | N |
| *Streptococcus* sp. CM6 | 1838 | HQ616372 | clade_98 | N | N |
| *Streptococcus* sp. ICM10 | 1840 | HQ616389 | clade_98 | N | N |
| *Streptococcus* sp. ICM12 | 1841 | HQ616390 | clade_98 | N | N |
| *Streptococcus* sp. ICM2 | 1842 | HQ616386 | clade_98 | N | N |
| *Streptococcus* sp. ICM4 | 1844 | HQ616387 | clade_98 | N | N |
| *Streptococcus* sp. ICM45 | 1843 | HQ616394 | clade_98 | N | N |
| *Streptococcus* sp. M143 | 1845 | ACRK01000025 | clade_98 | N | N |
| *Streptococcus* sp. M334 | 1846 | ACRL01000052 | clade_98 | N | N |
| *Streptococcus* sp. oral clone ASB02 | 1849 | AY923121 | clade_98 | N | N |
| *Streptococcus* sp. oral clone ASCA03 | 1850 | DQ272504 | clade_98 | N | N |
| *Streptococcus* sp. oral clone ASCA04 | 1851 | AY923116 | clade_98 | N | N |
| *Streptococcus* sp. oral clone ASCA09 | 1852 | AY923119 | clade_98 | N | N |
| *Streptococcus* sp. oral clone ASCB04 | 1853 | AY923123 | clade_98 | N | N |
| *Streptococcus* sp. oral clone ASCB06 | 1854 | AY923124 | clade_98 | N | N |
| *Streptococcus* sp. oral clone ASCC04 | 1855 | AY923127 | clade_98 | N | N |
| *Streptococcus* sp. oral clone ASCC05 | 1856 | AY923128 | clade_98 | N | N |
| *Streptococcus* sp. oral clone ASCC12 | 1857 | DQ272507 | clade_98 | N | N |
| *Streptococcus* sp. oral clone ASCD01 | 1858 | AY923129 | clade_98 | N | N |
| *Streptococcus* sp. oral clone ASCD09 | 1859 | AY923130 | clade_98 | N | N |
| *Streptococcus* sp. oral clone ASCD10 | 1860 | DQ272509 | clade_98 | N | N |
| *Streptococcus* sp. oral clone ASCE03 | 1861 | AY923134 | clade_98 | N | N |
| *Streptococcus* sp. oral clone ASCE04 | 1862 | AY953253 | clade_98 | N | N |
| *Streptococcus* sp. oral clone ASCE05 | 1863 | DQ272510 | clade_98 | N | N |
| *Streptococcus* sp. oral clone ASCE06 | 1864 | AY923135 | clade_98 | N | N |
| *Streptococcus* sp. oral clone ASCE09 | 1865 | AY923136 | clade_98 | N | N |
| *Streptococcus* sp. oral clone ASCE10 | 1866 | AY923137 | clade_98 | N | N |
| *Streptococcus* sp. oral clone ASCE12 | 1867 | AY923138 | clade_98 | N | N |
| *Streptococcus* sp. oral clone ASCF05 | 1868 | AY923140 | clade_98 | N | N |
| *Streptococcus* sp. oral clone ASCF07 | 1869 | AY953255 | clade_98 | N | N |
| *Streptococcus* sp. oral clone ASCF09 | 1870 | AY923142 | clade_98 | N | N |
| *Streptococcus* sp. oral clone ASCG04 | 1871 | AY923145 | clade_98 | N | N |
| *Streptococcus* sp. oral clone BW009 | 1872 | AY005042 | clade_98 | N | N |
| *Streptococcus* sp. oral clone CH016 | 1873 | AY005044 | clade_98 | N | N |
| *Streptococcus* sp. oral clone GK051 | 1874 | AY349413 | clade_98 | N | N |
| *Streptococcus* sp. oral clone GM006 | 1875 | AY349414 | clade_98 | N | N |
| *Streptococcus* sp. oral clone P2PA_41 P2 | 1876 | AY207051 | clade_98 | N | N |
| *Streptococcus* sp. oral clone P4PA_30 P4 | 1877 | AY207064 | clade_98 | N | N |
| *Streptococcus* sp. oral taxon 071 | 1878 | AEEP01000019 | clade_98 | N | N |
| *Streptococcus* sp. oral taxon G59 | 1879 | GU432132 | clade_98 | N | N |

TABLE 1-continued

See, e.g., WO 2014/121304

| OTU | SEQ ID Number | Public DB Accession | Clade | Spore Former | Pathogen Status |
|---|---|---|---|---|---|
| *Streptococcus* sp. oral taxon G62 | 1880 | GU432146 | clade_98 | N | N |
| *Streptococcus* sp. oral taxon G63 | 1881 | GU432150 | clade_98 | N | N |
| *Streptococcus suis* | 1882 | FM252032 | clade_98 | N | N |
| *Streptococcus thermophilus* | 1883 | CP000419 | clade_98 | N | N |
| *Streptococcus salivarius* | 1826 | AGBV01000001 | clade_98 | N | N |
| *Streptococcus uberis* | 1884 | HQ391900 | clade_98 | N | N |
| *Streptococcus urinalis* | 1885 | DQ303194 | clade_98 | N | N |
| *Streptococcus vestibularis* | 1886 | AEKO01000008 | clade_98 | N | N |
| *Streptococcus viridans* | 1887 | AF076036 | clade_98 | N | N |
| Synergistetes bacterium oral clone 03 5 D05 | 1908 | GU227192 | clade_98 | N | N |

TABLE 1A

Exemplary Immunomodulatory Bacterial Species

*Alkaliphilus metalliredigens*
*Ammonifex degensii*
*Anaerofustis stercorihominis*
*Anaerostipes caccae*
*Anaerotruncus colihominis*
*Bacillus amyloliquefaciens*
*Bacillus anthracis*
*Bacillus cellulosilyticus*
*Bacillus cereus*
*Bacillus clausii*
*Bacillus coagulans*
*Bacillus cytotoxicus*
*Bacillus halodurans*
*Bacillus licheniformis*
*Bacillus pumilus*
*Bacillus subtilis*
*Bacillus thuringiensis*
*Bacillus weihenstephanensis*
*Blautia (Ruminococcus) hansenii*
*Blautia (Ruminococcus) obeum*
*Brevibacillus brevis*
*Bryantella formatexigens*
*Caldicellulosiruptor saccharolyticus*
*Candidatus Desulforudis audaxviator*
*Carboxydibrachium pacificum*
*Carboxydothermus hydrogenoformans*
*Clostridium acetobutylicum*
*Clostridium asparagiforme*
*Clostridium bartlettii*
*Clostridium beijerinckii*
*Clostridium bolteae*
*Clostridium botulinum* A str. ATCC 19397
*Clostridium botulinum* B str. Eklund 17B
*Clostridium butyricum* pathogenic E4 str. BoNT BL5262
*Clostridium carboxid

TABLE 1B-continued

Exemplary Bacteria Useful in the Present Invention

*Bacteroides uniformis*
*Bacteroides vulgatus*
*Bifidobacterium adolescentis*
*Bifidobacterium bifidum*
*Bifidobacterium breve*
*Bifidobacterium faecale*
*Bifidobacterium kashiwanohense*
*Bifidobacterium longum* subsp. *longum*
*Bifidobacterium pseudocatenulatum*
*Bifidobacterium stercoris*
*Blautia (Ruminococcus) coccoides*
*Blautia faecis*
*Blautia glucerasea*
*Blautia (Ruminococcus) hansenii*
*Blautia hydrogenotrophica (Ruminococcus hydrogenotrophicus)*
*Blautia (Ruminococcus) luti*
*Blautia (Ruminococcus) obeum*
*Blautia producta (Ruminococcus productus)*
*Blautia (Ruminococcus) schinkii*
*Blautia stercoris*
*Blautia* uncultured *bacterium* clone BKLE_a03_2 (GenBank: EU469501.1)
*Blautia* uncultured *bacterium* clone SJTU_B_14_30 (GenBank: EF402926.1)
*Blautia* uncultured *bacterium* clone SJTU_C_14_16 (GenBank: EF404657.1)
*Blautia* uncultured *bacterium* clone S1-5 (GenBank: GQ898099.1)
*Blautia* uncultured PAC000178_s (www.ezbiocloud.net/eztaxon/hierarchy?m=browse&k=PAC000178&d=2)
*Blautia wexlerae*
*Candidatus Arthromitus* sp. SFB-mouse-Yit
*Catenibacterium mitsuokai*
Clostridiaceae *bacterium (Dielma fastidiosa)* JC13
Clostridiales *bacterium* 1_7_47FAA
*Clostridium asparagiforme*
*Clostridium bolteae*
*Clostridium clostridioforme*
*Clostridium glycyrrhizinilyticum*
*Clostridium (Hungatella) hathewayi*
*Clostridium histolyticum*
*Clostridium indolis*
*Clostridium leptum*
*Clostridium (Tyzzerella) nexile*
*Clostridium perfringens*
*Clostridium (Erysipelatoclostridium) ramosum*
*Clostridium scindens*
*Clostridium* sp. 14774
*Clostridium* sp. 7_3_54FAA
*Clostridium* sp. HGF2
*Clostridium symbiosum*
*Collinsella aerofaciens*
*Collinsella intestinalis*
*Coprobacillus* sp. D7
*Coprococcus catus*
*Coprococcus comes*
*Dorea formicigenerans*
*Dorea longicatena*
*Enterococcus faecalis*
*Enterococcus faecium*
Erysipelotrichaceae *bacterium* 3_1_53
*Escherichia coli*
*Escherichia coli* S88
*Eubacterium eligens*
*Eubacterium fissicatena*
*Eubacterium ramulus*
*Eubacterium rectale*
*Faecalibacterium prausnitzii*
*Flavonifractor plautii*
*Fusobacterium mortiferum*
*Fusobacterium nucleatum*
*Holdemania filiformis*
*Hydrogenoanaerobacterium saccharovorans*
*Klebsiella oxytoca*
Lachnospiraceae *bacterium* 3_1_57FAA_CT1
Lachnospiraceae *bacterium* 7_1_58FAA
Lachnospiraceae *bacterium* 5_1_57FAA
*Lactobacillus casei*
*Lactobacillus rhamnosus*

TABLE 1B-continued

Exemplary Bacteria Useful in the Present Invention

*Lactobacillus ruminis*
*Lactococcus casei*
*Odoribacter splanchnicus*
*Oscillibacter valericigenes*
*Parabacteroides gordonii*
*Parabacteroides johnsonii*
*Parabacteroides merdae*
*Pediococcus acidilactici*
*Peptostreptococcus asaccharolyticus*
*Propionibacterium granulosum*
*Roseburia intestinalis*
*Roseburia inulinivorans*
*Ruminococcus faecis*
*Ruminococcus gnavus*
*Ruminococcus* sp. ID8
*Ruminococcus torques*
*Slackia piriformis*
*Staphylococcus epidermidis*
*Staphylococcus saprophyticus*
*Streptococcus cristatus*
*Streptococcus dysgalactiae* subsp. *equisimilis*
*Streptococcus infantis*
*Streptococcus oralis*
*Streptococcus sanguinis*
*Streptococcus viridans*
*Streptococcus thermophilus*
*Veillonella dispar*

TABLE 1C

Exemplary Bacteria Useful in the Present Invention

*Anaerotruncus colihominis* strain 13
*Blautia producta* strain 6
*Clostridium bolteae* strain 7
Clostridiaceae *bacterium* JC13 strain 8
Clostridiales *bacterium* 1_7_47FAA strain 28
*Clostridium* sp. 7_3_54FAA strain 16
*Clostridium asparagiforme* strain 15
*Clostridium clostridioforme*
*Clostridium (Hungatella) hathewayi* strain 4
*Clostridium indolis* strain 9
*Clostridium (Erysipelatoclostridium) ramosum* strain 18
*Clostridium scindens* strain 26
*Clostridium* sp. 14774 strain 1
*Eubacterium fissicatena* strain 21
*Hydrogenoanaerobacterium saccharovorans*
Lachnospiraceae *bacterium* 3_1_57FAA strain 27
Lachnospiraceae *bacterium* 3_1_57FAA strain 29
Lachnospiraceae *bacterium* 7_1_58FAA strain 3
*Oscillibacter valericigenes*
*Ruminococcus* sp. ID8 strain 14

TABLE 1D

Exemplary Bacteria Useful in the Present Invention

*Bacteroides caccae*
*Bacteroides eggerthii*
*Bacteroides ovatus*
*Bacteroides* sp. 1_1_6
*Bacteroides* sp. 3_1_23
*Bacteroides* sp. D20
*Bacteroides vulgatus*
*Bifidobacterium adolescentis*
*Bifidobacterium pseudocatenulatum*
*Blautia (Ruminococcus) obeum*
*Blautia producta (Ruminococcus productus)*
*Blautia (Ruminococcus) schinkii*
*Clostridium (Hungatella) hathewayi*
*Clostridium (Tyzzerella) nexile*
*Clostridium* sp. HGF2
*Clostridium symbiosum*

TABLE 1D-continued

Exemplary Bacteria Useful in the Present Invention

*Collinsella aerofaciens*
*Coprobacillus* sp. D7
*Coprococcus catus*
*Coprococcus comes*
*Dorea formicigenerans*
*Dorea longicatena*
*Enterococcus faecalis*
Erysipelotrichaceae bacterium 3_1_53
*Escherichia coli*
*Escherichia coli* S88
*Eubacterium eligens*
*Eubacterium rectale*
*Faecalibacterium prausnitzii*
Lachnospiraceae bacterium 5_1_57FAA
*Odoribacter splanchnicus*
*Parabacteroides merdae*
*Roseburia intestinalis*
*Ruminococcus torques*
*Streptococcus thermophilus*

TABLE 1E

Exemplary Bacteria Useful in the Present Invention

*Akkermansia muciniphila*
*Enterococcus faecalis*
*Klebsiella oxytoca*
*Lactobacillus rhamnosus*
*Staphylococcus epidermidis*
*Streptococcus viridans*
*Veillonella dispar*

TABLE 1F

Exemplary Bacteria Useful in the Present Invention

*Acinetobacter baumannii*
*Acinetobacter lwoffii*
*Akkermansia muciniphila*
*Alistipes shahii*
*Anaerotruncus colihominis*
*Bacteroides caccae*
*Bacteroides dorei*
*Bacteroides eggerthii*
*Bacteroides finegoldii*
*Bacteroides fragilis*
*Bacteroides massiliensis*
*Bacteroides ovatus*
*Bacteroides salanitronis*
*Bacteroides* sp. 1_1_6
*Bacteroides* sp. 3_1_23
*Bacteroides* sp. D20
*Bacteroides thetaiotaomicron*
*Bacteroides uniformis*
*Bacteroides vulgatus*
*Bifidobacterium adolescentis*
*Bifidobacterium breve*
*Bifidobacterium pseudocatenulatum*
*Blautia (Ruminococcus) coccoides*
*Blautia faecis*
*Blautia glucerasea*
*Blautia (Ruminococcus) hansenii*
*Blautia hydrogenotrophica (Ruminococcus hydrogenotrophicus)*
*Blautia (Ruminococcus) luti*
*Blautia (Ruminococcus) obeum*
*Blautia producta (Ruminococcus productus)*
*Blautia (Ruminococcus) schinkii*
*Blautia stercoris*
*Blautia wexlerae*
*Candidatus Arthromitus* sp. SFB-mouse-Yit
Clostridiaceae bacterium (*Dielma fastidiosa*) JC13
Clostridiales bacterium 1_7_47FAA
*Clostridium asparagiforme*

TABLE 1F-continued

Exemplary Bacteria Useful in the Present Invention

*Clostridium bolteae*
*Clostridium clostridioforme*
*Clostridium (Hungatella) hathewayi*
*Clostridium histolyticum*
*Clostridium indolis*
*Clostridium leptum*
*Clostridium (Tyzzerella) nexile*
*Clostridium perfringens*
*Clostridium (Erysipelatoclostridium) ramosum*
*Clostridium scindens*
*Clostridium* sp. 14774
*Clostridium* sp. 7_3_54FAA
*Clostridium* sp. HGF2
*Clostridium symbiosum*
*Collinsella aerofaciens*
*Coprobacillus* sp. D7
*Coprococcus catus*
*Coprococcus comes*
*Dorea formicigenerans*
*Dorea longicatena*
*Enterococcus faecium*
Erysipelotrichaceae bacterium 3_1_53
*Escherichia coli*
*Escherichia coli* S88
*Eubacterium eligens*
*Eubacterium fissicatena*
*Eubacterium rectale*
*Faecalibacterium prausnitzii*
*Fusobacterium mortiferum*
*Fusobacterium nucleatum*
Hydrogenoanaerobacterium *saccharovorans*
Lachnospiraceae bacterium 3_1_57FAA_CT1
Lachnospiraceae bacterium 7_1_58FAA
Lachnospiraceae bacterium 5_1_57FAA
*Lactobacillus casei*
*Lactococcus casei*
*Odoribacter splanchnicus*
*Oscillibacter valericigenes*
*Parabacteroides johnsonii*
*Parabacteroides merdae*
*Pediococcus acidilactici*
*Peptostreptococcus asaccharolyticus*
*Propionibacterium granulosum*
*Roseburia intestinalis*
*Ruminococcus gnavus*
*Ruminococcus* sp. ID8
*Ruminococcus torques*
*Staphylococcus saprophyticus*
*Streptococcus thermophilus*

TABLE 2A

Species identified as germinable and sporulatable by colony picking

| OTU | BBA | GAM + FOS/inulin | M2GSC | Sweet B + FOS/Inulin | Sweet GAM | Total |
|---|---|---|---|---|---|---|
| *Blautia producta* | 1 | | | | | 1 |
| *Clostridium bartlettii* | 4 | | 1 | | | 5 |
| *Clostridium bolteae* | 2 | | | 5 | 1 | 8 |
| *Clostridium botulinum* | | | | 5 | | 5 |
| *Clostridium butyricum* | 37 | 43 | 8 | 1 | 33 | 122 |
| *Clostridium celatum* | 4 | | | | 1 | 5 |
| *Clostridium clostridioforme* | 1 | | | | 1 | 2 |
| *Clostridium disporicum* | 26 | 26 | 22 | 33 | 50 | 157 |
| *Clostridium glycolicum* | 4 | 9 | 14 | | | 27 |
| *Clostridium mayombei* | 2 | 2 | | | | 4 |
| *Clostridium paraputrificum* | 8 | 8 | 33 | 16 | 6 | 71 |
| *Clostridium sordellii* | | | 14 | | | 14 |
| *Clostridium* sp. 7_2_43FAA | | 1 | | | | 1 |
| *Clostridium symbiosum* | 3 | | | | | 3 |
| *Clostridium tertium* | | 1 | | 1 | | 2 |
| (blank) | | 2 | | 31 | | 33 |
| Totals | 92 | 92 | 92 | 92 | 92 | 460 |

TABLE 2B

| Species identified as germinable by 16S colony pick approach |
|---|
| *Clostridium paraputrificum* |
| *Clostridium disporicum* |
| *Clostridium glycolicum* |
| *Clostridium bartlettii* |
| *Clostridium butyricum* |
| *Ruminococcus bromii* |
| Lachnospiraceae bacterium 2_1_58FAA |
| *Eubacterium hadrum* |
| *Turicibacter sanguinis* |
| Lachnospiraceae bacterium oral taxon F15 |
| *Clostridium perfringens* |
| *Clostridium bifermentans* |
| *Roseburia* sp 11SE37 |
| *Clostridium quinii* |
| *Ruminococcus lactaris* |
| *Clostridium botulinum* |
| *Clostridium tyrobutyricum* |
| *Blautia hansenii* |
| *Clostridium kluyveri* |
| *Clostridium* sp JC122 |
| *Clostridium hylemonae* |
| *Clostridium celatum* |
| *Clostridium straminisolvens* |
| *Clostridium orbiscindens* |
| *Roseburia cecicola* |
| *Eubacterium tenue* |
| *Clostridium* sp. 7_2_43FAA |
| Lachnospiraceae bacterium 4_1_37FAA |
| *Eubacterium rectale* |
| *Clostridium viride* |
| *Ruminococcus* sp. K_1 |
| *Clostridium symbiosum* |
| *Ruminococcus torques* |
| *Clostridium algidicarnis* |

TABLE 2C

| Species identified as sporulatable by 16S NGS approach |
|---|
| *Clostridium paraputrificum* |
| *Clostridium bartlettii* |
| Lachnospiraceae bacterium 2_1_58FAA |
| *Clostridium disporicum* |
| *Ruminococcus bromii* |
| *Eubacterium hadrum* |
| *Clostridium butyricum* |
| *Roseburia* sp. 11SE37 |

TABLE 2C-continued

| Species identified as sporulatable by 16S NGS approach |
|---|
| *Clostridium perfringens* |
| *Clostridium glycolicum* |
| *Clostridium hylemonae* |
| *Clostridium orbiscindens* |
| *Ruminococcus lactaris* |
| *Clostridium symbiosum* |
| Lachnospiraceae bacterium oral taxon F15 |
| *Blautia hansenii* |
| *Turicibacter sanguinis* |
| *Clostridium straminisolvens* |
| *Clostridium botulinum* |
| Lachnospiraceae bacterium 4_1_37FAA |
| *Roseburia cecicola* |
| *Ruminococcus* sp. K_1 |
| *Clostridium bifermentans* |
| *Eubacterium rectale* |
| *Clostridium quinii* |
| *Clostridium viride* |
| *Clostridium kluyveri* |
| *Clostridium tyrobutyricum* |
| *Oscillibacter* sp. G2 |
| *Clostridium* sp. JC122 |
| Lachnospiraceae bacterium 3_1_57FAA |
| *Clostridium aldenense* |
| *Ruminococcus torques* |
| *Clostridium* sp. 7_2_43FAA |
| *Clostridium celatum* |
| *Eubacterium* sp. WAL_14571 |
| *Eubacterium tenue* |
| Lachnospiraceae bacterium 5_1_57FAA |
| *Clostridium clostridioforme* |
| *Clostridium* sp. YIT_12070 |
| *Blautia* sp. M25 |
| *Anaerostipes caccae* |
| *Roseburia inulinivorans* |
| *Clostridium* sp. D5 |
| *Clostridium asparagiforme* |
| *Coprobacillus* sp. D7 |
| *Clostridium* sp. HGF2 |
| *Clostridium citroniae* |
| *Clostridium difficile* |
| *Oscillibacter valericigenes* |
| *Clostridium algidicarnis* |

TABLE 3

Anaerobic bacterial species tested for carbon source usage (Biolog plates)

| Species purchased: | Species Freshly Isolated: |
|---|---|
| R. gnavus (EPV1) | Blautia luti BlnIX (EPV114) |
| E. rectale (EPV2) | Blautia luti ELU (EPV54) |
| B. luti (EPV3) | Ruminococcus gnavus (EPV102) |
| B. wexlerae (EPV5) | Blautia faecis (EPV78) |
| C. leptum (EPV6) | Ruminococcus torques (EPV76) |
| B. faecis (EPV15) | Blautia wexlerae SJTU1416 (EPV52) |
| B. obeum (EPV20) | Blautia WAL14507 (EPV64) |
| B. producta (EPV21) | Uncultured bacterium SJTU1416 (EPV51) |
| B. coccoides (EPV22) | Uncultured bacterium GQ8980099 (EPV47) |
| B. hydrogenotrophica (EPV23) | Eubacterium rectale (EPV35) |
| B. hansenii (EPV24) | |

TABLE 4

Exemplary Prebiotics/Carbon Sources

| Chemical | MoA |
|---|---|
| L-Arabinose | C-Source, carbohydrate |
| N-Acetyl-D-Glucosamine | C-Source, carbohydrate |
| D-Saccharic acid | C-Source, carboxylic acid |
| Succinic acid | C-Source, carboxylic acid |
| D-Galactose | C-Source, carbohydrate |
| L-Aspartic acid | C-Source, amino acid |
| L-Proline | C-Source, amino acid |
| D-Alanine | C-Source, amino acid |
| D-Trehalose | C-Source, carbohydrate |
| D-Mannose | C-Source, carbohydrate |
| Dulcitol | C-Source, carbohydrate |
| D-Serine | C-Source, amino acid |
| D-Sorbitol | C-Source, carbohydrate |
| Glycerol | C-Source, carbohydrate |
| L-Fucose | C-Source, carbohydrate |
| D-Glucuronic acid | C-Source, carboxylic acid |
| D-Gluconic acid | C-Source, carboxylic acid |
| DL-a-Glycerol Phosphate | C-Source, carbohydrate |
| D-Xylose | C-Source, carbohydrate |
| L-Lactic acid | C-Source, carboxylic acid |
| Formic acid | C-Source, carboxylic acid |
| D-Mannitol | C-Source, carbohydrate |
| L-Glutamic acid | C-Source, amino acid |
| D-Glucose-6-Phosphate | C-Source, carbohydrate |
| D-Galactonic acid-g-Lactone | C-Source, carboxylic acid |
| DL-Malic acid | C-Source, carboxylic acid |
| D-Ribose | C-Source, carbohydrate |
| Tween 20 | C-Source, fatty acid |
| L-Rhamnose | C-Source, carbohydrate |
| D-Fructose | C-Source, carbohydrate |
| Acetic acid | C-Source, carboxylic acid |
| a-D-Glucose | C-Source, carbohydrate |
| Maltose | C-Source, carbohydrate |
| D-Melibiose | C-Source, carbohydrate |
| Thymidine | C-Source, carbohydrate |
| L-Asparagine | C-Source, amino acid |
| D-Aspartic acid | C-Source, amino acid |
| D-Glucosaminic acid | C-Source, carboxylic acid |
| 1,2-Propanediol | C-Source, alcohol |
| Tween 40 | C-Source, fatty acid |
| a-Ketoglutaric acid | C-Source, carboxylic acid |
| a-Ketobutyric acid | C-Source, carboxylic acid |
| a-Methyl-D-Galactoside | C-Source, carbohydrate |
| a-D-Lactose | C-Source, carbohydrate |
| Lactulose | C-Source, carbohydrate |
| Sucrose | C-Source, carbohydrate |
| Uridine | C-Source, carbohydrate |
| L-Glutamine | C-Source, amino acid |
| m-Tartaric acid | C-Source, carboxylic acid |
| D-Glucose-1-Phosphate | C-Source, carbohydrate |
| D-Fructose-6-Phosphate | C-Source, carbohydrate |
| Tween 80 | C-Source, fatty acid |
| a-Hydroxyglutaric acid-g-Lactone | C-Source, carboxylic acid |
| a-Hydroxybutyric acid | C-Source, carboxylic acid |
| b-Methyl-D-Glucoside | C-Source, carbohydrate |
| Adonitol | C-Source, carbohydrate |
| Maltotriose | C-Source, carbohydrate |
| 2'-Deoxyadenosine | C-Source, carbohydrate |
| Adenosine | C-Source, carbohydrate |
| Gly-Asp | C-Source, amino acid |
| Citric acid | C-Source, carboxylic acid |
| m-Inositol | C-Source, carbohydrate |
| D-Threonine | C-Source, amino acid |
| Fumaric acid | C-Source, carboxylic acid |
| Bromosuccinic acid | C-Source, carboxylic acid |
| Propionic acid | C-Source, carboxylic acid |
| Mucic acid | C-Source, carboxylic acid |
| Glycolic acid | C-Source, carboxylic acid |
| Glyoxylic acid | C-Source, carboxylic acid |
| D-Cellobiose | C-Source, carbohydrate |
| Inosine | C-Source, carbohydrate |
| Gly-Glu | C-Source, amino acid |
| Tricarballylic acid | C-Source, carboxylic acid |
| L-Serine | C-Source, amino acid |
| L-Threonine | C-Source, amino acid |
| L-Alanine | C-Source, amino acid |
| Ala-Gly | C-Source, amino acid |
| Acetoacetic acid | C-Source, carboxylic acid |
| N-Acetyl-D-Mannosamine | C-Source, carbohydrate |
| Mono-Methylsuccinate | C-Source, carboxylic acid |
| Methylpyruvate | C-Source, ester |
| D-Malic acid | C-Source, carboxylic acid |
| L-Malic acid | C-Source, carboxylic acid |
| Gly-Pro | C-Source, amino acid |
| p-Hydroxyphenyl Acetic acid | C-Source, carboxylic acid |
| m-Hydroxyphenyl Acetic acid | C-Source, carboxylic acid |
| Tyramine | C-Source, amine |
| D-Psicose | C-Source, carbohydrate |
| L-Lyxose | C-Source, carbohydrate |
| Glucuronamide | C-Source, amide |
| Pyruvic acid | C-Source, carboxylic acid |
| L-Galactonic acid-g-Lactone | C-Source, carboxylic acid |
| D-Galacturonic acid | C-Source, carboxylic acid |
| Phenylethylamine | C-Source, amine |
| 2-Aminoethanol | C-Source, alcohol |
| Negative Control | C-Source, negative control |
| Chondroitin Sulfate C | C-Source, polymer |
| a-Cyclodextrin | C-Source, polymer |
| b-Cyclodextrin | C-Source, polymer |
| g-Cyclodextrin | C-Source, polymer |
| Dextrin | C-Source, polymer |
| Gelatin | C-Source, polymer |
| Glycogen | C-Source, polymer |
| Inulin | C-Source, polymer |
| Laminarin | C-Source, polymer |
| Mannan | C-Source, polymer |
| Pectin | C-Source, polymer |
| N-Acetyl-D-Galactosamine | C-Source, carbohydrate |
| N-Acetyl-Neuraminic acid | C-Source, carboxylic acid |
| b-D-Allose | C-Source, carbohydrate |
| Amygdalin | C-Source, carbohydrate |
| D-Arabinose | C-Source, carbohydrate |
| D-Arabitol | C-Source, carbohydrate |
| L-Arabitol | C-Source, carbohydrate |
| Arbutin | C-Source, carbohydrate |
| 2-Deoxy-D-Ribose | C-Source, carbohydrate |
| i-Erythritol | C-Source, carbohydrate |
| D-Fucose | C-Source, carbohydrate |
| 3-O-b-D-Galactopyranosyl-D-Arabinose | C-Source, carbohydrate |
| Gentiobiose | C-Source, carbohydrate |
| L-Glucose | C-Source, carbohydrate |
| D-Lactitol | C-Source, carbohydrate |
| D-Melezitose | C-Source, carbohydrate |
| Maltitol | C-Source, carbohydrate |
| a-Methyl-D-Glucoside | C-Source, carbohydrate |
| b-Methyl-D-Galactoside | C-Source, carbohydrate |
| 3-Methylglucose | C-Source, carbohydrate |
| b-Methyl-D-Glucuronic acid | C-Source, carboxylic acid |
| a-Methyl-D-Mannoside | C-Source, carbohydrate |

TABLE 4-continued

Exemplary Prebiotics/Carbon Sources

| Chemical | MoA |
|---|---|
| b-Methyl-D-Xyloside | C-Source, carbohydrate |
| Palatinose | C-Source, carbohydrate |
| D-Raffinose | C-Source, carbohydrate |
| Salicin | C-Source, carbohydrate |
| Sedoheptulosan | C-Source, carbohydrate |
| L-Sorbose | C-Source, carbohydrate |
| Stachyose | C-Source, carbohydrate |
| D-Tagatose | C-Source, carbohydrate |
| Turanose | C-Source, carbohydrate |
| Xylitol | C-Source, carbohydrate |
| N-Acetyl-D-Glucosaminitol | C-Source, carbohydrate |
| g-Amino-N-Butyric acid | C-Source, carboxylic acid |
| d-Amino Valeric acid | C-Source, carboxylic acid |
| Butyric acid | C-Source, carboxylic acid |
| Capric acid | C-Source, carboxylic acid |
| Caproic acid | C-Source, carboxylic acid |
| Citraconic acid | C-Source, carboxylic acid |
| Citramalic acid | C-Source, carboxylic acid |
| D-Glucosamine | C-Source, carbohydrate |
| 2-Hydroxybenzoic acid | C-Source, carboxylic acid |
| 4-Hydroxybenzoic acid | C-Source, carboxylic acid |
| b-Hydroxybutyric acid | C-Source, carboxylic acid |
| g-Hydroxybutyric acid | C-Source, carboxylic acid |
| a-Keto-Valeric acid | C-Source, carboxylic acid |
| Itaconic acid | C-Source, carboxylic acid |
| 5-Keto-D-Gluconic acid | C-Source, carboxylic acid |
| D-Lactic acid Methyl Ester | C-Source, ester |
| Malonic acid | C-Source, carboxylic acid |
| Melibionic acid | C-Source, carbohydrate |
| Oxalic acid | C-Source, carboxylic acid |
| Oxalomalic acid | C-Source, carboxylic acid |
| Quinic acid | C-Source, carboxylic acid |
| D-Ribono-1,4-Lactone | C-Source, carboxylic acid |
| Sebacic acid | C-Source, carboxylic acid |
| Sorbic acid | C-Source, carboxylic acid |
| Succinamic acid | C-Source, carboxylic acid |
| D-Tartaric acid | C-Source, carboxylic acid |
| L-Tartaric acid | C-Source, carboxylic acid |
| Acetamide | C-Source, amide |
| L-Alaninamide | C-Source, amide |
| N-Acetyl-L-Glutamic acid | C-Source, amino acid |
| L-Arginine | C-Source, amino acid |
| Glycine | C-Source, amino acid |
| L-Histidine | C-Source, amino acid |
| L-Homoserine | C-Source, amino acid |
| Hydroxy-L-Proline | C-Source, amino acid |
| L-Isoleucine | C-Source, amino acid |
| L-Leucine | C-Source, amino acid |
| L-Lysine | C-Source, amino acid |
| L-Methionine | C-Source, amino acid |
| L-Ornithine | C-Source, amino acid |
| L-Phenylalanine | C-Source, amino acid |
| L-Pyroglutamic acid | C-Source, amino acid |
| L-Valine | C-Source, amino acid |
| D,L-Carnitine | C-Source, carboxylic acid |
| sec-Butylamine | C-Source, amine |
| D,L-Octopamine | C-Source, amine |
| Putrescine | C-Source, amine |
| Dihydroxyacetone | C-Source, alcohol |
| 2,3-Butanediol | C-Source, alcohol |
| 2,3-Butanedione | C-Source, alcohol |
| 3-Hydroxy-2-butanone | C-Source, alcohol |

TABLE 5

Bacterial Species Detected at Low Frequency in Vaginal Samples from Vancomycin-Treated Mice

| Site | Group | Taxonomy | Mean abundance day 6 (out of 10,000) | Median abundance day 6 (out of 10,000) |
|---|---|---|---|---|
| vaginal | Vancomycin | KF008552.1.1432 D_0__Bacteria; D_1__Proteobacteria; D_2__Gammaproteobacteria; D_3__Enterobacteriales; D_4__Enterobacteriaceae; D_5__Klebsiella; D_6__Klebsiella pneumoniae | 0.291242675 | 0.024255713 |
| vaginal | Vancomycin | AB740357.1.1462 D_0__Bacteria; D_1__Proteobacteria; D_2__Gammaproteobacteria; D_3__Enterobacteriales; D_4__Enterobacteriaceae; D_5__Pantoea; D_6__Pantoea sp. NCCP-532 | 1.436524722 | 0 |
| vaginal | Vancomycin | DQ799428.1.1372 D_0__Bacteria; D_1__Verrucomicrobia; D_2__Verrucomicrobiae; D_3__Verrucomicrobiales; D_4__Verrucomicrobiaceae; D_5__Akkermansia; D_6__uncultured bacterium | 0.348310693 | 0 |
| vaginal | Vancomycin | JX094996.1.1390 D_0__Bacteria; D_1__Firmicutes; D_2__Clostridia; D_3__Clostridiales; D_4__Lachnospiraceae; D_5__Blautia; D_6__uncultured bacterium | 0.348310693 | 0 |
| vaginal | Vancomycin | EU459716.1.1286 D_0__Bacteria; D_1__Firmicutes; D_2__Clostridia; D_3__Clostridiales; D_4__Lachnospiraceae; D_5__uncultured; D_6__uncultured bacterium | 0.348310693 | 0 |
| vaginal | Vancomycin | EU457230.1.1391 D_0__Bacteria; D_1__Firmicutes; D_2__Clostridia; D_3__Clostridiales; D_4__Lachnospiraceae; | 0.696621386 | 0 |

TABLE 5-continued

Bacterial Species Detected at Low Frequency in Vaginal Samples from Vancomycin-Treated Mice

| Site | Group | Taxonomy | Mean abundance day 6 (out of 10,000) | Median abundance day 6 (out of 10,000) |
|---|---|---|---|---|
| vaginal | Vancomycin | D_5__Incertae Sedis; D_6__uncultured bacterium EU459317.1.1373 D_0__Bacteria; D_1__Firmicutes; D_2__Clostridia; D_3__Clostridiales; D_4__Clostridiaceae 1; D_5__Clostridium sensu stricto 1; D_6__uncultured bacterium | 0.348310693 | 0 |
| vaginal | Vancomycin | HM817954.1.1353 D_0__Bacteria; D_1__Firmicutes; D_2__Clostridia; D_3__Clostridiales; D_4__Lachnospiraceae; D_5__Roseburia; D_6__uncultured bacterium | 0.348310693 | 0 |
| vaginal | Vancomycin | GQ134873.1.1373 D_0__Bacteria; D_1__Firmicutes; D_2__Clostridia; D_3__Clostridiales; D_4__Clostridiaceae 1; D_5__Clostridium sensu stricto 1; D_6__uncultured bacterium | 0.348310693 | 0 |
| vaginal | Vancomycin | FJ879074.1.1494 D_0__Bacteria; D_1__Firmicutes; D_2__Clostridia; D_3__Clostridiales; D_4__Lachnospiraceae; D_5__uncultured; D_6__uncultured bacterium | 0.348310693 | 0 |
| vaginal | Vancomycin | EU774816.1.1381 D_0__Bacteria; D_1__Firmicutes; D_2__Clostridia; D_3__Clostridiales; D_4__Clostridiaceae 1; D_5__Clostridium sensu stricto 1; D_6__uncultured bacterium | 0.348310693 | 0 |
| vaginal | Vancomycin | EU775614.1.1398 D_0__Bacteria; D_1__Proteobacteria; D_2__Gammaproteobacteria; D_3__Enterobacteriales; D_4__Enterobacteriaceae; D_5__Enterobacter; D_6__uncultured bacterium | 0.417063419 | 0 |

Unless otherwise indicated, all numbers expressing quantities of ingredients, reaction conditions, and so forth used in the specification, including claims, are to be understood as being modified in all instances by the term "about." Accordingly, unless otherwise indicated to the contrary, the numerical parameters are approximations and may vary depending upon the desired properties sought to be obtained. At the very least, and not as an attempt to limit the application of the doctrine of equivalents to the scope of the claims, each numerical parameter should be construed in light of the number of significant digits and ordinary rounding approaches.

Unless otherwise indicated, the term "at least" preceding a series of elements is to be understood to refer to every element in the series.

While the invention has been particularly shown and described with reference to a preferred embodiment and various alternate embodiments, it will be understood by persons skilled in the relevant art that various changes in form and details can be made therein without departing from the spirit and scope of the invention.

All references, issued patents and patent applications cited within the body of the instant specification are hereby incorporated by reference in their entirety, for all purposes.

The foregoing description of the embodiments of the invention has been presented for the purpose of illustration; it is not intended to be exhaustive or to limit the invention to the precise forms disclosed. Persons skilled in the relevant art can appreciate that many modifications and variations are possible in light of the above disclosure. Finally, the language used in the specification has been principally selected for readability and instructional purposes, and it may not have been selected to delineate or circumscribe the inventive subject matter. It is therefore intended that the scope of the invention be limited not by this detailed description, but rather by any claims that issue on an application based hereon. Accordingly, the disclosure of the embodiments of the invention is intended to be illustrative, but not limiting, of the scope of the invention, which is set forth in the following claims.

SEQUENCE LISTING

The patent contains a lengthy "Sequence Listing" section. A copy of the "Sequence Listing" is available in electronic form from the USPTO web site (https://seqdata.uspto.gov/?pageRequest=docDetail&DocID=US11607432B2). An electronic copy of the "Sequence Listing" will also be available from the USPTO upon request and payment of the fee set forth in 37 CFR 1.19(b)(3).

The invention claimed is:

1. A method of treating dysbiosis in a subject in need thereof, the method comprising administering to the subject a pharmaceutical composition comprising a bacterial population of a single bacterial species, wherein said species is *Enterococcus gallinarum*, such that dysbiosis in the subject is treated.

2. The method of claim 1, wherein said administration increases secretion of at least one pro-inflammatory cytokine by immune cells of the subject.

3. The method of claim 2, wherein the pro-inflammatory cytokine is selected from IL-1a, IL-1b, IL6, IFN gamma and TNF alpha.

4. The method of claim 2, wherein the immune cells are peripheral blood mononuclear cells (PBMCs).

5. The method of claim 1, wherein said administration increases the proportion of Th1 cells in the subject.

6. The method of claim 1, wherein said administration decreases the proportion of Th2 cells in the subject.

7. The method of claim 1, wherein said administration increases the proportion of Th17 cells in the subject.

8. The method of claim 1, wherein the bacterial population is capable of increasing secretion by a population of human peripheral blood mononuclear cells (PBMCs) of a cytokine selected from the group consisting of IL-1b, IL6 and TNF alpha.

9. The method of claim 1, wherein each strain of bacteria in the composition is capable of increasing secretion by a population of human peripheral blood mononuclear cells (PBMCs) of a cytokine selected from the group consisting of IL-1b, IL6 and TNF alpha.

10. The method of claim 1, wherein the subject is human.

11. The method of claim 1, wherein the bacterial population is lyophilized.

12. The method of claim 1, wherein the pharmaceutical composition is in the form of a pill, tablet, capsule or lozenge.

13. The method of claim 1, wherein the pharmaceutical composition is administered orally.

14. The method of claim 1, wherein inflammation in the subject is reduced at a site distal to the gastrointestinal tract of the subject.

* * * * *